(12) United States Patent
Brooun et al.

(10) Patent No.: US 7,563,610 B1
(45) Date of Patent: Jul. 21, 2009

(54) CRYSTALLINE COMPOSITION OF FARSENYL PYROPHOSPHATE SYNTHASE (ISPA)

(75) Inventors: Alexei Brooun, San Diego, CA (US); Douglas R. Dougan, Calgary (CA); David Hosfield, San Diego, CA (US); Yanming Zhang, Tallahassee, FL (US)

(73) Assignee: Takeda San Diego, Inc., San Diego, CA (US)

( * ) Notice: Subject to any disclaimer, the term of this patent is extended or adjusted under 35 U.S.C. 154(b) by 439 days.

(21) Appl. No.: 10/651,668

(22) Filed: Aug. 28, 2003

(51) Int. Cl.
*C12N 9/12* (2006.01)
*C12N 9/00* (2006.01)

(52) U.S. Cl. .............................. 435/194; 435/183; 436/4

(58) Field of Classification Search ........................ None
See application file for complete search history.

(56) References Cited

OTHER PUBLICATIONS

Giege et al. (1994) Crystallogenesis of Biological Macromolecules: Facts and Perspectives. Acta Cryst., D50: 339-350.*
Branden et al. (1999) "Introduction to Protein Structure Second Edition", Garland Publishing Inc., New York, pp. 374-375.*
Drenth (1995) "Principles of Protein X-ray Crystallography", Springer, p. 1.*
Kierzek et al. (2001) Biophys Chem 91:1-20.*
Wiencek (1999) Ann Rev Biomed Eng 1:505-534.*
Hosfield et al. (2004) J.Biol.Chem. 279:8526-8529.*
Brunger, Axel T., "Crystallography & NMR System: A New Software Suite for Macromolecular Structure Determination" Acta. Cryst. (1998), D54, pp. 905-921.

* cited by examiner

*Primary Examiner*—David J Steadman
*Assistant Examiner*—Alexander D Kim
(74) *Attorney, Agent, or Firm*—David J. Weitz; David Stemerick; Mitchell R. Brustein

(57) ABSTRACT

Provided are crystals relating to Farsenyl Pyrophosphate Synthase (IspA) from *E. coli* and its various uses.

10 Claims, 199 Drawing Sheets

Amino acid sequence for full-length E. coli IspA (residues 16-314) with an N-terminal His-tag (residues 1-15, underlined)

[SEQ. ID No. 1]

MGSDKIIHHHHHHTLMDFPQQLEACVKQANQALSRFIAPLPFQNTPVVETMQYGALLGGK
RLRPFLVYATGHMFGVSTNTLDAPAAAVECIHAYSLIHDDLPAMDDDDLRRGLPTCHVKF
GEANAILAGDALQTLAFSILSDADMPEVSDRDRISMISELASASGIAGMCGGQALDLDAE
GKHVPLDALERIHRHKTGALIRAAVRLGALSAGDKGRRALPVLDKYAESIGLAFQVQDDI
LDVVGDTATLGKRQGADQQLGKSTYPALLGLEQARKKARDLIDDARQSLKQLAEQSLDTS
ALEALADYIIQRNK cDNA sequence encoding IspA (residues 46-945) with an N-terminal His-tag (residues 1-45; underlined)

[SEQ. ID No. 2]

ATGGGATCTGATAAAATTATTCACCATCACCATCACCATACCCTTATGGACTTTCCGCAG
CAACTCGAAGCCTGCGTTAAGCAGGCCAACCAGGCGCTGAGCCGTTTTATCGCCCCACTG
CCCTTTCAGAACACTCCCGTGGTCGAAACCATGCAGTATGGCGCATTATTAGGTGGTAAG
CGCCTGCGACCTTTCCTGGTTTATGCCACCGGTCATATGTTCGGCGTTAGCACAAACACG
CTGGACGCACCCGCTGCCGCCGTTGAGTGTATCCACGCTTACTCATTAATTCATGATGAT
TTACCGGCAATGGATGATGACGATCTGCGTCGCGGTTTGCCAACCTGCCATGTGAAGTTT
GGCGAAGCAAACGCGATTCTCGCTGGCGACGCTTTACAAACGCTGGCGTTCTCGATTTTA
AGCGATGCCGATATGCCGGAAGTGTCGGACCGCGACAGAATTTCGATGATTTCTGAACTG
GCGAGCGCCAGTGGTATTGCCGGAATGTGCGGTGGTCAGGCATTAGATTTAGACGCGGAA
GGCAAACACGTACCTCTGGACGCGCTTGAGCGTATTCATCGTCATAAAACCGGCGCATTG
ATTCGCGCCGCCGTTCGCCTTGGTGCATTAAGCGCCGGAGATAAAGGACGTCGTGCTCTG
CCGGTACTCGACAAGTATGCAGAGAGCATCGGCCTTGCCTTCCAGGTTCAGGATGACATC
CTGGATGTGGTGGGAGATACTGCAACGTTGGGAAAACGCCAGGGTGCCGACCAGCAACTT
GGTAAAAGTACCTACCCTGCACTTCTGGGTCTTGAGCAAGCCCGGAAGAAAGCCCGGGAT
CTGATCGACGATGCCCGTCAGTCGCTGAAACAACTGGCTGAACAGTCACTCGATACCTCG
GCACTGGAAGCGCTAGCGGACTACATCATCCAGCGTAATAAATAA

FIGURE 1

Amino acid sequence for full-length E. coli IspA (residues 16-314) with an N-terminal His-tag (residues 1-15, underlined)

[SEQ. ID No. 1]

MGSDKIIHHHHHHTLMDFPQQLEACVKQANQALSRFIAPLPFQNTPVVETMQYGALLGGK
RLRPFLVYATGHMFGVSTNTLDAPAAAVECIHAYSLIHDDLPAMDDDDLRRGLPTCHVKF
GEANAILAGDALQTLAFSILSDADMPEVSDRDRISMISELASASGIAGMCGGQALDLDAE
GKHVPLDALERIHRHKTGALIRAAVRLGALSAGDKGRRALPVLDKYAESIGLAFQVQDDI
LDVVGDTATLGKRQGADQQLGKSTYPALLGLEQARKKARDLIDDARQSLKQLAEQSLDTS
ALEALADYIIQRNK cDNA sequence encoding IspA (residues 46-945) with an N-terminal His-tag (residues 1-45; underlined)

[SEQ. ID No. 2]

ATGGGATCTGATAAAATTATTCACCATCACCATCACCATACCCTTATGGACTTTCCGCAG
CAACTCGAAGCCTGCGTTAAGCAGGCCAACCAGGCGCTGAGCCGTTTTATCGCCCCACTG
CCCTTTCAGAACACTCCCGTGGTCGAAACCATGCAGTATGGCGCATTATTAGGTGGTAAG
CGCCTGCGACCTTTCCTGGTTTATGCCACCGGTCATATGTTCGGCGTTAGCACAAACACG
CTGGACGCACCCGCTGCCGCCGTTGAGTGTATCCACGCTTACTCATTAATTCATGATGAT
TTACCGGCAATGGATGATGACGATCTGCGTCGCGGTTTGCCAACCTGCCATGTGAAGTTT
GGCGAAGCAAACGCGATTCTCGCTGGCGACGCTTTACAAACGCTGGCGTTCTCGATTTTA
AGCGATGCCGATATGCCGGAAGTGTCGGACCGCGACAGAATTTCGATGATTTCTGAACTG
GCGAGCGCCAGTGGTATTGCCGGAATGTGCGGTGGTCAGGCATTAGATTTAGACGCGGAA
GGCAAACACGTACCTCTGGACGCGCTTGAGCGTATTCATCGTCATAAAACCGGCGCATTG
ATTCGCGCCGCCGTTCGCCTTGGTGCATTAAGCGCCGGAGATAAAGGACGTCGTGCTCTG
CCGGTACTCGACAAGTATGCAGAGAGCATCGGCCTTGCCTTCCAGGTTCAGGATGACATC
CTGGATGTGGTGGGAGATACTGCAACGTTGGGAAAACGCCAGGGTGCCGACCAGCAACTT
GGTAAAAGTACCTACCCTGCACTTCTGGGTCTTGAGCAAGCCCGGAAGAAAGCCCGGGAT
CTGATCGACGATGCCCGTCAGTCGCTGAAACAACTGGCTGAACAGTCACTCGATACCTCG
GCACTGGAAGCGCTAGCGGACTACATCATCCAGCGTAATAAATAA

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | MET | A | 16 | 65.564 | 50.628 | -5.933 | 1.00 | 45.23 |
| 3 | CA | MET | A | 16 | 65.166 | 51.178 | -7.255 | 1.00 | 44.87 |
| 5 | CB | MET | A | 16 | 64.933 | 50.049 | -8.267 | 1.00 | 45.30 |
| 8 | CG | MET | A | 16 | 65.153 | 50.446 | -9.726 | 1.00 | 47.01 |
| 11 | SD | MET | A | 16 | 66.181 | 49.252 | -10.631 | 1.00 | 50.95 |
| 12 | CE | MET | A | 16 | 64.933 | 48.059 | -11.220 | 1.00 | 50.52 |
| 16 | C | MET | A | 16 | 63.907 | 52.030 | -7.120 | 1.00 | 43.94 |
| 17 | O | MET | A | 16 | 63.880 | 53.159 | -7.610 | 1.00 | 44.23 |
| 20 | N | ASP | A | 17 | 62.875 | 51.491 | -6.466 | 1.00 | 42.41 |
| 22 | CA | ASP | A | 17 | 61.591 | 52.188 | -6.366 | 1.00 | 41.35 |
| 24 | CB | ASP | A | 17 | 60.409 | 51.226 | -6.459 | 1.00 | 41.74 |
| 27 | CG | ASP | A | 17 | 59.134 | 51.926 | -6.899 | 1.00 | 43.33 |
| 28 | OD1 | ASP | A | 17 | 58.448 | 52.535 | -6.037 | 1.00 | 46.33 |
| 29 | OD2 | ASP | A | 17 | 58.753 | 51.939 | -8.093 | 1.00 | 45.52 |
| 30 | C | ASP | A | 17 | 61.486 | 52.990 | -5.079 | 1.00 | 39.80 |
| 31 | O | ASP | A | 17 | 61.195 | 52.441 | -4.005 | 1.00 | 38.54 |
| 32 | N | PHE | A | 18 | 61.672 | 54.298 | -5.210 | 1.00 | 38.05 |
| 34 | CA | PHE | A | 18 | 61.858 | 55.146 | -4.050 | 1.00 | 36.90 |
| 36 | CB | PHE | A | 18 | 62.429 | 56.514 | -4.427 | 1.00 | 36.92 |
| 39 | CG | PHE | A | 18 | 63.016 | 57.233 | -3.260 | 1.00 | 36.41 |
| 40 | CD1 | PHE | A | 18 | 64.116 | 56.707 | -2.609 | 1.00 | 37.05 |
| 42 | CE1 | PHE | A | 18 | 64.658 | 57.340 | -1.502 | 1.00 | 36.55 |
| 44 | CZ | PHE | A | 18 | 64.098 | 58.493 | -1.036 | 1.00 | 36.07 |
| 46 | CE2 | PHE | A | 18 | 62.988 | 59.025 | -1.664 | 1.00 | 36.56 |
| 48 | CD2 | PHE | A | 18 | 62.442 | 58.392 | -2.768 | 1.00 | 36.65 |
| 50 | C | PHE | A | 18 | 60.632 | 55.314 | -3.158 | 1.00 | 35.80 |
| 51 | O | PHE | A | 18 | 60.769 | 55.198 | -1.949 | 1.00 | 35.17 |
| 52 | N | PRO | A | 19 | 59.456 | 55.618 | -3.712 | 1.00 | 34.90 |
| 53 | CA | PRO | A | 19 | 58.239 | 55.676 | -2.889 | 1.00 | 34.06 |
| 55 | CB | PRO | A | 19 | 57.123 | 55.861 | -3.924 | 1.00 | 34.29 |
| 58 | CG | PRO | A | 19 | 57.782 | 56.558 | -5.047 | 1.00 | 34.27 |
| 61 | CD | PRO | A | 19 | 59.176 | 55.993 | -5.114 | 1.00 | 34.77 |
| 64 | C | PRO | A | 19 | 58.008 | 54.418 | -2.039 | 1.00 | 33.38 |
| 65 | O | PRO | A | 19 | 57.585 | 54.564 | -0.895 | 1.00 | 32.65 |
| 66 | N | GLN | A | 20 | 58.279 | 53.228 | -2.579 | 1.00 | 32.48 |
| 68 | CA | GLN | A | 20 | 58.126 | 51.981 | -1.815 | 1.00 | 32.23 |
| 70 | CB | GLN | A | 20 | 58.188 | 50.746 | -2.732 | 1.00 | 32.68 |
| 73 | CG | GLN | A | 20 | 56.883 | 50.493 | -3.534 | 1.00 | 35.01 |
| 76 | CD | GLN | A | 20 | 56.611 | 49.011 | -3.811 | 1.00 | 39.06 |
| 77 | OE1 | GLN | A | 20 | 55.463 | 48.546 | -3.685 | 1.00 | 41.57 |
| 78 | NE2 | GLN | A | 20 | 57.654 | 48.270 | -4.193 | 1.00 | 39.95 |
| 81 | C | GLN | A | 20 | 59.177 | 51.869 | -0.700 | 1.00 | 30.90 |
| 82 | O | GLN | A | 20 | 58.892 | 51.363 | 0.379 | 1.00 | 30.03 |

FIGURE 3 (Cont.)

| A | B | C | D | E | F | G | H | I | J |
|---|---|---|---|---|---|---|---|---|---|
| 83 | N | GLN | A | 21 | 60.385 | 52.351 | -0.959 | 1.00 | 29.82 |
| 85 | CA | GLN | A | 21 | 61.426 | 52.370 | 0.058 | 1.00 | 29.68 |
| 87 | CB | GLN | A | 21 | 62.783 | 52.738 | -0.560 | 1.00 | 29.82 |
| 90 | CG | GLN | A | 21 | 63.366 | 51.647 | -1.494 | 1.00 | 31.98 |
| 93 | CD | GLN | A | 21 | 63.920 | 50.425 | -0.746 | 1.00 | 34.89 |
| 94 | OE1 | GLN | A | 21 | 64.483 | 49.512 | -1.360 | 1.00 | 36.76 |
| 95 | NE2 | GLN | A | 21 | 63.762 | 50.412 | 0.572 | 1.00 | 37.29 |
| 98 | C | GLN | A | 21 | 61.065 | 53.323 | 1.204 | 1.00 | 28.61 |
| 99 | O | GLN | A | 21 | 61.214 | 52.973 | 2.372 | 1.00 | 28.03 |
| 100 | N | LEU | A | 22 | 60.588 | 54.513 | 0.863 | 1.00 | 27.80 |
| 102 | CA | LEU | A | 22 | 60.120 | 55.472 | 1.848 | 1.00 | 27.76 |
| 104 | CB | LEU | A | 22 | 59.582 | 56.740 | 1.169 | 1.00 | 28.15 |
| 107 | CG | LEU | A | 22 | 60.595 | 57.714 | 0.543 | 1.00 | 29.56 |
| 109 | CD1 | LEU | A | 22 | 59.880 | 58.764 | -0.297 | 1.00 | 30.48 |
| 113 | CD2 | LEU | A | 22 | 61.447 | 58.392 | 1.611 | 1.00 | 30.42 |
| 117 | C | LEU | A | 22 | 59.036 | 54.861 | 2.736 | 1.00 | 27.31 |
| 118 | O | LEU | A | 22 | 59.099 | 54.975 | 3.950 | 1.00 | 26.43 |
| 119 | N | GLU | A | 23 | 58.057 | 54.185 | 2.145 | 1.00 | 27.14 |
| 121 | CA | GLU | A | 23 | 56.973 | 53.627 | 2.952 | 1.00 | 27.44 |
| 123 | CB | GLU | A | 23 | 55.760 | 53.232 | 2.101 | 1.00 | 28.34 |
| 126 | CG | GLU | A | 23 | 54.798 | 52.234 | 2.759 | 1.00 | 31.44 |
| 129 | CD | GLU | A | 23 | 53.961 | 52.789 | 3.912 | 1.00 | 35.82 |
| 130 | OE1 | GLU | A | 23 | 52.791 | 52.370 | 4.024 | 1.00 | 38.87 |
| 131 | OE2 | GLU | A | 23 | 54.448 | 53.597 | 4.738 | 1.00 | 38.87 |
| 132 | C | GLU | A | 23 | 57.465 | 52.462 | 3.805 | 1.00 | 26.15 |
| 133 | O | GLU | A | 23 | 57.040 | 52.322 | 4.949 | 1.00 | 25.29 |
| 134 | N | ALA | A | 24 | 58.357 | 51.642 | 3.254 | 1.00 | 25.31 |
| 136 | CA | ALA | A | 24 | 59.018 | 50.578 | 4.013 | 1.00 | 24.72 |
| 138 | CB | ALA | A | 24 | 60.019 | 49.847 | 3.153 | 1.00 | 25.46 |
| 142 | C | ALA | A | 24 | 59.728 | 51.160 | 5.230 | 1.00 | 24.33 |
| 143 | O | ALA | A | 24 | 59.610 | 50.636 | 6.331 | 1.00 | 23.33 |
| 144 | N | CYS | A | 25 | 60.438 | 52.263 | 5.025 | 1.00 | 23.38 |
| 146 | CA | CYS | A | 25 | 61.130 | 52.944 | 6.115 | 1.00 | 23.00 |
| 148 | CB | CYS | A | 25 | 62.029 | 54.056 | 5.578 | 1.00 | 23.11 |
| 151 | SG | CYS | A | 25 | 62.861 | 54.980 | 6.885 | 1.00 | 21.11 |
| 152 | C | CYS | A | 25 | 60.147 | 53.499 | 7.162 | 1.00 | 22.39 |
| 153 | O | CYS | A | 25 | 60.368 | 53.344 | 8.351 | 1.00 | 22.44 |
| 154 | N | VAL | A | 26 | 59.051 | 54.105 | 6.725 | 1.00 | 22.24 |
| 156 | CA | VAL | A | 26 | 58.056 | 54.638 | 7.651 | 1.00 | 22.18 |
| 158 | CB | VAL | A | 26 | 56.889 | 55.349 | 6.902 | 1.00 | 22.57 |
| 160 | CG1 | VAL | A | 26 | 55.697 | 55.610 | 7.815 | 1.00 | 22.85 |
| 164 | CG2 | VAL | A | 26 | 57.368 | 56.650 | 6.293 | 1.00 | 22.19 |
| 168 | C | VAL | A | 26 | 57.534 | 53.530 | 8.580 | 1.00 | 21.91 |
| 169 | O | VAL | A | 26 | 57.440 | 53.722 | 9.789 | 1.00 | 21.65 |
| 170 | N | LYS | A | 27 | 57.235 | 52.369 | 8.011 | 1.00 | 21.41 |
| 172 | CA | LYS | A | 27 | 56.741 | 51.236 | 8.779 | 1.00 | 21.24 |
| 174 | CB | LYS | A | 27 | 56.273 | 50.127 | 7.836 | 1.00 | 22.15 |
| 177 | CG | LYS | A | 27 | 54.982 | 50.454 | 7.081 | 1.00 | 24.03 |
| 180 | CD | LYS | A | 27 | 54.467 | 49.210 | 6.340 | 1.00 | 28.62 |
| 183 | CE | LYS | A | 27 | 53.133 | 49.458 | 5.596 | 1.00 | 31.91 |
| 186 | NZ | LYS | A | 27 | 53.166 | 48.924 | 4.184 | 1.00 | 33.67 |
| 190 | C | LYS | A | 27 | 57.798 | 50.693 | 9.737 | 1.00 | 20.33 |

FIGURE 3 (Cont.)

| A | B | C | D | E | F | G | H | I | J |
|---|---|---|---|---|---|---|---|---|---|
| 191 | O | LYS | A | 27 | 57.499 | 50.428 | 10.910 | 1.00 | 19.84 |
| 192 | N | GLN | A | 28 | 59.022 | 50.536 | 9.244 | 1.00 | 19.37 |
| 194 | CA | GLN | A | 28 | 60.116 | 50.039 | 10.073 | 1.00 | 19.22 |
| 196 | CB | GLN | A | 28 | 61.413 | 49.892 | 9.264 | 1.00 | 19.05 |
| 199 | CG | GLN | A | 28 | 62.596 | 49.326 | 10.078 | 1.00 | 19.21 |
| 202 | CD | GLN | A | 28 | 62.485 | 47.814 | 10.392 | 1.00 | 20.65 |
| 203 | OE1 | GLN | A | 28 | 63.076 | 47.320 | 11.375 | 1.00 | 22.34 |
| 204 | NE2 | GLN | A | 28 | 61.792 | 47.087 | 9.537 | 1.00 | 16.09 |
| 207 | C | GLN | A | 28 | 60.340 | 50.985 | 11.258 | 1.00 | 18.67 |
| 208 | O | GLN | A | 28 | 60.392 | 50.549 | 12.386 | 1.00 | 18.19 |
| 209 | N | ALA | A | 29 | 60.465 | 52.278 | 10.985 | 1.00 | 18.55 |
| 211 | CA | ALA | A | 29 | 60.748 | 53.271 | 12.026 | 1.00 | 18.70 |
| 213 | CB | ALA | A | 29 | 61.022 | 54.625 | 11.403 | 1.00 | 18.98 |
| 217 | C | ALA | A | 29 | 59.626 | 53.382 | 13.036 | 1.00 | 19.64 |
| 218 | O | ALA | A | 29 | 59.875 | 53.535 | 14.238 | 1.00 | 19.64 |
| 219 | N | ASN | A | 30 | 58.386 | 53.300 | 12.564 | 1.00 | 19.52 |
| 221 | CA | ASN | A | 30 | 57.232 | 53.369 | 13.464 | 1.00 | 19.96 |
| 223 | CB | ASN | A | 30 | 55.920 | 53.446 | 12.688 | 1.00 | 19.83 |
| 226 | CG | ASN | A | 30 | 55.652 | 54.816 | 12.118 | 1.00 | 22.13 |
| 227 | OD1 | ASN | A | 30 | 56.322 | 55.792 | 12.458 | 1.00 | 23.82 |
| 228 | ND2 | ASN | A | 30 | 54.638 | 54.904 | 11.249 | 1.00 | 23.36 |
| 231 | C | ASN | A | 30 | 57.177 | 52.190 | 14.405 | 1.00 | 19.86 |
| 232 | O | ASN | A | 30 | 56.847 | 52.343 | 15.573 | 1.00 | 19.83 |
| 233 | N | GLN | A | 31 | 57.474 | 51.010 | 13.878 | 1.00 | 20.51 |
| 235 | CA | GLN | A | 31 | 57.584 | 49.779 | 14.679 | 1.00 | 21.34 |
| 237 | CB | GLN | A | 31 | 57.921 | 48.608 | 13.760 | 1.00 | 21.77 |
| 240 | CG | GLN | A | 31 | 57.882 | 47.246 | 14.412 | 1.00 | 24.92 |
| 243 | CD | GLN | A | 31 | 58.025 | 46.137 | 13.385 | 1.00 | 29.08 |
| 244 | OE1 | GLN | A | 31 | 59.120 | 45.918 | 12.832 | 1.00 | 33.06 |
| 245 | NE2 | GLN | A | 31 | 56.929 | 45.446 | 13.112 | 1.00 | 31.52 |
| 248 | C | GLN | A | 31 | 58.683 | 49.902 | 15.737 | 1.00 | 21.05 |
| 249 | O | GLN | A | 31 | 58.488 | 49.550 | 16.899 | 1.00 | 20.55 |
| 250 | N | ALA | A | 32 | 59.839 | 50.384 | 15.310 | 1.00 | 20.90 |
| 252 | CA | ALA | A | 32 | 60.957 | 50.629 | 16.213 | 1.00 | 21.59 |
| 254 | CB | ALA | A | 32 | 62.129 | 51.176 | 15.451 | 1.00 | 21.36 |
| 258 | C | ALA | A | 32 | 60.539 | 51.598 | 17.315 | 1.00 | 21.65 |
| 259 | O | ALA | A | 32 | 60.696 | 51.304 | 18.475 | 1.00 | 22.05 |
| 260 | N | LEU | A | 33 | 59.999 | 52.750 | 16.940 | 1.00 | 22.61 |
| 262 | CA | LEU | A | 33 | 59.575 | 53.760 | 17.906 | 1.00 | 23.19 |
| 264 | CB | LEU | A | 33 | 58.931 | 54.937 | 17.175 | 1.00 | 23.47 |
| 267 | CG | LEU | A | 33 | 59.879 | 55.966 | 16.574 | 1.00 | 24.21 |
| 269 | CD1 | LEU | A | 33 | 59.165 | 56.759 | 15.502 | 1.00 | 24.68 |
| 273 | CD2 | LEU | A | 33 | 60.391 | 56.887 | 17.685 | 1.00 | 26.09 |
| 277 | C | LEU | A | 33 | 58.555 | 53.183 | 18.890 | 1.00 | 24.35 |
| 278 | O | LEU | A | 33 | 58.659 | 53.391 | 20.094 | 1.00 | 23.66 |
| 279 | N | SER | A | 34 | 57.567 | 52.471 | 18.356 | 1.00 | 25.27 |
| 281 | CA | SER | A | 34 | 56.513 | 51.879 | 19.172 | 1.00 | 26.76 |
| 283 | CB | SER | A | 34 | 55.480 | 51.162 | 18.295 | 1.00 | 27.01 |
| 286 | OG | SER | A | 34 | 54.789 | 52.077 | 17.470 | 1.00 | 28.06 |
| 288 | C | SER | A | 34 | 57.070 | 50.896 | 20.194 | 1.00 | 27.73 |
| 289 | O | SER | A | 34 | 56.597 | 50.849 | 21.316 | 1.00 | 28.77 |
| 290 | N | ARG | A | 35 | 58.071 | 50.117 | 19.802 | 1.00 | 28.38 |

FIGURE 3 (Cont.)

| A | B | C | D | E | F | G | H | I | J |
|---|---|---|---|---|---|---|---|---|---|
| 292 | CA | ARG | A | 35 | 58.649 | 49.117 | 20.688 | 1.00 | 29.15 |
| 294 | CB | ARG | A | 35 | 59.580 | 48.182 | 19.915 | 1.00 | 29.68 |
| 297 | CG | ARG | A | 35 | 58.842 | 47.176 | 19.053 | 1.00 | 33.37 |
| 300 | CD | ARG | A | 35 | 59.681 | 46.648 | 17.895 | 1.00 | 36.27 |
| 303 | NE | ARG | A | 35 | 59.113 | 45.445 | 17.291 | 1.00 | 39.06 |
| 305 | CZ | ARG | A | 35 | 59.778 | 44.630 | 16.473 | 1.00 | 41.04 |
| 306 | NH1 | ARG | A | 35 | 61.046 | 44.878 | 16.153 | 1.00 | 42.52 |
| 309 | NH2 | ARG | A | 35 | 59.174 | 43.564 | 15.970 | 1.00 | 42.39 |
| 312 | C | ARG | A | 35 | 59.426 | 49.761 | 21.828 | 1.00 | 28.40 |
| 313 | O | ARG | A | 35 | 59.480 | 49.210 | 22.926 | 1.00 | 27.74 |
| 314 | N | PHE | A | 36 | 60.045 | 50.910 | 21.557 | 1.00 | 27.61 |
| 316 | CA | PHE | A | 36 | 60.785 | 51.634 | 22.587 | 1.00 | 27.39 |
| 318 | CB | PHE | A | 36 | 61.853 | 52.533 | 21.960 | 1.00 | 27.18 |
| 321 | CG | PHE | A | 36 | 62.924 | 51.766 | 21.240 | 1.00 | 25.69 |
| 322 | CD1 | PHE | A | 36 | 63.214 | 52.029 | 19.918 | 1.00 | 25.01 |
| 324 | CE1 | PHE | A | 36 | 64.194 | 51.311 | 19.253 | 1.00 | 25.43 |
| 326 | CZ | PHE | A | 36 | 64.881 | 50.295 | 19.910 | 1.00 | 26.41 |
| 328 | CE2 | PHE | A | 36 | 64.600 | 50.022 | 21.218 | 1.00 | 26.08 |
| 330 | CD2 | PHE | A | 36 | 63.624 | 50.755 | 21.886 | 1.00 | 25.98 |
| 332 | C | PHE | A | 36 | 59.855 | 52.427 | 23.491 | 1.00 | 27.72 |
| 333 | O | PHE | A | 36 | 60.189 | 52.684 | 24.642 | 1.00 | 27.44 |
| 334 | N | ILE | A | 37 | 58.679 | 52.775 | 22.979 | 1.00 | 27.76 |
| 336 | CA | ILE | A | 37 | 57.677 | 53.488 | 23.756 | 1.00 | 28.44 |
| 338 | CB | ILE | A | 37 | 56.779 | 54.342 | 22.815 | 1.00 | 28.50 |
| 340 | CG1 | ILE | A | 37 | 57.527 | 55.620 | 22.419 | 1.00 | 28.68 |
| 343 | CD1 | ILE | A | 37 | 56.932 | 56.377 | 21.266 | 1.00 | 29.67 |
| 347 | CG2 | ILE | A | 37 | 55.440 | 54.687 | 23.473 | 1.00 | 29.47 |
| 351 | C | ILE | A | 37 | 56.831 | 52.526 | 24.620 | 1.00 | 28.85 |
| 352 | O | ILE | A | 37 | 56.394 | 52.900 | 25.707 | 1.00 | 29.06 |
| 353 | N | ALA | A | 38 | 56.631 | 51.293 | 24.156 | 1.00 | 29.01 |
| 355 | CA | ALA | A | 38 | 55.688 | 50.357 | 24.797 | 1.00 | 29.51 |
| 357 | CB | ALA | A | 38 | 55.489 | 49.108 | 23.926 | 1.00 | 29.54 |
| 361 | C | ALA | A | 38 | 55.995 | 49.951 | 26.251 | 1.00 | 29.76 |
| 362 | O | ALA | A | 38 | 55.058 | 49.805 | 27.032 | 1.00 | 30.41 |
| 363 | N | PRO | A | 39 | 57.261 | 49.761 | 26.631 | 1.00 | 29.96 |
| 364 | CA | PRO | A | 39 | 57.590 | 49.430 | 28.028 | 1.00 | 29.81 |
| 366 | CB | PRO | A | 39 | 59.019 | 48.871 | 27.952 | 1.00 | 29.63 |
| 369 | CG | PRO | A | 39 | 59.465 | 48.986 | 26.511 | 1.00 | 30.25 |
| 372 | CD | PRO | A | 39 | 58.466 | 49.813 | 25.784 | 1.00 | 30.23 |
| 375 | C | PRO | A | 39 | 57.547 | 50.605 | 29.003 | 1.00 | 29.35 |
| 376 | O | PRO | A | 39 | 57.768 | 50.409 | 30.200 | 1.00 | 29.40 |
| 377 | N | LEU | A | 40 | 57.288 | 51.808 | 28.508 | 1.00 | 28.66 |
| 379 | CA | LEU | A | 40 | 57.243 | 52.978 | 29.364 | 1.00 | 27.78 |
| 381 | CB | LEU | A | 40 | 57.200 | 54.260 | 28.535 | 1.00 | 27.92 |
| 384 | CG | LEU | A | 40 | 58.410 | 54.574 | 27.654 | 1.00 | 28.42 |
| 386 | CD1 | LEU | A | 40 | 58.185 | 55.906 | 26.946 | 1.00 | 29.06 |
| 390 | CD2 | LEU | A | 40 | 59.716 | 54.573 | 28.481 | 1.00 | 28.93 |
| 394 | C | LEU | A | 40 | 56.009 | 52.911 | 30.243 | 1.00 | 27.39 |
| 395 | O | LEU | A | 40 | 54.962 | 52.410 | 29.814 | 1.00 | 27.10 |
| 396 | N | PRO | A | 41 | 56.115 | 53.412 | 31.471 | 1.00 | 26.65 |
| 397 | CA | PRO | A | 41 | 54.937 | 53.506 | 32.338 | 1.00 | 26.24 |
| 399 | CB | PRO | A | 41 | 55.528 | 53.818 | 33.719 | 1.00 | 26.42 |

FIGURE 3 (Cont.)

| A | B | C | D | E | F | G | H | I | J |
|---|---|---|---|---|---|---|---|---|---|
| 402 | CG | PRO | A | 41 | 56.887 | 54.444 | 33.440 | 1.00 | 26.56 |
| 405 | CD | PRO | A | 41 | 57.339 | 53.909 | 32.122 | 1.00 | 26.41 |
| 408 | C | PRO | A | 41 | 54.017 | 54.624 | 31.863 | 1.00 | 25.76 |
| 409 | O | PRO | A | 41 | 54.386 | 55.397 | 30.977 | 1.00 | 25.20 |
| 410 | N | PHE | A | 42 | 52.840 | 54.706 | 32.469 | 1.00 | 25.70 |
| 412 | CA | PHE | A | 42 | 51.873 | 55.765 | 32.212 | 1.00 | 25.79 |
| 414 | CB | PHE | A | 42 | 52.479 | 57.131 | 32.556 | 1.00 | 25.87 |
| 417 | CG | PHE | A | 42 | 53.188 | 57.147 | 33.878 | 1.00 | 25.55 |
| 418 | CD1 | PHE | A | 42 | 52.489 | 56.876 | 35.049 | 1.00 | 25.97 |
| 420 | CE1 | PHE | A | 42 | 53.131 | 56.864 | 36.274 | 1.00 | 25.51 |
| 422 | CZ | PHE | A | 42 | 54.480 | 57.116 | 36.349 | 1.00 | 25.34 |
| 424 | CE2 | PHE | A | 42 | 55.195 | 57.379 | 35.186 | 1.00 | 25.76 |
| 426 | CD2 | PHE | A | 42 | 54.551 | 57.383 | 33.959 | 1.00 | 24.78 |
| 428 | C | PHE | A | 42 | 51.323 | 55.730 | 30.787 | 1.00 | 25.98 |
| 429 | O | PHE | A | 42 | 50.987 | 56.762 | 30.226 | 1.00 | 25.18 |
| 430 | N | GLN | A | 43 | 51.222 | 54.528 | 30.221 | 1.00 | 26.46 |
| 432 | CA | GLN | A | 43 | 50.537 | 54.330 | 28.942 | 1.00 | 27.47 |
| 434 | CB | GLN | A | 43 | 50.502 | 52.854 | 28.527 | 1.00 | 27.56 |
| 437 | CG | GLN | A | 43 | 51.828 | 52.229 | 28.185 | 1.00 | 28.72 |
| 440 | CD | GLN | A | 43 | 52.596 | 52.968 | 27.106 | 1.00 | 30.09 |
| 441 | OE1 | GLN | A | 43 | 53.817 | 53.065 | 27.187 | 1.00 | 32.82 |
| 442 | NE2 | GLN | A | 43 | 51.897 | 53.475 | 26.096 | 1.00 | 30.99 |
| 445 | C | GLN | A | 43 | 49.111 | 54.786 | 29.106 | 1.00 | 28.28 |
| 446 | O | GLN | A | 43 | 48.511 | 54.598 | 30.172 | 1.00 | 28.52 |
| 447 | N | ASN | A | 44 | 48.579 | 55.403 | 28.060 | 1.00 | 28.97 |
| 449 | CA | ASN | A | 44 | 47.202 | 55.868 | 28.040 | 1.00 | 29.76 |
| 451 | CB | ASN | A | 44 | 46.212 | 54.687 | 28.180 | 1.00 | 30.31 |
| 454 | CG | ASN | A | 44 | 46.513 | 53.535 | 27.210 | 1.00 | 31.66 |
| 455 | OD1 | ASN | A | 44 | 46.576 | 53.726 | 25.997 | 1.00 | 36.40 |
| 456 | ND2 | ASN | A | 44 | 46.694 | 52.342 | 27.748 | 1.00 | 32.76 |
| 459 | C | ASN | A | 44 | 46.937 | 56.948 | 29.094 | 1.00 | 29.56 |
| 460 | O | ASN | A | 44 | 45.842 | 57.041 | 29.631 | 1.00 | 29.84 |
| 461 | N | THR | A | 45 | 47.958 | 57.750 | 29.393 | 1.00 | 29.02 |
| 463 | CA | THR | A | 45 | 47.782 | 59.023 | 30.090 | 1.00 | 28.55 |
| 465 | CB | THR | A | 45 | 48.663 | 59.090 | 31.346 | 1.00 | 28.99 |
| 467 | OG1 | THR | A | 45 | 50.045 | 59.094 | 30.966 | 1.00 | 29.70 |
| 469 | CG2 | THR | A | 45 | 48.504 | 57.836 | 32.213 | 1.00 | 29.52 |
| 473 | C | THR | A | 45 | 48.173 | 60.135 | 29.107 | 1.00 | 27.72 |
| 474 | O | THR | A | 45 | 48.886 | 59.861 | 28.147 | 1.00 | 27.59 |
| 475 | N | PRO | A | 46 | 47.713 | 61.371 | 29.316 | 1.00 | 26.46 |
| 476 | CA | PRO | A | 46 | 47.961 | 62.453 | 28.351 | 1.00 | 25.93 |
| 478 | CB | PRO | A | 46 | 47.404 | 63.699 | 29.061 | 1.00 | 25.92 |
| 481 | CG | PRO | A | 46 | 46.331 | 63.155 | 29.974 | 1.00 | 26.20 |
| 484 | CD | PRO | A | 46 | 46.879 | 61.831 | 30.447 | 1.00 | 26.74 |
| 487 | C | PRO | A | 46 | 49.419 | 62.688 | 27.918 | 1.00 | 25.28 |
| 488 | O | PRO | A | 46 | 49.638 | 62.912 | 26.731 | 1.00 | 24.82 |
| 489 | N | VAL | A | 47 | 50.389 | 62.661 | 28.824 | 1.00 | 24.84 |
| 491 | CA | VAL | A | 47 | 51.766 | 62.944 | 28.412 | 1.00 | 24.49 |
| 493 | CB | VAL | A | 47 | 52.711 | 63.189 | 29.616 | 1.00 | 24.35 |
| 495 | CG1 | VAL | A | 47 | 52.934 | 61.920 | 30.414 | 1.00 | 25.47 |
| 499 | CG2 | VAL | A | 47 | 54.047 | 63.752 | 29.131 | 1.00 | 25.13 |
| 503 | C | VAL | A | 47 | 52.317 | 61.860 | 27.460 | 1.00 | 23.84 |

FIGURE 3 (Cont.)

| A | B | C | D | E | F | G | H | I | J |
|---|---|---|---|---|---|---|---|---|---|
| 504 | O | VAL | A | 47 | 52.962 | 62.172 | 26.462 | 1.00 | 23.42 |
| 505 | N | VAL | A | 48 | 52.046 | 60.594 | 27.752 | 1.00 | 23.38 |
| 507 | CA | VAL | A | 48 | 52.505 | 59.516 | 26.878 | 1.00 | 23.48 |
| 509 | CB | VAL | A | 48 | 52.449 | 58.146 | 27.567 | 1.00 | 23.07 |
| 511 | CG1 | VAL | A | 48 | 52.773 | 57.012 | 26.566 | 1.00 | 23.03 |
| 515 | CG2 | VAL | A | 48 | 53.409 | 58.125 | 28.740 | 1.00 | 23.55 |
| 519 | C | VAL | A | 48 | 51.725 | 59.512 | 25.567 | 1.00 | 23.67 |
| 520 | O | VAL | A | 48 | 52.297 | 59.299 | 24.510 | 1.00 | 23.73 |
| 521 | N | GLU | A | 49 | 50.427 | 59.782 | 25.632 | 1.00 | 23.99 |
| 523 | CA | GLU | A | 49 | 49.629 | 59.897 | 24.417 | 1.00 | 24.17 |
| 525 | CB | GLU | A | 49 | 48.155 | 60.087 | 24.761 | 1.00 | 24.86 |
| 528 | CG | GLU | A | 49 | 47.534 | 58.863 | 25.404 | 1.00 | 27.67 |
| 531 | CD | GLU | A | 49 | 46.125 | 59.115 | 25.899 | 1.00 | 33.01 |
| 532 | OE1 | GLU | A | 49 | 45.337 | 58.140 | 25.909 | 1.00 | 36.58 |
| 533 | OE2 | GLU | A | 49 | 45.806 | 60.274 | 26.278 | 1.00 | 35.89 |
| 534 | C | GLU | A | 49 | 50.115 | 61.066 | 23.562 | 1.00 | 22.99 |
| 535 | O | GLU | A | 49 | 50.099 | 60.980 | 22.345 | 1.00 | 21.91 |
| 536 | N | THR | A | 50 | 50.574 | 62.139 | 24.208 | 1.00 | 22.14 |
| 538 | CA | THR | A | 50 | 51.147 | 63.270 | 23.497 | 1.00 | 21.71 |
| 540 | CB | THR | A | 50 | 51.426 | 64.447 | 24.442 | 1.00 | 21.87 |
| 542 | OG1 | THR | A | 50 | 50.218 | 64.833 | 25.112 | 1.00 | 21.63 |
| 544 | CG2 | THR | A | 50 | 51.861 | 65.695 | 23.647 | 1.00 | 21.55 |
| 548 | C | THR | A | 50 | 52.435 | 62.833 | 22.813 | 1.00 | 21.19 |
| 549 | O | THR | A | 50 | 52.658 | 63.152 | 21.667 | 1.00 | 20.77 |
| 550 | N | MET | A | 51 | 53.268 | 62.075 | 23.515 | 1.00 | 21.45 |
| 552 | CA | MET | A | 51 | 54.525 | 61.583 | 22.936 | 1.00 | 21.16 |
| 554 | CB | MET | A | 51 | 55.321 | 60.768 | 23.965 | 1.00 | 21.28 |
| 557 | CG | MET | A | 51 | 55.825 | 61.558 | 25.165 | 1.00 | 21.06 |
| 560 | SD | MET | A | 51 | 56.503 | 60.485 | 26.448 | 1.00 | 21.92 |
| 561 | CE | MET | A | 51 | 58.036 | 59.941 | 25.581 | 1.00 | 18.94 |
| 565 | C | MET | A | 51 | 54.227 | 60.713 | 21.704 | 1.00 | 21.05 |
| 566 | O | MET | A | 51 | 54.873 | 60.858 | 20.676 | 1.00 | 21.01 |
| 567 | N | GLN | A | 52 | 53.228 | 59.835 | 21.812 | 1.00 | 21.04 |
| 569 | CA | GLN | A | 52 | 52.882 | 58.908 | 20.737 | 1.00 | 21.29 |
| 571 | CB | GLN | A | 52 | 51.862 | 57.889 | 21.229 | 1.00 | 21.77 |
| 574 | CG | GLN | A | 52 | 52.407 | 56.822 | 22.155 | 1.00 | 23.17 |
| 577 | CD | GLN | A | 52 | 51.297 | 55.954 | 22.728 | 1.00 | 26.61 |
| 578 | OE1 | GLN | A | 52 | 51.254 | 54.743 | 22.480 | 1.00 | 30.25 |
| 579 | NE2 | GLN | A | 52 | 50.389 | 56.569 | 23.474 | 1.00 | 24.83 |
| 582 | C | GLN | A | 52 | 52.299 | 59.642 | 19.526 | 1.00 | 21.06 |
| 583 | O | GLN | A | 52 | 52.547 | 59.291 | 18.371 | 1.00 | 19.85 |
| 584 | N | TYR | A | 53 | 51.495 | 60.656 | 19.804 | 1.00 | 20.82 |
| 586 | CA | TYR | A | 53 | 50.887 | 61.466 | 18.760 | 1.00 | 21.28 |
| 588 | CB | TYR | A | 53 | 49.946 | 62.447 | 19.433 | 1.00 | 21.43 |
| 591 | CG | TYR | A | 53 | 49.135 | 63.357 | 18.555 | 1.00 | 23.00 |
| 592 | CD1 | TYR | A | 53 | 47.838 | 63.002 | 18.154 | 1.00 | 24.56 |
| 594 | CE1 | TYR | A | 53 | 47.069 | 63.859 | 17.385 | 1.00 | 24.49 |
| 596 | CZ | TYR | A | 53 | 47.562 | 65.107 | 17.052 | 1.00 | 25.48 |
| 597 | OH | TYR | A | 53 | 46.793 | 65.965 | 16.292 | 1.00 | 24.53 |
| 599 | CE2 | TYR | A | 53 | 48.844 | 65.484 | 17.445 | 1.00 | 23.07 |
| 601 | CD2 | TYR | A | 53 | 49.604 | 64.618 | 18.212 | 1.00 | 23.55 |
| 603 | C | TYR | A | 53 | 51.967 | 62.218 | 18.002 | 1.00 | 20.79 |

FIGURE 3 (Cont.)

| A | B | C | D | E | F | G | H | I | J |
|---|---|---|---|---|---|---|---|---|---|
| 604 | O | TYR | A | 53 | 52.033 | 62.184 | 16.765 | 1.00 | 20.35 |
| 605 | N | GLY | A | 54 | 52.811 | 62.910 | 18.761 | 1.00 | 20.69 |
| 607 | CA | GLY | A | 54 | 53.840 | 63.751 | 18.187 | 1.00 | 20.90 |
| 610 | C | GLY | A | 54 | 54.963 | 62.972 | 17.526 | 1.00 | 21.30 |
| 611 | O | GLY | A | 54 | 55.596 | 63.495 | 16.627 | 1.00 | 21.54 |
| 612 | N | ALA | A | 55 | 55.215 | 61.732 | 17.955 | 1.00 | 21.95 |
| 614 | CA | ALA | A | 55 | 56.315 | 60.942 | 17.389 | 1.00 | 22.16 |
| 616 | CB | ALA | A | 55 | 56.981 | 60.100 | 18.480 | 1.00 | 22.04 |
| 620 | C | ALA | A | 55 | 55.862 | 60.033 | 16.242 | 1.00 | 22.84 |
| 621 | O | ALA | A | 55 | 56.609 | 59.808 | 15.282 | 1.00 | 22.77 |
| 622 | N | LEU | A | 56 | 54.645 | 59.506 | 16.337 | 1.00 | 23.82 |
| 624 | CA | LEU | A | 56 | 54.227 | 58.413 | 15.446 | 1.00 | 25.01 |
| 626 | CB | LEU | A | 56 | 53.718 | 57.229 | 16.272 | 1.00 | 25.40 |
| 629 | CG | LEU | A | 56 | 54.803 | 56.448 | 16.999 | 1.00 | 26.02 |
| 631 | CD1 | LEU | A | 56 | 54.192 | 55.617 | 18.110 | 1.00 | 27.58 |
| 635 | CD2 | LEU | A | 56 | 55.583 | 55.570 | 16.011 | 1.00 | 26.63 |
| 639 | C | LEU | A | 56 | 53.188 | 58.758 | 14.386 | 1.00 | 25.71 |
| 640 | O | LEU | A | 56 | 53.144 | 58.088 | 13.352 | 1.00 | 25.79 |
| 641 | N | LEU | A | 57 | 52.351 | 59.772 | 14.626 | 1.00 | 26.23 |
| 643 | CA | LEU | A | 57 | 51.244 | 60.076 | 13.712 | 1.00 | 26.84 |
| 645 | CB | LEU | A | 57 | 50.045 | 60.627 | 14.487 | 1.00 | 27.25 |
| 648 | CG | LEU | A | 57 | 48.675 | 60.380 | 13.836 | 1.00 | 29.61 |
| 650 | CD1 | LEU | A | 57 | 48.417 | 58.886 | 13.617 | 1.00 | 30.97 |
| 654 | CD2 | LEU | A | 57 | 47.544 | 60.990 | 14.672 | 1.00 | 31.15 |
| 658 | C | LEU | A | 57 | 51.660 | 61.041 | 12.589 | 1.00 | 26.56 |
| 659 | O | LEU | A | 57 | 51.650 | 62.260 | 12.762 | 1.00 | 26.92 |
| 660 | N | GLY | A | 58 | 52.014 | 60.471 | 11.441 | 1.00 | 26.04 |
| 662 | CA | GLY | A | 58 | 52.480 | 61.230 | 10.294 | 1.00 | 25.24 |
| 665 | C | GLY | A | 58 | 53.983 | 61.421 | 10.347 | 1.00 | 24.44 |
| 666 | O | GLY | A | 58 | 54.635 | 61.015 | 11.301 | 1.00 | 24.64 |
| 667 | N | GLY | A | 59 | 54.513 | 62.081 | 9.331 | 1.00 | 23.73 |
| 669 | CA | GLY | A | 59 | 55.938 | 62.322 | 9.195 | 1.00 | 23.06 |
| 672 | C | GLY | A | 59 | 56.553 | 61.359 | 8.209 | 1.00 | 22.26 |
| 673 | O | GLY | A | 59 | 56.162 | 60.194 | 8.133 | 1.00 | 22.42 |
| 674 | N | LYS | A | 60 | 57.547 | 61.842 | 7.478 | 1.00 | 22.13 |
| 676 | CA | LYS | A | 60 | 58.154 | 61.112 | 6.374 | 1.00 | 21.99 |
| 678 | CB | LYS | A | 60 | 58.759 | 62.101 | 5.373 | 1.00 | 22.38 |
| 681 | CG | LYS | A | 60 | 57.740 | 63.053 | 4.741 | 1.00 | 22.42 |
| 684 | CD | LYS | A | 60 | 58.397 | 63.946 | 3.700 | 1.00 | 22.36 |
| 687 | CE | LYS | A | 60 | 59.309 | 65.000 | 4.315 | 1.00 | 22.65 |
| 690 | NZ | LYS | A | 60 | 58.610 | 65.764 | 5.390 | 1.00 | 22.32 |
| 694 | C | LYS | A | 60 | 59.236 | 60.121 | 6.820 | 1.00 | 21.22 |
| 695 | O | LYS | A | 60 | 59.639 | 59.250 | 6.044 | 1.00 | 21.45 |
| 696 | N | ARG | A | 61 | 59.679 | 60.268 | 8.064 | 1.00 | 20.48 |
| 698 | CA | ARG | A | 61 | 60.763 | 59.494 | 8.657 | 1.00 | 19.82 |
| 700 | CB | ARG | A | 61 | 60.347 | 58.035 | 8.877 | 1.00 | 19.66 |
| 703 | CG | ARG | A | 61 | 59.138 | 57.855 | 9.723 | 1.00 | 20.10 |
| 706 | CD | ARG | A | 61 | 59.272 | 58.230 | 11.192 | 1.00 | 20.40 |
| 709 | NE | ARG | A | 61 | 57.948 | 58.049 | 11.781 | 1.00 | 20.92 |
| 711 | CZ | ARG | A | 61 | 57.037 | 58.991 | 11.934 | 1.00 | 22.13 |
| 712 | NH1 | ARG | A | 61 | 57.298 | 60.255 | 11.645 | 1.00 | 23.06 |
| 715 | NH2 | ARG | A | 61 | 55.840 | 58.667 | 12.421 | 1.00 | 22.86 |

FIGURE 3 (Cont.)

| A | B | C | D | E | F | G | H | I | J |
|---|---|---|---|---|---|---|---|---|---|
| 718 | C | ARG | A | 61 | 62.061 | 59.514 | 7.860 | 1.00 | 19.24 |
| 719 | O | ARG | A | 61 | 62.738 | 58.501 | 7.779 | 1.00 | 18.48 |
| 720 | N | LEU | A | 62 | 62.432 | 60.666 | 7.307 | 1.00 | 18.87 |
| 722 | CA | LEU | A | 62 | 63.630 | 60.734 | 6.485 | 1.00 | 18.40 |
| 724 | CB | LEU | A | 62 | 63.643 | 61.988 | 5.629 | 1.00 | 18.86 |
| 727 | CG | LEU | A | 62 | 62.430 | 62.083 | 4.708 | 1.00 | 18.30 |
| 729 | CD1 | LEU | A | 62 | 62.550 | 63.320 | 3.821 | 1.00 | 18.04 |
| 733 | CD2 | LEU | A | 62 | 62.266 | 60.815 | 3.896 | 1.00 | 19.13 |
| 737 | C | LEU | A | 62 | 64.908 | 60.646 | 7.296 | 1.00 | 18.46 |
| 738 | O | LEU | A | 62 | 65.933 | 60.241 | 6.772 | 1.00 | 18.88 |
| 739 | N | ARG | A | 63 | 64.866 | 61.017 | 8.562 | 1.00 | 17.65 |
| 741 | CA | ARG | A | 63 | 66.054 | 60.871 | 9.384 | 1.00 | 17.87 |
| 743 | CB | ARG | A | 63 | 66.000 | 61.756 | 10.611 | 1.00 | 17.85 |
| 746 | CG | ARG | A | 63 | 66.045 | 63.219 | 10.223 | 1.00 | 17.38 |
| 749 | CD | ARG | A | 63 | 65.459 | 64.177 | 11.253 | 1.00 | 17.84 |
| 752 | NE | ARG | A | 63 | 65.361 | 65.533 | 10.704 | 1.00 | 19.01 |
| 754 | CZ | ARG | A | 63 | 64.417 | 65.941 | 9.863 | 1.00 | 20.05 |
| 755 | NH1 | ARG | A | 63 | 64.422 | 67.193 | 9.411 | 1.00 | 22.90 |
| 758 | NH2 | ARG | A | 63 | 63.449 | 65.123 | 9.477 | 1.00 | 21.09 |
| 761 | C | ARG | A | 63 | 66.322 | 59.401 | 9.705 | 1.00 | 17.71 |
| 762 | O | ARG | A | 63 | 67.454 | 58.951 | 9.531 | 1.00 | 18.10 |
| 763 | N | PRO | A | 64 | 65.329 | 58.645 | 10.163 | 1.00 | 17.51 |
| 764 | CA | PRO | A | 64 | 65.476 | 57.180 | 10.192 | 1.00 | 17.45 |
| 766 | CB | PRO | A | 64 | 64.070 | 56.703 | 10.531 | 1.00 | 17.56 |
| 769 | CG | PRO | A | 64 | 63.506 | 57.791 | 11.356 | 1.00 | 17.73 |
| 772 | CD | PRO | A | 64 | 64.052 | 59.064 | 10.767 | 1.00 | 17.18 |
| 775 | C | PRO | A | 64 | 65.936 | 56.615 | 8.859 | 1.00 | 17.33 |
| 776 | O | PRO | A | 64 | 66.816 | 55.755 | 8.854 | 1.00 | 17.25 |
| 777 | N | PHE | A | 65 | 65.376 | 57.104 | 7.754 | 1.00 | 17.93 |
| 779 | CA | PHE | A | 65 | 65.781 | 56.677 | 6.427 | 1.00 | 18.40 |
| 781 | CB | PHE | A | 65 | 65.044 | 57.457 | 5.338 | 1.00 | 19.10 |
| 784 | CG | PHE | A | 65 | 65.198 | 56.872 | 3.941 | 1.00 | 19.82 |
| 785 | CD1 | PHE | A | 65 | 66.425 | 56.898 | 3.278 | 1.00 | 21.48 |
| 787 | CE1 | PHE | A | 65 | 66.558 | 56.356 | 1.990 | 1.00 | 24.16 |
| 789 | CZ | PHE | A | 65 | 65.456 | 55.801 | 1.354 | 1.00 | 23.70 |
| 791 | CE2 | PHE | A | 65 | 64.232 | 55.787 | 2.000 | 1.00 | 24.40 |
| 793 | CD2 | PHE | A | 65 | 64.112 | 56.329 | 3.289 | 1.00 | 21.85 |
| 795 | C | PHE | A | 65 | 67.288 | 56.831 | 6.274 | 1.00 | 18.39 |
| 796 | O | PHE | A | 65 | 67.951 | 55.920 | 5.814 | 1.00 | 18.40 |
| 797 | N | LEU | A | 66 | 67.820 | 57.973 | 6.683 | 1.00 | 18.52 |
| 799 | CA | LEU | A | 66 | 69.255 | 58.228 | 6.643 | 1.00 | 18.77 |
| 801 | CB | LEU | A | 66 | 69.554 | 59.650 | 7.101 | 1.00 | 19.16 |
| 804 | CG | LEU | A | 66 | 69.280 | 60.737 | 6.070 | 1.00 | 20.56 |
| 806 | CD1 | LEU | A | 66 | 69.409 | 62.108 | 6.739 | 1.00 | 21.70 |
| 810 | CD2 | LEU | A | 66 | 70.233 | 60.611 | 4.897 | 1.00 | 21.14 |
| 814 | C | LEU | A | 66 | 70.063 | 57.274 | 7.512 | 1.00 | 18.22 |
| 815 | O | LEU | A | 66 | 71.162 | 56.862 | 7.131 | 1.00 | 17.84 |
| 816 | N | VAL | A | 67 | 69.546 | 56.973 | 8.693 | 1.00 | 16.88 |
| 818 | CA | VAL | A | 67 | 70.235 | 56.066 | 9.609 | 1.00 | 17.06 |
| 820 | CB | VAL | A | 67 | 69.512 | 56.001 | 10.969 | 1.00 | 16.98 |
| 822 | CG1 | VAL | A | 67 | 70.075 | 54.909 | 11.865 | 1.00 | 17.14 |
| 826 | CG2 | VAL | A | 67 | 69.621 | 57.337 | 11.679 | 1.00 | 16.69 |

FIGURE 3 (Cont.)

| A | B | C | D | E | F | G | H | I | J |
|---|---|---|---|---|---|---|---|---|---|
| 830 | C | VAL | A | 67 | 70.315 | 54.667 | 8.984 | 1.00 | 17.43 |
| 831 | O | VAL | A | 67 | 71.391 | 54.087 | 8.924 | 1.00 | 16.85 |
| 832 | N | TYR | A | 68 | 69.171 | 54.175 | 8.504 | 1.00 | 17.82 |
| 834 | CA | TYR | A | 68 | 69.049 | 52.853 | 7.890 | 1.00 | 18.73 |
| 836 | CB | TYR | A | 68 | 67.590 | 52.546 | 7.534 | 1.00 | 18.65 |
| 839 | CG | TYR | A | 68 | 66.682 | 52.294 | 8.706 | 1.00 | 17.77 |
| 840 | CD1 | TYR | A | 68 | 66.993 | 51.343 | 9.670 | 1.00 | 18.53 |
| 842 | CE1 | TYR | A | 68 | 66.152 | 51.109 | 10.734 | 1.00 | 19.24 |
| 844 | CZ | TYR | A | 68 | 64.967 | 51.819 | 10.844 | 1.00 | 17.86 |
| 845 | OH | TYR | A | 68 | 64.123 | 51.616 | 11.915 | 1.00 | 16.87 |
| 847 | CE2 | TYR | A | 68 | 64.650 | 52.774 | 9.914 | 1.00 | 18.34 |
| 849 | CD2 | TYR | A | 68 | 65.492 | 52.988 | 8.835 | 1.00 | 18.14 |
| 851 | C | TYR | A | 68 | 69.878 | 52.741 | 6.626 | 1.00 | 19.22 |
| 852 | O | TYR | A | 68 | 70.627 | 51.788 | 6.466 | 1.00 | 20.65 |
| 853 | N | ALA | A | 69 | 69.762 | 53.725 | 5.744 | 1.00 | 19.41 |
| 855 | CA | ALA | A | 69 | 70.470 | 53.707 | 4.474 | 1.00 | 19.53 |
| 857 | CB | ALA | A | 69 | 70.035 | 54.875 | 3.616 | 1.00 | 20.02 |
| 861 | C | ALA | A | 69 | 71.975 | 53.744 | 4.695 | 1.00 | 20.18 |
| 862 | O | ALA | A | 69 | 72.721 | 53.053 | 4.011 | 1.00 | 21.39 |
| 863 | N | THR | A | 70 | 72.423 | 54.545 | 5.656 | 1.00 | 20.00 |
| 865 | CA | THR | A | 70 | 73.841 | 54.656 | 5.930 | 1.00 | 20.26 |
| 867 | CB | THR | A | 70 | 74.124 | 55.842 | 6.828 | 1.00 | 20.06 |
| 869 | OG1 | THR | A | 70 | 73.742 | 57.060 | 6.143 | 1.00 | 19.95 |
| 871 | CG2 | THR | A | 70 | 75.624 | 55.979 | 7.077 | 1.00 | 20.73 |
| 875 | C | THR | A | 70 | 74.371 | 53.370 | 6.527 | 1.00 | 20.27 |
| 876 | O | THR | A | 70 | 75.330 | 52.821 | 6.025 | 1.00 | 20.97 |
| 877 | N | GLY | A | 71 | 73.743 | 52.886 | 7.588 | 1.00 | 20.36 |
| 879 | CA | GLY | A | 71 | 74.136 | 51.630 | 8.199 | 1.00 | 20.44 |
| 882 | C | GLY | A | 71 | 74.090 | 50.470 | 7.229 | 1.00 | 20.43 |
| 883 | O | GLY | A | 71 | 74.966 | 49.600 | 7.242 | 1.00 | 21.38 |
| 884 | N | HIS | A | 72 | 73.061 | 50.442 | 6.393 | 1.00 | 21.26 |
| 886 | CA | HIS | A | 72 | 72.886 | 49.367 | 5.401 | 1.00 | 21.95 |
| 888 | CB | HIS | A | 72 | 71.577 | 49.530 | 4.623 | 1.00 | 22.16 |
| 891 | CG | HIS | A | 72 | 70.369 | 49.049 | 5.362 | 1.00 | 21.95 |
| 892 | ND1 | HIS | A | 72 | 69.094 | 49.468 | 5.051 | 1.00 | 23.29 |
| 894 | CE1 | HIS | A | 72 | 68.231 | 48.892 | 5.869 | 1.00 | 23.63 |
| 896 | NE2 | HIS | A | 72 | 68.899 | 48.097 | 6.687 | 1.00 | 21.16 |
| 898 | CD2 | HIS | A | 72 | 70.238 | 48.181 | 6.394 | 1.00 | 22.72 |
| 900 | C | HIS | A | 72 | 74.054 | 49.313 | 4.421 | 1.00 | 22.56 |
| 901 | O | HIS | A | 72 | 74.455 | 48.228 | 3.995 | 1.00 | 21.64 |
| 902 | N | MET | A | 73 | 74.610 | 50.477 | 4.080 | 1.00 | 23.05 |
| 904 | CA | MET | A | 73 | 75.782 | 50.536 | 3.201 | 1.00 | 23.89 |
| 906 | CB | MET | A | 73 | 76.282 | 51.961 | 3.027 | 1.00 | 24.12 |
| 909 | CG | MET | A | 73 | 75.546 | 52.765 | 2.016 | 1.00 | 26.38 |
| 912 | SD | MET | A | 73 | 76.590 | 54.090 | 1.347 | 1.00 | 31.06 |
| 913 | CE | MET | A | 73 | 77.179 | 54.849 | 2.837 | 1.00 | 30.61 |
| 917 | C | MET | A | 73 | 76.944 | 49.713 | 3.732 | 1.00 | 24.04 |
| 918 | O | MET | A | 73 | 77.740 | 49.208 | 2.945 | 1.00 | 24.70 |
| 919 | N | PHE | A | 74 | 77.052 | 49.617 | 5.057 | 1.00 | 24.12 |
| 921 | CA | PHE | A | 74 | 78.122 | 48.863 | 5.723 | 1.00 | 24.15 |
| 923 | CB | PHE | A | 74 | 78.644 | 49.693 | 6.881 | 1.00 | 24.28 |
| 926 | CG | PHE | A | 74 | 79.127 | 51.040 | 6.455 | 1.00 | 25.09 |

FIGURE 3 (Cont.)

| A | B | C | D | E | F | G | H | I | J |
|---|---|---|---|---|---|---|---|---|---|
| 927 | CD1 | PHE | A | 74 | 78.410 | 52.183 | 6.759 | 1.00 | 25.88 |
| 929 | CE1 | PHE | A | 74 | 78.847 | 53.424 | 6.357 | 1.00 | 25.67 |
| 931 | CZ | PHE | A | 74 | 80.015 | 53.547 | 5.641 | 1.00 | 26.11 |
| 933 | CE2 | PHE | A | 74 | 80.751 | 52.415 | 5.330 | 1.00 | 26.51 |
| 935 | CD2 | PHE | A | 74 | 80.305 | 51.167 | 5.736 | 1.00 | 26.10 |
| 937 | C | PHE | A | 74 | 77.710 | 47.461 | 6.196 | 1.00 | 24.09 |
| 938 | O | PHE | A | 74 | 78.475 | 46.770 | 6.875 | 1.00 | 23.88 |
| 939 | N | GLY | A | 75 | 76.508 | 47.039 | 5.815 | 1.00 | 23.45 |
| 941 | CA | GLY | A | 75 | 76.025 | 45.708 | 6.114 | 1.00 | 23.38 |
| 944 | C | GLY | A | 75 | 75.544 | 45.539 | 7.545 | 1.00 | 23.11 |
| 945 | O | GLY | A | 75 | 75.412 | 44.415 | 8.032 | 1.00 | 22.14 |
| 946 | N | VAL | A | 76 | 75.261 | 46.636 | 8.241 | 1.00 | 22.50 |
| 948 | CA | VAL | A | 76 | 74.698 | 46.461 | 9.577 | 1.00 | 22.69 |
| 950 | CB | VAL | A | 76 | 75.093 | 47.576 | 10.642 | 1.00 | 22.92 |
| 952 | CG1 | VAL | A | 76 | 75.915 | 48.711 | 10.067 | 1.00 | 23.76 |
| 956 | CG2 | VAL | A | 76 | 73.908 | 48.074 | 11.396 | 1.00 | 22.71 |
| 960 | C | VAL | A | 76 | 73.194 | 46.144 | 9.484 | 1.00 | 21.96 |
| 961 | O | VAL | A | 76 | 72.487 | 46.604 | 8.591 | 1.00 | 21.42 |
| 962 | N | SER | A | 77 | 72.746 | 45.302 | 10.402 | 1.00 | 21.48 |
| 964 | CA | SER | A | 77 | 71.389 | 44.778 | 10.405 | 1.00 | 21.77 |
| 966 | CB | SER | A | 77 | 71.250 | 43.671 | 11.467 | 1.00 | 22.01 |
| 969 | OG | SER | A | 77 | 69.901 | 43.269 | 11.656 | 1.00 | 24.55 |
| 971 | C | SER | A | 77 | 70.388 | 45.893 | 10.669 | 1.00 | 21.66 |
| 972 | O | SER | A | 77 | 70.614 | 46.768 | 11.497 | 1.00 | 20.52 |
| 973 | N | THR | A | 78 | 69.280 | 45.849 | 9.950 | 1.00 | 21.30 |
| 975 | CA | THR | A | 78 | 68.197 | 46.782 | 10.145 | 1.00 | 21.37 |
| 977 | CB | THR | A | 78 | 67.041 | 46.395 | 9.243 | 1.00 | 21.59 |
| 979 | OG1 | THR | A | 78 | 67.522 | 46.238 | 7.898 | 1.00 | 20.65 |
| 981 | CG2 | THR | A | 78 | 66.004 | 47.531 | 9.175 | 1.00 | 21.88 |
| 985 | C | THR | A | 78 | 67.742 | 46.839 | 11.609 | 1.00 | 21.40 |
| 986 | O | THR | A | 78 | 67.457 | 47.919 | 12.127 | 1.00 | 20.26 |
| 987 | N | ASN | A | 79 | 67.712 | 45.681 | 12.273 | 1.00 | 20.85 |
| 989 | CA | ASN | A | 79 | 67.259 | 45.592 | 13.665 | 1.00 | 21.11 |
| 991 | CB | ASN | A | 79 | 67.155 | 44.113 | 14.110 | 1.00 | 20.78 |
| 994 | CG | ASN | A | 79 | 66.777 | 43.962 | 15.577 | 1.00 | 20.57 |
| 995 | OD1 | ASN | A | 79 | 65.629 | 44.176 | 15.960 | 1.00 | 20.74 |
| 996 | ND2 | ASN | A | 79 | 67.741 | 43.572 | 16.395 | 1.00 | 21.96 |
| 999 | C | ASN | A | 79 | 68.135 | 46.366 | 14.648 | 1.00 | 21.18 |
| 1000 | O | ASN | A | 79 | 67.630 | 46.935 | 15.589 | 1.00 | 21.24 |
| 1001 | N | THR | A | 80 | 69.445 | 46.363 | 14.445 | 1.00 | 21.31 |
| 1003 | CA | THR | A | 80 | 70.325 | 47.176 | 15.288 | 1.00 | 22.18 |
| 1005 | CB | THR | A | 80 | 71.831 | 46.719 | 15.233 | 1.00 | 23.07 |
| 1007 | OG1 | THR | A | 80 | 72.729 | 47.845 | 15.254 | 1.00 | 25.14 |
| 1009 | CG2 | THR | A | 80 | 72.163 | 46.051 | 13.972 | 1.00 | 25.36 |
| 1013 | C | THR | A | 80 | 70.149 | 48.653 | 14.952 | 1.00 | 21.28 |
| 1014 | O | THR | A | 80 | 70.191 | 49.488 | 15.836 | 1.00 | 21.18 |
| 1015 | N | LEU | A | 81 | 69.889 | 48.958 | 13.685 | 1.00 | 20.13 |
| 1017 | CA | LEU | A | 81 | 69.699 | 50.338 | 13.267 | 1.00 | 19.67 |
| 1019 | CB | LEU | A | 81 | 69.773 | 50.458 | 11.743 | 1.00 | 19.03 |
| 1022 | CG | LEU | A | 81 | 71.174 | 50.220 | 11.203 | 1.00 | 20.05 |
| 1024 | CD1 | LEU | A | 81 | 71.133 | 49.777 | 9.747 | 1.00 | 20.55 |
| 1028 | CD2 | LEU | A | 81 | 72.025 | 51.477 | 11.362 | 1.00 | 21.66 |

FIGURE 3 (Cont.)

| A | B | C | D | E | F | G | H | I | J |
|---|---|---|---|---|---|---|---|---|---|
| 1032 | C | LEU | A | 81 | 68.395 | 50.943 | 13.785 | 1.00 | 19.10 |
| 1033 | O | LEU | A | 81 | 68.266 | 52.154 | 13.797 | 1.00 | 17.73 |
| 1034 | N | ASP | A | 82 | 67.452 | 50.098 | 14.213 | 1.00 | 18.92 |
| 1036 | CA | ASP | A | 82 | 66.206 | 50.555 | 14.808 | 1.00 | 19.26 |
| 1038 | CB | ASP | A | 82 | 65.374 | 49.380 | 15.347 | 1.00 | 19.80 |
| 1041 | CG | ASP | A | 82 | 64.537 | 48.689 | 14.279 | 1.00 | 21.07 |
| 1042 | OD1 | ASP | A | 82 | 64.370 | 49.232 | 13.167 | 1.00 | 22.88 |
| 1043 | OD2 | ASP | A | 82 | 63.977 | 47.584 | 14.496 | 1.00 | 22.05 |
| 1044 | C | ASP | A | 82 | 66.491 | 51.503 | 15.972 | 1.00 | 18.72 |
| 1045 | O | ASP | A | 82 | 65.743 | 52.455 | 16.193 | 1.00 | 18.90 |
| 1046 | N | ALA | A | 83 | 67.551 | 51.227 | 16.724 | 1.00 | 18.47 |
| 1048 | CA | ALA | A | 83 | 67.879 | 52.031 | 17.902 | 1.00 | 18.05 |
| 1050 | CB | ALA | A | 83 | 68.957 | 51.350 | 18.777 | 1.00 | 18.08 |
| 1054 | C | ALA | A | 83 | 68.262 | 53.464 | 17.528 | 1.00 | 17.75 |
| 1055 | O | ALA | A | 83 | 67.571 | 54.391 | 17.954 | 1.00 | 16.58 |
| 1056 | N | PRO | A | 84 | 69.334 | 53.674 | 16.754 | 1.00 | 17.46 |
| 1057 | CA | PRO | A | 84 | 69.660 | 55.034 | 16.310 | 1.00 | 17.24 |
| 1059 | CB | PRO | A | 84 | 70.978 | 54.870 | 15.537 | 1.00 | 17.48 |
| 1062 | CG | PRO | A | 84 | 71.073 | 53.397 | 15.176 | 1.00 | 17.90 |
| 1065 | CD | PRO | A | 84 | 70.318 | 52.690 | 16.274 | 1.00 | 17.39 |
| 1068 | C | PRO | A | 84 | 68.570 | 55.674 | 15.452 | 1.00 | 17.54 |
| 1069 | O | PRO | A | 84 | 68.372 | 56.871 | 15.546 | 1.00 | 16.99 |
| 1070 | N | ALA | A | 85 | 67.881 | 54.899 | 14.617 | 1.00 | 17.55 |
| 1072 | CA | ALA | A | 85 | 66.786 | 55.439 | 13.827 | 1.00 | 17.51 |
| 1074 | CB | ALA | A | 85 | 66.196 | 54.371 | 12.908 | 1.00 | 17.15 |
| 1078 | C | ALA | A | 85 | 65.710 | 56.010 | 14.751 | 1.00 | 17.33 |
| 1079 | O | ALA | A | 85 | 65.235 | 57.120 | 14.540 | 1.00 | 17.48 |
| 1080 | N | ALA | A | 86 | 65.365 | 55.276 | 15.797 | 1.00 | 17.28 |
| 1082 | CA | ALA | A | 86 | 64.309 | 55.702 | 16.702 | 1.00 | 17.98 |
| 1084 | CB | ALA | A | 86 | 63.858 | 54.558 | 17.575 | 1.00 | 17.95 |
| 1088 | C | ALA | A | 86 | 64.764 | 56.881 | 17.559 | 1.00 | 18.07 |
| 1089 | O | ALA | A | 86 | 63.986 | 57.800 | 17.828 | 1.00 | 18.55 |
| 1090 | N | ALA | A | 87 | 66.027 | 56.852 | 17.965 | 1.00 | 17.63 |
| 1092 | CA | ALA | A | 87 | 66.612 | 57.905 | 18.776 | 1.00 | 17.90 |
| 1094 | CB | ALA | A | 87 | 68.016 | 57.551 | 19.129 | 1.00 | 17.89 |
| 1098 | C | ALA | A | 87 | 66.602 | 59.238 | 18.046 | 1.00 | 18.01 |
| 1099 | O | ALA | A | 87 | 66.199 | 60.258 | 18.611 | 1.00 | 16.96 |
| 1100 | N | VAL | A | 88 | 67.076 | 59.233 | 16.802 | 1.00 | 18.36 |
| 1102 | CA | VAL | A | 88 | 67.108 | 60.469 | 16.022 | 1.00 | 19.02 |
| 1104 | CB | VAL | A | 88 | 67.919 | 60.359 | 14.706 | 1.00 | 19.48 |
| 1106 | CG1 | VAL | A | 88 | 69.346 | 59.943 | 15.004 | 1.00 | 21.38 |
| 1110 | CG2 | VAL | A | 88 | 67.262 | 59.431 | 13.694 | 1.00 | 20.88 |
| 1114 | C | VAL | A | 88 | 65.697 | 60.984 | 15.728 | 1.00 | 18.91 |
| 1115 | O | VAL | A | 88 | 65.478 | 62.192 | 15.694 | 1.00 | 19.41 |
| 1116 | N | GLU | A | 89 | 64.755 | 60.075 | 15.506 | 1.00 | 18.77 |
| 1118 | CA | GLU | A | 89 | 63.371 | 60.460 | 15.281 | 1.00 | 19.03 |
| 1120 | CB | GLU | A | 89 | 62.580 | 59.307 | 14.672 | 1.00 | 19.35 |
| 1123 | CG | GLU | A | 89 | 61.202 | 59.659 | 14.140 | 1.00 | 20.47 |
| 1126 | CD | GLU | A | 89 | 61.187 | 60.686 | 13.014 | 1.00 | 23.08 |
| 1127 | OE1 | GLU | A | 89 | 60.085 | 61.188 | 12.699 | 1.00 | 21.79 |
| 1128 | OE2 | GLU | A | 89 | 62.243 | 61.001 | 12.436 | 1.00 | 22.95 |
| 1129 | C | GLU | A | 89 | 62.726 | 60.972 | 16.571 | 1.00 | 19.06 |

FIGURE 3 (Cont.)

| A | B | C | D | E | F | G | H | I | J |
|---|---|---|---|---|---|---|---|---|---|
| 1130 | O | GLU | A | 89 | 61.883 | 61.856 | 16.515 | 1.00 | 18.98 |
| 1131 | N | CYS | A | 90 | 63.154 | 60.466 | 17.724 | 1.00 | 19.07 |
| 1133 | CA | CYS | A | 90 | 62.684 | 61.026 | 18.999 | 1.00 | 19.48 |
| 1135 | CB | CYS | A | 90 | 63.154 | 60.218 | 20.204 | 1.00 | 19.62 |
| 1138 | SG | CYS | A | 90 | 62.240 | 58.692 | 20.462 | 1.00 | 21.40 |
| 1139 | C | CYS | A | 90 | 63.139 | 62.464 | 19.144 | 1.00 | 18.83 |
| 1140 | O | CYS | A | 90 | 62.348 | 63.311 | 19.526 | 1.00 | 19.11 |
| 1141 | N | ILE | A | 91 | 64.405 | 62.740 | 18.846 | 1.00 | 18.13 |
| 1143 | CA | ILE | A | 91 | 64.900 | 64.108 | 18.934 | 1.00 | 17.94 |
| 1145 | CB | ILE | A | 91 | 66.402 | 64.201 | 18.602 | 1.00 | 18.00 |
| 1147 | CG1 | ILE | A | 91 | 67.269 | 63.442 | 19.628 | 1.00 | 18.23 |
| 1150 | CD1 | ILE | A | 91 | 67.160 | 63.942 | 21.057 | 1.00 | 18.91 |
| 1154 | CG2 | ILE | A | 91 | 66.824 | 65.659 | 18.520 | 1.00 | 18.94 |
| 1158 | C | ILE | A | 91 | 64.117 | 64.994 | 17.959 | 1.00 | 17.15 |
| 1159 | O | ILE | A | 91 | 63.700 | 66.094 | 18.308 | 1.00 | 16.79 |
| 1160 | N | HIS | A | 92 | 63.952 | 64.506 | 16.732 | 1.00 | 16.32 |
| 1162 | CA | HIS | A | 92 | 63.238 | 65.238 | 15.701 | 1.00 | 16.58 |
| 1164 | CB | HIS | A | 92 | 63.182 | 64.438 | 14.409 | 1.00 | 16.65 |
| 1167 | CG | HIS | A | 92 | 62.424 | 65.119 | 13.321 | 1.00 | 16.27 |
| 1168 | ND1 | HIS | A | 92 | 61.352 | 64.536 | 12.675 | 1.00 | 17.53 |
| 1170 | CE1 | HIS | A | 92 | 60.892 | 65.378 | 11.761 | 1.00 | 15.88 |
| 1172 | NE2 | HIS | A | 92 | 61.620 | 66.480 | 11.800 | 1.00 | 17.29 |
| 1174 | CD2 | HIS | A | 92 | 62.573 | 66.348 | 12.779 | 1.00 | 15.01 |
| 1176 | C | HIS | A | 92 | 61.825 | 65.555 | 16.167 | 1.00 | 16.53 |
| 1177 | O | HIS | A | 92 | 61.399 | 66.712 | 16.151 | 1.00 | 16.57 |
| 1178 | N | ALA | A | 93 | 61.119 | 64.532 | 16.620 | 1.00 | 15.86 |
| 1180 | CA | ALA | A | 93 | 59.753 | 64.699 | 17.119 | 1.00 | 16.23 |
| 1182 | CB | ALA | A | 93 | 59.177 | 63.346 | 17.566 | 1.00 | 16.25 |
| 1186 | C | ALA | A | 93 | 59.671 | 65.720 | 18.251 | 1.00 | 16.36 |
| 1187 | O | ALA | A | 93 | 58.753 | 66.544 | 18.297 | 1.00 | 16.22 |
| 1188 | N | TYR | A | 94 | 60.632 | 65.668 | 19.168 | 1.00 | 16.81 |
| 1190 | CA | TYR | A | 94 | 60.653 | 66.585 | 20.289 | 1.00 | 17.25 |
| 1192 | CB | TYR | A | 94 | 61.742 | 66.187 | 21.312 | 1.00 | 18.09 |
| 1195 | CG | TYR | A | 94 | 62.785 | 67.233 | 21.639 | 1.00 | 18.65 |
| 1196 | CD1 | TYR | A | 94 | 62.444 | 68.391 | 22.309 | 1.00 | 20.51 |
| 1198 | CE1 | TYR | A | 94 | 63.388 | 69.341 | 22.613 | 1.00 | 22.48 |
| 1200 | CZ | TYR | A | 94 | 64.701 | 69.138 | 22.248 | 1.00 | 22.20 |
| 1201 | OH | TYR | A | 94 | 65.628 | 70.083 | 22.565 | 1.00 | 24.51 |
| 1203 | CE2 | TYR | A | 94 | 65.075 | 67.983 | 21.590 | 1.00 | 21.60 |
| 1205 | CD2 | TYR | A | 94 | 64.122 | 67.037 | 21.306 | 1.00 | 19.95 |
| 1207 | C | TYR | A | 94 | 60.837 | 68.001 | 19.766 | 1.00 | 17.28 |
| 1208 | O | TYR | A | 94 | 60.178 | 68.921 | 20.232 | 1.00 | 16.91 |
| 1209 | N | SER | A | 95 | 61.709 | 68.169 | 18.780 | 1.00 | 17.12 |
| 1211 | CA | SER | A | 95 | 62.028 | 69.486 | 18.281 | 1.00 | 17.61 |
| 1213 | CB | SER | A | 95 | 63.209 | 69.446 | 17.312 | 1.00 | 17.91 |
| 1216 | OG | SER | A | 95 | 62.859 | 68.946 | 16.045 | 1.00 | 19.03 |
| 1218 | C | SER | A | 95 | 60.787 | 70.161 | 17.665 | 1.00 | 18.18 |
| 1219 | O | SER | A | 95 | 60.591 | 71.367 | 17.826 | 1.00 | 17.08 |
| 1220 | N | LEU | A | 96 | 59.936 | 69.376 | 17.021 | 1.00 | 18.08 |
| 1222 | CA | LEU | A | 96 | 58.748 | 69.937 | 16.356 | 1.00 | 18.75 |
| 1224 | CB | LEU | A | 96 | 58.168 | 68.946 | 15.359 | 1.00 | 18.81 |
| 1227 | CG | LEU | A | 96 | 59.159 | 68.371 | 14.350 | 1.00 | 19.61 |

FIGURE 3 (Cont.)

| A | B | C | D | E | F | G | H | I | J |
|---|---|---|---|---|---|---|---|---|---|
| 1229 | CD1 | LEU | A | 96 | 58.421 | 67.472 | 13.385 | 1.00 | 19.87 |
| 1233 | CD2 | LEU | A | 96 | 59.901 | 69.477 | 13.628 | 1.00 | 20.82 |
| 1237 | C | LEU | A | 96 | 57.676 | 70.285 | 17.371 | 1.00 | 18.79 |
| 1238 | O | LEU | A | 96 | 56.928 | 71.252 | 17.192 | 1.00 | 19.67 |
| 1239 | N | ILE | A | 97 | 57.581 | 69.478 | 18.422 | 1.00 | 18.80 |
| 1241 | CA | ILE | A | 97 | 56.574 | 69.704 | 19.448 | 1.00 | 18.69 |
| 1243 | CB | ILE | A | 97 | 56.590 | 68.612 | 20.520 | 1.00 | 18.23 |
| 1245 | CG1 | ILE | A | 97 | 56.062 | 67.307 | 19.941 | 1.00 | 17.66 |
| 1248 | CD1 | ILE | A | 97 | 56.017 | 66.149 | 20.924 | 1.00 | 19.38 |
| 1252 | CG2 | ILE | A | 97 | 55.756 | 69.050 | 21.746 | 1.00 | 18.51 |
| 1256 | C | ILE | A | 97 | 56.844 | 71.069 | 20.071 | 1.00 | 19.44 |
| 1257 | O | ILE | A | 97 | 55.925 | 71.851 | 20.233 | 1.00 | 19.55 |
| 1258 | N | HIS | A | 98 | 58.108 | 71.358 | 20.383 | 1.00 | 19.42 |
| 1260 | CA | HIS | A | 98 | 58.452 | 72.609 | 21.039 | 1.00 | 20.66 |
| 1262 | CB | HIS | A | 98 | 59.797 | 72.507 | 21.730 | 1.00 | 21.50 |
| 1265 | CG | HIS | A | 98 | 59.735 | 71.795 | 23.045 | 1.00 | 25.90 |
| 1266 | ND1 | HIS | A | 98 | 59.610 | 70.432 | 23.149 | 1.00 | 34.19 |
| 1268 | CE1 | HIS | A | 98 | 59.570 | 70.087 | 24.425 | 1.00 | 32.41 |
| 1270 | NE2 | HIS | A | 98 | 59.660 | 71.175 | 25.149 | 1.00 | 32.34 |
| 1272 | CD2 | HIS | A | 98 | 59.748 | 72.261 | 24.312 | 1.00 | 32.88 |
| 1274 | C | HIS | A | 98 | 58.437 | 73.774 | 20.072 | 1.00 | 20.22 |
| 1275 | O | HIS | A | 98 | 58.095 | 74.880 | 20.444 | 1.00 | 20.04 |
| 1276 | N | ASP | A | 99 | 58.809 | 73.500 | 18.829 | 1.00 | 20.34 |
| 1278 | CA | ASP | A | 99 | 58.834 | 74.488 | 17.772 | 1.00 | 20.27 |
| 1280 | CB | ASP | A | 99 | 59.394 | 73.845 | 16.496 | 1.00 | 20.14 |
| 1283 | CG | ASP | A | 99 | 59.438 | 74.806 | 15.326 | 1.00 | 19.89 |
| 1284 | OD1 | ASP | A | 99 | 58.542 | 74.720 | 14.458 | 1.00 | 20.18 |
| 1285 | OD2 | ASP | A | 99 | 60.332 | 75.665 | 15.194 | 1.00 | 18.02 |
| 1286 | C | ASP | A | 99 | 57.447 | 75.081 | 17.512 | 1.00 | 20.91 |
| 1287 | O | ASP | A | 99 | 57.322 | 76.277 | 17.253 | 1.00 | 21.26 |
| 1288 | N | ASP | A | 100 | 56.410 | 74.254 | 17.580 | 1.00 | 21.41 |
| 1290 | CA | ASP | A | 100 | 55.037 | 74.718 | 17.328 | 1.00 | 21.41 |
| 1292 | CB | ASP | A | 100 | 54.098 | 73.551 | 17.048 | 1.00 | 21.45 |
| 1295 | CG | ASP | A | 100 | 54.436 | 72.819 | 15.799 | 1.00 | 20.29 |
| 1296 | OD1 | ASP | A | 100 | 54.167 | 71.594 | 15.734 | 1.00 | 20.18 |
| 1297 | OD2 | ASP | A | 100 | 54.978 | 73.379 | 14.841 | 1.00 | 19.29 |
| 1298 | C | ASP | A | 100 | 54.428 | 75.500 | 18.483 | 1.00 | 21.71 |
| 1299 | O | ASP | A | 100 | 53.395 | 76.123 | 18.301 | 1.00 | 22.06 |
| 1300 | N | LEU | A | 101 | 55.039 | 75.467 | 19.664 | 1.00 | 21.73 |
| 1302 | CA | LEU | A | 101 | 54.463 | 76.129 | 20.837 | 1.00 | 21.71 |
| 1304 | CB | LEU | A | 101 | 55.389 | 76.027 | 22.052 | 1.00 | 21.29 |
| 1307 | CG | LEU | A | 101 | 55.643 | 74.639 | 22.631 | 1.00 | 21.02 |
| 1309 | CD1 | LEU | A | 101 | 56.681 | 74.748 | 23.744 | 1.00 | 21.63 |
| 1313 | CD2 | LEU | A | 101 | 54.375 | 73.987 | 23.130 | 1.00 | 21.37 |
| 1317 | C | LEU | A | 101 | 54.173 | 77.611 | 20.587 | 1.00 | 22.13 |
| 1318 | O | LEU | A | 101 | 54.852 | 78.255 | 19.795 | 1.00 | 21.48 |
| 1319 | N | PRO | A | 102 | 53.167 | 78.152 | 21.273 | 1.00 | 23.19 |
| 1320 | CA | PRO | A | 102 | 52.850 | 79.588 | 21.175 | 1.00 | 23.59 |
| 1322 | CB | PRO | A | 102 | 51.811 | 79.779 | 22.282 | 1.00 | 24.00 |
| 1325 | CG | PRO | A | 102 | 51.099 | 78.464 | 22.308 | 1.00 | 23.90 |
| 1328 | CD | PRO | A | 102 | 52.216 | 77.443 | 22.149 | 1.00 | 22.62 |
| 1331 | C | PRO | A | 102 | 54.045 | 80.533 | 21.348 | 1.00 | 24.21 |

FIGURE 3 (Cont.)

| A | B | C | D | E | F | G | H | I | J |
|---|---|---|---|---|---|---|---|---|---|
| 1332 | O | PRO | A | 102 | 54.148 | 81.494 | 20.599 | 1.00 | 25.11 |
| 1333 | N | ALA | A | 103 | 54.943 | 80.255 | 22.285 | 1.00 | 24.74 |
| 1335 | CA | ALA | A | 103 | 56.123 | 81.094 | 22.516 | 1.00 | 25.23 |
| 1337 | CB | ALA | A | 103 | 56.753 | 80.737 | 23.867 | 1.00 | 25.78 |
| 1341 | C | ALA | A | 103 | 57.176 | 80.941 | 21.417 | 1.00 | 25.46 |
| 1342 | O | ALA | A | 103 | 58.093 | 81.742 | 21.317 | 1.00 | 24.70 |
| 1343 | N | MET | A | 104 | 57.053 | 79.879 | 20.626 | 1.00 | 25.19 |
| 1345 | CA | MET | A | 104 | 57.981 | 79.590 | 19.550 | 1.00 | 26.00 |
| 1347 | CB | MET | A | 104 | 58.362 | 78.109 | 19.598 | 1.00 | 25.79 |
| 1350 | CG | MET | A | 104 | 58.997 | 77.719 | 20.916 | 1.00 | 27.52 |
| 1353 | SD | MET | A | 104 | 60.690 | 78.194 | 20.987 | 1.00 | 31.55 |
| 1354 | CE | MET | A | 104 | 61.411 | 77.093 | 19.688 | 1.00 | 31.97 |
| 1358 | C | MET | A | 104 | 57.345 | 79.995 | 18.207 | 1.00 | 25.73 |
| 1359 | O | MET | A | 104 | 57.213 | 81.186 | 17.942 | 1.00 | 25.54 |
| 1360 | N | ASP | A | 105 | 56.937 | 79.038 | 17.374 | 1.00 | 25.29 |
| 1362 | CA | ASP | A | 105 | 56.373 | 79.388 | 16.061 | 1.00 | 25.81 |
| 1364 | CB | ASP | A | 105 | 56.832 | 78.419 | 14.969 | 1.00 | 25.24 |
| 1367 | CG | ASP | A | 105 | 58.319 | 78.496 | 14.716 | 1.00 | 24.83 |
| 1368 | OD1 | ASP | A | 105 | 58.853 | 77.642 | 13.954 | 1.00 | 22.09 |
| 1369 | OD2 | ASP | A | 105 | 59.049 | 79.364 | 15.253 | 1.00 | 25.62 |
| 1370 | C | ASP | A | 105 | 54.851 | 79.525 | 16.069 | 1.00 | 25.92 |
| 1371 | O | ASP | A | 105 | 54.289 | 80.054 | 15.126 | 1.00 | 26.07 |
| 1372 | N | ASP | A | 106 | 54.206 | 79.043 | 17.125 | 1.00 | 26.89 |
| 1374 | CA | ASP | A | 106 | 52.759 | 79.211 | 17.350 | 1.00 | 27.69 |
| 1376 | CB | ASP | A | 106 | 52.419 | 80.670 | 17.671 | 1.00 | 28.12 |
| 1379 | CG | ASP | A | 106 | 51.000 | 80.840 | 18.202 | 1.00 | 29.63 |
| 1380 | OD1 | ASP | A | 106 | 50.458 | 81.960 | 18.094 | 1.00 | 31.75 |
| 1381 | OD2 | ASP | A | 106 | 50.342 | 79.911 | 18.732 | 1.00 | 31.76 |
| 1382 | C | ASP | A | 106 | 51.952 | 78.715 | 16.157 | 1.00 | 28.05 |
| 1383 | O | ASP | A | 106 | 51.159 | 79.450 | 15.549 | 1.00 | 28.01 |
| 1384 | N | ASP | A | 107 | 52.190 | 77.456 | 15.809 | 1.00 | 28.07 |
| 1386 | CA | ASP | A | 107 | 51.534 | 76.822 | 14.686 | 1.00 | 27.99 |
| 1388 | CB | ASP | A | 107 | 52.553 | 76.037 | 13.855 | 1.00 | 28.56 |
| 1391 | CG | ASP | A | 107 | 53.069 | 76.830 | 12.677 | 1.00 | 29.78 |
| 1392 | OD1 | ASP | A | 107 | 52.257 | 77.111 | 11.774 | 1.00 | 33.36 |
| 1393 | OD2 | ASP | A | 107 | 54.255 | 77.210 | 12.549 | 1.00 | 31.90 |
| 1394 | C | ASP | A | 107 | 50.478 | 75.882 | 15.230 | 1.00 | 27.64 |
| 1395 | O | ASP | A | 107 | 50.693 | 75.218 | 16.248 | 1.00 | 26.98 |
| 1396 | N | ASP | A | 108 | 49.334 | 75.823 | 14.559 | 1.00 | 26.95 |
| 1398 | CA | ASP | A | 108 | 48.242 | 74.989 | 15.031 | 1.00 | 26.81 |
| 1400 | CB | ASP | A | 108 | 46.929 | 75.778 | 15.089 | 1.00 | 27.66 |
| 1403 | CG | ASP | A | 108 | 46.453 | 76.241 | 13.725 | 1.00 | 30.37 |
| 1404 | OD1 | ASP | A | 108 | 45.282 | 76.700 | 13.645 | 1.00 | 33.61 |
| 1405 | OD2 | ASP | A | 108 | 47.165 | 76.194 | 12.690 | 1.00 | 32.04 |
| 1406 | C | ASP | A | 108 | 48.075 | 73.702 | 14.236 | 1.00 | 25.96 |
| 1407 | O | ASP | A | 108 | 47.283 | 72.856 | 14.631 | 1.00 | 25.76 |
| 1408 | N | LEU | A | 109 | 48.818 | 73.559 | 13.136 | 1.00 | 25.04 |
| 1410 | CA | LEU | A | 109 | 48.751 | 72.367 | 12.298 | 1.00 | 24.85 |
| 1412 | CB | LEU | A | 109 | 48.106 | 72.694 | 10.945 | 1.00 | 25.33 |
| 1415 | CG | LEU | A | 109 | 46.598 | 72.821 | 10.810 | 1.00 | 26.83 |
| 1417 | CD1 | LEU | A | 109 | 46.260 | 73.283 | 9.399 | 1.00 | 29.44 |
| 1421 | CD2 | LEU | A | 109 | 45.903 | 71.492 | 11.089 | 1.00 | 27.95 |

FIGURE 3 (Cont.)

| A | B | C | D | E | F | G | H | I | J |
|---|---|---|---|---|---|---|---|---|---|
| 1425 | C | LEU | A | 109 | 50.144 | 71.781 | 12.034 | 1.00 | 23.64 |
| 1426 | O | LEU | A | 109 | 51.094 | 72.514 | 11.790 | 1.00 | 23.64 |
| 1427 | N | ARG | A | 110 | 50.237 | 70.454 | 12.081 | 1.00 | 22.79 |
| 1429 | CA | ARG | A | 110 | 51.401 | 69.715 | 11.603 | 1.00 | 22.20 |
| 1431 | CB | ARG | A | 110 | 52.479 | 69.644 | 12.672 | 1.00 | 21.90 |
| 1434 | CG | ARG | A | 110 | 53.742 | 69.015 | 12.166 | 1.00 | 21.62 |
| 1437 | CD | ARG | A | 110 | 54.820 | 68.975 | 13.195 | 1.00 | 21.16 |
| 1440 | NE | ARG | A | 110 | 55.377 | 70.290 | 13.472 | 1.00 | 19.55 |
| 1442 | CZ | ARG | A | 110 | 56.277 | 70.905 | 12.721 | 1.00 | 21.19 |
| 1443 | NH1 | ARG | A | 110 | 56.740 | 72.082 | 13.111 | 1.00 | 21.55 |
| 1446 | NH2 | ARG | A | 110 | 56.737 | 70.355 | 11.590 | 1.00 | 21.98 |
| 1449 | C | ARG | A | 110 | 50.997 | 68.301 | 11.215 | 1.00 | 21.87 |
| 1450 | O | ARG | A | 110 | 50.184 | 67.686 | 11.876 | 1.00 | 20.97 |
| 1451 | N | ARG | A | 111 | 51.566 | 67.807 | 10.122 | 1.00 | 22.79 |
| 1453 | CA | ARG | A | 111 | 51.237 | 66.489 | 9.580 | 1.00 | 23.42 |
| 1455 | CB | ARG | A | 111 | 51.814 | 65.407 | 10.477 | 1.00 | 23.33 |
| 1458 | CG | ARG | A | 111 | 53.310 | 65.424 | 10.531 | 1.00 | 22.10 |
| 1461 | CD | ARG | A | 111 | 53.841 | 64.752 | 11.768 | 1.00 | 21.59 |
| 1464 | NE | ARG | A | 111 | 55.282 | 64.632 | 11.726 | 1.00 | 21.10 |
| 1466 | CZ | ARG | A | 111 | 56.009 | 64.082 | 12.681 | 1.00 | 21.03 |
| 1467 | NH1 | ARG | A | 111 | 55.438 | 63.576 | 13.760 | 1.00 | 20.75 |
| 1470 | NH2 | ARG | A | 111 | 57.323 | 64.020 | 12.544 | 1.00 | 22.79 |
| 1473 | C | ARG | A | 111 | 49.733 | 66.284 | 9.374 | 1.00 | 24.49 |
| 1474 | O | ARG | A | 111 | 49.216 | 65.181 | 9.528 | 1.00 | 24.90 |
| 1475 | N | GLY | A | 112 | 49.048 | 67.375 | 9.037 | 1.00 | 25.84 |
| 1477 | CA | GLY | A | 112 | 47.641 | 67.363 | 8.673 | 1.00 | 26.45 |
| 1480 | C | GLY | A | 112 | 46.709 | 67.432 | 9.854 | 1.00 | 27.01 |
| 1481 | O | GLY | A | 112 | 45.500 | 67.383 | 9.663 | 1.00 | 27.66 |
| 1482 | N | LEU | A | 113 | 47.258 | 67.574 | 11.066 | 1.00 | 27.18 |
| 1484 | CA | LEU | A | 113 | 46.478 | 67.445 | 12.301 | 1.00 | 27.29 |
| 1486 | CB | LEU | A | 113 | 46.778 | 66.104 | 12.965 | 1.00 | 27.61 |
| 1489 | CG | LEU | A | 113 | 46.308 | 64.849 | 12.230 | 1.00 | 29.25 |
| 1491 | CD1 | LEU | A | 113 | 46.956 | 63.639 | 12.826 | 1.00 | 29.40 |
| 1495 | CD2 | LEU | A | 113 | 44.799 | 64.723 | 12.297 | 1.00 | 30.33 |
| 1499 | C | LEU | A | 113 | 46.783 | 68.580 | 13.279 | 1.00 | 26.95 |
| 1500 | O | LEU | A | 113 | 47.781 | 69.273 | 13.134 | 1.00 | 26.97 |
| 1501 | N | PRO | A | 114 | 45.911 | 68.807 | 14.256 | 1.00 | 26.77 |
| 1502 | CA | PRO | A | 114 | 46.242 | 69.737 | 15.341 | 1.00 | 26.42 |
| 1504 | CB | PRO | A | 114 | 45.151 | 69.465 | 16.391 | 1.00 | 26.39 |
| 1507 | CG | PRO | A | 114 | 43.997 | 68.927 | 15.636 | 1.00 | 27.10 |
| 1510 | CD | PRO | A | 114 | 44.540 | 68.278 | 14.377 | 1.00 | 27.03 |
| 1513 | C | PRO | A | 114 | 47.644 | 69.428 | 15.902 | 1.00 | 25.96 |
| 1514 | O | PRO | A | 114 | 47.988 | 68.247 | 16.088 | 1.00 | 25.12 |
| 1515 | N | THR | A | 115 | 48.433 | 70.470 | 16.131 | 1.00 | 25.63 |
| 1517 | CA | THR | A | 115 | 49.730 | 70.336 | 16.803 | 1.00 | 25.53 |
| 1519 | CB | THR | A | 115 | 50.478 | 71.668 | 16.835 | 1.00 | 25.67 |
| 1521 | OG1 | THR | A | 115 | 49.605 | 72.715 | 17.288 | 1.00 | 26.41 |
| 1523 | CG2 | THR | A | 115 | 50.901 | 72.085 | 15.442 | 1.00 | 25.77 |
| 1527 | C | THR | A | 115 | 49.531 | 69.838 | 18.228 | 1.00 | 25.27 |
| 1528 | O | THR | A | 115 | 48.430 | 69.941 | 18.787 | 1.00 | 24.78 |
| 1529 | N | CYS | A | 116 | 50.600 | 69.305 | 18.817 | 1.00 | 24.89 |
| 1531 | CA | CYS | A | 116 | 50.523 | 68.697 | 20.137 | 1.00 | 24.95 |

FIGURE 3 (Cont.)

| A | B | C | D | E | F | G | H | I | J |
|---|---|---|---|---|---|---|---|---|---|
| 1533 | CB | CYS | A | 116 | 51.895 | 68.165 | 20.581 | 1.00 | 24.90 |
| 1536 | SG | CYS | A | 116 | 52.285 | 66.565 | 19.821 | 1.00 | 24.91 |
| 1537 | C | CYS | A | 116 | 49.933 | 69.634 | 21.182 | 1.00 | 24.97 |
| 1538 | O | CYS | A | 116 | 49.096 | 69.228 | 21.971 | 1.00 | 24.71 |
| 1539 | N | HIS | A | 117 | 50.346 | 70.894 | 21.168 | 1.00 | 25.78 |
| 1541 | CA | HIS | A | 117 | 49.925 | 71.820 | 22.208 | 1.00 | 26.16 |
| 1543 | CB | HIS | A | 117 | 50.836 | 73.054 | 22.246 | 1.00 | 26.51 |
| 1546 | CG | HIS | A | 117 | 50.548 | 74.067 | 21.186 | 1.00 | 27.10 |
| 1547 | ND1 | HIS | A | 117 | 50.785 | 73.840 | 19.849 | 1.00 | 30.89 |
| 1549 | CE1 | HIS | A | 117 | 50.441 | 74.911 | 19.156 | 1.00 | 30.52 |
| 1551 | NE2 | HIS | A | 117 | 50.007 | 75.831 | 19.996 | 1.00 | 30.35 |
| 1553 | CD2 | HIS | A | 117 | 50.066 | 75.327 | 21.272 | 1.00 | 29.44 |
| 1555 | C | HIS | A | 117 | 48.433 | 72.162 | 22.054 | 1.00 | 26.69 |
| 1556 | O | HIS | A | 117 | 47.747 | 72.385 | 23.040 | 1.00 | 26.52 |
| 1557 | N | VAL | A | 118 | 47.938 | 72.180 | 20.820 | 1.00 | 27.17 |
| 1559 | CA | VAL | A | 118 | 46.510 | 72.380 | 20.577 | 1.00 | 27.86 |
| 1561 | CB | VAL | A | 118 | 46.217 | 72.617 | 19.078 | 1.00 | 27.70 |
| 1563 | CG1 | VAL | A | 118 | 44.701 | 72.510 | 18.774 | 1.00 | 28.86 |
| 1567 | CG2 | VAL | A | 118 | 46.737 | 73.972 | 18.645 | 1.00 | 28.14 |
| 1571 | C | VAL | A | 118 | 45.695 | 71.196 | 21.131 | 1.00 | 28.24 |
| 1572 | O | VAL | A | 118 | 44.784 | 71.396 | 21.935 | 1.00 | 28.47 |
| 1573 | N | LYS | A | 119 | 46.040 | 69.973 | 20.733 | 1.00 | 28.54 |
| 1575 | CA | LYS | A | 119 | 45.245 | 68.798 | 21.101 | 1.00 | 29.34 |
| 1577 | CB | LYS | A | 119 | 45.617 | 67.583 | 20.241 | 1.00 | 29.61 |
| 1580 | CG | LYS | A | 119 | 44.863 | 66.301 | 20.626 | 1.00 | 30.82 |
| 1583 | CD | LYS | A | 119 | 45.106 | 65.186 | 19.627 | 1.00 | 32.53 |
| 1586 | CE | LYS | A | 119 | 44.199 | 63.976 | 19.839 | 1.00 | 33.76 |
| 1589 | NZ | LYS | A | 119 | 43.344 | 64.050 | 21.054 | 1.00 | 36.05 |
| 1593 | C | LYS | A | 119 | 45.371 | 68.422 | 22.581 | 1.00 | 29.59 |
| 1594 | O | LYS | A | 119 | 44.383 | 68.012 | 23.194 | 1.00 | 29.82 |
| 1595 | N | PHE | A | 120 | 46.575 | 68.551 | 23.146 | 1.00 | 28.84 |
| 1597 | CA | PHE | A | 120 | 46.839 | 68.108 | 24.519 | 1.00 | 28.62 |
| 1599 | CB | PHE | A | 120 | 47.984 | 67.096 | 24.529 | 1.00 | 28.31 |
| 1602 | CG | PHE | A | 120 | 47.722 | 65.880 | 23.711 | 1.00 | 27.28 |
| 1603 | CD1 | PHE | A | 120 | 47.055 | 64.787 | 24.261 | 1.00 | 27.38 |
| 1605 | CE1 | PHE | A | 120 | 46.831 | 63.631 | 23.508 | 1.00 | 27.16 |
| 1607 | CZ | PHE | A | 120 | 47.271 | 63.563 | 22.198 | 1.00 | 27.58 |
| 1609 | CE2 | PHE | A | 120 | 47.932 | 64.648 | 21.636 | 1.00 | 27.23 |
| 1611 | CD2 | PHE | A | 120 | 48.163 | 65.804 | 22.399 | 1.00 | 27.44 |
| 1613 | C | PHE | A | 120 | 47.185 | 69.217 | 25.515 | 1.00 | 28.26 |
| 1614 | O | PHE | A | 120 | 47.341 | 68.943 | 26.706 | 1.00 | 29.25 |
| 1615 | N | GLY | A | 121 | 47.299 | 70.452 | 25.042 | 1.00 | 27.60 |
| 1617 | CA | GLY | A | 121 | 47.659 | 71.575 | 25.896 | 1.00 | 26.94 |
| 1620 | C | GLY | A | 121 | 49.155 | 71.840 | 25.860 | 1.00 | 26.46 |
| 1621 | O | GLY | A | 121 | 49.958 | 70.992 | 25.438 | 1.00 | 26.06 |
| 1622 | N | GLU | A | 122 | 49.536 | 73.009 | 26.340 | 1.00 | 25.72 |
| 1624 | CA | GLU | A | 122 | 50.910 | 73.462 | 26.248 | 1.00 | 25.58 |
| 1626 | CB | GLU | A | 122 | 51.007 | 74.958 | 26.519 | 1.00 | 25.87 |
| 1629 | CG | GLU | A | 122 | 50.483 | 75.783 | 25.358 | 1.00 | 29.11 |
| 1632 | CD | GLU | A | 122 | 50.355 | 77.241 | 25.698 | 1.00 | 33.26 |
| 1633 | OE1 | GLU | A | 122 | 51.247 | 77.754 | 26.399 | 1.00 | 35.51 |
| 1634 | OE2 | GLU | A | 122 | 49.349 | 77.861 | 25.269 | 1.00 | 37.97 |

FIGURE 3 (Cont.)

| A | B | C | D | E | F | G | H | I | J |
|---|---|---|---|---|---|---|---|---|---|
| 1635 | C | GLU | A | 122 | 51.798 | 72.689 | 27.211 | 1.00 | 24.80 |
| 1636 | O | GLU | A | 122 | 52.899 | 72.300 | 26.840 | 1.00 | 24.40 |
| 1637 | N | ALA | A | 123 | 51.320 | 72.474 | 28.436 | 1.00 | 23.77 |
| 1639 | CA | ALA | A | 123 | 52.098 | 71.760 | 29.447 | 1.00 | 23.73 |
| 1641 | CB | ALA | A | 123 | 51.353 | 71.711 | 30.776 | 1.00 | 23.98 |
| 1645 | C | ALA | A | 123 | 52.441 | 70.343 | 28.968 | 1.00 | 23.81 |
| 1646 | O | ALA | A | 123 | 53.603 | 69.943 | 29.024 | 1.00 | 24.19 |
| 1647 | N | ASN | A | 124 | 51.442 | 69.609 | 28.479 | 1.00 | 22.86 |
| 1649 | CA | ASN | A | 124 | 51.654 | 68.270 | 27.947 | 1.00 | 22.86 |
| 1651 | CB | ASN | A | 124 | 50.345 | 67.623 | 27.491 | 1.00 | 23.02 |
| 1654 | CG | ASN | A | 124 | 49.539 | 67.041 | 28.635 | 1.00 | 24.68 |
| 1655 | OD1 | ASN | A | 124 | 48.304 | 67.110 | 28.640 | 1.00 | 27.85 |
| 1656 | ND2 | ASN | A | 124 | 50.220 | 66.461 | 29.600 | 1.00 | 25.67 |
| 1659 | C | ASN | A | 124 | 52.631 | 68.261 | 26.779 | 1.00 | 21.84 |
| 1660 | O | ASN | A | 124 | 53.428 | 67.339 | 26.667 | 1.00 | 22.15 |
| 1661 | N | ALA | A | 125 | 52.543 | 69.263 | 25.908 | 1.00 | 20.33 |
| 1663 | CA | ALA | A | 125 | 53.457 | 69.399 | 24.788 | 1.00 | 20.39 |
| 1665 | CB | ALA | A | 125 | 52.984 | 70.529 | 23.886 | 1.00 | 20.63 |
| 1669 | C | ALA | A | 125 | 54.925 | 69.621 | 25.250 | 1.00 | 19.95 |
| 1670 | O | ALA | A | 125 | 55.856 | 68.974 | 24.760 | 1.00 | 19.97 |
| 1671 | N | ILE | A | 126 | 55.117 | 70.509 | 26.218 | 1.00 | 19.41 |
| 1673 | CA | ILE | A | 126 | 56.434 | 70.769 | 26.790 | 1.00 | 19.39 |
| 1675 | CB | ILE | A | 126 | 56.357 | 71.842 | 27.880 | 1.00 | 19.07 |
| 1677 | CG1 | ILE | A | 126 | 56.032 | 73.214 | 27.267 | 1.00 | 20.58 |
| 1680 | CD1 | ILE | A | 126 | 55.450 | 74.180 | 28.244 | 1.00 | 22.11 |
| 1684 | CG2 | ILE | A | 126 | 57.668 | 71.944 | 28.623 | 1.00 | 19.77 |
| 1688 | C | ILE | A | 126 | 57.011 | 69.487 | 27.378 | 1.00 | 19.19 |
| 1689 | O | ILE | A | 126 | 58.134 | 69.105 | 27.069 | 1.00 | 18.97 |
| 1690 | N | LEU | A | 127 | 56.229 | 68.824 | 28.211 | 1.00 | 18.52 |
| 1692 | CA | LEU | A | 127 | 56.694 | 67.637 | 28.913 | 1.00 | 19.19 |
| 1694 | CB | LEU | A | 127 | 55.716 | 67.252 | 30.029 | 1.00 | 19.06 |
| 1697 | CG | LEU | A | 127 | 55.616 | 68.280 | 31.166 | 1.00 | 20.37 |
| 1699 | CD1 | LEU | A | 127 | 56.961 | 68.500 | 31.859 | 1.00 | 22.60 |
| 1703 | CD2 | LEU | A | 127 | 54.595 | 67.820 | 32.159 | 1.00 | 21.48 |
| 1707 | C | LEU | A | 127 | 56.907 | 66.470 | 27.966 | 1.00 | 18.53 |
| 1708 | O | LEU | A | 127 | 57.856 | 65.723 | 28.126 | 1.00 | 18.41 |
| 1709 | N | ALA | A | 128 | 56.033 | 66.320 | 26.973 | 1.00 | 17.92 |
| 1711 | CA | ALA | A | 128 | 56.179 | 65.228 | 26.012 | 1.00 | 17.62 |
| 1713 | CB | ALA | A | 128 | 54.947 | 65.115 | 25.104 | 1.00 | 17.67 |
| 1717 | C | ALA | A | 128 | 57.434 | 65.418 | 25.168 | 1.00 | 17.09 |
| 1718 | O | ALA | A | 128 | 58.108 | 64.461 | 24.828 | 1.00 | 17.12 |
| 1719 | N | GLY | A | 129 | 57.740 | 66.649 | 24.807 | 1.00 | 16.81 |
| 1721 | CA | GLY | A | 129 | 58.945 | 66.914 | 24.059 | 1.00 | 16.96 |
| 1724 | C | GLY | A | 129 | 60.155 | 66.651 | 24.946 | 1.00 | 17.30 |
| 1725 | O | GLY | A | 129 | 61.102 | 66.022 | 24.500 | 1.00 | 17.59 |
| 1726 | N | ASP | A | 130 | 60.106 | 67.121 | 26.193 | 1.00 | 17.16 |
| 1728 | CA | ASP | A | 130 | 61.139 | 66.853 | 27.190 | 1.00 | 17.77 |
| 1730 | CB | ASP | A | 130 | 60.717 | 67.383 | 28.562 | 1.00 | 18.20 |
| 1733 | CG | ASP | A | 130 | 60.801 | 68.881 | 28.661 | 1.00 | 19.18 |
| 1734 | OD1 | ASP | A | 130 | 61.407 | 69.492 | 27.759 | 1.00 | 21.99 |
| 1735 | OD2 | ASP | A | 130 | 60.295 | 69.527 | 29.612 | 1.00 | 19.91 |
| 1736 | C | ASP | A | 130 | 61.410 | 65.359 | 27.301 | 1.00 | 17.64 |

FIGURE 3 (Cont.)

| A | B | C | D | E | F | G | H | I | J |
|---|---|---|---|---|---|---|---|---|---|
| 1737 | O | ASP | A | 130 | 62.548 | 64.927 | 27.230 | 1.00 | 17.90 |
| 1738 | N | ALA | A | 131 | 60.343 | 64.584 | 27.447 | 1.00 | 17.42 |
| 1740 | CA | ALA | A | 131 | 60.438 | 63.146 | 27.633 | 1.00 | 17.39 |
| 1742 | CB | ALA | A | 131 | 59.098 | 62.582 | 28.089 | 1.00 | 17.97 |
| 1746 | C | ALA | A | 131 | 60.910 | 62.429 | 26.378 | 1.00 | 17.06 |
| 1747 | O | ALA | A | 131 | 61.576 | 61.425 | 26.482 | 1.00 | 16.51 |
| 1748 | N | LEU | A | 132 | 60.525 | 62.918 | 25.197 | 1.00 | 17.23 |
| 1750 | CA | LEU | A | 132 | 61.005 | 62.333 | 23.947 | 1.00 | 17.60 |
| 1752 | CB | LEU | A | 132 | 60.265 | 62.904 | 22.740 | 1.00 | 17.59 |
| 1755 | CG | LEU | A | 132 | 58.930 | 62.247 | 22.427 | 1.00 | 17.08 |
| 1757 | CD1 | LEU | A | 132 | 58.170 | 63.044 | 21.399 | 1.00 | 18.87 |
| 1761 | CD2 | LEU | A | 132 | 59.126 | 60.798 | 21.970 | 1.00 | 18.78 |
| 1765 | C | LEU | A | 132 | 62.515 | 62.534 | 23.779 | 1.00 | 17.74 |
| 1766 | O | LEU | A | 132 | 63.197 | 61.641 | 23.297 | 1.00 | 17.61 |
| 1767 | N | GLN | A | 133 | 63.036 | 63.695 | 24.185 | 1.00 | 17.96 |
| 1769 | CA | GLN | A | 133 | 64.483 | 63.926 | 24.148 | 1.00 | 18.23 |
| 1771 | CB | GLN | A | 133 | 64.894 | 65.366 | 24.559 | 1.00 | 18.28 |
| 1774 | CG | GLN | A | 133 | 66.427 | 65.512 | 24.520 | 1.00 | 19.50 |
| 1777 | CD | GLN | A | 133 | 67.021 | 66.816 | 25.074 | 1.00 | 22.38 |
| 1778 | OE1 | GLN | A | 133 | 66.350 | 67.833 | 25.237 | 1.00 | 19.65 |
| 1779 | NE2 | GLN | A | 133 | 68.322 | 66.768 | 25.346 | 1.00 | 23.26 |
| 1782 | C | GLN | A | 133 | 65.165 | 62.906 | 25.043 | 1.00 | 17.62 |
| 1783 | O | GLN | A | 133 | 66.132 | 62.284 | 24.645 | 1.00 | 17.06 |
| 1784 | N | THR | A | 134 | 64.650 | 62.736 | 26.258 | 1.00 | 18.05 |
| 1786 | CA | THR | A | 134 | 65.220 | 61.790 | 27.201 | 1.00 | 18.07 |
| 1788 | CB | THR | A | 134 | 64.461 | 61.797 | 28.520 | 1.00 | 18.89 |
| 1790 | OG1 | THR | A | 134 | 64.445 | 63.109 | 29.073 | 1.00 | 17.91 |
| 1792 | CG2 | THR | A | 134 | 65.189 | 60.940 | 29.551 | 1.00 | 18.65 |
| 1796 | C | THR | A | 134 | 65.165 | 60.373 | 26.665 | 1.00 | 17.74 |
| 1797 | O | THR | A | 134 | 66.111 | 59.615 | 26.829 | 1.00 | 17.70 |
| 1798 | N | LEU | A | 135 | 64.056 | 60.037 | 26.016 | 1.00 | 17.32 |
| 1800 | CA | LEU | A | 135 | 63.863 | 58.698 | 25.487 | 1.00 | 17.21 |
| 1802 | CB | LEU | A | 135 | 62.450 | 58.554 | 24.899 | 1.00 | 16.68 |
| 1805 | CG | LEU | A | 135 | 62.102 | 57.160 | 24.360 | 1.00 | 17.14 |
| 1807 | CD1 | LEU | A | 135 | 62.252 | 56.096 | 25.413 | 1.00 | 17.24 |
| 1811 | CD2 | LEU | A | 135 | 60.691 | 57.141 | 23.772 | 1.00 | 17.71 |
| 1815 | C | LEU | A | 135 | 64.934 | 58.362 | 24.443 | 1.00 | 16.99 |
| 1816 | O | LEU | A | 135 | 65.396 | 57.234 | 24.373 | 1.00 | 17.51 |
| 1817 | N | ALA | A | 136 | 65.311 | 59.345 | 23.637 | 1.00 | 16.86 |
| 1819 | CA | ALA | A | 136 | 66.350 | 59.191 | 22.640 | 1.00 | 16.98 |
| 1821 | CB | ALA | A | 136 | 66.617 | 60.525 | 21.936 | 1.00 | 16.96 |
| 1825 | C | ALA | A | 136 | 67.629 | 58.656 | 23.286 | 1.00 | 17.44 |
| 1826 | O | ALA | A | 136 | 68.269 | 57.772 | 22.741 | 1.00 | 17.77 |
| 1827 | N | PHE | A | 137 | 67.982 | 59.193 | 24.449 | 1.00 | 17.78 |
| 1829 | CA | PHE | A | 137 | 69.179 | 58.770 | 25.172 | 1.00 | 18.09 |
| 1831 | CB | PHE | A | 137 | 69.700 | 59.891 | 26.062 | 1.00 | 18.06 |
| 1834 | CG | PHE | A | 137 | 70.113 | 61.073 | 25.279 | 1.00 | 18.66 |
| 1835 | CD1 | PHE | A | 137 | 69.308 | 62.203 | 25.215 | 1.00 | 17.95 |
| 1837 | CE1 | PHE | A | 137 | 69.672 | 63.284 | 24.422 | 1.00 | 18.78 |
| 1839 | CZ | PHE | A | 137 | 70.834 | 63.241 | 23.689 | 1.00 | 18.81 |
| 1841 | CE2 | PHE | A | 137 | 71.647 | 62.108 | 23.742 | 1.00 | 19.03 |
| 1843 | CD2 | PHE | A | 137 | 71.277 | 61.031 | 24.526 | 1.00 | 19.55 |

FIGURE 3 (Cont.)

| A | B | C | D | E | F | G | H | I | J |
|---|---|---|---|---|---|---|---|---|---|
| 1845 | C | PHE | A | 137 | 69.000 | 57.481 | 25.944 | 1.00 | 17.78 |
| 1846 | O | PHE | A | 137 | 69.967 | 56.741 | 26.093 | 1.00 | 19.01 |
| 1847 | N | SER | A | 138 | 67.783 | 57.181 | 26.383 | 1.00 | 17.63 |
| 1849 | CA | SER | A | 138 | 67.480 | 55.853 | 26.930 | 1.00 | 17.81 |
| 1851 | CB | SER | A | 138 | 66.064 | 55.790 | 27.503 | 1.00 | 18.14 |
| 1854 | OG | SER | A | 138 | 65.998 | 56.474 | 28.749 | 1.00 | 19.62 |
| 1856 | C | SER | A | 138 | 67.634 | 54.788 | 25.860 | 1.00 | 17.61 |
| 1857 | O | SER | A | 138 | 68.139 | 53.706 | 26.127 | 1.00 | 17.31 |
| 1858 | N | ILE | A | 139 | 67.202 | 55.100 | 24.646 | 1.00 | 17.34 |
| 1860 | CA | ILE | A | 139 | 67.275 | 54.150 | 23.545 | 1.00 | 18.07 |
| 1862 | CB | ILE | A | 139 | 66.528 | 54.676 | 22.286 | 1.00 | 18.17 |
| 1864 | CG1 | ILE | A | 139 | 65.001 | 54.638 | 22.531 | 1.00 | 18.76 |
| 1867 | CD1 | ILE | A | 139 | 64.188 | 55.429 | 21.499 | 1.00 | 19.79 |
| 1871 | CG2 | ILE | A | 139 | 66.878 | 53.836 | 21.073 | 1.00 | 19.10 |
| 1875 | C | ILE | A | 139 | 68.732 | 53.827 | 23.237 | 1.00 | 17.54 |
| 1876 | O | ILE | A | 139 | 69.102 | 52.663 | 23.207 | 1.00 | 17.29 |
| 1877 | N | LEU | A | 140 | 69.556 | 54.854 | 23.081 | 1.00 | 17.52 |
| 1879 | CA | LEU | A | 140 | 70.961 | 54.677 | 22.710 | 1.00 | 18.26 |
| 1881 | CB | LEU | A | 140 | 71.607 | 56.028 | 22.388 | 1.00 | 18.48 |
| 1884 | CG | LEU | A | 140 | 71.151 | 56.649 | 21.066 | 1.00 | 18.76 |
| 1886 | CD1 | LEU | A | 140 | 71.890 | 57.952 | 20.786 | 1.00 | 19.92 |
| 1890 | CD2 | LEU | A | 140 | 71.349 | 55.663 | 19.939 | 1.00 | 19.54 |
| 1894 | C | LEU | A | 140 | 71.775 | 53.986 | 23.786 | 1.00 | 18.96 |
| 1895 | O | LEU | A | 140 | 72.715 | 53.265 | 23.476 | 1.00 | 18.14 |
| 1896 | N | SER | A | 141 | 71.414 | 54.201 | 25.046 | 1.00 | 19.45 |
| 1898 | CA | SER | A | 141 | 72.165 | 53.596 | 26.142 | 1.00 | 20.52 |
| 1900 | CB | SER | A | 141 | 72.125 | 54.482 | 27.404 | 1.00 | 20.39 |
| 1903 | OG | SER | A | 141 | 70.812 | 54.763 | 27.813 | 1.00 | 22.72 |
| 1905 | C | SER | A | 141 | 71.707 | 52.157 | 26.439 | 1.00 | 20.99 |
| 1906 | O | SER | A | 141 | 72.535 | 51.344 | 26.874 | 1.00 | 21.12 |
| 1907 | N | ASP | A | 142 | 70.435 | 51.840 | 26.157 | 1.00 | 20.94 |
| 1909 | CA | ASP | A | 142 | 69.803 | 50.583 | 26.617 | 1.00 | 21.52 |
| 1911 | CB | ASP | A | 142 | 68.510 | 50.885 | 27.360 | 1.00 | 21.35 |
| 1914 | CG | ASP | A | 142 | 68.740 | 51.573 | 28.668 | 1.00 | 23.16 |
| 1915 | OD1 | ASP | A | 142 | 67.745 | 52.038 | 29.261 | 1.00 | 22.75 |
| 1916 | OD2 | ASP | A | 142 | 69.871 | 51.678 | 29.188 | 1.00 | 24.41 |
| 1917 | C | ASP | A | 142 | 69.436 | 49.569 | 25.557 | 1.00 | 21.65 |
| 1918 | O | ASP | A | 142 | 69.308 | 48.382 | 25.850 | 1.00 | 20.45 |
| 1919 | N | ALA | A | 143 | 69.203 | 50.033 | 24.342 | 1.00 | 22.42 |
| 1921 | CA | ALA | A | 143 | 68.645 | 49.176 | 23.301 | 1.00 | 23.31 |
| 1923 | CB | ALA | A | 143 | 68.113 | 50.004 | 22.165 | 1.00 | 22.74 |
| 1927 | C | ALA | A | 143 | 69.698 | 48.200 | 22.795 | 1.00 | 24.09 |
| 1928 | O | ALA | A | 143 | 70.895 | 48.453 | 22.888 | 1.00 | 24.03 |
| 1929 | N | ASP | A | 144 | 69.228 | 47.087 | 22.256 | 1.00 | 25.84 |
| 1931 | CA | ASP | A | 144 | 70.096 | 46.051 | 21.707 | 1.00 | 27.11 |
| 1933 | CB | ASP | A | 144 | 69.309 | 44.768 | 21.402 | 1.00 | 27.68 |
| 1936 | CG | ASP | A | 144 | 68.293 | 44.426 | 22.469 | 1.00 | 31.56 |
| 1937 | OD1 | ASP | A | 144 | 67.116 | 44.829 | 22.309 | 1.00 | 38.25 |
| 1938 | OD2 | ASP | A | 144 | 68.558 | 43.752 | 23.487 | 1.00 | 35.92 |
| 1939 | C | ASP | A | 144 | 70.716 | 46.563 | 20.420 | 1.00 | 26.94 |
| 1940 | O | ASP | A | 144 | 69.995 | 46.966 | 19.504 | 1.00 | 27.42 |
| 1941 | N | MET | A | 145 | 72.044 | 46.586 | 20.374 | 1.00 | 27.00 |

FIGURE 3 (Cont.)

| A | B | C | D | E | F | G | H | I | J |
|---|---|---|---|---|---|---|---|---|---|
| 1943 | CA | MET | A | 145 | 72.794 | 46.828 | 19.148 | 1.00 | 27.40 |
| 1945 | CB | MET | A | 145 | 73.297 | 48.273 | 19.105 | 1.00 | 27.32 |
| 1948 | CG | MET | A | 145 | 72.199 | 49.301 | 19.048 | 1.00 | 27.17 |
| 1951 | SD | MET | A | 145 | 72.806 | 50.970 | 18.731 | 1.00 | 27.97 |
| 1952 | CE | MET | A | 145 | 73.747 | 51.294 | 20.169 | 1.00 | 26.35 |
| 1956 | C | MET | A | 145 | 73.972 | 45.850 | 19.125 | 1.00 | 28.08 |
| 1957 | O | MET | A | 145 | 75.099 | 46.213 | 19.487 | 1.00 | 27.86 |
| 1958 | N | PRO | A | 146 | 73.702 | 44.596 | 18.768 | 1.00 | 28.99 |
| 1959 | CA | PRO | A | 146 | 74.700 | 43.519 | 18.900 | 1.00 | 29.80 |
| 1961 | CB | PRO | A | 146 | 74.018 | 42.301 | 18.244 | 1.00 | 30.17 |
| 1964 | CG | PRO | A | 146 | 72.730 | 42.788 | 17.654 | 1.00 | 29.78 |
| 1967 | CD | PRO | A | 146 | 72.402 | 44.090 | 18.296 | 1.00 | 29.22 |
| 1970 | C | PRO | A | 146 | 76.088 | 43.778 | 18.280 | 1.00 | 29.90 |
| 1971 | O | PRO | A | 146 | 77.081 | 43.394 | 18.874 | 1.00 | 30.77 |
| 1972 | N | GLU | A | 147 | 76.176 | 44.452 | 17.149 | 1.00 | 30.07 |
| 1974 | CA | GLU | A | 147 | 77.488 | 44.605 | 16.495 | 1.00 | 30.29 |
| 1976 | CB | GLU | A | 147 | 77.348 | 44.666 | 14.970 | 1.00 | 30.88 |
| 1979 | CG | GLU | A | 147 | 76.419 | 43.625 | 14.368 | 1.00 | 33.60 |
| 1982 | CD | GLU | A | 147 | 74.996 | 44.126 | 14.226 | 1.00 | 36.03 |
| 1983 | OE1 | GLU | A | 147 | 74.447 | 44.088 | 13.102 | 1.00 | 38.00 |
| 1984 | OE2 | GLU | A | 147 | 74.433 | 44.556 | 15.252 | 1.00 | 37.12 |
| 1985 | C | GLU | A | 147 | 78.224 | 45.857 | 16.976 | 1.00 | 28.68 |
| 1986 | O | GLU | A | 147 | 79.335 | 46.129 | 16.528 | 1.00 | 28.50 |
| 1987 | N | VAL | A | 148 | 77.599 | 46.613 | 17.879 | 1.00 | 26.68 |
| 1989 | CA | VAL | A | 148 | 78.056 | 47.949 | 18.205 | 1.00 | 25.01 |
| 1991 | CB | VAL | A | 148 | 76.886 | 48.966 | 18.244 | 1.00 | 25.12 |
| 1993 | CG1 | VAL | A | 148 | 77.404 | 50.369 | 18.438 | 1.00 | 24.25 |
| 1997 | CG2 | VAL | A | 148 | 76.049 | 48.887 | 16.950 | 1.00 | 24.80 |
| 2001 | C | VAL | A | 148 | 78.819 | 47.927 | 19.526 | 1.00 | 23.84 |
| 2002 | O | VAL | A | 148 | 78.271 | 47.605 | 20.585 | 1.00 | 23.11 |
| 2003 | N | SER | A | 149 | 80.098 | 48.254 | 19.440 | 1.00 | 22.76 |
| 2005 | CA | SER | A | 149 | 80.952 | 48.338 | 20.613 | 1.00 | 22.78 |
| 2007 | CB | SER | A | 149 | 82.404 | 48.597 | 20.186 | 1.00 | 22.49 |
| 2010 | OG | SER | A | 149 | 82.568 | 49.915 | 19.707 | 1.00 | 21.57 |
| 2012 | C | SER | A | 149 | 80.458 | 49.448 | 21.539 | 1.00 | 23.11 |
| 2013 | O | SER | A | 149 | 79.794 | 50.402 | 21.099 | 1.00 | 21.95 |
| 2014 | N | ASP | A | 150 | 80.777 | 49.313 | 22.817 | 1.00 | 23.66 |
| 2016 | CA | ASP | A | 150 | 80.499 | 50.348 | 23.801 | 1.00 | 24.49 |
| 2018 | CB | ASP | A | 150 | 81.010 | 49.930 | 25.172 | 1.00 | 25.14 |
| 2021 | CG | ASP | A | 150 | 80.256 | 48.733 | 25.735 | 1.00 | 27.65 |
| 2022 | OD1 | ASP | A | 150 | 80.719 | 48.186 | 26.762 | 1.00 | 31.30 |
| 2023 | OD2 | ASP | A | 150 | 79.201 | 48.281 | 25.225 | 1.00 | 27.89 |
| 2024 | C | ASP | A | 150 | 81.115 | 51.680 | 23.394 | 1.00 | 24.45 |
| 2025 | O | ASP | A | 150 | 80.499 | 52.725 | 23.568 | 1.00 | 23.41 |
| 2026 | N | ARG | A | 151 | 82.319 | 51.639 | 22.827 | 1.00 | 24.28 |
| 2028 | CA | ARG | A | 151 | 82.973 | 52.844 | 22.355 | 1.00 | 24.79 |
| 2030 | CB | ARG | A | 151 | 84.352 | 52.508 | 21.759 | 1.00 | 26.00 |
| 2033 | CG | ARG | A | 151 | 85.134 | 53.699 | 21.268 | 1.00 | 28.93 |
| 2036 | CD | ARG | A | 151 | 85.432 | 54.712 | 22.350 | 1.00 | 34.80 |
| 2039 | NE | ARG | A | 151 | 84.576 | 55.893 | 22.233 | 1.00 | 38.89 |
| 2041 | CZ | ARG | A | 151 | 84.277 | 56.711 | 23.229 | 1.00 | 42.07 |
| 2042 | NH1 | ARG | A | 151 | 83.494 | 57.756 | 22.989 | 1.00 | 43.97 |

FIGURE 3 (Cont.)

| A | B | C | D | E | F | G | H | I | J |
|---|---|---|---|---|---|---|---|---|---|
| 2045 | NH2 | ARG | A | 151 | 84.754 | 56.502 | 24.462 | 1.00 | 42.69 |
| 2048 | C | ARG | A | 151 | 82.119 | 53.534 | 21.303 | 1.00 | 23.63 |
| 2049 | O | ARG | A | 151 | 81.949 | 54.749 | 21.330 | 1.00 | 22.68 |
| 2050 | N | ASP | A | 152 | 81.578 | 52.751 | 20.377 | 1.00 | 22.64 |
| 2052 | CA | ASP | A | 152 | 80.765 | 53.305 | 19.316 | 1.00 | 22.05 |
| 2054 | CB | ASP | A | 152 | 80.695 | 52.351 | 18.126 | 1.00 | 22.68 |
| 2057 | CG | ASP | A | 152 | 82.013 | 52.303 | 17.348 | 1.00 | 24.58 |
| 2058 | OD1 | ASP | A | 152 | 82.780 | 53.285 | 17.412 | 1.00 | 24.51 |
| 2059 | OD2 | ASP | A | 152 | 82.369 | 51.328 | 16.654 | 1.00 | 27.53 |
| 2060 | C | ASP | A | 152 | 79.380 | 53.730 | 19.832 | 1.00 | 20.89 |
| 2061 | O | ASP | A | 152 | 78.829 | 54.703 | 19.348 | 1.00 | 19.41 |
| 2062 | N | ARG | A | 153 | 78.855 | 53.043 | 20.844 | 1.00 | 19.83 |
| 2064 | CA | ARG | A | 153 | 77.577 | 53.435 | 21.459 | 1.00 | 18.66 |
| 2066 | CB | ARG | A | 153 | 77.116 | 52.390 | 22.450 | 1.00 | 18.96 |
| 2069 | CG | ARG | A | 153 | 75.734 | 52.644 | 23.008 | 1.00 | 18.87 |
| 2072 | CD | ARG | A | 153 | 75.377 | 51.687 | 24.112 | 1.00 | 19.73 |
| 2075 | NE | ARG | A | 153 | 75.180 | 50.322 | 23.630 | 1.00 | 20.07 |
| 2077 | CZ | ARG | A | 153 | 73.991 | 49.773 | 23.369 | 1.00 | 22.06 |
| 2078 | NH1 | ARG | A | 153 | 73.929 | 48.516 | 22.949 | 1.00 | 20.83 |
| 2081 | NH2 | ARG | A | 153 | 72.862 | 50.466 | 23.521 | 1.00 | 23.23 |
| 2084 | C | ARG | A | 153 | 77.724 | 54.771 | 22.171 | 1.00 | 18.18 |
| 2085 | O | ARG | A | 153 | 76.842 | 55.612 | 22.081 | 1.00 | 17.20 |
| 2086 | N | ILE | A | 154 | 78.847 | 54.959 | 22.869 | 1.00 | 17.73 |
| 2088 | CA | ILE | A | 154 | 79.141 | 56.223 | 23.542 | 1.00 | 18.41 |
| 2090 | CB | ILE | A | 154 | 80.414 | 56.100 | 24.449 | 1.00 | 18.14 |
| 2092 | CG1 | ILE | A | 154 | 80.092 | 55.249 | 25.684 | 1.00 | 19.24 |
| 2095 | CD1 | ILE | A | 154 | 81.307 | 54.703 | 26.408 | 1.00 | 20.01 |
| 2099 | CG2 | ILE | A | 154 | 80.932 | 57.468 | 24.875 | 1.00 | 19.53 |
| 2103 | C | ILE | A | 154 | 79.277 | 57.343 | 22.505 | 1.00 | 17.74 |
| 2104 | O | ILE | A | 154 | 78.757 | 58.424 | 22.698 | 1.00 | 18.17 |
| 2105 | N | SER | A | 155 | 79.934 | 57.063 | 21.388 | 1.00 | 18.18 |
| 2107 | CA | SER | A | 155 | 80.095 | 58.043 | 20.323 | 1.00 | 18.52 |
| 2109 | CB | SER | A | 155 | 81.020 | 57.511 | 19.236 | 1.00 | 18.63 |
| 2112 | OG | SER | A | 155 | 82.330 | 57.395 | 19.748 | 1.00 | 18.50 |
| 2114 | C | SER | A | 155 | 78.744 | 58.437 | 19.718 | 1.00 | 19.05 |
| 2115 | O | SER | A | 155 | 78.538 | 59.594 | 19.368 | 1.00 | 19.13 |
| 2116 | N | MET | A | 156 | 77.836 | 57.476 | 19.618 | 1.00 | 19.12 |
| 2118 | CA | MET | A | 156 | 76.482 | 57.743 | 19.135 | 1.00 | 19.40 |
| 2120 | CB | MET | A | 156 | 75.674 | 56.461 | 19.063 | 1.00 | 19.56 |
| 2123 | CG | MET | A | 156 | 76.083 | 55.564 | 17.948 | 1.00 | 22.23 |
| 2126 | SD | MET | A | 156 | 74.922 | 54.182 | 17.803 | 1.00 | 28.16 |
| 2127 | CE | MET | A | 156 | 75.814 | 53.241 | 16.666 | 1.00 | 26.77 |
| 2131 | C | MET | A | 156 | 75.746 | 58.693 | 20.039 | 1.00 | 18.61 |
| 2132 | O | MET | A | 156 | 75.101 | 59.609 | 19.567 | 1.00 | 18.79 |
| 2133 | N | ILE | A | 157 | 75.826 | 58.439 | 21.342 | 1.00 | 18.55 |
| 2135 | CA | ILE | A | 157 | 75.194 | 59.281 | 22.349 | 1.00 | 17.91 |
| 2137 | CB | ILE | A | 157 | 75.342 | 58.649 | 23.752 | 1.00 | 17.84 |
| 2139 | CG1 | ILE | A | 157 | 74.511 | 57.360 | 23.840 | 1.00 | 18.27 |
| 2142 | CD1 | ILE | A | 157 | 74.814 | 56.495 | 25.017 | 1.00 | 18.88 |
| 2146 | CG2 | ILE | A | 157 | 74.941 | 59.646 | 24.845 | 1.00 | 17.97 |
| 2150 | C | ILE | A | 157 | 75.804 | 60.685 | 22.313 | 1.00 | 17.61 |
| 2151 | O | ILE | A | 157 | 75.087 | 61.683 | 22.308 | 1.00 | 16.93 |

FIGURE 3 (Cont.)

| A | B | C | D | E | F | G | H | I | J |
|---|---|---|---|---|---|---|---|---|---|
| 2152 | N | SER | A | 158 | 77.136 | 60.749 | 22.290 | 1.00 | 17.36 |
| 2154 | CA | SER | A | 158 | 77.856 | 62.012 | 22.247 | 1.00 | 17.24 |
| 2156 | CB | SER | A | 158 | 79.372 | 61.759 | 22.292 | 1.00 | 17.57 |
| 2159 | OG | SER | A | 158 | 80.087 | 62.908 | 21.936 | 1.00 | 16.92 |
| 2161 | C | SER | A | 158 | 77.487 | 62.819 | 21.007 | 1.00 | 17.58 |
| 2162 | O | SER | A | 158 | 77.266 | 64.003 | 21.093 | 1.00 | 17.17 |
| 2163 | N | GLU | A | 159 | 77.408 | 62.163 | 19.856 | 1.00 | 18.38 |
| 2165 | CA | GLU | A | 159 | 77.042 | 62.833 | 18.616 | 1.00 | 18.63 |
| 2167 | CB | GLU | A | 159 | 77.242 | 61.904 | 17.409 | 1.00 | 19.18 |
| 2170 | CG | GLU | A | 159 | 76.518 | 62.361 | 16.145 | 1.00 | 20.77 |
| 2173 | CD | GLU | A | 159 | 76.979 | 63.726 | 15.666 | 1.00 | 23.75 |
| 2174 | OE1 | GLU | A | 159 | 78.105 | 64.141 | 16.022 | 1.00 | 24.45 |
| 2175 | OE2 | GLU | A | 159 | 76.233 | 64.384 | 14.918 | 1.00 | 26.52 |
| 2176 | C | GLU | A | 159 | 75.592 | 63.324 | 18.648 | 1.00 | 18.90 |
| 2177 | O | GLU | A | 159 | 75.311 | 64.455 | 18.224 | 1.00 | 18.41 |
| 2178 | N | LEU | A | 160 | 74.671 | 62.489 | 19.122 | 1.00 | 18.15 |
| 2180 | CA | LEU | A | 160 | 73.274 | 62.921 | 19.169 | 1.00 | 18.98 |
| 2182 | CB | LEU | A | 160 | 72.333 | 61.801 | 19.559 | 1.00 | 19.20 |
| 2185 | CG | LEU | A | 160 | 70.845 | 62.123 | 19.337 | 1.00 | 20.03 |
| 2187 | CD1 | LEU | A | 160 | 70.528 | 62.479 | 17.890 | 1.00 | 20.04 |
| 2191 | CD2 | LEU | A | 160 | 70.015 | 60.977 | 19.795 | 1.00 | 21.02 |
| 2195 | C | LEU | A | 160 | 73.119 | 64.115 | 20.113 | 1.00 | 19.39 |
| 2196 | O | LEU | A | 160 | 72.388 | 65.058 | 19.808 | 1.00 | 19.39 |
| 2197 | N | ALA | A | 161 | 73.832 | 64.078 | 21.234 | 1.00 | 19.92 |
| 2199 | CA | ALA | A | 161 | 73.814 | 65.162 | 22.208 | 1.00 | 20.54 |
| 2201 | CB | ALA | A | 161 | 74.591 | 64.764 | 23.463 | 1.00 | 20.76 |
| 2205 | C | ALA | A | 161 | 74.362 | 66.466 | 21.621 | 1.00 | 20.84 |
| 2206 | O | ALA | A | 161 | 73.690 | 67.496 | 21.678 | 1.00 | 21.05 |
| 2207 | N | SER | A | 162 | 75.554 | 66.431 | 21.027 | 1.00 | 21.51 |
| 2209 | CA | SER | A | 162 | 76.138 | 67.660 | 20.486 | 1.00 | 22.08 |
| 2211 | CB | SER | A | 162 | 77.614 | 67.492 | 20.063 | 1.00 | 22.37 |
| 2214 | OG | SER | A | 162 | 77.809 | 66.365 | 19.248 | 1.00 | 24.18 |
| 2216 | C | SER | A | 162 | 75.286 | 68.207 | 19.336 | 1.00 | 21.42 |
| 2217 | O | SER | A | 162 | 75.142 | 69.415 | 19.197 | 1.00 | 21.65 |
| 2218 | N | ALA | A | 163 | 74.700 | 67.316 | 18.539 | 1.00 | 20.43 |
| 2220 | CA | ALA | A | 163 | 73.906 | 67.716 | 17.379 | 1.00 | 20.07 |
| 2222 | CB | ALA | A | 163 | 73.732 | 66.523 | 16.438 | 1.00 | 20.07 |
| 2226 | C | ALA | A | 163 | 72.537 | 68.265 | 17.768 | 1.00 | 19.77 |
| 2227 | O | ALA | A | 163 | 71.937 | 69.041 | 17.026 | 1.00 | 18.96 |
| 2228 | N | SER | A | 164 | 72.026 | 67.836 | 18.922 | 1.00 | 19.92 |
| 2230 | CA | SER | A | 164 | 70.677 | 68.207 | 19.366 | 1.00 | 19.71 |
| 2232 | CB | SER | A | 164 | 70.061 | 67.027 | 20.112 | 1.00 | 20.08 |
| 2235 | OG | SER | A | 164 | 70.098 | 65.862 | 19.285 | 1.00 | 21.77 |
| 2237 | C | SER | A | 164 | 70.655 | 69.452 | 20.246 | 1.00 | 20.10 |
| 2238 | O | SER | A | 164 | 69.661 | 70.210 | 20.271 | 1.00 | 18.98 |
| 2239 | N | GLY | A | 165 | 71.757 | 69.676 | 20.958 | 1.00 | 19.76 |
| 2241 | CA | GLY | A | 165 | 71.846 | 70.733 | 21.939 | 1.00 | 20.35 |
| 2244 | C | GLY | A | 165 | 72.244 | 72.081 | 21.365 | 1.00 | 20.96 |
| 2245 | O | GLY | A | 165 | 71.982 | 72.393 | 20.203 | 1.00 | 20.86 |
| 2246 | N | ILE | A | 166 | 72.900 | 72.879 | 22.200 | 1.00 | 21.84 |
| 2248 | CA | ILE | A | 166 | 73.170 | 74.280 | 21.914 | 1.00 | 22.71 |
| 2250 | CB | ILE | A | 166 | 73.611 | 74.975 | 23.242 | 1.00 | 23.10 |

FIGURE 3 (Cont.)

| A | B | C | D | E | F | G | H | I | J |
|---|---|---|---|---|---|---|---|---|---|
| 2252 | CG1 | ILE | A | 166 | 73.194 | 76.437 | 23.239 | 1.00 | 23.87 |
| 2255 | CD1 | ILE | A | 166 | 71.710 | 76.610 | 23.444 | 1.00 | 23.14 |
| 2259 | CG2 | ILE | A | 166 | 75.109 | 74.770 | 23.489 | 1.00 | 25.44 |
| 2263 | C | ILE | A | 166 | 74.197 | 74.443 | 20.769 | 1.00 | 22.75 |
| 2264 | O | ILE | A | 166 | 74.206 | 75.456 | 20.057 | 1.00 | 23.12 |
| 2265 | N | ALA | A | 167 | 75.027 | 73.422 | 20.572 | 1.00 | 22.36 |
| 2267 | CA | ALA | A | 167 | 75.954 | 73.367 | 19.451 | 1.00 | 22.62 |
| 2269 | CB | ALA | A | 167 | 77.109 | 72.455 | 19.770 | 1.00 | 22.85 |
| 2273 | C | ALA | A | 167 | 75.285 | 72.916 | 18.152 | 1.00 | 22.34 |
| 2274 | O | ALA | A | 167 | 75.905 | 72.963 | 17.111 | 1.00 | 22.65 |
| 2275 | N | GLY | A | 168 | 74.028 | 72.488 | 18.212 | 1.00 | 21.57 |
| 2277 | CA | GLY | A | 168 | 73.304 | 72.064 | 17.022 | 1.00 | 21.12 |
| 2280 | C | GLY | A | 168 | 71.883 | 72.588 | 16.982 | 1.00 | 20.68 |
| 2281 | O | GLY | A | 168 | 71.665 | 73.785 | 16.956 | 1.00 | 19.79 |
| 2282 | N | MET | A | 169 | 70.914 | 71.682 | 17.005 | 1.00 | 20.95 |
| 2284 | CA | MET | A | 169 | 69.501 | 72.019 | 16.812 | 1.00 | 20.87 |
| 2286 | CB | MET | A | 169 | 68.655 | 70.757 | 16.927 | 1.00 | 21.21 |
| 2289 | CG | MET | A | 169 | 67.183 | 70.922 | 16.531 | 1.00 | 22.91 |
| 2292 | SD | MET | A | 169 | 66.208 | 71.479 | 17.897 | 1.00 | 28.34 |
| 2293 | CE | MET | A | 169 | 66.254 | 69.967 | 19.003 | 1.00 | 25.97 |
| 2297 | C | MET | A | 169 | 68.952 | 73.140 | 17.721 | 1.00 | 20.52 |
| 2298 | O | MET | A | 169 | 68.310 | 74.072 | 17.224 | 1.00 | 19.77 |
| 2299 | N | CYS | A | 170 | 69.200 | 73.059 | 19.028 | 1.00 | 20.60 |
| 2301 | CA | CYS | A | 170 | 68.689 | 74.061 | 19.977 | 1.00 | 20.42 |
| 2303 | CB | BCYS | A | 170 | 68.958 | 73.590 | 21.405 | 0.35 | 20.62 |
| 2304 | CB | ACYS | A | 170 | 68.958 | 73.668 | 21.427 | 0.65 | 20.89 |
| 2309 | SG | BCYS | A | 170 | 67.803 | 74.234 | 22.609 | 0.35 | 20.91 |
| 2310 | SG | ACYS | A | 170 | 67.804 | 72.489 | 22.098 | 0.65 | 22.71 |
| 2311 | C | CYS | A | 170 | 69.332 | 75.426 | 19.744 | 1.00 | 20.33 |
| 2312 | O | CYS | A | 170 | 68.665 | 76.459 | 19.811 | 1.00 | 18.74 |
| 2313 | N | GLY | A | 171 | 70.650 | 75.414 | 19.539 | 1.00 | 20.11 |
| 2315 | CA | GLY | A | 171 | 71.384 | 76.605 | 19.172 | 1.00 | 20.26 |
| 2318 | C | GLY | A | 171 | 70.807 | 77.252 | 17.932 | 1.00 | 20.35 |
| 2319 | O | GLY | A | 171 | 70.645 | 78.473 | 17.877 | 1.00 | 19.82 |
| 2320 | N | GLY | A | 172 | 70.470 | 76.425 | 16.948 | 1.00 | 20.20 |
| 2322 | CA | GLY | A | 172 | 69.875 | 76.891 | 15.715 | 1.00 | 20.43 |
| 2325 | C | GLY | A | 172 | 68.484 | 77.441 | 15.920 | 1.00 | 20.51 |
| 2326 | O | GLY | A | 172 | 68.117 | 78.435 | 15.303 | 1.00 | 20.93 |
| 2327 | N | GLN | A | 173 | 67.716 | 76.816 | 16.800 | 1.00 | 20.70 |
| 2329 | CA | GLN | A | 173 | 66.397 | 77.327 | 17.168 | 1.00 | 21.15 |
| 2331 | CB | GLN | A | 173 | 65.684 | 76.383 | 18.149 | 1.00 | 21.47 |
| 2334 | CG | GLN | A | 173 | 65.165 | 75.072 | 17.546 | 1.00 | 21.62 |
| 2337 | CD | GLN | A | 173 | 64.102 | 75.279 | 16.494 | 1.00 | 22.97 |
| 2338 | OE1 | GLN | A | 173 | 64.417 | 75.656 | 15.362 | 1.00 | 27.11 |
| 2339 | NE2 | GLN | A | 173 | 62.845 | 75.031 | 16.850 | 1.00 | 22.24 |
| 2342 | C | GLN | A | 173 | 66.514 | 78.725 | 17.794 | 1.00 | 21.59 |
| 2343 | O | GLN | A | 173 | 65.695 | 79.609 | 17.513 | 1.00 | 22.14 |
| 2344 | N | ALA | A | 174 | 67.532 | 78.931 | 18.622 | 1.00 | 21.59 |
| 2346 | CA | ALA | A | 174 | 67.766 | 80.245 | 19.230 | 1.00 | 21.99 |
| 2348 | CB | ALA | A | 174 | 68.847 | 80.166 | 20.296 | 1.00 | 22.20 |
| 2352 | C | ALA | A | 174 | 68.152 | 81.269 | 18.164 | 1.00 | 22.07 |
| 2353 | O | ALA | A | 174 | 67.683 | 82.380 | 18.206 | 1.00 | 21.87 |

FIGURE 3 (Cont.)

| A | B | C | D | E | F | G | H | I | J |
|---|---|---|---|---|---|---|---|---|---|
| 2354 | N | LEU | A | 175 | 69.001 | 80.885 | 17.212 | 1.00 | 22.13 |
| 2356 | CA | LEU | A | 175 | 69.369 | 81.776 | 16.106 | 1.00 | 23.00 |
| 2358 | CB | LEU | A | 175 | 70.449 | 81.144 | 15.233 | 1.00 | 23.09 |
| 2361 | CG | LEU | A | 175 | 71.824 | 80.871 | 15.840 | 1.00 | 22.66 |
| 2363 | CD1 | LEU | A | 175 | 72.668 | 80.085 | 14.817 | 1.00 | 24.29 |
| 2367 | CD2 | LEU | A | 175 | 72.522 | 82.155 | 16.235 | 1.00 | 22.45 |
| 2371 | C | LEU | A | 175 | 68.163 | 82.119 | 15.240 | 1.00 | 23.28 |
| 2372 | O | LEU | A | 175 | 68.003 | 83.265 | 14.805 | 1.00 | 23.62 |
| 2373 | N | ASP | A | 176 | 67.314 | 81.123 | 15.002 | 1.00 | 23.53 |
| 2375 | CA | ASP | A | 176 | 66.112 | 81.280 | 14.197 | 1.00 | 24.49 |
| 2377 | CB | ASP | A | 176 | 65.382 | 79.934 | 14.080 | 1.00 | 24.90 |
| 2380 | CG | ASP | A | 176 | 64.004 | 80.064 | 13.491 | 1.00 | 25.57 |
| 2381 | OD1 | ASP | A | 176 | 63.830 | 79.750 | 12.287 | 1.00 | 28.64 |
| 2382 | OD2 | ASP | A | 176 | 63.023 | 80.441 | 14.162 | 1.00 | 28.54 |
| 2383 | C | ASP | A | 176 | 65.187 | 82.320 | 14.841 | 1.00 | 24.97 |
| 2384 | O | ASP | A | 176 | 64.683 | 83.222 | 14.178 | 1.00 | 24.47 |
| 2385 | N | LEU | A | 177 | 64.974 | 82.168 | 16.138 | 1.00 | 25.23 |
| 2387 | CA | LEU | A | 177 | 64.127 | 83.083 | 16.905 | 1.00 | 26.68 |
| 2389 | CB | LEU | A | 177 | 63.977 | 82.575 | 18.343 | 1.00 | 26.78 |
| 2392 | CG | LEU | A | 177 | 62.658 | 81.902 | 18.734 | 1.00 | 28.22 |
| 2394 | CD1 | LEU | A | 177 | 62.016 | 81.077 | 17.633 | 1.00 | 29.14 |
| 2398 | CD2 | LEU | A | 177 | 62.892 | 81.055 | 19.970 | 1.00 | 29.13 |
| 2402 | C | LEU | A | 177 | 64.686 | 84.512 | 16.914 | 1.00 | 26.76 |
| 2403 | O | LEU | A | 177 | 63.936 | 85.474 | 16.784 | 1.00 | 26.89 |
| 2404 | N | ASP | A | 178 | 66.002 | 84.640 | 17.050 | 1.00 | 27.40 |
| 2406 | CA | ASP | A | 178 | 66.636 | 85.952 | 17.078 | 1.00 | 28.30 |
| 2408 | CB | ASP | A | 178 | 68.107 | 85.827 | 17.459 | 1.00 | 28.53 |
| 2411 | CG | ASP | A | 178 | 68.753 | 87.176 | 17.720 | 1.00 | 31.35 |
| 2412 | OD1 | ASP | A | 178 | 69.682 | 87.571 | 16.965 | 1.00 | 33.39 |
| 2413 | OD2 | ASP | A | 178 | 68.389 | 87.907 | 18.667 | 1.00 | 33.95 |
| 2414 | C | ASP | A | 178 | 66.513 | 86.681 | 15.734 | 1.00 | 28.03 |
| 2415 | O | ASP | A | 178 | 66.398 | 87.907 | 15.689 | 1.00 | 27.69 |
| 2416 | N | ALA | A | 179 | 66.525 | 85.915 | 14.648 | 1.00 | 27.46 |
| 2418 | CA | ALA | A | 179 | 66.499 | 86.467 | 13.300 | 1.00 | 27.69 |
| 2420 | CB | ALA | A | 179 | 67.174 | 85.479 | 12.330 | 1.00 | 27.70 |
| 2424 | C | ALA | A | 179 | 65.089 | 86.843 | 12.796 | 1.00 | 27.58 |
| 2425 | O | ALA | A | 179 | 64.946 | 87.351 | 11.683 | 1.00 | 27.80 |
| 2426 | N | GLU | A | 180 | 64.057 | 86.590 | 13.596 | 1.00 | 27.88 |
| 2428 | CA | GLU | A | 180 | 62.702 | 87.040 | 13.277 | 1.00 | 28.36 |
| 2430 | CB | GLU | A | 180 | 61.710 | 86.633 | 14.367 | 1.00 | 28.57 |
| 2433 | CG | GLU | A | 180 | 61.415 | 85.151 | 14.422 | 1.00 | 29.97 |
| 2436 | CD | GLU | A | 180 | 60.434 | 84.780 | 15.517 | 1.00 | 32.47 |
| 2437 | OE1 | GLU | A | 180 | 60.070 | 85.661 | 16.338 | 1.00 | 34.93 |
| 2438 | OE2 | GLU | A | 180 | 60.026 | 83.598 | 15.558 | 1.00 | 32.41 |
| 2439 | C | GLU | A | 180 | 62.695 | 88.560 | 13.162 | 1.00 | 28.40 |
| 2440 | O | GLU | A | 180 | 63.140 | 89.252 | 14.075 | 1.00 | 27.70 |
| 2441 | N | GLY | A | 181 | 62.227 | 89.057 | 12.020 | 1.00 | 28.55 |
| 2443 | CA | GLY | A | 181 | 62.105 | 90.477 | 11.766 | 1.00 | 29.05 |
| 2446 | C | GLY | A | 181 | 63.391 | 91.173 | 11.391 | 1.00 | 29.41 |
| 2447 | O | GLY | A | 181 | 63.379 | 92.382 | 11.129 | 1.00 | 30.34 |
| 2448 | N | LYS | A | 182 | 64.501 | 90.437 | 11.353 | 1.00 | 29.52 |
| 2450 | CA | LYS | A | 182 | 65.818 | 91.032 | 11.137 | 1.00 | 29.58 |

FIGURE 3 (Cont.)

| A | B | C | D | E | F | G | H | I | J |
|---|---|---|---|---|---|---|---|---|---|
| 2452 | CB | LYS | A | 182 | 66.807 | 90.510 | 12.175 | 1.00 | 30.25 |
| 2455 | CG | LYS | A | 182 | 66.415 | 90.819 | 13.604 | 1.00 | 31.19 |
| 2458 | CD | LYS | A | 182 | 67.528 | 90.474 | 14.569 | 1.00 | 33.42 |
| 2461 | CE | LYS | A | 182 | 67.168 | 90.894 | 16.009 | 1.00 | 34.43 |
| 2464 | NZ | LYS | A | 182 | 65.969 | 90.178 | 16.544 | 1.00 | 36.01 |
| 2468 | C | LYS | A | 182 | 66.375 | 90.797 | 9.730 | 1.00 | 29.61 |
| 2469 | O | LYS | A | 182 | 67.389 | 91.383 | 9.367 | 1.00 | 29.31 |
| 2470 | N | HIS | A | 183 | 65.725 | 89.944 | 8.947 | 1.00 | 29.18 |
| 2472 | CA | HIS | A | 183 | 66.098 | 89.736 | 7.546 | 1.00 | 29.54 |
| 2474 | CB | HIS | A | 183 | 65.574 | 90.895 | 6.688 | 1.00 | 29.50 |
| 2477 | CG | HIS | A | 183 | 64.099 | 91.086 | 6.806 | 1.00 | 29.04 |
| 2478 | ND1 | HIS | A | 183 | 63.217 | 90.679 | 5.835 | 1.00 | 29.33 |
| 2480 | CE1 | HIS | A | 183 | 61.982 | 90.944 | 6.226 | 1.00 | 30.87 |
| 2482 | NE2 | HIS | A | 183 | 62.033 | 91.486 | 7.429 | 1.00 | 30.77 |
| 2484 | CD2 | HIS | A | 183 | 63.346 | 91.580 | 7.816 | 1.00 | 30.69 |
| 2486 | C | HIS | A | 183 | 67.598 | 89.588 | 7.410 | 1.00 | 29.56 |
| 2487 | O | HIS | A | 183 | 68.261 | 90.375 | 6.732 | 1.00 | 29.82 |
| 2488 | N | VAL | A | 184 | 68.136 | 88.569 | 8.067 | 1.00 | 29.52 |
| 2490 | CA | VAL | A | 184 | 69.580 | 88.461 | 8.215 | 1.00 | 29.40 |
| 2492 | CB | VAL | A | 184 | 69.976 | 87.488 | 9.352 | 1.00 | 29.29 |
| 2494 | CG1 | VAL | A | 184 | 69.310 | 87.904 | 10.659 | 1.00 | 29.32 |
| 2498 | CG2 | VAL | A | 184 | 69.645 | 86.033 | 8.998 | 1.00 | 28.66 |
| 2502 | C | VAL | A | 184 | 70.233 | 88.072 | 6.886 | 1.00 | 29.41 |
| 2503 | O | VAL | A | 184 | 69.586 | 87.448 | 6.037 | 1.00 | 29.64 |
| 2504 | N | PRO | A | 185 | 71.501 | 88.441 | 6.701 | 1.00 | 29.70 |
| 2505 | CA | PRO | A | 185 | 72.217 | -88.146 | 5.458 | 1.00 | 29.74 |
| 2507 | CB | PRO | A | 185 | 73.565 | 88.851 | 5.643 | 1.00 | 29.72 |
| 2510 | CG | PRO | A | 185 | 73.389 | 89.766 | 6.777 | 1.00 | 30.18 |
| 2513 | CD | PRO | A | 185 | 72.357 | 89.168 | 7.653 | 1.00 | 30.09 |
| 2516 | C | PRO | A | 185 | 72.448 | 86.659 | 5.266 | 1.00 | 29.95 |
| 2517 | O | PRO | A | 185 | 72.317 | 85.896 | 6.224 | 1.00 | 29.23 |
| 2518 | N | LEU | A | 186 | 72.843 | 86.279 | 4.059 | 1.00 | 30.11 |
| 2520 | CA | LEU | A | 186 | 73.010 | 84.873 | 3.690 | 1.00 | 30.66 |
| 2522 | CB | LEU | A | 186 | 73.595 | 84.765 | 2.281 | 1.00 | 30.90 |
| 2525 | CG | LEU | A | 186 | 73.604 | 83.417 | 1.548 | 1.00 | 32.07 |
| 2527 | CD1 | LEU | A | 186 | 74.931 | 82.695 | 1.750 | 1.00 | 34.56 |
| 2531 | CD2 | LEU | A | 186 | 72.438 | 82.535 | 1.942 | 1.00 | 31.83 |
| 2535 | C | LEU | A | 186 | 73.875 | 84.071 | 4.670 | 1.00 | 30.74 |
| 2536 | O | LEU | A | 186 | 73.472 | 82.997 | 5.093 | 1.00 | 30.04 |
| 2537 | N | ASP | A | 187 | 75.058 | 84.584 | 5.009 | 1.00 | 30.98 |
| 2539 | CA | ASP | A | 187 | 75.951 | 83.903 | 5.945 | 1.00 | 31.77 |
| 2541 | CB | ASP | A | 187 | 77.278 | 84.667 | 6.143 | 1.00 | 32.58 |
| 2544 | CG | ASP | A | 187 | 77.097 | 86.128 | 6.641 | 1.00 | 34.74 |
| 2545 | OD1 | ASP | A | 187 | 75.963 | 86.630 | 6.812 | 1.00 | 37.70 |
| 2546 | OD2 | ASP | A | 187 | 78.079 | 86.866 | 6.881 | 1.00 | 39.45 |
| 2547 | C | ASP | A | 187 | 75.295 | 83.578 | 7.301 | 1.00 | 31.43 |
| 2548 | O | ASP | A | 187 | 75.516 | 82.494 | 7.847 | 1.00 | 31.36 |
| 2549 | N | ALA | A | 188 | 74.493 | 84.505 | 7.823 | 1.00 | 30.71 |
| 2551 | CA | ALA | A | 188 | 73.781 | 84.297 | 9.082 | 1.00 | 30.32 |
| 2553 | CB | ALA | A | 188 | 73.271 | 85.624 | 9.641 | 1.00 | 30.46 |
| 2557 | C | ALA | A | 188 | 72.627 | 83.331 | 8.870 | 1.00 | 29.80 |
| 2558 | O | ALA | A | 188 | 72.328 | 82.505 | 9.731 | 1.00 | 28.47 |

FIGURE 3 (Cont.)

| A | B | C | D | E | F | G | H | I | J |
|---|---|---|---|---|---|---|---|---|---|
| 2559 | N | LEU | A | 189 | 71.990 | 83.427 | 7.708 | 1.00 | 29.23 |
| 2561 | CA | LEU | A | 189 | 70.902 | 82.529 | 7.358 | 1.00 | 29.70 |
| 2563 | CB | LEU | A | 189 | 70.360 | 82.867 | 5.971 | 1.00 | 30.15 |
| 2566 | CG | LEU | A | 189 | 68.870 | 83.128 | 5.772 | 1.00 | 31.79 |
| 2568 | CD1 | LEU | A | 189 | 68.545 | 82.912 | 4.280 | 1.00 | 32.57 |
| 2572 | CD2 | LEU | A | 189 | 67.958 | 82.296 | 6.672 | 1.00 | 32.39 |
| 2576 | C | LEU | A | 189 | 71.397 | 81.077 | 7.356 | 1.00 | 29.25 |
| 2577 | O | LEU | A | 189 | 70.766 | 80.182 | 7.923 | 1.00 | 27.68 |
| 2578 | N | GLU | A | 190 | 72.539 | 80.867 | 6.712 | 1.00 | 28.91 |
| 2580 | CA | GLU | A | 190 | 73.138 | 79.547 | 6.604 | 1.00 | 28.82 |
| 2582 | CB | GLU | A | 190 | 74.362 | 79.609 | 5.697 | 1.00 | 29.44 |
| 2585 | CG | GLU | A | 190 | 74.926 | 78.249 | 5.322 | 1.00 | 31.65 |
| 2588 | CD | GLU | A | 190 | 76.119 | 78.345 | 4.382 | 1.00 | 35.05 |
| 2589 | OE1 | GLU | A | 190 | 76.048 | 79.127 | 3.405 | 1.00 | 36.65 |
| 2590 | OE2 | GLU | A | 190 | 77.126 | 77.631 | 4.625 | 1.00 | 37.41 |
| 2591 | C | GLU | A | 190 | 73.524 | 78.996 | 7.972 | 1.00 | 28.22 |
| 2592 | O | GLU | A | 190 | 73.406 | 77.807 | 8.220 | 1.00 | 27.03 |
| 2593 | N | ARG | A | 191 | 74.001 | 79.866 | 8.856 | 1.00 | 27.79 |
| 2595 | CA | ARG | A | 191 | 74.342 | 79.454 | 10.210 | 1.00 | 27.69 |
| 2597 | CB | ARG | A | 191 | 75.021 | 80.585 | 10.988 | 1.00 | 28.29 |
| 2600 | CG | ARG | A | 191 | 76.429 | 80.908 | 10.483 | 1.00 | 32.30 |
| 2603 | CD | ARG | A | 191 | 77.323 | 81.682 | 11.474 | 1.00 | 35.96 |
| 2606 | NE | ARG | A | 191 | 78.509 | 80.902 | 11.831 | 1.00 | 39.49 |
| 2608 | CZ | ARG | A | 191 | 79.520 | 80.619 | 11.005 | 1.00 | 42.00 |
| 2609 | NH1 | ARG | A | 191 | 79.524 | 81.054 | 9.748 | 1.00 | 43.12 |
| 2612 | NH2 | ARG | A | 191 | 80.539 | 79.889 | 11.440 | 1.00 | 42.49 |
| 2615 | C | ARG | A | 191 | 73.100 | 78.970 | 10.948 | 1.00 | 26.20 |
| 2616 | O | ARG | A | 191 | 73.153 | 77.952 | 11.634 | 1.00 | 25.47 |
| 2617 | N | ILE | A | 192 | 71.985 | 79.681 | 10.787 | 1.00 | 25.12 |
| 2619 | CA | ILE | A | 192 | 70.719 | 79.254 | 11.387 | 1.00 | 24.45 |
| 2621 | CB | ILE | A | 192 | 69.546 | 80.183 | 11.009 | 1.00 | 24.28 |
| 2623 | CG1 | ILE | A | 192 | 69.717 | 81.579 | 11.619 | 1.00 | 25.03 |
| 2626 | CD1 | ILE | A | 192 | 68.851 | 82.624 | 10.981 | 1.00 | 25.02 |
| 2630 | CG2 | ILE | A | 192 | 68.222 | 79.577 | 11.474 | 1.00 | 24.54 |
| 2634 | C | ILE | A | 192 | 70.385 | 77.842 | 10.906 | 1.00 | 24.27 |
| 2635 | O | ILE | A | 192 | 70.205 | 76.928 | 11.699 | 1.00 | 23.05 |
| 2636 | N | HIS | A | 193 | 70.289 | 77.701 | 9.590 | 1.00 | 23.44 |
| 2638 | CA | HIS | A | 193 | 69.789 | 76.477 | 8.976 | 1.00 | 23.31 |
| 2640 | CB | HIS | A | 193 | 69.573 | 76.731 | 7.485 | 1.00 | 23.43 |
| 2643 | CG | HIS | A | 193 | 68.349 | 77.547 | 7.209 | 1.00 | 24.48 |
| 2644 | ND1 | HIS | A | 193 | 67.494 | 77.964 | 8.208 | 1.00 | 25.73 |
| 2646 | CE1 | HIS | A | 193 | 66.480 | 78.623 | 7.675 | 1.00 | 26.42 |
| 2648 | NE2 | HIS | A | 193 | 66.659 | 78.669 | 6.367 | 1.00 | 25.37 |
| 2650 | CD2 | HIS | A | 193 | 67.817 | 77.999 | 6.052 | 1.00 | 25.77 |
| 2652 | C | HIS | A | 193 | 70.678 | 75.264 | 9.230 | 1.00 | 22.37 |
| 2653 | O | HIS | A | 193 | 70.179 | 74.181 | 9.534 | 1.00 | 22.47 |
| 2654 | N | ARG | A | 194 | 71.986 | 75.445 | 9.128 | 1.00 | 21.53 |
| 2656 | CA | ARG | A | 194 | 72.919 | 74.362 | 9.391 | 1.00 | 21.47 |
| 2658 | CB | ARG | A | 194 | 74.358 | 74.778 | 9.120 | 1.00 | 20.83 |
| 2661 | CG | ARG | A | 194 | 74.700 | 74.835 | 7.656 | 1.00 | 21.22 |
| 2664 | CD | ARG | A | 194 | 76.180 | 74.847 | 7.423 | 1.00 | 22.88 |
| 2667 | NE | ARG | A | 194 | 76.501 | 75.077 | 6.022 | 1.00 | 24.27 |

FIGURE 3 (Cont.)

| A | B | C | D | E | F | G | H | I | J |
|---|---|---|---|---|---|---|---|---|---|
| 2669 | CZ | ARG | A | 194 | 76.459 | 74.147 | 5.092 | 1.00 | 25.12 |
| 2670 | NH1 | ARG | A | 194 | 76.120 | 72.904 | 5.398 | 1.00 | 25.42 |
| 2673 | NH2 | ARG | A | 194 | 76.784 | 74.455 | 3.840 | 1.00 | 28.83 |
| 2676 | C | ARG | A | 194 | 72.780 | 73.872 | 10.829 | 1.00 | 21.18 |
| 2677 | O | ARG | A | 194 | 72.861 | 72.681 | 11.071 | 1.00 | 20.79 |
| 2678 | N | HIS | A | 195 | 72.583 | 74.777 | 11.784 | 1.00 | 21.00 |
| 2680 | CA | HIS | A | 195 | 72.436 | 74.337 | 13.171 | 1.00 | 21.63 |
| 2682 | CB | HIS | A | 195 | 72.773 | 75.458 | 14.158 | 1.00 | 21.62 |
| 2685 | CG | HIS | A | 195 | 74.232 | 75.787 | 14.215 | 1.00 | 24.46 |
| 2686 | ND1 | HIS | A | 195 | 74.944 | 75.833 | 15.394 | 1.00 | 28.06 |
| 2688 | CE1 | HIS | A | 195 | 76.201 | 76.148 | 15.134 | 1.00 | 28.87 |
| 2690 | NE2 | HIS | A | 195 | 76.330 | 76.304 | 13.831 | 1.00 | 29.50 |
| 2692 | CD2 | HIS | A | 195 | 75.113 | 76.086 | 13.233 | 1.00 | 27.40 |
| 2694 | C | HIS | A | 195 | 71.050 | 73.751 | 13.451 | 1.00 | 21.00 |
| 2695 | O | HIS | A | 195 | 70.948 | 72.646 | 13.985 | 1.00 | 20.86 |
| 2696 | N | LYS | A | 196 | 69.985 | 74.462 | 13.087 | 1.00 | 20.63 |
| 2698 | CA | LYS | A | 196 | 68.642 | 74.022 | 13.489 | 1.00 | 20.10 |
| 2700 | CB | LYS | A | 196 | 67.590 | 75.123 | 13.367 | 1.00 | 19.88 |
| 2703 | CG | LYS | A | 196 | 66.987 | 75.363 | 11.997 | 1.00 | 19.59 |
| 2706 | CD | LYS | A | 196 | 65.944 | 76.473 | 12.065 | 1.00 | 19.02 |
| 2709 | CE | LYS | A | 196 | 65.416 | 76.847 | 10.672 | 1.00 | 18.63 |
| 2712 | NZ | LYS | A | 196 | 64.064 | 77.494 | 10.673 | 1.00 | 19.09 |
| 2716 | C | LYS | A | 196 | 68.215 | 72.756 | 12.758 | 1.00 | 20.00 |
| 2717 | O | LYS | A | 196 | 67.491 | 71.960 | 13.307 | 1.00 | 20.23 |
| 2718 | N | THR | A | 197 | 68.705 | 72.557 | 11.539 | 1.00 | 19.63 |
| 2720 | CA | THR | A | 197 | 68.278 | 71.433 | 10.726 | 1.00 | 19.13 |
| 2722 | CB | THR | A | 197 | 67.408 | 71.938 | 9.580 | 1.00 | 19.35 |
| 2724 | OG1 | THR | A | 197 | 66.166 | 72.400 | 10.127 | 1.00 | 18.33 |
| 2726 | CG2 | THR | A | 197 | 67.021 | 70.812 | 8.618 | 1.00 | 18.67 |
| 2730 | C | THR | A | 197 | 69.413 | 70.554 | 10.226 | 1.00 | 19.03 |
| 2731 | O | THR | A | 197 | 69.275 | 69.332 | 10.223 | 1.00 | 18.17 |
| 2732 | N | GLY | A | 198 | 70.522 | 71.167 | 9.812 | 1.00 | 19.30 |
| 2734 | CA | GLY | A | 198 | 71.667 | 70.421 | 9.316 | 1.00 | 19.16 |
| 2737 | C | GLY | A | 198 | 72.260 | 69.466 | 10.329 | 1.00 | 19.28 |
| 2738 | O | GLY | A | 198 | 72.580 | 68.330 | 9.987 | 1.00 | 19.12 |
| 2739 | N | ALA | A | 199 | 72.371 | 69.910 | 11.576 | 1.00 | 19.18 |
| 2741 | CA | ALA | A | 199 | 73.129 | 69.182 | 12.585 | 1.00 | 19.36 |
| 2743 | CB | ALA | A | 199 | 73.245 | 70.005 | 13.861 | 1.00 | 19.70 |
| 2747 | C | ALA | A | 199 | 72.505 | 67.816 | 12.897 | 1.00 | 19.34 |
| 2748 | O | ALA | A | 199 | 73.224 | 66.830 | 13.057 | 1.00 | 19.28 |
| 2749 | N | LEU | A | 200 | 71.177 | 67.768 | 12.994 | 1.00 | 19.51 |
| 2751 | CA | LEU | A | 200 | 70.476 | 66.522 | 13.302 | 1.00 | 19.63 |
| 2753 | CB | LEU | A | 200 | 69.016 | 66.775 | 13.700 | 1.00 | 19.77 |
| 2756 | CG | LEU | A | 200 | 68.261 | 65.516 | 14.183 | 1.00 | 20.34 |
| 2758 | CD1 | LEU | A | 200 | 68.918 | 64.931 | 15.431 | 1.00 | 20.63 |
| 2762 | CD2 | LEU | A | 200 | 66.799 | 65.855 | 14.449 | 1.00 | 20.55 |
| 2766 | C | LEU | A | 200 | 70.514 | 65.563 | 12.125 | 1.00 | 19.55 |
| 2767 | O | LEU | A | 200 | 70.590 | 64.336 | 12.312 | 1.00 | 19.72 |
| 2768 | N | ILE | A | 201 | 70.462 | 66.114 | 10.919 | 1.00 | 19.19 |
| 2770 | CA | ILE | A | 201 | 70.556 | 65.299 | 9.706 | 1.00 | 19.51 |
| 2772 | CB | ILE | A | 201 | 70.178 | 66.143 | 8.471 | 1.00 | 19.64 |
| 2774 | CG1 | ILE | A | 201 | 68.659 | 66.197 | 8.372 | 1.00 | 20.21 |

FIGURE 3 (Cont.)

| A | B | C | D | E | F | G | H | I | J |
|---|---|---|---|---|---|---|---|---|---|
| 2777 | CD1 | ILE | A | 201 | 68.149 | 67.249 | 7.449 | 1.00 | 21.65 |
| 2781 | CG2 | ILE | A | 201 | 70.782 | 65.578 | 7.169 | 1.00 | 20.92 |
| 2785 | C | ILE | A | 201 | 71.941 | 64.661 | 9.604 | 1.00 | 19.17 |
| 2786 | O | ILE | A | 201 | 72.066 | 63.504 | 9.227 | 1.00 | 18.77 |
| 2787 | N | ARG | A | 202 | 72.970 | 65.420 | 9.963 | 1.00 | 19.39 |
| 2789 | CA | ARG | A | 202 | 74.323 | 64.891 | 10.001 | 1.00 | 19.72 |
| 2791 | CB | ARG | A | 202 | 75.343 | 66.008 | 10.148 | 1.00 | 20.03 |
| 2794 | CG | ARG | A | 202 | 76.774 | 65.526 | 10.119 | 1.00 | 21.06 |
| 2797 | CD | ARG | A | 202 | 77.777 | 66.638 | 10.165 | 1.00 | 20.98 |
| 2800 | NE | ARG | A | 202 | 77.824 | 67.265 | 11.473 | 1.00 | 23.53 |
| 2802 | CZ | ARG | A | 202 | 78.617 | 68.294 | 11.789 | 1.00 | 25.30 |
| 2803 | NH1 | ARG | A | 202 | 78.580 | 68.800 | 13.012 | 1.00 | 23.66 |
| 2806 | NH2 | ARG | A | 202 | 79.445 | 68.815 | 10.891 | 1.00 | 26.69 |
| 2809 | C | ARG | A | 202 | 74.453 | 63.843 | 11.113 | 1.00 | 19.73 |
| 2810 | O | ARG | A | 202 | 75.153 | 62.859 | 10.935 | 1.00 | 19.84 |
| 2811 | N | ALA | A | 203 | 73.741 | 64.027 | 12.226 | 1.00 | 19.24 |
| 2813 | CA | ALA | A | 203 | 73.713 | 63.009 | 13.276 | 1.00 | 18.65 |
| 2815 | CB | ALA | A | 203 | 73.001 | 63.513 | 14.517 | 1.00 | 19.04 |
| 2819 | C | ALA | A | 203 | 73.097 | 61.696 | 12.824 | 1.00 | 18.20 |
| 2820 | O | ALA | A | 203 | 73.582 | 60.644 | 13.210 | 1.00 | 18.83 |
| 2821 | N | ALA | A | 204 | 72.025 | 61.740 | 12.043 | 1.00 | 18.01 |
| 2823 | CA | ALA | A | 204 | 71.441 | 60.524 | 11.485 | 1.00 | 18.08 |
| 2825 | CB | ALA | A | 204 | 70.268 | 60.868 | 10.588 | 1.00 | 18.17 |
| 2829 | C | ALA | A | 204 | 72.481 | 59.738 | 10.700 | 1.00 | 18.04 |
| 2830 | O | ALA | A | 204 | 72.645 | 58.522 | 10.879 | 1.00 | 17.73 |
| 2831 | N | VAL | A | 205 | 73.170 | 60.430 | 9.809 | 1.00 | 17.87 |
| 2833 | CA | VAL | A | 205 | 74.174 | 59.786 | 8.990 | 1.00 | 18.48 |
| 2835 | CB | VAL | A | 205 | 74.659 | 60.714 | 7.874 | 1.00 | 18.22 |
| 2837 | CG1 | VAL | A | 205 | 75.791 | 60.079 | 7.109 | 1.00 | 18.92 |
| 2841 | CG2 | VAL | A | 205 | 73.476 | 61.057 | 6.930 | 1.00 | 17.58 |
| 2845 | C | VAL | A | 205 | 75.314 | 59.238 | 9.852 | 1.00 | 18.69 |
| 2846 | O | VAL | A | 205 | 75.716 | 58.086 | 9.677 | 1.00 | 20.23 |
| 2847 | N | ARG | A | 206 | 75.783 | 60.032 | 10.808 | 1.00 | 18.74 |
| 2849 | CA | ARG | A | 206 | 76.862 | 59.629 | 11.702 | 1.00 | 18.96 |
| 2851 | CB | ARG | A | 206 | 77.274 | 60.778 | 12.615 | 1.00 | 18.76 |
| 2854 | CG | ARG | A | 206 | 78.157 | 61.792 | 11.948 | 1.00 | 19.71 |
| 2857 | CD | ARG | A | 206 | 78.477 | 63.008 | 12.803 | 1.00 | 19.66 |
| 2860 | NE | ARG | A | 206 | 79.481 | 63.857 | 12.167 | 1.00 | 21.03 |
| 2862 | CZ | ARG | A | 206 | 80.008 | 64.936 | 12.737 | 1.00 | 22.60 |
| 2863 | NH1 | ARG | A | 206 | 79.659 | 65.289 | 13.965 | 1.00 | 22.08 |
| 2866 | NH2 | ARG | A | 206 | 80.903 | 65.660 | 12.079 | 1.00 | 21.63 |
| 2869 | C | ARG | A | 206 | 76.481 | 58.427 | 12.549 | 1.00 | 19.18 |
| 2870 | O | ARG | A | 206 | 77.283 | 57.530 | 12.757 | 1.00 | 18.61 |
| 2871 | N | LEU | A | 207 | 75.244 | 58.394 | 13.014 | 1.00 | 19.73 |
| 2873 | CA | LEU | A | 207 | 74.790 | 57.288 | 13.850 | 1.00 | 20.29 |
| 2875 | CB | LEU | A | 207 | 73.426 | 57.600 | 14.481 | 1.00 | 20.21 |
| 2878 | CG | LEU | A | 207 | 73.432 | 58.067 | 15.944 | 1.00 | 21.69 |
| 2880 | CD1 | LEU | A | 207 | 74.453 | 59.147 | 16.210 | 1.00 | 22.70 |
| 2884 | CD2 | LEU | A | 207 | 72.044 | 58.554 | 16.298 | 1.00 | 23.52 |
| 2888 | C | LEU | A | 207 | 74.715 | 56.013 | 13.013 | 1.00 | 20.31 |
| 2889 | O | LEU | A | 207 | 75.049 | 54.941 | 13.486 | 1.00 | 19.90 |
| 2890 | N | GLY | A | 208 | 74.273 | 56.131 | 11.772 | 1.00 | 20.46 |

FIGURE 3 (Cont.)

| A | B | C | D | E | F | G | H | I | J |
|---|---|---|---|---|---|---|---|---|---|
| 2892 | CA | GLY | A | 208 | 74.297 | 55.000 | 10.861 | 1.00 | 21.15 |
| 2895 | C | GLY | A | 208 | 75.703 | 54.457 | 10.656 | 1.00 | 21.20 |
| 2896 | O | GLY | A | 208 | 75.933 | 53.240 | 10.737 | 1.00 | 22.15 |
| 2897 | N | ALA | A | 209 | 76.643 | 55.362 | 10.419 | 1.00 | 21.27 |
| 2899 | CA | ALA | A | 209 | 78.046 | 55.006 | 10.215 | 1.00 | 22.05 |
| 2901 | CB | ALA | A | 209 | 78.813 | 56.193 | 9.733 | 1.00 | 21.96 |
| 2905 | C | ALA | A | 209 | 78.700 | 54.419 | 11.480 | 1.00 | 22.41 |
| 2906 | O | ALA | A | 209 | 79.383 | 53.398 | 11.411 | 1.00 | 22.53 |
| 2907 | N | LEU | A | 210 | 78.471 | 55.041 | 12.635 | 1.00 | 22.29 |
| 2909 | CA | LEU | A | 210 | 79.090 | 54.580 | 13.877 | 1.00 | 22.51 |
| 2911 | CB | LEU | A | 210 | 78.775 | 55.522 | 15.039 | 1.00 | 22.37 |
| 2914 | CG | LEU | A | 210 | 79.513 | 56.853 | 14.977 | 1.00 | 22.40 |
| 2916 | CD1 | LEU | A | 210 | 78.845 | 57.900 | 15.863 | 1.00 | 22.42 |
| 2920 | CD2 | LEU | A | 210 | 81.004 | 56.689 | 15.372 | 1.00 | 22.32 |
| 2924 | C | LEU | A | 210 | 78.642 | 53.168 | 14.213 | 1.00 | 23.22 |
| 2925 | O | LEU | A | 210 | 79.383 | 52.408 | 14.830 | 1.00 | 23.30 |
| 2926 | N | SER | A | 211 | 77.430 | 52.809 | 13.786 | 1.00 | 24.01 |
| 2928 | CA | SER | A | 211 | 76.914 | 51.469 | 13.999 | 1.00 | 24.10 |
| 2930 | CB | SER | A | 211 | 75.478 | 51.347 | 13.496 | 1.00 | 24.10 |
| 2933 | OG | SER | A | 211 | 75.459 | 51.162 | 12.104 | 1.00 | 25.59 |
| 2935 | C | SER | A | 211 | 77.764 | 50.397 | 13.335 | 1.00 | 24.24 |
| 2936 | O | SER | A | 211 | 77.746 | 49.254 | 13.778 | 1.00 | 23.60 |
| 2937 | N | ALA | A | 212 | 78.464 | 50.782 | 12.269 | 1.00 | 24.79 |
| 2939 | CA | ALA | A | 212 | 79.332 | 49.906 | 11.496 | 1.00 | 25.88 |
| 2941 | CB | ALA | A | 212 | 79.361 | 50.376 | 10.050 | 1.00 | 26.06 |
| 2945 | C | ALA | A | 212 | 80.762 | 49.837 | 12.044 | 1.00 | 26.25 |
| 2946 | O | ALA | A | 212 | 81.602 | 49.130 | 11.490 | 1.00 | 27.04 |
| 2947 | N | GLY | A | 213 | 81.051 | 50.586 | 13.100 | 1.00 | 26.38 |
| 2949 | CA | GLY | A | 213 | 82.373 | 50.574 | 13.692 | 1.00 | 27.08 |
| 2952 | C | GLY | A | 213 | 83.427 | 51.209 | 12.809 | 1.00 | 27.54 |
| 2953 | O | GLY | A | 213 | 83.193 | 52.242 | 12.199 | 1.00 | 27.58 |
| 2954 | N | ASP | A | 214 | 84.584 | 50.570 | 12.718 | 1.00 | 28.92 |
| 2956 | CA | ASP | A | 214 | 85.758 | 51.188 | 12.105 | 1.00 | 29.67 |
| 2958 | CB | ASP | A | 214 | 86.993 | 50.294 | 12.281 | 1.00 | 30.31 |
| 2961 | CG | ASP | A | 214 | 87.596 | 50.413 | 13.666 | 1.00 | 33.03 |
| 2962 | OD1 | ASP | A | 214 | 88.445 | 49.568 | 14.020 | 1.00 | 37.45 |
| 2963 | OD2 | ASP | A | 214 | 87.285 | 51.318 | 14.478 | 1.00 | 35.85 |
| 2964 | C | ASP | A | 214 | 85.530 | 51.523 | 10.650 | 1.00 | 29.40 |
| 2965 | O | ASP | A | 214 | 85.907 | 52.596 | 10.203 | 1.00 | 29.23 |
| 2966 | N | LYS | A | 215 | 84.879 | 50.625 | 9.921 | 1.00 | 29.50 |
| 2968 | CA | LYS | A | 215 | 84.593 | 50.862 | 8.505 | 1.00 | 29.92 |
| 2970 | CB | LYS | A | 215 | 84.019 | 49.610 | 7.839 | 1.00 | 30.45 |
| 2973 | CG | LYS | A | 215 | 85.103 | 48.766 | 7.182 | 1.00 | 33.43 |
| 2976 | CD | LYS | A | 215 | 84.685 | 47.310 | 6.964 | 1.00 | 36.17 |
| 2979 | CE | LYS | A | 215 | 85.888 | 46.439 | 6.568 | 1.00 | 37.55 |
| 2982 | NZ | LYS | A | 215 | 85.967 | 45.213 | 7.416 | 1.00 | 39.13 |
| 2986 | C | LYS | A | 215 | 83.672 | 52.076 | 8.312 | 1.00 | 29.02 |
| 2987 | O | LYS | A | 215 | 83.851 | 52.860 | 7.384 | 1.00 | 27.84 |
| 2988 | N | GLY | A | 216 | 82.696 | 52.241 | 9.198 | 1.00 | 28.66 |
| 2990 | CA | GLY | A | 216 | 81.855 | 53.429 | 9.162 | 1.00 | 28.17 |
| 2993 | C | GLY | A | 216 | 82.647 | 54.692 | 9.471 | 1.00 | 27.77 |
| 2994 | O | GLY | A | 216 | 82.503 | 55.719 | 8.812 | 1.00 | 27.08 |

FIGURE 3 (Cont.)

| A | B | C | D | E | F | G | H | I | J |
|---|---|---|---|---|---|---|---|---|---|
| 2995 | N | ARG | A | 217 | 83.498 | 54.609 | 10.482 | 1.00 | 27.98 |
| 2997 | CA | ARG | A | 217 | 84.306 | 55.751 | 10.900 | 1.00 | 28.29 |
| 2999 | CB | ARG | A | 217 | 85.165 | 55.391 | 12.106 | 1.00 | 28.55 |
| 3002 | CG | ARG | A | 217 | 84.449 | 55.520 | 13.428 | 1.00 | 28.34 |
| 3005 | CD | ARG | A | 217 | 85.328 | 55.173 | 14.580 | 1.00 | 29.33 |
| 3008 | NE | ARG | A | 217 | 84.577 | 55.110 | 15.826 | 1.00 | 29.90 |
| 3010 | CZ | ARG | A | 217 | 84.375 | 56.148 | 16.637 | 1.00 | 29.01 |
| 3011 | NH1 | ARG | A | 217 | 84.836 | 57.359 | 16.334 | 1.00 | 29.10 |
| 3014 | NH2 | ARG | A | 217 | 83.671 | 55.980 | 17.743 | 1.00 | 28.00 |
| 3017 | C | ARG | A | 217 | 85.201 | 56.266 | 9.783 | 1.00 | 28.80 |
| 3018 | O | ARG | A | 217 | 85.367 | 57.476 | 9.645 | 1.00 | 28.97 |
| 3019 | N | ARG | A | 218 | 85.752 | 55.354 | 8.978 | 1.00 | 29.00 |
| 3021 | CA | ARG | A | 218 | 86.622 | 55.726 | 7.853 | 1.00 | 29.76 |
| 3023 | CB | ARG | A | 218 | 87.268 | 54.483 | 7.223 | 1.00 | 30.54 |
| 3026 | CG | ARG | A | 218 | 88.351 | 53.812 | 8.069 | 1.00 | 33.89 |
| 3029 | CD | ARG | A | 218 | 88.273 | 52.280 | 8.115 | 1.00 | 38.26 |
| 3032 | NE | ARG | A | 218 | 88.914 | 51.617 | 6.975 | 1.00 | 41.13 |
| 3034 | CZ | ARG | A | 218 | 88.318 | 51.290 | 5.817 | 1.00 | 44.61 |
| 3035 | NH1 | ARG | A | 218 | 89.023 | 50.681 | 4.862 | 1.00 | 46.06 |
| 3038 | NH2 | ARG | A | 218 | 87.037 | 51.564 | 5.587 | 1.00 | 45.97 |
| 3041 | C | ARG | A | 218 | 85.866 | 56.481 | 6.765 | 1.00 | 29.10 |
| 3042 | O | ARG | A | 218 | 86.460 | 57.283 | 6.034 | 1.00 | 29.09 |
| 3043 | N | ALA | A | 219 | 84.565 | 56.209 | 6.646 | 1.00 | 27.99 |
| 3045 | CA | ALA | A | 219 | 83.720 | 56.894 | 5.669 | 1.00 | 27.60 |
| 3047 | CB | ALA | A | 219 | 82.532 | 56.030 | 5.313 | 1.00 | 27.48 |
| 3051 | C | ALA | A | 219 | 83.234 | 58.253 | 6.142 | 1.00 | 27.24 |
| 3052 | O | ALA | A | 219 | 82.710 | 59.018 | 5.344 | 1.00 | 26.75 |
| 3053 | N | LEU | A | 220 | 83.394 | 58.543 | 7.433 | 1.00 | 27.30 |
| 3055 | CA | LEU | A | 220 | 82.807 | 59.736 | 8.036 | 1.00 | 27.51 |
| 3057 | CB | LEU | A | 220 | 83.061 | 59.804 | 9.546 | 1.00 | 27.81 |
| 3060 | CG | LEU | A | 220 | 82.127 | 58.960 | 10.416 | 1.00 | 29.69 |
| 3062 | CD1 | LEU | A | 220 | 82.573 | 59.004 | 11.889 | 1.00 | 30.50 |
| 3066 | CD2 | LEU | A | 220 | 80.677 | 59.411 | 10.271 | 1.00 | 30.60 |
| 3070 | C | LEU | A | 220 | 83.226 | 61.045 | 7.400 | 1.00 | 26.87 |
| 3071 | O | LEU | A | 220 | 82.380 | 61.901 | 7.232 | 1.00 | 27.16 |
| 3072 | N | PRO | A | 221 | 84.502 | 61.248 | 7.067 | 1.00 | 26.59 |
| 3073 | CA | PRO | A | 221 | 84.879 | 62.502 | 6.399 | 1.00 | 26.30 |
| 3075 | CB | PRO | A | 221 | 86.349 | 62.269 | 6.006 | 1.00 | 26.54 |
| 3078 | CG | PRO | A | 221 | 86.853 | 61.366 | 7.081 | 1.00 | 27.08 |
| 3081 | CD | PRO | A | 221 | 85.685 | 60.415 | 7.352 | 1.00 | 26.58 |
| 3084 | C | PRO | A | 221 | 83.996 | 62.758 | 5.195 | 1.00 | 25.66 |
| 3085 | O | PRO | A | 221 | 83.479 | 63.859 | 5.044 | 1.00 | 26.22 |
| 3086 | N | VAL | A | 222 | 83.770 | 61.735 | 4.381 | 1.00 | 24.71 |
| 3088 | CA | VAL | A | 222 | 82.965 | 61.910 | 3.181 | 1.00 | 24.34 |
| 3090 | CB | VAL | A | 222 | 83.272 | 60.835 | 2.139 | 1.00 | 24.09 |
| 3092 | CG1 | VAL | A | 222 | 82.302 | 60.927 | 0.999 | 1.00 | 23.94 |
| 3096 | CG2 | VAL | A | 222 | 84.718 | 60.988 | 1.655 | 1.00 | 25.44 |
| 3100 | C | VAL | A | 222 | 81.465 | 61.955 | 3.470 | 1.00 | 23.78 |
| 3101 | O | VAL | A | 222 | 80.754 | 62.771 | 2.885 | 1.00 | 23.40 |
| 3102 | N | LEU | A | 223 | 80.978 | 61.096 | 4.362 | 1.00 | 23.25 |
| 3104 | CA | LEU | A | 223 | 79.552 | 61.118 | 4.707 | 1.00 | 22.90 |
| 3106 | CB | LEU | A | 223 | 79.179 | 59.955 | 5.627 | 1.00 | 23.13 |

FIGURE 3 (Cont.)

| A | B | C | D | E | F | G | H | I | J |
|---|---|---|---|---|---|---|---|---|---|
| 3109 | CG | LEU | A | 223 | 79.130 | 58.583 | 4.947 | 1.00 | 22.78 |
| 3111 | CD1 | LEU | A | 223 | 79.022 | 57.462 | 5.987 | 1.00 | 23.57 |
| 3115 | CD2 | LEU | A | 223 | 77.991 | 58.484 | 3.975 | 1.00 | 23.72 |
| 3119 | C | LEU | A | 223 | 79.159 | 62.441 | 5.346 | 1.00 | 23.02 |
| 3120 | O | LEU | A | 223 | 78.023 | 62.903 | 5.182 | 1.00 | 22.74 |
| 3121 | N | ASP | A | 224 | 80.081 | 63.036 | 6.093 | 1.00 | 23.24 |
| 3123 | CA | ASP | A | 224 | 79.838 | 64.328 | 6.722 | 1.00 | 23.61 |
| 3125 | CB | ASP | A | 224 | 81.028 | 64.753 | 7.588 | 1.00 | 23.94 |
| 3128 | CG | ASP | A | 224 | 81.009 | 64.118 | 8.974 | 1.00 | 25.27 |
| 3129 | OD1 | ASP | A | 224 | 79.961 | 63.561 | 9.379 | 1.00 | 25.31 |
| 3130 | OD2 | ASP | A | 224 | 81.989 | 64.158 | 9.749 | 1.00 | 27.02 |
| 3131 | C | ASP | A | 224 | 79.568 | 65.385 | 5.654 | 1.00 | 23.60 |
| 3132 | O | ASP | A | 224 | 78.630 | 66.175 | 5.772 | 1.00 | 22.89 |
| 3133 | N | LYS | A | 225 | 80.373 | 65.377 | 4.599 | 1.00 | 23.58 |
| 3135 | CA | LYS | A | 225 | 80.234 | 66.391 | 3.557 | 1.00 | 24.32 |
| 3137 | CB | LYS | A | 225 | 81.439 | 66.381 | 2.594 | 1.00 | 24.94 |
| 3140 | CG | LYS | A | 225 | 82.825 | 66.478 | 3.298 | 1.00 | 27.64 |
| 3143 | CD | LYS | A | 225 | 83.113 | 67.828 | 4.009 | 1.00 | 31.84 |
| 3146 | CE | LYS | A | 225 | 83.516 | 67.719 | 5.546 | 1.00 | 32.28 |
| 3149 | NZ | LYS | A | 225 | 84.063 | 66.374 | 6.064 | 1.00 | 30.63 |
| 3153 | C | LYS | A | 225 | 78.901 | 66.207 | 2.842 | 1.00 | 23.43 |
| 3154 | O | LYS | A | 225 | 78.205 | 67.177 | 2.548 | 1.00 | 23.79 |
| 3155 | N | TYR | A | 226 | 78.521 | 64.955 | 2.612 | 1.00 | 22.64 |
| 3157 | CA | TYR | A | 226 | 77.214 | 64.632 | 2.063 | 1.00 | 21.59 |
| 3159 | CB | TYR | A | 226 | 77.075 | 63.114 | 1.881 | 1.00 | 21.93 |
| 3162 | CG | TYR | A | 226 | 75.645 | 62.633 | 1.753 | 1.00 | 20.62 |
| 3163 | CD1 | TYR | A | 226 | 75.021 | 62.606 | 0.523 | 1.00 | 21.37 |
| 3165 | CE1 | TYR | A | 226 | 73.736 | 62.160 | 0.386 | 1.00 | 20.90 |
| 3167 | CZ | TYR | A | 226 | 73.030 | 61.727 | 1.487 | 1.00 | 20.66 |
| 3168 | OH | TYR | A | 226 | 71.737 | 61.289 | 1.311 | 1.00 | 21.67 |
| 3170 | CE2 | TYR | A | 226 | 73.617 | 61.727 | 2.730 | 1.00 | 21.12 |
| 3172 | CD2 | TYR | A | 226 | 74.933 | 62.174 | 2.862 | 1.00 | 20.69 |
| 3174 | C | TYR | A | 226 | 76.098 | 65.121 | 2.979 | 1.00 | 21.19 |
| 3175 | O | TYR | A | 226 | 75.156 | 65.754 | 2.523 | 1.00 | 21.30 |
| 3176 | N | ALA | A | 227 | 76.208 | 64.804 | 4.261 | 1.00 | 20.68 |
| 3178 | CA | ALA | A | 227 | 75.173 | 65.126 | 5.240 | 1.00 | 20.41 |
| 3180 | CB | ALA | A | 227 | 75.503 | 64.513 | 6.581 | 1.00 | 20.07 |
| 3184 | C | ALA | A | 227 | 75.007 | 66.627 | 5.390 | 1.00 | 20.36 |
| 3185 | O | ALA | A | 227 | 73.893 | 67.123 | 5.485 | 1.00 | 19.95 |
| 3186 | N | GLU | A | 228 | 76.132 | 67.326 | 5.407 | 1.00 | 20.85 |
| 3188 | CA | GLU | A | 228 | 76.160 | 68.786 | 5.503 | 1.00 | 21.65 |
| 3190 | CB | GLU | A | 228 | 77.601 | 69.285 | 5.581 | 1.00 | 21.59 |
| 3193 | CG | GLU | A | 228 | 78.225 | 69.020 | 6.940 | 1.00 | 23.51 |
| 3196 | CD | GLU | A | 228 | 79.737 | 68.868 | 6.911 | 1.00 | 25.72 |
| 3197 | OE1 | GLU | A | 228 | 80.292 | 68.333 | 7.899 | 1.00 | 25.16 |
| 3198 | OE2 | GLU | A | 228 | 80.367 | 69.272 | 5.910 | 1.00 | 28.53 |
| 3199 | C | GLU | A | 228 | 75.411 | 69.428 | 4.340 | 1.00 | 21.53 |
| 3200 | O | GLU | A | 228 | 74.644 | 70.370 | 4.532 | 1.00 | 22.09 |
| 3201 | N | SER | A | 229 | 75.600 | 68.899 | 3.141 | 1.00 | 21.49 |
| 3203 | CA | SER | A | 229 | 74.922 | 69.459 | 1.985 | 1.00 | 21.57 |
| 3205 | CB | SER | A | 229 | 75.598 | 69.036 | 0.695 | 1.00 | 21.17 |
| 3208 | OG | SER | A | 229 | 76.870 | 69.647 | 0.589 | 1.00 | 22.38 |

FIGURE 3 (Cont.)

| A | B | C | D | E | F | G | H | I | J |
|---|---|---|---|---|---|---|---|---|---|
| 3210 | C | SER | A | 229 | 73.432 | 69.119 | 1.967 | 1.00 | 21.32 |
| 3211 | O | SER | A | 229 | 72.629 | 69.993 | 1.719 | 1.00 | 20.51 |
| 3212 | N | ILE | A | 230 | 73.044 | 67.871 | 2.238 | 1.00 | 21.52 |
| 3214 | CA | ILE | A | 230 | 71.610 | 67.562 | 2.236 | 1.00 | 21.70 |
| 3216 | CB | ILE | A | 230 | 71.318 | 66.049 | 2.154 | 1.00 | 21.58 |
| 3218 | CG1 | ILE | A | 230 | 71.881 | 65.279 | 3.347 | 1.00 | 22.85 |
| 3221 | CD1 | ILE | A | 230 | 71.069 | 64.038 | 3.669 | 1.00 | 22.81 |
| 3225 | CG2 | ILE | A | 230 | 71.815 | 65.486 | 0.849 | 1.00 | 21.97 |
| 3229 | C | ILE | A | 230 | 70.874 | 68.190 | 3.421 | 1.00 | 21.12 |
| 3230 | O | ILE | A | 230 | 69.684 | 68.467 | 3.337 | 1.00 | 21.31 |
| 3231 | N | GLY | A | 231 | 71.583 | 68.412 | 4.520 | 1.00 | 21.08 |
| 3233 | CA | GLY | A | 231 | 70.983 | 68.977 | 5.714 | 1.00 | 21.32 |
| 3236 | C | GLY | A | 231 | 70.607 | 70.441 | 5.534 | 1.00 | 21.14 |
| 3237 | O | GLY | A | 231 | 69.514 | 70.877 | 5.917 | 1.00 | 21.86 |
| 3238 | N | LEU | A | 232 | 71.513 | 71.205 | 4.939 | 1.00 | 21.35 |
| 3240 | CA | LEU | A | 232 | 71.214 | 72.583 | 4.595 | 1.00 | 21.18 |
| 3242 | CB | LEU | A | 232 | 72.467 | 73.318 | 4.127 | 1.00 | 21.49 |
| 3245 | CG | LEU | A | 232 | 72.250 | 74.769 | 3.712 | 1.00 | 21.63 |
| 3247 | CD1 | LEU | A | 232 | 71.601 | 75.564 | 4.829 | 1.00 | 22.56 |
| 3251 | CD2 | LEU | A | 232 | 73.571 | 75.361 | 3.320 | 1.00 | 23.37 |
| 3255 | C | LEU | A | 232 | 70.134 | 72.604 | 3.521 | 1.00 | 20.95 |
| 3256 | O | LEU | A | 232 | 69.171 | 73.324 | 3.659 | 1.00 | 20.57 |
| 3257 | N | ALA | A | 233 | 70.270 | 71.766 | 2.488 | 1.00 | 20.80 |
| 3259 | CA | ALA | A | 233 | 69.271 | 71.677 | 1.424 | 1.00 | 20.94 |
| 3261 | CB | ALA | A | 233 | 69.674 | 70.639 | 0.373 | 1.00 | 21.23 |
| 3265 | C | ALA | A | 233 | 67.885 | 71.350 | 1.966 | 1.00 | 20.81 |
| 3266 | O | ALA | A | 233 | 66.878 | 71.812 | 1.442 | 1.00 | 20.67 |
| 3267 | N | PHE | A | 234 | 67.840 | 70.554 | 3.029 | 1.00 | 20.67 |
| 3269 | CA | PHE | A | 234 | 66.568 | 70.166 | 3.634 | 1.00 | 20.70 |
| 3271 | CB | PHE | A | 234 | 66.798 | 69.201 | 4.785 | 1.00 | 20.78 |
| 3274 | CG | PHE | A | 234 | 65.600 | 68.375 | 5.131 | 1.00 | 22.14 |
| 3275 | CD1 | PHE | A | 234 | 65.546 | 67.041 | 4.768 | 1.00 | 23.74 |
| 3277 | CE1 | PHE | A | 234 | 64.455 | 66.267 | 5.103 | 1.00 | 25.17 |
| 3279 | CZ | PHE | A | 234 | 63.407 | 66.817 | 5.797 | 1.00 | 23.85 |
| 3281 | CE2 | PHE | A | 234 | 63.462 | 68.143 | 6.173 | 1.00 | 23.26 |
| 3283 | CD2 | PHE | A | 234 | 64.551 | 68.907 | 5.851 | 1.00 | 21.11 |
| 3285 | C | PHE | A | 234 | 65.812 | 71.378 | 4.147 | 1.00 | 20.30 |
| 3286 | O | PHE | A | 234 | 64.590 | 71.496 | 3.939 | 1.00 | 19.63 |
| 3287 | N | GLN | A | 235 | 66.523 | 72.269 | 4.835 | 1.00 | 20.63 |
| 3289 | CA | GLN | A | 235 | 65.874 | 73.456 | 5.381 | 1.00 | 21.12 |
| 3291 | CB | GLN | A | 235 | 66.699 | 74.091 | 6.503 | 1.00 | 21.39 |
| 3294 | CG | GLN | A | 235 | 65.944 | 75.205 | 7.276 | 1.00 | 21.45 |
| 3297 | CD | GLN | A | 235 | 64.668 | 74.715 | 7.926 | 1.00 | 23.00 |
| 3298 | OE1 | GLN | A | 235 | 64.650 | 73.654 | 8.548 | 1.00 | 23.23 |
| 3299 | NE2 | GLN | A | 235 | 63.595 | 75.490 | 7.795 | 1.00 | 20.99 |
| 3302 | C | GLN | A | 235 | 65.546 | 74.494 | 4.300 | 1.00 | 21.77 |
| 3303 | O | GLN | A | 235 | 64.511 | 75.148 | 4.375 | 1.00 | 22.39 |
| 3304 | N | VAL | A | 236 | 66.402 | 74.641 | 3.299 | 1.00 | 22.51 |
| 3306 | CA | VAL | A | 236 | 66.066 | 75.543 | 2.184 | 1.00 | 22.92 |
| 3308 | CB | VAL | A | 236 | 67.260 | 75.840 | 1.212 | 1.00 | 23.27 |
| 3310 | CG1 | VAL | A | 236 | 68.054 | 74.664 | 0.922 | 1.00 | 26.25 |
| 3314 | CG2 | VAL | A | 236 | 66.794 | 76.486 | -0.102 | 1.00 | 23.71 |

FIGURE 3 (Cont.)

| A | B | C | D | E | F | G | H | I | J |
|---|---|---|---|---|---|---|---|---|---|
| 3318 | C | VAL | A | 236 | 64.794 | 75.075 | 1.478 | 1.00 | 22.84 |
| 3319 | O | VAL | A | 236 | 63.936 | 75.893 | 1.150 | 1.00 | 22.34 |
| 3320 | N | GLN | A | 237 | 64.635 | 73.761 | 1.307 | 1.00 | 23.02 |
| 3322 | CA | GLN | A | 237 | 63.413 | 73.222 | 0.738 | 1.00 | 23.04 |
| 3324 | CB | GLN | A | 237 | 63.538 | 71.727 | 0.418 | 1.00 | 23.87 |
| 3327 | CG | GLN | A | 237 | 62.276 | 71.128 | -0.198 | 1.00 | 25.59 |
| 3330 | CD | GLN | A | 237 | 62.058 | 71.593 | -1.623 | 1.00 | 29.42 |
| 3331 | OE1 | GLN | A | 237 | 62.818 | 72.426 | -2.133 | 1.00 | 30.57 |
| 3332 | NE2 | GLN | A | 237 | 61.025 | 71.053 | -2.275 | 1.00 | 28.29 |
| 3335 | C | GLN | A | 237 | 62.241 | 73.441 | 1.671 | 1.00 | 22.23 |
| 3336 | O | GLN | A | 237 | 61.140 | 73.709 | 1.213 | 1.00 | 22.37 |
| 3337 | N | ASP | A | 238 | 62.467 | 73.315 | 2.977 | 1.00 | 21.60 |
| 3339 | CA | ASP | A | 238 | 61.409 | 73.564 | 3.954 | 1.00 | 21.14 |
| 3341 | CB | ASP | A | 238 | 61.898 | 73.263 | 5.372 | 1.00 | 20.81 |
| 3344 | CG | ASP | A | 238 | 60.808 | 73.400 | 6.393 | 1.00 | 20.15 |
| 3345 | OD1 | ASP | A | 238 | 59.877 | 72.588 | 6.376 | 1.00 | 22.40 |
| 3346 | OD2 | ASP | A | 238 | 60.774 | 74.310 | 7.250 | 1.00 | 23.26 |
| 3347 | C | ASP | A | 238 | 60.904 | 75.018 | 3.848 | 1.00 | 21.37 |
| 3348 | O | ASP | A | 238 | 59.701 | 75.260 | 3.866 | 1.00 | 21.86 |
| 3349 | N | ASP | A | 239 | 61.820 | 75.966 | 3.694 | 1.00 | 21.89 |
| 3351 | CA | ASP | A | 239 | 61.446 | 77.379 | 3.534 | 1.00 | 22.75 |
| 3353 | CB | ASP | A | 239 | 62.674 | 78.275 | 3.478 | 1.00 | 22.66 |
| 3356 | CG | ASP | A | 239 | 63.436 | 78.375 | 4.789 | 1.00 | 23.92 |
| 3357 | OD1 | ASP | A | 239 | 62.965 | 77.899 | 5.859 | 1.00 | 26.27 |
| 3358 | OD2 | ASP | A | 239 | 64.542 | 78.966 | 4.821 | 1.00 | 23.49 |
| 3359 | C | ASP | A | 239 | 60.679 | 77.596 | 2.219 | 1.00 | 23.14 |
| 3360 | O | ASP | A | 239 | 59.719 | 78.357 | 2.158 | 1.00 | 23.09 |
| 3361 | N | ILE | A | 240 | 61.129 | 76.934 | 1.162 | 1.00 | 24.22 |
| 3363 | CA | ILE | A | 240 | 60.507 | 77.067 | -0.150 | 1.00 | 24.50 |
| 3365 | CB | ILE | A | 240 | 61.358 | 76.356 | -1.230 | 1.00 | 24.79 |
| 3367 | CG1 | ILE | A | 240 | 62.593 | 77.200 | -1.545 | 1.00 | 25.00 |
| 3370 | CD1 | ILE | A | 240 | 63.697 | 76.444 | -2.246 | 1.00 | 25.62 |
| 3374 | CG2 | ILE | A | 240 | 60.548 | 76.118 | -2.518 | 1.00 | 24.83 |
| 3378 | C | ILE | A | 240 | 59.094 | 76.529 | -0.095 | 1.00 | 24.74 |
| 3379 | O | ILE | A | 240 | 58.168 | 77.162 | -0.598 | 1.00 | 24.41 |
| 3380 | N | LEU | A | 241 | 58.920 | 75.380 | 0.561 | 1.00 | 24.90 |
| 3382 | CA | LEU | A | 241 | 57.608 | 74.763 | 0.702 | 1.00 | 25.47 |
| 3384 | CB | LEU | A | 241 | 57.721 | 73.376 | 1.346 | 1.00 | 25.41 |
| 3387 | CG | LEU | A | 241 | 58.364 | 72.296 | 0.469 | 1.00 | 26.20 |
| 3389 | CD1 | LEU | A | 241 | 58.592 | 71.012 | 1.275 | 1.00 | 26.19 |
| 3393 | CD2 | LEU | A | 241 | 57.523 | 72.032 | -0.762 | 1.00 | 26.28 |
| 3397 | C | LEU | A | 241 | 56.677 | 75.637 | 1.517 | 1.00 | 25.82 |
| 3398 | O | LEU | A | 241 | 55.463 | 75.646 | 1.296 | 1.00 | 26.02 |
| 3399 | N | ASP | A | 242 | 57.238 | 76.375 | 2.461 | 1.00 | 26.06 |
| 3401 | CA | ASP | A | 242 | 56.422 | 77.233 | 3.298 | 1.00 | 27.02 |
| 3403 | CB | ASP | A | 242 | 57.239 | 77.832 | 4.426 | 1.00 | 26.69 |
| 3406 | CG | ASP | A | 242 | 56.390 | 78.176 | 5.607 | 1.00 | 28.82 |
| 3407 | OD1 | ASP | A | 242 | 55.886 | 79.319 | 5.636 | 1.00 | 29.75 |
| 3408 | OD2 | ASP | A | 242 | 56.148 | 77.365 | 6.534 | 1.00 | 31.49 |
| 3409 | C | ASP | A | 242 | 55.765 | 78.333 | 2.458 | 1.00 | 27.65 |
| 3410 | O | ASP | A | 242 | 54.622 | 78.689 | 2.698 | 1.00 | 28.08 |
| 3411 | N | VAL | A | 243 | 56.481 | 78.823 | 1.454 | 1.00 | 28.57 |

FIGURE 3 (Cont.)

| A | B | C | D | E | F | G | H | I | J |
|---|---|---|---|---|---|---|---|---|---|
| 3413 | CA | VAL | A | 243 | 55.949 | 79.838 | 0.542 | 1.00 | 29.59 |
| 3415 | CB | VAL | A | 243 | 57.091 | 80.577 | -0.188 | 1.00 | 29.49 |
| 3417 | CG1 | VAL | A | 243 | 56.537 | 81.656 | -1.140 | 1.00 | 29.98 |
| 3421 | CG2 | VAL | A | 243 | 58.062 | 81.200 | 0.825 | 1.00 | 29.51 |
| 3425 | C | VAL | A | 243 | 54.951 | 79.248 | -0.477 | 1.00 | 30.63 |
| 3426 | O | VAL | A | 243 | 53.791 | 79.669 | -0.525 | 1.00 | 30.78 |
| 3427 | N | VAL | A | 244 | 55.388 | 78.253 | -1.250 | 1.00 | 31.44 |
| 3429 | CA | VAL | A | 244 | 54.642 | 77.785 | -2.427 | 1.00 | 32.17 |
| 3431 | CB | VAL | A | 244 | 55.605 | 77.525 | -3.617 | 1.00 | 32.40 |
| 3433 | CG1 | VAL | A | 244 | 56.588 | 78.680 | -3.768 | 1.00 | 32.66 |
| 3437 | CG2 | VAL | A | 244 | 56.349 | 76.185 | -3.462 | 1.00 | 32.82 |
| 3441 | C | VAL | A | 244 | 53.766 | 76.543 | -2.233 | 1.00 | 32.47 |
| 3442 | O | VAL | A | 244 | 52.963 | 76.204 | -3.110 | 1.00 | 32.70 |
| 3443 | N | GLY | A | 245 | 53.915 | 75.854 | -1.105 | 1.00 | 32.77 |
| 3445 | CA | GLY | A | 245 | 53.200 | 74.611 | -0.879 | 1.00 | 33.14 |
| 3448 | C | GLY | A | 245 | 51.784 | 74.871 | -0.407 | 1.00 | 33.82 |
| 3449 | O | GLY | A | 245 | 51.515 | 75.920 | 0.162 | 1.00 | 34.10 |
| 3450 | N | ASP | A | 246 | 50.887 | 73.920 | -0.656 | 1.00 | 34.38 |
| 3452 | CA | ASP | A | 246 | 49.489 | 73.995 | -0.211 | 1.00 | 34.75 |
| 3454 | CB | ASP | A | 246 | 48.602 | 73.159 | -1.151 | 1.00 | 35.30 |
| 3457 | CG | ASP | A | 246 | 47.185 | 73.699 | -1.272 | 1.00 | 38.65 |
| 3458 | OD1 | ASP | A | 246 | 46.738 | 73.925 | -2.425 | 1.00 | 42.04 |
| 3459 | OD2 | ASP | A | 246 | 46.433 | 73.914 | -0.284 | 1.00 | 42.91 |
| 3460 | C | ASP | A | 246 | 49.431 | 73.410 | 1.198 | 1.00 | 33.97 |
| 3461 | O | ASP | A | 246 | 50.088 | 72.411 | 1.456 | 1.00 | 33.79 |
| 3462 | N | THR | A | 247 | 48.643 | 74.009 | 2.089 | 1.00 | 33.08 |
| 3464 | CA | THR | A | 247 | 48.489 | 73.517 | 3.465 | 1.00 | 32.87 |
| 3466 | CB | THR | A | 247 | 47.476 | 74.394 | 4.249 | 1.00 | 32.46 |
| 3468 | OG1 | THR | A | 247 | 48.002 | 75.710 | 4.420 | 1.00 | 32.70 |
| 3470 | CG2 | THR | A | 247 | 47.288 | 73.901 | 5.684 | 1.00 | 32.42 |
| 3474 | C | THR | A | 247 | 48.061 | 72.041 | 3.542 | 1.00 | 32.67 |
| 3475 | O | THR | A | 247 | 48.561 | 71.297 | 4.377 | 1.00 | 32.65 |
| 3476 | N | ALA | A | 248 | 47.141 | 71.617 | 2.677 | 1.00 | 32.34 |
| 3478 | CA | ALA | A | 248 | 46.651 | 70.240 | 2.709 | 1.00 | 32.14 |
| 3480 | CB | ALA | A | 248 | 45.388 | 70.095 | 1.857 | 1.00 | 32.51 |
| 3484 | C | ALA | A | 248 | 47.724 | 69.228 | 2.271 | 1.00 | 31.60 |
| 3485 | O | ALA | A | 248 | 47.692 | 68.073 | 2.678 | 1.00 | 31.38 |
| 3486 | N | THR | A | 249 | 48.668 | 69.666 | 1.447 | 1.00 | 31.12 |
| 3488 | CA | THR | A | 249 | 49.785 | 68.815 | 1.025 | 1.00 | 31.09 |
| 3490 | CB | THR | A | 249 | 50.269 | 69.251 | -0.371 | 1.00 | 31.32 |
| 3492 | OG1 | THR | A | 249 | 49.192 | 69.112 | -1.313 | 1.00 | 33.79 |
| 3494 | CG2 | THR | A | 249 | 51.348 | 68.308 | -0.917 | 1.00 | 31.41 |
| 3498 | C | THR | A | 249 | 50.943 | 68.825 | 2.045 | 1.00 | 30.23 |
| 3499 | O | THR | A | 249 | 51.483 | 67.768 | 2.391 | 1.00 | 30.03 |
| 3500 | N | LEU | A | 250 | 51.312 | 70.017 | 2.520 | 1.00 | 29.30 |
| 3502 | CA | LEU | A | 250 | 52.358 | 70.175 | 3.539 | 1.00 | 28.64 |
| 3504 | CB | LEU | A | 250 | 52.668 | 71.653 | 3.766 | 1.00 | 28.31 |
| 3507 | CG | LEU | A | 250 | 53.253 | 72.412 | 2.577 | 1.00 | 29.19 |
| 3509 | CD1 | LEU | A | 250 | 53.329 | 73.903 | 2.883 | 1.00 | 29.07 |
| 3513 | CD2 | LEU | A | 250 | 54.620 | 71.880 | 2.197 | 1.00 | 29.56 |
| 3517 | C | LEU | A | 250 | 52.007 | 69.554 | 4.880 | 1.00 | 27.73 |
| 3518 | O | LEU | A | 250 | 52.877 | 69.038 | 5.578 | 1.00 | 27.92 |

FIGURE 3 (Cont.)

| A | B | C | D | E | F | G | H | I | J |
|---|---|---|---|---|---|---|---|---|---|
| 3519 | N | GLY | A | 251 | 50.732 | 69.613 | 5.240 | 1.00 | 26.76 |
| 3521 | CA | GLY | A | 251 | 50.277 | 69.195 | 6.546 | 1.00 | 26.19 |
| 3524 | C | GLY | A | 251 | 50.485 | 70.266 | 7.601 | 1.00 | 25.80 |
| 3525 | O | GLY | A | 251 | 50.150 | 70.053 | 8.757 | 1.00 | 24.95 |
| 3526 | N | LYS | A | 252 | 51.071 | 71.388 | 7.197 | 1.00 | 25.86 |
| 3528 | CA | LYS | A | 252 | 51.273 | 72.556 | 8.052 | 1.00 | 26.53 |
| 3530 | CB | LYS | A | 252 | 52.701 | 72.588 | 8.628 | 1.00 | 25.80 |
| 3533 | CG | LYS | A | 252 | 53.804 | 72.498 | 7.579 | 1.00 | 25.64 |
| 3536 | CD | LYS | A | 252 | 55.183 | 72.231 | 8.200 | 1.00 | 23.61 |
| 3539 | CE | LYS | A | 252 | 56.297 | 72.507 | 7.205 | 1.00 | 22.86 |
| 3542 | NZ | LYS | A | 252 | 57.604 | 71.866 | 7.602 | 1.00 | 21.94 |
| 3546 | C | LYS | A | 252 | 50.992 | 73.813 | 7.223 | 1.00 | 27.55 |
| 3547 | O | LYS | A | 252 | 51.046 | 73.781 | 5.982 | 1.00 | 28.12 |
| 3548 | N | ARG | A | 253 | 50.721 | 74.918 | 7.905 | 1.00 | 28.61 |
| 3550 | CA | ARG | A | 253 | 50.217 | 76.128 | 7.249 | 1.00 | 29.63 |
| 3552 | CB | ARG | A | 253 | 49.658 | 77.096 | 8.287 | 1.00 | 30.10 |
| 3555 | CG | ARG | A | 253 | 48.370 | 76.612 | 8.875 | 1.00 | 32.12 |
| 3558 | CD | ARG | A | 253 | 47.441 | 77.693 | 9.362 | 1.00 | 35.28 |
| 3561 | NE | ARG | A | 253 | 46.380 | 77.104 | 10.175 | 1.00 | 38.07 |
| 3563 | CZ | ARG | A | 253 | 45.308 | 76.476 | 9.688 | 1.00 | 40.08 |
| 3564 | NH1 | ARG | A | 253 | 45.095 | 76.378 | 8.376 | 1.00 | 39.60 |
| 3567 | NH2 | ARG | A | 253 | 44.419 | 75.962 | 10.533 | 1.00 | 40.97 |
| 3570 | C | ARG | A | 253 | 51.223 | 76.852 | 6.360 | 1.00 | 29.71 |
| 3571 | O | ARG | A | 253 | 52.306 | 77.274 | 6.806 | 1.00 | 29.38 |
| 3572 | N | GLN | A | 254 | 50.847 | 76.966 | 5.084 | 1.00 | 30.10 |
| 3574 | CA | GLN | A | 254 | 51.544 | 77.794 | 4.108 | 1.00 | 29.94 |
| 3576 | CB | GLN | A | 254 | 50.816 | 77.731 | 2.754 | 1.00 | 30.17 |
| 3579 | CG | GLN | A | 254 | 51.436 | 78.643 | 1.649 | 1.00 | 31.83 |
| 3582 | CD | GLN | A | 254 | 50.618 | 78.716 | 0.357 | 1.00 | 34.25 |
| 3583 | OE1 | GLN | A | 254 | 51.157 | 79.057 | -0.705 | 1.00 | 35.57 |
| 3584 | NE2 | GLN | A | 254 | 49.333 | 78.396 | 0.439 | 1.00 | 35.68 |
| 3587 | C | GLN | A | 254 | 51.586 | 79.238 | 4.601 | 1.00 | 29.79 |
| 3588 | O | GLN | A | 254 | 50.625 | 79.733 | 5.193 | 1.00 | 29.82 |
| 3589 | N | GLY | A | 255 | 52.705 | 79.907 | 4.369 | 1.00 | 29.23 |
| 3591 | CA | GLY | A | 255 | 52.843 | 81.298 | 4.740 | 1.00 | 29.36 |
| 3594 | C | GLY | A | 255 | 53.063 | 81.513 | 6.230 | 1.00 | 29.17 |
| 3595 | O | GLY | A | 255 | 52.963 | 82.630 | 6.708 | 1.00 | 28.41 |
| 3596 | N | ALA | A | 256 | 53.372 | 80.453 | 6.971 | 1.00 | 29.32 |
| 3598 | CA | ALA | A | 256 | 53.670 | 80.594 | 8.395 | 1.00 | 29.31 |
| 3600 | CB | ALA | A | 256 | 53.865 | 79.216 | 9.032 | 1.00 | 29.54 |
| 3604 | C | ALA | A | 256 | 54.900 | 81.481 | 8.638 | 1.00 | 29.48 |
| 3605 | O | ALA | A | 256 | 54.915 | 82.276 | 9.569 | 1.00 | 30.09 |
| 3606 | N | ASP | A | 257 | 55.925 | 81.350 | 7.805 | 1.00 | 29.41 |
| 3608 | CA | ASP | A | 257 | 57.170 | 82.079 | 8.006 | 1.00 | 29.43 |
| 3610 | CB | ASP | A | 257 | 58.242 | 81.581 | 7.053 | 1.00 | 29.35 |
| 3613 | CG | ASP | A | 257 | 58.770 | 80.208 | 7.420 | 1.00 | 28.93 |
| 3614 | OD1 | ASP | A | 257 | 58.493 | 79.724 | 8.552 | 1.00 | 27.10 |
| 3615 | OD2 | ASP | A | 257 | 59.480 | 79.562 | 6.613 | 1.00 | 25.07 |
| 3616 | C | ASP | A | 257 | 56.992 | 83.576 | 7.772 | 1.00 | 30.15 |
| 3617 | O | ASP | A | 257 | 57.516 | 84.404 | 8.505 | 1.00 | 28.74 |
| 3618 | N | GLN | A | 258 | 56.258 | 83.887 | 6.717 | 1.00 | 31.27 |
| 3620 | CA | GLN | A | 258 | 56.003 | 85.254 | 6.311 | 1.00 | 32.11 |

FIGURE 3 (Cont.)

| A | B | C | D | E | F | G | H | I | J |
|---|---|---|---|---|---|---|---|---|---|
| 3622 | CB | BGLN | A | 258 | 55.223 | 85.271 | 4.997 | 0.35 | 32.00 |
| 3623 | CB | AGLN | A | 258 | 55.313 | 85.259 | 4.930 | 0.65 | 32.18 |
| 3628 | CG | BGLN | A | 258 | 55.115 | 86.632 | 4.342 | 0.35 | 31.76 |
| 3629 | CG | AGLN | A | 258 | 56.317 | 84.920 | 3.801 | 0.65 | 32.43 |
| 3634 | CD | BGLN | A | 258 | 54.771 | 86.519 | 2.876 | 0.35 | 31.23 |
| 3635 | CD | AGLN | A | 258 | 55.724 | 84.264 | 2.547 | 0.65 | 32.97 |
| 3636 | OE1 | BGLN | A | 258 | 55.645 | 86.639 | 2.016 | 0.35 | 30.93 |
| 3637 | OE1 | AGLN | A | 258 | 54.977 | 83.279 | 2.618 | 0.65 | 32.08 |
| 3638 | NE2 | BGLN | A | 258 | 53.503 | 86.266 | 2.585 | 0.35 | 30.18 |
| 3639 | NE2 | AGLN | A | 258 | 56.103 | 84.792 | 1.389 | 0.65 | 33.37 |
| 3644 | C | GLN | A | 258 | 55.203 | 85.967 | 7.400 | 1.00 | 32.82 |
| 3645 | O | GLN | A | 258 | 55.460 | 87.123 | 7.720 | 1.00 | 33.46 |
| 3646 | N | GLN | A | 259 | 54.266 | 85.249 | 8.000 | 1.00 | 33.70 |
| 3648 | CA | GLN | A | 259 | 53.452 | 85.780 | 9.084 | 1.00 | 34.64 |
| 3650 | CB | GLN | A | 259 | 52.395 | 84.756 | 9.463 | 1.00 | 35.35 |
| 3653 | CG | GLN | A | 259 | 51.346 | 85.257 | 10.436 | 1.00 | 38.57 |
| 3656 | CD | GLN | A | 259 | 50.161 | 84.331 | 10.482 | 1.00 | 42.61 |
| 3657 | OE1 | GLN | A | 259 | 49.161 | 84.555 | 9.787 | 1.00 | 45.33 |
| 3658 | NE2 | GLN | A | 259 | 50.272 | 83.263 | 11.278 | 1.00 | 44.63 |
| 3661 | C | GLN | A | 259 | 54.281 | 86.173 | 10.320 | 1.00 | 34.20 |
| 3662 | O | GLN | A | 259 | 53.948 | 87.154 | 10.990 | 1.00 | 33.93 |
| 3663 | N | LEU | A | 260 | 55.347 | 85.419 | 10.613 | 1.00 | 33.21 |
| 3665 | CA | LEU | A | 260 | 56.247 | 85.737 | 11.734 | 1.00 | 32.74 |
| 3667 | CB | LEU | A | 260 | 56.676 | 84.463 | 12.474 | 1.00 | 32.73 |
| 3670 | CG | LEU | A | 260 | 55.629 | 83.549 | 13.112 | 1.00 | 34.09 |
| 3672 | CD1 | LEU | A | 260 | 56.300 | 82.734 | 14.206 | 1.00 | 35.07 |
| 3676 | CD2 | LEU | A | 260 | 54.412 | 84.295 | 13.676 | 1.00 | 35.20 |
| 3680 | C | LEU | A | 260 | 57.514 | 86.495 | 11.326 | 1.00 | 31.74 |
| 3681 | O | LEU | A | 260 | 58.348 | 86.790 | 12.172 | 1.00 | 31.90 |
| 3682 | N | GLY | A | 261 | 57.670 | 86.808 | 10.043 | 1.00 | 30.66 |
| 3684 | CA | GLY | A | 261 | 58.858 | 87.495 | 9.565 | 1.00 | 29.51 |
| 3687 | C | GLY | A | 261 | 60.157 | 86.732 | 9.759 | 1.00 | 28.74 |
| 3688 | O | GLY | A | 261 | 61.198 | 87.333 | 9.998 | 1.00 | 28.52 |
| 3689 | N | LYS | A | 262 | 60.099 | 85.405 | 9.649 | 1.00 | 27.62 |
| 3691 | CA | LYS | A | 262 | 61.296 | 84.575 | 9.707 | 1.00 | 26.77 |
| 3693 | CB | LYS | A | 262 | 60.934 | 83.092 | 9.572 | 1.00 | 26.29 |
| 3696 | CG | LYS | A | 262 | 60.021 | 82.536 | 10.642 | 1.00 | 25.90 |
| 3699 | CD | LYS | A | 262 | 60.797 | 82.141 | 11.884 | 1.00 | 26.17 |
| 3702 | CE | LYS | A | 262 | 59.882 | 81.593 | 12.965 | 1.00 | 26.68 |
| 3705 | NZ | LYS | A | 262 | 60.644 | 81.319 | 14.214 | 1.00 | 25.74 |
| 3709 | C | LYS | A | 262 | 62.280 | 84.943 | 8.595 | 1.00 | 26.39 |
| 3710 | O | LYS | A | 262 | 61.884 | 85.161 | 7.445 | 1.00 | 26.03 |
| 3711 | N | SER | A | 263 | 63.563 | 85.005 | 8.943 | 1.00 | 26.23 |
| 3713 | CA | SER | A | 263 | 64.629 | 85.019 | 7.944 | 1.00 | 26.10 |
| 3715 | CB | SER | A | 263 | 65.975 | 85.311 | 8.586 | 1.00 | 26.43 |
| 3718 | OG | SER | A | 263 | 65.979 | 86.581 | 9.207 | 1.00 | 26.96 |
| 3720 | C | SER | A | 263 | 64.666 | 83.652 | 7.247 | 1.00 | 26.21 |
| 3721 | O | SER | A | 263 | 64.899 | 82.629 | 7.898 | 1.00 | 25.19 |
| 3722 | N | THR | A | 264 | 64.388 | 83.642 | 5.942 | 1.00 | 25.65 |
| 3724 | CA | THR | A | 264 | 64.408 | 82.408 | 5.149 | 1.00 | 25.89 |
| 3726 | CB | THR | A | 264 | 62.975 | 81.922 | 4.812 | 1.00 | 26.14 |
| 3728 | OG1 | THR | A | 264 | 62.368 | 82.789 | 3.847 | 1.00 | 26.91 |

FIGURE 3 (Cont.)

| A | B | C | D | E | F | G | H | I | J |
|---|---|---|---|---|---|---|---|---|---|
| 3730 | CG2 | THR | A | 264 | 62.046 | 81.992 | 6.033 | 1.00 | 26.45 |
| 3734 | C | THR | A | 264 | 65.189 | 82.591 | 3.856 | 1.00 | 25.77 |
| 3735 | O | THR | A | 264 | 65.538 | 83.722 | 3.472 | 1.00 | 25.52 |
| 3736 | N | TYR | A | 265 | 65.479 | 81.471 | 3.195 | 1.00 | 25.31 |
| 3738 | CA | TYR | A | 265 | 66.114 | 81.507 | 1.886 | 1.00 | 25.24 |
| 3740 | CB | TYR | A | 265 | 66.555 | 80.104 | 1.428 | 1.00 | 24.84 |
| 3743 | CG | TYR | A | 265 | 67.953 | 79.767 | 1.902 | 1.00 | 24.29 |
| 3744 | CD1 | TYR | A | 265 | 69.012 | 79.698 | 1.010 | 1.00 | 23.63 |
| 3746 | CE1 | TYR | A | 265 | 70.282 | 79.407 | 1.423 | 1.00 | 24.04 |
| 3748 | CZ | TYR | A | 265 | 70.545 | 79.200 | 2.759 | 1.00 | 24.29 |
| 3749 | OH | TYR | A | 265 | 71.827 | 78.928 | 3.168 | 1.00 | 24.41 |
| 3751 | CE2 | TYR | A | 265 | 69.521 | 79.276 | 3.685 | 1.00 | 24.92 |
| 3753 | CD2 | TYR | A | 265 | 68.225 | 79.566 | 3.250 | 1.00 | 23.77 |
| 3755 | C | TYR | A | 265 | 65.240 | 82.222 | 0.843 | 1.00 | 25.25 |
| 3756 | O | TYR | A | 265 | 65.717 | 83.149 | 0.211 | 1.00 | 25.83 |
| 3757 | N | PRO | A | 266 | 63.982 | 81.823 | 0.658 | 1.00 | 25.61 |
| 3758 | CA | PRO | A | 266 | 63.108 | 82.515 | -0.307 | 1.00 | 25.70 |
| 3760 | CB | PRO | A | 266 | 61.812 | 81.700 | -0.284 | 1.00 | 26.04 |
| 3763 | CG | PRO | A | 266 | 61.876 | 80.854 | 0.923 | 1.00 | 26.04 |
| 3766 | CD | PRO | A | 266 | 63.311 | 80.683 | 1.293 | 1.00 | 25.37 |
| 3769 | C | PRO | A | 266 | 62.825 | 83.980 | 0.027 | 1.00 | 25.95 |
| 3770 | O | PRO | A | 266 | 62.702 | 84.784 | -0.900 | 1.00 | 25.00 |
| 3771 | N | ALA | A | 267 | 62.738 | 84.326 | 1.311 | 1.00 | 26.04 |
| 3773 | CA | ALA | A | 267 | 62.503 | 85.719 | 1.697 | 1.00 | 26.33 |
| 3775 | CB | ALA | A | 267 | 62.193 | 85.853 | 3.166 | 1.00 | 26.37 |
| 3779 | C | ALA | A | 267 | 63.694 | 86.578 | 1.309 | 1.00 | 26.47 |
| 3780 | O | ALA | A | 267 | 63.512 | 87.637 | 0.734 | 1.00 | 26.90 |
| 3781 | N | LEU | A | 268 | 64.906 | 86.094 | 1.574 | 1.00 | 26.35 |
| 3783 | CA | LEU | A | 268 | 66.124 | 86.814 | 1.213 | 1.00 | 26.27 |
| 3785 | CB | LEU | A | 268 | 67.337 | 86.201 | 1.924 | 1.00 | 26.30 |
| 3788 | CG | LEU | A | 268 | 68.691 | 86.873 | 1.690 | 1.00 | 27.65 |
| 3790 | CD1 | LEU | A | 268 | 68.728 | 88.322 | 2.211 | 1.00 | 28.07 |
| 3794 | CD2 | LEU | A | 268 | 69.803 | 86.053 | 2.316 | 1.00 | 28.26 |
| 3798 | C | LEU | A | 268 | 66.386 | 86.828 | -0.294 | 1.00 | 26.01 |
| 3799 | O | LEU | A | 268 | 66.541 | 87.899 | -0.898 | 1.00 | 25.44 |
| 3800 | N | LEU | A | 269 | 66.439 | 85.633 | -0.881 | 1.00 | 25.58 |
| 3802 | CA | LEU | A | 269 | 66.963 | 85.430 | -2.234 | 1.00 | 25.43 |
| 3804 | CB | LEU | A | 269 | 67.755 | 84.113 | -2.298 | 1.00 | 25.44 |
| 3807 | CG | LEU | A | 269 | 68.906 | 83.896 | -1.320 | 1.00 | 26.67 |
| 3809 | CD1 | LEU | A | 269 | 69.520 | 82.486 | -1.510 | 1.00 | 25.96 |
| 3813 | CD2 | LEU | A | 269 | 69.960 | 84.976 | -1.479 | 1.00 | 27.24 |
| 3817 | C | LEU | A | 269 | 65.902 | 85.380 | -3.316 | 1.00 | 24.91 |
| 3818 | O | LEU | A | 269 | 66.226 | 85.454 | -4.490 | 1.00 | 24.92 |
| 3819 | N | GLY | A | 270 | 64.640 | 85.253 | -2.933 | 1.00 | 24.87 |
| 3821 | CA | GLY | A | 270 | 63.584 | 84.945 | -3.884 | 1.00 | 24.94 |
| 3824 | C | GLY | A | 270 | 63.529 | 83.446 | -4.151 | 1.00 | 25.33 |
| 3825 | O | GLY | A | 270 | 64.488 | 82.724 | -3.871 | 1.00 | 25.08 |
| 3826 | N | LEU | A | 271 | 62.415 | 82.985 | -4.699 | 1.00 | 25.79 |
| 3828 | CA | LEU | A | 271 | 62.170 | 81.567 | -4.899 | 1.00 | 26.67 |
| 3830 | CB | LEU | A | 271 | 60.732 | 81.320 | -5.383 | 1.00 | 27.35 |
| 3833 | CG | LEU | A | 271 | 59.602 | 81.477 | -4.365 | 1.00 | 28.42 |
| 3835 | CD1 | LEU | A | 271 | 58.252 | 81.403 | -5.068 | 1.00 | 29.93 |

FIGURE 3 (Cont.)

| A | B | C | D | E | F | G | H | I | J |
|---|---|---|---|---|---|---|---|---|---|
| 3839 | CD2 | LEU | A | 271 | 59.687 | 80.413 | -3.279 | 1.00 | 28.63 |
| 3843 | C | LEU | A | 271 | 63.162 | 80.914 | -5.853 | 1.00 | 27.13 |
| 3844 | O | LEU | A | 271 | 63.593 | 79.796 | -5.591 | 1.00 | 27.11 |
| 3845 | N | GLU | A | 272 | 63.536 | 81.599 | -6.938 | 1.00 | 27.48 |
| 3847 | CA | GLU | A | 272 | 64.429 | 81.018 | -7.956 | 1.00 | 28.05 |
| 3849 | CB | GLU | A | 272 | 64.488 | 81.905 | -9.229 | 1.00 | 28.98 |
| 3852 | CG | GLU | A | 272 | 65.687 | 81.611 | -10.148 | 1.00 | 31.69 |
| 3855 | CD | GLU | A | 272 | 65.592 | 82.253 | -11.528 | 1.00 | 35.38 |
| 3856 | OE1 | GLU | A | 272 | 66.103 | 81.648 | -12.499 | 1.00 | 39.00 |
| 3857 | OE2 | GLU | A | 272 | 65.013 | 83.354 | -11.655 | 1.00 | 37.35 |
| 3858 | C | GLU | A | 272 | 65.850 | 80.739 | -7.455 | 1.00 | 27.43 |
| 3859 | O | GLU | A | 272 | 66.427 | 79.668 | -7.745 | 1.00 | 27.14 |
| 3860 | N | GLN | A | 273 | 66.432 | 81.697 | -6.743 | 1.00 | 26.16 |
| 3862 | CA | GLN | A | 273 | 67.799 | 81.563 | -6.250 | 1.00 | 26.17 |
| 3864 | CB | GLN | A | 273 | 68.364 | 82.909 | -5.793 | 1.00 | 26.14 |
| 3867 | CG | GLN | A | 273 | 68.642 | 83.881 | -6.920 | 1.00 | 29.26 |
| 3870 | CD | GLN | A | 273 | 69.025 | 85.266 | -6.418 | 1.00 | 32.23 |
| 3871 | OE1 | GLN | A | 273 | 69.828 | 85.405 | -5.485 | 1.00 | 34.54 |
| 3872 | NE2 | GLN | A | 273 | 68.464 | 86.295 | -7.046 | 1.00 | 34.59 |
| 3875 | C | GLN | A | 273 | 67.854 | 80.566 | -5.092 | 1.00 | 25.40 |
| 3876 | O | GLN | A | 273 | 68.856 | 79.905 | -4.900 | 1.00 | 25.15 |
| 3877 | N | ALA | A | 274 | 66.776 | 80.485 | -4.318 | 1.00 | 25.33 |
| 3879 | CA | ALA | A | 274 | 66.681 | 79.514 | -3.239 | 1.00 | 25.32 |
| 3881 | CB | ALA | A | 274 | 65.429 | 79.770 | -2.427 | 1.00 | 25.59 |
| 3885 | C | ALA | A | 274 | 66.665 | 78.097 | -3.837 | 1.00 | 25.68 |
| 3886 | O | ALA | A | 274 | 67.388 | 77.213 | -3.385 | 1.00 | 25.35 |
| 3887 | N | ARG | A | 275 | 65.860 | 77.913 | -4.878 | 1.00 | 25.78 |
| 3889 | CA | ARG | A | 275 | 65.753 | 76.631 | -5.564 | 1.00 | 26.49 |
| 3891 | CB | ARG | A | 275 | 64.725 | 76.697 | -6.683 | 1.00 | 26.59 |
| 3894 | CG | ARG | A | 275 | 63.311 | 76.604 | -6.197 | 1.00 | 27.19 |
| 3897 | CD | ARG | A | 275 | 62.284 | 76.791 | -7.294 | 1.00 | 29.91 |
| 3900 | NE | ARG | A | 275 | 60.926 | 76.575 | -6.799 | 1.00 | 31.85 |
| 3902 | CZ | ARG | A | 275 | 59.886 | 77.379 | -7.009 | 1.00 | 34.22 |
| 3903 | NH1 | ARG | A | 275 | 59.998 | 78.504 | -7.720 | 1.00 | 35.16 |
| 3906 | NH2 | ARG | A | 275 | 58.706 | 77.047 | -6.491 | 1.00 | 35.99 |
| 3909 | C | ARG | A | 275 | 67.091 | 76.201 | -6.109 | 1.00 | 26.94 |
| 3910 | O | ARG | A | 275 | 67.468 | 75.039 | -5.985 | 1.00 | 27.03 |
| 3911 | N | LYS | A | 276 | 67.816 | 77.155 | -6.679 | 1.00 | 27.58 |
| 3913 | CA | LYS | A | 276 | 69.145 | 76.929 | -7.218 | 1.00 | 28.35 |
| 3915 | CB | LYS | A | 276 | 69.641 | 78.193 | -7.934 | 1.00 | 29.25 |
| 3918 | CG | LYS | A | 276 | 71.101 | 78.163 | -8.408 | 1.00 | 31.10 |
| 3921 | CD | LYS | A | 276 | 71.288 | 77.283 | -9.637 | 1.00 | 34.04 |
| 3924 | CE | LYS | A | 276 | 72.514 | 77.689 | -10.473 | 1.00 | 35.05 |
| 3927 | NZ | LYS | A | 276 | 73.803 | 77.493 | -9.748 | 1.00 | 35.48 |
| 3931 | C | LYS | A | 276 | 70.130 | 76.552 | -6.132 | 1.00 | 28.37 |
| 3932 | O | LYS | A | 276 | 70.987 | 75.692 | -6.347 | 1.00 | 28.80 |
| 3933 | N | LYS | A | 277 | 70.054 | 77.222 | -4.986 | 1.00 | 28.08 |
| 3935 | CA | LYS | A | 277 | 70.938 | 76.890 | -3.873 | 1.00 | 27.92 |
| 3937 | CB | LYS | A | 277 | 70.723 | 77.824 | -2.675 | 1.00 | 28.22 |
| 3940 | CG | LYS | A | 277 | 71.163 | 79.279 | -2.921 | 1.00 | 30.08 |
| 3943 | CD | LYS | A | 277 | 72.546 | 79.581 | -2.376 | 1.00 | 31.98 |
| 3946 | CE | LYS | A | 277 | 72.871 | 81.085 | -2.414 | 1.00 | 32.86 |

FIGURE 3 (Cont.)

| A | B | C | D | E | F | G | H | I | J |
|---|---|---|---|---|---|---|---|---|---|
| 3949 | NZ | LYS | A | 277 | 74.277 | 81.323 | -2.846 | 1.00 | 33.80 |
| 3953 | C | LYS | A | 277 | 70.680 | 75.438 | -3.453 | 1.00 | 27.24 |
| 3954 | O | LYS | A | 277 | 71.620 | 74.699 | -3.201 | 1.00 | 26.52 |
| 3955 | N | ALA | A | 278 | 69.411 | 75.041 | -3.393 | 1.00 | 26.71 |
| 3957 | CA | ALA | A | 278 | 69.053 | 73.682 | -2.960 | 1.00 | 26.99 |
| 3959 | CB | ALA | A | 278 | 67.544 | 73.546 | -2.823 | 1.00 | 26.84 |
| 3963 | C | ALA | A | 278 | 69.589 | 72.651 | -3.949 | 1.00 | 27.26 |
| 3964 | O | ALA | A | 278 | 70.141 | 71.636 | -3.566 | 1.00 | 26.69 |
| 3965 | N | ARG | A | 279 | 69.427 | 72.948 | -5.234 | 1.00 | 27.61 |
| 3967 | CA | ARG | A | 279 | 69.869 | 72.070 | -6.311 | 1.00 | 28.16 |
| 3969 | CB | ARG | A | 279 | 69.332 | 72.603 | -7.641 | 1.00 | 28.87 |
| 3972 | CG | ARG | A | 279 | 69.910 | 71.996 | -8.886 | 1.00 | 32.19 |
| 3975 | CD | ARG | A | 279 | 69.160 | 72.414 | -10.158 | 1.00 | 35.33 |
| 3978 | NE | ARG | A | 279 | 68.039 | 73.319 | -9.871 | 1.00 | 38.00 |
| 3980 | CZ | ARG | A | 279 | 68.005 | 74.632 | -10.133 | 1.00 | 38.95 |
| 3981 | NH1 | ARG | A | 279 | 69.027 | 75.256 | -10.711 | 1.00 | 40.27 |
| 3984 | NH2 | ARG | A | 279 | 66.924 | 75.329 | -9.815 | 1.00 | 38.71 |
| 3987 | C | ARG | A | 279 | 71.389 | 71.923 | -6.336 | 1.00 | 27.24 |
| 3988 | O | ARG | A | 279 | 71.885 | 70.819 | -6.512 | 1.00 | 27.02 |
| 3989 | N | ASP | A | 280 | 72.116 | 73.021 | -6.128 | 1.00 | 26.36 |
| 3991 | CA | ASP | A | 280 | 73.586 | 72.995 | -6.059 | 1.00 | 25.90 |
| 3993 | CB | ASP | A | 280 | 74.150 | 74.420 | -6.005 | 1.00 | 26.39 |
| 3996 | CG | ASP | A | 280 | 74.006 | 75.175 | -7.335 | 1.00 | 28.03 |
| 3997 | OD1 | ASP | A | 280 | 74.090 | 76.423 | -7.315 | 1.00 | 30.25 |
| 3998 | OD2 | ASP | A | 280 | 73.790 | 74.623 | -8.433 | 1.00 | 28.83 |
| 3999 | C | ASP | A | 280 | 74.086 | 72.217 | -4.828 | 1.00 | 25.37 |
| 4000 | O | ASP | A | 280 | 75.128 | 71.557 | -4.873 | 1.00 | 24.74 |
| 4001 | N | LEU | A | 281 | 73.346 | 72.307 | -3.727 | 1.00 | 24.45 |
| 4003 | CA | LEU | A | 281 | 73.688 | 71.553 | -2.529 | 1.00 | 24.47 |
| 4005 | CB | LEU | A | 281 | 72.825 | 71.999 | -1.335 | 1.00 | 24.55 |
| 4008 | CG | LEU | A | 281 | 73.246 | 73.324 | -0.700 | 1.00 | 23.94 |
| 4010 | CD1 | LEU | A | 281 | 72.129 | 73.904 | 0.129 | 1.00 | 23.80 |
| 4014 | CD2 | LEU | A | 281 | 74.506 | 73.133 | 0.150 | 1.00 | 23.78 |
| 4018 | C | LEU | A | 281 | 73.526 | 70.048 | -2.781 | 1.00 | 24.25 |
| 4019 | O | LEU | A | 281 | 74.364 | 69.262 | -2.353 | 1.00 | 23.54 |
| 4020 | N | ILE | A | 282 | 72.459 | 69.660 | -3.475 | 1.00 | 24.75 |
| 4022 | CA | ILE | A | 282 | 72.221 | 68.242 | -3.788 | 1.00 | 25.66 |
| 4024 | CB | ILE | A | 282 | 70.771 | 67.998 | -4.289 | 1.00 | 25.32 |
| 4026 | CG1 | ILE | A | 282 | 69.745 | 68.291 | -3.185 | 1.00 | 25.41 |
| 4029 | CD1 | ILE | A | 282 | 70.153 | 67.917 | -1.800 | 1.00 | 25.34 |
| 4033 | CG2 | ILE | A | 282 | 70.592 | 66.548 | -4.826 | 1.00 | 25.27 |
| 4037 | C | ILE | A | 282 | 73.241 | 67.719 | -4.788 | 1.00 | 26.42 |
| 4038 | O | ILE | A | 282 | 73.728 | 66.602 | -4.641 | 1.00 | 26.98 |
| 4039 | N | ASP | A | 283 | 73.571 | 68.511 | -5.802 | 1.00 | 27.38 |
| 4041 | CA | ASP | A | 283 | 74.607 | 68.111 | -6.753 | 1.00 | 28.16 |
| 4043 | CB | ASP | A | 283 | 74.799 | 69.165 | -7.851 | 1.00 | 28.99 |
| 4046 | CG | ASP | A | 283 | 73.578 | 69.319 | -8.758 | 1.00 | 31.72 |
| 4047 | OD1 | ASP | A | 283 | 73.510 | 70.341 | -9.477 | 1.00 | 36.96 |
| 4048 | OD2 | ASP | A | 283 | 72.644 | 68.493 | -8.830 | 1.00 | 35.17 |
| 4049 | C | ASP | A | 283 | 75.929 | 67.903 | -5.997 | 1.00 | 27.86 |
| 4050 | O | ASP | A | 283 | 76.696 | 67.003 | -6.319 | 1.00 | 27.48 |
| 4051 | N | ASP | A | 284 | 76.189 | 68.740 | -4.988 | 1.00 | 27.56 |

FIGURE 3 (Cont.)

| A | B | C | D | E | F | G | H | I | J |
|---|---|---|---|---|---|---|---|---|---|
| 4053 | CA | ASP | A | 284 | 77.405 | 68.623 | -4.177 | 1.00 | 27.43 |
| 4055 | CB | ASP | A | 284 | 77.573 | 69.869 | -3.296 | 1.00 | 27.98 |
| 4058 | CG | ASP | A | 284 | 78.753 | 69.774 | -2.351 | 1.00 | 29.55 |
| 4059 | OD1 | ASP | A | 284 | 79.871 | 70.166 | -2.754 | 1.00 | 34.48 |
| 4060 | OD2 | ASP | A | 284 | 78.662 | 69.347 | -1.179 | 1.00 | 30.96 |
| 4061 | C | ASP | A | 284 | 77.344 | 67.351 | -3.320 | 1.00 | 26.91 |
| 4062 | O | ASP | A | 284 | 78.347 | 66.666 | -3.137 | 1.00 | 26.70 |
| 4063 | N | ALA | A | 285 | 76.154 | 67.039 | -2.817 | 1.00 | 26.35 |
| 4065 | CA | ALA | A | 285 | 75.935 | 65.830 | -2.041 | 1.00 | 26.26 |
| 4067 | CB | ALA | A | 285 | 74.514 | 65.811 | -1.452 | 1.00 | 26.18 |
| 4071 | C | ALA | A | 285 | 76.164 | 64.607 | -2.913 | 1.00 | 26.41 |
| 4072 | O | ALA | A | 285 | 76.774 | 63.648 | -2.469 | 1.00 | 26.46 |
| 4073 | N | ARG | A | 286 | 75.687 | 64.647 | -4.156 | 1.00 | 26.93 |
| 4075 | CA | ARG | A | 286 | 75.888 | 63.543 | -5.095 | 1.00 | 27.77 |
| 4077 | CB | ARG | A | 286 | 75.153 | 63.778 | -6.413 | 1.00 | 28.06 |
| 4080 | CG | ARG | A | 286 | 73.650 | 63.500 | -6.353 | 1.00 | 30.42 |
| 4083 | CD | ARG | A | 286 | 72.949 | 63.511 | -7.727 | 1.00 | 33.16 |
| 4086 | NE | ARG | A | 286 | 71.739 | 62.694 | -7.695 | 1.00 | 35.04 |
| 4088 | CZ | ARG | A | 286 | 71.709 | 61.365 | -7.828 | 1.00 | 37.56 |
| 4089 | NH1 | ARG | A | 286 | 72.820 | 60.653 | -8.041 | 1.00 | 37.77 |
| 4092 | NH2 | ARG | A | 286 | 70.544 | 60.731 | -7.757 | 1.00 | 37.95 |
| 4095 | C | ARG | A | 286 | 77.377 | 63.333 | -5.364 | 1.00 | 28.02 |
| 4096 | O | ARG | A | 286 | 77.837 | 62.202 | -5.438 | 1.00 | 27.64 |
| 4097 | N | GLN | A | 287 | 78.120 | 64.427 | -5.478 | 1.00 | 28.41 |
| 4099 | CA | GLN | A | 287 | 79.550 | 64.352 | -5.768 | 1.00 | 29.05 |
| 4101 | CB | GLN | A | 287 | 80.163 | 65.742 | -5.984 | 1.00 | 29.26 |
| 4104 | CG | GLN | A | 287 | 79.870 | 66.348 | -7.343 | 1.00 | 31.16 |
| 4107 | CD | GLN | A | 287 | 80.342 | 65.469 | -8.494 | 1.00 | 34.10 |
| 4108 | OE1 | GLN | A | 287 | 81.544 | 65.280 | -8.687 | 1.00 | 36.57 |
| 4109 | NE2 | GLN | A | 287 | 79.396 | 64.921 | -9.248 | 1.00 | 34.65 |
| 4112 | C | GLN | A | 287 | 80.260 | 63.638 | -4.645 | 1.00 | 28.84 |
| 4113 | O | GLN | A | 287 | 81.060 | 62.747 | -4.898 | 1.00 | 29.43 |
| 4114 | N | SER | A | 288 | 79.946 | 64.002 | -3.403 | 1.00 | 28.72 |
| 4116 | CA | SER | A | 288 | 80.514 | 63.331 | -2.234 | 1.00 | 28.70 |
| 4118 | CB | SER | A | 288 | 79.948 | 63.912 | -0.930 | 1.00 | 28.50 |
| 4121 | OG | SER | A | 288 | 80.451 | 65.214 | -0.693 | 1.00 | 28.19 |
| 4123 | C | SER | A | 288 | 80.254 | 61.824 | -2.255 | 1.00 | 28.86 |
| 4124 | O | SER | A | 288 | 81.143 | 61.046 | -1.948 | 1.00 | 28.79 |
| 4125 | N | LEU | A | 289 | 79.028 | 61.428 | -2.579 | 1.00 | 29.44 |
| 4127 | CA | LEU | A | 289 | 78.666 | 60.005 | -2.650 | 1.00 | 29.79 |
| 4129 | CB | LEU | A | 289 | 77.163 | 59.818 | -2.910 | 1.00 | 29.50 |
| 4132 | CG | LEU | A | 289 | 76.184 | 60.273 | -1.815 | 1.00 | 28.59 |
| 4134 | CD1 | LEU | A | 289 | 74.747 | 60.026 | -2.249 | 1.00 | 28.94 |
| 4138 | CD2 | LEU | A | 289 | 76.473 | 59.585 | -0.493 | 1.00 | 27.92 |
| 4142 | C | LEU | A | 289 | 79.472 | 59.246 | -3.717 | 1.00 | 30.81 |
| 4143 | O | LEU | A | 289 | 79.732 | 58.062 | -3.545 | 1.00 | 30.71 |
| 4144 | N | LYS | A | 290 | 79.870 | 59.919 | -4.800 | 1.00 | 31.59 |
| 4146 | CA | LYS | A | 290 | 80.704 | 59.288 | -5.837 | 1.00 | 32.26 |
| 4148 | CB | LYS | A | 290 | 80.998 | 60.268 | -6.989 | 1.00 | 32.55 |
| 4151 | CG | LYS | A | 290 | 79.794 | 60.560 | -7.898 | 1.00 | 34.13 |
| 4154 | CD | LYS | A | 290 | 80.188 | 61.386 | -9.153 | 1.00 | 35.23 |
| 4157 | CE | LYS | A | 290 | 79.129 | 61.238 | -10.259 | 1.00 | 36.81 |

FIGURE 3 (Cont.)

| A | B | C | D | E | F | G | H | I | J |
|---|---|---|---|---|---|---|---|---|---|
| 4160 | NZ | LYS | A | 290 | 79.083 | 62.387 | -11.229 | 1.00 | 37.86 |
| 4164 | C | LYS | A | 290 | 82.012 | 58.741 | -5.256 | 1.00 | 32.60 |
| 4165 | O | LYS | A | 290 | 82.471 | 57.679 | -5.650 | 1.00 | 33.03 |
| 4166 | N | GLN | A | 291 | 82.589 | 59.462 | -4.300 | 1.00 | 33.38 |
| 4168 | CA | GLN | A | 291 | 83.796 | 59.026 | -3.599 | 1.00 | 34.01 |
| 4170 | CB | GLN | A | 291 | 84.253 | 60.103 | -2.607 | 1.00 | 34.60 |
| 4173 | CG | GLN | A | 291 | 84.614 | 61.448 | -3.230 | 1.00 | 35.87 |
| 4176 | CD | GLN | A | 291 | 85.108 | 62.446 | -2.197 | 1.00 | 37.47 |
| 4177 | OE1 | GLN | A | 291 | 86.039 | 62.155 | -1.446 | 1.00 | 39.36 |
| 4178 | NE2 | GLN | A | 291 | 84.483 | 63.615 | -2.149 | 1.00 | 39.06 |
| 4181 | C | GLN | A | 291 | 83.589 | 57.715 | -2.830 | 1.00 | 34.18 |
| 4182 | O | GLN | A | 291 | 84.513 | 56.909 | -2.707 | 1.00 | 34.15 |
| 4183 | N | LEU | A | 292 | 82.385 | 57.520 | -2.294 | 1.00 | 33.99 |
| 4185 | CA | LEU | A | 292 | 82.047 | 56.287 | -1.591 | 1.00 | 34.26 |
| 4187 | CB | LEU | A | 292 | 80.849 | 56.509 | -0.670 | 1.00 | 33.95 |
| 4190 | CG | LEU | A | 292 | 81.061 | 57.578 | 0.398 | 1.00 | 33.40 |
| 4192 | CD1 | LEU | A | 292 | 79.805 | 57.720 | 1.223 | 1.00 | 33.09 |
| 4196 | CD2 | LEU | A | 292 | 82.269 | 57.242 | 1.274 | 1.00 | 33.91 |
| 4200 | C | LEU | A | 292 | 81.738 | 55.137 | -2.533 | 1.00 | 34.79 |
| 4201 | O | LEU | A | 292 | 82.073 | 53.989 | -2.239 | 1.00 | 34.64 |
| 4202 | N | ALA | A | 293 | 81.072 | 55.445 | -3.642 | 1.00 | 35.56 |
| 4204 | CA | ALA | A | 293 | 80.741 | 54.450 | -4.660 | 1.00 | 36.49 |
| 4206 | CB | ALA | A | 293 | 79.825 | 55.061 | -5.712 | 1.00 | 36.38 |
| 4210 | C | ALA | A | 293 | 82.012 | 53.886 | -5.311 | 1.00 | 37.32 |
| 4211 | O | ALA | A | 293 | 82.015 | 52.758 | -5.799 | 1.00 | 37.70 |
| 4212 | N | GLU | A | 294 | 83.075 | 54.690 | -5.296 | 1.00 | 38.52 |
| 4214 | CA | GLU | A | 294 | 84.421 | 54.297 | -5.744 | 1.00 | 39.54 |
| 4216 | CB | GLU | A | 294 | 85.353 | 55.513 | -5.677 | 1.00 | 39.78 |
| 4219 | CG | GLU | A | 294 | 86.404 | 55.572 | -6.767 | 1.00 | 41.97 |
| 4222 | CD | GLU | A | 294 | 86.407 | 56.897 | -7.488 | 1.00 | 43.76 |
| 4223 | OE1 | GLU | A | 294 | 86.681 | 57.915 | -6.825 | 1.00 | 46.66 |
| 4224 | OE2 | GLU | A | 294 | 86.129 | 56.921 | -8.705 | 1.00 | 45.53 |
| 4225 | C | GLU | A | 294 | 85.034 | 53.179 | -4.895 | 1.00 | 39.49 |
| 4226 | O | GLU | A | 294 | 85.883 | 52.422 | -5.363 | 1.00 | 40.00 |
| 4227 | N | GLN | A | 295 | 84.617 | 53.112 | -3.638 | 1.00 | 39.43 |
| 4229 | CA | GLN | A | 295 | 85.085 | 52.109 | -2.700 | 1.00 | 39.30 |
| 4231 | CB | GLN | A | 295 | 85.306 | 52.752 | -1.324 | 1.00 | 39.51 |
| 4234 | CG | GLN | A | 295 | 86.094 | 54.061 | -1.348 | 1.00 | 40.85 |
| 4237 | CD | GLN | A | 295 | 86.003 | 54.825 | -0.033 | 1.00 | 42.68 |
| 4238 | OE1 | GLN | A | 295 | 85.958 | 54.217 | 1.037 | 1.00 | 44.83 |
| 4239 | NE2 | GLN | A | 295 | 85.983 | 56.156 | -0.110 | 1.00 | 42.30 |
| 4242 | C | GLN | A | 295 | 84.087 | 50.944 | -2.594 | 1.00 | 38.62 |
| 4243 | O | GLN | A | 295 | 84.083 | 50.210 | -1.605 | 1.00 | 38.99 |
| 4244 | N | SER | A | 296 | 83.250 | 50.794 | -3.616 | 1.00 | 37.61 |
| 4246 | CA | SER | A | 296 | 82.260 | 49.718 | -3.721 | 1.00 | 36.98 |
| 4248 | CB | SER | A | 296 | 82.963 | 48.362 | -3.884 | 1.00 | 37.17 |
| 4251 | OG | SER | A | 296 | 83.487 | 48.241 | -5.197 | 1.00 | 38.77 |
| 4253 | C | SER | A | 296 | 81.210 | 49.685 | -2.598 | 1.00 | 35.68 |
| 4254 | O | SER | A | 296 | 80.722 | 48.617 | -2.206 | 1.00 | 35.55 |
| 4255 | N | LEU | A | 297 | 80.867 | 50.865 | -2.092 | 1.00 | 34.25 |
| 4257 | CA | LEU | A | 297 | 79.710 | 51.032 | -1.218 | 1.00 | 32.88 |
| 4259 | CB | LEU | A | 297 | 79.997 | 52.090 | -0.161 | 1.00 | 32.92 |

FIGURE 3 (Cont.)

| A | B | C | D | E | F | G | H | I | J |
|---|---|---|---|---|---|---|---|---|---|
| 4262 | CG | LEU | A | 297 | 81.178 | 51.793 | 0.755 | 1.00 | 33.21 |
| 4264 | CD1 | LEU | A | 297 | 81.567 | 53.040 | 1.532 | 1.00 | 33.05 |
| 4268 | CD2 | LEU | A | 297 | 80.872 | 50.609 | 1.704 | 1.00 | 33.61 |
| 4272 | C | LEU | A | 297 | 78.507 | 51.432 | -2.074 | 1.00 | 31.66 |
| 4273 | O | LEU | A | 297 | 78.621 | 52.255 | -2.988 | 1.00 | 31.32 |
| 4274 | N | ASP | A | 298 | 77.361 | 50.827 | -1.799 | 1.00 | 30.63 |
| 4276 | CA | ASP | A | 298 | 76.127 | 51.123 | -2.528 | 1.00 | 29.60 |
| 4278 | CB | ASP | A | 298 | 75.150 | 49.956 | -2.371 | 1.00 | 29.83 |
| 4281 | CG | ASP | A | 298 | 73.911 | 50.089 | -3.251 | 1.00 | 30.98 |
| 4282 | OD1 | ASP | A | 298 | 73.673 | 51.177 | -3.843 | 1.00 | 30.78 |
| 4283 | OD2 | ASP | A | 298 | 73.117 | 49.135 | -3.407 | 1.00 | 32.78 |
| 4284 | C | ASP | A | 298 | 75.516 | 52.431 | -2.021 | 1.00 | 28.62 |
| 4285 | O | ASP | A | 298 | 74.919 | 52.474 | -0.953 | 1.00 | 27.93 |
| 4286 | N | THR | A | 299 | 75.655 | 53.496 | -2.801 | 1.00 | 27.78 |
| 4288 | CA | THR | A | 299 | 75.152 | 54.812 | -2.395 | 1.00 | 27.48 |
| 4290 | CB | THR | A | 299 | 76.121 | 55.907 | -2.850 | 1.00 | 27.79 |
| 4292 | OG1 | THR | A | 299 | 76.198 | 55.923 | -4.282 | 1.00 | 27.64 |
| 4294 | CG2 | THR | A | 299 | 77.522 | 55.612 | -2.397 | 1.00 | 27.86 |
| 4298 | C | THR | A | 299 | 73.775 | 55.130 | -2.963 | 1.00 | 26.98 |
| 4299 | O | THR | A | 299 | 73.314 | 56.269 | -2.852 | 1.00 | 26.90 |
| 4300 | N | SER | A | 300 | 73.115 | 54.136 | -3.549 | 1.00 | 25.87 |
| 4302 | CA | SER | A | 300 | 71.884 | 54.371 | -4.303 | 1.00 | 25.78 |
| 4304 | CB | SER | A | 300 | 71.469 | 53.116 | -5.083 | 1.00 | 25.66 |
| 4307 | OG | SER | A | 300 | 71.181 | 52.042 | -4.210 | 1.00 | 28.03 |
| 4309 | C | SER | A | 300 | 70.718 | 54.922 | -3.460 | 1.00 | 24.86 |
| 4310 | O | SER | A | 300 | 69.989 | 55.799 | -3.922 | 1.00 | 24.04 |
| 4311 | N | ALA | A | 301 | 70.538 | 54.423 | -2.237 | 1.00 | 24.31 |
| 4313 | CA | ALA | A | 301 | 69.491 | 54.957 | -1.356 | 1.00 | 23.85 |
| 4315 | CB | ALA | A | 301 | 69.266 | 54.058 | -0.138 | 1.00 | 23.74 |
| 4319 | C | ALA | A | 301 | 69.813 | 56.402 | -0.925 | 1.00 | 23.51 |
| 4320 | O | ALA | A | 301 | 68.927 | 57.234 | -0.865 | 1.00 | 22.49 |
| 4321 | N | LEU | A | 302 | 71.082 | 56.696 | -0.670 | 1.00 | 23.59 |
| 4323 | CA | LEU | A | 302 | 71.476 | 58.050 | -0.254 | 1.00 | 24.04 |
| 4325 | CB | LEU | A | 302 | 72.893 | 58.059 | 0.321 | 1.00 | 23.68 |
| 4328 | CG | LEU | A | 302 | 73.047 | 57.380 | 1.677 | 1.00 | 24.07 |
| 4330 | CD1 | LEU | A | 302 | 74.495 | 57.511 | 2.165 | 1.00 | 25.59 |
| 4334 | CD2 | LEU | A | 302 | 72.085 | 57.972 | 2.680 | 1.00 | 24.26 |
| 4338 | C | LEU | A | 302 | 71.375 | 59.070 | -1.370 | 1.00 | 24.05 |
| 4339 | O | LEU | A | 302 | 71.128 | 60.238 | -1.104 | 1.00 | 24.30 |
| 4340 | N | GLU | A | 303 | 71.575 | 58.648 | -2.614 | 1.00 | 24.92 |
| 4342 | CA | GLU | A | 303 | 71.455 | 59.578 | -3.734 | 1.00 | 25.79 |
| 4344 | CB | GLU | A | 303 | 72.238 | 59.158 | -4.988 | 1.00 | 26.38 |
| 4347 | CG | GLU | A | 303 | 72.152 | 57.732 | -5.448 | 1.00 | 28.99 |
| 4350 | CD | GLU | A | 303 | 73.344 | 57.345 | -6.333 | 1.00 | 31.29 |
| 4351 | OE1 | GLU | A | 303 | 73.673 | 58.127 | -7.247 | 1.00 | 31.21 |
| 4352 | OE2 | GLU | A | 303 | 73.966 | 56.274 | -6.098 | 1.00 | 33.39 |
| 4353 | C | GLU | A | 303 | 69.982 | 59.834 | -4.045 | 1.00 | 25.52 |
| 4354 | O | GLU | A | 303 | 69.605 | 60.961 | -4.347 | 1.00 | 25.13 |
| 4355 | N | ALA | A | 304 | 69.152 | 58.797 | -3.927 | 1.00 | 25.73 |
| 4357 | CA | ALA | A | 304 | 67.709 | 58.953 | -4.149 | 1.00 | 25.33 |
| 4359 | CB | ALA | A | 304 | 67.020 | 57.609 | -4.201 | 1.00 | 25.75 |
| 4363 | C | ALA | A | 304 | 67.099 | 59.830 | -3.059 | 1.00 | 25.32 |

FIGURE 3 (Cont.)

| A | B | C | D | E | F | G | H | I | J |
|---|---|---|---|---|---|---|---|---|---|
| 4364 | O | ALA | A | 304 | 66.202 | 60.633 | -3.328 | 1.00 | 24.76 |
| 4365 | N | LEU | A | 305 | 67.591 | 59.677 | -1.828 | 1.00 | 25.18 |
| 4367 | CA | LEU | A | 305 | 67.117 | 60.499 | -0.711 | 1.00 | 25.23 |
| 4369 | CB | LEU | A | 305 | 67.707 | 59.988 | 0.608 | 1.00 | 25.28 |
| 4372 | CG | LEU | A | 305 | 67.209 | 60.548 | 1.945 | 1.00 | 27.23 |
| 4374 | CD1 | LEU | A | 305 | 67.788 | 61.919 | 2.199 | 1.00 | 29.43 |
| 4378 | CD2 | LEU | A | 305 | 65.687 | 60.595 | 2.012 | 1.00 | 28.69 |
| 4382 | C | LEU | A | 305 | 67.520 | 61.954 | -0.959 | 1.00 | 24.32 |
| 4383 | O | LEU | A | 305 | 66.719 | 62.872 | -0.780 | 1.00 | 23.70 |
| 4384 | N | ALA | A | 306 | 68.758 | 62.146 | -1.399 | 1.00 | 23.80 |
| 4386 | CA | ALA | A | 306 | 69.282 | 63.481 | -1.672 | 1.00 | 24.14 |
| 4388 | CB | ALA | A | 306 | 70.733 | 63.405 | -2.153 | 1.00 | 24.17 |
| 4392 | C | ALA | A | 306 | 68.410 | 64.218 | -2.687 | 1.00 | 24.07 |
| 4393 | O | ALA | A | 306 | 68.063 | 65.382 | -2.480 | 1.00 | 23.69 |
| 4394 | N | ASP | A | 307 | 68.027 | 63.538 | -3.761 | 1.00 | 24.24 |
| 4396 | CA | ASP | A | 307 | 67.146 | 64.143 | -4.772 | 1.00 | 24.99 |
| 4398 | CB | ASP | A | 307 | 67.015 | 63.231 | -5.990 | 1.00 | 25.46 |
| 4401 | CG | ASP | A | 307 | 68.259 | 63.225 | -6.840 | 1.00 | 27.73 |
| 4402 | OD1 | ASP | A | 307 | 68.311 | 62.445 | -7.819 | 1.00 | 32.11 |
| 4403 | OD2 | ASP | A | 307 | 69.231 | 63.968 | -6.614 | 1.00 | 30.06 |
| 4404 | C | ASP | A | 307 | 65.751 | 64.427 | -4.242 | 1.00 | 24.15 |
| 4405 | O | ASP | A | 307 | 65.146 | 65.464 | -4.565 | 1.00 | 23.53 |
| 4406 | N | TYR | A | 308 | 65.233 | 63.497 | -3.445 | 1.00 | 23.64 |
| 4408 | CA | TYR | A | 308 | 63.890 | 63.636 | -2.889 | 1.00 | 23.49 |
| 4410 | CB | TYR | A | 308 | 63.465 | 62.369 | -2.150 | 1.00 | 23.53 |
| 4413 | CG | TYR | A | 308 | 62.066 | 62.432 | -1.543 | 1.00 | 23.83 |
| 4414 | CD1 | TYR | A | 308 | 61.882 | 62.358 | -0.171 | 1.00 | 24.83 |
| 4416 | CE1 | TYR | A | 308 | 60.607 | 62.425 | 0.392 | 1.00 | 25.12 |
| 4418 | CZ | TYR | A | 308 | 59.501 | 62.553 | -0.424 | 1.00 | 26.00 |
| 4419 | OH | TYR | A | 308 | 58.239 | 62.602 | 0.134 | 1.00 | 26.70 |
| 4421 | CE2 | TYR | A | 308 | 59.660 | 62.622 | -1.798 | 1.00 | 25.30 |
| 4423 | CD2 | TYR | A | 308 | 60.939 | 62.568 | -2.344 | 1.00 | 23.99 |
| 4425 | C | TYR | A | 308 | 63.824 | 64.844 | -1.957 | 1.00 | 23.57 |
| 4426 | O | TYR | A | 308 | 62.829 | 65.529 | -1.919 | 1.00 | 22.72 |
| 4427 | N | ILE | A | 309 | 64.902 | 65.112 | -1.229 | 1.00 | 24.12 |
| 4429 | CA | ILE | A | 309 | 64.949 | 66.247 | -0.301 | 1.00 | 24.93 |
| 4431 | CB | ILE | A | 309 | 66.333 | 66.304 | 0.411 | 1.00 | 24.90 |
| 4433 | CG1 | ILE | A | 309 | 66.333 | 65.285 | 1.553 | 1.00 | 25.34 |
| 4436 | CD1 | ILE | A | 309 | 67.675 | 65.077 | 2.197 | 1.00 | 27.41 |
| 4440 | CG2 | ILE | A | 309 | 66.639 | 67.710 | 0.943 | 1.00 | 25.11 |
| 4444 | C | ILE | A | 309 | 64.575 | 67.576 | -0.977 | 1.00 | 25.41 |
| 4445 | O | ILE | A | 309 | 64.017 | 68.468 | -0.326 | 1.00 | 25.21 |
| 4446 | N | ILE | A | 310 | 64.848 | 67.702 | -2.274 | 1.00 | 25.98 |
| 4448 | CA | ILE | A | 310 | 64.481 | 68.928 | -3.003 | 1.00 | 26.46 |
| 4450 | CB | ILE | A | 310 | 65.736 | 69.586 | -3.590 | 1.00 | 26.50 |
| 4452 | CG1 | ILE | A | 310 | 66.349 | 68.722 | -4.700 | 1.00 | 26.76 |
| 4455 | CD1 | ILE | A | 310 | 67.350 | 69.472 | -5.530 | 1.00 | 27.27 |
| 4459 | CG2 | ILE | A | 310 | 66.729 | 69.819 | -2.491 | 1.00 | 26.11 |
| 4463 | C | ILE | A | 310 | 63.393 | 68.781 | -4.066 | 1.00 | 26.91 |
| 4464 | O | ILE | A | 310 | 62.930 | 69.779 | -4.622 | 1.00 | 26.80 |
| 4465 | N | GLN | A | 311 | 62.982 | 67.543 | -4.337 | 1.00 | 26.94 |
| 4467 | CA | GLN | A | 311 | 61.911 | 67.267 | -5.284 | 1.00 | 27.25 |

FIGURE 3 (Cont.)

| A | B | C | D | E | F | G | H | I | J |
|---|---|---|---|---|---|---|---|---|---|
| 4469 | CB | GLN | A | 311 | 62.217 | 65.999 | -6.089 | 1.00 | 27.44 |
| 4472 | CG | GLN | A | 311 | 63.241 | 66.219 | -7.186 | 1.00 | 30.05 |
| 4475 | CD | GLN | A | 311 | 63.720 | 64.922 | -7.830 | 1.00 | 33.37 |
| 4476 | OE1 | GLN | A | 311 | 64.730 | 64.920 | -8.521 | 1.00 | 36.33 |
| 4477 | NE2 | GLN | A | 311 | 62.999 | 63.828 | -7.606 | 1.00 | 34.01 |
| 4480 | C | GLN | A | 311 | 60.573 | 67.102 | -4.575 | 1.00 | 26.71 |
| 4481 | O | GLN | A | 311 | 59.514 | 67.225 | -5.193 | 1.00 | 27.01 |
| 4482 | N | ARG | A | 312 | 60.620 | 66.825 | -3.280 | 1.00 | 26.09 |
| 4484 | CA | ARG | A | 312 | 59.418 | 66.570 | -2.503 | 1.00 | 25.94 |
| 4486 | CB | ARG | A | 312 | 59.774 | 66.077 | -1.098 | 1.00 | 25.87 |
| 4489 | CG | ARG | A | 312 | 60.382 | 67.160 | -0.225 | 1.00 | 25.06 |
| 4492 | CD | ARG | A | 312 | 61.211 | 66.630 | 0.914 | 1.00 | 23.99 |
| 4495 | NE | ARG | A | 312 | 61.963 | 67.704 | 1.555 | 1.00 | 22.64 |
| 4497 | CZ | ARG | A | 312 | 61.503 | 68.481 | 2.528 | 1.00 | 19.61 |
| 4498 | NH1 | ARG | A | 312 | 62.286 | 69.429 | 3.025 | 1.00 | 20.15 |
| 4501 | NH2 | ARG | A | 312 | 60.289 | 68.325 | 3.008 | 1.00 | 19.15 |
| 4504 | C | ARG | A | 312 | 58.558 | 67.817 | -2.386 | 1.00 | 26.24 |
| 4505 | O | ARG | A | 312 | 59.053 | 68.938 | -2.448 | 1.00 | 25.48 |
| 4506 | N | ASN | A | 313 | 57.269 | 67.601 | -2.191 | 1.00 | 26.97 |
| 4508 | CA | ASN | A | 313 | 56.321 | 68.702 | -2.054 | 1.00 | 28.44 |
| 4510 | CB | ASN | A | 313 | 55.255 | 68.594 | -3.128 | 1.00 | 28.90 |
| 4513 | CG | ASN | A | 313 | 55.820 | 68.829 | -4.487 | 1.00 | 31.25 |
| 4514 | OD1 | ASN | A | 313 | 56.328 | 69.921 | -4.771 | 1.00 | 36.72 |
| 4515 | ND2 | ASN | A | 313 | 55.782 | 67.807 | -5.337 | 1.00 | 35.16 |
| 4518 | C | ASN | A | 313 | 55.711 | 68.729 | -0.676 | 1.00 | 28.47 |
| 4519 | O | ASN | A | 313 | 54.731 | 69.426 | -0.440 | 1.00 | 28.00 |
| 4520 | N | LYS | A | 314 | 56.326 | 67.972 | 0.234 | 1.00 | 29.44 |
| 4522 | CA | LYS | A | 314 | 55.925 | 67.944 | 1.642 | 1.00 | 30.19 |
| 4524 | CB | LYS | A | 314 | 54.722 | 67.029 | 1.835 | 1.00 | 30.27 |
| 4527 | CG | LYS | A | 314 | 54.874 | 65.638 | 1.202 | 1.00 | 32.14 |
| 4530 | CD | LYS | A | 314 | 54.635 | 64.498 | 2.180 | 1.00 | 34.17 |
| 4533 | CE | LYS | A | 314 | 53.660 | 63.459 | 1.652 | 1.00 | 35.54 |
| 4536 | NZ | LYS | A | 314 | 54.228 | 62.656 | 0.542 | 1.00 | 36.19 |
| 4540 | C | LYS | A | 314 | 57.081 | 67.487 | 2.528 | 1.00 | 30.38 |
| 4541 | O | LYS | A | 314 | 56.992 | 67.504 | 3.759 | 1.00 | 30.94 |
| 4542 | OXT | LYS | A | 314 | 58.130 | 67.081 | 2.028 | 1.00 | 30.00 |
| 4543 | N | ASP | B | 17 | 19.060 | 6.498 | -16.010 | 1.00 | 36.37 |
| 4545 | CA | ASP | B | 17 | 17.827 | 7.340 | -15.968 | 1.00 | 36.07 |
| 4547 | CB | ASP | B | 17 | 16.585 | 6.454 | -15.910 | 1.00 | 36.75 |
| 4550 | CG | ASP | B | 17 | 15.301 | 7.258 | -15.889 | 1.00 | 38.21 |
| 4551 | OD1 | ASP | B | 17 | 15.288 | 8.356 | -16.476 | 1.00 | 42.09 |
| 4552 | OD2 | ASP | B | 17 | 14.258 | 6.882 | -15.321 | 1.00 | 41.73 |
| 4553 | C | ASP | B | 17 | 17.853 | 8.266 | -14.742 | 1.00 | 35.62 |
| 4554 | O | ASP | B | 17 | 17.713 | 7.800 | -13.603 | 1.00 | 35.09 |
| 4557 | N | PHE | B | 18 | 18.002 | 9.572 | -14.969 | 1.00 | 34.42 |
| 4559 | CA | PHE | B | 18 | 18.233 | 10.472 | -13.845 | 1.00 | 33.65 |
| 4561 | CB | PHE | B | 18 | 18.831 | 11.812 | -14.264 | 1.00 | 33.54 |
| 4564 | CG | PHE | B | 18 | 19.286 | 12.629 | -13.097 | 1.00 | 32.06 |
| 4565 | CD1 | PHE | B | 18 | 20.342 | 12.202 | -12.312 | 1.00 | 31.59 |
| 4567 | CE1 | PHE | B | 18 | 20.747 | 12.940 | -11.217 | 1.00 | 31.53 |
| 4569 | CZ | PHE | B | 18 | 20.080 | 14.100 | -10.888 | 1.00 | 30.24 |
| 4571 | CE2 | PHE | B | 18 | 19.029 | 14.516 | -11.638 | 1.00 | 31.16 |

FIGURE 3 (Cont.)

| A | B | C | D | E | F | G | H | I | J |
|---|---|---|---|---|---|---|---|---|---|
| 4573 | CD2 | PHE | B | 18 | 18.621 | 13.779 | -12.739 | 1.00 | 32.52 |
| 4575 | C | PHE | B | 18 | 17.015 | 10.695 | -12.946 | 1.00 | 33.05 |
| 4576 | O | PHE | B | 18 | 17.179 | 10.672 | -11.738 | 1.00 | 32.55 |
| 4577 | N | PRO | B | 19 | 15.817 | 10.901 | -13.503 | 1.00 | 32.85 |
| 4578 | CA | PRO | B | 19 | 14.606 | 11.056 | -12.680 | 1.00 | 32.66 |
| 4580 | CB | PRO | B | 19 | 13.497 | 11.261 | -13.722 | 1.00 | 32.79 |
| 4583 | CG | PRO | B | 19 | 14.213 | 11.795 | -14.914 | 1.00 | 33.05 |
| 4586 | CD | PRO | B | 19 | 15.508 | 11.051 | -14.936 | 1.00 | 32.96 |
| 4589 | C | PRO | B | 19 | 14.285 | 9.869 | -11.768 | 1.00 | 32.36 |
| 4590 | O | PRO | B | 19 | 13.759 | 10.093 | -10.685 | 1.00 | 31.80 |
| 4591 | N | GLN | B | 20 | 14.594 | 8.643 | -12.190 | 1.00 | 31.98 |
| 4593 | CA | GLN | B | 20 | 14.399 | 7.478 | -11.329 | 1.00 | 32.12 |
| 4595 | CB | GLN | B | 20 | 14.282 | 6.175 | -12.145 | 1.00 | 32.62 |
| 4598 | CG | GLN | B | 20 | 12.872 | 5.922 | -12.758 | 1.00 | 35.79 |
| 4601 | CD | GLN | B | 20 | 11.784 | 5.507 | -11.736 | 1.00 | 38.90 |
| 4602 | OE1 | GLN | B | 20 | 11.382 | 4.327 | -11.677 | 1.00 | 40.51 |
| 4603 | NE2 | GLN | B | 20 | 11.292 | 6.479 | -10.956 | 1.00 | 40.37 |
| 4606 | C | GLN | B | 20 | 15.524 | 7.368 | -10.279 | 1.00 | 30.90 |
| 4607 | O | GLN | B | 20 | 15.304 | 6.829 | -9.213 | 1.00 | 30.46 |
| 4608 | N | GLN | B | 21 | 16.715 | 7.872 | -10.583 | 1.00 | 30.18 |
| 4610 | CA | GLN | B | 21 | 17.778 | 7.963 | -9.575 | 1.00 | 30.30 |
| 4612 | CB | GLN | B | 21 | 19.108 | 8.421 | -10.180 | 1.00 | 30.56 |
| 4615 | CG | GLN | B | 21 | 19.929 | 7.310 | -10.799 | 1.00 | 33.30 |
| 4618 | CD | GLN | B | 21 | 20.971 | 6.745 | -9.843 | 1.00 | 36.37 |
| 4619 | OE1 | GLN | B | 21 | 21.903 | 7.457 | -9.441 | 1.00 | 39.14 |
| 4620 | NE2 | GLN | B | 21 | 20.822 | 5.474 | -9.479 | 1.00 | 36.91 |
| 4623 | C | GLN | B | 21 | 17.364 | 8.924 | -8.464 | 1.00 | 29.14 |
| 4624 | O | GLN | B | 21 | 17.509 | 8.604 | -7.285 | 1.00 | 29.47 |
| 4625 | N | LEU | B | 22 | 16.838 | 10.086 | -8.841 | 1.00 | 27.84 |
| 4627 | CA | LEU | B | 22 | 16.384 | 11.074 | -7.864 | 1.00 | 27.57 |
| 4629 | CB | LEU | B | 22 | 15.793 | 12.309 | -8.546 | 1.00 | 27.88 |
| 4632 | CG | LEU | B | 22 | 16.740 | 13.324 | -9.180 | 1.00 | 28.18 |
| 4634 | CD1 | LEU | B | 22 | 15.884 | 14.370 | -9.884 | 1.00 | 28.62 |
| 4638 | CD2 | LEU | B | 22 | 17.667 | 13.973 | -8.145 | 1.00 | 28.38 |
| 4642 | C | LEU | B | 22 | 15.317 | 10.478 | -6.961 | 1.00 | 27.38 |
| 4643 | O | LEU | B | 22 | 15.364 | 10.643 | -5.741 | 1.00 | 26.09 |
| 4644 | N | GLU | B | 23 | 14.358 | 9.786 | -7.573 | 1.00 | 27.02 |
| 4646 | CA | GLU | B | 23 | 13.207 | 9.269 | -6.847 | 1.00 | 27.65 |
| 4648 | CB | GLU | B | 23 | 12.098 | 8.855 | -7.825 | 1.00 | 28.49 |
| 4651 | CG | GLU | B | 23 | 11.022 | 7.981 | -7.212 | 1.00 | 32.02 |
| 4654 | CD | GLU | B | 23 | 9.646 | 8.256 | -7.782 | 1.00 | 37.15 |
| 4655 | OE1 | GLU | B | 23 | 9.109 | 9.364 | -7.545 | 1.00 | 42.58 |
| 4656 | OE2 | GLU | B | 23 | 9.100 | 7.363 | -8.463 | 1.00 | 41.15 |
| 4657 | C | GLU | B | 23 | 13.618 | 8.112 | -5.938 | 1.00 | 26.50 |
| 4658 | O | GLU | B | 23 | 13.115 | 8.008 | -4.823 | 1.00 | 26.62 |
| 4659 | N | ALA | B | 24 | 14.513 | 7.250 | -6.421 | 1.00 | 25.43 |
| 4661 | CA | ALA | B | 24 | 15.092 | 6.179 | -5.610 | 1.00 | 24.85 |
| 4663 | CB | ALA | B | 24 | 16.021 | 5.297 | -6.443 | 1.00 | 24.98 |
| 4667 | C | ALA | B | 24 | 15.864 | 6.765 | -4.421 | 1.00 | 24.65 |
| 4668 | O | ALA | B | 24 | 15.827 | 6.211 | -3.318 | 1.00 | 23.25 |
| 4669 | N | CYS | B | 25 | 16.556 | 7.885 | -4.650 | 1.00 | 24.00 |
| 4671 | CA | CYS | B | 25 | 17.315 | 8.544 | -3.589 | 1.00 | 23.64 |

FIGURE 3 (Cont.)

| A | B | C | D | E | F | G | H | I | J |
|---|---|---|---|---|---|---|---|---|---|
| 4673 | CB | CYS | B | 25 | 18.217 | 9.650 | -4.152 | 1.00 | 23.72 |
| 4676 | SG | CYS | B | 25 | 19.117 | 10.582 | -2.885 | 1.00 | 22.22 |
| 4677 | C | CYS | B | 25 | 16.374 | 9.096 | -2.524 | 1.00 | 23.27 |
| 4678 | O | CYS | B | 25 | 16.578 | 8.876 | -1.336 | 1.00 | 23.22 |
| 4679 | N | VAL | B | 26 | 15.323 | 9.779 | -2.945 | 1.00 | 23.25 |
| 4681 | CA | VAL | B | 26 | 14.334 | 10.280 | -2.006 | 1.00 | 23.43 |
| 4683 | CB | VAL | B | 26 | 13.175 | 10.997 | -2.725 | 1.00 | 23.51 |
| 4685 | CG1 | VAL | B | 26 | 12.005 | 11.220 | -1.804 | 1.00 | 24.68 |
| 4689 | CG2 | VAL | B | 26 | 13.650 | 12.324 | -3.276 | 1.00 | 23.07 |
| 4693 | C | VAL | B | 26 | 13.811 | 9.132 | -1.138 | 1.00 | 23.73 |
| 4694 | O | VAL | B | 26 | 13.641 | 9.300 | 0.067 | 1.00 | 23.38 |
| 4695 | N | LYS | B | 27 | 13.581 | 7.964 | -1.737 | 1.00 | 23.54 |
| 4697 | CA | LYS | B | 27 | 13.012 | 6.852 | -0.972 | 1.00 | 24.03 |
| 4699 | CB | LYS | B | 27 | 12.440 | 5.765 | -1.891 | 1.00 | 24.27 |
| 4702 | CG | LYS | B | 27 | 10.995 | 6.086 | -2.256 | 1.00 | 27.21 |
| 4705 | CD | LYS | B | 27 | 10.544 | 5.567 | -3.606 | 1.00 | 31.82 |
| 4708 | CE | LYS | B | 27 | 9.032 | 5.811 | -3.762 | 1.00 | 33.94 |
| 4711 | NZ | LYS | B | 27 | 8.488 | 5.279 | -5.045 | 1.00 | 37.62 |
| 4715 | C | LYS | B | 27 | 14.026 | 6.287 | -0.004 | 1.00 | 22.89 |
| 4716 | O | LYS | B | 27 | 13.699 | 6.017 | 1.145 | 1.00 | 23.39 |
| 4717 | N | GLN | B | 28 | 15.257 | 6.124 | -0.468 | 1.00 | 22.27 |
| 4719 | CA | GLN | B | 28 | 16.335 | 5.645 | 0.380 | 1.00 | 21.89 |
| 4721 | CB | GLN | B | 28 | 17.623 | 5.496 | -0.423 | 1.00 | 21.61 |
| 4724 | CG | GLN | B | 28 | 18.810 | 4.946 | 0.352 | 1.00 | 21.80 |
| 4727 | CD | GLN | B | 28 | 18.683 | 3.471 | 0.705 | 1.00 | 23.69 |
| 4728 | OE1 | GLN | B | 28 | 19.316 | 2.999 | 1.657 | 1.00 | 25.82 |
| 4729 | NE2 | GLN | B | 28 | 17.882 | 2.742 | -0.054 | 1.00 | 22.57 |
| 4732 | C | GLN | B | 28 | 16.518 | 6.604 | 1.561 | 1.00 | 21.61 |
| 4733 | O | GLN | B | 28 | 16.596 | 6.163 | 2.704 | 1.00 | 21.00 |
| 4734 | N | ALA | B | 29 | 16.556 | 7.906 | 1.285 | 1.00 | 21.58 |
| 4736 | CA | ALA | B | 29 | 16.835 | 8.916 | 2.323 | 1.00 | 21.82 |
| 4738 | CB | ALA | B | 29 | 17.120 | 10.295 | 1.691 | 1.00 | 21.91 |
| 4742 | C | ALA | B | 29 | 15.684 | 9.025 | 3.317 | 1.00 | 21.73 |
| 4743 | O | ALA | B | 29 | 15.897 | 9.174 | 4.508 | 1.00 | 21.94 |
| 4744 | N | ASN | B | 30 | 14.461 | 8.963 | 2.822 | 1.00 | 22.10 |
| 4746 | CA | ASN | B | 30 | 13.289 | 8.996 | 3.699 | 1.00 | 22.38 |
| 4748 | CB | ASN | B | 30 | 12.013 | 9.035 | 2.869 | 1.00 | 22.05 |
| 4751 | CG | ASN | B | 30 | 11.720 | 10.416 | 2.319 | 1.00 | 23.08 |
| 4752 | OD1 | ASN | B | 30 | 12.374 | 11.387 | 2.689 | 1.00 | 22.74 |
| 4753 | ND2 | ASN | B | 30 | 10.732 | 10.510 | 1.424 | 1.00 | 22.09 |
| 4756 | C | ASN | B | 30 | 13.237 | 7.812 | 4.655 | 1.00 | 22.64 |
| 4757 | O | ASN | B | 30 | 12.857 | 7.962 | 5.811 | 1.00 | 22.97 |
| 4758 | N | GLN | B | 31 | 13.604 | 6.637 | 4.160 | 1.00 | 22.84 |
| 4760 | CA | GLN | B | 31 | 13.624 | 5.438 | 4.978 | 1.00 | 23.34 |
| 4762 | CB | GLN | B | 31 | 13.859 | 4.210 | 4.085 | 1.00 | 23.43 |
| 4765 | CG | GLN | B | 31 | 14.118 | 2.893 | 4.795 | 1.00 | 26.33 |
| 4768 | CD | GLN | B | 31 | 14.528 | 1.795 | 3.815 | 1.00 | 28.80 |
| 4769 | OE1 | GLN | B | 31 | 15.700 | 1.679 | 3.443 | 1.00 | 33.07 |
| 4770 | NE2 | GLN | B | 31 | 13.560 | 1.007 | 3.378 | 1.00 | 32.12 |
| 4773 | C | GLN | B | 31 | 14.720 | 5.582 | 6.039 | 1.00 | 23.12 |
| 4774 | O | GLN | B | 31 | 14.542 | 5.183 | 7.178 | 1.00 | 23.43 |
| 4775 | N | ALA | B | 32 | 15.855 | 6.146 | 5.653 | 1.00 | 22.32 |

FIGURE 3 (Cont.)

| A | B | C | D | E | F | G | H | I | J |
|---|---|---|---|---|---|---|---|---|---|
| 4777 | CA | ALA | B | 32 | 16.974 | 6.318 | 6.569 | 1.00 | 22.90 |
| 4779 | CB | ALA | B | 32 | 18.199 | 6.814 | 5.818 | 1.00 | 22.55 |
| 4783 | C | ALA | B | 32 | 16.590 | 7.296 | 7.679 | 1.00 | 22.66 |
| 4784 | O | ALA | B | 32 | 16.750 | 6.992 | 8.861 | 1.00 | 22.59 |
| 4785 | N | LEU | B | 33 | 16.069 | 8.457 | 7.288 | 1.00 | 22.88 |
| 4787 | CA | LEU | B | 33 | 15.603 | 9.462 | 8.244 | 1.00 | 23.19 |
| 4789 | CB | LEU | B | 33 | 14.980 | 10.661 | 7.521 | 1.00 | 23.23 |
| 4792 | CG | LEU | B | 33 | 15.948 | 11.654 | 6.869 | 1.00 | 24.18 |
| 4794 | CD1 | LEU | B | 33 | 15.253 | 12.531 | 5.850 | 1.00 | 25.04 |
| 4798 | CD2 | LEU | B | 33 | 16.610 | 12.528 | 7.925 | 1.00 | 25.95 |
| 4802 | C | LEU | B | 33 | 14.565 | 8.869 | 9.206 | 1.00 | 23.67 |
| 4803 | O | LEU | B | 33 | 14.665 | 9.037 | 10.415 | 1.00 | 22.94 |
| 4804 | N | SER | B | 34 | 13.573 | 8.180 | 8.654 | 1.00 | 24.43 |
| 4806 | CA | SER | B | 34 | 12.506 | 7.580 | 9.458 | 1.00 | 25.35 |
| 4808 | CB | SER | B | 34 | 11.490 | 6.887 | 8.551 | 1.00 | 25.51 |
| 4811 | OG | SER | B | 34 | 10.877 | 7.830 | 7.706 | 1.00 | 26.80 |
| 4813 | C | SER | B | 34 | 13.043 | 6.579 | 10.487 | 1.00 | 25.98 |
| 4814 | O | SER | B | 34 | 12.547 | 6.525 | 11.610 | 1.00 | 26.04 |
| 4815 | N | ARG | B | 35 | 14.062 | 5.813 | 10.094 | 1.00 | 26.60 |
| 4817 | CA | ARG | B | 35 | 14.700 | 4.820 | 10.962 | 1.00 | 27.70 |
| 4819 | CB | ARG | B | 35 | 15.743 | 3.993 | 10.185 | 1.00 | 28.27 |
| 4822 | CG | ARG | B | 35 | 15.205 | 2.761 | 9.484 | 1.00 | 31.67 |
| 4825 | CD | ARG | B | 35 | 16.207 | 1.605 | 9.357 | 1.00 | 34.70 |
| 4828 | NE | ARG | B | 35 | 17.593 | 2.056 | 9.140 | 1.00 | 36.06 |
| 4830 | CZ | ARG | B | 35 | 18.083 | 2.498 | 7.984 | 1.00 | 33.83 |
| 4831 | NH1 | ARG | B | 35 | 17.320 | 2.570 | 6.914 | 1.00 | 34.48 |
| 4834 | NH2 | ARG | B | 35 | 19.354 | 2.876 | 7.903 | 1.00 | 33.58 |
| 4837 | C | ARG | B | 35 | 15.407 | 5.464 | 12.148 | 1.00 | 27.46 |
| 4838 | O | ARG | B | 35 | 15.465 | 4.877 | 13.237 | 1.00 | 27.43 |
| 4839 | N | PHE | B | 36 | 15.967 | 6.655 | 11.926 | 1.00 | 27.31 |
| 4841 | CA | PHE | B | 36 | 16.692 | 7.373 | 12.965 | 1.00 | 26.91 |
| 4843 | CB | PHE | B | 36 | 17.758 | 8.289 | 12.356 | 1.00 | 26.72 |
| 4846 | CG | PHE | B | 36 | 18.835 | 7.547 | 11.623 | 1.00 | 24.89 |
| 4847 | CD1 | PHE | B | 36 | 19.206 | 7.916 | 10.343 | 1.00 | 22.57 |
| 4849 | CE1 | PHE | B | 36 | 20.201 | 7.220 | 9.656 | 1.00 | 22.79 |
| 4851 | CZ | PHE | B | 36 | 20.845 | 6.150 | 10.267 | 1.00 | 23.00 |
| 4853 | CE2 | PHE | B | 36 | 20.493 | 5.777 | 11.546 | 1.00 | 24.18 |
| 4855 | CD2 | PHE | B | 36 | 19.488 | 6.473 | 12.224 | 1.00 | 24.53 |
| 4857 | C | PHE | B | 36 | 15.763 | 8.164 | 13.851 | 1.00 | 27.56 |
| 4858 | O | PHE | B | 36 | 16.136 | 8.505 | 14.964 | 1.00 | 28.14 |
| 4859 | N | ILE | B | 37 | 14.563 | 8.457 | 13.357 | 1.00 | 28.06 |
| 4861 | CA | ILE | B | 37 | 13.570 | 9.208 | 14.113 | 1.00 | 29.01 |
| 4863 | CB | ILE | B | 37 | 12.677 | 10.054 | 13.160 | 1.00 | 29.24 |
| 4865 | CG1 | ILE | B | 37 | 13.470 | 11.240 | 12.608 | 1.00 | 28.43 |
| 4868 | CD1 | ILE | B | 37 | 12.767 | 12.003 | 11.524 | 1.00 | 29.06 |
| 4872 | CG2 | ILE | B | 37 | 11.412 | 10.552 | 13.876 | 1.00 | 30.14 |
| 4876 | C | ILE | B | 37 | 12.719 | 8.257 | 14.959 | 1.00 | 29.75 |
| 4877 | O | ILE | B | 37 | 12.120 | 8.678 | 15.948 | 1.00 | 30.10 |
| 4878 | N | ALA | B | 38 | 12.698 | 6.977 | 14.580 | 1.00 | 30.36 |
| 4880 | CA | ALA | B | 38 | 11.784 | 5.995 | 15.172 | 1.00 | 30.63 |
| 4882 | CB | ALA | B | 38 | 11.849 | 4.666 | 14.409 | 1.00 | 30.80 |
| 4886 | C | ALA | B | 38 | 12.021 | 5.762 | 16.651 | 1.00 | 30.90 |

FIGURE 3 (Cont.)

| A | B | C | D | E | F | G | H | I | J |
|---|---|---|---|---|---|---|---|---|---|
| 4887 | O | ALA | B | 38 | 11.052 | 5.739 | 17.415 | 1.00 | 31.31 |
| 4888 | N | PRO | B | 39 | 13.278 | 5.595 | 17.074 | 1.00 | 31.28 |
| 4889 | CA | PRO | B | 39 | 13.573 | 5.370 | 18.494 | 1.00 | 31.54 |
| 4891 | CB | PRO | B | 39 | 15.045 | 4.922 | 18.489 | 1.00 | 31.77 |
| 4894 | CG | PRO | B | 39 | 15.425 | 4.741 | 17.062 | 1.00 | 32.00 |
| 4897 | CD | PRO | B | 39 | 14.512 | 5.594 | 16.270 | 1.00 | 31.28 |
| 4900 | C | PRO | B | 39 | 13.423 | 6.610 | 19.377 | 1.00 | 31.62 |
| 4901 | O | PRO | B | 39 | 13.551 | 6.466 | 20.594 | 1.00 | 32.39 |
| 4902 | N | LEU | B | 40 | 13.184 | 7.790 | 18.794 | 1.00 | 30.70 |
| 4904 | CA | LEU | B | 40 | 13.053 | 9.012 | 19.575 | 1.00 | 30.07 |
| 4906 | CB | LEU | B | 40 | 12.980 | 10.253 | 18.670 | 1.00 | 30.11 |
| 4909 | CG | LEU | B | 40 | 14.228 | 10.593 | 17.836 | 1.00 | 30.37 |
| 4911 | CD1 | LEU | B | 40 | 13.985 | 11.886 | 17.056 | 1.00 | 30.25 |
| 4915 | CD2 | LEU | B | 40 | 15.502 | 10.691 | 18.687 | 1.00 | 30.52 |
| 4919 | C | LEU | B | 40 | 11.801 | 8.963 | 20.448 | 1.00 | 29.37 |
| 4920 | O | LEU | B | 40 | 10.747 | 8.494 | 20.005 | 1.00 | 29.73 |
| 4921 | N | PRO | B | 41 | 11.903 | 9.477 | 21.669 | 1.00 | 28.40 |
| 4922 | CA | PRO | B | 41 | 10.738 | 9.551 | 22.553 | 1.00 | 28.09 |
| 4924 | CB | PRO | B | 41 | 11.355 | 9.872 | 23.921 | 1.00 | 28.24 |
| 4927 | CG | PRO | B | 41 | 12.658 | 10.565 | 23.613 | 1.00 | 28.08 |
| 4930 | CD | PRO | B | 41 | 13.115 | 10.033 | 22.301 | 1.00 | 28.09 |
| 4933 | C | PRO | B | 41 | 9.796 | 10.657 | 22.100 | 1.00 | 27.75 |
| 4934 | O | PRO | B | 41 | 10.119 | 11.411 | 21.154 | 1.00 | 26.90 |
| 4935 | N | PHE | B | 42 | 8.630 | 10.724 | 22.739 | 1.00 | 27.16 |
| 4937 | CA | PHE | B | 42 | 7.644 | 11.774 | 22.477 | 1.00 | 27.19 |
| 4939 | CB | PHE | B | 42 | 8.224 | 13.158 | 22.776 | 1.00 | 27.06 |
| 4942 | CG | PHE | B | 42 | 8.887 | 13.259 | 24.118 | 1.00 | 27.64 |
| 4943 | CD1 | PHE | B | 42 | 8.136 | 13.124 | 25.279 | 1.00 | 28.66 |
| 4945 | CE1 | PHE | B | 42 | 8.732 | 13.207 | 26.518 | 1.00 | 29.45 |
| 4947 | CZ | PHE | B | 42 | 10.096 | 13.439 | 26.617 | 1.00 | 28.49 |
| 4949 | CE2 | PHE | B | 42 | 10.863 | 13.574 | 25.475 | 1.00 | 27.66 |
| 4951 | CD2 | PHE | B | 42 | 10.260 | 13.485 | 24.226 | 1.00 | 27.57 |
| 4953 | C | PHE | B | 42 | 7.094 | 11.730 | 21.053 | 1.00 | 27.15 |
| 4954 | O | PHE | B | 42 | 6.729 | 12.755 | 20.491 | 1.00 | 26.43 |
| 4955 | N | GLN | B | 43 | 7.015 | 10.534 | 20.489 | 1.00 | 27.91 |
| 4957 | CA | GLN | B | 43 | 6.310 | 10.320 | 19.224 | 1.00 | 28.60 |
| 4959 | CB | GLN | B | 43 | 6.294 | 8.834 | 18.858 | 1.00 | 28.40 |
| 4962 | CG | GLN | B | 43 | 7.659 | 8.201 | 18.665 | 1.00 | 28.70 |
| 4965 | CD | GLN | B | 43 | 8.379 | 8.718 | 17.438 | 1.00 | 28.74 |
| 4966 | OE1 | GLN | B | 43 | 7.765 | 8.927 | 16.394 | 1.00 | 29.53 |
| 4967 | NE2 | GLN | B | 43 | 9.685 | 8.915 | 17.558 | 1.00 | 28.45 |
| 4970 | C | GLN | B | 43 | 4.868 | 10.796 | 19.363 | 1.00 | 29.43 |
| 4971 | O | GLN | B | 43 | 4.275 | 10.720 | 20.449 | 1.00 | 30.02 |
| 4972 | N | ASN | B | 44 | 4.311 | 11.291 | 18.268 | 1.00 | 30.07 |
| 4974 | CA | ASN | B | 44 | 2.942 | 11.787 | 18.226 | 1.00 | 30.82 |
| 4976 | CB | ASN | B | 44 | 1.943 | 10.631 | 18.396 | 1.00 | 31.34 |
| 4979 | CG | ASN | B | 44 | 2.264 | 9.445 | 17.492 | 1.00 | 32.36 |
| 4980 | OD1 | ASN | B | 44 | 2.338 | 9.579 | 16.261 | 1.00 | 35.83 |
| 4981 | ND2 | ASN | B | 44 | 2.480 | 8.288 | 18.096 | 1.00 | 33.67 |
| 4984 | C | ASN | B | 44 | 2.684 | 12.898 | 19.244 | 1.00 | 30.94 |
| 4985 | O | ASN | B | 44 | 1.596 | 12.983 | 19.805 | 1.00 | 31.98 |
| 4986 | N | THR | B | 45 | 3.705 | 13.716 | 19.507 | 1.00 | 30.13 |

FIGURE 3 (Cont.)

| A | B | C | D | E | F | G | H | I | J |
|---|---|---|---|---|---|---|---|---|---|
| 4988 | CA | THR | B | 45 | 3.529 | 14.982 | 20.201 | 1.00 | 29.44 |
| 4990 | CB | THR | B | 45 | 4.399 | 15.055 | 21.470 | 1.00 | 29.55 |
| 4992 | OG1 | THR | B | 45 | 5.790 | 15.106 | 21.123 | 1.00 | 29.59 |
| 4994 | CG2 | THR | B | 45 | 4.249 | 13.787 | 22.313 | 1.00 | 30.13 |
| 4998 | C | THR | B | 45 | 3.901 | 16.083 | 19.216 | 1.00 | 28.76 |
| 4999 | O | THR | B | 45 | 4.574 | 15.800 | 18.231 | 1.00 | 29.08 |
| 5000 | N | PRO | B | 46 | 3.458 | 17.318 | 19.450 | 1.00 | 28.09 |
| 5001 | CA | PRO | B | 46 | 3.684 | 18.421 | 18.494 | 1.00 | 27.28 |
| 5003 | CB | PRO | B | 46 | 3.174 | 19.652 | 19.252 | 1.00 | 27.82 |
| 5006 | CG | PRO | B | 46 | 2.115 | 19.111 | 20.181 | 1.00 | 28.40 |
| 5009 | CD | PRO | B | 46 | 2.640 | 17.750 | 20.605 | 1.00 | 28.19 |
| 5012 | C | PRO | B | 46 | 5.135 | 18.643 | 18.041 | 1.00 | 26.19 |
| 5013 | O | PRO | B | 46 | 5.357 | 18.854 | 16.853 | 1.00 | 25.60 |
| 5014 | N | VAL | B | 47 | 6.100 | 18.595 | 18.957 | 1.00 | 24.76 |
| 5016 | CA | VAL | B | 47 | 7.479 | 18.902 | 18.602 | 1.00 | 23.94 |
| 5018 | CB | VAL | B | 47 | 8.365 | 19.173 | 19.859 | 1.00 | 24.25 |
| 5020 | CG1 | VAL | B | 47 | 8.593 | 17.904 | 20.684 | 1.00 | 24.46 |
| 5024 | CG2 | VAL | B | 47 | 9.678 | 19.801 | 19.452 | 1.00 | 25.37 |
| 5028 | C | VAL | B | 47 | 8.074 | 17.824 | 17.690 | 1.00 | 22.86 |
| 5029 | O | VAL | B | 47 | 8.719 | 18.150 | 16.704 | 1.00 | 21.98 |
| 5030 | N | VAL | B | 48 | 7.822 | 16.549 | 17.991 | 1.00 | 22.17 |
| 5032 | CA | VAL | B | 48 | 8.303 | 15.456 | 17.145 | 1.00 | 22.05 |
| 5034 | CB | VAL | B | 48 | 8.227 | 14.101 | 17.872 | 1.00 | 22.22 |
| 5036 | CG1 | VAL | B | 48 | 8.620 | 12.960 | 16.951 | 1.00 | 22.38 |
| 5040 | CG2 | VAL | B | 48 | 9.132 | 14.128 | 19.090 | 1.00 | 22.62 |
| 5044 | C | VAL | B | 48 | 7.547 | 15.414 | 15.816 | 1.00 | 22.15 |
| 5045 | O | VAL | B | 48 | 8.108 | 15.076 | 14.775 | 1.00 | 21.53 |
| 5046 | N | GLU | B | 49 | 6.273 | 15.760 | 15.844 | 1.00 | 22.30 |
| 5048 | CA | GLU | B | 49 | 5.501 | 15.839 | 14.612 | 1.00 | 23.31 |
| 5050 | CB | GLU | B | 49 | 4.020 | 16.062 | 14.906 | 1.00 | 23.97 |
| 5053 | CG | GLU | B | 49 | 3.349 | 14.847 | 15.529 | 1.00 | 27.97 |
| 5056 | CD | GLU | B | 49 | 1.902 | 15.107 | 15.899 | 1.00 | 32.93 |
| 5057 | OE1 | GLU | B | 49 | 1.410 | 16.237 | 15.650 | 1.00 | 37.74 |
| 5058 | OE2 | GLU | B | 49 | 1.263 | 14.182 | 16.446 | 1.00 | 36.88 |
| 5059 | C | GLU | B | 49 | 6.023 | 16.965 | 13.727 | 1.00 | 22.40 |
| 5060 | O | GLU | B | 49 | 6.016 | 16.837 | 12.516 | 1.00 | 21.26 |
| 5061 | N | THR | B | 50 | 6.497 | 18.044 | 14.344 | 1.00 | 21.39 |
| 5063 | CA | THR | B | 50 | 7.105 | 19.143 | 13.607 | 1.00 | 21.78 |
| 5065 | CB | THR | B | 50 | 7.382 | 20.353 | 14.534 | 1.00 | 22.24 |
| 5067 | OG1 | THR | B | 50 | 6.174 | 20.767 | 15.191 | 1.00 | 21.33 |
| 5069 | CG2 | THR | B | 50 | 7.803 | 21.573 | 13.727 | 1.00 | 22.96 |
| 5073 | C | THR | B | 50 | 8.406 | 18.684 | 12.964 | 1.00 | 21.83 |
| 5074 | O | THR | B | 50 | 8.671 | 19.001 | 11.808 | 1.00 | 21.23 |
| 5075 | N | MET | B | 51 | 9.220 | 17.953 | 13.728 | 1.00 | 21.95 |
| 5077 | CA | MET | B | 51 | 10.470 | 17.408 | 13.215 | 1.00 | 21.91 |
| 5079 | CB | MET | B | 51 | 11.207 | 16.630 | 14.299 | 1.00 | 21.87 |
| 5082 | CG | MET | B | 51 | 11.735 | 17.485 | 15.441 | 1.00 | 20.93 |
| 5085 | SD | MET | B | 51 | 12.315 | 16.444 | 16.774 | 1.00 | 22.35 |
| 5086 | CE | MET | B | 51 | 13.754 | 15.689 | 16.047 | 1.00 | 23.07 |
| 5090 | C | MET | B | 51 | 10.221 | 16.502 | 12.014 | 1.00 | 22.56 |
| 5091 | O | MET | B | 51 | 10.951 | 16.565 | 11.024 | 1.00 | 22.83 |
| 5092 | N | GLN | B | 52 | 9.179 | 15.676 | 12.088 | 1.00 | 23.09 |

FIGURE 3 (Cont.)

| A | B | C | D | E | F | G | H | I | J |
|---|---|---|---|---|---|---|---|---|---|
| 5094 | CA | GLN | B | 52 | 8.895 | 14.714 | 11.016 | 1.00 | 23.09 |
| 5096 | CB | GLN | B | 52 | 7.843 | 13.694 | 11.460 | 1.00 | 23.18 |
| 5099 | CG | GLN | B | 52 | 8.386 | 12.700 | 12.456 | 1.00 | 24.11 |
| 5102 | CD | GLN | B | 52 | 7.334 | 11.743 | 12.961 | 1.00 | 26.66 |
| 5103 | OE1 | GLN | B | 52 | 7.463 | 10.525 | 12.791 | 1.00 | 28.62 |
| 5104 | NE2 | GLN | B | 52 | 6.304 | 12.280 | 13.601 | 1.00 | 23.91 |
| 5107 | C | GLN | B | 52 | 8.393 | 15.435 | 9.787 | 1.00 | 22.65 |
| 5108 | O | GLN | B | 52 | 8.764 | 15.123 | 8.661 | 1.00 | 22.15 |
| 5109 | N | TYR | B | 53 | 7.531 | 16.402 | 10.028 | 1.00 | 22.64 |
| 5111 | CA | TYR | B | 53 | 6.942 | 17.213 | 8.974 | 1.00 | 22.81 |
| 5113 | CB | TYR | B | 53 | 5.939 | 18.145 | 9.647 | 1.00 | 23.23 |
| 5116 | CG | TYR | B | 53 | 5.133 | 19.066 | 8.784 | 1.00 | 24.77 |
| 5117 | CD1 | TYR | B | 53 | 3.855 | 18.706 | 8.346 | 1.00 | 27.29 |
| 5119 | CE1 | TYR | B | 53 | 3.089 | 19.572 | 7.587 | 1.00 | 28.69 |
| 5121 | CZ | TYR | B | 53 | 3.582 | 20.820 | 7.286 | 1.00 | 28.49 |
| 5122 | OH | TYR | B | 53 | 2.827 | 21.673 | 6.537 | 1.00 | 28.74 |
| 5124 | CE2 | TYR | B | 53 | 4.844 | 21.209 | 7.727 | 1.00 | 27.93 |
| 5126 | CD2 | TYR | B | 53 | 5.600 | 20.335 | 8.477 | 1.00 | 26.79 |
| 5128 | C | TYR | B | 53 | 8.051 | 17.978 | 8.237 | 1.00 | 22.85 |
| 5129 | O | TYR | B | 53 | 8.114 | 17.976 | 7.010 | 1.00 | 22.68 |
| 5130 | N | GLY | B | 54 | 8.948 | 18.591 | 9.005 | 1.00 | 22.75 |
| 5132 | CA | GLY | B | 54 | 10.014 | 19.408 | 8.455 | 1.00 | 22.25 |
| 5135 | C | GLY | B | 54 | 11.071 | 18.608 | 7.738 | 1.00 | 22.08 |
| 5136 | O | GLY | B | 54 | 11.669 | 19.088 | 6.782 | 1.00 | 21.36 |
| 5137 | N | ALA | B | 55 | 11.310 | 17.384 | 8.201 | 1.00 | 22.33 |
| 5139 | CA | ALA | B | 55 | 12.382 | 16.568 | 7.656 | 1.00 | 22.52 |
| 5141 | CB | ALA | B | 55 | 12.996 | 15.714 | 8.733 | 1.00 | 22.31 |
| 5145 | C | ALA | B | 55 | 11.925 | 15.698 | 6.492 | 1.00 | 23.07 |
| 5146 | O | ALA | B | 55 | 12.692 | 15.487 | 5.548 | 1.00 | 22.77 |
| 5147 | N | LEU | B | 56 | 10.682 | 15.220 | 6.538 | 1.00 | 23.33 |
| 5149 | CA | LEU | B | 56 | 10.265 | 14.079 | 5.705 | 1.00 | 24.30 |
| 5151 | CB | LEU | B | 56 | 9.706 | 12.960 | 6.586 | 1.00 | 24.12 |
| 5154 | CG | LEU | B | 56 | 10.789 | 12.220 | 7.367 | 1.00 | 24.95 |
| 5156 | CD1 | LEU | B | 56 | 10.177 | 11.362 | 8.448 | 1.00 | 25.81 |
| 5160 | CD2 | LEU | B | 56 | 11.624 | 11.386 | 6.415 | 1.00 | 25.72 |
| 5164 | C | LEU | B | 56 | 9.241 | 14.390 | 4.610 | 1.00 | 24.83 |
| 5165 | O | LEU | B | 56 | 9.168 | 13.668 | 3.615 | 1.00 | 24.82 |
| 5166 | N | LEU | B | 57 | 8.480 | 15.459 | 4.784 | 1.00 | 25.44 |
| 5168 | CA | LEU | B | 57 | 7.363 | 15.761 | 3.890 | 1.00 | 26.38 |
| 5170 | CB | LEU | B | 57 | 6.196 | 16.353 | 4.683 | 1.00 | 26.51 |
| 5173 | CG | LEU | B | 57 | 4.851 | 15.625 | 4.607 | 1.00 | 29.53 |
| 5175 | CD1 | LEU | B | 57 | 4.953 | 14.108 | 4.807 | 1.00 | 30.58 |
| 5179 | CD2 | LEU | B | 57 | 3.880 | 16.228 | 5.625 | 1.00 | 30.77 |
| 5183 | C | LEU | B | 57 | 7.833 | 16.671 | 2.741 | 1.00 | 26.06 |
| 5184 | O | LEU | B | 57 | 7.862 | 17.895 | 2.846 | 1.00 | 27.01 |
| 5185 | N | GLY | B | 58 | 8.237 | 16.048 | 1.651 | 1.00 | 25.60 |
| 5187 | CA | GLY | B | 58 | 8.677 | 16.778 | 0.477 | 1.00 | 25.47 |
| 5190 | C | GLY | B | 58 | 10.152 | 17.095 | 0.529 | 1.00 | 24.67 |
| 5191 | O | GLY | B | 58 | 10.821 | 16.878 | 1.542 | 1.00 | 24.85 |
| 5192 | N | GLY | B | 59 | 10.655 | 17.628 | -0.575 | 1.00 | 24.17 |
| 5194 | CA | GLY | B | 59 | 12.046 | 18.001 | -0.702 | 1.00 | 23.50 |
| 5197 | C | GLY | B | 59 | 12.688 | 17.037 | -1.671 | 1.00 | 23.34 |

FIGURE 3 (Cont.)

| A | B | C | D | E | F | G | H | I | J |
|---|---|---|---|---|---|---|---|---|---|
| 5198 | O | GLY | B | 59 | 12.221 | 15.901 | -1.822 | 1.00 | 23.79 |
| 5199 | N | LYS | B | 60 | 13.776 | 17.465 | -2.305 | 1.00 | 22.25 |
| 5201 | CA | LYS | B | 60 | 14.378 | 16.698 | -3.397 | 1.00 | 21.47 |
| 5203 | CB | LYS | B | 60 | 14.964 | 17.634 | -4.446 | 1.00 | 21.33 |
| 5206 | CG | LYS | B | 60 | 13.989 | 18.633 | -5.009 | 1.00 | 21.64 |
| 5209 | CD | LYS | B | 60 | 14.690 | 19.563 | -5.983 | 1.00 | 20.05 |
| 5212 | CE | LYS | B | 60 | 15.503 | 20.635 | -5.285 | 1.00 | 20.61 |
| 5215 | NZ | LYS | B | 60 | 14.661 | 21.571 | -4.488 | 1.00 | 18.47 |
| 5219 | C | LYS | B | 60 | 15.473 | 15.764 | -2.916 | 1.00 | 20.81 |
| 5220 | O | LYS | B | 60 | 15.930 | 14.904 | -3.680 | 1.00 | 19.71 |
| 5221 | N | ARG | B | 61 | 15.873 | 15.934 | -1.651 | 1.00 | 19.67 |
| 5223 | CA | ARG | B | 61 | 16.956 | 15.168 | -1.037 | 1.00 | 19.66 |
| 5225 | CB | ARG | B | 61 | 16.531 | 13.713 | -0.785 | 1.00 | 19.62 |
| 5228 | CG | ARG | B | 61 | 15.280 | 13.581 | 0.031 | 1.00 | 20.32 |
| 5231 | CD | ARG | B | 61 | 15.456 | 13.814 | 1.534 | 1.00 | 21.36 |
| 5234 | NE | ARG | B | 61 | 14.145 | 13.667 | 2.159 | 1.00 | 22.35 |
| 5236 | CZ | ARG | B | 61 | 13.232 | 14.625 | 2.243 | 1.00 | 24.57 |
| 5237 | NH1 | ARG | B | 61 | 13.491 | 15.867 | 1.836 | 1.00 | 25.55 |
| 5240 | NH2 | ARG | B | 61 | 12.042 | 14.347 | 2.754 | 1.00 | 25.42 |
| 5243 | C | ARG | B | 61 | 18.218 | 15.188 | -1.878 | 1.00 | 19.19 |
| 5244 | O | ARG | B | 61 | 18.871 | 14.162 | -2.042 | 1.00 | 19.59 |
| 5245 | N | LEU | B | 62 | 18.575 | 16.345 | -2.419 | 1.00 | 18.57 |
| 5247 | CA | LEU | B | 62 | 19.781 | 16.421 | -3.233 | 1.00 | 18.09 |
| 5249 | CB | LEU | B | 62 | 19.801 | 17.700 | -4.043 | 1.00 | 18.16 |
| 5252 | CG | LEU | B | 62 | 18.659 | 17.854 | -5.069 | 1.00 | 17.75 |
| 5254 | CD1 | LEU | B | 62 | 18.918 | 19.010 | -5.960 | 1.00 | 17.68 |
| 5258 | CD2 | LEU | B | 62 | 18.460 | 16.582 | -5.902 | 1.00 | 17.92 |
| 5262 | C | LEU | B | 62 | 21.050 | 16.265 | -2.398 | 1.00 | 18.27 |
| 5263 | O | LEU | B | 62 | 22.075 | 15.828 | -2.904 | 1.00 | 19.36 |
| 5264 | N | ARG | B | 63 | 20.984 | 16.589 | -1.118 | 1.00 | 18.60 |
| 5266 | CA | ARG | B | 63 | 22.152 | 16.472 | -0.263 | 1.00 | 18.77 |
| 5268 | CB | ARG | B | 63 | 22.052 | 17.389 | 0.948 | 1.00 | 18.34 |
| 5271 | CG | ARG | B | 63 | 22.255 | 18.855 | 0.557 | 1.00 | 18.92 |
| 5274 | CD | ARG | B | 63 | 21.763 | 19.861 | 1.576 | 1.00 | 19.63 |
| 5277 | NE | ARG | B | 63 | 21.626 | 21.189 | 0.993 | 1.00 | 18.86 |
| 5279 | CZ | ARG | B | 63 | 20.623 | 21.574 | 0.213 | 1.00 | 20.23 |
| 5280 | NH1 | ARG | B | 63 | 20.591 | 22.816 | -0.258 | 1.00 | 20.75 |
| 5283 | NH2 | ARG | B | 63 | 19.642 | 20.736 | -0.106 | 1.00 | 20.23 |
| 5286 | C | ARG | B | 63 | 22.421 | 14.999 | 0.076 | 1.00 | 19.10 |
| 5287 | O | ARG | B | 63 | 23.547 | 14.561 | -0.077 | 1.00 | 19.88 |
| 5288 | N | PRO | B | 64 | 21.423 | 14.225 | 0.504 | 1.00 | 19.43 |
| 5289 | CA | PRO | B | 64 | 21.571 | 12.764 | 0.495 | 1.00 | 19.41 |
| 5291 | CB | PRO | B | 64 | 20.168 | 12.271 | 0.822 | 1.00 | 20.11 |
| 5294 | CG | PRO | B | 64 | 19.619 | 13.337 | 1.712 | 1.00 | 19.65 |
| 5297 | CD | PRO | B | 64 | 20.136 | 14.628 | 1.091 | 1.00 | 19.55 |
| 5300 | C | PRO | B | 64 | 22.061 | 12.230 | -0.851 | 1.00 | 18.78 |
| 5301 | O | PRO | B | 64 | 22.971 | 11.411 | -0.850 | 1.00 | 19.31 |
| 5302 | N | PHE | B | 65 | 21.512 | 12.708 | -1.965 | 1.00 | 18.78 |
| 5304 | CA | PHE | B | 65 | 21.994 | 12.301 | -3.290 | 1.00 | 18.13 |
| 5306 | CB | PHE | B | 65 | 21.301 | 13.089 | -4.406 | 1.00 | 18.17 |
| 5309 | CG | PHE | B | 65 | 21.440 | 12.462 | -5.768 | 1.00 | 19.67 |
| 5310 | CD1 | PHE | B | 65 | 22.618 | 12.595 | -6.496 | 1.00 | 21.70 |

FIGURE 3 (Cont.)

| A | B | C | D | E | F | G | H | I | J |
|---|---|---|---|---|---|---|---|---|---|
| 5312 | CE1 | PHE | B | 65 | 22.745 | 12.007 | -7.755 | 1.00 | 22.62 |
| 5314 | CZ | PHE | B | 65 | 21.697 | 11.280 | -8.296 | 1.00 | 23.33 |
| 5316 | CE2 | PHE | B | 65 | 20.532 | 11.138 | -7.587 | 1.00 | 23.93 |
| 5318 | CD2 | PHE | B | 65 | 20.400 | 11.730 | -6.324 | 1.00 | 22.20 |
| 5320 | C | PHE | B | 65 | 23.518 | 12.444 | -3.401 | 1.00 | 18.01 |
| 5321 | O | PHE | B | 65 | 24.194 | 11.528 | -3.851 | 1.00 | 17.71 |
| 5322 | N | LEU | B | 66 | 24.042 | 13.591 | -2.986 | 1.00 | 17.36 |
| 5324 | CA | LEU | B | 66 | 25.470 | 13.851 | -3.011 | 1.00 | 17.79 |
| 5326 | CB | LEU | B | 66 | 25.775 | 15.297 | -2.615 | 1.00 | 17.54 |
| 5329 | CG | LEU | B | 66 | 25.431 | 16.355 | -3.650 | 1.00 | 18.09 |
| 5331 | CD1 | LEU | B | 66 | 25.477 | 17.733 | -3.004 | 1.00 | 20.27 |
| 5335 | CD2 | LEU | B | 66 | 26.378 | 16.312 | -4.830 | 1.00 | 18.85 |
| 5339 | C | LEU | B | 66 | 26.245 | 12.913 | -2.104 | 1.00 | 17.24 |
| 5340 | O | LEU | B | 66 | 27.325 | 12.470 | -2.464 | 1.00 | 17.66 |
| 5341 | N | VAL | B | 67 | 25.717 | 12.633 | -0.920 | 1.00 | 16.80 |
| 5343 | CA | VAL | B | 67 | 26.388 | 11.711 | -0.011 | 1.00 | 16.74 |
| 5345 | CB | VAL | B | 67 | 25.658 | 11.640 | 1.340 | 1.00 | 16.98 |
| 5347 | CG1 | VAL | B | 67 | 26.180 | 10.504 | 2.196 | 1.00 | 16.26 |
| 5351 | CG2 | VAL | B | 67 | 25.754 | 13.004 | 2.088 | 1.00 | 17.68 |
| 5355 | C | VAL | B | 67 | 26.465 | 10.322 | -0.656 | 1.00 | 16.74 |
| 5356 | O | VAL | B | 67 | 27.536 | 9.725 | -0.718 | 1.00 | 15.63 |
| 5357 | N | TYR | B | 68 | 25.315 | 9.830 | -1.120 | 1.00 | 17.27 |
| 5359 | CA | TYR | B | 68 | 25.226 | 8.520 | -1.767 | 1.00 | 18.14 |
| 5361 | CB | TYR | B | 68 | 23.790 | 8.181 | -2.162 | 1.00 | 18.15 |
| 5364 | CG | TYR | B | 68 | 22.884 | 7.903 | -1.001 | 1.00 | 17.89 |
| 5365 | CD1 | TYR | B | 68 | 23.205 | 6.940 | -0.059 | 1.00 | 19.51 |
| 5367 | CE1 | TYR | B | 68 | 22.357 | 6.678 | 1.022 | 1.00 | 18.10 |
| 5369 | CZ | TYR | B | 68 | 21.198 | 7.396 | 1.155 | 1.00 | 18.28 |
| 5370 | OH | TYR | B | 68 | 20.351 | 7.135 | 2.215 | 1.00 | 19.90 |
| 5372 | CE2 | TYR | B | 68 | 20.866 | 8.363 | 0.221 | 1.00 | 18.45 |
| 5374 | CD2 | TYR | B | 68 | 21.699 | 8.599 | -0.846 | 1.00 | 18.98 |
| 5376 | C | TYR | B | 68 | 26.082 | 8.438 | -3.015 | 1.00 | 17.83 |
| 5377 | O | TYR | B | 68 | 26.788 | 7.478 | -3.201 | 1.00 | 17.93 |
| 5378 | N | ALA | B | 69 | 26.031 | 9.456 | -3.868 | 1.00 | 18.14 |
| 5380 | CA | ALA | B | 69 | 26.687 | 9.377 | -5.168 | 1.00 | 17.87 |
| 5382 | CB | ALA | B | 69 | 26.264 | 10.525 | -6.039 | 1.00 | 18.36 |
| 5386 | C | ALA | B | 69 | 28.200 | 9.387 | -4.975 | 1.00 | 18.40 |
| 5387 | O | ALA | B | 69 | 28.960 | 8.703 | -5.696 | 1.00 | 18.10 |
| 5388 | N | THR | B | 70 | 28.639 | 10.155 | -3.985 | 1.00 | 18.02 |
| 5390 | CA | THR | B | 70 | 30.055 | 10.258 | -3.691 | 1.00 | 18.66 |
| 5392 | CB | THR | B | 70 | 30.300 | 11.424 | -2.750 | 1.00 | 17.72 |
| 5394 | OG1 | THR | B | 70 | 29.858 | 12.636 | -3.373 | 1.00 | 18.73 |
| 5396 | CG2 | THR | B | 70 | 31.801 | 11.638 | -2.534 | 1.00 | 19.07 |
| 5400 | C | THR | B | 70 | 30.634 | 8.968 | -3.097 | 1.00 | 19.24 |
| 5401 | O | THR | B | 70 | 31.644 | 8.449 | -3.592 | 1.00 | 19.75 |
| 5402 | N | GLY | B | 71 | 29.999 | 8.474 | -2.036 | 1.00 | 19.50 |
| 5404 | CA | GLY | B | 71 | 30.432 | 7.259 | -1.389 | 1.00 | 20.08 |
| 5407 | C | GLY | B | 71 | 30.417 | 6.071 | -2.343 | 1.00 | 20.27 |
| 5408 | O | GLY | B | 71 | 31.314 | 5.231 | -2.310 | 1.00 | 20.87 |
| 5409 | N | HIS | B | 72 | 29.379 | 6.008 | -3.169 | 1.00 | 20.75 |
| 5411 | CA | HIS | B | 72 | 29.201 | 4.952 | -4.163 | 1.00 | 21.28 |
| 5413 | CB | HIS | B | 72 | 27.909 | 5.167 | -4.955 | 1.00 | 20.79 |

FIGURE 3 (Cont.)

| A | B | C | D | E | F | G | H | I | J |
|---|---|---|---|---|---|---|---|---|---|
| 5416 | CG | HIS | B | 72 | 26.666 | 4.749 | -4.233 | 1.00 | 20.15 |
| 5417 | ND1 | HIS | B | 72 | 25.407 | 4.975 | -4.744 | 1.00 | 18.98 |
| 5419 | CE1 | HIS | B | 72 | 24.500 | 4.502 | -3.911 | 1.00 | 20.13 |
| 5421 | NE2 | HIS | B | 72 | 25.126 | 3.949 | -2.887 | 1.00 | 20.74 |
| 5423 | CD2 | HIS | B | 72 | 26.482 | 4.101 | -3.059 | 1.00 | 21.64 |
| 5425 | C | HIS | B | 72 | 30.361 | 4.878 | -5.151 | 1.00 | 21.89 |
| 5426 | O | HIS | B | 72 | 30.692 | 3.791 | -5.606 | 1.00 | 21.76 |
| 5427 | N | MET | B | 73 | 30.960 | 6.023 | -5.493 | 1.00 | 22.15 |
| 5429 | CA | MET | B | 73 | 32.157 | 6.051 | -6.357 | 1.00 | 23.42 |
| 5431 | CB | MET | B | 73 | 32.672 | 7.481 | -6.565 | 1.00 | 23.57 |
| 5434 | CG | MET | B | 73 | 31.804 | 8.325 | -7.471 | 1.00 | 24.99 |
| 5437 | SD | MET | B | 73 | 32.611 | 9.844 | -8.067 | 1.00 | 26.07 |
| 5438 | CE | MET | B | 73 | 33.270 | 10.463 | -6.588 | 1.00 | 25.93 |
| 5442 | C | MET | B | 73 | 33.303 | 5.200 | -5.819 | 1.00 | 23.68 |
| 5443 | O | MET | B | 73 | 34.094 | 4.657 | -6.595 | 1.00 | 24.77 |
| 5444 | N | PHE | B | 74 | 33.405 | 5.105 | -4.502 | 1.00 | 23.69 |
| 5446 | CA | PHE | B | 74 | 34.474 | 4.342 | -3.856 | 1.00 | 23.70 |
| 5448 | CB | PHE | B | 74 | 35.073 | 5.171 | -2.720 | 1.00 | 23.12 |
| 5451 | CG | PHE | B | 74 | 35.419 | 6.571 | -3.134 | 1.00 | 23.22 |
| 5452 | CD1 | PHE | B | 74 | 34.539 | 7.620 | -2.887 | 1.00 | 22.52 |
| 5454 | CE1 | PHE | B | 74 | 34.842 | 8.909 | -3.297 | 1.00 | 21.95 |
| 5456 | CZ | PHE | B | 74 | 36.029 | 9.160 | -3.967 | 1.00 | 23.61 |
| 5458 | CE2 | PHE | B | 74 | 36.910 | 8.116 | -4.230 | 1.00 | 22.42 |
| 5460 | CD2 | PHE | B | 74 | 36.604 | 6.834 | -3.818 | 1.00 | 23.20 |
| 5462 | C | PHE | B | 74 | 34.016 | 2.986 | -3.339 | 1.00 | 23.73 |
| 5463 | O | PHE | B | 74 | 34.751 | 2.309 | -2.625 | 1.00 | 23.67 |
| 5464 | N | GLY | B | 75 | 32.791 | 2.607 | -3.686 | 1.00 | 23.96 |
| 5466 | CA | GLY | B | 75 | 32.273 | 1.287 | -3.397 | 1.00 | 24.04 |
| 5469 | C | GLY | B | 75 | 31.674 | 1.153 | -2.023 | 1.00 | 23.99 |
| 5470 | O | GLY | B | 75 | 31.462 | 0.038 | -1.543 | 1.00 | 23.68 |
| 5471 | N | VAL | B | 76 | 31.385 | 2.278 | -1.375 | 1.00 | 23.71 |
| 5473 | CA | VAL | B | 76 | 30.866 | 2.207 | -0.020 | 1.00 | 23.08 |
| 5475 | CB | BVAL | B | 76 | 31.048 | 3.547 | 0.736 | 0.35 | 22.92 |
| 5476 | CB | AVAL | B | 76 | 31.192 | 3.459 | 0.840 | 0.65 | 23.42 |
| 5479 | CG1 | BVAL | B | 76 | 30.368 | 3.508 | 2.114 | 0.35 | 22.09 |
| 5480 | CG1 | AVAL | B | 76 | 32.625 | 3.934 | 0.590 | 0.65 | 23.81 |
| 5487 | CG2 | BVAL | B | 76 | 32.527 | 3.883 | 0.872 | 0.35 | 23.15 |
| 5488 | CG2 | AVAL | B | 76 | 30.219 | 4.544 | 0.625 | 0.65 | 24.67 |
| 5495 | C | VAL | B | 76 | 29.387 | 1.847 | -0.088 | 1.00 | 22.55 |
| 5496 | O | VAL | B | 76 | 28.660 | 2.300 | -0.965 | 1.00 | 21.42 |
| 5497 | N | SER | B | 77 | 28.987 | 0.968 | 0.819 | 1.00 | 22.22 |
| 5499 | CA | SER | B | 77 | 27.645 | 0.429 | 0.868 | 1.00 | 22.25 |
| 5501 | CB | SER | B | 77 | 27.539 | -0.621 | 1.979 | 1.00 | 22.22 |
| 5504 | OG | SER | B | 77 | 26.202 | -1.078 | 2.137 | 1.00 | 22.42 |
| 5506 | C | SER | B | 77 | 26.656 | 1.550 | 1.108 | 1.00 | 22.33 |
| 5507 | O | SER | B | 77 | 26.919 | 2.462 | 1.898 | 1.00 | 21.77 |
| 5508 | N | THR | B | 78 | 25.534 | 1.480 | 0.394 | 1.00 | 21.99 |
| 5510 | CA | THR | B | 78 | 24.431 | 2.400 | 0.559 | 1.00 | 22.06 |
| 5512 | CB | THR | B | 78 | 23.259 | 1.990 | -0.367 | 1.00 | 22.16 |
| 5514 | OG1 | THR | B | 78 | 23.685 | 2.032 | -1.732 | 1.00 | 23.21 |
| 5516 | CG2 | THR | B | 78 | 22.126 | 2.999 | -0.303 | 1.00 | 22.58 |
| 5520 | C | THR | B | 78 | 23.949 | 2.433 | 1.997 | 1.00 | 21.59 |

FIGURE 3 (Cont.)

| A | B | C | D | E | F | G | H | I | J |
|---|---|---|---|---|---|---|---|---|---|
| 5521 | O | THR | B | 78 | 23.618 | 3.500 | 2.527 | 1.00 | 21.04 |
| 5522 | N | ASN | B | 79 | 23.897 | 1.261 | 2.628 | 1.00 | 21.29 |
| 5524 | CA | ASN | B | 79 | 23.467 | 1.170 | 4.022 | 1.00 | 21.08 |
| 5526 | CB | ASN | B | 79 | 23.358 | -0.293 | 4.454 | 1.00 | 21.68 |
| 5529 | CG | ASN | B | 79 | 23.046 | -0.442 | 5.923 | 1.00 | 21.92 |
| 5530 | OD1 | ASN | B | 79 | 21.903 | -0.297 | 6.343 | 1.00 | 23.33 |
| 5531 | ND2 | ASN | B | 79 | 24.060 | -0.747 | 6.706 | 1.00 | 22.60 |
| 5534 | C | ASN | B | 79 | 24.404 | 1.930 | 4.963 | 1.00 | 20.60 |
| 5535 | O | ASN | B | 79 | 23.950 | 2.532 | 5.920 | 1.00 | 19.95 |
| 5536 | N | THR | B | 80 | 25.708 | 1.876 | 4.708 | 1.00 | 20.20 |
| 5538 | CA | THR | B | 80 | 26.661 | 2.698 | 5.453 | 1.00 | 20.29 |
| 5540 | CB | THR | B | 80 | 28.086 | 2.339 | 5.017 | 1.00 | 20.31 |
| 5542 | OG1 | THR | B | 80 | 28.386 | 1.014 | 5.482 | 1.00 | 20.98 |
| 5544 | CG2 | THR | B | 80 | 29.139 | 3.242 | 5.699 | 1.00 | 21.55 |
| 5548 | C | THR | B | 80 | 26.390 | 4.199 | 5.257 | 1.00 | 20.17 |
| 5549 | O | THR | B | 80 | 26.440 | 4.994 | 6.218 | 1.00 | 20.64 |
| 5550 | N | LEU | B | 81 | 26.078 | 4.560 | 4.013 | 1.00 | 19.46 |
| 5552 | CA | LEU | B | 81 | 25.883 | 5.947 | 3.604 | 1.00 | 19.22 |
| 5554 | CB | LEU | B | 81 | 25.952 | 6.044 | 2.077 | 1.00 | 18.97 |
| 5557 | CG | LEU | B | 81 | 27.376 | 5.905 | 1.533 | 1.00 | 19.26 |
| 5559 | CD1 | LEU | B | 81 | 27.370 | 5.638 | 0.037 | 1.00 | 20.15 |
| 5563 | CD2 | LEU | B | 81 | 28.251 | 7.121 | 1.875 | 1.00 | 20.46 |
| 5567 | C | LEU | B | 81 | 24.584 | 6.574 | 4.113 | 1.00 | 19.19 |
| 5568 | O | LEU | B | 81 | 24.445 | 7.794 | 4.139 | 1.00 | 18.91 |
| 5569 | N | ASP | B | 82 | 23.641 | 5.746 | 4.523 | 1.00 | 19.51 |
| 5571 | CA | ASP | B | 82 | 22.393 | 6.219 | 5.106 | 1.00 | 19.28 |
| 5573 | CB | ASP | B | 82 | 21.559 | 5.046 | 5.616 | 1.00 | 19.89 |
| 5576 | CG | ASP | B | 82 | 20.654 | 4.406 | 4.552 | 1.00 | 21.00 |
| 5577 | OD1 | ASP | B | 82 | 20.591 | 4.823 | 3.365 | 1.00 | 21.03 |
| 5578 | OD2 | ASP | B | 82 | 19.938 | 3.431 | 4.867 | 1.00 | 24.24 |
| 5579 | C | ASP | B | 82 | 22.645 | 7.167 | 6.297 | 1.00 | 18.72 |
| 5580 | O | ASP | B | 82 | 21.924 | 8.147 | 6.462 | 1.00 | 18.18 |
| 5581 | N | ALA | B | 83 | 23.639 | 6.861 | 7.130 | 1.00 | 18.70 |
| 5583 | CA | ALA | B | 83 | 23.955 | 7.700 | 8.290 | 1.00 | 19.48 |
| 5585 | CB | ALA | B | 83 | 25.006 | 7.061 | 9.204 | 1.00 | 19.64 |
| 5589 | C | ALA | B | 83 | 24.360 | 9.113 | 7.894 | 1.00 | 19.16 |
| 5590 | O | ALA | B | 83 | 23.679 | 10.049 | 8.257 | 1.00 | 18.92 |
| 5591 | N | PRO | B | 84 | 25.451 | 9.305 | 7.163 | 1.00 | 19.56 |
| 5592 | CA | PRO | B | 84 | 25.781 | 10.672 | 6.739 | 1.00 | 19.16 |
| 5594 | CB | PRO | B | 84 | 27.114 | 10.519 | 6.004 | 1.00 | 19.21 |
| 5597 | CG | PRO | B | 84 | 27.166 | 9.070 | 5.606 | 1.00 | 19.67 |
| 5600 | CD | PRO | B | 84 | 26.446 | 8.323 | 6.694 | 1.00 | 19.64 |
| 5603 | C | PRO | B | 84 | 24.692 | 11.299 | 5.856 | 1.00 | 18.58 |
| 5604 | O | PRO | B | 84 | 24.509 | 12.510 | 5.924 | 1.00 | 18.13 |
| 5605 | N | ALA | B | 85 | 23.975 | 10.506 | 5.063 | 1.00 | 18.37 |
| 5607 | CA | ALA | B | 85 | 22.891 | 11.038 | 4.225 | 1.00 | 18.51 |
| 5609 | CB | ALA | B | 85 | 22.314 | 9.952 | 3.312 | 1.00 | 18.83 |
| 5613 | C | ALA | B | 85 | 21.790 | 11.644 | 5.073 | 1.00 | 18.64 |
| 5614 | O | ALA | B | 85 | 21.313 | 12.749 | 4.811 | 1.00 | 19.06 |
| 5615 | N | ALA | B | 86 | 21.407 | 10.928 | 6.114 | 1.00 | 18.40 |
| 5617 | CA | ALA | B | 86 | 20.360 | 11.383 | 7.010 | 1.00 | 18.11 |
| 5619 | CB | ALA | B | 86 | 19.906 | 10.245 | 7.903 | 1.00 | 18.05 |

FIGURE 3 (Cont.)

| A | B | C | D | E | F | G | H | I | J |
|---|---|---|---|---|---|---|---|---|---|
| 5623 | C | ALA | B | 86 | 20.855 | 12.566 | 7.841 | 1.00 | 17.48 |
| 5624 | O | ALA | B | 86 | 20.123 | 13.505 | 8.071 | 1.00 | 16.95 |
| 5625 | N | ALA | B | 87 | 22.105 | 12.525 | 8.281 | 1.00 | 17.41 |
| 5627 | CA | ALA | B | 87 | 22.630 | 13.600 | 9.115 | 1.00 | 17.40 |
| 5629 | CB | ALA | B | 87 | 23.982 | 13.244 | 9.638 | 1.00 | 17.13 |
| 5633 | C | ALA | B | 87 | 22.680 | 14.917 | 8.335 | 1.00 | 17.61 |
| 5634 | O | ALA | B | 87 | 22.298 | 15.947 | 8.858 | 1.00 | 17.33 |
| 5635 | N | VAL | B | 88 | 23.143 | 14.893 | 7.091 | 1.00 | 18.42 |
| 5637 | CA | VAL | B | 88 | 23.208 | 16.146 | 6.304 | 1.00 | 18.96 |
| 5639 | CB | BVAL | B | 88 | 24.038 | 16.002 | 4.993 | 0.35 | 18.97 |
| 5640 | CB | AVAL | B | 88 | 23.983 | 16.016 | 4.957 | 0.65 | 19.14 |
| 5643 | CG1 | BVAL | B | 88 | 23.256 | 15.295 | 3.906 | 0.35 | 19.73 |
| 5644 | CG1 | AVAL | B | 88 | 25.429 | 15.726 | 5.214 | 0.65 | 19.11 |
| 5651 | CG2 | BVAL | B | 88 | 24.517 | 17.378 | 4.509 | 0.35 | 18.57 |
| 5652 | CG2 | AVAL | B | 88 | 23.381 | 14.977 | 4.031 | 0.65 | 20.34 |
| 5659 | C | VAL | B | 88 | 21.813 | 16.685 | 6.031 | 1.00 | 19.05 |
| 5660 | O | VAL | B | 88 | 21.610 | 17.902 | 6.048 | 1.00 | 19.83 |
| 5661 | N | GLU | B | 89 | 20.858 | 15.786 | 5.828 | 1.00 | 18.96 |
| 5663 | CA | GLU | B | 89 | 19.479 | 16.181 | 5.611 | 1.00 | 19.29 |
| 5665 | CB | GLU | B | 89 | 18.657 | 15.024 | 5.045 | 1.00 | 19.83 |
| 5668 | CG | GLU | B | 89 | 17.271 | 15.429 | 4.550 | 1.00 | 20.18 |
| 5671 | CD | GLU | B | 89 | 17.276 | 16.380 | 3.353 | 1.00 | 21.04 |
| 5672 | OE1 | GLU | B | 89 | 16.175 | 16.831 | 2.956 | 1.00 | 20.80 |
| 5673 | OE2 | GLU | B | 89 | 18.352 | 16.669 | 2.784 | 1.00 | 22.55 |
| 5674 | C | GLU | B | 89 | 18.816 | 16.727 | 6.868 | 1.00 | 19.09 |
| 5675 | O | GLU | B | 89 | 17.964 | 17.587 | 6.761 | 1.00 | 18.76 |
| 5676 | N | CYS | B | 90 | 19.205 | 16.246 | 8.053 | 1.00 | 19.19 |
| 5678 | CA | CYS | B | 90 | 18.694 | 16.808 | 9.313 | 1.00 | 18.68 |
| 5680 | CB | CYS | B | 90 | 19.186 | 16.019 | 10.519 | 1.00 | 19.12 |
| 5683 | SG | CYS | B | 90 | 18.326 | 14.474 | 10.771 | 1.00 | 22.59 |
| 5684 | C | CYS | B | 90 | 19.160 | 18.255 | 9.485 | 1.00 | 17.90 |
| 5685 | O | CYS | B | 90 | 18.407 | 19.095 | 9.978 | 1.00 | 17.58 |
| 5686 | N | ILE | B | 91 | 20.416 | 18.524 | 9.129 | 1.00 | 16.55 |
| 5688 | CA | ILE | B | 91 | 20.951 | 19.877 | 9.214 | 1.00 | 16.20 |
| 5690 | CB | ILE | B | 91 | 22.468 | 19.934 | 8.896 | 1.00 | 15.98 |
| 5692 | CG1 | ILE | B | 91 | 23.261 | 19.204 | 9.970 | 1.00 | 15.40 |
| 5695 | CD1 | ILE | B | 91 | 23.203 | 19.886 | 11.342 | 1.00 | 17.23 |
| 5699 | CG2 | ILE | B | 91 | 22.941 | 21.391 | 8.777 | 1.00 | 15.29 |
| 5703 | C | ILE | B | 91 | 20.200 | 20.722 | 8.215 | 1.00 | 15.87 |
| 5704 | O | ILE | B | 91 | 19.770 | 21.815 | 8.533 | 1.00 | 15.70 |
| 5705 | N | HIS | B | 92 | 20.067 | 20.215 | 6.992 | 1.00 | 15.91 |
| 5707 | CA | HIS | B | 92 | 19.330 | 20.914 | 5.957 | 1.00 | 16.10 |
| 5709 | CB | HIS | B | 92 | 19.247 | 20.072 | 4.687 | 1.00 | 16.66 |
| 5712 | CG | HIS | B | 92 | 18.572 | 20.782 | 3.567 | 1.00 | 15.86 |
| 5713 | ND1 | HIS | B | 92 | 17.518 | 20.240 | 2.860 | 1.00 | 19.53 |
| 5715 | CE1 | HIS | B | 92 | 17.127 | 21.104 | 1.941 | 1.00 | 17.62 |
| 5717 | NE2 | HIS | B | 92 | 17.871 | 22.190 | 2.043 | 1.00 | 19.93 |
| 5719 | CD2 | HIS | B | 92 | 18.776 | 22.017 | 3.057 | 1.00 | 15.34 |
| 5721 | C | HIS | B | 92 | 17.923 | 21.259 | 6.424 | 1.00 | 17.04 |
| 5722 | O | HIS | B | 92 | 17.524 | 22.425 | 6.412 | 1.00 | 16.67 |
| 5723 | N | ALA | B | 93 | 17.193 | 20.243 | 6.885 | 1.00 | 17.19 |
| 5725 | CA | ALA | B | 93 | 15.809 | 20.414 | 7.334 | 1.00 | 17.14 |

FIGURE 3 (Cont.)

| A | B | C | D | E | F | G | H | I | J |
|---|---|---|---|---|---|---|---|---|---|
| 5727 | CB | ALA | B | 93 | 15.236 | 19.074 | 7.793 | 1.00 | 17.69 |
| 5731 | C | ALA | B | 93 | 15.681 | 21.456 | 8.452 | 1.00 | 17.97 |
| 5732 | O | ALA | B | 93 | 14.806 | 22.325 | 8.400 | 1.00 | 17.24 |
| 5733 | N | TYR | B | 94 | 16.570 | 21.389 | 9.449 | 1.00 | 17.80 |
| 5735 | CA | TYR | B | 94 | 16.550 | 22.348 | 10.560 | 1.00 | 17.32 |
| 5737 | CB | TYR | B | 94 | 17.580 | 21.968 | 11.647 | 1.00 | 18.17 |
| 5740 | CG | TYR | B | 94 | 18.635 | 23.015 | 11.933 | 1.00 | 19.38 |
| 5741 | CD1 | TYR | B | 94 | 18.308 | 24.219 | 12.556 | 1.00 | 22.96 |
| 5743 | CE1 | TYR | B | 94 | 19.290 | 25.186 | 12.809 | 1.00 | 23.47 |
| 5745 | CZ | TYR | B | 94 | 20.601 | 24.932 | 12.424 | 1.00 | 23.58 |
| 5746 | OH | TYR | B | 94 | 21.596 | 25.839 | 12.653 | 1.00 | 22.83 |
| 5748 | CE2 | TYR | B | 94 | 20.935 | 23.736 | 11.815 | 1.00 | 21.94 |
| 5750 | CD2 | TYR | B | 94 | 19.963 | 22.802 | 11.571 | 1.00 | 20.83 |
| 5752 | C | TYR | B | 94 | 16.810 | 23.765 | 10.042 | 1.00 | 16.90 |
| 5753 | O | TYR | B | 94 | 16.187 | 24.727 | 10.489 | 1.00 | 16.75 |
| 5754 | N | SER | B | 95 | 17.730 | 23.891 | 9.098 | 1.00 | 16.44 |
| 5756 | CA | SER | B | 95 | 18.097 | 25.192 | 8.581 | 1.00 | 17.14 |
| 5758 | CB | SER | B | 95 | 19.263 | 25.083 | 7.593 | 1.00 | 16.73 |
| 5761 | OG | SER | B | 95 | 18.840 | 24.597 | 6.337 | 1.00 | 18.73 |
| 5763 | C | SER | B | 95 | 16.887 | 25.851 | 7.924 | 1.00 | 17.47 |
| 5764 | O | SER | B | 95 | 16.686 | 27.050 | 8.047 | 1.00 | 17.44 |
| 5765 | N | LEU | B | 96 | 16.089 | 25.064 | 7.224 | 1.00 | 18.06 |
| 5767 | CA | LEU | B | 96 | 14.897 | 25.584 | 6.562 | 1.00 | 18.72 |
| 5769 | CB | LEU | B | 96 | 14.324 | 24.528 | 5.642 | 1.00 | 19.20 |
| 5772 | CG | LEU | B | 96 | 15.224 | 23.982 | 4.548 | 1.00 | 19.55 |
| 5774 | CD1 | LEU | B | 96 | 14.392 | 23.084 | 3.642 | 1.00 | 21.29 |
| 5778 | CD2 | LEU | B | 96 | 15.912 | 25.114 | 3.771 | 1.00 | 19.66 |
| 5782 | C | LEU | B | 96 | 13.814 | 26.018 | 7.551 | 1.00 | 18.78 |
| 5783 | O | LEU | B | 96 | 13.179 | 27.057 | 7.360 | 1.00 | 19.38 |
| 5784 | N | ILE | B | 97 | 13.607 | 25.227 | 8.599 | 1.00 | 18.35 |
| 5786 | CA | ILE | B | 97 | 12.581 | 25.536 | 9.612 | 1.00 | 18.39 |
| 5788 | CB | ILE | B | 97 | 12.525 | 24.456 | 10.724 | 1.00 | 18.49 |
| 5790 | CG1 | ILE | B | 97 | 12.050 | 23.122 | 10.161 | 1.00 | 19.38 |
| 5793 | CD1 | ILE | B | 97 | 12.339 | 21.950 | 11.075 | 1.00 | 20.40 |
| 5797 | CG2 | ILE | B | 97 | 11.617 | 24.887 | 11.862 | 1.00 | 18.22 |
| 5801 | C | ILE | B | 97 | 12.874 | 26.891 | 10.247 | 1.00 | 18.35 |
| 5802 | O | ILE | B | 97 | 11.976 | 27.698 | 10.437 | 1.00 | 18.38 |
| 5803 | N | HIS | B | 98 | 14.142 | 27.127 | 10.568 | 1.00 | 18.85 |
| 5805 | CA | HIS | B | 98 | 14.554 | 28.377 | 11.204 | 1.00 | 18.52 |
| 5807 | CB | HIS | B | 98 | 15.891 | 28.199 | 11.898 | 1.00 | 19.08 |
| 5810 | CG | HIS | B | 98 | 15.787 | 27.494 | 13.204 | 1.00 | 18.65 |
| 5811 | ND1 | HIS | B | 98 | 16.798 | 27.505 | 14.135 | 1.00 | 19.24 |
| 5813 | CE1 | HIS | B | 98 | 16.422 | 26.803 | 15.188 | 1.00 | 20.04 |
| 5815 | NE2 | HIS | B | 98 | 15.204 | 26.341 | 14.976 | 1.00 | 19.64 |
| 5817 | CD2 | HIS | B | 98 | 14.785 | 26.756 | 13.738 | 1.00 | 20.54 |
| 5819 | C | HIS | B | 98 | 14.588 | 29.526 | 10.189 | 1.00 | 18.70 |
| 5820 | O | HIS | B | 98 | 14.261 | 30.658 | 10.527 | 1.00 | 18.65 |
| 5821 | N | ASP | B | 99 | 14.949 | 29.218 | 8.946 | 1.00 | 18.55 |
| 5823 | CA | ASP | B | 99 | 14.971 | 30.199 | 7.861 | 1.00 | 18.61 |
| 5825 | CB | ASP | B | 99 | 15.515 | 29.530 | 6.605 | 1.00 | 18.44 |
| 5828 | CG | ASP | B | 99 | 15.629 | 30.470 | 5.456 | 1.00 | 18.37 |
| 5829 | OD1 | ASP | B | 99 | 14.710 | 30.462 | 4.590 | 1.00 | 16.28 |

FIGURE 3 (Cont.)

| A | B | C | D | E | F | G | H | I | J |
|---|---|---|---|---|---|---|---|---|---|
| 5830 | OD2 | ASP | B | 99 | 16.618 | 31.233 | 5.324 | 1.00 | 20.63 |
| 5831 | C | ASP | B | 99 | 13.581 | 30.809 | 7.572 | 1.00 | 18.97 |
| 5832 | O | ASP | B | 99 | 13.471 | 31.985 | 7.256 | 1.00 | 19.10 |
| 5833 | N | ASP | B | 100 | 12.537 | 30.007 | 7.703 | 1.00 | 19.32 |
| 5835 | CA | ASP | B | 100 | 11.172 | 30.446 | 7.448 | 1.00 | 20.42 |
| 5837 | CB | ASP | B | 100 | 10.283 | 29.224 | 7.206 | 1.00 | 20.29 |
| 5840 | CG | ASP | B | 100 | 10.566 | 28.544 | 5.883 | 1.00 | 20.45 |
| 5841 | OD1 | ASP | B | 100 | 10.363 | 27.303 | 5.791 | 1.00 | 21.30 |
| 5842 | OD2 | ASP | B | 100 | 10.981 | 29.158 | 4.885 | 1.00 | 20.64 |
| 5843 | C | ASP | B | 100 | 10.524 | 31.287 | 8.577 | 1.00 | 20.97 |
| 5844 | O | ASP | B | 100 | 9.465 | 31.874 | 8.372 | 1.00 | 21.34 |
| 5845 | N | LEU | B | 101 | 11.150 | 31.332 | 9.748 | 1.00 | 21.55 |
| 5847 | CA | LEU | B | 101 | 10.588 | 31.991 | 10.925 | 1.00 | 22.27 |
| 5849 | CB | LEU | B | 101 | 11.551 | 31.861 | 12.120 | 1.00 | 22.07 |
| 5852 | CG | LEU | B | 101 | 11.746 | 30.451 | 12.684 | 1.00 | 22.57 |
| 5854 | CD1 | LEU | B | 101 | 12.901 | 30.397 | 13.690 | 1.00 | 21.96 |
| 5858 | CD2 | LEU | B | 101 | 10.471 | 29.947 | 13.317 | 1.00 | 23.63 |
| 5862 | C | LEU | B | 101 | 10.313 | 33.470 | 10.646 | 1.00 | 22.59 |
| 5863 | O | LEU | B | 101 | 11.025 | 34.078 | 9.870 | 1.00 | 22.10 |
| 5864 | N | PRO | B | 102 | 9.262 | 34.035 | 11.242 | 1.00 | 23.34 |
| 5865 | CA | PRO | B | 102 | 8.959 | 35.467 | 11.096 | 1.00 | 23.88 |
| 5867 | CB | PRO | B | 102 | 7.886 | 35.698 | 12.152 | 1.00 | 23.65 |
| 5870 | CG | PRO | B | 102 | 7.151 | 34.422 | 12.154 | 1.00 | 24.22 |
| 5873 | CD | PRO | B | 102 | 8.225 | 33.347 | 12.024 | 1.00 | 23.27 |
| 5876 | C | PRO | B | 102 | 10.131 | 36.428 | 11.282 | 1.00 | 24.08 |
| 5877 | O | PRO | B | 102 | 10.211 | 37.387 | 10.523 | 1.00 | 24.64 |
| 5878 | N | ALA | B | 103 | 11.019 | 36.183 | 12.243 | 1.00 | 24.21 |
| 5880 | CA | ALA | B | 103 | 12.179 | 37.054 | 12.450 | 1.00 | 24.56 |
| 5882 | CB | ALA | B | 103 | 12.804 | 36.795 | 13.823 | 1.00 | 24.65 |
| 5886 | C | ALA | B | 103 | 13.235 | 36.885 | 11.364 | 1.00 | 24.37 |
| 5887 | O | ALA | B | 103 | 14.092 | 37.756 | 11.188 | 1.00 | 25.00 |
| 5888 | N | MET | B | 104 | 13.193 | 35.747 | 10.674 | 1.00 | 23.93 |
| 5890 | CA | MET | B | 104 | 14.111 | 35.445 | 9.578 | 1.00 | 24.35 |
| 5892 | CB | MET | B | 104 | 14.527 | 33.969 | 9.642 | 1.00 | 24.14 |
| 5895 | CG | MET | B | 104 | 15.317 | 33.629 | 10.912 | 1.00 | 26.61 |
| 5898 | SD | MET | B | 104 | 17.063 | 34.058 | 10.820 | 1.00 | 29.08 |
| 5899 | CE | MET | B | 104 | 17.584 | 33.058 | 9.452 | 1.00 | 29.15 |
| 5903 | C | MET | B | 104 | 13.463 | 35.845 | 8.237 | 1.00 | 23.69 |
| 5904 | O | MET | B | 104 | 13.310 | 37.040 | 7.995 | 1.00 | 23.79 |
| 5905 | N | ASP | B | 105 | 13.044 | 34.885 | 7.404 | 1.00 | 23.23 |
| 5907 | CA | ASP | B | 105 | 12.489 | 35.198 | 6.073 | 1.00 | 22.98 |
| 5909 | CB | ASP | B | 105 | 12.936 | 34.167 | 5.016 | 1.00 | 22.62 |
| 5912 | CG | ASP | B | 105 | 14.429 | 34.138 | 4.838 | 1.00 | 21.61 |
| 5913 | OD1 | ASP | B | 105 | 14.957 | 33.260 | 4.090 | 1.00 | 18.84 |
| 5914 | OD2 | ASP | B | 105 | 15.163 | 34.963 | 5.413 | 1.00 | 21.22 |
| 5915 | C | ASP | B | 105 | 10.967 | 35.289 | 6.067 | 1.00 | 23.49 |
| 5916 | O | ASP | B | 105 | 10.365 | 35.645 | 5.054 | 1.00 | 22.75 |
| 5917 | N | ASP | B | 106 | 10.348 | 34.950 | 7.185 | 1.00 | 23.98 |
| 5919 | CA | ASP | B | 106 | 8.907 | 35.099 | 7.339 | 1.00 | 25.41 |
| 5921 | CB | ASP | B | 106 | 8.567 | 36.597 | 7.503 | 1.00 | 25.60 |
| 5924 | CG | ASP | B | 106 | 7.203 | 36.817 | 8.103 | 1.00 | 27.51 |
| 5925 | OD1 | ASP | B | 106 | 6.682 | 37.941 | 7.973 | 1.00 | 29.77 |

FIGURE 3 (Cont.)

| A | B | C | D | E | F | G | H | I | J |
|---|---|---|---|---|---|---|---|---|---|
| 5926 | OD2 | ASP | B | 106 | 6.583 | 35.930 | 8.728 | 1.00 | 28.05 |
| 5927 | C | ASP | B | 106 | 8.126 | 34.503 | 6.172 | 1.00 | 25.57 |
| 5928 | O | ASP | B | 106 | 7.385 | 35.206 | 5.498 | 1.00 | 25.87 |
| 5929 | N | ASP | B | 107 | 8.309 | 33.203 | 5.936 | 1.00 | 26.04 |
| 5931 | CA | ASP | B | 107 | 7.630 | 32.487 | 4.861 | 1.00 | 25.95 |
| 5933 | CB | ASP | B | 107 | 8.641 | 31.685 | 4.032 | 1.00 | 26.04 |
| 5936 | CG | ASP | B | 107 | 9.212 | 32.477 | 2.895 | 1.00 | 26.93 |
| 5937 | OD1 | ASP | B | 107 | 8.428 | 32.869 | 2.004 | 1.00 | 30.09 |
| 5938 | OD2 | ASP | B | 107 | 10.426 | 32.755 | 2.786 | 1.00 | 25.96 |
| 5939 | C | ASP | B | 107 | 6.573 | 31.549 | 5.403 | 1.00 | 26.02 |
| 5940 | O | ASP | B | 107 | 6.773 | 30.883 | 6.425 | 1.00 | 26.50 |
| 5941 | N | ASP | B | 108 | 5.443 | 31.487 | 4.703 | 1.00 | 25.79 |
| 5943 | CA | ASP | B | 108 | 4.331 | 30.628 | 5.107 | 1.00 | 25.53 |
| 5945 | CB | ASP | B | 108 | 3.012 | 31.404 | 5.131 | 1.00 | 25.80 |
| 5948 | CG | ASP | B | 108 | 2.611 | 31.970 | 3.766 | 1.00 | 28.04 |
| 5949 | OD1 | ASP | B | 108 | 1.460 | 32.426 | 3.651 | 1.00 | 30.10 |
| 5950 | OD2 | ASP | B | 108 | 3.356 | 32.024 | 2.762 | 1.00 | 28.90 |
| 5951 | C | ASP | B | 108 | 4.183 | 29.359 | 4.260 | 1.00 | 24.50 |
| 5952 | O | ASP | B | 108 | 3.362 | 28.516 | 4.588 | 1.00 | 23.73 |
| 5953 | N | LEU | B | 109 | 4.975 | 29.228 | 3.197 | 1.00 | 23.97 |
| 5955 | CA | LEU | B | 109 | 4.939 | 28.054 | 2.323 | 1.00 | 23.69 |
| 5957 | CB | LEU | B | 109 | 4.386 | 28.414 | 0.940 | 1.00 | 24.10 |
| 5960 | CG | LEU | B | 109 | 2.907 | 28.201 | 0.569 | 1.00 | 27.09 |
| 5962 | CD1 | LEU | B | 109 | 2.748 | 28.570 | -0.917 | 1.00 | 27.23 |
| 5966 | CD2 | LEU | B | 109 | 2.367 | 26.794 | 0.840 | 1.00 | 25.73 |
| 5970 | C | LEU | B | 109 | 6.329 | 27.462 | 2.103 | 1.00 | 22.98 |
| 5971 | O | LEU | B | 109 | 7.271 | 28.178 | 1.813 | 1.00 | 22.51 |
| 5972 | N | ARG | B | 110 | 6.426 | 26.146 | 2.208 | 1.00 | 22.68 |
| 5974 | CA | ARG | B | 110 | 7.609 | 25.422 | 1.776 | 1.00 | 22.37 |
| 5976 | CB | ARG | B | 110 | 8.662 | 25.359 | 2.878 | 1.00 | 22.08 |
| 5979 | CG | ARG | B | 110 | 9.916 | 24.624 | 2.441 | 1.00 | 21.74 |
| 5982 | CD | ARG | B | 110 | 11.021 | 24.622 | 3.487 | 1.00 | 19.15 |
| 5985 | NE | ARG | B | 110 | 11.586 | 25.949 | 3.737 | 1.00 | 17.98 |
| 5987 | CZ | ARG | B | 110 | 12.421 | 26.579 | 2.911 | 1.00 | 18.36 |
| 5988 | NH1 | ARG | B | 110 | 12.900 | 27.771 | 3.239 | 1.00 | 19.16 |
| 5991 | NH2 | ARG | B | 110 | 12.789 | 26.027 | 1.770 | 1.00 | 18.06 |
| 5994 | C | ARG | B | 110 | 7.210 | 24.022 | 1.382 | 1.00 | 22.36 |
| 5995 | O | ARG | B | 110 | 6.409 | 23.385 | 2.071 | 1.00 | 22.81 |
| 5996 | N | ARG | B | 111 | 7.789 | 23.549 | 0.283 | 1.00 | 22.18 |
| 5998 | CA | ARG | B | 111 | 7.542 | 22.212 | -0.244 | 1.00 | 22.54 |
| 6000 | CB | ARG | B | 111 | 8.143 | 21.147 | 0.679 | 1.00 | 22.32 |
| 6003 | CG | ARG | B | 111 | 9.662 | 21.147 | 0.734 | 1.00 | 21.77 |
| 6006 | CD | ARG | B | 111 | 10.202 | 20.545 | 2.021 | 1.00 | 21.80 |
| 6009 | NE | ARG | B | 111 | 11.633 | 20.275 | 1.973 | 1.00 | 20.78 |
| 6011 | CZ | ARG | B | 111 | 12.305 | 19.671 | 2.947 | 1.00 | 20.45 |
| 6012 | NH1 | ARG | B | 111 | 11.688 | 19.269 | 4.048 | 1.00 | 18.82 |
| 6015 | NH2 | ARG | B | 111 | 13.608 | 19.464 | 2.826 | 1.00 | 19.98 |
| 6018 | C | ARG | B | 111 | 6.042 | 21.973 | -0.465 | 1.00 | 23.08 |
| 6019 | O | ARG | B | 111 | 5.544 | 20.861 | -0.338 | 1.00 | 22.39 |
| 6020 | N | GLY | B | 112 | 5.335 | 23.042 | -0.807 | 1.00 | 23.92 |
| 6022 | CA | GLY | B | 112 | 3.921 | 22.975 | -1.135 | 1.00 | 24.69 |
| 6025 | C | GLY | B | 112 | 3.010 | 23.023 | 0.070 | 1.00 | 24.98 |

FIGURE 3 (Cont.)

| A | B | C | D | E | F | G | H | I | J |
|---|---|---|---|---|---|---|---|---|---|
| 6026 | O | GLY | B | 112 | 1.808 | 22.978 | -0.089 | 1.00 | 25.54 |
| 6027 | N | LEU | B | 113 | 3.578 | 23.126 | 1.268 | 1.00 | 25.57 |
| 6029 | CA | LEU | B | 113 | 2.813 | 23.045 | 2.508 | 1.00 | 25.94 |
| 6031 | CB | LEU | B | 113 | 3.226 | 21.797 | 3.283 | 1.00 | 26.65 |
| 6034 | CG | LEU | B | 113 | 3.068 | 20.468 | 2.548 | 1.00 | 29.36 |
| 6036 | CD1 | LEU | B | 113 | 3.750 | 19.369 | 3.338 | 1.00 | 31.10 |
| 6040 | CD2 | LEU | B | 113 | 1.599 | 20.127 | 2.336 | 1.00 | 31.06 |
| 6044 | C | LEU | B | 113 | 3.043 | 24.272 | 3.388 | 1.00 | 25.32 |
| 6045 | O | LEU | B | 113 | 4.027 | 24.999 | 3.216 | 1.00 | 24.34 |
| 6046 | N | PRO | B | 114 | 2.153 | 24.497 | 4.355 | 1.00 | 25.34 |
| 6047 | CA | PRO | B | 114 | 2.425 | 25.500 | 5.383 | 1.00 | 24.92 |
| 6049 | CB | PRO | B | 114 | 1.261 | 25.331 | 6.348 | 1.00 | 25.42 |
| 6052 | CG | PRO | B | 114 | 0.165 | 24.734 | 5.503 | 1.00 | 25.33 |
| 6055 | CD | PRO | B | 114 | 0.862 | 23.812 | 4.575 | 1.00 | 25.09 |
| 6058 | C | PRO | B | 114 | 3.764 | 25.201 | 6.077 | 1.00 | 24.65 |
| 6059 | O | PRO | B | 114 | 4.051 | 24.057 | 6.403 | 1.00 | 24.29 |
| 6060 | N | THR | B | 115 | 4.583 | 26.222 | 6.259 | 1.00 | 24.42 |
| 6062 | CA | THR | B | 115 | 5.850 | 26.062 | 6.966 | 1.00 | 24.49 |
| 6064 | CB | THR | B | 115 | 6.635 | 27.364 | 6.990 | 1.00 | 24.32 |
| 6066 | OG1 | THR | B | 115 | 5.798 | 28.437 | 7.465 | 1.00 | 26.32 |
| 6068 | CG2 | THR | B | 115 | 7.058 | 27.773 | 5.573 | 1.00 | 24.50 |
| 6072 | C | THR | B | 115 | 5.607 | 25.577 | 8.387 | 1.00 | 24.50 |
| 6073 | O | THR | B | 115 | 4.512 | 25.721 | 8.944 | 1.00 | 23.20 |
| 6074 | N | CYS | B | 116 | 6.641 | 24.995 | 8.969 | 1.00 | 24.26 |
| 6076 | CA | CYS | B | 116 | 6.537 | 24.419 | 10.297 | 1.00 | 24.93 |
| 6078 | CB | CYS | B | 116 | 7.885 | 23.869 | 10.759 | 1.00 | 24.70 |
| 6081 | SG | CYS | B | 116 | 8.346 | 22.384 | 9.881 | 1.00 | 26.74 |
| 6082 | C | CYS | B | 116 | 6.002 | 25.412 | 11.305 | 1.00 | 24.67 |
| 6083 | O | CYS | B | 116 | 5.204 | 25.042 | 12.148 | 1.00 | 25.48 |
| 6084 | N | HIS | B | 117 | 6.408 | 26.672 | 11.212 | 1.00 | 24.78 |
| 6086 | CA | HIS | B | 117 | 5.981 | 27.647 | 12.214 | 1.00 | 25.04 |
| 6088 | CB | HIS | B | 117 | 6.888 | 28.867 | 12.233 | 1.00 | 25.27 |
| 6091 | CG | HIS | B | 117 | 6.649 | 29.828 | 11.116 | 1.00 | 25.24 |
| 6092 | ND1 | HIS | B | 117 | 5.983 | 31.018 | 11.293 | 1.00 | 26.70 |
| 6094 | CE1 | HIS | B | 117 | 5.924 | 31.663 | 10.141 | 1.00 | 27.42 |
| 6096 | NE2 | HIS | B | 117 | 6.532 | 30.935 | 9.226 | 1.00 | 26.41 |
| 6098 | CD2 | HIS | B | 117 | 6.985 | 29.776 | 9.807 | 1.00 | 26.27 |
| 6100 | C | HIS | B | 117 | 4.539 | 28.076 | 12.018 | 1.00 | 25.01 |
| 6101 | O | HIS | B | 117 | 3.891 | 28.466 | 12.971 | 1.00 | 25.49 |
| 6102 | N | VAL | B | 118 | 4.051 | 28.021 | 10.784 | 1.00 | 25.12 |
| 6104 | CA | VAL | B | 118 | 2.631 | 28.253 | 10.508 | 1.00 | 25.25 |
| 6106 | CB | VAL | B | 118 | 2.394 | 28.567 | 9.018 | 1.00 | 25.46 |
| 6108 | CG1 | VAL | B | 118 | 0.884 | 28.609 | 8.673 | 1.00 | 26.21 |
| 6112 | CG2 | VAL | B | 118 | 3.035 | 29.894 | 8.681 | 1.00 | 25.70 |
| 6116 | C | VAL | B | 118 | 1.786 | 27.078 | 10.999 | 1.00 | 25.08 |
| 6117 | O | VAL | B | 118 | 0.821 | 27.285 | 11.720 | 1.00 | 24.86 |
| 6118 | N | LYS | B | 119 | 2.167 | 25.856 | 10.639 | 1.00 | 25.25 |
| 6120 | CA | LYS | B | 119 | 1.439 | 24.654 | 11.042 | 1.00 | 25.87 |
| 6122 | CB | LYS | B | 119 | 1.935 | 23.428 | 10.263 | 1.00 | 26.25 |
| 6125 | CG | LYS | B | 119 | 0.884 | 22.726 | 9.418 | 1.00 | 28.80 |
| 6128 | CD | LYS | B | 119 | -0.165 | 22.025 | 10.250 | 1.00 | 31.95 |
| 6131 | CE | LYS | B | 119 | -0.978 | 21.015 | 9.432 | 1.00 | 33.31 |

FIGURE 3 (Cont.)

| A | B | C | D | E | F | G | H | I | J |
|---|---|---|---|---|---|---|---|---|---|
| 6134 | NZ | LYS | B | 119 | -1.864 | 21.671 | 8.417 | 1.00 | 34.97 |
| 6138 | C | LYS | B | 119 | 1.468 | 24.365 | 12.564 | 1.00 | 25.31 |
| 6139 | O | LYS | B | 119 | 0.445 | 24.061 | 13.161 | 1.00 | 24.99 |
| 6140 | N | PHE | B | 120 | 2.626 | 24.488 | 13.193 | 1.00 | 24.69 |
| 6142 | CA | PHE | B | 120 | 2.789 | 24.032 | 14.567 | 1.00 | 24.30 |
| 6144 | CB | PHE | B | 120 | 3.908 | 22.993 | 14.616 | 1.00 | 24.16 |
| 6147 | CG | PHE | B | 120 | 3.639 | 21.763 | 13.799 | 1.00 | 24.65 |
| 6148 | CD1 | PHE | B | 120 | 2.915 | 20.704 | 14.332 | 1.00 | 26.16 |
| 6150 | CE1 | PHE | B | 120 | 2.690 | 19.541 | 13.582 | 1.00 | 25.66 |
| 6152 | CZ | PHE | B | 120 | 3.192 | 19.441 | 12.311 | 1.00 | 25.37 |
| 6154 | CE2 | PHE | B | 120 | 3.930 | 20.494 | 11.767 | 1.00 | 24.54 |
| 6156 | CD2 | PHE | B | 120 | 4.158 | 21.637 | 12.513 | 1.00 | 25.35 |
| 6158 | C | PHE | B | 120 | 3.084 | 25.165 | 15.565 | 1.00 | 23.77 |
| 6159 | O | PHE | B | 120 | 3.155 | 24.927 | 16.752 | 1.00 | 23.66 |
| 6160 | N | GLY | B | 121 | 3.250 | 26.391 | 15.083 | 1.00 | 23.69 |
| 6162 | CA | GLY | B | 121 | 3.622 | 27.516 | 15.935 | 1.00 | 23.51 |
| 6165 | C | GLY | B | 121 | 5.130 | 27.773 | 15.955 | 1.00 | 23.55 |
| 6166 | O | GLY | B | 121 | 5.927 | 26.892 | 15.652 | 1.00 | 22.34 |
| 6167 | N | GLU | B | 122 | 5.518 | 28.986 | 16.320 | 1.00 | 23.70 |
| 6169 | CA | GLU | B | 122 | 6.934 | 29.381 | 16.314 | 1.00 | 24.67 |
| 6171 | CB | GLU | B | 122 | 7.091 | 30.868 | 16.639 | 1.00 | 24.89 |
| 6174 | CG | GLU | B | 122 | 6.990 | 31.777 | 15.427 | 1.00 | 27.84 |
| 6177 | CD | GLU | B | 122 | 7.069 | 33.248 | 15.796 | 1.00 | 30.34 |
| 6178 | OE1 | GLU | B | 122 | 8.174 | 33.721 | 16.136 | 1.00 | 35.10 |
| 6179 | OE2 | GLU | B | 122 | 6.033 | 33.931 | 15.743 | 1.00 | 32.39 |
| 6180 | C | GLU | B | 122 | 7.792 | 28.558 | 17.283 | 1.00 | 24.12 |
| 6181 | O | GLU | B | 122 | 8.925 | 28.199 | 16.955 | 1.00 | 23.74 |
| 6182 | N | ALA | B | 123 | 7.249 | 28.292 | 18.469 | 1.00 | 23.52 |
| 6184 | CA | ALA | B | 123 | 7.968 | 27.587 | 19.526 | 1.00 | 23.88 |
| 6186 | CB | ALA | B | 123 | 7.156 | 27.594 | 20.816 | 1.00 | 23.93 |
| 6190 | C | ALA | B | 123 | 8.287 | 26.159 | 19.098 | 1.00 | 23.98 |
| 6191 | O | ALA | B | 123 | 9.417 | 25.688 | 19.247 | 1.00 | 22.97 |
| 6192 | N | ASN | B | 124 | 7.290 | 25.494 | 18.524 | 1.00 | 23.86 |
| 6194 | CA | ASN | B | 124 | 7.484 | 24.159 | 17.980 | 1.00 | 24.09 |
| 6196 | CB | ASN | B | 124 | 6.165 | 23.561 | 17.486 | 1.00 | 24.26 |
| 6199 | CG | ASN | B | 124 | 5.365 | 22.896 | 18.601 | 1.00 | 26.12 |
| 6200 | OD1 | ASN | B | 124 | 4.125 | 22.946 | 18.602 | 1.00 | 27.70 |
| 6201 | ND2 | ASN | B | 124 | 6.064 | 22.278 | 19.561 | 1.00 | 23.40 |
| 6204 | C | ASN | B | 124 | 8.508 | 24.168 | 16.849 | 1.00 | 23.11 |
| 6205 | O | ASN | B | 124 | 9.294 | 23.250 | 16.750 | 1.00 | 22.29 |
| 6206 | N | ALA | B | 125 | 8.496 | 25.208 | 16.015 | 1.00 | 22.58 |
| 6208 | CA | ALA | B | 125 | 9.430 | 25.303 | 14.896 | 1.00 | 22.31 |
| 6210 | CB | ALA | B | 125 | 9.043 | 26.425 | 13.953 | 1.00 | 23.02 |
| 6214 | C | ALA | B | 125 | 10.836 | 25.526 | 15.405 | 1.00 | 21.81 |
| 6215 | O | ALA | B | 125 | 11.766 | 24.906 | 14.932 | 1.00 | 21.37 |
| 6216 | N | ILE | B | 126 | 10.985 | 26.419 | 16.371 | 1.00 | 21.15 |
| 6218 | CA | ILE | B | 126 | 12.293 | 26.701 | 16.936 | 1.00 | 20.84 |
| 6220 | CB | ILE | B | 126 | 12.177 | 27.795 | 18.007 | 1.00 | 20.71 |
| 6222 | CG1 | ILE | B | 126 | 11.994 | 29.168 | 17.339 | 1.00 | 21.50 |
| 6225 | CD1 | ILE | B | 126 | 11.342 | 30.199 | 18.243 | 1.00 | 22.29 |
| 6229 | CG2 | ILE | B | 126 | 13.395 | 27.816 | 18.903 | 1.00 | 21.11 |
| 6233 | C | ILE | B | 126 | 12.888 | 25.423 | 17.523 | 1.00 | 19.99 |

FIGURE 3 (Cont.)

| A | B | C | D | E | F | G | H | I | J |
|---|---|---|---|---|---|---|---|---|---|
| 6234 | O | ILE | B | 126 | 14.037 | 25.072 | 17.234 | 1.00 | 19.91 |
| 6235 | N | LEU | B | 127 | 12.094 | 24.746 | 18.342 | 1.00 | 19.38 |
| 6237 | CA | LEU | B | 127 | 12.522 | 23.553 | 19.061 | 1.00 | 19.20 |
| 6239 | CB | LEU | B | 127 | 11.477 | 23.141 | 20.106 | 1.00 | 19.23 |
| 6242 | CG | LEU | B | 127 | 11.417 | 24.029 | 21.357 | 1.00 | 20.75 |
| 6244 | CD1 | LEU | B | 127 | 12.776 | 24.131 | 22.047 | 1.00 | 22.13 |
| 6248 | CD2 | LEU | B | 127 | 10.382 | 23.528 | 22.321 | 1.00 | 22.65 |
| 6252 | C | LEU | B | 127 | 12.776 | 22.413 | 18.096 | 1.00 | 19.26 |
| 6253 | O | LEU | B | 127 | 13.757 | 21.682 | 18.244 | 1.00 | 19.51 |
| 6254 | N | ALA | B | 128 | 11.926 | 22.286 | 17.082 | 1.00 | 18.61 |
| 6256 | CA | ALA | B | 128 | 12.073 | 21.218 | 16.108 | 1.00 | 19.13 |
| 6258 | CB | ALA | B | 128 | 10.873 | 21.183 | 15.181 | 1.00 | 18.64 |
| 6262 | C | ALA | B | 128 | 13.373 | 21.368 | 15.315 | 1.00 | 18.57 |
| 6263 | O | ALA | B | 128 | 14.079 | 20.387 | 15.065 | 1.00 | 18.99 |
| 6264 | N | GLY | B | 129 | 13.685 | 22.595 | 14.916 | 1.00 | 18.91 |
| 6266 | CA | GLY | B | 129 | 14.948 | 22.879 | 14.272 | 1.00 | 18.59 |
| 6269 | C | GLY | B | 129 | 16.117 | 22.574 | 15.200 | 1.00 | 18.99 |
| 6270 | O | GLY | B | 129 | 17.098 | 21.959 | 14.790 | 1.00 | 18.66 |
| 6271 | N | ASP | B | 130 | 16.001 | 22.986 | 16.459 | 1.00 | 19.11 |
| 6273 | CA | ASP | B | 130 | 17.061 | 22.771 | 17.457 | 1.00 | 19.02 |
| 6275 | CB | ASP | B | 130 | 16.652 | 23.327 | 18.829 | 1.00 | 18.48 |
| 6278 | CG | ASP | B | 130 | 16.654 | 24.851 | 18.881 | 1.00 | 20.10 |
| 6279 | OD1 | ASP | B | 130 | 17.086 | 25.482 | 17.880 | 1.00 | 19.13 |
| 6280 | OD2 | ASP | B | 130 | 16.221 | 25.488 | 19.889 | 1.00 | 20.44 |
| 6281 | C | ASP | B | 130 | 17.344 | 21.283 | 17.586 | 1.00 | 18.66 |
| 6282 | O | ASP | B | 130 | 18.481 | 20.860 | 17.541 | 1.00 | 18.36 |
| 6283 | N | ALA | B | 131 | 16.274 | 20.506 | 17.675 | 1.00 | 18.43 |
| 6285 | CA | ALA | B | 131 | 16.347 | 19.069 | 17.878 | 1.00 | 18.51 |
| 6287 | CB | ALA | B | 131 | 15.012 | 18.540 | 18.344 | 1.00 | 18.33 |
| 6291 | C | ALA | B | 131 | 16.808 | 18.315 | 16.629 | 1.00 | 18.44 |
| 6292 | O | ALA | B | 131 | 17.407 | 17.248 | 16.748 | 1.00 | 18.67 |
| 6293 | N | LEU | B | 132 | 16.518 | 18.850 | 15.445 | 1.00 | 18.17 |
| 6295 | CA | LEU | B | 132 | 16.970 | 18.235 | 14.207 | 1.00 | 18.20 |
| 6297 | CB | LEU | B | 132 | 16.213 | 18.786 | 12.995 | 1.00 | 18.38 |
| 6300 | CG | LEU | B | 132 | 14.853 | 18.138 | 12.732 | 1.00 | 17.74 |
| 6302 | CD1 | LEU | B | 132 | 14.127 | 18.905 | 11.651 | 1.00 | 17.44 |
| 6306 | CD2 | LEU | B | 132 | 15.017 | 16.674 | 12.341 | 1.00 | 18.02 |
| 6310 | C | LEU | B | 132 | 18.467 | 18.452 | 14.034 | 1.00 | 18.06 |
| 6311 | O | LEU | B | 132 | 19.167 | 17.572 | 13.544 | 1.00 | 18.16 |
| 6312 | N | GLN | B | 133 | 18.969 | 19.610 | 14.447 | 1.00 | 17.91 |
| 6314 | CA | GLN | B | 133 | 20.412 | 19.804 | 14.412 | 1.00 | 18.74 |
| 6316 | CB | GLN | B | 133 | 20.838 | 21.223 | 14.800 | 1.00 | 18.78 |
| 6319 | CG | GLN | B | 133 | 22.358 | 21.369 | 14.668 | 1.00 | 21.69 |
| 6322 | CD | GLN | B | 133 | 22.953 | 22.631 | 15.232 | 1.00 | 23.34 |
| 6323 | OE1 | GLN | B | 133 | 22.274 | 23.644 | 15.458 | 1.00 | 24.32 |
| 6324 | NE2 | GLN | B | 133 | 24.255 | 22.578 | 15.452 | 1.00 | 26.40 |
| 6327 | C | GLN | B | 133 | 21.094 | 18.762 | 15.319 | 1.00 | 18.33 |
| 6328 | O | GLN | B | 133 | 22.086 | 18.144 | 14.926 | 1.00 | 18.38 |
| 6329 | N | THR | B | 134 | 20.542 | 18.560 | 16.508 | 1.00 | 17.86 |
| 6331 | CA | THR | B | 134 | 21.121 | 17.657 | 17.476 | 1.00 | 18.15 |
| 6333 | CB | THR | B | 134 | 20.384 | 17.734 | 18.820 | 1.00 | 18.21 |
| 6335 | OG1 | THR | B | 134 | 20.296 | 19.101 | 19.283 | 1.00 | 18.94 |

FIGURE 3 (Cont.)

| A | B | C | D | E | F | G | H | I | J |
|---|---|---|---|---|---|---|---|---|---|
| 6337 | CG2 | THR | B | 134 | 21.169 | 17.017 | 19.864 | 1.00 | 19.06 |
| 6341 | C | THR | B | 134 | 21.060 | 16.225 | 16.950 | 1.00 | 18.22 |
| 6342 | O | THR | B | 134 | 22.014 | 15.474 | 17.106 | 1.00 | 18.09 |
| 6343 | N | LEU | B | 135 | 19.936 | 15.870 | 16.322 | 1.00 | 17.83 |
| 6345 | CA | LEU | B | 135 | 19.739 | 14.530 | 15.781 | 1.00 | 17.43 |
| 6347 | CB | LEU | B | 135 | 18.336 | 14.416 | 15.184 | 1.00 | 17.61 |
| 6350 | CG | LEU | B | 135 | 18.006 | 13.113 | 14.455 | 1.00 | 18.78 |
| 6352 | CD1 | LEU | B | 135 | 18.167 | 11.908 | 15.367 | 1.00 | 18.23 |
| 6356 | CD2 | LEU | B | 135 | 16.619 | 13.201 | 13.912 | 1.00 | 19.31 |
| 6360 | C | LEU | B | 135 | 20.818 | 14.186 | 14.743 | 1.00 | 16.77 |
| 6361 | O | LEU | B | 135 | 21.287 | 13.045 | 14.664 | 1.00 | 16.01 |
| 6362 | N | ALA | B | 136 | 21.243 | 15.179 | 13.970 | 1.00 | 16.82 |
| 6364 | CA | ALA | B | 136 | 22.280 | 14.960 | 12.974 | 1.00 | 16.89 |
| 6366 | CB | ALA | B | 136 | 22.581 | 16.241 | 12.231 | 1.00 | 17.47 |
| 6370 | C | ALA | B | 136 | 23.548 | 14.406 | 13.625 | 1.00 | 17.27 |
| 6371 | O | ALA | B | 136 | 24.184 | 13.484 | 13.091 | 1.00 | 17.46 |
| 6372 | N | PHE | B | 137 | 23.888 | 14.943 | 14.789 | 1.00 | 17.08 |
| 6374 | CA | PHE | B | 137 | 25.088 | 14.528 | 15.496 | 1.00 | 17.65 |
| 6376 | CB | PHE | B | 137 | 25.593 | 15.666 | 16.381 | 1.00 | 18.03 |
| 6379 | CG | PHE | B | 137 | 26.007 | 16.880 | 15.584 | 1.00 | 18.67 |
| 6380 | CD1 | PHE | B | 137 | 25.230 | 18.019 | 15.566 | 1.00 | 18.86 |
| 6382 | CE1 | PHE | B | 137 | 25.605 | 19.122 | 14.809 | 1.00 | 19.97 |
| 6384 | CZ | PHE | B | 137 | 26.757 | 19.070 | 14.029 | 1.00 | 19.23 |
| 6386 | CE2 | PHE | B | 137 | 27.526 | 17.940 | 14.023 | 1.00 | 19.82 |
| 6388 | CD2 | PHE | B | 137 | 27.140 | 16.835 | 14.788 | 1.00 | 21.06 |
| 6390 | C | PHE | B | 137 | 24.848 | 13.218 | 16.260 | 1.00 | 17.89 |
| 6391 | O | PHE | B | 137 | 25.764 | 12.440 | 16.419 | 1.00 | 17.92 |
| 6392 | N | SER | B | 138 | 23.613 | 12.966 | 16.699 | 1.00 | 18.09 |
| 6394 | CA | SER | B | 138 | 23.275 | 11.661 | 17.269 | 1.00 | 18.71 |
| 6396 | CB | SER | B | 138 | 21.839 | 11.634 | 17.769 | 1.00 | 18.28 |
| 6399 | OG | SER | B | 138 | 21.712 | 12.386 | 18.950 | 1.00 | 19.32 |
| 6401 | C | SER | B | 138 | 23.466 | 10.571 | 16.212 | 1.00 | 18.94 |
| 6402 | O | SER | B | 138 | 24.084 | 9.555 | 16.485 | 1.00 | 19.25 |
| 6403 | N | ILE | B | 139 | 22.967 | 10.819 | 15.001 | 1.00 | 19.22 |
| 6405 | CA | ILE | B | 139 | 23.123 | 9.884 | 13.890 | 1.00 | 19.25 |
| 6407 | CB | ILE | B | 139 | 22.430 | 10.403 | 12.622 | 1.00 | 19.39 |
| 6409 | CG1 | ILE | B | 139 | 20.916 | 10.363 | 12.822 | 1.00 | 18.95 |
| 6412 | CD1 | ILE | B | 139 | 20.144 | 11.100 | 11.805 | 1.00 | 21.43 |
| 6416 | CG2 | ILE | B | 139 | 22.848 | 9.571 | 11.387 | 1.00 | 17.88 |
| 6420 | C | ILE | B | 139 | 24.606 | 9.609 | 13.612 | 1.00 | 19.87 |
| 6421 | O | ILE | B | 139 | 25.021 | 8.461 | 13.593 | 1.00 | 19.68 |
| 6422 | N | LEU | B | 140 | 25.397 | 10.648 | 13.393 | 1.00 | 19.88 |
| 6424 | CA | LEU | B | 140 | 26.799 | 10.451 | 13.025 | 1.00 | 20.40 |
| 6426 | CB | LEU | B | 140 | 27.452 | 11.764 | 12.620 | 1.00 | 20.25 |
| 6429 | CG | LEU | B | 140 | 27.071 | 12.298 | 11.246 | 1.00 | 20.51 |
| 6431 | CD1 | LEU | B | 140 | 27.798 | 13.593 | 11.005 | 1.00 | 23.24 |
| 6435 | CD2 | LEU | B | 140 | 27.402 | 11.299 | 10.149 | 1.00 | 21.98 |
| 6439 | C | LEU | B | 140 | 27.600 | 9.803 | 14.145 | 1.00 | 20.89 |
| 6440 | O | LEU | B | 140 | 28.572 | 9.088 | 13.876 | 1.00 | 21.00 |
| 6441 | N | SER | B | 141 | 27.211 | 10.045 | 15.396 | 1.00 | 21.26 |
| 6443 | CA | SER | B | 141 | 27.933 | 9.439 | 16.514 | 1.00 | 22.16 |
| 6445 | CB | SER | B | 141 | 27.926 | 10.329 | 17.756 | 1.00 | 21.93 |

FIGURE 3 (Cont.)

| A | B | C | D | E | F | G | H | I | J |
|---|---|---|---|---|---|---|---|---|---|
| 6448 | OG | SER | B | 141 | 26.615 | 10.552 | 18.225 | 1.00 | 23.99 |
| 6450 | C | SER | B | 141 | 27.456 | 8.023 | 16.856 | 1.00 | 22.90 |
| 6451 | O | SER | B | 141 | 28.248 | 7.250 | 17.390 | 1.00 | 22.85 |
| 6452 | N | ASP | B | 142 | 26.203 | 7.678 | 16.538 | 1.00 | 23.91 |
| 6454 | CA | ASP | B | 142 | 25.580 | 6.411 | 16.991 | 1.00 | 24.85 |
| 6456 | CB | ASP | B | 142 | 24.270 | 6.674 | 17.745 | 1.00 | 25.39 |
| 6459 | CG | ASP | B | 142 | 24.464 | 7.509 | 18.995 | 1.00 | 26.64 |
| 6460 | OD1 | ASP | B | 142 | 23.535 | 8.249 | 19.365 | 1.00 | 25.98 |
| 6461 | OD2 | ASP | B | 142 | 25.516 | 7.497 | 19.667 | 1.00 | 29.60 |
| 6462 | C | ASP | B | 142 | 25.262 | 5.407 | 15.890 | 1.00 | 25.42 |
| 6463 | O | ASP | B | 142 | 25.185 | 4.202 | 16.158 | 1.00 | 25.21 |
| 6464 | N | ALA | B | 143 | 25.052 | 5.887 | 14.663 | 1.00 | 25.69 |
| 6466 | CA | ALA | B | 143 | 24.533 | 5.031 | 13.592 | 1.00 | 26.20 |
| 6468 | CB | ALA | B | 143 | 24.187 | 5.840 | 12.367 | 1.00 | 26.13 |
| 6472 | C | ALA | B | 143 | 25.542 | 3.965 | 13.226 | 1.00 | 26.52 |
| 6473 | O | ALA | B | 143 | 26.739 | 4.190 | 13.292 | 1.00 | 26.08 |
| 6474 | N | ASP | B | 144 | 25.051 | 2.790 | 12.862 | 1.00 | 27.00 |
| 6476 | CA | ASP | B | 144 | 25.908 | 1.760 | 12.308 | 1.00 | 27.79 |
| 6478 | CB | ASP | B | 144 | 25.084 | 0.487 | 12.088 | 1.00 | 28.61 |
| 6481 | CG | ASP | B | 144 | 25.935 | -0.733 | 11.853 | 1.00 | 30.23 |
| 6482 | OD1 | ASP | B | 144 | 27.147 | -0.714 | 12.160 | 1.00 | 33.26 |
| 6483 | OD2 | ASP | B | 144 | 25.452 | -1.776 | 11.358 | 1.00 | 34.68 |
| 6484 | C | ASP | B | 144 | 26.531 | 2.247 | 10.992 | 1.00 | 27.76 |
| 6485 | O | ASP | B | 144 | 25.825 | 2.652 | 10.050 | 1.00 | 27.93 |
| 6486 | N | MET | B | 145 | 27.856 | 2.247 | 10.951 | 1.00 | 27.25 |
| 6488 | CA | MET | B | 145 | 28.612 | 2.526 | 9.743 | 1.00 | 27.33 |
| 6490 | CB | MET | B | 145 | 29.181 | 3.936 | 9.772 | 1.00 | 26.88 |
| 6493 | CG | MET | B | 145 | 28.129 | 5.014 | 9.664 | 1.00 | 26.79 |
| 6496 | SD | MET | B | 145 | 28.859 | 6.646 | 9.270 | 1.00 | 27.26 |
| 6497 | CE | MET | B | 145 | 29.830 | 6.916 | 10.701 | 1.00 | 23.05 |
| 6501 | C | MET | B | 145 | 29.737 | 1.508 | 9.657 | 1.00 | 27.62 |
| 6502 | O | MET | B | 145 | 30.895 | 1.812 | 9.936 | 1.00 | 26.26 |
| 6503 | N | PRO | B | 146 | 29.393 | 0.291 | 9.256 | 1.00 | 28.79 |
| 6504 | CA | PRO | B | 146 | 30.354 | -0.815 | 9.234 | 1.00 | 29.73 |
| 6506 | CB | PRO | B | 146 | 29.669 | -1.832 | 8.320 | 1.00 | 29.99 |
| 6509 | CG | PRO | B | 146 | 28.228 | -1.630 | 8.593 | 1.00 | 29.30 |
| 6512 | CD | PRO | B | 146 | 28.060 | -0.137 | 8.799 | 1.00 | 29.11 |
| 6515 | C | PRO | B | 146 | 31.733 | -0.464 | 8.696 | 1.00 | 30.46 |
| 6516 | O | PRO | B | 146 | 32.732 | -0.822 | 9.317 | 1.00 | 30.83 |
| 6517 | N | GLU | B | 147 | 31.801 | 0.253 | 7.586 | 1.00 | 31.81 |
| 6519 | CA | GLU | B | 147 | 33.089 | 0.431 | 6.905 | 1.00 | 33.36 |
| 6521 | CB | GLU | B | 147 | 32.889 | 0.840 | 5.426 | 1.00 | 34.57 |
| 6524 | CG | GLU | B | 147 | 31.629 | 0.304 | 4.730 | 1.00 | 37.40 |
| 6527 | CD | GLU | B | 147 | 31.768 | 0.264 | 3.209 | 1.00 | 41.76 |
| 6528 | OE1 | GLU | B | 147 | 30.918 | -0.387 | 2.543 | 1.00 | 42.19 |
| 6529 | OE2 | GLU | B | 147 | 32.733 | 0.877 | 2.676 | 1.00 | 43.49 |
| 6530 | C | GLU | B | 147 | 34.030 | 1.449 | 7.587 | 1.00 | 32.65 |
| 6531 | O | GLU | B | 147 | 35.172 | 1.605 | 7.155 | 1.00 | 33.17 |
| 6532 | N | VAL | B | 148 | 33.572 | 2.099 | 8.660 | 1.00 | 31.25 |
| 6534 | CA | VAL | B | 148 | 34.097 | 3.410 | 9.043 | 1.00 | 30.18 |
| 6536 | CB | VAL | B | 148 | 32.970 | 4.456 | 9.012 | 1.00 | 30.21 |
| 6538 | CG1 | VAL | B | 148 | 33.501 | 5.842 | 9.381 | 1.00 | 29.95 |

FIGURE 3 (Cont.)

| A | B | C | D | E | F | G | H | I | J |
|---|---|---|---|---|---|---|---|---|---|
| 6542 | CG2 | VAL | B | 148 | 32.310 | 4.467 | 7.634 | 1.00 | 30.63 |
| 6546 | C | VAL | B | 148 | 34.767 | 3.425 | 10.417 | 1.00 | 28.89 |
| 6547 | O | VAL | B | 148 | 34.131 | 3.174 | 11.431 | 1.00 | 27.43 |
| 6548 | N | SER | B | 149 | 36.057 | 3.755 | 10.435 | 1.00 | 28.02 |
| 6550 | CA | SER | B | 149 | 36.806 | 3.836 | 11.681 | 1.00 | 27.32 |
| 6552 | CB | SER | B | 149 | 38.302 | 4.022 | 11.413 | 1.00 | 27.23 |
| 6555 | OG | SER | B | 149 | 38.554 | 5.276 | 10.811 | 1.00 | 25.67 |
| 6557 | C | SER | B | 149 | 36.295 | 4.984 | 12.540 | 1.00 | 27.03 |
| 6558 | O | SER | B | 149 | 35.651 | 5.906 | 12.045 | 1.00 | 26.50 |
| 6559 | N | ASP | B | 150 | 36.601 | 4.899 | 13.831 | 1.00 | 26.71 |
| 6561 | CA | ASP | B | 150 | 36.236 | 5.914 | 14.810 | 1.00 | 26.65 |
| 6563 | CB | ASP | B | 150 | 36.729 | 5.509 | 16.194 | 1.00 | 26.35 |
| 6566 | CG | ASP | B | 150 | 35.776 | 4.575 | 16.906 | 1.00 | 28.03 |
| 6567 | OD1 | ASP | B | 150 | 36.086 | 4.216 | 18.054 | 1.00 | 30.17 |
| 6568 | OD2 | ASP | B | 150 | 34.692 | 4.157 | 16.424 | 1.00 | 29.62 |
| 6569 | C | ASP | B | 150 | 36.824 | 7.253 | 14.407 | 1.00 | 26.23 |
| 6570 | O | ASP | B | 150 | 36.146 | 8.269 | 14.454 | 1.00 | 25.29 |
| 6571 | N | ARG | B | 151 | 38.077 | 7.229 | 13.970 | 1.00 | 26.28 |
| 6573 | CA | ARG | B | 151 | 38.745 | 8.409 | 13.442 | 1.00 | 26.55 |
| 6575 | CB | ARG | B | 151 | 40.172 | 8.069 | 13.019 | 1.00 | 27.45 |
| 6578 | CG | ARG | B | 151 | 41.099 | 9.254 | 13.054 | 1.00 | 30.78 |
| 6581 | CD | ARG | B | 151 | 41.726 | 9.500 | 14.416 | 1.00 | 34.73 |
| 6584 | NE | ARG | B | 151 | 41.001 | 10.520 | 15.179 | 1.00 | 38.97 |
| 6586 | CZ | ARG | B | 151 | 41.152 | 11.835 | 15.043 | 1.00 | 42.64 |
| 6587 | NH1 | ARG | B | 151 | 42.000 | 12.354 | 14.148 | 1.00 | 45.06 |
| 6590 | NH2 | ARG | B | 151 | 40.435 | 12.651 | 15.801 | 1.00 | 43.15 |
| 6593 | C | ARG | B | 151 | 38.004 | 9.052 | 12.268 | 1.00 | 25.50 |
| 6594 | O | ARG | B | 151 | 37.870 | 10.265 | 12.211 | 1.00 | 25.19 |
| 6595 | N | ASP | B | 152 | 37.540 | 8.252 | 11.315 | 1.00 | 24.83 |
| 6597 | CA | ASP | B | 152 | 36.823 | 8.813 | 10.171 | 1.00 | 24.18 |
| 6599 | CB | ASP | B | 152 | 36.747 | 7.809 | 9.030 | 1.00 | 24.78 |
| 6602 | CG | ASP | B | 152 | 38.117 | 7.499 | 8.443 | 1.00 | 26.32 |
| 6603 | OD1 | ASP | B | 152 | 39.074 | 8.280 | 8.679 | 1.00 | 29.38 |
| 6604 | OD2 | ASP | B | 152 | 38.329 | 6.479 | 7.758 | 1.00 | 28.43 |
| 6605 | C | ASP | B | 152 | 35.427 | 9.290 | 10.562 | 1.00 | 22.75 |
| 6606 | O | ASP | B | 152 | 34.923 | 10.240 | 10.007 | 1.00 | 22.39 |
| 6607 | N | ARG | B | 153 | 34.810 | 8.619 | 11.521 | 1.00 | 21.86 |
| 6609 | CA | ARG | B | 153 | 33.532 | 9.053 | 12.064 | 1.00 | 20.79 |
| 6611 | CB | ARG | B | 153 | 33.022 | 8.054 | 13.088 | 1.00 | 20.74 |
| 6614 | CG | ARG | B | 153 | 31.647 | 8.375 | 13.651 | 1.00 | 20.82 |
| 6617 | CD | ARG | B | 153 | 31.205 | 7.399 | 14.704 | 1.00 | 20.94 |
| 6620 | NE | ARG | B | 153 | 30.980 | 6.045 | 14.173 | 1.00 | 22.48 |
| 6622 | CZ | ARG | B | 153 | 29.790 | 5.511 | 13.895 | 1.00 | 23.71 |
| 6623 | NH1 | ARG | B | 153 | 29.723 | 4.256 | 13.448 | 1.00 | 25.23 |
| 6626 | NH2 | ARG | B | 153 | 28.671 | 6.205 | 14.046 | 1.00 | 20.67 |
| 6629 | C | ARG | B | 153 | 33.676 | 10.426 | 12.714 | 1.00 | 20.58 |
| 6630 | O | ARG | B | 153 | 32.833 | 11.297 | 12.519 | 1.00 | 18.98 |
| 6631 | N | ILE | B | 154 | 34.752 | 10.610 | 13.483 | 1.00 | 20.29 |
| 6633 | CA | ILE | B | 154 | 35.016 | 11.891 | 14.124 | 1.00 | 20.38 |
| 6635 | CB | ILE | B | 154 | 36.209 | 11.808 | 15.090 | 1.00 | 20.21 |
| 6637 | CG1 | ILE | B | 154 | 35.848 | 10.962 | 16.319 | 1.00 | 20.02 |
| 6640 | CD1 | ILE | B | 154 | 37.077 | 10.390 | 17.035 | 1.00 | 21.78 |

FIGURE 3 (Cont.)

| A | B | C | D | E | F | G | H | I | J |
|---|---|---|---|---|---|---|---|---|---|
| 6644 | CG2 | ILE | B | 154 | 36.656 | 13.203 | 15.514 | 1.00 | 21.46 |
| 6648 | C | ILE | B | 154 | 35.247 | 12.940 | 13.051 | 1.00 | 20.53 |
| 6649 | O | ILE | B | 154 | 34.737 | 14.018 | 13.158 | 1.00 | 20.41 |
| 6650 | N | SER | B | 155 | 35.976 | 12.593 | 11.996 | 1.00 | 21.07 |
| 6652 | CA | SER | B | 155 | 36.182 | 13.485 | 10.864 | 1.00 | 21.78 |
| 6654 | CB | SER | B | 155 | 37.097 | 12.822 | 9.824 | 1.00 | 22.36 |
| 6657 | OG | SER | B | 155 | 38.452 | 13.117 | 10.107 | 1.00 | 25.91 |
| 6659 | C | SER | B | 155 | 34.867 | 13.924 | 10.186 | 1.00 | 21.46 |
| 6660 | O | SER | B | 155 | 34.771 | 15.053 | 9.711 | 1.00 | 21.56 |
| 6661 | N | MET | B | 156 | 33.886 | 13.029 | 10.125 | 1.00 | 21.47 |
| 6663 | CA | MET | B | 156 | 32.569 | 13.337 | 9.576 | 1.00 | 21.23 |
| 6665 | CB | MET | B | 156 | 31.726 | 12.079 | 9.403 | 1.00 | 21.94 |
| 6668 | CG | MET | B | 156 | 32.183 | 11.183 | 8.281 | 1.00 | 24.79 |
| 6671 | SD | MET | B | 156 | 31.189 | 9.677 | 8.224 | 1.00 | 31.73 |
| 6672 | CE | MET | B | 156 | 32.337 | 8.674 | 7.553 | 1.00 | 32.04 |
| 6676 | C | MET | B | 156 | 31.815 | 14.278 | 10.480 | 1.00 | 20.18 |
| 6677 | O | MET | B | 156 | 31.164 | 15.191 | 10.005 | 1.00 | 20.12 |
| 6678 | N | ILE | B | 157 | 31.894 | 14.045 | 11.782 | 1.00 | 20.00 |
| 6680 | CA | ILE | B | 157 | 31.238 | 14.915 | 12.744 | 1.00 | 19.69 |
| 6682 | CB | ILE | B | 157 | 31.290 | 14.326 | 14.178 | 1.00 | 19.62 |
| 6684 | CG1 | ILE | B | 157 | 30.466 | 13.047 | 14.259 | 1.00 | 19.47 |
| 6687 | CD1 | ILE | B | 157 | 30.741 | 12.182 | 15.483 | 1.00 | 21.29 |
| 6691 | CG2 | ILE | B | 157 | 30.763 | 15.332 | 15.177 | 1.00 | 18.69 |
| 6695 | C | ILE | B | 157 | 31.878 | 16.289 | 12.688 | 1.00 | 19.80 |
| 6696 | O | ILE | B | 157 | 31.182 | 17.300 | 12.684 | 1.00 | 20.00 |
| 6697 | N | SER | B | 158 | 33.204 | 16.340 | 12.640 | 1.00 | 19.73 |
| 6699 | CA | SER | B | 158 | 33.894 | 17.619 | 12.559 | 1.00 | 19.44 |
| 6701 | CB | SER | B | 158 | 35.410 | 17.419 | 12.507 | 1.00 | 19.53 |
| 6704 | OG | SER | B | 158 | 36.053 | 18.665 | 12.347 | 1.00 | 19.74 |
| 6706 | C | SER | B | 158 | 33.469 | 18.403 | 11.325 | 1.00 | 19.46 |
| 6707 | O | SER | B | 158 | 33.193 | 19.587 | 11.408 | 1.00 | 18.61 |
| 6708 | N | GLU | B | 159 | 33.429 | 17.734 | 10.181 | 1.00 | 20.02 |
| 6710 | CA | GLU | B | 159 | 33.084 | 18.384 | 8.932 | 1.00 | 20.06 |
| 6712 | CB | GLU | B | 159 | 33.224 | 17.423 | 7.757 | 1.00 | 20.49 |
| 6715 | CG | GLU | B | 159 | 32.576 | 17.922 | 6.472 | 1.00 | 21.89 |
| 6718 | CD | GLU | B | 159 | 33.103 | 19.290 | 6.041 | 1.00 | 23.61 |
| 6719 | OE1 | GLU | B | 159 | 34.281 | 19.584 | 6.322 | 1.00 | 24.99 |
| 6720 | OE2 | GLU | B | 159 | 32.347 | 20.067 | 5.426 | 1.00 | 25.28 |
| 6721 | C | GLU | B | 159 | 31.658 | 18.934 | 8.990 | 1.00 | 19.72 |
| 6722 | O | GLU | B | 159 | 31.422 | 20.062 | 8.577 | 1.00 | 19.69 |
| 6723 | N | LEU | B | 160 | 30.720 | 18.140 | 9.494 | 1.00 | 18.90 |
| 6725 | CA | LEU | B | 160 | 29.324 | 18.550 | 9.526 | 1.00 | 18.94 |
| 6727 | CB | LEU | B | 160 | 28.406 | 17.404 | 9.956 | 1.00 | 18.87 |
| 6730 | CG | LEU | B | 160 | 26.915 | 17.695 | 9.771 | 1.00 | 19.53 |
| 6732 | CD1 | LEU | B | 160 | 26.644 | 18.166 | 8.357 | 1.00 | 19.83 |
| 6736 | CD2 | LEU | B | 160 | 26.076 | 16.470 | 10.093 | 1.00 | 20.63 |
| 6740 | C | LEU | B | 160 | 29.158 | 19.736 | 10.458 | 1.00 | 18.48 |
| 6741 | O | LEU | B | 160 | 28.486 | 20.694 | 10.130 | 1.00 | 18.99 |
| 6742 | N | ALA | B | 161 | 29.803 | 19.673 | 11.612 | 1.00 | 18.69 |
| 6744 | CA | ALA | B | 161 | 29.769 | 20.773 | 12.560 | 1.00 | 18.51 |
| 6746 | CB | ALA | B | 161 | 30.446 | 20.384 | 13.872 | 1.00 | 18.21 |
| 6750 | C | ALA | B | 161 | 30.377 | 22.045 | 11.970 | 1.00 | 19.04 |

FIGURE 3 (Cont.)

| A | B | C | D | E | F | G | H | I | J |
|---|---|---|---|---|---|---|---|---|---|
| 6751 | O | ALA | B | 161 | 29.749 | 23.095 | 12.012 | 1.00 | 18.97 |
| 6752 | N | SER | B | 162 | 31.573 | 21.976 | 11.387 | 1.00 | 19.49 |
| 6754 | CA | SER | B | 162 | 32.161 | 23.190 | 10.838 | 1.00 | 19.97 |
| 6756 | CB | SER | B | 162 | 33.630 | 22.988 | 10.472 | 1.00 | 20.60 |
| 6759 | OG | SER | B | 162 | 33.756 | 21.975 | 9.518 | 1.00 | 24.18 |
| 6761 | C | SER | B | 162 | 31.348 | 23.734 | 9.643 | 1.00 | 19.40 |
| 6762 | O | SER | B | 162 | 31.186 | 24.958 | 9.482 | 1.00 | 18.70 |
| 6763 | N | ALA | B | 163 | 30.813 | 22.832 | 8.825 | 1.00 | 19.19 |
| 6765 | CA | ALA | B | 163 | 29.974 | 23.225 | 7.690 | 1.00 | 18.98 |
| 6767 | CB | ALA | B | 163 | 29.671 | 22.011 | 6.798 | 1.00 | 19.19 |
| 6771 | C | ALA | B | 163 | 28.672 | 23.907 | 8.081 | 1.00 | 18.85 |
| 6772 | O | ALA | B | 163 | 28.157 | 24.742 | 7.341 | 1.00 | 19.30 |
| 6773 | N | SER | B | 164 | 28.135 | 23.537 | 9.228 | 1.00 | 18.81 |
| 6775 | CA | SER | B | 164 | 26.788 | 23.931 | 9.638 | 1.00 | 18.52 |
| 6777 | CB | SER | B | 164 | 26.128 | 22.787 | 10.405 | 1.00 | 18.45 |
| 6780 | OG | SER | B | 164 | 26.073 | 21.610 | 9.622 | 1.00 | 18.06 |
| 6782 | C | SER | B | 164 | 26.780 | 25.159 | 10.526 | 1.00 | 18.48 |
| 6783 | O | SER | B | 164 | 25.779 | 25.828 | 10.630 | 1.00 | 18.20 |
| 6784 | N | GLY | B | 165 | 27.902 | 25.438 | 11.177 | 1.00 | 19.42 |
| 6786 | CA | GLY | B | 165 | 27.950 | 26.481 | 12.175 | 1.00 | 19.70 |
| 6789 | C | GLY | B | 165 | 28.359 | 27.810 | 11.598 | 1.00 | 20.33 |
| 6790 | O | GLY | B | 165 | 28.096 | 28.122 | 10.441 | 1.00 | 19.41 |
| 6791 | N | ILE | B | 166 | 29.018 | 28.604 | 12.424 | 1.00 | 21.45 |
| 6793 | CA | ILE | B | 166 | 29.348 | 29.976 | 12.074 | 1.00 | 22.91 |
| 6795 | CB | ILE | B | 166 | 29.846 | 30.707 | 13.354 | 1.00 | 23.50 |
| 6797 | CG1 | ILE | B | 166 | 29.737 | 32.206 | 13.173 | 1.00 | 25.77 |
| 6800 | CD1 | ILE | B | 166 | 28.314 | 32.688 | 13.353 | 1.00 | 25.49 |
| 6804 | CG2 | ILE | B | 166 | 31.229 | 30.245 | 13.727 | 1.00 | 24.89 |
| 6808 | C | ILE | B | 166 | 30.354 | 30.068 | 10.916 | 1.00 | 22.56 |
| 6809 | O | ILE | B | 166 | 30.335 | 31.016 | 10.141 | 1.00 | 22.77 |
| 6810 | N | ALA | B | 167 | 31.207 | 29.059 | 10.771 | 1.00 | 22.49 |
| 6812 | CA | ALA | B | 167 | 32.152 | 29.006 | 9.656 | 1.00 | 22.06 |
| 6814 | CB | ALA | B | 167 | 33.324 | 28.148 | 10.023 | 1.00 | 21.92 |
| 6818 | C | ALA | B | 167 | 31.490 | 28.488 | 8.383 | 1.00 | 22.04 |
| 6819 | O | ALA | B | 167 | 32.146 | 28.318 | 7.376 | 1.00 | 22.97 |
| 6820 | N | GLY | B | 168 | 30.181 | 28.252 | 8.430 | 1.00 | 21.24 |
| 6822 | CA | GLY | B | 168 | 29.464 | 27.684 | 7.313 | 1.00 | 20.53 |
| 6825 | C | GLY | B | 168 | 28.034 | 28.189 | 7.292 | 1.00 | 20.28 |
| 6826 | O | GLY | B | 168 | 27.804 | 29.394 | 7.295 | 1.00 | 19.03 |
| 6827 | N | MET | B | 169 | 27.082 | 27.265 | 7.340 | 1.00 | 20.39 |
| 6829 | CA | MET | B | 169 | 25.676 | 27.559 | 7.077 | 1.00 | 21.14 |
| 6831 | CB | MET | B | 169 | 24.855 | 26.298 | 7.278 | 1.00 | 21.40 |
| 6834 | CG | MET | B | 169 | 23.410 | 26.392 | 6.837 | 1.00 | 23.14 |
| 6837 | SD | MET | B | 169 | 22.401 | 27.153 | 8.090 | 1.00 | 26.74 |
| 6838 | CE | MET | B | 169 | 22.407 | 25.862 | 9.410 | 1.00 | 26.17 |
| 6842 | C | MET | B | 169 | 25.147 | 28.696 | 7.938 | 1.00 | 21.67 |
| 6843 | O | MET | B | 169 | 24.556 | 29.644 | 7.436 | 1.00 | 21.21 |
| 6844 | N | CYS | B | 170 | 25.367 | 28.594 | 9.239 | 1.00 | 22.13 |
| 6846 | CA | CYS | B | 170 | 24.827 | 29.556 | 10.170 | 1.00 | 22.50 |
| 6848 | CB | BCYS | B | 170 | 25.042 | 29.096 | 11.614 | 0.35 | 22.49 |
| 6849 | CB | ACYS | B | 170 | 25.010 | 29.057 | 11.596 | 0.65 | 22.96 |
| 6854 | SG | BCYS | B | 170 | 23.609 | 28.307 | 12.340 | 0.35 | 22.05 |

FIGURE 3 (Cont.)

| A | B | C | D | E | F | G | H | I | J |
|---|---|---|---|---|---|---|---|---|---|
| 6855 | SG | ACYS | B | 170 | 24.028 | 29.996 | 12.749 | 0.65 | 25.42 |
| 6856 | C | CYS | B | 170 | 25.460 | 30.935 | 9.997 | 1.00 | 21.94 |
| 6857 | O | CYS | B | 170 | 24.775 | 31.934 | 10.105 | 1.00 | 22.08 |
| 6858 | N | GLY | B | 171 | 26.767 | 30.980 | 9.758 | 1.00 | 21.27 |
| 6860 | CA | GLY | B | 171 | 27.453 | 32.231 | 9.504 | 1.00 | 21.35 |
| 6863 | C | GLY | B | 171 | 26.951 | 32.858 | 8.218 | 1.00 | 20.97 |
| 6864 | O | GLY | B | 171 | 26.839 | 34.081 | 8.111 | 1.00 | 20.81 |
| 6865 | N | GLY | B | 172 | 26.643 | 32.009 | 7.249 | 1.00 | 20.08 |
| 6867 | CA | GLY | B | 172 | 26.027 | 32.440 | 6.009 | 1.00 | 19.62 |
| 6870 | C | GLY | B | 172 | 24.641 | 33.007 | 6.215 | 1.00 | 19.25 |
| 6871 | O | GLY | B | 172 | 24.288 | 34.011 | 5.605 | 1.00 | 18.27 |
| 6872 | N | GLN | B | 173 | 23.858 | 32.380 | 7.084 | 1.00 | 18.75 |
| 6874 | CA | GLN | B | 173 | 22.535 | 32.890 | 7.404 | 1.00 | 19.22 |
| 6876 | CB | GLN | B | 173 | 21.787 | 31.947 | 8.348 | 1.00 | 19.67 |
| 6879 | CG | GLN | B | 173 | 21.349 | 30.652 | 7.682 | 1.00 | 20.18 |
| 6882 | CD | GLN | B | 173 | 20.333 | 30.899 | 6.597 | 1.00 | 20.92 |
| 6883 | OE1 | GLN | B | 173 | 20.701 | 31.297 | 5.496 | 1.00 | 21.77 |
| 6884 | NE2 | GLN | B | 173 | 19.047 | 30.712 | 6.914 | 1.00 | 19.90 |
| 6887 | C | GLN | B | 173 | 22.632 | 34.281 | 8.002 | 1.00 | 19.31 |
| 6888 | O | GLN | B | 173 | 21.805 | 35.146 | 7.691 | 1.00 | 18.98 |
| 6889 | N | ALA | B | 174 | 23.667 | 34.503 | 8.810 | 1.00 | 19.26 |
| 6891 | CA | ALA | B | 174 | 23.894 | 35.813 | 9.437 | 1.00 | 20.09 |
| 6893 | CB | ALA | B | 174 | 24.956 | 35.725 | 10.526 | 1.00 | 19.57 |
| 6897 | C | ALA | B | 174 | 24.292 | 36.845 | 8.387 | 1.00 | 20.47 |
| 6898 | O | ALA | B | 174 | 23.826 | 37.969 | 8.440 | 1.00 | 21.60 |
| 6899 | N | LEU | B | 175 | 25.143 | 36.464 | 7.436 | 1.00 | 21.00 |
| 6901 | CA | LEU | B | 175 | 25.561 | 37.384 | 6.371 | 1.00 | 21.21 |
| 6903 | CB | LEU | B | 175 | 26.646 | 36.753 | 5.497 | 1.00 | 21.41 |
| 6906 | CG | LEU | B | 175 | 28.026 | 36.557 | 6.121 | 1.00 | 23.45 |
| 6908 | CD1 | LEU | B | 175 | 28.948 | 35.855 | 5.138 | 1.00 | 24.47 |
| 6912 | CD2 | LEU | B | 175 | 28.630 | 37.913 | 6.562 | 1.00 | 24.78 |
| 6916 | C | LEU | B | 175 | 24.358 | 37.776 | 5.519 | 1.00 | 21.36 |
| 6917 | O | LEU | B | 175 | 24.210 | 38.942 | 5.118 | 1.00 | 20.88 |
| 6918 | N | ASP | B | 176 | 23.498 | 36.794 | 5.258 | 1.00 | 21.82 |
| 6920 | CA | ASP | B | 176 | 22.291 | 36.980 | 4.466 | 1.00 | 22.30 |
| 6922 | CB | ASP | B | 176 | 21.615 | 35.625 | 4.252 | 1.00 | 22.47 |
| 6925 | CG | ASP | B | 176 | 20.205 | 35.739 | 3.779 | 1.00 | 21.57 |
| 6926 | OD1 | ASP | B | 176 | 19.938 | 35.449 | 2.588 | 1.00 | 22.94 |
| 6927 | OD2 | ASP | B | 176 | 19.281 | 36.072 | 4.540 | 1.00 | 25.04 |
| 6928 | C | ASP | B | 176 | 21.356 | 37.989 | 5.138 | 1.00 | 23.38 |
| 6929 | O | ASP | B | 176 | 20.856 | 38.927 | 4.499 | 1.00 | 23.61 |
| 6930 | N | LEU | B | 177 | 21.131 | 37.814 | 6.429 | 1.00 | 24.61 |
| 6932 | CA | LEU | B | 177 | 20.296 | 38.751 | 7.181 | 1.00 | 26.08 |
| 6934 | CB | LEU | B | 177 | 20.112 | 38.267 | 8.621 | 1.00 | 26.86 |
| 6937 | CG | LEU | B | 177 | 18.842 | 37.475 | 8.968 | 1.00 | 28.65 |
| 6939 | CD1 | LEU | B | 177 | 18.029 | 36.990 | 7.768 | 1.00 | 30.94 |
| 6943 | CD2 | LEU | B | 177 | 19.243 | 36.330 | 9.825 | 1.00 | 29.29 |
| 6947 | C | LEU | B | 177 | 20.891 | 40.147 | 7.193 | 1.00 | 26.38 |
| 6948 | O | LEU | B | 177 | 20.176 | 41.134 | 7.048 | 1.00 | 27.18 |
| 6949 | N | ASP | B | 178 | 22.203 | 40.228 | 7.355 | 1.00 | 27.07 |
| 6951 | CA | ASP | B | 178 | 22.893 | 41.513 | 7.389 | 1.00 | 27.97 |
| 6953 | CB | ASP | B | 178 | 24.336 | 41.337 | 7.864 | 1.00 | 28.49 |

FIGURE 3 (Cont.)

| A | B | C | D | E | F | G | H | I | J |
|---|---|---|---|---|---|---|---|---|---|
| 6956 | CG | ASP | B | 178 | 24.926 | 42.624 | 8.427 | 1.00 | 31.55 |
| 6957 | OD1 | ASP | B | 178 | 25.937 | 43.106 | 7.874 | 1.00 | 34.43 |
| 6958 | OD2 | ASP | B | 178 | 24.447 | 43.218 | 9.419 | 1.00 | 36.43 |
| 6959 | C | ASP | B | 178 | 22.865 | 42.228 | 6.034 | 1.00 | 27.98 |
| 6960 | O | ASP | B | 178 | 22.853 | 43.454 | 5.993 | 1.00 | 27.47 |
| 6961 | N | ALA | B | 179 | 22.828 | 41.462 | 4.936 | 1.00 | 27.64 |
| 6963 | CA | ALA | B | 179 | 22.818 | 42.026 | 3.576 | 1.00 | 27.64 |
| 6965 | CB | ALA | B | 179 | 23.397 | 41.024 | 2.579 | 1.00 | 27.26 |
| 6969 | C | ALA | B | 179 | 21.415 | 42.474 | 3.118 | 1.00 | 27.90 |
| 6970 | O | ALA | B | 179 | 21.288 | 43.142 | 2.109 | 1.00 | 27.38 |
| 6971 | N | GLU | B | 180 | 20.374 | 42.097 | 3.852 | 1.00 | 28.50 |
| 6973 | CA | GLU | B | 180 | 19.006 | 42.515 | 3.535 | 1.00 | 29.13 |
| 6975 | CB | GLU | B | 180 | 18.031 | 42.069 | 4.629 | 1.00 | 29.71 |
| 6978 | CG | GLU | B | 180 | 17.071 | 40.969 | 4.234 | 1.00 | 31.66 |
| 6981 | CD | GLU | B | 180 | 16.175 | 40.534 | 5.384 | 1.00 | 33.14 |
| 6982 | OE1 | GLU | B | 180 | 15.509 | 41.400 | 5.995 | 1.00 | 35.30 |
| 6983 | OE2 | GLU | B | 180 | 16.149 | 39.324 | 5.684 | 1.00 | 32.62 |
| 6984 | C | GLU | B | 180 | 18.922 | 44.041 | 3.418 | 1.00 | 29.49 |
| 6985 | O | GLU | B | 180 | 19.290 | 44.755 | 4.348 | 1.00 | 28.60 |
| 6986 | N | GLY | B | 181 | 18.454 | 44.518 | 2.264 | 1.00 | 29.61 |
| 6988 | CA | GLY | B | 181 | 18.279 | 45.935 | 1.997 | 1.00 | 29.83 |
| 6991 | C | GLY | B | 181 | 19.560 | 46.670 | 1.658 | 1.00 | 30.04 |
| 6992 | O | GLY | B | 181 | 19.532 | 47.871 | 1.420 | 1.00 | 30.48 |
| 6993 | N | LYS | B | 182 | 20.681 | 45.954 | 1.622 | 1.00 | 30.21 |
| 6995 | CA | LYS | B | 182 | 21.992 | 46.573 | 1.506 | 1.00 | 30.46 |
| 6997 | CB | LYS | B | 182 | 22.959 | 45.982 | 2.526 | 1.00 | 30.97 |
| 7000 | CG | LYS | B | 182 | 22.593 | 46.287 | 3.973 | 1.00 | 32.58 |
| 7003 | CD | LYS | B | 182 | 23.830 | 46.343 | 4.864 | 1.00 | 34.32 |
| 7006 | CE | LYS | B | 182 | 23.490 | 46.882 | 6.259 | 1.00 | 35.98 |
| 7009 | NZ | LYS | B | 182 | 23.339 | 45.804 | 7.290 | 1.00 | 36.88 |
| 7013 | C | LYS | B | 182 | 22.573 | 46.427 | 0.116 | 1.00 | 30.22 |
| 7014 | O | LYS | B | 182 | 23.559 | 47.083 | -0.203 | 1.00 | 30.23 |
| 7015 | N | HIS | B | 183 | 21.984 | 45.555 | -0.700 | 1.00 | 29.28 |
| 7017 | CA | HIS | B | 183 | 22.375 | 45.441 | -2.093 | 1.00 | 29.34 |
| 7019 | CB | HIS | B | 183 | 21.892 | 46.684 | -2.856 | 1.00 | 29.70 |
| 7022 | CG | HIS | B | 183 | 20.410 | 46.833 | -2.832 | 1.00 | 30.08 |
| 7023 | ND1 | HIS | B | 183 | 19.699 | 47.003 | -1.668 | 1.00 | 32.28 |
| 7025 | CE1 | HIS | B | 183 | 18.412 | 47.068 | -1.942 | 1.00 | 31.16 |
| 7027 | NE2 | HIS | B | 183 | 18.261 | 46.940 | -3.244 | 1.00 | 32.50 |
| 7029 | CD2 | HIS | B | 183 | 19.497 | 46.782 | -3.821 | 1.00 | 32.70 |
| 7031 | C | HIS | B | 183 | 23.887 | 45.297 | -2.191 | 1.00 | 28.93 |
| 7032 | O | HIS | B | 183 | 24.558 | 46.097 | -2.847 | 1.00 | 29.19 |
| 7033 | N | VAL | B | 184 | 24.415 | 44.274 | -1.522 | 1.00 | 27.85 |
| 7035 | CA | VAL | B | 184 | 25.850 | 44.103 | -1.417 | 1.00 | 27.29 |
| 7037 | CB | VAL | B | 184 | 26.247 | 43.065 | -0.319 | 1.00 | 27.33 |
| 7039 | CG1 | VAL | B | 184 | 25.636 | 43.452 | 1.052 | 1.00 | 27.10 |
| 7043 | CG2 | VAL | B | 184 | 25.860 | 41.634 | -0.722 | 1.00 | 27.05 |
| 7047 | C | VAL | B | 184 | 26.419 | 43.723 | -2.779 | 1.00 | 26.86 |
| 7048 | O | VAL | B | 184 | 25.733 | 43.075 | -3.577 | 1.00 | 26.12 |
| 7049 | N | PRO | B | 185 | 27.663 | 44.126 | -3.051 | 1.00 | 26.31 |
| 7050 | CA | PRO | B | 185 | 28.314 | 43.792 | -4.319 | 1.00 | 26.16 |
| 7052 | CB | PRO | B | 185 | 29.596 | 44.623 | -4.284 | 1.00 | 26.24 |

FIGURE 3 (Cont.)

| A | B | C | D | E | F | G | H | I | J |
|---|---|---|---|---|---|---|---|---|---|
| 7055 | CG | PRO | B | 185 | 29.892 | 44.801 | -2.835 | 1.00 | 26.65 |
| 7058 | CD | PRO | B | 185 | 28.552 | 44.905 | -2.168 | 1.00 | 26.81 |
| 7061 | C | PRO | B | 185 | 28.646 | 42.297 | -4.436 | 1.00 | 25.85 |
| 7062 | O | PRO | B | 185 | 28.521 | 41.553 | -3.475 | 1.00 | 24.67 |
| 7063 | N | LEU | B | 186 | 29.106 | 41.908 | -5.616 | 1.00 | 26.22 |
| 7065 | CA | LEU | B | 186 | 29.284 | 40.509 | -6.002 | 1.00 | 26.42 |
| 7067 | CB | LEU | B | 186 | 29.859 | 40.422 | -7.424 | 1.00 | 26.65 |
| 7070 | CG | LEU | B | 186 | 29.462 | 39.279 | -8.371 | 1.00 | 28.07 |
| 7072 | CD1 | LEU | B | 186 | 30.565 | 39.033 | -9.399 | 1.00 | 29.61 |
| 7076 | CD2 | LEU | B | 186 | 29.105 | 38.004 | -7.671 | 1.00 | 28.33 |
| 7080 | C | LEU | B | 186 | 30.183 | 39.726 | -5.048 | 1.00 | 26.27 |
| 7081 | O | LEU | B | 186 | 29.890 | 38.580 | -4.737 | 1.00 | 25.80 |
| 7082 | N | ASP | B | 187 | 31.286 | 40.317 | -4.590 | 1.00 | 26.90 |
| 7084 | CA | ASP | B | 187 | 32.198 | 39.558 | -3.721 | 1.00 | 27.11 |
| 7086 | CB | ASP | B | 187 | 33.567 | 40.236 | -3.526 | 1.00 | 27.85 |
| 7089 | CG | ASP | B | 187 | 33.480 | 41.648 | -2.951 | 1.00 | 30.82 |
| 7090 | OD1 | ASP | B | 187 | 34.555 | 42.173 | -2.574 | 1.00 | 36.51 |
| 7091 | OD2 | ASP | B | 187 | 32.435 | 42.331 | -2.848 | 1.00 | 35.53 |
| 7092 | C | ASP | B | 187 | 31.554 | 39.180 | -2.380 | 1.00 | 26.24 |
| 7093 | O | ASP | B | 187 | 31.729 | 38.053 | -1.900 | 1.00 | 25.65 |
| 7094 | N | ALA | B | 188 | 30.809 | 40.117 | -1.799 | 1.00 | 25.42 |
| 7096 | CA | ALA | B | 188 | 30.097 | 39.892 | -0.548 | 1.00 | 24.85 |
| 7098 | CB | ALA | B | 188 | 29.610 | 41.221 | 0.019 | 1.00 | 24.84 |
| 7102 | C | ALA | B | 188 | 28.915 | 38.951 | -0.774 | 1.00 | 24.38 |
| 7103 | O | ALA | B | 188 | 28.578 | 38.154 | 0.081 | 1.00 | 24.14 |
| 7104 | N | LEU | B | 189 | 28.291 | 39.059 | -1.942 | 1.00 | 24.33 |
| 7106 | CA | LEU | B | 189 | 27.156 | 38.230 | -2.286 | 1.00 | 24.42 |
| 7108 | CB | LEU | B | 189 | 26.530 | 38.741 | -3.577 | 1.00 | 24.99 |
| 7111 | CG | LEU | B | 189 | 25.509 | 37.865 | -4.268 | 1.00 | 25.94 |
| 7113 | CD1 | LEU | B | 189 | 24.317 | 37.593 | -3.350 | 1.00 | 26.65 |
| 7117 | CD2 | LEU | B | 189 | 25.072 | 38.566 | -5.566 | 1.00 | 26.30 |
| 7121 | C | LEU | B | 189 | 27.607 | 36.783 | -2.435 | 1.00 | 23.85 |
| 7122 | O | LEU | B | 189 | 26.965 | 35.863 | -1.918 | 1.00 | 23.56 |
| 7123 | N | GLU | B | 190 | 28.727 | 36.590 | -3.115 | 1.00 | 23.22 |
| 7125 | CA | GLU | B | 190 | 29.301 | 35.269 | -3.280 | 1.00 | 23.29 |
| 7127 | CB | GLU | B | 190 | 30.566 | 35.331 | -4.135 | 1.00 | 23.75 |
| 7130 | CG | GLU | B | 190 | 31.070 | 33.963 | -4.535 | 1.00 | 25.63 |
| 7133 | CD | GLU | B | 190 | 32.356 | 33.994 | -5.339 | 1.00 | 28.46 |
| 7134 | OE1 | GLU | B | 190 | 33.201 | 33.121 | -5.090 | 1.00 | 31.64 |
| 7135 | OE2 | GLU | B | 190 | 32.522 | 34.854 | -6.226 | 1.00 | 32.12 |
| 7136 | C | GLU | B | 190 | 29.625 | 34.655 | -1.917 | 1.00 | 22.85 |
| 7137 | O | GLU | B | 190 | 29.434 | 33.459 | -1.699 | 1.00 | 20.62 |
| 7138 | N | ARG | B | 191 | 30.114 | 35.490 | -1.009 | 1.00 | 22.57 |
| 7140 | CA | ARG | B | 191 | 30.499 | 35.041 | 0.315 | 1.00 | 22.97 |
| 7142 | CB | ARG | B | 191 | 31.169 | 36.171 | 1.077 | 1.00 | 23.59 |
| 7145 | CG | ARG | B | 191 | 31.646 | 35.789 | 2.444 | 1.00 | 26.56 |
| 7148 | CD | ARG | B | 191 | 32.707 | 36.714 | 3.004 | 1.00 | 31.42 |
| 7151 | NE | ARG | B | 191 | 32.158 | 37.666 | 3.962 | 1.00 | 35.82 |
| 7153 | CZ | ARG | B | 191 | 32.874 | 38.304 | 4.891 | 1.00 | 38.83 |
| 7154 | NH1 | ARG | B | 191 | 34.184 | 38.105 | 5.012 | 1.00 | 39.90 |
| 7157 | NH2 | ARG | B | 191 | 32.270 | 39.150 | 5.712 | 1.00 | 40.92 |
| 7160 | C | ARG | B | 191 | 29.282 | 34.546 | 1.087 | 1.00 | 21.94 |

FIGURE 3 (Cont.)

| A | B | C | D | E | F | G | H | I | J |
|---|---|---|---|---|---|---|---|---|---|
| 7161 | O | ARG | B | 191 | 29.357 | 33.536 | 1.770 | 1.00 | 22.24 |
| 7162 | N | ILE | B | 192 | 28.160 | 35.246 | 0.947 | 1.00 | 21.11 |
| 7164 | CA | ILE | B | 192 | 26.916 | 34.836 | 1.574 | 1.00 | 19.99 |
| 7166 | CB | ILE | B | 192 | 25.763 | 35.775 | 1.186 | 1.00 | 19.92 |
| 7168 | CG1 | ILE | B | 192 | 25.925 | 37.151 | 1.835 | 1.00 | 20.88 |
| 7171 | CD1 | ILE | B | 192 | 25.092 | 38.196 | 1.195 | 1.00 | 21.97 |
| 7175 | CG2 | ILE | B | 192 | 24.408 | 35.196 | 1.598 | 1.00 | 19.49 |
| 7179 | C | ILE | B | 192 | 26.589 | 33.421 | 1.107 | 1.00 | 19.95 |
| 7180 | O | ILE | B | 192 | 26.387 | 32.538 | 1.914 | 1.00 | 19.48 |
| 7181 | N | HIS | B | 193 | 26.542 | 33.231 | -0.207 | 1.00 | 19.56 |
| 7183 | CA | HIS | B | 193 | 26.027 | 31.999 | -0.802 | 1.00 | 18.94 |
| 7185 | CB | HIS | B | 193 | 25.801 | 32.209 | -2.298 | 1.00 | 19.11 |
| 7188 | CG | HIS | B | 193 | 24.584 | 33.024 | -2.606 | 1.00 | 17.67 |
| 7189 | ND1 | HIS | B | 193 | 23.920 | 33.755 | -1.647 | 1.00 | 19.83 |
| 7191 | CE1 | HIS | B | 193 | 22.873 | 34.349 | -2.191 | 1.00 | 19.06 |
| 7193 | NE2 | HIS | B | 193 | 22.821 | 34.013 | -3.467 | 1.00 | 19.16 |
| 7195 | CD2 | HIS | B | 193 | 23.882 | 33.186 | -3.754 | 1.00 | 19.39 |
| 7197 | C | HIS | B | 193 | 26.913 | 30.802 | -0.543 | 1.00 | 18.45 |
| 7198 | O | HIS | B | 193 | 26.422 | 29.700 | -0.294 | 1.00 | 18.16 |
| 7199 | N | ARG | B | 194 | 28.221 | 31.017 | -0.579 | 1.00 | 18.21 |
| 7201 | CA | ARG | B | 194 | 29.157 | 29.954 | -0.301 | 1.00 | 18.14 |
| 7203 | CB | ARG | B | 194 | 30.582 | 30.396 | -0.588 | 1.00 | 18.28 |
| 7206 | CG | ARG | B | 194 | 30.894 | 30.549 | -2.059 | 1.00 | 18.14 |
| 7209 | CD | ARG | B | 194 | 32.368 | 30.534 | -2.332 | 1.00 | 19.86 |
| 7212 | NE | ARG | B | 194 | 32.685 | 30.696 | -3.740 | 1.00 | 20.51 |
| 7214 | CZ | ARG | B | 194 | 32.656 | 29.723 | -4.648 | 1.00 | 23.08 |
| 7215 | NH1 | ARG | B | 194 | 32.326 | 28.482 | -4.320 | 1.00 | 24.68 |
| 7218 | NH2 | ARG | B | 194 | 32.981 | 29.995 | -5.900 | 1.00 | 25.18 |
| 7221 | C | ARG | B | 194 | 29.003 | 29.465 | 1.143 | 1.00 | 18.28 |
| 7222 | O | ARG | B | 194 | 29.037 | 28.267 | 1.392 | 1.00 | 18.15 |
| 7223 | N | HIS | B | 195 | 28.782 | 30.390 | 2.079 | 1.00 | 18.49 |
| 7225 | CA | HIS | B | 195 | 28.558 | 30.036 | 3.479 | 1.00 | 18.76 |
| 7227 | CB | HIS | B | 195 | 28.786 | 31.251 | 4.390 | 1.00 | 18.80 |
| 7230 | CG | HIS | B | 195 | 30.224 | 31.612 | 4.533 | 1.00 | 19.89 |
| 7231 | ND1 | HIS | B | 195 | 30.934 | 32.241 | 3.533 | 1.00 | 21.51 |
| 7233 | CE1 | HIS | B | 195 | 32.186 | 32.408 | 3.925 | 1.00 | 21.57 |
| 7235 | NE2 | HIS | B | 195 | 32.311 | 31.910 | 5.142 | 1.00 | 21.37 |
| 7237 | CD2 | HIS | B | 195 | 31.103 | 31.395 | 5.541 | 1.00 | 21.40 |
| 7239 | C | HIS | B | 195 | 27.170 | 29.430 | 3.697 | 1.00 | 18.88 |
| 7240 | O | HIS | B | 195 | 27.050 | 28.298 | 4.182 | 1.00 | 19.41 |
| 7241 | N | LYS | B | 196 | 26.117 | 30.122 | 3.293 | 1.00 | 18.32 |
| 7243 | CA | LYS | B | 196 | 24.778 | 29.672 | 3.686 | 1.00 | 18.29 |
| 7245 | CB | LYS | B | 196 | 23.725 | 30.764 | 3.506 | 1.00 | 18.11 |
| 7248 | CG | LYS | B | 196 | 23.241 | 31.027 | 2.080 | 1.00 | 17.45 |
| 7251 | CD | LYS | B | 196 | 22.081 | 32.049 | 2.131 | 1.00 | 17.15 |
| 7254 | CE | LYS | B | 196 | 21.634 | 32.547 | 0.768 | 1.00 | 15.61 |
| 7257 | NZ | LYS | B | 196 | 20.235 | 33.122 | 0.794 | 1.00 | 15.01 |
| 7261 | C | LYS | B | 196 | 24.322 | 28.389 | 3.006 | 1.00 | 18.44 |
| 7262 | O | LYS | B | 196 | 23.466 | 27.688 | 3.541 | 1.00 | 18.43 |
| 7263 | N | THR | B | 197 | 24.898 | 28.098 | 1.841 | 1.00 | 17.92 |
| 7265 | CA | THR | B | 197 | 24.454 | 27.009 | 0.983 | 1.00 | 18.22 |
| 7267 | CB | THR | B | 197 | 23.686 | 27.598 | -0.203 | 1.00 | 17.81 |

FIGURE 3 (Cont.)

| A | B | C | D | E | F | G | H | I | J |
|---|---|---|---|---|---|---|---|---|---|
| 7269 | OG1 | THR | B | 197 | 22.429 | 28.070 | 0.261 | 1.00 | 18.26 |
| 7271 | CG2 | THR | B | 197 | 23.322 | 26.539 | -1.246 | 1.00 | 18.58 |
| 7275 | C | THR | B | 197 | 25.601 | 26.129 | 0.504 | 1.00 | 17.84 |
| 7276 | O | THR | B | 197 | 25.482 | 24.907 | 0.475 | 1.00 | 18.55 |
| 7277 | N | GLY | B | 198 | 26.703 | 26.746 | 0.104 | 1.00 | 17.60 |
| 7279 | CA | GLY | B | 198 | 27.854 | 26.006 | -0.358 | 1.00 | 17.04 |
| 7282 | C | GLY | B | 198 | 28.469 | 25.112 | 0.708 | 1.00 | 16.72 |
| 7283 | O | GLY | B | 198 | 28.863 | 23.993 | 0.415 | 1.00 | 15.65 |
| 7284 | N | ALA | B | 199 | 28.523 | 25.581 | 1.951 | 1.00 | 16.19 |
| 7286 | CA | ALA | B | 199 | 29.239 | 24.837 | 2.993 | 1.00 | 16.23 |
| 7288 | CB | ALA | B | 199 | 29.265 | 25.611 | 4.271 | 1.00 | 16.00 |
| 7292 | C | ALA | B | 199 | 28.633 | 23.441 | 3.200 | 1.00 | 16.09 |
| 7293 | O | ALA | B | 199 | 29.357 | 22.445 | 3.312 | 1.00 | 16.00 |
| 7294 | N | LEU | B | 200 | 27.309 | 23.363 | 3.200 | 1.00 | 15.80 |
| 7296 | CA | LEU | B | 200 | 26.623 | 22.126 | 3.536 | 1.00 | 16.20 |
| 7298 | CB | LEU | B | 200 | 25.202 | 22.408 | 4.018 | 1.00 | 16.05 |
| 7301 | CG | LEU | B | 200 | 24.363 | 21.238 | 4.540 | 1.00 | 18.16 |
| 7303 | CD1 | LEU | B | 200 | 25.019 | 20.573 | 5.727 | 1.00 | 18.85 |
| 7307 | CD2 | LEU | B | 200 | 22.989 | 21.735 | 4.928 | 1.00 | 18.03 |
| 7311 | C | LEU | B | 200 | 26.593 | 21.206 | 2.332 | 1.00 | 16.19 |
| 7312 | O | LEU | B | 200 | 26.544 | 19.993 | 2.479 | 1.00 | 15.79 |
| 7313 | N | ILE | B | 201 | 26.615 | 21.769 | 1.136 | 1.00 | 16.74 |
| 7315 | CA | ILE | B | 201 | 26.723 | 20.928 | -0.052 | 1.00 | 17.10 |
| 7317 | CB | ILE | B | 201 | 26.341 | 21.713 | -1.305 | 1.00 | 17.41 |
| 7319 | CG1 | ILE | B | 201 | 24.806 | 21.764 | -1.403 | 1.00 | 18.09 |
| 7322 | CD1 | ILE | B | 201 | 24.283 | 22.985 | -2.120 | 1.00 | 19.65 |
| 7326 | CG2 | ILE | B | 201 | 26.936 | 21.073 | -2.581 | 1.00 | 16.41 |
| 7330 | C | ILE | B | 201 | 28.130 | 20.312 | -0.110 | 1.00 | 17.27 |
| 7331 | O | ILE | B | 201 | 28.289 | 19.126 | -0.436 | 1.00 | 16.47 |
| 7332 | N | ARG | B | 202 | 29.139 | 21.098 | 0.240 | 1.00 | 17.03 |
| 7334 | CA | ARG | B | 202 | 30.468 | 20.539 | 0.389 | 1.00 | 17.33 |
| 7336 | CB | ARG | B | 202 | 31.516 | 21.598 | 0.645 | 1.00 | 17.65 |
| 7339 | CG | ARG | B | 202 | 32.956 | 20.997 | 0.625 | 1.00 | 18.08 |
| 7342 | CD | ARG | B | 202 | 34.038 | 22.029 | 0.637 | 1.00 | 19.46 |
| 7345 | NE | ARG | B | 202 | 33.985 | 22.829 | 1.854 | 1.00 | 21.33 |
| 7347 | CZ | ARG | B | 202 | 34.772 | 23.882 | 2.089 | 1.00 | 22.51 |
| 7348 | NH1 | ARG | B | 202 | 34.662 | 24.547 | 3.222 | 1.00 | 23.90 |
| 7351 | NH2 | ARG | B | 202 | 35.663 | 24.271 | 1.199 | 1.00 | 21.54 |
| 7354 | C | ARG | B | 202 | 30.517 | 19.475 | 1.475 | 1.00 | 17.44 |
| 7355 | O | ARG | B | 202 | 31.179 | 18.451 | 1.295 | 1.00 | 17.53 |
| 7356 | N | ALA | B | 203 | 29.804 | 19.689 | 2.580 | 1.00 | 17.13 |
| 7358 | CA | ALA | B | 203 | 29.776 | 18.709 | 3.658 | 1.00 | 16.93 |
| 7360 | CB | ALA | B | 203 | 28.967 | 19.200 | 4.832 | 1.00 | 17.56 |
| 7364 | C | ALA | B | 203 | 29.211 | 17.389 | 3.179 | 1.00 | 17.03 |
| 7365 | O | ALA | B | 203 | 29.704 | 16.351 | 3.574 | 1.00 | 15.70 |
| 7366 | N | ALA | B | 204 | 28.154 | 17.439 | 2.368 | 1.00 | 16.79 |
| 7368 | CA | ALA | B | 204 | 27.548 | 16.224 | 1.799 | 1.00 | 17.41 |
| 7370 | CB | ALA | B | 204 | 26.386 | 16.572 | 0.915 | 1.00 | 17.51 |
| 7374 | C | ALA | B | 204 | 28.560 | 15.419 | 1.002 | 1.00 | 17.70 |
| 7375 | O | ALA | B | 204 | 28.698 | 14.197 | 1.200 | 1.00 | 17.88 |
| 7376 | N | VAL | B | 205 | 29.268 | 16.107 | 0.109 | 1.00 | 17.07 |
| 7378 | CA | VAL | B | 205 | 30.282 | 15.471 | -0.724 | 1.00 | 17.54 |

FIGURE 3 (Cont.)

| A | B | C | D | E | F | G | H | I | J |
|---|---|---|---|---|---|---|---|---|---|
| 7380 | CB | VAL | B | 205 | 30.849 | 16.429 | -1.793 | 1.00 | 17.01 |
| 7382 | CG1 | VAL | B | 205 | 31.962 | 15.769 | -2.607 | 1.00 | 17.61 |
| 7386 | CG2 | VAL | B | 205 | 29.750 | 16.884 | -2.730 | 1.00 | 17.80 |
| 7390 | C | VAL | B | 205 | 31.400 | 14.924 | 0.150 | 1.00 | 18.04 |
| 7391 | O | VAL | B | 205 | 31.802 | 13.766 | -0.005 | 1.00 | 17.71 |
| 7392 | N | ARG | B | 206 | 31.887 | 15.748 | 1.078 | 1.00 | 18.26 |
| 7394 | CA | ARG | B | 206 | 32.974 | 15.348 | 1.963 | 1.00 | 18.54 |
| 7396 | CB | ARG | B | 206 | 33.393 | 16.497 | 2.878 | 1.00 | 19.04 |
| 7399 | CG | ARG | B | 206 | 34.211 | 17.532 | 2.179 | 1.00 | 18.96 |
| 7402 | CD | ARG | B | 206 | 34.665 | 18.637 | 3.113 | 1.00 | 20.46 |
| 7405 | NE | ARG | B | 206 | 35.712 | 19.448 | 2.531 | 1.00 | 20.99 |
| 7407 | CZ | ARG | B | 206 | 36.218 | 20.545 | 3.102 | 1.00 | 21.01 |
| 7408 | NH1 | ARG | B | 206 | 35.771 | 20.974 | 4.275 | 1.00 | 20.38 |
| 7411 | NH2 | ARG | B | 206 | 37.190 | 21.204 | 2.495 | 1.00 | 20.62 |
| 7414 | C | ARG | B | 206 | 32.582 | 14.152 | 2.795 | 1.00 | 18.87 |
| 7415 | O | ARG | B | 206 | 33.368 | 13.219 | 2.935 | 1.00 | 18.67 |
| 7416 | N | LEU | B | 207 | 31.346 | 14.136 | 3.289 | 1.00 | 19.33 |
| 7418 | CA | LEU | B | 207 | 30.896 | 13.036 | 4.141 | 1.00 | 20.12 |
| 7420 | CB | LEU | B | 207 | 29.516 | 13.310 | 4.738 | 1.00 | 19.99 |
| 7423 | CG | LEU | B | 207 | 29.431 | 13.776 | 6.203 | 1.00 | 22.44 |
| 7425 | CD1 | LEU | B | 207 | 30.464 | 14.770 | 6.559 | 1.00 | 24.69 |
| 7429 | CD2 | LEU | B | 207 | 28.046 | 14.364 | 6.440 | 1.00 | 24.61 |
| 7433 | C | LEU | B | 207 | 30.887 | 11.715 | 3.370 | 1.00 | 20.21 |
| 7434 | O | LEU | B | 207 | 31.247 | 10.668 | 3.922 | 1.00 | 20.74 |
| 7435 | N | GLY | B | 208 | 30.461 | 11.750 | 2.110 | 1.00 | 20.90 |
| 7437 | CA | GLY | B | 208 | 30.546 | 10.578 | 1.246 | 1.00 | 21.11 |
| 7440 | C | GLY | B | 208 | 31.979 | 10.097 | 1.066 | 1.00 | 21.83 |
| 7441 | O | GLY | B | 208 | 32.263 | 8.898 | 1.152 | 1.00 | 22.91 |
| 7442 | N | ALA | B | 209 | 32.892 | 11.029 | 0.821 | 1.00 | 21.98 |
| 7444 | CA | ALA | B | 209 | 34.292 | 10.688 | 0.627 | 1.00 | 22.48 |
| 7446 | CB | ALA | B | 209 | 35.059 | 11.868 | 0.052 | 1.00 | 22.44 |
| 7450 | C | ALA | B | 209 | 34.934 | 10.189 | 1.928 | 1.00 | 23.19 |
| 7451 | O | ALA | B | 209 | 35.703 | 9.232 | 1.906 | 1.00 | 23.21 |
| 7452 | N | LEU | B | 210 | 34.582 | 10.804 | 3.058 | 1.00 | 23.38 |
| 7454 | CA | LEU | B | 210 | 35.144 | 10.429 | 4.355 | 1.00 | 23.77 |
| 7456 | CB | LEU | B | 210 | 34.733 | 11.429 | 5.440 | 1.00 | 23.69 |
| 7459 | CG | LEU | B | 210 | 35.459 | 12.768 | 5.355 | 1.00 | 23.52 |
| 7461 | CD1 | LEU | B | 210 | 34.830 | 13.745 | 6.336 | 1.00 | 22.14 |
| 7465 | CD2 | LEU | B | 210 | 36.962 | 12.569 | 5.630 | 1.00 | 24.32 |
| 7469 | C | LEU | B | 210 | 34.721 | 9.031 | 4.780 | 1.00 | 24.42 |
| 7470 | O | LEU | B | 210 | 35.379 | 8.410 | 5.603 | 1.00 | 24.38 |
| 7471 | N | SER | B | 211 | 33.627 | 8.541 | 4.211 | 1.00 | 25.75 |
| 7473 | CA | SER | B | 211 | 33.176 | 7.180 | 4.458 | 1.00 | 26.29 |
| 7475 | CB | BSER | B | 211 | 31.724 | 6.990 | 3.992 | 0.35 | 26.33 |
| 7476 | CB | ASER | B | 211 | 31.733 | 7.003 | 3.960 | 0.65 | 26.73 |
| 7481 | OG | BSER | B | 211 | 31.635 | 6.814 | 2.589 | 0.35 | 25.17 |
| 7482 | OG | ASER | B | 211 | 30.884 | 8.043 | 4.437 | 0.65 | 28.22 |
| 7485 | C | SER | B | 211 | 34.096 | 6.146 | 3.779 | 1.00 | 26.79 |
| 7486 | O | SER | B | 211 | 33.943 | 4.960 | 4.011 | 1.00 | 27.11 |
| 7487 | N | ALA | B | 212 | 35.052 | 6.609 | 2.971 | 1.00 | 27.48 |
| 7489 | CA | ALA | B | 212 | 35.807 | 5.765 | 2.045 | 1.00 | 28.00 |
| 7491 | CB | ALA | B | 212 | 35.502 | 6.200 | 0.610 | 1.00 | 27.64 |

FIGURE 3 (Cont.)

| A | B | C | D | E | F | G | H | I | J |
|---|---|---|---|---|---|---|---|---|---|
| 7495 | C | ALA | B | 212 | 37.330 | 5.735 | 2.259 | 1.00 | 28.36 |
| 7496 | O | ALA | B | 212 | 38.075 | 5.478 | 1.305 | 1.00 | 28.63 |
| 7497 | N | GLY | B | 213 | 37.793 | 6.017 | 3.480 | 1.00 | 28.63 |
| 7499 | CA | GLY | B | 213 | 39.190 | 5.812 | 3.848 | 1.00 | 28.66 |
| 7502 | C | GLY | B | 213 | 40.160 | 6.623 | 3.013 | 1.00 | 29.30 |
| 7503 | O | GLY | B | 213 | 39.829 | 7.754 | 2.628 | 1.00 | 29.18 |
| 7504 | N | ASP | B | 214 | 41.337 | 6.047 | 2.725 | 1.00 | 29.91 |
| 7506 | CA | ASP | B | 214 | 42.401 | 6.716 | 1.945 | 1.00 | 30.40 |
| 7508 | CB | ASP | B | 214 | 43.629 | 5.798 | 1.749 | 1.00 | 31.13 |
| 7511 | CG | ASP | B | 214 | 44.248 | 5.315 | 3.055 | 1.00 | 32.74 |
| 7512 | OD1 | ASP | B | 214 | 44.060 | 5.963 | 4.113 | 1.00 | 34.47 |
| 7513 | OD2 | ASP | B | 214 | 44.958 | 4.280 | 3.097 | 1.00 | 35.20 |
| 7514 | C | ASP | B | 214 | 41.960 | 7.157 | 0.541 | 1.00 | 30.05 |
| 7515 | O | ASP | B | 214 | 42.333 | 8.224 | 0.068 | 1.00 | 29.72 |
| 7516 | N | LYS | B | 215 | 41.203 | 6.319 | -0.150 | 1.00 | 30.05 |
| 7518 | CA | LYS | B | 215 | 40.854 | 6.614 | -1.546 | 1.00 | 29.92 |
| 7520 | CB | LYS | B | 215 | 40.230 | 5.391 | -2.199 | 1.00 | 30.71 |
| 7523 | CG | LYS | B | 215 | 40.214 | 5.394 | -3.723 | 1.00 | 32.45 |
| 7526 | CD | LYS | B | 215 | 39.887 | 3.980 | -4.222 | 1.00 | 34.64 |
| 7529 | CE | LYS | B | 215 | 39.790 | 3.882 | -5.732 | 1.00 | 36.80 |
| 7532 | NZ | LYS | B | 215 | 39.315 | 2.521 | -6.190 | 1.00 | 38.07 |
| 7536 | C | LYS | B | 215 | 39.906 | 7.821 | -1.634 | 1.00 | 28.89 |
| 7537 | O | LYS | B | 215 | 40.045 | 8.661 | -2.525 | 1.00 | 28.45 |
| 7538 | N | GLY | B | 216 | 38.972 | 7.902 | -0.689 | 1.00 | 27.81 |
| 7540 | CA | GLY | B | 216 | 38.049 | 9.018 | -0.591 | 1.00 | 27.11 |
| 7543 | C | GLY | B | 216 | 38.781 | 10.292 | -0.243 | 1.00 | 26.53 |
| 7544 | O | GLY | B | 216 | 38.559 | 11.333 | -0.840 | 1.00 | 26.52 |
| 7545 | N | ARG | B | 217 | 39.690 | 10.198 | 0.720 | 1.00 | 26.28 |
| 7547 | CA | ARG | B | 217 | 40.519 | 11.340 | 1.099 | 1.00 | 25.74 |
| 7549 | CB | ARG | B | 217 | 41.263 | 11.018 | 2.393 | 1.00 | 25.35 |
| 7552 | CG | ARG | B | 217 | 40.332 | 11.005 | 3.598 | 1.00 | 28.38 |
| 7555 | CD | ARG | B | 217 | 40.945 | 10.453 | 4.857 | 1.00 | 31.47 |
| 7558 | NE | ARG | B | 217 | 40.208 | 10.787 | 6.078 | 1.00 | 33.37 |
| 7560 | CZ | ARG | B | 217 | 40.258 | 11.974 | 6.697 | 1.00 | 36.00 |
| 7561 | NH1 | ARG | B | 217 | 40.977 | 12.979 | 6.200 | 1.00 | 39.28 |
| 7564 | NH2 | ARG | B | 217 | 39.575 | 12.170 | 7.810 | 1.00 | 34.96 |
| 7567 | C | ARG | B | 217 | 41.471 | 11.800 | -0.027 | 1.00 | 24.69 |
| 7568 | O | ARG | B | 217 | 41.743 | 12.983 | -0.161 | 1.00 | 24.52 |
| 7569 | N | ARG | B | 218 | 41.956 | 10.873 | -0.844 | 1.00 | 24.21 |
| 7571 | CA | ARG | B | 218 | 42.809 | 11.210 | -1.983 | 1.00 | 23.79 |
| 7573 | CB | ARG | B | 218 | 43.340 | 9.927 | -2.637 | 1.00 | 24.37 |
| 7576 | CG | ARG | B | 218 | 44.257 | 10.097 | -3.872 | 1.00 | 27.47 |
| 7579 | CD | ARG | B | 218 | 43.908 | 9.115 | -5.003 | 1.00 | 32.66 |
| 7582 | NE | ARG | B | 218 | 45.013 | 8.799 | -5.908 | 1.00 | 36.58 |
| 7584 | CZ | ARG | B | 218 | 45.406 | 9.552 | -6.933 | 1.00 | 39.40 |
| 7585 | NH1 | ARG | B | 218 | 46.425 | 9.145 | -7.688 | 1.00 | 40.57 |
| 7588 | NH2 | ARG | B | 218 | 44.809 | 10.714 | -7.204 | 1.00 | 39.74 |
| 7591 | C | ARG | B | 218 | 42.025 | 12.047 | -3.005 | 1.00 | 22.91 |
| 7592 | O | ARG | B | 218 | 42.599 | 12.928 | -3.640 | 1.00 | 22.18 |
| 7593 | N | ALA | B | 219 | 40.726 | 11.759 | -3.149 | 1.00 | 21.70 |
| 7595 | CA | ALA | B | 219 | 39.845 | 12.476 | -4.066 | 1.00 | 21.49 |
| 7597 | CB | ALA | B | 219 | 38.667 | 11.618 | -4.422 | 1.00 | 21.35 |

FIGURE 3 (Cont.)

| A | B | C | D | E | F | G | H | I | J |
|---|---|---|---|---|---|---|---|---|---|
| 7601 | C | ALA | B | 219 | 39.340 | 13.818 | -3.523 | 1.00 | 21.64 |
| 7602 | O | ALA | B | 219 | 38.756 | 14.587 | -4.270 | 1.00 | 20.84 |
| 7603 | N | LEU | B | 220 | 39.563 | 14.090 | -2.240 | 1.00 | 21.58 |
| 7605 | CA | LEU | B | 220 | 39.003 | 15.285 | -1.600 | 1.00 | 22.20 |
| 7607 | CB | LEU | B | 220 | 39.340 | 15.335 | -0.110 | 1.00 | 22.43 |
| 7610 | CG | LEU | B | 220 | 38.407 | 14.580 | 0.840 | 1.00 | 22.95 |
| 7612 | CD1 | LEU | B | 220 | 38.991 | 14.642 | 2.244 | 1.00 | 24.14 |
| 7616 | CD2 | LEU | B | 220 | 37.002 | 15.153 | 0.810 | 1.00 | 24.62 |
| 7620 | C | LEU | B | 220 | 39.364 | 16.616 | -2.239 | 1.00 | 21.85 |
| 7621 | O | LEU | B | 220 | 38.482 | 17.438 | -2.393 | 1.00 | 22.54 |
| 7622 | N | PRO | B | 221 | 40.627 | 16.872 | -2.583 | 1.00 | 22.19 |
| 7623 | CA | PRO | B | 221 | 40.969 | 18.150 | -3.227 | 1.00 | 22.28 |
| 7625 | CB | PRO | B | 221 | 42.442 | 17.987 | -3.589 | 1.00 | 22.39 |
| 7628 | CG | PRO | B | 221 | 42.951 | 16.960 | -2.616 | 1.00 | 23.34 |
| 7631 | CD | PRO | B | 221 | 41.812 | 16.025 | -2.379 | 1.00 | 22.27 |
| 7634 | C | PRO | B | 221 | 40.115 | 18.420 | -4.460 | 1.00 | 21.79 |
| 7635 | O | PRO | B | 221 | 39.580 | 19.513 | -4.592 | 1.00 | 21.54 |
| 7636 | N | VAL | B | 222 | 39.945 | 17.431 | -5.331 | 1.00 | 21.34 |
| 7638 | CA | VAL | B | 222 | 39.131 | 17.616 | -6.533 | 1.00 | 20.96 |
| 7640 | CB | VAL | B | 222 | 39.431 | 16.533 | -7.601 | 1.00 | 21.09 |
| 7642 | CG1 | VAL | B | 222 | 38.492 | 16.664 | -8.787 | 1.00 | 20.79 |
| 7646 | CG2 | VAL | B | 222 | 40.885 | 16.668 | -8.085 | 1.00 | 22.50 |
| 7650 | C | VAL | B | 222 | 37.620 | 17.635 | -6.214 | 1.00 | 20.48 |
| 7651 | O | VAL | B | 222 | 36.877 | 18.411 | -6.804 | 1.00 | 20.29 |
| 7652 | N | LEU | B | 223 | 37.172 | 16.773 | -5.307 | 1.00 | 20.17 |
| 7654 | CA | LEU | B | 223 | 35.750 | 16.717 | -4.924 | 1.00 | 19.91 |
| 7656 | CB | LEU | B | 223 | 35.466 | 15.562 | -3.957 | 1.00 | 20.52 |
| 7659 | CG | LEU | B | 223 | 35.293 | 14.173 | -4.587 | 1.00 | 21.95 |
| 7661 | CD1 | LEU | B | 223 | 35.296 | 13.095 | -3.512 | 1.00 | 22.04 |
| 7665 | CD2 | LEU | B | 223 | 34.039 | 14.111 | -5.407 | 1.00 | 23.07 |
| 7669 | C | LEU | B | 223 | 35.327 | 18.015 | -4.253 | 1.00 | 19.72 |
| 7670 | O | LEU | B | 223 | 34.188 | 18.456 | -4.381 | 1.00 | 19.07 |
| 7671 | N | ASP | B | 224 | 36.250 | 18.599 | -3.503 | 1.00 | 19.68 |
| 7673 | CA | ASP | B | 224 | 36.042 | 19.893 | -2.883 | 1.00 | 19.94 |
| 7675 | CB | ASP | B | 224 | 37.272 | 20.287 | -2.069 | 1.00 | 19.86 |
| 7678 | CG | ASP | B | 224 | 37.289 | 19.671 | -0.705 | 1.00 | 22.67 |
| 7679 | OD1 | ASP | B | 224 | 36.256 | 19.094 | -0.288 | 1.00 | 23.35 |
| 7680 | OD2 | ASP | B | 224 | 38.304 | 19.744 | 0.036 | 1.00 | 25.14 |
| 7681 | C | ASP | B | 224 | 35.778 | 20.972 | -3.908 | 1.00 | 19.81 |
| 7682 | O | ASP | B | 224 | 34.910 | 21.795 | -3.702 | 1.00 | 19.95 |
| 7683 | N | LYS | B | 225 | 36.541 | 20.990 | -4.996 | 1.00 | 19.94 |
| 7685 | CA | LYS | B | 225 | 36.368 | 22.027 | -6.013 | 1.00 | 20.31 |
| 7687 | CB | LYS | B | 225 | 37.525 | 22.048 | -7.022 | 1.00 | 20.63 |
| 7690 | CG | LYS | B | 225 | 38.973 | 22.184 | -6.439 | 1.00 | 22.72 |
| 7693 | CD | BLYS | B | 225 | 39.100 | 23.053 | -5.155 | 0.35 | 21.46 |
| 7694 | CD | ALYS | B | 225 | 39.001 | 22.753 | -5.014 | 0.65 | 25.09 |
| 7699 | CE | BLYS | B | 225 | 39.223 | 22.270 | -3.837 | 0.35 | 19.92 |
| 7700 | CE | ALYS | B | 225 | 39.871 | 23.974 | -4.801 | 0.65 | 25.51 |
| 7705 | NZ | BLYS | B | 225 | 40.570 | 21.728 | -3.502 | 0.35 | 14.63 |
| 7706 | NZ | ALYS | B | 225 | 39.377 | 24.575 | -3.546 | 0.65 | 24.29 |
| 7713 | C | LYS | B | 225 | 35.049 | 21.804 | -6.718 | 1.00 | 19.81 |
| 7714 | O | LYS | B | 225 | 34.320 | 22.762 | -6.982 | 1.00 | 19.64 |

FIGURE 3 (Cont.)

| A | B | C | D | E | F | G | H | I | J |
|---|---|---|---|---|---|---|---|---|---|
| 7715 | N | TYR | B | 226 | 34.733 | 20.536 | -6.979 | 1.00 | 19.10 |
| 7717 | CA | TYR | B | 226 | 33.437 | 20.151 | -7.525 | 1.00 | 18.47 |
| 7719 | CB | TYR | B | 226 | 33.307 | 18.624 | -7.646 | 1.00 | 18.62 |
| 7722 | CG | TYR | B | 226 | 31.883 | 18.168 | -7.875 | 1.00 | 17.81 |
| 7723 | CD1 | TYR | B | 226 | 31.300 | 18.256 | -9.132 | 1.00 | 17.52 |
| 7725 | CE1 | TYR | B | 226 | 29.994 | 17.859 | -9.337 | 1.00 | 20.05 |
| 7727 | CZ | TYR | B | 226 | 29.232 | 17.374 | -8.279 | 1.00 | 18.47 |
| 7728 | OH | TYR | B | 226 | 27.919 | 16.982 | -8.500 | 1.00 | 17.52 |
| 7730 | CE2 | TYR | B | 226 | 29.785 | 17.299 | -7.026 | 1.00 | 17.57 |
| 7732 | CD2 | TYR | B | 226 | 31.112 | 17.694 | -6.829 | 1.00 | 17.49 |
| 7734 | C | TYR | B | 226 | 32.331 | 20.699 | -6.643 | 1.00 | 18.41 |
| 7735 | O | TYR | B | 226 | 31.452 | 21.411 | -7.122 | 1.00 | 18.11 |
| 7736 | N | ALA | B | 227 | 32.417 | 20.408 | -5.345 | 1.00 | 18.13 |
| 7738 | CA | ALA | B | 227 | 31.403 | 20.799 | -4.377 | 1.00 | 18.18 |
| 7740 | CB | ALA | B | 227 | 31.723 | 20.221 | -3.021 | 1.00 | 17.94 |
| 7744 | C | ALA | B | 227 | 31.281 | 22.316 | -4.251 | 1.00 | 18.61 |
| 7745 | O | ALA | B | 227 | 30.196 | 22.851 | -4.063 | 1.00 | 18.11 |
| 7746 | N | GLU | B | 228 | 32.407 | 22.996 | -4.328 | 1.00 | 19.06 |
| 7748 | CA | GLU | B | 228 | 32.418 | 24.439 | -4.177 | 1.00 | 20.24 |
| 7750 | CB | GLU | B | 228 | 33.864 | 24.949 | -4.123 | 1.00 | 20.64 |
| 7753 | CG | GLU | B | 228 | 34.451 | 24.809 | -2.730 | 1.00 | 23.29 |
| 7756 | CD | GLU | B | 228 | 35.947 | 24.586 | -2.731 | 1.00 | 26.70 |
| 7757 | OE1 | GLU | B | 228 | 36.464 | 23.942 | -1.768 | 1.00 | 29.92 |
| 7758 | OE2 | GLU | B | 228 | 36.592 | 25.044 | -3.686 | 1.00 | 27.85 |
| 7759 | C | GLU | B | 228 | 31.636 | 25.080 | -5.300 | 1.00 | 20.03 |
| 7760 | O | GLU | B | 228 | 30.842 | 25.982 | -5.063 | 1.00 | 20.42 |
| 7761 | N | SER | B | 229 | 31.824 | 24.584 | -6.521 | 1.00 | 20.10 |
| 7763 | CA | SER | B | 229 | 31.140 | 25.146 | -7.663 | 1.00 | 20.21 |
| 7765 | CB | SER | B | 229 | 31.838 | 24.755 | -8.958 | 1.00 | 20.74 |
| 7768 | OG | SER | B | 229 | 33.134 | 25.319 | -8.986 | 1.00 | 21.81 |
| 7770 | C | SER | B | 229 | 29.655 | 24.795 | -7.704 | 1.00 | 19.69 |
| 7771 | O | SER | B | 229 | 28.845 | 25.675 | -7.972 | 1.00 | 19.58 |
| 7772 | N | ILE | B | 230 | 29.283 | 23.538 | -7.451 | 1.00 | 19.26 |
| 7774 | CA | ILE | B | 230 | 27.855 | 23.173 | -7.467 | 1.00 | 19.00 |
| 7776 | CB | ILE | B | 230 | 27.588 | 21.634 | -7.493 | 1.00 | 19.39 |
| 7778 | CG1 | ILE | B | 230 | 28.132 | 20.922 | -6.249 | 1.00 | 19.42 |
| 7781 | CD1 | ILE | B | 230 | 27.348 | 19.661 | -5.883 | 1.00 | 19.21 |
| 7785 | CG2 | ILE | B | 230 | 28.145 | 20.996 | -8.778 | 1.00 | 20.74 |
| 7789 | C | ILE | B | 230 | 27.118 | 23.798 | -6.292 | 1.00 | 18.75 |
| 7790 | O | ILE | B | 230 | 25.934 | 24.062 | -6.404 | 1.00 | 18.69 |
| 7791 | N | GLY | B | 231 | 27.825 | 24.000 | -5.179 | 1.00 | 17.92 |
| 7793 | CA | GLY | B | 231 | 27.260 | 24.588 | -3.977 | 1.00 | 18.54 |
| 7796 | C | GLY | B | 231 | 26.885 | 26.044 | -4.189 | 1.00 | 18.41 |
| 7797 | O | GLY | B | 231 | 25.776 | 26.467 | -3.838 | 1.00 | 18.39 |
| 7798 | N | LEU | B | 232 | 27.791 | 26.809 | -4.801 | 1.00 | 18.03 |
| 7800 | CA | LEU | B | 232 | 27.463 | 28.191 | -5.176 | 1.00 | 17.92 |
| 7802 | CB | LEU | B | 232 | 28.697 | 28.973 | -5.644 | 1.00 | 17.76 |
| 7805 | CG | LEU | B | 232 | 28.471 | 30.416 | -6.137 | 1.00 | 18.58 |
| 7807 | CD1 | LEU | B | 232 | 27.676 | 31.245 | -5.123 | 1.00 | 20.10 |
| 7811 | CD2 | LEU | B | 232 | 29.783 | 31.085 | -6.471 | 1.00 | 19.77 |
| 7815 | C | LEU | B | 232 | 26.371 | 28.184 | -6.232 | 1.00 | 17.69 |
| 7816 | O | LEU | B | 232 | 25.391 | 28.929 | -6.125 | 1.00 | 17.69 |

FIGURE 3 (Cont.)

| A | B | C | D | E | F | G | H | I | J |
|---|---|---|---|---|---|---|---|---|---|
| 7817 | N | ALA | B | 233 | 26.520 | 27.332 | -7.243 | 1.00 | 17.54 |
| 7819 | CA | ALA | B | 233 | 25.535 | 27.255 | -8.330 | 1.00 | 17.52 |
| 7821 | CB | ALA | B | 233 | 25.937 | 26.175 | -9.322 | 1.00 | 17.72 |
| 7825 | C | ALA | B | 233 | 24.133 | 26.996 | -7.801 | 1.00 | 16.87 |
| 7826 | O | ALA | B | 233 | 23.149 | 27.503 | -8.321 | 1.00 | 16.72 |
| 7827 | N | PHE | B | 234 | 24.055 | 26.207 | -6.738 | 1.00 | 17.20 |
| 7829 | CA | PHE | B | 234 | 22.796 | 25.770 | -6.175 | 1.00 | 17.20 |
| 7831 | CB | PHE | B | 234 | 23.077 | 24.798 | -5.020 | 1.00 | 17.86 |
| 7834 | CG | PHE | B | 234 | 21.913 | 23.952 | -4.635 | 1.00 | 19.19 |
| 7835 | CD1 | PHE | B | 234 | 21.908 | 22.595 | -4.939 | 1.00 | 23.96 |
| 7837 | CE1 | PHE | B | 234 | 20.833 | 21.786 | -4.576 | 1.00 | 25.08 |
| 7839 | CZ | PHE | B | 234 | 19.753 | 22.346 | -3.895 | 1.00 | 23.44 |
| 7841 | CE2 | PHE | B | 234 | 19.766 | 23.705 | -3.578 | 1.00 | 21.13 |
| 7843 | CD2 | PHE | B | 234 | 20.837 | 24.489 | -3.936 | 1.00 | 19.81 |
| 7845 | C | PHE | B | 234 | 22.023 | 26.972 | -5.659 | 1.00 | 17.12 |
| 7846 | O | PHE | B | 234 | 20.817 | 27.075 | -5.856 | 1.00 | 16.09 |
| 7847 | N | GLN | B | 235 | 22.724 | 27.860 | -4.969 | 1.00 | 16.71 |
| 7849 | CA | GLN | B | 235 | 22.093 | 29.040 | -4.427 | 1.00 | 17.18 |
| 7851 | CB | GLN | B | 235 | 22.918 | 29.661 | -3.304 | 1.00 | 16.88 |
| 7854 | CG | GLN | B | 235 | 22.173 | 30.781 | -2.566 | 1.00 | 16.78 |
| 7857 | CD | GLN | B | 235 | 20.856 | 30.332 | -1.970 | 1.00 | 18.18 |
| 7858 | OE1 | GLN | B | 235 | 20.783 | 29.271 | -1.353 | 1.00 | 17.96 |
| 7859 | NE2 | GLN | B | 235 | 19.818 | 31.140 | -2.138 | 1.00 | 15.32 |
| 7862 | C | GLN | B | 235 | 21.821 | 30.089 | -5.501 | 1.00 | 16.98 |
| 7863 | O | GLN | B | 235 | 20.842 | 30.800 | -5.392 | 1.00 | 16.15 |
| 7864 | N | VAL | B | 236 | 22.640 | 30.184 | -6.544 | 1.00 | 17.46 |
| 7866 | CA | VAL | B | 236 | 22.265 | 31.160 | -7.590 | 1.00 | 18.23 |
| 7868 | CB | VAL | B | 236 | 23.405 | 31.708 | -8.547 | 1.00 | 18.68 |
| 7870 | CG1 | VAL | B | 236 | 24.747 | 31.119 | -8.271 | 1.00 | 19.87 |
| 7874 | CG2 | VAL | B | 236 | 23.019 | 31.733 | -10.030 | 1.00 | 19.70 |
| 7878 | C | VAL | B | 236 | 21.003 | 30.665 | -8.279 | 1.00 | 17.45 |
| 7879 | O | VAL | B | 236 | 20.139 | 31.457 | -8.531 | 1.00 | 17.04 |
| 7880 | N | GLN | B | 237 | 20.856 | 29.350 | -8.447 | 1.00 | 17.88 |
| 7882 | CA | GLN | B | 237 | 19.649 | 28.785 | -9.035 | 1.00 | 18.28 |
| 7884 | CB | GLN | B | 237 | 19.783 | 27.288 | -9.337 | 1.00 | 18.86 |
| 7887 | CG | GLN | B | 237 | 18.561 | 26.715 | -10.056 | 1.00 | 20.61 |
| 7890 | CD | GLN | B | 237 | 18.402 | 27.211 | -11.478 | 1.00 | 23.91 |
| 7891 | OE1 | GLN | B | 237 | 19.207 | 27.995 | -11.962 | 1.00 | 27.71 |
| 7892 | NE2 | GLN | B | 237 | 17.361 | 26.738 | -12.157 | 1.00 | 25.53 |
| 7895 | C | GLN | B | 237 | 18.469 | 29.005 | -8.135 | 1.00 | 17.68 |
| 7896 | O | GLN | B | 237 | 17.381 | 29.326 | -8.612 | 1.00 | 18.18 |
| 7897 | N | ASP | B | 238 | 18.673 | 28.830 | -6.832 | 1.00 | 16.95 |
| 7899 | CA | ASP | B | 238 | 17.624 | 29.133 | -5.872 | 1.00 | 16.59 |
| 7901 | CB | ASP | B | 238 | 18.084 | 28.803 | -4.452 | 1.00 | 15.86 |
| 7904 | CG | ASP | B | 238 | 16.988 | 28.976 | -3.451 | 1.00 | 16.32 |
| 7905 | OD1 | ASP | B | 238 | 16.037 | 28.162 | -3.445 | 1.00 | 17.49 |
| 7906 | OD2 | ASP | B | 238 | 16.959 | 29.929 | -2.651 | 1.00 | 18.97 |
| 7907 | C | ASP | B | 238 | 17.186 | 30.610 | -5.985 | 1.00 | 16.34 |
| 7908 | O | ASP | B | 238 | 16.001 | 30.905 | -5.932 | 1.00 | 15.59 |
| 7909 | N | ASP | B | 239 | 18.135 | 31.526 | -6.146 | 1.00 | 17.76 |
| 7911 | CA | ASP | B | 239 | 17.799 | 32.959 | -6.321 | 1.00 | 18.83 |
| 7913 | CB | ASP | B | 239 | 19.044 | 33.819 | -6.384 | 1.00 | 19.28 |

FIGURE 3 (Cont.)

| A | B | C | D | E | F | G | H | I | J |
|---|---|---|---|---|---|---|---|---|---|
| 7916 | CG | ASP | B | 239 | 19.766 | 33.928 | -5.070 | 1.00 | 19.95 |
| 7917 | OD1 | ASP | B | 239 | 19.251 | 33.447 | -4.018 | 1.00 | 23.46 |
| 7918 | OD2 | ASP | B | 239 | 20.886 | 34.480 | -5.016 | 1.00 | 19.63 |
| 7919 | C | ASP | B | 239 | 17.021 | 33.192 | -7.610 | 1.00 | 19.87 |
| 7920 | O | ASP | B | 239 | 16.020 | 33.917 | -7.629 | 1.00 | 20.25 |
| 7921 | N | ILE | B | 240 | 17.492 | 32.570 | -8.687 | 1.00 | 19.96 |
| 7923 | CA | ILE | B | 240 | 16.845 | 32.676 | -9.986 | 1.00 | 20.61 |
| 7925 | CB | ILE | B | 240 | 17.647 | 31.902 | -11.039 | 1.00 | 20.77 |
| 7927 | CG1 | ILE | B | 240 | 18.945 | 32.645 | -11.363 | 1.00 | 20.81 |
| 7930 | CD1 | ILE | B | 240 | 19.974 | 31.792 | -11.997 | 1.00 | 21.71 |
| 7934 | CG2 | ILE | B | 240 | 16.821 | 31.682 | -12.304 | 1.00 | 21.31 |
| 7938 | C | ILE | B | 240 | 15.413 | 32.161 | -9.932 | 1.00 | 20.80 |
| 7939 | O | ILE | B | 240 | 14.506 | 32.784 | -10.482 | 1.00 | 20.05 |
| 7940 | N | LEU | B | 241 | 15.214 | 31.014 | -9.283 | 1.00 | 21.23 |
| 7942 | CA | LEU | B | 241 | 13.904 | 30.394 | -9.206 | 1.00 | 21.82 |
| 7944 | CB | LEU | B | 241 | 14.009 | 28.986 | -8.620 | 1.00 | 22.08 |
| 7947 | CG | LEU | B | 241 | 14.569 | 27.953 | -9.600 | 1.00 | 23.04 |
| 7949 | CD1 | LEU | B | 241 | 14.635 | 26.592 | -8.926 | 1.00 | 25.03 |
| 7953 | CD2 | LEU | B | 241 | 13.740 | 27.874 | -10.869 | 1.00 | 23.91 |
| 7957 | C | LEU | B | 241 | 12.955 | 31.226 | -8.384 | 1.00 | 22.17 |
| 7958 | O | LEU | B | 241 | 11.759 | 31.219 | -8.613 | 1.00 | 22.86 |
| 7959 | N | ASP | B | 242 | 13.487 | 31.928 | -7.401 | 1.00 | 22.89 |
| 7961 | CA | ASP | B | 242 | 12.680 | 32.816 | -6.597 | 1.00 | 23.68 |
| 7963 | CB | ASP | B | 242 | 13.538 | 33.476 | -5.526 | 1.00 | 24.26 |
| 7966 | CG | ASP | B | 242 | 12.782 | 33.732 | -4.261 | 1.00 | 26.59 |
| 7967 | OD1 | ASP | B | 242 | 12.339 | 34.885 | -4.081 | 1.00 | 29.09 |
| 7968 | OD2 | ASP | B | 242 | 12.586 | 32.842 | -3.395 | 1.00 | 30.35 |
| 7969 | C | ASP | B | 242 | 12.018 | 33.889 | -7.468 | 1.00 | 24.03 |
| 7970 | O | ASP | B | 242 | 10.872 | 34.264 | -7.225 | 1.00 | 23.75 |
| 7971 | N | VAL | B | 243 | 12.722 | 34.380 | -8.478 | 1.00 | 24.22 |
| 7973 | CA | VAL | B | 243 | 12.133 | 35.431 | -9.334 | 1.00 | 25.09 |
| 7975 | CB | BVAL | B | 243 | 13.207 | 36.455 | -9.871 | 0.35 | 24.92 |
| 7976 | CB | AVAL | B | 243 | 13.180 | 36.479 | -9.849 | 0.65 | 25.18 |
| 7979 | CG1 | BVAL | B | 243 | 14.454 | 35.767 | -10.368 | 0.35 | 24.74 |
| 7980 | CG1 | AVAL | B | 243 | 14.270 | 36.727 | -8.817 | 0.65 | 24.27 |
| 7987 | CG2 | BVAL | B | 243 | 12.633 | 37.361 | -10.975 | 0.35 | 23.96 |
| 7988 | CG2 | AVAL | B | 243 | 13.775 | 36.088 | -11.166 | 0.65 | 25.87 |
| 7995 | C | VAL | B | 243 | 11.271 | 34.851 | -10.474 | 1.00 | 25.74 |
| 7996 | O | VAL | B | 243 | 10.167 | 35.330 | -10.688 | 1.00 | 25.89 |
| 7997 | N | VAL | B | 244 | 11.745 | 33.812 | -11.160 | 1.00 | 26.96 |
| 7999 | CA | VAL | B | 244 | 11.065 | 33.282 | -12.350 | 1.00 | 27.89 |
| 8001 | CB | VAL | B | 244 | 12.069 | 32.914 | -13.472 | 1.00 | 28.15 |
| 8003 | CG1 | VAL | B | 244 | 12.996 | 34.083 | -13.769 | 1.00 | 29.48 |
| 8007 | CG2 | VAL | B | 244 | 12.852 | 31.642 | -13.143 | 1.00 | 28.31 |
| 8011 | C | VAL | B | 244 | 10.158 | 32.066 | -12.136 | 1.00 | 28.41 |
| 8012 | O | VAL | B | 244 | 9.330 | 31.776 | -12.983 | 1.00 | 28.51 |
| 8013 | N | GLY | B | 245 | 10.331 | 31.335 | -11.038 | 1.00 | 29.07 |
| 8015 | CA | GLY | B | 245 | 9.583 | 30.107 | -10.813 | 1.00 | 29.72 |
| 8018 | C | GLY | B | 245 | 8.131 | 30.378 | -10.460 | 1.00 | 30.36 |
| 8019 | O | GLY | B | 245 | 7.793 | 31.482 | -10.070 | 1.00 | 31.39 |
| 8020 | N | ASP | B | 246 | 7.276 | 29.376 | -10.613 | 1.00 | 30.83 |
| 8022 | CA | ASP | B | 246 | 5.885 | 29.465 | -10.194 | 1.00 | 31.66 |

FIGURE 3 (Cont.)

| A | B | C | D | E | F | G | H | I | J |
|---|---|---|---|---|---|---|---|---|---|
| 8024 | CB | ASP | B | 246 | 4.996 | 28.632 | -11.128 | 1.00 | 32.32 |
| 8027 | CG | ASP | B | 246 | 3.527 | 29.006 | -11.027 | 1.00 | 35.80 |
| 8028 | OD1 | ASP | B | 246 | 2.981 | 29.516 | -12.041 | 1.00 | 41.36 |
| 8029 | OD2 | ASP | B | 246 | 2.818 | 28.820 | -9.997 | 1.00 | 39.19 |
| 8030 | C | ASP | B | 246 | 5.782 | 28.894 | -8.790 | 1.00 | 30.65 |
| 8031 | O | ASP | B | 246 | 6.321 | 27.842 | -8.546 | 1.00 | 30.56 |
| 8032 | N | THR | B | 247 | 5.072 | 29.572 | -7.892 | 1.00 | 29.92 |
| 8034 | CA | THR | B | 247 | 4.846 | 29.080 | -6.533 | 1.00 | 29.76 |
| 8036 | CB | THR | B | 247 | 3.814 | 29.975 | -5.811 | 1.00 | 29.87 |
| 8038 | OG1 | THR | B | 247 | 4.378 | 31.272 | -5.593 | 1.00 | 31.54 |
| 8040 | CG2 | THR | B | 247 | 3.502 | 29.459 | -4.399 | 1.00 | 30.40 |
| 8044 | C | THR | B | 247 | 4.401 | 27.611 | -6.492 | 1.00 | 28.88 |
| 8045 | O | THR | B | 247 | 4.911 | 26.844 | -5.685 | 1.00 | 28.30 |
| 8046 | N | ALA | B | 248 | 3.465 | 27.222 | -7.358 | 1.00 | 28.23 |
| 8048 | CA | ALA | B | 248 | 2.932 | 25.852 | -7.367 | 1.00 | 28.33 |
| 8050 | CB | ALA | B | 248 | 1.809 | 25.708 | -8.391 | 1.00 | 28.17 |
| 8054 | C | ALA | B | 248 | 4.007 | 24.805 | -7.644 | 1.00 | 28.26 |
| 8055 | O | ALA | B | 248 | 3.925 | 23.687 | -7.143 | 1.00 | 28.69 |
| 8056 | N | THR | B | 249 | 4.985 | 25.172 | -8.466 | 1.00 | 27.77 |
| 8058 | CA | THR | B | 249 | 6.091 | 24.292 | -8.824 | 1.00 | 27.75 |
| 8060 | CB | THR | B | 249 | 6.638 | 24.726 | -10.188 | 1.00 | 27.90 |
| 8062 | OG1 | THR | B | 249 | 5.596 | 24.624 | -11.164 | 1.00 | 30.21 |
| 8064 | CG2 | THR | B | 249 | 7.706 | 23.767 | -10.678 | 1.00 | 28.58 |
| 8068 | C | THR | B | 249 | 7.223 | 24.275 | -7.773 | 1.00 | 26.85 |
| 8069 | O | THR | B | 249 | 7.671 | 23.202 | -7.356 | 1.00 | 26.31 |
| 8070 | N | LEU | B | 250 | 7.654 | 25.463 | -7.348 | 1.00 | 25.98 |
| 8072 | CA | LEU | B | 250 | 8.706 | 25.627 | -6.328 | 1.00 | 25.67 |
| 8074 | CB | LEU | B | 250 | 8.994 | 27.116 | -6.091 | 1.00 | 25.92 |
| 8077 | CG | LEU | B | 250 | 9.408 | 28.030 | -7.239 | 1.00 | 27.52 |
| 8079 | CD1 | LEU | B | 250 | 9.656 | 29.433 | -6.691 | 1.00 | 27.93 |
| 8083 | CD2 | LEU | B | 250 | 10.625 | 27.516 | -7.954 | 1.00 | 28.70 |
| 8087 | C | LEU | B | 250 | 8.359 | 25.039 | -4.965 | 1.00 | 24.61 |
| 8088 | O | LEU | B | 250 | 9.244 | 24.625 | -4.217 | 1.00 | 22.99 |
| 8089 | N | GLY | B | 251 | 7.077 | 25.078 | -4.612 | 1.00 | 23.96 |
| 8091 | CA | GLY | B | 251 | 6.636 | 24.759 | -3.265 | 1.00 | 23.66 |
| 8094 | C | GLY | B | 251 | 6.808 | 25.892 | -2.263 | 1.00 | 23.66 |
| 8095 | O | GLY | B | 251 | 6.449 | 25.748 | -1.105 | 1.00 | 23.25 |
| 8096 | N | LYS | B | 252 | 7.310 | 27.036 | -2.721 | 1.00 | 23.45 |
| 8098 | CA | LYS | B | 252 | 7.499 | 28.207 | -1.881 | 1.00 | 23.55 |
| 8100 | CB | LYS | B | 252 | 8.913 | 28.217 | -1.262 | 1.00 | 23.19 |
| 8103 | CG | LYS | B | 252 | 10.065 | 28.100 | -2.279 | 1.00 | 22.81 |
| 8106 | CD | LYS | B | 252 | 11.443 | 27.892 | -1.587 | 1.00 | 21.30 |
| 8109 | CE | LYS | B | 252 | 12.575 | 28.125 | -2.537 | 1.00 | 19.95 |
| 8112 | NZ | LYS | B | 252 | 13.876 | 27.549 | -2.087 | 1.00 | 18.06 |
| 8116 | C | LYS | B | 252 | 7.248 | 29.466 | -2.729 | 1.00 | 24.42 |
| 8117 | O | LYS | B | 252 | 7.280 | 29.414 | -3.961 | 1.00 | 24.38 |
| 8118 | N | ARG | B | 253 | 7.024 | 30.592 | -2.066 | 1.00 | 25.44 |
| 8120 | CA | ARG | B | 253 | 6.534 | 31.795 | -2.744 | 1.00 | 26.73 |
| 8122 | CB | ARG | B | 253 | 6.006 | 32.830 | -1.737 | 1.00 | 27.67 |
| 8125 | CG | ARG | B | 253 | 4.510 | 33.101 | -1.907 | 1.00 | 31.24 |
| 8128 | CD | ARG | B | 253 | 3.825 | 33.710 | -0.700 | 1.00 | 35.52 |
| 8131 | NE | ARG | B | 253 | 3.150 | 32.704 | 0.116 | 1.00 | 37.39 |

FIGURE 3 (Cont.)

| A | B | C | D | E | F | G | H | I | J |
|---|---|---|---|---|---|---|---|---|---|
| 8133 | CZ | ARG | B | 253 | 2.036 | 32.056 | -0.235 | 1.00 | 39.88 |
| 8134 | NH1 | ARG | B | 253 | 1.451 | 32.263 | -1.417 | 1.00 | 41.43 |
| 8137 | NH2 | ARG | B | 253 | 1.518 | 31.167 | 0.605 | 1.00 | 41.57 |
| 8140 | C | ARG | B | 253 | 7.550 | 32.432 | -3.685 | 1.00 | 25.93 |
| 8141 | O | ARG | B | 253 | 8.642 | 32.852 | -3.283 | 1.00 | 25.79 |
| 8142 | N | GLN | B | 254 | 7.176 | 32.480 | -4.955 | 1.00 | 25.68 |
| 8144 | CA | GLN | B | 254 | 7.848 | 33.323 | -5.931 | 1.00 | 25.41 |
| 8146 | CB | GLN | B | 254 | 7.076 | 33.337 | -7.255 | 1.00 | 25.85 |
| 8149 | CG | BGLN | B | 254 | 7.707 | 34.187 | -8.363 | 0.35 | 25.46 |
| 8150 | CG | AGLN | B | 254 | 7.696 | 34.266 | -8.323 | 0.65 | 26.52 |
| 8155 | CD | BGLN | B | 254 | 7.388 | 35.665 | -8.261 | 0.35 | 25.75 |
| 8156 | CD | AGLN | B | 254 | 6.858 | 34.376 | -9.595 | 0.65 | 29.40 |
| 8157 | OE1 | BGLN | B | 254 | 8.227 | 36.501 | -8.593 | 0.35 | 26.04 |
| 8158 | OE1 | AGLN | B | 254 | 7.335 | 34.901 | -10.609 | 0.65 | 30.77 |
| 8159 | NE2 | BGLN | B | 254 | 6.180 | 35.993 | -7.809 | 0.35 | 25.98 |
| 8160 | NE2 | AGLN | B | 254 | 5.622 | 33.888 | -9.547 | 0.65 | 29.10 |
| 8165 | C | GLN | B | 254 | 7.900 | 34.730 | -5.369 | 1.00 | 24.67 |
| 8166 | O | GLN | B | 254 | 6.942 | 35.184 | -4.755 | 1.00 | 24.03 |
| 8167 | N | GLY | B | 255 | 9.023 | 35.413 | -5.565 | 1.00 | 24.23 |
| 8169 | CA | GLY | B | 255 | 9.107 | 36.829 | -5.264 | 1.00 | 24.15 |
| 8172 | C | GLY | B | 255 | 9.417 | 37.151 | -3.816 | 1.00 | 24.34 |
| 8173 | O | GLY | B | 255 | 9.464 | 38.307 | -3.465 | 1.00 | 24.07 |
| 8174 | N | ALA | B | 256 | 9.656 | 36.142 | -2.983 | 1.00 | 24.66 |
| 8176 | CA | ALA | B | 256 | 9.909 | 36.359 | -1.559 | 1.00 | 25.08 |
| 8178 | CB | ALA | B | 256 | 9.978 | 35.024 | -0.833 | 1.00 | 24.93 |
| 8182 | C | ALA | B | 256 | 11.179 | 37.180 | -1.288 | 1.00 | 25.56 |
| 8183 | O | ALA | B | 256 | 11.213 | 37.979 | -0.353 | 1.00 | 26.42 |
| 8184 | N | ASP | B | 257 | 12.210 | 37.000 | -2.105 | 1.00 | 25.88 |
| 8186 | CA | ASP | B | 257 | 13.466 | 37.739 | -1.932 | 1.00 | 26.25 |
| 8188 | CB | ASP | B | 257 | 14.564 | 37.191 | -2.848 | 1.00 | 26.11 |
| 8191 | CG | ASP | B | 257 | 15.025 | 35.791 | -2.463 | 1.00 | 26.45 |
| 8192 | OD1 | ASP | B | 257 | 14.815 | 35.353 | -1.299 | 1.00 | 26.12 |
| 8193 | OD2 | ASP | B | 257 | 15.602 | 35.054 | -3.292 | 1.00 | 25.40 |
| 8194 | C | ASP | B | 257 | 13.286 | 39.221 | -2.241 | 1.00 | 27.05 |
| 8195 | O | ASP | B | 257 | 13.823 | 40.074 | -1.549 | 1.00 | 26.45 |
| 8196 | N | GLN | B | 258 | 12.545 | 39.520 | -3.304 | 1.00 | 28.65 |
| 8198 | CA | GLN | B | 258 | 12.278 | 40.908 | -3.691 | 1.00 | 29.67 |
| 8200 | CB | BGLN | B | 258 | 11.590 | 40.972 | -5.061 | 0.35 | 29.64 |
| 8201 | CB | AGLN | B | 258 | 11.557 | 40.939 | -5.046 | 0.65 | 30.10 |
| 8206 | CG | BGLN | B | 258 | 12.546 | 40.710 | -6.226 | 0.35 | 29.64 |
| 8207 | CG | AGLN | B | 258 | 11.357 | 42.333 | -5.625 | 0.65 | 31.67 |
| 8212 | CD | BGLN | B | 258 | 11.961 | 41.060 | -7.589 | 0.35 | 29.88 |
| 8213 | CD | AGLN | B | 258 | 9.896 | 42.666 | -5.883 | 0.65 | 33.37 |
| 8214 | OE1 | BGLN | B | 258 | 12.242 | 40.380 | -8.581 | 0.35 | 29.18 |
| 8215 | OE1 | AGLN | B | 258 | 9.502 | 42.893 | -7.025 | 0.65 | 34.64 |
| 8216 | NE2 | BGLN | B | 258 | 11.163 | 42.126 | -7.646 | 0.35 | 29.79 |
| 8217 | NE2 | AGLN | B | 258 | 9.094 | 42.705 | -4.820 | 0.65 | 34.91 |
| 8222 | C | GLN | B | 258 | 11.455 | 41.638 | -2.614 | 1.00 | 29.97 |
| 8223 | O | GLN | B | 258 | 11.755 | 42.780 | -2.274 | 1.00 | 29.34 |
| 8224 | N | GLN | B | 259 | 10.439 | 40.957 | -2.080 | 1.00 | 30.70 |
| 8226 | CA | GLN | B | 259 | 9.658 | 41.427 | -0.922 | 1.00 | 31.61 |
| 8228 | CB | GLN | B | 259 | 8.769 | 40.285 | -0.410 | 1.00 | 32.41 |

FIGURE 3 (Cont.)

| A | B | C | D | E | F | G | H | I | J |
|---|---|---|---|---|---|---|---|---|---|
| 8231 | CG | GLN | B | 259 | 7.466 | 40.703 | 0.244 | 1.00 | 35.31 |
| 8234 | CD | GLN | B | 259 | 6.317 | 40.769 | -0.744 | 1.00 | 39.68 |
| 8235 | OE1 | GLN | B | 259 | 5.925 | 41.861 | -1.174 | 1.00 | 43.25 |
| 8236 | NE2 | GLN | B | 259 | 5.780 | 39.605 | -1.119 | 1.00 | 42.40 |
| 8239 | C | GLN | B | 259 | 10.546 | 41.934 | 0.242 | 1.00 | 31.29 |
| 8240 | O | GLN | B | 259 | 10.321 | 43.032 | 0.776 | 1.00 | 31.47 |
| 8241 | N | LEU | B | 260 | 11.552 | 41.135 | 0.612 | 1.00 | 30.18 |
| 8243 | CA | LEU | B | 260 | 12.421 | 41.420 | 1.761 | 1.00 | 29.88 |
| 8245 | CB | LEU | B | 260 | 12.851 | 40.109 | 2.446 | 1.00 | 29.79 |
| 8248 | CG | LEU | B | 260 | 11.792 | 39.268 | 3.160 | 1.00 | 30.18 |
| 8250 | CD1 | LEU | B | 260 | 12.453 | 38.363 | 4.192 | 1.00 | 29.62 |
| 8254 | CD2 | LEU | B | 260 | 10.742 | 40.140 | 3.817 | 1.00 | 31.47 |
| 8258 | C | LEU | B | 260 | 13.681 | 42.207 | 1.413 | 1.00 | 28.94 |
| 8259 | O | LEU | B | 260 | 14.431 | 42.593 | 2.307 | 1.00 | 29.69 |
| 8260 | N | GLY | B | 261 | 13.921 | 42.429 | 0.128 | 1.00 | 27.95 |
| 8262 | CA | GLY | B | 261 | 15.133 | 43.084 | -0.333 | 1.00 | 26.93 |
| 8265 | C | GLY | B | 261 | 16.398 | 42.279 | -0.094 | 1.00 | 25.88 |
| 8266 | O | GLY | B | 261 | 17.436 | 42.845 | 0.261 | 1.00 | 25.61 |
| 8267 | N | LYS | B | 262 | 16.325 | 40.959 | -0.277 | 1.00 | 24.82 |
| 8269 | CA | LYS | B | 262 | 17.501 | 40.115 | -0.136 | 1.00 | 23.75 |
| 8271 | CB | LYS | B | 262 | 17.153 | 38.627 | -0.295 | 1.00 | 23.56 |
| 8274 | CG | LYS | B | 262 | 16.230 | 38.069 | 0.762 | 1.00 | 23.25 |
| 8277 | CD | LYS | B | 262 | 16.916 | 37.862 | 2.096 | 1.00 | 21.56 |
| 8280 | CE | LYS | B | 262 | 15.901 | 37.433 | 3.158 | 1.00 | 23.14 |
| 8283 | NZ | LYS | B | 262 | 16.536 | 37.070 | 4.482 | 1.00 | 21.85 |
| 8287 | C | LYS | B | 262 | 18.515 | 40.497 | -1.195 | 1.00 | 23.58 |
| 8288 | O | LYS | B | 262 | 18.145 | 40.845 | -2.337 | 1.00 | 23.29 |
| 8289 | N | SER | B | 263 | 19.785 | 40.474 | -0.803 | 1.00 | 22.82 |
| 8291 | CA | SER | B | 263 | 20.885 | 40.514 | -1.746 | 1.00 | 22.51 |
| 8293 | CB | SER | B | 263 | 22.206 | 40.785 | -1.035 | 1.00 | 22.93 |
| 8296 | OG | SER | B | 263 | 22.263 | 42.141 | -0.613 | 1.00 | 23.10 |
| 8298 | C | SER | B | 263 | 20.934 | 39.170 | -2.452 | 1.00 | 22.79 |
| 8299 | O | SER | B | 263 | 21.051 | 38.122 | -1.784 | 1.00 | 22.61 |
| 8300 | N | THR | B | 264 | 20.786 | 39.194 | -3.782 | 1.00 | 21.90 |
| 8302 | CA | THR | B | 264 | 20.764 | 37.973 | -4.593 | 1.00 | 22.01 |
| 8304 | CB | THR | B | 264 | 19.304 | 37.496 | -4.909 | 1.00 | 22.17 |
| 8306 | OG1 | THR | B | 264 | 18.667 | 38.392 | -5.827 | 1.00 | 23.42 |
| 8308 | CG2 | THR | B | 264 | 18.386 | 37.525 | -3.707 | 1.00 | 21.68 |
| 8312 | C | THR | B | 264 | 21.499 | 38.175 | -5.908 | 1.00 | 21.99 |
| 8313 | O | THR | B | 264 | 21.731 | 39.306 | -6.354 | 1.00 | 21.16 |
| 8314 | N | TYR | B | 265 | 21.841 | 37.066 | -6.553 | 1.00 | 21.84 |
| 8316 | CA | TYR | B | 265 | 22.470 | 37.134 | -7.864 | 1.00 | 22.04 |
| 8318 | CB | TYR | B | 265 | 22.959 | 35.754 | -8.319 | 1.00 | 21.34 |
| 8321 | CG | TYR | B | 265 | 24.340 | 35.435 | -7.803 | 1.00 | 20.33 |
| 8322 | CD1 | TYR | B | 265 | 25.430 | 35.422 | -8.654 | 1.00 | 20.38 |
| 8324 | CE1 | TYR | B | 265 | 26.686 | 35.129 | -8.197 | 1.00 | 20.95 |
| 8326 | CZ | TYR | B | 265 | 26.877 | 34.859 | -6.866 | 1.00 | 20.10 |
| 8327 | OH | TYR | B | 265 | 28.142 | 34.576 | -6.417 | 1.00 | 24.40 |
| 8329 | CE2 | TYR | B | 265 | 25.818 | 34.876 | -5.989 | 1.00 | 19.89 |
| 8331 | CD2 | TYR | B | 265 | 24.561 | 35.161 | -6.455 | 1.00 | 18.52 |
| 8333 | C | TYR | B | 265 | 21.588 | 37.816 | -8.933 | 1.00 | 22.40 |
| 8334 | O | TYR | B | 265 | 22.075 | 38.711 | -9.612 | 1.00 | 22.20 |

FIGURE 3 (Cont.)

| A | B | C | D | E | F | G | H | I | J |
|---|---|---|---|---|---|---|---|---|---|
| 8335 | N | PRO | B | 266 | 20.328 | 37.413 | -9.102 | 1.00 | 22.68 |
| 8336 | CA | PRO | B | 266 | 19.448 | 38.083 | -10.073 | 1.00 | 23.28 |
| 8338 | CB | PRO | B | 266 | 18.131 | 37.309 | -9.984 | 1.00 | 23.44 |
| 8341 | CG | PRO | B | 266 | 18.438 | 36.064 | -9.253 | 1.00 | 23.26 |
| 8344 | CD | PRO | B | 266 | 19.635 | 36.319 | -8.412 | 1.00 | 23.08 |
| 8347 | C | PRO | B | 266 | 19.193 | 39.550 | -9.744 | 1.00 | 23.45 |
| 8348 | O | PRO | B | 266 | 19.084 | 40.350 | -10.668 | 1.00 | 23.18 |
| 8349 | N | ALA | B | 267 | 19.099 | 39.890 | -8.460 | 1.00 | 23.47 |
| 8351 | CA | ALA | B | 267 | 18.821 | 41.268 | -8.062 | 1.00 | 23.58 |
| 8353 | CB | ALA | B | 267 | 18.569 | 41.386 | -6.560 | 1.00 | 23.84 |
| 8357 | C | ALA | B | 267 | 19.962 | 42.155 | -8.483 | 1.00 | 23.82 |
| 8358 | O | ALA | B | 267 | 19.742 | 43.216 | -9.062 | 1.00 | 24.38 |
| 8359 | N | LEU | B | 268 | 21.184 | 41.692 | -8.247 | 1.00 | 23.53 |
| 8361 | CA | LEU | B | 268 | 22.375 | 42.447 | -8.586 | 1.00 | 23.59 |
| 8363 | CB | LEU | B | 268 | 23.566 | 41.908 | -7.798 | 1.00 | 23.51 |
| 8366 | CG | LEU | B | 268 | 24.934 | 42.511 | -8.113 | 1.00 | 23.92 |
| 8368 | CD1 | LEU | B | 268 | 24.947 | 44.021 | -7.830 | 1.00 | 24.92 |
| 8372 | CD2 | LEU | B | 268 | 26.012 | 41.800 | -7.318 | 1.00 | 24.12 |
| 8376 | C | LEU | B | 268 | 22.704 | 42.437 | -10.082 | 1.00 | 23.25 |
| 8377 | O | LEU | B | 268 | 22.964 | 43.479 | -10.664 | 1.00 | 23.31 |
| 8378 | N | LEU | B | 269 | 22.693 | 41.253 | -10.683 | 1.00 | 22.76 |
| 8380 | CA | LEU | B | 269 | 23.281 | 41.018 | -11.995 | 1.00 | 22.56 |
| 8382 | CB | LEU | B | 269 | 24.093 | 39.726 | -11.983 | 1.00 | 22.53 |
| 8385 | CG | LEU | B | 269 | 25.314 | 39.686 | -11.062 | 1.00 | 24.16 |
| 8387 | CD1 | LEU | B | 269 | 25.881 | 38.277 | -11.022 | 1.00 | 25.08 |
| 8391 | CD2 | LEU | B | 269 | 26.394 | 40.674 | -11.518 | 1.00 | 25.88 |
| 8395 | C | LEU | B | 269 | 22.237 | 40.925 | -13.089 | 1.00 | 21.93 |
| 8396 | O | LEU | B | 269 | 22.567 | 40.925 | -14.273 | 1.00 | 21.98 |
| 8397 | N | GLY | B | 270 | 20.981 | 40.880 | -12.696 | 1.00 | 21.10 |
| 8399 | CA | GLY | B | 270 | 19.925 | 40.537 | -13.619 | 1.00 | 21.48 |
| 8402 | C | GLY | B | 270 | 19.923 | 39.035 | -13.860 | 1.00 | 21.79 |
| 8403 | O | GLY | B | 270 | 20.883 | 38.320 | -13.530 | 1.00 | 20.41 |
| 8404 | N | LEU | B | 271 | 18.831 | 38.570 | -14.445 | 1.00 | 22.27 |
| 8406 | CA | LEU | B | 271 | 18.587 | 37.145 | -14.645 | 1.00 | 23.11 |
| 8408 | CB | LEU | B | 271 | 17.169 | 36.923 | -15.161 | 1.00 | 23.57 |
| 8411 | CG | LEU | B | 271 | 16.145 | 36.966 | -14.051 | 1.00 | 23.96 |
| 8413 | CD1 | LEU | B | 271 | 14.712 | 36.988 | -14.638 | 1.00 | 25.68 |
| 8417 | CD2 | LEU | B | 271 | 16.375 | 35.748 | -13.152 | 1.00 | 24.82 |
| 8421 | C | LEU | B | 271 | 19.554 | 36.493 | -15.601 | 1.00 | 23.62 |
| 8422 | O | LEU | B | 271 | 19.999 | 35.393 | -15.348 | 1.00 | 22.96 |
| 8423 | N | GLU | B | 272 | 19.885 | 37.158 | -16.704 | 1.00 | 24.28 |
| 8425 | CA | GLU | B | 272 | 20.703 | 36.498 | -17.715 | 1.00 | 25.35 |
| 8427 | CB | GLU | B | 272 | 20.712 | 37.237 | -19.049 | 1.00 | 26.22 |
| 8430 | CG | GLU | B | 272 | 21.247 | 36.373 | -20.184 | 1.00 | 30.72 |
| 8433 | CD | GLU | B | 272 | 20.177 | 35.523 | -20.858 | 1.00 | 36.13 |
| 8434 | OE1 | GLU | B | 272 | 19.801 | 35.857 | -22.020 | 1.00 | 40.61 |
| 8435 | OE2 | GLU | B | 272 | 19.725 | 34.513 | -20.244 | 1.00 | 38.13 |
| 8436 | C | GLU | B | 272 | 22.116 | 36.293 | -17.220 | 1.00 | 24.46 |
| 8437 | O | GLU | B | 272 | 22.658 | 35.215 | -17.405 | 1.00 | 23.99 |
| 8438 | N | GLN | B | 273 | 22.707 | 37.305 | -16.582 | 1.00 | 23.54 |
| 8440 | CA | GLN | B | 273 | 24.052 | 37.148 | -16.019 | 1.00 | 23.89 |
| 8442 | CB | GLN | B | 273 | 24.640 | 38.488 | -15.569 | 1.00 | 23.95 |

FIGURE 3 (Cont.)

| A | B | C | D | E | F | G | H | I | J |
|---|---|---|---|---|---|---|---|---|---|
| 8445 | CG | GLN | B | 273 | 25.057 | 39.407 | -16.701 | 1.00 | 26.62 |
| 8448 | CD | GLN | B | 273 | 25.436 | 40.804 | -16.197 | 1.00 | 29.62 |
| 8449 | OE1 | GLN | B | 273 | 26.041 | 40.939 | -15.140 | 1.00 | 29.56 |
| 8450 | NE2 | GLN | B | 273 | 25.046 | 41.834 | -16.941 | 1.00 | 32.63 |
| 8453 | C | GLN | B | 273 | 24.042 | 36.157 | -14.848 | 1.00 | 23.16 |
| 8454 | O | GLN | B | 273 | 24.994 | 35.428 | -14.656 | 1.00 | 23.94 |
| 8455 | N | ALA | B | 274 | 22.968 | 36.130 | -14.071 | 1.00 | 22.86 |
| 8457 | CA | ALA | B | 274 | 22.852 | 35.161 | -12.985 | 1.00 | 22.78 |
| 8459 | CB | ALA | B | 274 | 21.591 | 35.413 | -12.169 | 1.00 | 22.56 |
| 8463 | C | ALA | B | 274 | 22.848 | 33.738 | -13.565 | 1.00 | 22.60 |
| 8464 | O | ALA | B | 274 | 23.542 | 32.873 | -13.071 | 1.00 | 22.64 |
| 8465 | N | ARG | B | 275 | 22.085 | 33.520 | -14.632 | 1.00 | 22.89 |
| 8467 | CA | ARG | B | 275 | 22.048 | 32.213 | -15.299 | 1.00 | 23.30 |
| 8469 | CB | ARG | B | 275 | 21.012 | 32.205 | -16.431 | 1.00 | 23.67 |
| 8472 | CG | ARG | B | 275 | 19.594 | 32.090 | -15.944 | 1.00 | 25.28 |
| 8475 | CD | ARG | B | 275 | 18.542 | 32.199 | -17.031 | 1.00 | 27.92 |
| 8478 | NE | ARG | B | 275 | 17.209 | 31.888 | -16.503 | 1.00 | 30.36 |
| 8480 | CZ | ARG | B | 275 | 16.104 | 32.616 | -16.697 | 1.00 | 32.35 |
| 8481 | NH1 | ARG | B | 275 | 16.121 | 33.727 | -17.423 | 1.00 | 31.95 |
| 8484 | NH2 | ARG | B | 275 | 14.954 | 32.217 | -16.160 | 1.00 | 34.03 |
| 8487 | C | ARG | B | 275 | 23.424 | 31.827 | -15.854 | 1.00 | 23.20 |
| 8488 | O | ARG | B | 275 | 23.843 | 30.669 | -15.783 | 1.00 | 22.27 |
| 8489 | N | LYS | B | 276 | 24.111 | 32.807 | -16.421 | 1.00 | 23.01 |
| 8491 | CA | LYS | B | 276 | 25.418 | 32.595 | -16.998 | 1.00 | 22.90 |
| 8493 | CB | LYS | B | 276 | 25.870 | 33.833 | -17.774 | 1.00 | 23.16 |
| 8496 | CG | LYS | B | 276 | 27.307 | 33.794 | -18.251 | 1.00 | 24.89 |
| 8499 | CD | LYS | B | 276 | 27.542 | 32.619 | -19.190 | 1.00 | 28.29 |
| 8502 | CE | LYS | B | 276 | 28.672 | 32.892 | -20.166 | 1.00 | 29.58 |
| 8505 | NZ | LYS | B | 276 | 29.948 | 33.113 | -19.451 | 1.00 | 30.99 |
| 8509 | C | LYS | B | 276 | 26.422 | 32.253 | -15.893 | 1.00 | 22.40 |
| 8510 | O | LYS | B | 276 | 27.270 | 31.400 | -16.086 | 1.00 | 22.05 |
| 8511 | N | LYS | B | 277 | 26.312 | 32.901 | -14.742 | 1.00 | 21.92 |
| 8513 | CA | LYS | B | 277 | 27.191 | 32.604 | -13.612 | 1.00 | 22.26 |
| 8515 | CB | LYS | B | 277 | 26.959 | 33.566 | -12.444 | 1.00 | 22.86 |
| 8518 | CG | LYS | B | 277 | 27.325 | 35.029 | -12.759 | 1.00 | 26.57 |
| 8521 | CD | LYS | B | 277 | 28.574 | 35.530 | -12.019 | 1.00 | 30.08 |
| 8524 | CE | LYS | B | 277 | 29.067 | 36.885 | -12.583 | 1.00 | 31.95 |
| 8527 | NZ | LYS | B | 277 | 30.540 | 37.060 | -12.449 | 1.00 | 33.10 |
| 8531 | C | LYS | B | 277 | 26.982 | 31.151 | -13.175 | 1.00 | 21.47 |
| 8532 | O | LYS | B | 277 | 27.939 | 30.422 | -12.944 | 1.00 | 21.43 |
| 8533 | N | ALA | B | 278 | 25.725 | 30.729 | -13.101 | 1.00 | 20.57 |
| 8535 | CA | ALA | B | 278 | 25.408 | 29.366 | -12.697 | 1.00 | 20.64 |
| 8537 | CB | ALA | B | 278 | 23.881 | 29.171 | -12.552 | 1.00 | 20.42 |
| 8541 | C | ALA | B | 278 | 25.990 | 28.377 | -13.699 | 1.00 | 20.27 |
| 8542 | O | ALA | B | 278 | 26.607 | 27.383 | -13.306 | 1.00 | 19.24 |
| 8543 | N | ARG | B | 279 | 25.819 | 28.639 | -14.990 | 1.00 | 20.74 |
| 8545 | CA | ARG | B | 279 | 26.307 | 27.695 | -15.997 | 1.00 | 21.12 |
| 8547 | CB | ARG | B | 279 | 25.765 | 28.003 | -17.392 | 1.00 | 21.76 |
| 8550 | CG | ARG | B | 279 | 26.088 | 26.897 | -18.402 | 1.00 | 22.89 |
| 8553 | CD | ARG | B | 279 | 25.654 | 27.222 | -19.814 | 1.00 | 25.89 |
| 8556 | NE | ARG | B | 279 | 26.498 | 28.272 | -20.382 | 1.00 | 26.63 |
| 8558 | CZ | ARG | B | 279 | 26.296 | 28.833 | -21.562 | 1.00 | 26.13 |

FIGURE 3 (Cont.)

| A | B | C | D | E | F | G | H | I | J |
|---|---|---|---|---|---|---|---|---|---|
| 8559 | NH1 | ARG | B | 279 | 25.253 | 28.490 | -22.311 | 1.00 | 24.20 |
| 8562 | NH2 | ARG | B | 279 | 27.138 | 29.760 | -21.981 | 1.00 | 25.45 |
| 8565 | C | ARG | B | 279 | 27.831 | 27.650 | -16.001 | 1.00 | 21.30 |
| 8566 | O | ARG | B | 279 | 28.416 | 26.590 | -16.177 | 1.00 | 21.07 |
| 8567 | N | ASP | B | 280 | 28.461 | 28.795 | -15.766 | 1.00 | 21.40 |
| 8569 | CA | ASP | B | 280 | 29.915 | 28.874 | -15.595 | 1.00 | 21.87 |
| 8571 | CB | ASP | B | 280 | 30.335 | 30.327 | -15.313 | 1.00 | 22.54 |
| 8574 | CG | ASP | B | 280 | 30.370 | 31.200 | -16.579 | 1.00 | 25.24 |
| 8575 | OD1 | ASP | B | 280 | 30.630 | 32.424 | -16.457 | 1.00 | 28.05 |
| 8576 | OD2 | ASP | B | 280 | 30.138 | 30.759 | -17.724 | 1.00 | 26.91 |
| 8577 | C | ASP | B | 280 | 30.401 | 27.958 | -14.456 | 1.00 | 21.04 |
| 8578 | O | ASP | B | 280 | 31.440 | 27.297 | -14.562 | 1.00 | 20.76 |
| 8579 | N | LEU | B | 281 | 29.633 | 27.922 | -13.372 | 1.00 | 20.21 |
| 8581 | CA | LEU | B | 281 | 29.994 | 27.151 | -12.188 | 1.00 | 19.69 |
| 8583 | CB | LEU | B | 281 | 29.141 | 27.569 | -10.992 | 1.00 | 19.82 |
| 8586 | CG | LEU | B | 281 | 29.530 | 28.953 | -10.452 | 1.00 | 18.53 |
| 8588 | CD1 | LEU | B | 281 | 28.423 | 29.532 | -9.589 | 1.00 | 19.63 |
| 8592 | CD2 | LEU | B | 281 | 30.812 | 28.869 | -9.646 | 1.00 | 19.99 |
| 8596 | C | LEU | B | 281 | 29.838 | 25.670 | -12.468 | 1.00 | 19.73 |
| 8597 | O | LEU | B | 281 | 30.671 | 24.889 | -12.094 | 1.00 | 20.05 |
| 8598 | N | ILE | B | 282 | 28.774 | 25.295 | -13.150 | 1.00 | 20.33 |
| 8600 | CA | ILE | B | 282 | 28.597 | 23.906 | -13.555 | 1.00 | 21.14 |
| 8602 | CB | ILE | B | 282 | 27.190 | 23.672 | -14.076 | 1.00 | 21.02 |
| 8604 | CG1 | ILE | B | 282 | 26.178 | 23.925 | -12.949 | 1.00 | 22.56 |
| 8607 | CD1 | ILE | B | 282 | 26.532 | 23.265 | -11.610 | 1.00 | 22.71 |
| 8611 | CG2 | ILE | B | 282 | 27.041 | 22.244 | -14.624 | 1.00 | 21.66 |
| 8615 | C | ILE | B | 282 | 29.659 | 23.477 | -14.566 | 1.00 | 21.32 |
| 8616 | O | ILE | B | 282 | 30.149 | 22.359 | -14.488 | 1.00 | 21.92 |
| 8617 | N | ASP | B | 283 | 30.032 | 24.358 | -15.487 | 1.00 | 21.87 |
| 8619 | CA | ASP | B | 283 | 31.112 | 24.056 | -16.430 | 1.00 | 22.32 |
| 8621 | CB | ASP | B | 283 | 31.436 | 25.261 | -17.330 | 1.00 | 22.60 |
| 8624 | CG | ASP | B | 283 | 30.410 | 25.503 | -18.417 | 1.00 | 23.70 |
| 8625 | OD1 | ASP | B | 283 | 30.445 | 26.623 | -18.989 | 1.00 | 26.27 |
| 8626 | OD2 | ASP | B | 283 | 29.548 | 24.676 | -18.786 | 1.00 | 22.23 |
| 8627 | C | ASP | B | 283 | 32.369 | 23.705 | -15.624 | 1.00 | 22.25 |
| 8628 | O | ASP | B | 283 | 33.066 | 22.756 | -15.928 | 1.00 | 21.47 |
| 8629 | N | ASP | B | 284 | 32.636 | 24.490 | -14.588 | 1.00 | 22.34 |
| 8631 | CA | ASP | B | 284 | 33.793 | 24.291 | -13.731 | 1.00 | 23.23 |
| 8633 | CB | ASP | B | 284 | 33.980 | 25.509 | -12.820 | 1.00 | 23.34 |
| 8636 | CG | ASP | B | 284 | 35.161 | 25.368 | -11.918 | 1.00 | 26.31 |
| 8637 | OD1 | ASP | B | 284 | 36.305 | 25.530 | -12.420 | 1.00 | 28.34 |
| 8638 | OD2 | ASP | B | 284 | 35.037 | 25.088 | -10.697 | 1.00 | 28.06 |
| 8639 | C | ASP | B | 284 | 33.670 | 22.986 | -12.925 | 1.00 | 22.69 |
| 8640 | O | ASP | B | 284 | 34.641 | 22.234 | -12.816 | 1.00 | 22.49 |
| 8641 | N | ALA | B | 285 | 32.474 | 22.703 | -12.405 | 1.00 | 22.19 |
| 8643 | CA | ALA | B | 285 | 32.204 | 21.431 | -11.725 | 1.00 | 22.57 |
| 8645 | CB | ALA | B | 285 | 30.752 | 21.361 | -11.263 | 1.00 | 22.03 |
| 8649 | C | ALA | B | 285 | 32.524 | 20.233 | -12.631 | 1.00 | 22.99 |
| 8650 | O | ALA | B | 285 | 33.151 | 19.270 | -12.190 | 1.00 | 22.66 |
| 8651 | N | ARG | B | 286 | 32.115 | 20.321 | -13.895 | 1.00 | 23.78 |
| 8653 | CA | ARG | B | 286 | 32.394 | 19.283 | -14.883 | 1.00 | 25.16 |
| 8655 | CB | ARG | B | 286 | 31.628 | 19.550 | -16.180 | 1.00 | 25.91 |

FIGURE 3 (Cont.)

| A | B | C | D | E | F | G | H | I | J |
|---|---|---|---|---|---|---|---|---|---|
| 8658 | CG | ARG | B | 286 | 30.138 | 19.170 | -16.097 | 1.00 | 28.32 |
| 8661 | CD | BARG | B | 286 | 29.468 | 18.992 | -17.466 | 0.35 | 29.52 |
| 8662 | CD | AARG | B | 286 | 29.453 | 19.007 | -17.451 | 0.65 | 30.92 |
| 8667 | NE | BARG | B | 286 | 29.262 | 20.264 | -18.163 | 0.35 | 29.83 |
| 8668 | NE | AARG | B | 286 | 28.271 | 18.146 | -17.365 | 0.65 | 31.71 |
| 8671 | CZ | BARG | B | 286 | 28.839 | 20.386 | -19.423 | 0.35 | 30.53 |
| 8672 | CZ | AARG | B | 286 | 28.231 | 16.856 | -17.684 | 0.65 | 33.32 |
| 8673 | NH1 | BARG | B | 286 | 28.567 | 19.313 | -20.165 | 0.35 | 30.23 |
| 8674 | NH1 | AARG | B | 286 | 29.309 | 16.209 | -18.125 | 0.65 | 33.00 |
| 8679 | NH2 | BARG | B | 286 | 28.688 | 21.596 | -19.951 | 0.35 | 30.87 |
| 8680 | NH2 | AARG | B | 286 | 27.089 | 16.195 | -17.563 | 0.65 | 33.96 |
| 8685 | C | ARG | B | 286 | 33.894 | 19.108 | -15.170 | 1.00 | 25.22 |
| 8686 | O | ARG | B | 286 | 34.349 | 17.988 | -15.388 | 1.00 | 24.81 |
| 8687 | N | GLN | B | 287 | 34.651 | 20.204 | -15.171 | 1.00 | 25.23 |
| 8689 | CA | GLN | B | 287 | 36.100 | 20.116 | -15.322 | 1.00 | 25.93 |
| 8691 | CB | GLN | B | 287 | 36.756 | 21.497 | -15.472 | 1.00 | 26.28 |
| 8694 | CG | GLN | B | 287 | 36.425 | 22.206 | -16.775 | 1.00 | 29.31 |
| 8697 | CD | GLN | B | 287 | 37.009 | 21.533 | -18.012 | 1.00 | 32.74 |
| 8698 | OE1 | GLN | B | 287 | 38.047 | 20.880 | -17.945 | 1.00 | 35.76 |
| 8699 | NE2 | GLN | B | 287 | 36.340 | 21.706 | -19.144 | 1.00 | 35.59 |
| 8702 | C | GLN | B | 287 | 36.706 | 19.364 | -14.131 | 1.00 | 25.31 |
| 8703 | O | GLN | B | 287 | 37.565 | 18.521 | -14.333 | 1.00 | 24.00 |
| 8704 | N | SER | B | 288 | 36.241 | 19.658 | -12.905 | 1.00 | 25.12 |
| 8706 | CA | SER | B | 288 | 36.665 | 18.911 | -11.720 | 1.00 | 25.39 |
| 8708 | CB | SER | B | 288 | 36.105 | 19.510 | -10.414 | 1.00 | 25.38 |
| 8711 | OG | SER | B | 288 | 36.557 | 20.834 | -10.215 | 1.00 | 24.82 |
| 8713 | C | SER | B | 288 | 36.289 | 17.433 | -11.820 | 1.00 | 25.78 |
| 8714 | O | SER | B | 288 | 37.077 | 16.569 | -11.459 | 1.00 | 25.49 |
| 8715 | N | LEU | B | 289 | 35.098 | 17.125 | -12.321 | 1.00 | 26.38 |
| 8717 | CA | LEU | B | 289 | 34.709 | 15.726 | -12.441 | 1.00 | 27.10 |
| 8719 | CB | LEU | B | 289 | 33.237 | 15.580 | -12.838 | 1.00 | 26.93 |
| 8722 | CG | LEU | B | 289 | 32.258 | 15.977 | -11.729 | 1.00 | 25.30 |
| 8724 | CD1 | LEU | B | 289 | 30.821 | 15.804 | -12.200 | 1.00 | 25.85 |
| 8728 | CD2 | LEU | B | 289 | 32.524 | 15.189 | -10.431 | 1.00 | 25.23 |
| 8732 | C | LEU | B | 289 | 35.635 | 14.995 | -13.425 | 1.00 | 28.16 |
| 8733 | O | LEU | B | 289 | 35.998 | 13.854 | -13.186 | 1.00 | 28.16 |
| 8734 | N | LYS | B | 290 | 36.053 | 15.677 | -14.487 | 1.00 | 29.02 |
| 8736 | CA | LYS | B | 290 | 36.961 | 15.096 | -15.481 | 1.00 | 30.79 |
| 8738 | CB | LYS | B | 290 | 37.313 | 16.118 | -16.587 | 1.00 | 30.97 |
| 8741 | CG | LYS | B | 290 | 36.966 | 15.687 | -18.011 | 1.00 | 33.97 |
| 8744 | CD | LYS | B | 290 | 36.614 | 16.900 | -18.921 | 1.00 | 36.64 |
| 8747 | CE | LYS | B | 290 | 35.099 | 17.019 | -19.182 | 1.00 | 37.79 |
| 8750 | NZ | LYS | B | 290 | 34.637 | 18.445 | -19.343 | 1.00 | 38.84 |
| 8754 | C | LYS | B | 290 | 38.244 | 14.611 | -14.809 | 1.00 | 31.28 |
| 8755 | O | LYS | B | 290 | 38.750 | 13.544 | -15.141 | 1.00 | 31.44 |
| 8756 | N | GLN | B | 291 | 38.759 | 15.401 | -13.869 | 1.00 | 32.13 |
| 8758 | CA | GLN | B | 291 | 39.978 | 15.054 | -13.152 | 1.00 | 33.58 |
| 8760 | CB | GLN | B | 291 | 40.470 | 16.251 | -12.326 | 1.00 | 33.80 |
| 8763 | CG | GLN | B | 291 | 40.818 | 17.493 | -13.167 | 1.00 | 35.12 |
| 8766 | CD | GLN | B | 291 | 40.846 | 18.775 | -12.353 | 1.00 | 36.83 |
| 8767 | OE1 | GLN | B | 291 | 41.175 | 18.756 | -11.168 | 1.00 | 36.95 |
| 8768 | NE2 | GLN | B | 291 | 40.495 | 19.893 | -12.985 | 1.00 | 38.40 |

FIGURE 3 (Cont.)

| A | B | C | D | E | F | G | H | I | J |
|---|---|---|---|---|---|---|---|---|---|
| 8771 | C | GLN | B | 291 | 39.800 | 13.810 | -12.265 | 1.00 | 34.42 |
| 8772 | O | GLN | B | 291 | 40.764 | 13.098 | -12.013 | 1.00 | 34.62 |
| 8773 | N | LEU | B | 292 | 38.577 | 13.568 | -11.784 | 1.00 | 35.42 |
| 8775 | CA | LEU | B | 292 | 38.248 | 12.364 | -10.999 | 1.00 | 36.35 |
| 8777 | CB | LEU | B | 292 | 36.931 | 12.542 | -10.251 | 1.00 | 36.39 |
| 8780 | CG | LEU | B | 292 | 36.924 | 13.515 | -9.082 | 1.00 | 36.49 |
| 8782 | CD1 | LEU | B | 292 | 35.562 | 13.491 | -8.411 | 1.00 | 36.85 |
| 8786 | CD2 | LEU | B | 292 | 38.023 | 13.153 | -8.101 | 1.00 | 36.84 |
| 8790 | C | LEU | B | 292 | 38.141 | 11.088 | -11.820 | 1.00 | 37.54 |
| 8791 | O | LEU | B | 292 | 38.519 | 10.015 | -11.352 | 1.00 | 37.33 |
| 8792 | N | ALA | B | 293 | 37.598 | 11.193 | -13.028 | 1.00 | 38.95 |
| 8794 | CA | ALA | B | 293 | 37.635 | 10.088 | -13.974 | 1.00 | 40.14 |
| 8796 | CB | ALA | B | 293 | 36.587 | 10.291 | -15.078 | 1.00 | 40.36 |
| 8800 | C | ALA | B | 293 | 39.045 | 9.950 | -14.565 | 1.00 | 40.76 |
| 8801 | O | ALA | B | 293 | 39.206 | 9.462 | -15.677 | 1.00 | 41.94 |
| 8802 | N | GLU | B | 294 | 40.045 | 10.442 | -13.834 | 1.00 | 41.22 |
| 8804 | CA | GLU | B | 294 | 41.456 | 10.118 | -14.039 | 1.00 | 41.53 |
| 8806 | CB | GLU | B | 294 | 42.240 | 11.402 | -14.318 | 1.00 | 41.94 |
| 8809 | CG | GLU | B | 294 | 43.620 | 11.186 | -14.911 | 1.00 | 44.01 |
| 8812 | CD | GLU | B | 294 | 44.144 | 12.428 | -15.604 | 1.00 | 45.96 |
| 8813 | OE1 | GLU | B | 294 | 44.166 | 13.499 | -14.953 | 1.00 | 48.06 |
| 8814 | OE2 | GLU | B | 294 | 44.528 | 12.332 | -16.794 | 1.00 | 47.73 |
| 8815 | C | GLU | B | 294 | 42.047 | 9.414 | -12.808 | 1.00 | 40.89 |
| 8816 | O | GLU | B | 294 | 43.185 | 8.941 | -12.846 | 1.00 | 41.57 |
| 8817 | N | GLN | B | 295 | 41.295 | 9.399 | -11.705 | 1.00 | 39.90 |
| 8819 | CA | GLN | B | 295 | 41.549 | 8.516 | -10.565 | 1.00 | 38.66 |
| 8821 | CB | GLN | B | 295 | 41.248 | 9.243 | -9.243 | 1.00 | 38.65 |
| 8824 | CG | GLN | B | 295 | 41.958 | 10.592 | -9.083 | 1.00 | 38.47 |
| 8827 | CD | GLN | B | 295 | 41.556 | 11.354 | -7.816 | 1.00 | 37.66 |
| 8828 | OE1 | GLN | B | 295 | 41.179 | 10.751 | -6.807 | 1.00 | 36.11 |
| 8829 | NE2 | GLN | B | 295 | 41.658 | 12.686 | -7.867 | 1.00 | 36.75 |
| 8832 | C | GLN | B | 295 | 40.681 | 7.258 | -10.689 | 1.00 | 37.75 |
| 8833 | O | GLN | B | 295 | 40.432 | 6.560 | -9.698 | 1.00 | 37.50 |
| 8834 | N | SER | B | 296 | 40.220 | 6.995 | -11.914 | 1.00 | 36.44 |
| 8836 | CA | SER | B | 296 | 39.373 | 5.852 | -12.261 | 1.00 | 35.92 |
| 8838 | CB | SER | B | 296 | 40.117 | 4.541 | -12.022 | 1.00 | 36.22 |
| 8841 | OG | SER | B | 296 | 39.666 | 3.572 | -12.955 | 1.00 | 38.05 |
| 8843 | C | SER | B | 296 | 38.003 | 5.810 | -11.566 | 1.00 | 34.56 |
| 8844 | O | SER | B | 296 | 37.551 | 4.753 | -11.143 | 1.00 | 34.47 |
| 8845 | N | LEU | B | 297 | 37.330 | 6.952 | -11.485 | 1.00 | 32.72 |
| 8847 | CA | LEU | B | 297 | 36.060 | 7.022 | -10.773 | 1.00 | 31.10 |
| 8849 | CB | LEU | B | 297 | 36.114 | 8.107 | -9.699 | 1.00 | 30.86 |
| 8852 | CG | LEU | B | 297 | 37.166 | 7.891 | -8.611 | 1.00 | 30.39 |
| 8854 | CD1 | LEU | B | 297 | 37.381 | 9.150 | -7.786 | 1.00 | 30.04 |
| 8858 | CD2 | LEU | B | 297 | 36.771 | 6.739 | -7.721 | 1.00 | 30.69 |
| 8862 | C | LEU | B | 297 | 34.910 | 7.286 | -11.724 | 1.00 | 30.21 |
| 8863 | O | LEU | B | 297 | 35.045 | 8.047 | -12.684 | 1.00 | 29.81 |
| 8864 | N | ASP | B | 298 | 33.776 | 6.655 | -11.425 | 1.00 | 28.91 |
| 8866 | CA | ASP | B | 298 | 32.541 | 6.834 | -12.171 | 1.00 | 28.55 |
| 8868 | CB | ASP | B | 298 | 31.659 | 5.597 | -12.005 | 1.00 | 28.67 |
| 8871 | CG | ASP | B | 298 | 30.377 | 5.661 | -12.823 | 1.00 | 30.58 |
| 8872 | OD1 | ASP | B | 298 | 30.141 | 6.682 | -13.512 | 1.00 | 31.79 |

FIGURE 3 (Cont.)

| A | B | C | D | E | F | G | H | I | J |
|---|---|---|---|---|---|---|---|---|---|
| 8873 | OD2 | ASP | B | 298 | 29.534 | 4.729 | -12.815 | 1.00 | 33.35 |
| 8874 | C | ASP | B | 298 | 31.830 | 8.086 | -11.662 | 1.00 | 27.64 |
| 8875 | O | ASP | B | 298 | 31.132 | 8.050 | -10.649 | 1.00 | 26.94 |
| 8876 | N | THR | B | 299 | 32.007 | 9.187 | -12.390 | 1.00 | 26.96 |
| 8878 | CA | THR | B | 299 | 31.424 | 10.478 | -12.020 | 1.00 | 26.33 |
| 8880 | CB | THR | B | 299 | 32.352 | 11.615 | -12.471 | 1.00 | 26.05 |
| 8882 | OG1 | THR | B | 299 | 32.571 | 11.538 | -13.882 | 1.00 | 27.18 |
| 8884 | CG2 | THR | B | 299 | 33.740 | 11.457 | -11.879 | 1.00 | 26.15 |
| 8888 | C | THR | B | 299 | 30.006 | 10.704 | -12.588 | 1.00 | 25.98 |
| 8889 | O | THR | B | 299 | 29.464 | 11.785 | -12.453 | 1.00 | 25.98 |
| 8890 | N | SER | B | 300 | 29.392 | 9.682 | -13.176 | 1.00 | 25.39 |
| 8892 | CA | SER | B | 300 | 28.130 | 9.855 | -13.906 | 1.00 | 25.11 |
| 8894 | CB | SER | B | 300 | 27.672 | 8.535 | -14.531 | 1.00 | 25.29 |
| 8897 | OG | SER | B | 300 | 27.346 | 7.581 | -13.529 | 1.00 | 27.52 |
| 8899 | C | SER | B | 300 | 27.004 | 10.479 | -13.077 | 1.00 | 24.18 |
| 8900 | O | SER | B | 300 | 26.340 | 11.391 | -13.553 | 1.00 | 23.89 |
| 8901 | N | ALA | B | 301 | 26.788 | 10.001 | -11.850 | 1.00 | 23.33 |
| 8903 | CA | ALA | B | 301 | 25.756 | 10.590 | -10.983 | 1.00 | 22.98 |
| 8905 | CB | ALA | B | 301 | 25.555 | 9.776 | -9.736 | 1.00 | 22.98 |
| 8909 | C | ALA | B | 301 | 26.051 | 12.044 | -10.605 | 1.00 | 22.43 |
| 8910 | O | ALA | B | 301 | 25.138 | 12.850 | -10.585 | 1.00 | 21.51 |
| 8911 | N | LEU | B | 302 | 27.321 | 12.361 | -10.309 | 1.00 | 22.10 |
| 8913 | CA | LEU | B | 302 | 27.705 | 13.698 | -9.887 | 1.00 | 21.91 |
| 8915 | CB | LEU | B | 302 | 29.102 | 13.715 | -9.268 | 1.00 | 21.74 |
| 8918 | CG | LEU | B | 302 | 29.295 | 12.964 | -7.951 | 1.00 | 22.89 |
| 8920 | CD1 | LEU | B | 302 | 30.736 | 13.126 | -7.523 | 1.00 | 23.47 |
| 8924 | CD2 | LEU | B | 302 | 28.338 | 13.420 | -6.858 | 1.00 | 23.02 |
| 8928 | C | LEU | B | 302 | 27.651 | 14.663 | -11.058 | 1.00 | 22.32 |
| 8929 | O | LEU | B | 302 | 27.411 | 15.858 | -10.863 | 1.00 | 21.59 |
| 8930 | N | GLU | B | 303 | 27.861 | 14.144 | -12.270 | 1.00 | 22.83 |
| 8932 | CA | GLU | B | 303 | 27.716 | 14.933 | -13.480 | 1.00 | 23.58 |
| 8934 | CB | GLU | B | 303 | 28.227 | 14.192 | -14.720 | 1.00 | 24.19 |
| 8937 | CG | GLU | B | 303 | 29.708 | 13.867 | -14.789 | 1.00 | 27.75 |
| 8940 | CD | GLU | B | 303 | 30.025 | 12.941 | -15.962 | 1.00 | 31.36 |
| 8941 | OE1 | GLU | B | 303 | 29.515 | 13.205 | -17.070 | 1.00 | 34.68 |
| 8942 | OE2 | GLU | B | 303 | 30.758 | 11.938 | -15.784 | 1.00 | 33.57 |
| 8943 | C | GLU | B | 303 | 26.241 | 15.247 | -13.705 | 1.00 | 23.21 |
| 8944 | O | GLU | B | 303 | 25.897 | 16.382 | -14.000 | 1.00 | 23.30 |
| 8945 | N | ALA | B | 304 | 25.378 | 14.238 | -13.592 | 1.00 | 22.93 |
| 8947 | CA | ALA | B | 304 | 23.954 | 14.418 | -13.865 | 1.00 | 23.17 |
| 8949 | CB | ALA | B | 304 | 23.219 | 13.063 | -13.846 | 1.00 | 23.72 |
| 8953 | C | ALA | B | 304 | 23.348 | 15.383 | -12.844 | 1.00 | 22.99 |
| 8954 | O | ALA | B | 304 | 22.530 | 16.240 | -13.186 | 1.00 | 22.84 |
| 8955 | N | LEU | B | 305 | 23.786 | 15.250 | -11.596 | 1.00 | 22.47 |
| 8957 | CA | LEU | B | 305 | 23.331 | 16.111 | -10.518 | 1.00 | 22.39 |
| 8959 | CB | LEU | B | 305 | 23.841 | 15.623 | -9.166 | 1.00 | 22.42 |
| 8962 | CG | LEU | B | 305 | 23.319 | 16.420 | -7.973 | 1.00 | 23.49 |
| 8964 | CD1 | LEU | B | 305 | 21.813 | 16.473 | -7.938 | 1.00 | 26.09 |
| 8968 | CD2 | LEU | B | 305 | 23.835 | 15.859 | -6.701 | 1.00 | 25.91 |
| 8972 | C | LEU | B | 305 | 23.766 | 17.540 | -10.732 | 1.00 | 21.68 |
| 8973 | O | LEU | B | 305 | 22.993 | 18.452 | -10.511 | 1.00 | 21.68 |
| 8974 | N | ALA | B | 306 | 25.002 | 17.742 | -11.173 | 1.00 | 21.62 |

FIGURE 3 (Cont.)

| A | B | C | D | E | F | G | H | I | J |
|---|---|---|---|---|---|---|---|---|---|
| 8976 | CA | ALA | B | 306 | 25.507 | 19.094 | -11.401 | 1.00 | 21.18 |
| 8978 | CB | ALA | B | 306 | 26.970 | 19.055 | -11.829 | 1.00 | 20.99 |
| 8982 | C | ALA | B | 306 | 24.649 | 19.827 | -12.437 | 1.00 | 21.29 |
| 8983 | O | ALA | B | 306 | 24.260 | 20.978 | -12.221 | 1.00 | 20.84 |
| 8984 | N | ASP | B | 307 | 24.356 | 19.157 | -13.557 | 1.00 | 21.52 |
| 8986 | CA | ASP | B | 307 | 23.462 | 19.700 | -14.575 | 1.00 | 21.89 |
| 8988 | CB | ASP | B | 307 | 23.298 | 18.717 | -15.749 | 1.00 | 22.19 |
| 8991 | CG | ASP | B | 307 | 24.484 | 18.721 | -16.695 | 1.00 | 24.91 |
| 8992 | OD1 | ASP | B | 307 | 25.217 | 19.734 | -16.774 | 1.00 | 27.76 |
| 8993 | OD2 | ASP | B | 307 | 24.754 | 17.744 | -17.418 | 1.00 | 28.49 |
| 8994 | C | ASP | B | 307 | 22.091 | 19.989 | -13.985 | 1.00 | 21.17 |
| 8995 | O | ASP | B | 307 | 21.517 | 21.065 | -14.199 | 1.00 | 21.04 |
| 8996 | N | TYR | B | 308 | 21.566 | 19.037 | -13.226 | 1.00 | 20.68 |
| 8998 | CA | TYR | B | 308 | 20.230 | 19.196 | -12.667 | 1.00 | 21.00 |
| 9000 | CB | TYR | B | 308 | 19.804 | 17.946 | -11.921 | 1.00 | 20.75 |
| 9003 | CG | TYR | B | 308 | 18.419 | 18.039 | -11.344 | 1.00 | 21.19 |
| 9004 | CD1 | TYR | B | 308 | 18.220 | 18.052 | -9.966 | 1.00 | 20.91 |
| 9006 | CE1 | TYR | B | 308 | 16.956 | 18.127 | -9.432 | 1.00 | 21.89 |
| 9008 | CZ | TYR | B | 308 | 15.853 | 18.187 | -10.268 | 1.00 | 24.30 |
| 9009 | OH | TYR | B | 308 | 14.587 | 18.254 | -9.704 | 1.00 | 26.37 |
| 9011 | CE2 | TYR | B | 308 | 16.020 | 18.192 | -11.643 | 1.00 | 23.04 |
| 9013 | CD2 | TYR | B | 308 | 17.299 | 18.112 | -12.174 | 1.00 | 22.71 |
| 9015 | C | TYR | B | 308 | 20.145 | 20.397 | -11.726 | 1.00 | 21.05 |
| 9016 | O | TYR | B | 308 | 19.109 | 21.018 | -11.613 | 1.00 | 20.68 |
| 9017 | N | ILE | B | 309 | 21.239 | 20.713 | -11.043 | 1.00 | 21.13 |
| 9019 | CA | ILE | B | 309 | 21.245 | 21.825 | -10.102 | 1.00 | 21.51 |
| 9021 | CB | ILE | B | 309 | 22.635 | 21.881 | -9.382 | 1.00 | 21.42 |
| 9023 | CG1 | ILE | B | 309 | 22.663 | 20.817 | -8.279 | 1.00 | 21.51 |
| 9026 | CD1 | ILE | B | 309 | 24.007 | 20.664 | -7.593 | 1.00 | 22.06 |
| 9030 | CG2 | ILE | B | 309 | 22.891 | 23.256 | -8.766 | 1.00 | 22.35 |
| 9034 | C | ILE | B | 309 | 20.874 | 23.159 | -10.774 | 1.00 | 21.80 |
| 9035 | O | ILE | B | 309 | 20.237 | 24.017 | -10.162 | 1.00 | 21.41 |
| 9036 | N | ILE | B | 310 | 21.245 | 23.328 | -12.041 | 1.00 | 22.74 |
| 9038 | CA | ILE | B | 310 | 20.886 | 24.542 | -12.765 | 1.00 | 23.55 |
| 9040 | CB | ILE | B | 310 | 22.148 | 25.209 | -13.364 | 1.00 | 23.89 |
| 9042 | CG1 | ILE | B | 310 | 22.714 | 24.400 | -14.540 | 1.00 | 24.25 |
| 9045 | CD1 | ILE | B | 310 | 23.776 | 25.141 | -15.342 | 1.00 | 24.35 |
| 9049 | CG2 | ILE | B | 310 | 23.190 | 25.406 | -12.269 | 1.00 | 24.66 |
| 9053 | C | ILE | B | 310 | 19.799 | 24.344 | -13.828 | 1.00 | 23.85 |
| 9054 | O | ILE | B | 310 | 19.400 | 25.315 | -14.470 | 1.00 | 24.70 |
| 9055 | N | GLN | B | 311 | 19.319 | 23.110 | -14.015 | 1.00 | 23.74 |
| 9057 | CA | GLN | B | 311 | 18.251 | 22.833 | -14.990 | 1.00 | 23.91 |
| 9059 | CB | GLN | B | 311 | 18.584 | 21.602 | -15.821 | 1.00 | 24.17 |
| 9062 | CG | GLN | B | 311 | 19.713 | 21.884 | -16.815 | 1.00 | 26.77 |
| 9065 | CD | GLN | B | 311 | 20.172 | 20.670 | -17.588 | 1.00 | 28.31 |
| 9066 | OE1 | GLN | B | 311 | 21.115 | 20.760 | -18.367 | 1.00 | 33.64 |
| 9067 | NE2 | GLN | B | 311 | 19.520 | 19.540 | -17.382 | 1.00 | 32.21 |
| 9070 | C | GLN | B | 311 | 16.887 | 22.687 | -14.329 | 1.00 | 23.46 |
| 9071 | O | GLN | B | 311 | 15.857 | 22.873 | -14.981 | 1.00 | 23.30 |
| 9072 | N | ARG | B | 312 | 16.889 | 22.369 | -13.033 | 1.00 | 23.14 |
| 9074 | CA | ARG | B | 312 | 15.666 | 22.175 | -12.249 | 1.00 | 22.83 |
| 9076 | CB | ARG | B | 312 | 16.010 | 21.784 | -10.806 | 1.00 | 22.67 |

FIGURE 3 (Cont.)

| A | B | C | D | E | F | G | H | I | J |
|---|---|---|---|---|---|---|---|---|---|
| 9079 | CG | ARG | B | 312 | 16.722 | 22.887 | -10.002 | 1.00 | 21.91 |
| 9082 | CD | ARG | B | 312 | 17.584 | 22.348 | -8.871 | 1.00 | 20.80 |
| 9085 | NE | ARG | B | 312 | 18.319 | 23.405 | -8.180 | 1.00 | 19.32 |
| 9087 | CZ | ARG | B | 312 | 17.807 | 24.145 | -7.212 | 1.00 | 19.88 |
| 9088 | NH1 | ARG | B | 312 | 18.559 | 25.083 | -6.640 | 1.00 | 20.86 |
| 9091 | NH2 | ARG | B | 312 | 16.547 | 23.956 | -6.806 | 1.00 | 18.83 |
| 9094 | C | ARG | B | 312 | 14.826 | 23.434 | -12.199 | 1.00 | 23.29 |
| 9095 | O | ARG | B | 312 | 15.361 | 24.542 | -12.222 | 1.00 | 22.52 |
| 9096 | N | ASN | B | 313 | 13.513 | 23.232 | -12.116 | 1.00 | 24.23 |
| 9098 | CA | ASN | B | 313 | 12.519 | 24.294 | -11.967 | 1.00 | 25.30 |
| 9100 | CB | ASN | B | 313 | 11.404 | 24.132 | -13.023 | 1.00 | 25.73 |
| 9103 | CG | ASN | B | 313 | 10.586 | 22.855 | -12.843 | 1.00 | 27.06 |
| 9104 | OD1 | ASN | B | 313 | 10.893 | 22.015 | -12.003 | 1.00 | 30.28 |
| 9105 | ND2 | ASN | B | 313 | 9.526 | 22.712 | -13.642 | 1.00 | 30.33 |
| 9108 | C | ASN | B | 313 | 11.922 | 24.303 | -10.550 | 1.00 | 26.15 |
| 9109 | O | ASN | B | 313 | 10.931 | 24.991 | -10.282 | 1.00 | 26.07 |
| 9110 | N | LYS | B | 314 | 12.523 | 23.510 | -9.663 | 1.00 | 26.76 |
| 9112 | CA | LYS | B | 314 | 12.057 | 23.349 | -8.295 | 1.00 | 27.55 |
| 9114 | CB | LYS | B | 314 | 10.997 | 22.245 | -8.214 | 1.00 | 28.24 |
| 9117 | CG | LYS | B | 314 | 11.437 | 20.876 | -8.748 | 1.00 | 30.42 |
| 9120 | CD | LYS | B | 314 | 10.388 | 19.777 | -8.483 | 1.00 | 34.02 |
| 9123 | CE | LYS | B | 314 | 9.281 | 19.733 | -9.557 | 1.00 | 35.81 |
| 9126 | NZ | LYS | B | 314 | 9.763 | 19.297 | -10.914 | 1.00 | 37.55 |
| 9130 | C | LYS | B | 314 | 13.212 | 23.017 | -7.370 | 1.00 | 27.53 |
| 9131 | O | LYS | B | 314 | 13.045 | 23.018 | -6.148 | 1.00 | 27.94 |
| 9132 | OXT | LYS | B | 314 | 14.311 | 22.729 | -7.848 | 1.00 | 26.55 |
| 9133 | O9 | ipp | X | 900 | 59.879 | 67.784 | 6.844 | 1.00 | 22.62 |
| 9134 | P7 | ipp | X | 900 | 60.281 | 67.030 | 8.078 | 1.00 | 20.44 |
| 9135 | O8 | ipp | X | 900 | 61.128 | 65.793 | 7.905 | 1.00 | 20.16 |
| 9136 | O10 | ipp | X | 900 | 58.921 | 66.747 | 8.923 | 1.00 | 20.32 |
| 9137 | P11 | ipp | X | 900 | 58.096 | 65.364 | 9.039 | 1.00 | 20.72 |
| 9138 | O13 | ipp | X | 900 | 58.271 | 64.667 | 7.712 | 1.00 | 21.48 |
| 9139 | O12 | ipp | X | 900 | 58.760 | 64.598 | 10.167 | 1.00 | 20.42 |
| 9140 | O14 | ipp | X | 900 | 56.677 | 65.719 | 9.388 | 1.00 | 19.87 |
| 9141 | O6 | ipp | X | 900 | 61.085 | 68.067 | 9.000 | 1.00 | 23.40 |
| 9142 | C5 | ipp | X | 900 | 60.446 | 69.278 | 9.396 | 1.00 | 22.55 |
| 9145 | C4 | ipp | X | 900 | 61.386 | 70.077 | 10.277 | 1.00 | 23.87 |
| 9148 | C2 | ipp | X | 900 | 62.729 | 70.303 | 9.627 | 1.00 | 24.00 |
| 9149 | C3 | ipp | X | 900 | 62.847 | 70.872 | 8.237 | 1.00 | 23.48 |
| 9153 | C1 | ipp | X | 900 | 63.818 | 70.021 | 10.311 | 1.00 | 24.77 |
| 9156 | O12 | ris | X | 901 | 57.820 | 74.304 | 11.572 | 1.00 | 21.28 |
| 9157 | P9 | ris | X | 901 | 58.623 | 73.691 | 10.433 | 1.00 | 21.35 |
| 9158 | O11 | ris | X | 901 | 58.329 | 74.511 | 8.992 | 1.00 | 22.29 |
| 9160 | O10 | ris | X | 901 | 58.206 | 72.094 | 10.263 | 1.00 | 22.10 |
| 9162 | C8 | ris | X | 901 | 60.334 | 73.798 | 10.791 | 1.00 | 20.58 |
| 9163 | O13 | ris | X | 901 | 61.051 | 73.167 | 9.710 | 1.00 | 21.47 |
| 9165 | P14 | ris | X | 901 | 60.832 | 75.467 | 10.955 | 1.00 | 21.49 |
| 9166 | O16 | ris | X | 901 | 60.487 | 76.175 | 9.664 | 1.00 | 20.67 |
| 9167 | O15 | ris | X | 901 | 60.014 | 76.127 | 12.259 | 1.00 | 20.29 |
| 9169 | O17 | ris | X | 901 | 62.473 | 75.654 | 11.235 | 1.00 | 16.79 |
| 9171 | C7 | ris | X | 901 | 60.517 | 73.036 | 12.110 | 1.00 | 20.01 |
| 9174 | C2 | ris | X | 901 | 61.916 | 72.843 | 12.658 | 1.00 | 20.04 |

FIGURE 3 (Cont.)

| A | B | C | D | E | F | G | H | I | J |
|---|---|---|---|---|---|---|---|---|---|
| 9175 | C1 | ris | X | 901 | 62.030 | 72.693 | 14.038 | 1.00 | 22.23 |
| 9177 | C6 | ris | X | 901 | 63.284 | 72.496 | 14.614 | 1.00 | 21.92 |
| 9179 | C5 | ris | X | 901 | 64.396 | 72.454 | 13.790 | 1.00 | 21.90 |
| 9181 | N4 | ris | X | 901 | 64.272 | 72.597 | 12.461 | 1.00 | 20.50 |
| 9182 | C3 | ris | X | 901 | 63.073 | 72.787 | 11.887 | 1.00 | 20.38 |
| 9184 | O9 | ipp | X | 902 | 16.064 | 23.295 | -2.975 | 1.00 | 21.48 |
| 9185 | P7 | ipp | X | 902 | 16.496 | 22.587 | -1.731 | 1.00 | 20.32 |
| 9186 | O8 | ipp | X | 902 | 17.402 | 21.368 | -1.817 | 1.00 | 20.60 |
| 9187 | O10 | ipp | X | 902 | 15.180 | 22.297 | -0.852 | 1.00 | 19.29 |
| 9188 | P11 | ipp | X | 902 | 14.357 | 20.933 | -0.731 | 1.00 | 21.41 |
| 9189 | O13 | ipp | X | 902 | 14.501 | 20.303 | -2.099 | 1.00 | 21.14 |
| 9190 | O12 | ipp | X | 902 | 15.018 | 20.139 | 0.361 | 1.00 | 19.56 |
| 9191 | O14 | ipp | X | 902 | 12.943 | 21.318 | -0.386 | 1.00 | 20.18 |
| 9192 | O6 | ipp | X | 902 | 17.282 | 23.658 | -0.828 | 1.00 | 21.57 |
| 9193 | C5 | ipp | X | 902 | 16.665 | 24.901 | -0.520 | 1.00 | 20.59 |
| 9196 | C4 | ipp | X | 902 | 17.539 | 25.684 | 0.451 | 1.00 | 20.72 |
| 9199 | C2 | ipp | X | 902 | 18.923 | 25.954 | -0.086 | 1.00 | 20.12 |
| 9200 | C3 | ipp | X | 902 | 19.094 | 26.613 | -1.425 | 1.00 | 20.10 |
| 9204 | C1 | ipp | X | 902 | 19.970 | 25.641 | 0.637 | 1.00 | 19.72 |
| 9207 | O12 | ris | X | 903 | 13.949 | 29.944 | 1.653 | 1.00 | 18.96 |
| 9208 | P9 | ris | X | 903 | 14.827 | 29.319 | 0.595 | 1.00 | 18.15 |
| 9209 | O11 | ris | X | 903 | 14.564 | 30.066 | -0.891 | 1.00 | 17.76 |
| 9211 | O10 | ris | X | 903 | 14.479 | 27.699 | 0.371 | 1.00 | 17.12 |
| 9213 | C8 | ris | X | 903 | 16.543 | 29.484 | 1.000 | 1.00 | 16.83 |
| 9214 | O13 | ris | X | 903 | 17.268 | 28.905 | -0.099 | 1.00 | 14.71 |
| 9216 | P14 | ris | X | 903 | 17.105 | 31.143 | 1.147 | 1.00 | 16.07 |
| 9217 | O16 | ris | X | 903 | 16.424 | 31.703 | 2.361 | 1.00 | 18.08 |
| 9218 | O15 | ris | X | 903 | 18.754 | 31.239 | 1.421 | 1.00 | 20.15 |
| 9220 | O17 | ris | X | 903 | 16.681 | 31.883 | -0.303 | 1.00 | 17.24 |
| 9222 | C7 | ris | X | 903 | 16.736 | 28.711 | 2.310 | 1.00 | 15.64 |
| 9225 | C2 | ris | X | 903 | 18.144 | 28.461 | 2.843 | 1.00 | 17.89 |
| 9226 | C1 | ris | X | 903 | 18.231 | 28.146 | 4.193 | 1.00 | 17.51 |
| 9228 | C6 | ris | X | 903 | 19.477 | 27.908 | 4.776 | 1.00 | 17.87 |
| 9230 | C5 | ris | X | 903 | 20.612 | 27.985 | 3.980 | 1.00 | 18.68 |
| 9232 | N4 | ris | X | 903 | 20.535 | 28.281 | 2.665 | 1.00 | 18.45 |
| 9233 | C3 | ris | X | 903 | 19.332 | 28.506 | 2.084 | 1.00 | 18.77 |
| 9235 | MG | MG | X | 904 | 15.574 | 31.310 | -1.873 | 1.00 | 21.07 |
| 9236 | MG | MG | X | 905 | 17.080 | 32.751 | 3.968 | 1.00 | 17.94 |
| 9237 | MG | MG | X | 906 | 14.279 | 31.564 | 2.944 | 1.00 | 18.98 |
| 9238 | MG | MG | X | 907 | 58.027 | 75.928 | 12.811 | 1.00 | 21.97 |
| 9239 | MG | MG | X | 908 | 59.508 | 75.731 | 8.080 | 1.00 | 25.32 |
| 9240 | MG | MG | X | 909 | 60.807 | 77.116 | 13.792 | 1.00 | 19.86 |
| 9241 | OW0 | HOH | X | 1 | 69.581 | 70.101 | 13.536 | 1.00 | 18.91 |
| 9244 | OW0 | HOH | X | 2 | 62.678 | 62.339 | 10.204 | 1.00 | 15.42 |
| 9247 | OW0 | HOH | X | 3 | 25.799 | 25.747 | 3.926 | 1.00 | 15.73 |
| 9250 | OW0 | HOH | X | 4 | 59.333 | 62.010 | 10.213 | 1.00 | 18.17 |
| 9253 | OW0 | HOH | X | 5 | 18.822 | 17.964 | 0.386 | 1.00 | 18.32 |
| 9256 | OW0 | HOH | X | 6 | 13.596 | 24.842 | -2.548 | 1.00 | 13.98 |
| 9259 | OW0 | HOH | X | 7 | 60.443 | 70.120 | 5.487 | 1.00 | 20.05 |
| 9262 | OW0 | HOH | X | 8 | 67.024 | 68.022 | 10.947 | 1.00 | 18.31 |
| 9265 | OW0 | HOH | X | 9 | 75.891 | 66.532 | 13.529 | 1.00 | 16.24 |
| 9268 | OW0 | HOH | X | 10 | 61.389 | 59.407 | 28.540 | 1.00 | 15.76 |

FIGURE 3 (Cont.)

| A | B | C | D | E | F | G | H | I | J |
|---|---|---|---|---|---|---|---|---|---|
| 9271 | OW0 | HOH | X | 11 | 16.713 | 25.479 | -4.403 | 1.00 | 16.69 |
| 9274 | OW0 | HOH | X | 12 | 17.228 | 19.008 | -1.948 | 1.00 | 17.97 |
| 9277 | OW0 | HOH | X | 13 | 60.948 | 63.338 | 7.816 | 1.00 | 17.21 |
| 9280 | OW0 | HOH | X | 14 | 12.537 | 21.690 | 6.873 | 1.00 | 20.29 |
| 9283 | OW0 | HOH | X | 15 | 17.395 | 34.432 | 2.680 | 1.00 | 15.95 |
| 9286 | OW0 | HOH | X | 16 | 22.715 | 24.983 | 3.509 | 1.00 | 21.00 |
| 9289 | OW0 | HOH | X | 17 | 23.103 | 23.679 | 1.175 | 1.00 | 16.66 |
| 9292 | OW0 | HOH | X | 18 | 60.488 | 77.235 | 6.934 | 1.00 | 16.27 |
| 9295 | OW0 | HOH | X | 19 | 57.327 | 69.233 | 7.233 | 1.00 | 17.06 |
| 9298 | OW0 | HOH | X | 20 | 15.505 | 17.649 | 0.655 | 1.00 | 17.89 |
| 9301 | OW0 | HOH | X | 21 | 34.673 | 22.728 | -9.839 | 1.00 | 22.21 |
| 9304 | OW0 | HOH | X | 22 | 12.191 | 23.940 | -0.324 | 1.00 | 14.99 |
| 9307 | OW0 | HOH | X | 23 | 4.461 | 26.280 | 19.031 | 1.00 | 23.20 |
| 9310 | OW0 | HOH | X | 24 | 72.420 | 88.509 | 2.009 | 1.00 | 28.92 |
| 9313 | OW0 | HOH | X | 25 | 73.365 | 71.690 | 24.882 | 1.00 | 15.83 |
| 9316 | OW0 | HOH | X | 26 | 9.311 | 27.134 | 10.014 | 1.00 | 16.86 |
| 9319 | OW0 | HOH | X | 27 | 33.303 | 4.388 | 14.111 | 1.00 | 23.61 |
| 9322 | OW0 | HOH | X | 28 | 9.972 | 29.039 | 2.416 | 1.00 | 19.40 |
| 9325 | OW0 | HOH | X | 29 | 20.315 | 24.167 | 4.178 | 1.00 | 21.86 |
| 9328 | OW0 | HOH | X | 30 | 23.161 | 10.579 | 20.659 | 1.00 | 23.73 |
| 9331 | OW0 | HOH | X | 31 | 62.889 | 76.521 | 13.608 | 1.00 | 18.10 |
| 9334 | OW0 | HOH | X | 32 | 14.368 | 17.510 | 4.944 | 1.00 | 24.43 |
| 9337 | OW0 | HOH | X | 33 | 31.222 | 26.334 | 11.934 | 1.00 | 21.87 |
| 9340 | OW0 | HOH | X | 34 | 17.123 | 34.428 | -0.050 | 1.00 | 18.82 |
| 9343 | OW0 | HOH | X | 35 | 65.244 | 84.346 | -6.827 | 1.00 | 23.12 |
| 9346 | OW0 | HOH | X | 36 | 53.273 | 71.292 | 19.938 | 1.00 | 20.38 |
| 9349 | OW0 | HOH | X | 37 | 75.108 | 70.654 | 21.698 | 1.00 | 19.01 |
| 9352 | OW0 | HOH | X | 38 | 61.370 | 78.383 | 15.450 | 1.00 | 24.45 |
| 9355 | OW0 | HOH | X | 39 | 64.170 | 68.585 | 13.753 | 1.00 | 23.11 |
| 9358 | OW0 | HOH | X | 40 | 15.187 | 3.524 | -3.226 | 1.00 | 21.48 |
| 9361 | OW0 | HOH | X | 41 | 20.358 | 39.276 | 1.884 | 1.00 | 22.25 |
| 9364 | OW0 | HOH | X | 42 | 59.729 | 80.370 | 3.839 | 1.00 | 25.41 |
| 9367 | OW0 | HOH | X | 43 | 9.394 | 25.625 | 7.660 | 1.00 | 19.98 |
| 9370 | OW0 | HOH | X | 44 | 19.279 | 13.591 | 19.445 | 1.00 | 25.74 |
| 9373 | OW0 | HOH | X | 45 | 18.592 | 28.894 | 9.372 | 1.00 | 21.52 |
| 9376 | OW0 | HOH | X | 46 | 16.733 | 32.742 | -2.993 | 1.00 | 17.70 |
| 9379 | OW0 | HOH | X | 47 | 28.337 | 35.553 | 9.793 | 1.00 | 24.55 |
| 9382 | OW0 | HOH | X | 48 | 71.766 | 52.024 | 1.660 | 1.00 | 25.10 |
| 9385 | OW0 | HOH | X | 49 | 5.509 | 18.812 | 21.857 | 1.00 | 25.11 |
| 9388 | OW0 | HOH | X | 50 | 25.249 | 44.467 | -11.635 | 1.00 | 22.90 |
| 9391 | OW0 | HOH | X | 51 | 16.089 | 35.932 | -5.867 | 1.00 | 20.15 |
| 9394 | OW0 | HOH | X | 52 | 50.870 | 75.101 | 10.886 | 1.00 | 22.51 |
| 9397 | OW0 | HOH | X | 53 | 58.111 | 59.051 | 3.773 | 1.00 | 23.52 |
| 9400 | OW0 | HOH | X | 54 | 84.343 | 49.350 | 23.069 | 1.00 | 19.58 |
| 9403 | OW0 | HOH | X | 55 | 56.087 | 75.553 | 13.615 | 1.00 | 15.17 |
| 9406 | OW0 | HOH | X | 56 | 19.494 | 34.654 | -1.382 | 1.00 | 20.86 |
| 9409 | OW0 | HOH | X | 57 | 8.799 | 19.400 | 4.773 | 1.00 | 21.44 |
| 9412 | OW0 | HOH | X | 58 | 39.726 | 12.512 | 12.694 | 1.00 | 37.61 |
| 9415 | OW0 | HOH | X | 59 | 12.786 | 3.396 | 7.777 | 1.00 | 28.21 |
| 9418 | OW0 | HOH | X | 61 | 33.547 | 28.085 | -16.167 | 1.00 | 24.17 |
| 9421 | OW0 | HOH | X | 62 | 60.548 | 68.421 | 32.431 | 1.00 | 22.66 |
| 9424 | OW0 | HOH | X | 63 | 52.652 | 63.594 | 14.580 | 1.00 | 21.16 |

FIGURE 3 (Cont.)

| A | B | C | D | E | F | G | H | I | J |
|---|---|---|---|---|---|---|---|---|---|
| 9427 | OW0 | HOH | X | 64 | 63.267 | 78.956 | 8.228 | 1.00 | 23.96 |
| 9430 | OW0 | HOH | X | 65 | 21.674 | 40.154 | -16.591 | 1.00 | 19.82 |
| 9433 | OW0 | HOH | X | 66 | 62.524 | 73.265 | 19.235 | 1.00 | 24.72 |
| 9436 | OW0 | HOH | X | 67 | 50.175 | 67.476 | 14.681 | 1.00 | 24.07 |
| 9439 | OW0 | HOH | X | 68 | 16.317 | 24.542 | 22.592 | 1.00 | 24.88 |
| 9442 | OW0 | HOH | X | 70 | 13.596 | 32.913 | 1.425 | 1.00 | 18.95 |
| 9445 | OW0 | HOH | X | 71 | 33.743 | 4.683 | -9.292 | 1.00 | 21.88 |
| 9448 | OW0 | HOH | X | 72 | 84.877 | 52.105 | 15.691 | 1.00 | 35.89 |
| 9451 | OW0 | HOH | X | 73 | 28.069 | 7.721 | -7.921 | 1.00 | 22.28 |
| 9454 | OW0 | HOH | X | 74 | 29.256 | 1.053 | 13.166 | 1.00 | 28.61 |
| 9457 | OW0 | HOH | X | 75 | 26.790 | -1.137 | 5.597 | 1.00 | 33.71 |
| 9460 | OW0 | HOH | X | 76 | 33.840 | 27.398 | -6.991 | 1.00 | 26.70 |
| 9463 | OW0 | HOH | X | 77 | 20.039 | 38.545 | -21.843 | 1.00 | 59.27 |
| 9466 | OW0 | HOH | X | 78 | 49.910 | 55.142 | 25.447 | 1.00 | 26.46 |
| 9469 | OW0 | HOH | X | 79 | 9.843 | 14.477 | -1.615 | 1.00 | 27.96 |
| 9472 | OW0 | HOH | X | 80 | 36.808 | 16.350 | 8.648 | 1.00 | 22.19 |
| 9475 | OW0 | HOH | X | 81 | 43.245 | 14.999 | 0.753 | 1.00 | 22.13 |
| 9478 | OW0 | HOH | X | 82 | 57.361 | 79.956 | 11.239 | 1.00 | 25.78 |
| 9481 | OW0 | HOH | X | 83 | 9.775 | 24.342 | -1.506 | 1.00 | 22.49 |
| 9484 | OW0 | HOH | X | 84 | 68.131 | 69.501 | 22.346 | 1.00 | 28.17 |
| 9487 | OW0 | HOH | X | 85 | 64.173 | 83.689 | 11.530 | 1.00 | 19.53 |
| 9490 | OW0 | HOH | X | 86 | 58.920 | 48.042 | 6.438 | 1.00 | 22.32 |
| 9493 | OW0 | HOH | X | 87 | 57.493 | 77.168 | 11.232 | 1.00 | 19.16 |
| 9496 | OW0 | HOH | X | 88 | 77.326 | 71.627 | 2.643 | 1.00 | 27.72 |
| 9499 | OW0 | HOH | X | 89 | 74.547 | 71.580 | 7.451 | 1.00 | 24.66 |
| 9502 | OW0 | HOH | X | 91 | 48.469 | 59.380 | 21.046 | 1.00 | 23.24 |
| 9505 | OW0 | HOH | X | 92 | 59.723 | 83.049 | 3.647 | 1.00 | 26.08 |
| 9508 | OW0 | HOH | X | 93 | 29.853 | 24.288 | -1.800 | 1.00 | 33.40 |
| 9511 | O | HOH | X | 94 | 56.128 | 56.547 | -0.069 | 1.00 | 31.76 |
| 9514 | O | HOH | X | 95 | 60.992 | 57.155 | 5.055 | 1.00 | 25.17 |
| 9517 | O | HOH | X | 96 | 57.412 | 60.876 | 1.767 | 1.00 | 27.49 |
| 9520 | O | HOH | X | 98 | 10.425 | 34.341 | 14.720 | 1.00 | 25.28 |
| 9523 | O | HOH | X | 99 | 58.393 | 61.924 | 14.465 | 1.00 | 21.57 |
| 9526 | O | HOH | X | 100 | 15.514 | 40.203 | -8.447 | 1.00 | 25.83 |
| 9529 | O | HOH | X | 101 | 71.395 | 44.872 | 6.706 | 1.00 | 23.21 |
| 9532 | O | HOH | X | 102 | 59.088 | 84.453 | 1.416 | 1.00 | 21.13 |
| 9535 | O | HOH | X | 103 | 10.805 | 35.476 | 2.484 | 1.00 | 30.21 |
| 9538 | O | HOH | X | 104 | 78.675 | 67.094 | -0.168 | 1.00 | 30.94 |
| 9541 | O | HOH | X | 105 | 53.216 | 69.834 | 17.573 | 1.00 | 21.88 |
| 9544 | O | HOH | X | 106 | 11.540 | 21.193 | -2.775 | 1.00 | 23.63 |
| 9547 | O | HOH | X | 107 | 56.434 | 66.036 | 16.603 | 1.00 | 21.18 |
| 9550 | O | HOH | X | 108 | 53.589 | 69.002 | 8.469 | 1.00 | 26.03 |
| 9553 | O | HOH | X | 109 | 22.171 | 2.588 | 12.364 | 1.00 | 25.07 |
| 9556 | O | HOH | X | 110 | 77.332 | 49.094 | 0.357 | 1.00 | 25.35 |
| 9559 | O | HOH | X | 111 | 33.771 | 36.319 | -2.063 | 1.00 | 30.82 |
| 9562 | O | HOH | X | 112 | 12.214 | 37.251 | -5.519 | 1.00 | 20.62 |
| 9565 | O | HOH | X | 113 | 68.012 | 47.978 | 18.112 | 1.00 | 22.53 |
| 9568 | O | HOH | X | 114 | 52.583 | 66.344 | 14.741 | 1.00 | 24.60 |
| 9571 | O | HOH | X | 115 | 54.317 | 78.524 | 24.510 | 1.00 | 28.76 |
| 9574 | O | HOH | X | 116 | 17.315 | 3.665 | 4.180 | 1.00 | 31.96 |
| 9577 | O | HOH | X | 117 | 41.900 | 14.903 | -5.570 | 1.00 | 23.73 |
| 9580 | O | HOH | X | 118 | 25.232 | 6.606 | -7.167 | 1.00 | 24.37 |

FIGURE 3 (Cont.)

| A | B | C | D | E | F | G | H | I | J |
|---|---|---|---|---|---|---|---|---|---|
| 9583 | O | HOH | X | 119 | 69.198 | 51.022 | 2.442 | 1.00 | 32.30 |
| 9586 | O | HOH | X | 120 | 54.454 | 75.970 | 7.898 | 1.00 | 29.61 |
| 9589 | O | HOH | X | 121 | 72.835 | 54.092 | -0.028 | 1.00 | 28.37 |
| 9592 | O | HOH | X | 122 | 13.624 | 16.407 | -7.904 | 1.00 | 26.27 |
| 9595 | O | HOH | X | 123 | 52.606 | 51.548 | 23.966 | 1.00 | 31.75 |
| 9598 | O | HOH | X | 124 | 64.545 | 60.261 | -5.452 | 1.00 | 26.24 |
| 9601 | O | HOH | X | 125 | 48.485 | 73.411 | 29.403 | 1.00 | 35.53 |
| 9604 | O | HOH | X | 126 | 73.394 | 45.286 | 22.697 | 1.00 | 31.73 |
| 9607 | O | HOH | X | 127 | 1.619 | 16.387 | 23.748 | 1.00 | 35.87 |
| 9610 | O | HOH | X | 128 | 51.331 | 52.037 | 31.882 | 1.00 | 32.80 |
| 9613 | O | HOH | X | 130 | 59.702 | 84.785 | 5.880 | 1.00 | 28.09 |
| 9616 | O | HOH | X | 131 | 35.875 | 32.733 | -2.230 | 1.00 | 41.90 |
| 9619 | O | HOH | X | 132 | 56.078 | 68.294 | 9.410 | 1.00 | 23.25 |
| 9622 | O | HOH | X | 133 | 68.940 | 88.925 | -1.936 | 1.00 | 24.65 |
| 9625 | O | HOH | X | 134 | 66.234 | 47.041 | 21.983 | 1.00 | 27.75 |
| 9628 | O | HOH | X | 135 | 61.333 | 46.476 | 6.833 | 1.00 | 25.98 |
| 9631 | O | HOH | X | 136 | 67.556 | 54.792 | 30.084 | 1.00 | 27.45 |
| 9634 | O | HOH | X | 137 | 40.092 | 4.846 | 14.202 | 1.00 | 33.56 |
| 9637 | O | HOH | X | 138 | 6.434 | 23.324 | 4.635 | 1.00 | 23.23 |
| 9640 | O | HOH | X | 139 | 53.326 | 52.199 | 10.569 | 1.00 | 27.46 |
| 9643 | O | HOH | X | 140 | 16.797 | 40.699 | -15.388 | 1.00 | 31.25 |
| 9646 | O | HOH | X | 141 | 55.505 | 68.569 | 5.472 | 1.00 | 31.05 |
| 9649 | O | HOH | X | 142 | 19.829 | 28.141 | -14.550 | 1.00 | 32.03 |
| 9652 | O | HOH | X | 143 | 72.192 | 80.036 | 19.386 | 1.00 | 26.69 |
| 9655 | O | HOH | X | 144 | 49.567 | 62.818 | 10.675 | 1.00 | 36.36 |
| 9658 | O | HOH | X | 145 | 77.624 | 80.795 | 7.572 | 1.00 | 30.84 |
| 9661 | O | HOH | X | 146 | 70.251 | 84.697 | 14.333 | 1.00 | 29.10 |
| 9664 | O | HOH | X | 147 | 22.147 | 28.439 | -15.860 | 1.00 | 25.06 |
| 9667 | O | HOH | X | 149 | 13.634 | 35.572 | 1.265 | 1.00 | 25.62 |
| 9670 | O | HOH | X | 150 | 82.244 | 46.629 | 23.769 | 1.00 | 35.68 |
| 9673 | O | HOH | X | 151 | 63.846 | 88.990 | 3.561 | 1.00 | 28.36 |
| 9676 | O | HOH | X | 152 | 64.405 | 73.293 | -9.004 | 1.00 | 59.74 |
| 9679 | O | HOH | X | 153 | 19.585 | 44.233 | -0.968 | 1.00 | 31.22 |
| 9682 | O | HOH | X | 154 | 17.128 | 12.637 | -4.589 | 1.00 | 25.38 |
| 9685 | O | HOH | X | 155 | 5.113 | 33.908 | 7.713 | 1.00 | 38.08 |
| 9688 | O | HOH | X | 156 | 30.306 | 34.937 | -7.899 | 1.00 | 34.44 |
| 9691 | O | HOH | X | 157 | 3.129 | 22.986 | -4.541 | 1.00 | 39.21 |
| 9694 | O | HOH | X | 158 | 66.626 | 69.399 | 13.372 | 1.00 | 23.00 |
| 9697 | O | HOH | X | 159 | 63.446 | 57.641 | 29.205 | 1.00 | 27.23 |
| 9700 | O | HOH | X | 160 | 54.243 | 50.317 | 14.175 | 1.00 | 34.68 |
| 9703 | O | HOH | X | 161 | 66.368 | 78.182 | -9.856 | 1.00 | 26.10 |
| 9706 | O | HOH | X | 162 | 53.159 | 57.048 | 10.179 | 1.00 | 27.95 |
| 9709 | O | HOH | X | 163 | 44.219 | 16.007 | -6.192 | 1.00 | 25.11 |
| 9712 | O | HOH | X | 164 | 80.589 | 61.008 | 18.291 | 1.00 | 25.88 |
| 9715 | O | HOH | X | 165 | 28.989 | 38.706 | 2.563 | 1.00 | 25.75 |
| 9718 | O | HOH | X | 166 | 11.238 | 30.773 | 0.615 | 1.00 | 24.14 |
| 9721 | O | HOH | X | 167 | 53.608 | 73.127 | 12.234 | 1.00 | 26.24 |
| 9724 | O | HOH | X | 169 | 63.586 | 45.033 | 14.349 | 1.00 | 31.13 |
| 9727 | O | HOH | X | 170 | 77.596 | 48.785 | 23.097 | 1.00 | 26.73 |
| 9730 | O | HOH | X | 171 | 84.848 | 48.026 | 14.304 | 1.00 | 29.46 |
| 9733 | O | HOH | X | 172 | 4.265 | 15.315 | 11.290 | 1.00 | 29.33 |
| 9736 | O | HOH | X | 173 | 3.381 | 31.069 | 16.737 | 1.00 | 33.72 |

FIGURE 3 (Cont.)

| A | B | C | D | E | F | G | H | I | J |
|---|---|---|---|---|---|---|---|---|---|
| 9739 | O | HOH | X | 174 | 55.238 | 65.487 | 7.142 | 1.00 | 31.03 |
| 9742 | O | HOH | X | 175 | 9.341 | 26.913 | -11.288 | 1.00 | 29.49 |
| 9745 | O | HOH | X | 176 | 53.199 | 53.483 | 20.584 | 1.00 | 32.49 |
| 9748 | O | HOH | X | 177 | 14.338 | 14.643 | -5.988 | 1.00 | 23.99 |
| 9751 | O | HOH | X | 178 | 38.329 | 22.112 | -11.565 | 1.00 | 45.14 |
| 9754 | O | HOH | X | 179 | 39.337 | 18.256 | 2.081 | 1.00 | 27.57 |
| 9757 | O | HOH | X | 180 | 56.191 | 81.845 | 4.467 | 1.00 | 30.98 |
| 9760 | O | HOH | X | 181 | 20.859 | 16.036 | -15.248 | 1.00 | 24.19 |
| 9763 | O | HOH | X | 182 | 52.592 | 52.636 | 34.412 | 1.00 | 33.36 |
| 9766 | O | HOH | X | 183 | 8.751 | 22.025 | 4.991 | 1.00 | 21.08 |
| 9769 | O | HOH | X | 184 | 63.183 | 88.654 | 8.668 | 1.00 | 32.88 |
| 9772 | O | HOH | X | 185 | 23.296 | 39.123 | 11.088 | 1.00 | 28.53 |
| 9775 | O | HOH | X | 186 | 21.029 | 42.374 | -4.623 | 1.00 | 40.24 |
| 9778 | O | HOH | X | 187 | 61.193 | 73.706 | -5.808 | 1.00 | 35.26 |
| 9781 | O | HOH | X | 188 | 55.468 | 47.798 | 19.949 | 1.00 | 28.75 |
| 9784 | O | HOH | X | 189 | 35.734 | 28.370 | -1.891 | 1.00 | 42.91 |
| 9787 | O | HOH | X | 190 | 28.941 | 9.752 | -9.745 | 1.00 | 28.83 |
| 9790 | O | HOH | X | 191 | 60.836 | 85.243 | -5.478 | 1.00 | 33.63 |
| 9793 | O | HOH | X | 193 | 85.606 | 61.921 | 11.265 | 1.00 | 33.58 |
| 9796 | O | HOH | X | 194 | 78.387 | 74.119 | -1.722 | 1.00 | 50.78 |
| 9799 | O | HOH | X | 195 | 7.183 | 30.679 | 0.916 | 1.00 | 33.15 |
| 9802 | O | HOH | X | 196 | 32.652 | 28.076 | -18.831 | 1.00 | 28.06 |
| 9805 | O | HOH | X | 197 | 53.948 | 51.530 | 21.729 | 1.00 | 30.16 |
| 9808 | O | HOH | X | 198 | 3.740 | 12.442 | 13.203 | 1.00 | 38.10 |
| 9811 | O | HOH | X | 199 | 81.671 | 47.299 | 9.794 | 1.00 | 39.29 |
| 9814 | O | HOH | X | 200 | 76.149 | 46.441 | 21.909 | 1.00 | 32.74 |
| 9817 | O | HOH | X | 201 | 61.151 | 42.663 | 13.748 | 1.00 | 62.81 |
| 9820 | O | HOH | X | 202 | 54.688 | 79.719 | 12.391 | 1.00 | 30.29 |
| 9823 | O | HOH | X | 203 | 51.275 | 79.190 | 10.957 | 1.00 | 40.83 |
| 9826 | O | HOH | X | 204 | 14.506 | 30.823 | -3.503 | 1.00 | 21.42 |
| 9829 | O | HOH | X | 205 | 14.195 | 32.814 | -1.332 | 1.00 | 19.33 |
| 9832 | O | HOH | X | 206 | 12.434 | 31.396 | 3.683 | 1.00 | 16.08 |
| 9835 | O | HOH | X | 207 | 18.969 | 32.213 | 3.765 | 1.00 | 20.53 |
| 9838 | O | HOH | X | 208 | 17.536 | 34.005 | 5.600 | 1.00 | 16.75 |
| 9841 | O | HOH | X | 209 | 33.461 | 39.878 | 0.879 | 1.00 | 48.09 |
| 9844 | O | HOH | X | 210 | 78.263 | 66.876 | 16.527 | 1.00 | 37.29 |
| 9847 | O | HOH | X | 211 | 80.975 | 67.293 | 15.894 | 1.00 | 39.50 |
| 9850 | O | HOH | X | 212 | 82.405 | 67.613 | 13.856 | 1.00 | 46.74 |
| 9853 | O | HOH | X | 213 | 50.671 | 57.527 | 11.069 | 1.00 | 40.42 |
| 9856 | O | HOH | X | 214 | 51.601 | 55.517 | 13.513 | 1.00 | 33.26 |
| 9859 | O | HOH | X | 215 | 62.729 | 54.517 | 30.771 | 1.00 | 40.62 |
| 9862 | O | HOH | X | 216 | 60.331 | 52.329 | 31.300 | 1.00 | 52.01 |
| 9865 | O | HOH | X | 217 | 31.078 | 32.997 | -9.951 | 1.00 | 29.54 |
| 9868 | O | HOH | X | 218 | 33.614 | 33.829 | -1.558 | 1.00 | 23.66 |
| 9871 | O | HOH | X | 219 | 3.882 | 31.855 | 12.746 | 1.00 | 38.99 |
| 9874 | O | HOH | X | 220 | 15.840 | 40.330 | -3.855 | 1.00 | 26.18 |
| 9877 | O | HOH | X | 221 | 15.995 | 38.459 | -6.211 | 1.00 | 24.53 |
| 9880 | O | HOH | X | 222 | 63.555 | 73.039 | -4.552 | 1.00 | 36.76 |
| 9883 | O | HOH | X | 223 | 65.686 | 72.948 | -6.046 | 1.00 | 30.87 |
| 9886 | O | HOH | X | 224 | 61.071 | 89.367 | 2.768 | 1.00 | 33.44 |
| 9889 | O | HOH | X | 225 | 85.368 | 50.306 | 25.290 | 1.00 | 39.68 |
| 9892 | O | HOH | X | 226 | 10.770 | 31.661 | -1.862 | 1.00 | 30.59 |

FIGURE 3 (Cont.)

| A | B | C | D | E | F | G | H | I | J |
|---|---|---|---|---|---|---|---|---|---|
| 9895 | O | HOH | X | 227 | 67.074 | 86.090 | 20.611 | 1.00 | 47.90 |
| 9898 | O | HOH | X | 228 | 72.225 | 82.393 | 20.309 | 1.00 | 28.15 |
| 9901 | O | HOH | X | 229 | 23.258 | 30.948 | -19.639 | 1.00 | 37.49 |
| 9904 | O | HOH | X | 230 | 18.514 | 43.214 | -15.138 | 1.00 | 25.15 |
| 9907 | O | HOH | X | 231 | 18.316 | 39.793 | -17.580 | 1.00 | 30.27 |
| 9910 | O | HOH | X | 232 | 18.565 | 40.376 | -20.157 | 1.00 | 27.88 |
| 9913 | O | HOH | X | 233 | 10.124 | 22.994 | 6.965 | 1.00 | 22.65 |
| 9916 | O | HOH | X | 234 | 40.682 | 5.559 | 16.461 | 1.00 | 35.43 |
| 9919 | O | HOH | X | 235 | 60.087 | 44.060 | 7.813 | 1.00 | 29.04 |
| 9922 | O | HOH | X | 236 | 65.753 | 46.800 | 19.256 | 1.00 | 33.55 |
| 9925 | O | HOH | X | 237 | 47.350 | 74.880 | 26.880 | 1.00 | 40.56 |
| 9928 | O | HOH | X | 238 | 48.590 | 70.295 | 28.815 | 1.00 | 22.47 |
| 9931 | O | HOH | X | 239 | 62.111 | 62.571 | -5.691 | 1.00 | 41.29 |
| 9934 | O | HOH | X | 240 | 58.266 | 75.096 | 6.385 | 1.00 | 20.97 |
| 9937 | O | HOH | X | 241 | 57.930 | 77.196 | 8.555 | 1.00 | 21.06 |
| 9940 | O | HOH | X | 242 | 60.766 | 78.814 | 9.905 | 1.00 | 24.54 |
| 9943 | O | HOH | X | 243 | 61.087 | 78.751 | 12.516 | 1.00 | 17.96 |
| 9946 | O | HOH | X | 244 | 66.063 | 45.873 | 5.892 | 1.00 | 30.86 |
| 9949 | O | HOH | X | 245 | 68.834 | 44.595 | 6.140 | 1.00 | 27.12 |
| 9952 | O | HOH | X | 246 | 40.240 | 21.104 | -0.696 | 1.00 | 29.77 |
| 9955 | O | HOH | X | 247 | 54.038 | 67.321 | 16.979 | 1.00 | 23.18 |
| 9958 | O | HOH | X | 248 | 6.161 | 36.828 | -2.610 | 1.00 | 45.75 |
| 9961 | O | HOH | X | 249 | 32.414 | 42.931 | -5.770 | 1.00 | 26.20 |
| 9964 | O | HOH | X | 250 | 8.263 | 18.675 | -2.300 | 1.00 | 37.46 |
| 9967 | O | HOH | X | 251 | 57.682 | 88.576 | 6.524 | 1.00 | 41.67 |
| 9970 | O | HOH | X | 252 | 9.403 | 38.851 | 14.485 | 1.00 | 38.72 |
| 9973 | O | HOH | X | 253 | 7.150 | 40.262 | 16.390 | 1.00 | 45.72 |
| 9976 | O | HOH | X | 254 | 53.657 | 64.735 | -1.870 | 1.00 | 50.87 |
| 9979 | O | HOH | X | 255 | 54.909 | 49.982 | 11.303 | 1.00 | 29.97 |
| 9982 | O | HOH | X | 256 | 54.469 | 48.142 | 15.766 | 1.00 | 35.94 |
| 9985 | O | HOH | X | 257 | 64.819 | 51.877 | 25.591 | 1.00 | 48.64 |
| 9988 | O | HOH | X | 258 | 48.466 | 60.211 | 34.761 | 1.00 | 34.69 |
| 9991 | O | HOH | X | 259 | 50.594 | 60.418 | 33.231 | 1.00 | 29.29 |
| 9994 | O | HOH | X | 260 | 44.303 | 61.380 | 23.666 | 1.00 | 50.60 |
| 9997 | O | HOH | X | 261 | 42.915 | 58.238 | 26.279 | 1.00 | 44.44 |
| 10000 | O | HOH | X | 262 | 52.554 | 63.196 | 6.954 | 1.00 | 45.59 |
| 10003 | O | HOH | X | 263 | 75.789 | 43.073 | 11.027 | 1.00 | 45.52 |
| 10006 | O | HOH | X | 264 | 63.099 | 46.831 | 5.108 | 1.00 | 38.28 |
| 10009 | O | HOH | X | 265 | 44.196 | 64.994 | 15.827 | 1.00 | 37.65 |
| 10012 | O | HOH | X | 266 | 43.951 | 62.363 | 16.102 | 1.00 | 46.48 |
| 10015 | O | HOH | X | 267 | 39.222 | 63.891 | 21.996 | 1.00 | 52.12 |
| 10018 | O | HOH | X | 268 | 42.850 | 63.664 | 23.396 | 1.00 | 50.80 |
| 10021 | O | HOH | X | 269 | 48.526 | 74.293 | 31.675 | 1.00 | 36.34 |
| 10024 | O | HOH | X | 270 | 67.670 | 48.672 | 31.258 | 1.00 | 51.39 |
| 10027 | O | HOH | X | 271 | 81.199 | 48.984 | 16.751 | 1.00 | 28.66 |
| 10030 | O | HOH | X | 272 | 79.911 | 47.943 | 14.775 | 1.00 | 31.46 |
| 10033 | O | HOH | X | 273 | 85.017 | 50.279 | 19.126 | 1.00 | 30.80 |
| 10036 | O | HOH | X | 274 | 64.657 | 81.303 | 10.384 | 1.00 | 30.96 |
| 10039 | O | HOH | X | 275 | 62.329 | 87.607 | 6.341 | 1.00 | 31.55 |
| 10042 | O | HOH | X | 276 | 64.640 | 86.808 | 5.080 | 1.00 | 34.11 |
| 10045 | O | HOH | X | 277 | 60.179 | 93.225 | 8.295 | 1.00 | 40.09 |
| 10048 | O | HOH | X | 278 | 73.593 | 79.168 | 1.381 | 1.00 | 35.41 |

FIGURE 3 (Cont.)

| A | B | C | D | E | F | G | H | I | J |
|---|---|---|---|---|---|---|---|---|---|
| 10051 | O | HOH | X | 279 | 74.858 | 77.325 | -0.481 | 1.00 | 41.75 |
| 10054 | O | HOH | X | 280 | 77.068 | 76.446 | 0.836 | 1.00 | 38.59 |
| 10057 | O | HOH | X | 281 | 74.159 | 76.085 | -2.785 | 1.00 | 31.06 |
| 10060 | O | HOH | X | 282 | 79.283 | 78.702 | 16.390 | 1.00 | 38.20 |
| 10063 | O | HOH | X | 283 | 77.257 | 76.993 | 10.420 | 1.00 | 32.78 |
| 10066 | O | HOH | X | 284 | 77.239 | 78.246 | 8.067 | 1.00 | 37.50 |
| 10069 | O | HOH | X | 285 | 73.948 | 68.872 | 7.682 | 1.00 | 33.72 |
| 10072 | O | HOH | X | 286 | 77.608 | 62.256 | 8.543 | 1.00 | 45.53 |
| 10075 | O | HOH | X | 287 | 84.634 | 47.863 | 10.649 | 1.00 | 33.57 |
| 10078 | O | HOH | X | 288 | 89.171 | 59.221 | 10.145 | 1.00 | 51.60 |
| 10081 | O | HOH | X | 289 | 88.540 | 58.568 | 7.606 | 1.00 | 57.77 |
| 10084 | O | HOH | X | 290 | 44.965 | 73.834 | 1.582 | 1.00 | 48.13 |
| 10087 | O | HOH | X | 291 | 49.561 | 81.495 | 7.222 | 1.00 | 45.30 |
| 10090 | O | HOH | X | 292 | 70.469 | 68.660 | -8.004 | 1.00 | 41.08 |
| 10093 | O | HOH | X | 293 | 81.881 | 67.174 | -2.963 | 1.00 | 39.74 |
| 10096 | O | HOH | X | 294 | 77.288 | 57.817 | -5.855 | 1.00 | 32.90 |
| 10099 | O | HOH | X | 295 | 76.204 | 60.286 | -6.405 | 1.00 | 33.62 |
| 10102 | O | HOH | X | 296 | 72.178 | 51.978 | -1.088 | 1.00 | 40.76 |
| 10105 | O | HOH | X | 297 | 69.367 | 55.952 | -6.441 | 1.00 | 41.52 |
| 10108 | O | HOH | X | 298 | 66.145 | 60.092 | -7.585 | 1.00 | 37.64 |
| 10111 | O | HOH | X | 299 | 58.836 | 67.727 | -7.779 | 1.00 | 45.55 |
| 10114 | O | HOH | X | 300 | 13.363 | 3.105 | -5.157 | 1.00 | 38.92 |
| 10117 | O | HOH | X | 301 | 13.794 | 2.664 | -0.805 | 1.00 | 33.87 |
| 10120 | O | HOH | X | 302 | 15.442 | 1.396 | 0.758 | 1.00 | 53.73 |
| 10123 | O | HOH | X | 303 | 17.525 | -0.047 | 0.589 | 1.00 | 35.96 |
| 10126 | O | HOH | X | 304 | 13.277 | 5.297 | -9.056 | 1.00 | 41.07 |
| 10129 | O | HOH | X | 305 | 10.451 | 8.808 | -4.245 | 1.00 | 33.55 |
| 10132 | O | HOH | X | 306 | 11.127 | 5.641 | 1.860 | 1.00 | 28.72 |
| 10135 | O | HOH | X | 307 | 17.465 | 2.139 | -2.799 | 1.00 | 30.54 |
| 10138 | O | HOH | X | 308 | 19.535 | 2.393 | -4.513 | 1.00 | 33.31 |
| 10141 | O | HOH | X | 309 | 9.312 | 12.628 | 0.396 | 1.00 | 37.60 |
| 10144 | O | HOH | X | 310 | 7.665 | 11.510 | 3.549 | 1.00 | 34.31 |
| 10147 | O | HOH | X | 311 | 6.051 | 11.080 | 6.071 | 1.00 | 39.84 |
| 10150 | O | HOH | X | 312 | 10.116 | 7.158 | 11.883 | 1.00 | 33.40 |
| 10153 | O | HOH | X | 313 | 9.385 | 9.324 | 10.796 | 1.00 | 36.05 |
| 10156 | O | HOH | X | 314 | 14.622 | 2.412 | 13.739 | 1.00 | 31.45 |
| 10159 | O | HOH | X | 315 | 13.037 | 2.160 | 16.038 | 1.00 | 41.01 |
| 10162 | O | HOH | X | 316 | 5.930 | 10.969 | 15.786 | 1.00 | 34.44 |
| 10165 | O | HOH | X | 317 | 4.581 | 9.801 | 22.907 | 1.00 | 46.13 |
| 10168 | O | HOH | X | 318 | 1.584 | 18.885 | -1.559 | 1.00 | 52.72 |
| 10171 | O | HOH | X | 319 | 37.184 | 2.115 | -2.954 | 1.00 | 43.48 |
| 10174 | O | HOH | X | 320 | 36.733 | 3.493 | -6.561 | 1.00 | 45.09 |
| 10177 | O | HOH | X | 321 | 20.082 | 0.677 | 4.712 | 1.00 | 26.47 |
| 10180 | O | HOH | X | 322 | 20.457 | 8.134 | 16.042 | 1.00 | 46.78 |
| 10183 | O | HOH | X | 323 | 19.090 | 10.262 | 18.888 | 1.00 | 37.59 |
| 10186 | O | HOH | X | 324 | 24.214 | 25.499 | 12.581 | 1.00 | 29.01 |
| 10189 | O | HOH | X | 325 | 14.989 | 39.048 | 7.973 | 1.00 | 31.76 |
| 10192 | O | HOH | X | 326 | 11.756 | 39.045 | 9.415 | 1.00 | 50.88 |
| 10195 | O | HOH | X | 327 | 7.810 | 36.884 | 3.543 | 1.00 | 43.84 |
| 10198 | O | HOH | X | 328 | 3.242 | 25.497 | -3.703 | 1.00 | 29.56 |
| 10201 | O | HOH | X | 329 | 1.219 | 33.875 | 16.266 | 1.00 | 46.56 |
| 10204 | O | HOH | X | 330 | 1.544 | 29.687 | 13.872 | 1.00 | 40.23 |

FIGURE 3 (Cont.)

| A | B | C | D | E | F | G | H | I | J |
|---|---|---|---|---|---|---|---|---|---|
| 10207 | O | HOH | X | 331 | -0.474 | 27.413 | 15.144 | 1.00 | 54.89 |
| 10210 | O | HOH | X | 332 | 4.337 | 28.953 | 19.199 | 1.00 | 36.94 |
| 10213 | O | HOH | X | 333 | -1.539 | 27.356 | 11.980 | 1.00 | 45.30 |
| 10216 | O | HOH | X | 334 | -2.107 | 24.658 | 12.397 | 1.00 | 38.86 |
| 10219 | O | HOH | X | 335 | 2.398 | 22.547 | 20.759 | 1.00 | 43.49 |
| 10222 | O | HOH | X | 336 | 4.084 | 16.237 | 25.067 | 1.00 | 35.34 |
| 10225 | O | HOH | X | 337 | 3.978 | 13.588 | 25.815 | 1.00 | 45.80 |
| 10228 | O | HOH | X | 338 | 3.094 | 17.271 | 27.390 | 1.00 | 40.72 |
| 10231 | O | HOH | X | 339 | 4.241 | 24.783 | 21.717 | 1.00 | 35.53 |
| 10234 | O | HOH | X | 340 | 37.329 | 4.276 | 7.908 | 1.00 | 35.31 |
| 10237 | O | HOH | X | 341 | 39.684 | 14.815 | 17.121 | 1.00 | 27.65 |
| 10240 | O | HOH | X | 342 | 36.317 | 20.283 | 10.218 | 1.00 | 40.32 |
| 10243 | O | HOH | X | 343 | 32.070 | 22.082 | 3.932 | 1.00 | 19.26 |
| 10246 | O | HOH | X | 344 | 32.703 | 24.069 | 5.500 | 1.00 | 30.65 |
| 10249 | O | HOH | X | 345 | 21.195 | 37.054 | 0.700 | 1.00 | 23.85 |
| 10252 | O | HOH | X | 346 | 26.360 | 48.147 | -1.801 | 1.00 | 37.57 |
| 10255 | O | HOH | X | 347 | 23.190 | 43.465 | -4.592 | 1.00 | 34.90 |
| 10258 | O | HOH | X | 348 | 18.440 | 43.181 | -3.522 | 1.00 | 30.15 |
| 10261 | O | HOH | X | 349 | 15.607 | 42.903 | -4.850 | 1.00 | 31.05 |
| 10264 | O | HOH | X | 350 | 13.692 | 44.194 | -3.391 | 1.00 | 41.66 |
| 10267 | O | HOH | X | 351 | 31.128 | 44.045 | -7.531 | 1.00 | 41.41 |
| 10270 | O | HOH | X | 352 | 31.689 | 47.433 | -4.627 | 1.00 | 30.20 |
| 10273 | O | HOH | X | 353 | 32.993 | 49.163 | -3.190 | 1.00 | 38.18 |
| 10276 | O | HOH | X | 354 | 27.426 | 44.095 | -10.304 | 1.00 | 33.92 |
| 10279 | O | HOH | X | 355 | 43.796 | 13.725 | 3.108 | 1.00 | 23.99 |
| 10282 | O | HOH | X | 356 | 42.070 | 17.335 | 1.525 | 1.00 | 30.43 |
| 10285 | O | HOH | X | 357 | 43.287 | 19.448 | 0.553 | 1.00 | 33.75 |
| 10288 | O | HOH | X | 358 | 39.828 | 16.002 | 5.397 | 1.00 | 35.08 |
| 10291 | O | HOH | X | 359 | 38.165 | 17.818 | 4.577 | 1.00 | 37.82 |
| 10294 | O | HOH | X | 360 | 33.950 | 17.800 | -1.148 | 1.00 | 45.50 |
| 10297 | O | HOH | X | 361 | 11.762 | 24.758 | -4.528 | 1.00 | 31.90 |
| 10300 | O | HOH | X | 362 | 3.975 | 32.061 | -8.760 | 1.00 | 36.38 |
| 10303 | O | HOH | X | 363 | 15.528 | 42.830 | -7.772 | 1.00 | 35.25 |
| 10306 | O | HOH | X | 364 | 14.500 | 29.223 | -15.075 | 1.00 | 41.38 |
| 10309 | O | HOH | X | 365 | 32.850 | 21.982 | -18.707 | 1.00 | 37.44 |
| 10312 | O | HOH | X | 366 | 40.592 | 8.573 | -5.209 | 1.00 | 37.21 |
| 10315 | O | HOH | X | 367 | 25.811 | 11.663 | -16.176 | 1.00 | 30.06 |
| 10318 | O | HOH | X | 368 | 26.945 | 13.028 | -17.719 | 1.00 | 49.20 |
| 10321 | O | HOH | X | 369 | 24.479 | 22.182 | -17.748 | 1.00 | 49.87 |
| 10324 | O | HOH | X | 370 | 21.021 | 17.997 | -19.491 | 1.00 | 46.80 |
| 10327 | O | HOH | X | 371 | 23.217 | 19.367 | -20.360 | 1.00 | 51.32 |
| 10330 | O | HOH | X | 372 | 22.674 | 25.397 | -19.288 | 1.00 | 43.41 |
| 10333 | O | HOH | X | 373 | 12.811 | 20.249 | -12.633 | 1.00 | 35.30 |
| 10336 | O | HOH | X | 374 | 55.709 | 88.998 | 19.001 | 1.00 | 47.10 |
| 10339 | O | HOH | X | 375 | 54.100 | 84.683 | 17.666 | 1.00 | 43.29 |
| 10342 | O | HOH | X | 376 | 48.970 | 77.908 | 17.748 | 1.00 | 39.82 |
| 10345 | O | HOH | X | 377 | 41.899 | 65.707 | 18.118 | 1.00 | 46.67 |
| 10348 | O | HOH | X | 378 | 48.368 | 58.949 | 18.441 | 1.00 | 30.58 |
| 10351 | O | HOH | X | 379 | 48.070 | 56.991 | 22.120 | 1.00 | 35.54 |
| 10354 | O | HOH | X | 380 | 47.998 | 54.800 | 20.225 | 1.00 | 42.38 |
| 10357 | O | HOH | X | 381 | 50.349 | 57.710 | 17.797 | 1.00 | 39.16 |
| 10360 | O | HOH | X | 382 | 32.392 | 26.723 | 0.642 | 1.00 | 35.35 |

FIGURE 3 (Cont.)

| A | B | C | D | E | F | G | H | I | J |
|---|---|---|---|---|---|---|---|---|---|
| 10363 | O | HOH | X | 383 | 30.720 | 27.097 | -2.250 | 1.00 | 27.18 |
| 10366 | O | HOH | X | 384 | 37.015 | 26.821 | 2.778 | 1.00 | 49.37 |
| 10369 | O | HOH | X | 385 | 38.443 | 23.443 | 3.534 | 1.00 | 33.87 |
| 10372 | O | HOH | X | 386 | 38.669 | 19.697 | 6.394 | 1.00 | 36.31 |
| 10375 | O | HOH | X | 387 | 30.186 | -3.337 | 5.179 | 1.00 | 43.04 |
| 10378 | O | HOH | X | 388 | 36.379 | 2.179 | 1.556 | 1.00 | 42.15 |
| 10381 | O | HOH | X | 389 | 41.111 | 3.324 | 0.448 | 1.00 | 36.90 |
| 10384 | O | HOH | X | 390 | 43.161 | 2.676 | -1.085 | 1.00 | 38.66 |
| 10387 | O | HOH | X | 391 | 62.047 | 69.399 | 25.389 | 1.00 | 88.66 |
| 10390 | O | HOH | X | 392 | 64.141 | 69.344 | 27.823 | 1.00 | 41.19 |
| 10393 | O | HOH | X | 393 | 58.875 | 89.405 | 12.710 | 1.00 | 64.96 |
| 10396 | O | HOH | X | 394 | 52.351 | 74.162 | -4.548 | 1.00 | 47.29 |
| 10399 | O | HOH | X | 395 | 53.730 | 70.282 | -5.715 | 1.00 | 55.71 |
| 10402 | O | HOH | X | 396 | 47.666 | 76.863 | 1.325 | 1.00 | 34.63 |
| 10405 | O | HOH | X | 397 | 59.660 | 75.843 | -9.785 | 1.00 | 41.09 |
| 10408 | O | HOH | X | 398 | 62.561 | 78.886 | -9.940 | 1.00 | 50.51 |
| 10411 | O | HOH | X | 399 | 30.260 | 2.431 | -11.763 | 1.00 | 34.80 |
| 10414 | O | HOH | X | 400 | 27.528 | 3.971 | -14.875 | 1.00 | 45.91 |
| 10417 | O | HOH | X | 401 | 33.506 | 13.418 | -15.971 | 1.00 | 38.77 |
| 10420 | O | HOH | X | 402 | 41.028 | 6.141 | -7.128 | 1.00 | 49.46 |
| 10423 | O | HOH | X | 403 | 28.710 | 29.035 | -18.837 | 1.00 | 26.44 |
| 10426 | O | HOH | X | 404 | 29.796 | 34.872 | -15.688 | 1.00 | 37.98 |
| 10429 | O | HOH | X | 405 | 27.243 | 36.476 | -15.645 | 1.00 | 37.96 |
| 10432 | O | HOH | X | 406 | 31.047 | 35.920 | -10.224 | 1.00 | 55.58 |
| 10435 | O | HOH | X | 407 | 33.680 | 38.851 | -7.405 | 1.00 | 50.01 |
| 10438 | O | HOH | X | 408 | 25.402 | 37.066 | -19.531 | 1.00 | 37.00 |
| 10441 | O | HOH | X | 409 | 35.153 | 33.776 | 5.764 | 1.00 | 48.02 |
| 10444 | O | HOH | X | 410 | 35.151 | 34.064 | 2.494 | 1.00 | 34.05 |
| 10447 | O | HOH | X | 411 | 34.154 | 30.349 | 7.013 | 1.00 | 44.18 |
| 10450 | O | HOH | X | 412 | 8.762 | 37.486 | 1.397 | 1.00 | 38.43 |
| 10453 | O | HOH | X | 413 | 7.201 | 35.165 | 1.535 | 1.00 | 41.39 |
| 10456 | O | HOH | X | 414 | 26.384 | 40.391 | 4.437 | 1.00 | 36.18 |
| 10459 | O | HOH | X | 415 | 51.309 | 51.810 | -0.301 | 1.00 | 39.62 |
| 10462 | O | HOH | X | 416 | 29.679 | 4.776 | 17.263 | 1.00 | 29.29 |
| 10465 | O | HOH | X | 417 | 28.029 | 5.806 | 20.001 | 1.00 | 42.73 |
| 10468 | O | HOH | X | 418 | 20.603 | 24.902 | 18.280 | 1.00 | 45.48 |
| 10471 | O | HOH | X | 419 | 56.231 | 57.185 | 2.974 | 1.00 | 32.25 |
| 10474 | O | HOH | X | 420 | 53.164 | 57.686 | 5.692 | 1.00 | 35.05 |
| 10477 | O | HOH | X | 421 | 65.428 | 51.862 | 28.325 | 1.00 | 40.33 |

FIGURE 3AA

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | MET | A | 16 | 65.564 | 50.628 | -5.933 | 1.00 | 45.23 |
| 3 | CA | MET | A | 16 | 65.166 | 51.178 | -7.255 | 1.00 | 44.87 |
| 5 | CB | MET | A | 16 | 64.933 | 50.049 | -8.267 | 1.00 | 45.30 |
| 8 | CG | MET | A | 16 | 65.153 | 50.446 | -9.726 | 1.00 | 47.01 |
| 11 | SD | MET | A | 16 | 66.181 | 49.252 | -10.631 | 1.00 | 50.95 |
| 12 | CE | MET | A | 16 | 64.933 | 48.059 | -11.220 | 1.00 | 50.52 |
| 16 | C | MET | A | 16 | 63.907 | 52.030 | -7.120 | 1.00 | 43.94 |
| 17 | O | MET | A | 16 | 63.880 | 53.159 | -7.610 | 1.00 | 44.23 |
| 20 | N | ASP | A | 17 | 62.875 | 51.491 | -6.466 | 1.00 | 42.41 |
| 22 | CA | ASP | A | 17 | 61.591 | 52.188 | -6.366 | 1.00 | 41.35 |
| 24 | CB | ASP | A | 17 | 60.409 | 51.226 | -6.459 | 1.00 | 41.74 |
| 27 | CG | ASP | A | 17 | 59.134 | 51.926 | -6.899 | 1.00 | 43.33 |
| 28 | OD1 | ASP | A | 17 | 58.448 | 52.535 | -6.037 | 1.00 | 46.33 |
| 29 | OD2 | ASP | A | 17 | 58.753 | 51.939 | -8.093 | 1.00 | 45.52 |
| 30 | C | ASP | A | 17 | 61.486 | 52.990 | -5.079 | 1.00 | 39.80 |
| 31 | O | ASP | A | 17 | 61.195 | 52.441 | -4.005 | 1.00 | 38.54 |
| 32 | N | PHE | A | 18 | 61.672 | 54.298 | -5.210 | 1.00 | 38.05 |
| 34 | CA | PHE | A | 18 | 61.858 | 55.146 | -4.050 | 1.00 | 36.90 |
| 36 | CB | PHE | A | 18 | 62.429 | 56.514 | -4.427 | 1.00 | 36.92 |
| 39 | CG | PHE | A | 18 | 63.016 | 57.233 | -3.260 | 1.00 | 36.41 |
| 40 | CD1 | PHE | A | 18 | 64.116 | 56.707 | -2.609 | 1.00 | 37.05 |
| 42 | CE1 | PHE | A | 18 | 64.658 | 57.340 | -1.502 | 1.00 | 36.55 |
| 44 | CZ | PHE | A | 18 | 64.098 | 58.493 | -1.036 | 1.00 | 36.07 |
| 46 | CE2 | PHE | A | 18 | 62.988 | 59.025 | -1.664 | 1.00 | 36.56 |
| 48 | CD2 | PHE | A | 18 | 62.442 | 58.392 | -2.768 | 1.00 | 36.65 |
| 50 | C | PHE | A | 18 | 60.632 | 55.314 | -3.158 | 1.00 | 35.80 |
| 51 | O | PHE | A | 18 | 60.769 | 55.198 | -1.949 | 1.00 | 35.17 |
| 52 | N | PRO | A | 19 | 59.456 | 55.618 | -3.712 | 1.00 | 34.90 |
| 53 | CA | PRO | A | 19 | 58.239 | 55.676 | -2.889 | 1.00 | 34.06 |
| 55 | CB | PRO | A | 19 | 57.123 | 55.861 | -3.924 | 1.00 | 34.29 |
| 58 | CG | PRO | A | 19 | 57.782 | 56.558 | -5.047 | 1.00 | 34.27 |
| 61 | CD | PRO | A | 19 | 59.176 | 55.993 | -5.114 | 1.00 | 34.77 |
| 64 | C | PRO | A | 19 | 58.008 | 54.418 | -2.039 | 1.00 | 33.38 |
| 65 | O | PRO | A | 19 | 57.585 | 54.564 | -0.895 | 1.00 | 32.65 |
| 66 | N | GLN | A | 20 | 58.279 | 53.228 | -2.579 | 1.00 | 32.48 |
| 68 | CA | GLN | A | 20 | 58.126 | 51.981 | -1.815 | 1.00 | 32.23 |
| 70 | CB | GLN | A | 20 | 58.188 | 50.746 | -2.732 | 1.00 | 32.68 |
| 73 | CG | GLN | A | 20 | 56.883 | 50.493 | -3.534 | 1.00 | 35.01 |
| 76 | CD | GLN | A | 20 | 56.611 | 49.011 | -3.811 | 1.00 | 39.06 |
| 77 | OE1 | GLN | A | 20 | 55.463 | 48.546 | -3.685 | 1.00 | 41.57 |
| 78 | NE2 | GLN | A | 20 | 57.654 | 48.270 | -4.193 | 1.00 | 39.95 |
| 81 | C | GLN | A | 20 | 59.177 | 51.869 | -0.700 | 1.00 | 30.90 |
| 82 | O | GLN | A | 20 | 58.892 | 51.363 | 0.379 | 1.00 | 30.03 |

FIGURE 3 AB

| A | B | C | D | E | F | G | H | I | J |
|---|---|---|---|---|---|---|---|---|---|
| 83 | N | GLN | A | 21 | 60.385 | 52.351 | -0.959 | 1.00 | 29.82 |
| 85 | CA | GLN | A | 21 | 61.426 | 52.370 | 0.058 | 1.00 | 29.68 |
| 87 | CB | GLN | A | 21 | 62.783 | 52.738 | -0.560 | 1.00 | 29.82 |
| 90 | CG | GLN | A | 21 | 63.366 | 51.647 | -1.494 | 1.00 | 31.98 |
| 93 | CD | GLN | A | 21 | 63.920 | 50.425 | -0.746 | 1.00 | 34.89 |
| 94 | OE1 | GLN | A | 21 | 64.483 | 49.512 | -1.360 | 1.00 | 36.76 |
| 95 | NE2 | GLN | A | 21 | 63.762 | 50.412 | 0.572 | 1.00 | 37.29 |
| 98 | C | GLN | A | 21 | 61.065 | 53.323 | 1.204 | 1.00 | 28.61 |
| 99 | O | GLN | A | 21 | 61.214 | 52.973 | 2.372 | 1.00 | 28.03 |
| 100 | N | LEU | A | 22 | 60.588 | 54.513 | 0.863 | 1.00 | 27.80 |
| 102 | CA | LEU | A | 22 | 60.120 | 55.472 | 1.848 | 1.00 | 27.76 |
| 104 | CB | LEU | A | 22 | 59.582 | 56.740 | 1.169 | 1.00 | 28.15 |
| 107 | CG | LEU | A | 22 | 60.595 | 57.714 | 0.543 | 1.00 | 29.56 |
| 109 | CD1 | LEU | A | 22 | 59.880 | 58.764 | -0.297 | 1.00 | 30.48 |
| 113 | CD2 | LEU | A | 22 | 61.447 | 58.392 | 1.611 | 1.00 | 30.42 |
| 117 | C | LEU | A | 22 | 59.036 | 54.861 | 2.736 | 1.00 | 27.31 |
| 118 | O | LEU | A | 22 | 59.099 | 54.975 | 3.950 | 1.00 | 26.43 |
| 119 | N | GLU | A | 23 | 58.057 | 54.185 | 2.145 | 1.00 | 27.14 |
| 121 | CA | GLU | A | 23 | 56.973 | 53.627 | 2.952 | 1.00 | 27.44 |
| 123 | CB | GLU | A | 23 | 55.760 | 53.232 | 2.101 | 1.00 | 28.34 |
| 126 | CG | GLU | A | 23 | 54.798 | 52.234 | 2.759 | 1.00 | 31.44 |
| 129 | CD | GLU | A | 23 | 53.961 | 52.789 | 3.912 | 1.00 | 35.82 |
| 130 | OE1 | GLU | A | 23 | 52.791 | 52.370 | 4.024 | 1.00 | 38.87 |
| 131 | OE2 | GLU | A | 23 | 54.448 | 53.597 | 4.738 | 1.00 | 38.87 |
| 132 | C | GLU | A | 23 | 57.465 | 52.462 | 3.805 | 1.00 | 26.15 |
| 133 | O | GLU | A | 23 | 57.040 | 52.322 | 4.949 | 1.00 | 25.29 |
| 134 | N | ALA | A | 24 | 58.357 | 51.642 | 3.254 | 1.00 | 25.31 |
| 136 | CA | ALA | A | 24 | 59.018 | 50.578 | 4.013 | 1.00 | 24.72 |
| 138 | CB | ALA | A | 24 | 60.019 | 49.847 | 3.153 | 1.00 | 25.46 |
| 142 | C | ALA | A | 24 | 59.728 | 51.160 | 5.230 | 1.00 | 24.33 |
| 143 | O | ALA | A | 24 | 59.610 | 50.636 | 6.331 | 1.00 | 23.33 |
| 144 | N | CYS | A | 25 | 60.438 | 52.263 | 5.025 | 1.00 | 23.38 |
| 146 | CA | CYS | A | 25 | 61.130 | 52.944 | 6.115 | 1.00 | 23.00 |
| 148 | CB | CYS | A | 25 | 62.029 | 54.056 | 5.578 | 1.00 | 23.11 |
| 151 | SG | CYS | A | 25 | 62.861 | 54.980 | 6.885 | 1.00 | 21.11 |
| 152 | C | CYS | A | 25 | 60.147 | 53.499 | 7.162 | 1.00 | 22.39 |
| 153 | O | CYS | A | 25 | 60.368 | 53.344 | 8.351 | 1.00 | 22.44 |
| 154 | N | VAL | A | 26 | 59.051 | 54.105 | 6.725 | 1.00 | 22.24 |
| 156 | CA | VAL | A | 26 | 58.056 | 54.638 | 7.651 | 1.00 | 22.18 |
| 158 | CB | VAL | A | 26 | 56.889 | 55.349 | 6.902 | 1.00 | 22.57 |
| 160 | CG1 | VAL | A | 26 | 55.697 | 55.610 | 7.815 | 1.00 | 22.85 |
| 164 | CG2 | VAL | A | 26 | 57.368 | 56.650 | 6.293 | 1.00 | 22.19 |
| 168 | C | VAL | A | 26 | 57.534 | 53.530 | 8.580 | 1.00 | 21.91 |
| 169 | O | VAL | A | 26 | 57.440 | 53.722 | 9.789 | 1.00 | 21.65 |
| 170 | N | LYS | A | 27 | 57.235 | 52.369 | 8.011 | 1.00 | 21.41 |
| 172 | CA | LYS | A | 27 | 56.741 | 51.236 | 8.779 | 1.00 | 21.24 |
| 174 | CB | LYS | A | 27 | 56.273 | 50.127 | 7.836 | 1.00 | 22.15 |
| 177 | CG | LYS | A | 27 | 54.982 | 50.454 | 7.081 | 1.00 | 24.03 |
| 180 | CD | LYS | A | 27 | 54.467 | 49.210 | 6.340 | 1.00 | 28.62 |
| 183 | CE | LYS | A | 27 | 53.133 | 49.458 | 5.596 | 1.00 | 31.91 |
| 186 | NZ | LYS | A | 27 | 53.166 | 48.924 | 4.184 | 1.00 | 33.67 |
| 190 | C | LYS | A | 27 | 57.798 | 50.693 | 9.737 | 1.00 | 20.33 |

FIGURE 3 AC

| A | B | C | D | E | F | G | H | I | J |
|---|---|---|---|---|---|---|---|---|---|
| 191 | O   | LYS | A | 27 | 57.499 | 50.428 | 10.910 | 1.00 | 19.84 |
| 192 | N   | GLN | A | 28 | 59.022 | 50.536 |  9.244 | 1.00 | 19.37 |
| 194 | CA  | GLN | A | 28 | 60.116 | 50.039 | 10.073 | 1.00 | 19.22 |
| 196 | CB  | GLN | A | 28 | 61.413 | 49.892 |  9.264 | 1.00 | 19.05 |
| 199 | CG  | GLN | A | 28 | 62.596 | 49.326 | 10.078 | 1.00 | 19.21 |
| 202 | CD  | GLN | A | 28 | 62.485 | 47.814 | 10.392 | 1.00 | 20.65 |
| 203 | OE1 | GLN | A | 28 | 63.076 | 47.320 | 11.375 | 1.00 | 22.34 |
| 204 | NE2 | GLN | A | 28 | 61.792 | 47.087 |  9.537 | 1.00 | 16.09 |
| 207 | C   | GLN | A | 28 | 60.340 | 50.985 | 11.258 | 1.00 | 18.67 |
| 208 | O   | GLN | A | 28 | 60.392 | 50.549 | 12.386 | 1.00 | 18.19 |
| 209 | N   | ALA | A | 29 | 60.465 | 52.278 | 10.985 | 1.00 | 18.55 |
| 211 | CA  | ALA | A | 29 | 60.748 | 53.271 | 12.026 | 1.00 | 18.70 |
| 213 | CB  | ALA | A | 29 | 61.022 | 54.625 | 11.403 | 1.00 | 18.98 |
| 217 | C   | ALA | A | 29 | 59.626 | 53.382 | 13.036 | 1.00 | 19.64 |
| 218 | O   | ALA | A | 29 | 59.875 | 53.535 | 14.238 | 1.00 | 19.64 |
| 219 | N   | ASN | A | 30 | 58.386 | 53.300 | 12.564 | 1.00 | 19.52 |
| 221 | CA  | ASN | A | 30 | 57.232 | 53.369 | 13.464 | 1.00 | 19.96 |
| 223 | CB  | ASN | A | 30 | 55.920 | 53.446 | 12.688 | 1.00 | 19.83 |
| 226 | CG  | ASN | A | 30 | 55.652 | 54.816 | 12.118 | 1.00 | 22.13 |
| 227 | OD1 | ASN | A | 30 | 56.322 | 55.792 | 12.458 | 1.00 | 23.82 |
| 228 | ND2 | ASN | A | 30 | 54.638 | 54.904 | 11.249 | 1.00 | 23.36 |
| 231 | C   | ASN | A | 30 | 57.177 | 52.190 | 14.405 | 1.00 | 19.86 |
| 232 | O   | ASN | A | 30 | 56.847 | 52.343 | 15.573 | 1.00 | 19.83 |
| 233 | N   | GLN | A | 31 | 57.474 | 51.010 | 13.878 | 1.00 | 20.51 |
| 235 | CA  | GLN | A | 31 | 57.584 | 49.779 | 14.679 | 1.00 | 21.34 |
| 237 | CB  | GLN | A | 31 | 57.921 | 48.608 | 13.760 | 1.00 | 21.77 |
| 240 | CG  | GLN | A | 31 | 57.882 | 47.246 | 14.412 | 1.00 | 24.92 |
| 243 | CD  | GLN | A | 31 | 58.025 | 46.137 | 13.385 | 1.00 | 29.08 |
| 244 | OE1 | GLN | A | 31 | 59.120 | 45.918 | 12.832 | 1.00 | 33.06 |
| 245 | NE2 | GLN | A | 31 | 56.929 | 45.446 | 13.112 | 1.00 | 31.52 |
| 248 | C   | GLN | A | 31 | 58.683 | 49.902 | 15.737 | 1.00 | 21.05 |
| 249 | O   | GLN | A | 31 | 58.488 | 49.550 | 16.899 | 1.00 | 20.55 |
| 250 | N   | ALA | A | 32 | 59.839 | 50.384 | 15.310 | 1.00 | 20.90 |
| 252 | CA  | ALA | A | 32 | 60.957 | 50.629 | 16.213 | 1.00 | 21.59 |
| 254 | CB  | ALA | A | 32 | 62.129 | 51.176 | 15.451 | 1.00 | 21.36 |
| 258 | C   | ALA | A | 32 | 60.539 | 51.598 | 17.315 | 1.00 | 21.65 |
| 259 | O   | ALA | A | 32 | 60.696 | 51.304 | 18.475 | 1.00 | 22.05 |
| 260 | N   | LEU | A | 33 | 59.999 | 52.750 | 16.940 | 1.00 | 22.61 |
| 262 | CA  | LEU | A | 33 | 59.575 | 53.760 | 17.906 | 1.00 | 23.19 |
| 264 | CB  | LEU | A | 33 | 58.931 | 54.937 | 17.175 | 1.00 | 23.47 |
| 267 | CG  | LEU | A | 33 | 59.879 | 55.966 | 16.574 | 1.00 | 24.21 |
| 269 | CD1 | LEU | A | 33 | 59.165 | 56.759 | 15.502 | 1.00 | 24.68 |
| 273 | CD2 | LEU | A | 33 | 60.391 | 56.887 | 17.685 | 1.00 | 26.09 |
| 277 | C   | LEU | A | 33 | 58.555 | 53.183 | 18.890 | 1.00 | 24.35 |
| 278 | O   | LEU | A | 33 | 58.659 | 53.391 | 20.094 | 1.00 | 23.66 |
| 279 | N   | SER | A | 34 | 57.567 | 52.471 | 18.356 | 1.00 | 25.27 |
| 281 | CA  | SER | A | 34 | 56.513 | 51.879 | 19.172 | 1.00 | 26.76 |
| 283 | CB  | SER | A | 34 | 55.480 | 51.162 | 18.295 | 1.00 | 27.01 |
| 286 | OG  | SER | A | 34 | 54.789 | 52.077 | 17.470 | 1.00 | 28.06 |
| 288 | C   | SER | A | 34 | 57.070 | 50.896 | 20.194 | 1.00 | 27.73 |
| 289 | O   | SER | A | 34 | 56.597 | 50.849 | 21.316 | 1.00 | 28.77 |
| 290 | N   | ARG | A | 35 | 58.071 | 50.117 | 19.802 | 1.00 | 28.38 |

FIGURE 3 AD

| A | B | C | D | E | F | G | H | I | J |
|---|---|---|---|---|---|---|---|---|---|
| 292 | CA | ARG | A | 35 | 58.649 | 49.117 | 20.688 | 1.00 | 29.15 |
| 294 | CB | ARG | A | 35 | 59.580 | 48.182 | 19.915 | 1.00 | 29.68 |
| 297 | CG | ARG | A | 35 | 58.842 | 47.176 | 19.053 | 1.00 | 33.37 |
| 300 | CD | ARG | A | 35 | 59.681 | 46.648 | 17.895 | 1.00 | 36.27 |
| 303 | NE | ARG | A | 35 | 59.113 | 45.445 | 17.291 | 1.00 | 39.06 |
| 305 | CZ | ARG | A | 35 | 59.778 | 44.630 | 16.473 | 1.00 | 41.04 |
| 306 | NH1 | ARG | A | 35 | 61.046 | 44.878 | 16.153 | 1.00 | 42.52 |
| 309 | NH2 | ARG | A | 35 | 59.174 | 43.564 | 15.970 | 1.00 | 42.39 |
| 312 | C | ARG | A | 35 | 59.426 | 49.761 | 21.828 | 1.00 | 28.40 |
| 313 | O | ARG | A | 35 | 59.480 | 49.210 | 22.926 | 1.00 | 27.74 |
| 314 | N | PHE | A | 36 | 60.045 | 50.910 | 21.557 | 1.00 | 27.61 |
| 316 | CA | PHE | A | 36 | 60.785 | 51.634 | 22.587 | 1.00 | 27.39 |
| 318 | CB | PHE | A | 36 | 61.853 | 52.533 | 21.960 | 1.00 | 27.18 |
| 321 | CG | PHE | A | 36 | 62.924 | 51.766 | 21.240 | 1.00 | 25.69 |
| 322 | CD1 | PHE | A | 36 | 63.214 | 52.029 | 19.918 | 1.00 | 25.01 |
| 324 | CE1 | PHE | A | 36 | 64.194 | 51.311 | 19.253 | 1.00 | 25.43 |
| 326 | CZ | PHE | A | 36 | 64.881 | 50.295 | 19.910 | 1.00 | 26.41 |
| 328 | CE2 | PHE | A | 36 | 64.600 | 50.022 | 21.218 | 1.00 | 26.08 |
| 330 | CD2 | PHE | A | 36 | 63.624 | 50.755 | 21.886 | 1.00 | 25.98 |
| 332 | C | PHE | A | 36 | 59.855 | 52.427 | 23.491 | 1.00 | 27.72 |
| 333 | O | PHE | A | 36 | 60.189 | 52.684 | 24.642 | 1.00 | 27.44 |
| 334 | N | ILE | A | 37 | 58.679 | 52.775 | 22.979 | 1.00 | 27.76 |
| 336 | CA | ILE | A | 37 | 57.677 | 53.488 | 23.756 | 1.00 | 28.44 |
| 338 | CB | ILE | A | 37 | 56.779 | 54.342 | 22.815 | 1.00 | 28.50 |
| 340 | CG1 | ILE | A | 37 | 57.527 | 55.620 | 22.419 | 1.00 | 28.68 |
| 343 | CD1 | ILE | A | 37 | 56.932 | 56.377 | 21.266 | 1.00 | 29.67 |
| 347 | CG2 | ILE | A | 37 | 55.440 | 54.687 | 23.473 | 1.00 | 29.47 |
| 351 | C | ILE | A | 37 | 56.831 | 52.526 | 24.620 | 1.00 | 28.85 |
| 352 | O | ILE | A | 37 | 56.394 | 52.900 | 25.707 | 1.00 | 29.06 |
| 353 | N | ALA | A | 38 | 56.631 | 51.293 | 24.156 | 1.00 | 29.01 |
| 355 | CA | ALA | A | 38 | 55.688 | 50.357 | 24.797 | 1.00 | 29.51 |
| 357 | CB | ALA | A | 38 | 55.489 | 49.108 | 23.926 | 1.00 | 29.54 |
| 361 | C | ALA | A | 38 | 55.995 | 49.951 | 26.251 | 1.00 | 29.76 |
| 362 | O | ALA | A | 38 | 55.058 | 49.805 | 27.032 | 1.00 | 30.41 |
| 363 | N | PRO | A | 39 | 57.261 | 49.761 | 26.631 | 1.00 | 29.96 |
| 364 | CA | PRO | A | 39 | 57.590 | 49.430 | 28.028 | 1.00 | 29.81 |
| 366 | CB | PRO | A | 39 | 59.019 | 48.871 | 27.952 | 1.00 | 29.63 |
| 369 | CG | PRO | A | 39 | 59.465 | 48.986 | 26.511 | 1.00 | 30.25 |
| 372 | CD | PRO | A | 39 | 58.466 | 49.813 | 25.784 | 1.00 | 30.23 |
| 375 | C | PRO | A | 39 | 57.547 | 50.605 | 29.003 | 1.00 | 29.35 |
| 376 | O | PRO | A | 39 | 57.768 | 50.409 | 30.200 | 1.00 | 29.40 |
| 377 | N | LEU | A | 40 | 57.288 | 51.808 | 28.508 | 1.00 | 28.66 |
| 379 | CA | LEU | A | 40 | 57.243 | 52.978 | 29.364 | 1.00 | 27.78 |
| 381 | CB | LEU | A | 40 | 57.200 | 54.260 | 28.535 | 1.00 | 27.92 |
| 384 | CG | LEU | A | 40 | 58.410 | 54.574 | 27.654 | 1.00 | 28.42 |
| 386 | CD1 | LEU | A | 40 | 58.185 | 55.906 | 26.946 | 1.00 | 29.06 |
| 390 | CD2 | LEU | A | 40 | 59.716 | 54.573 | 28.481 | 1.00 | 28.93 |
| 394 | C | LEU | A | 40 | 56.009 | 52.911 | 30.243 | 1.00 | 27.39 |
| 395 | O | LEU | A | 40 | 54.962 | 52.410 | 29.814 | 1.00 | 27.10 |
| 396 | N | PRO | A | 41 | 56.115 | 53.412 | 31.471 | 1.00 | 26.65 |
| 397 | CA | PRO | A | 41 | 54.937 | 53.506 | 32.338 | 1.00 | 26.24 |
| 399 | CB | PRO | A | 41 | 55.528 | 53.818 | 33.719 | 1.00 | 26.42 |

FIGURE 3 AE

| A | B | C | D | E | F | G | H | I | J |
|---|---|---|---|---|---|---|---|---|---|
| 402 | CG | PRO | A | 41 | 56.887 | 54.444 | 33.440 | 1.00 | 26.56 |
| 405 | CD | PRO | A | 41 | 57.339 | 53.909 | 32.122 | 1.00 | 26.41 |
| 408 | C | PRO | A | 41 | 54.017 | 54.624 | 31.863 | 1.00 | 25.76 |
| 409 | O | PRO | A | 41 | 54.386 | 55.397 | 30.977 | 1.00 | 25.20 |
| 410 | N | PHE | A | 42 | 52.840 | 54.706 | 32.469 | 1.00 | 25.70 |
| 412 | CA | PHE | A | 42 | 51.873 | 55.765 | 32.212 | 1.00 | 25.79 |
| 414 | CB | PHE | A | 42 | 52.479 | 57.131 | 32.556 | 1.00 | 25.87 |
| 417 | CG | PHE | A | 42 | 53.188 | 57.147 | 33.878 | 1.00 | 25.55 |
| 418 | CD1 | PHE | A | 42 | 52.489 | 56.876 | 35.049 | 1.00 | 25.97 |
| 420 | CE1 | PHE | A | 42 | 53.131 | 56.864 | 36.274 | 1.00 | 25.51 |
| 422 | CZ | PHE | A | 42 | 54.480 | 57.116 | 36.349 | 1.00 | 25.34 |
| 424 | CE2 | PHE | A | 42 | 55.195 | 57.379 | 35.186 | 1.00 | 25.76 |
| 426 | CD2 | PHE | A | 42 | 54.551 | 57.383 | 33.959 | 1.00 | 24.78 |
| 428 | C | PHE | A | 42 | 51.323 | 55.730 | 30.787 | 1.00 | 25.98 |
| 429 | O | PHE | A | 42 | 50.987 | 56.762 | 30.226 | 1.00 | 25.18 |
| 430 | N | GLN | A | 43 | 51.222 | 54.528 | 30.221 | 1.00 | 26.46 |
| 432 | CA | GLN | A | 43 | 50.537 | 54.330 | 28.942 | 1.00 | 27.47 |
| 434 | CB | GLN | A | 43 | 50.502 | 52.854 | 28.527 | 1.00 | 27.56 |
| 437 | CG | GLN | A | 43 | 51.828 | 52.229 | 28.185 | 1.00 | 28.72 |
| 440 | CD | GLN | A | 43 | 52.596 | 52.968 | 27.106 | 1.00 | 30.09 |
| 441 | OE1 | GLN | A | 43 | 53.817 | 53.065 | 27.187 | 1.00 | 32.82 |
| 442 | NE2 | GLN | A | 43 | 51.897 | 53.475 | 26.096 | 1.00 | 30.99 |
| 445 | C | GLN | A | 43 | 49.111 | 54.786 | 29.106 | 1.00 | 28.28 |
| 446 | O | GLN | A | 43 | 48.511 | 54.598 | 30.172 | 1.00 | 28.52 |
| 447 | N | ASN | A | 44 | 48.579 | 55.403 | 28.060 | 1.00 | 28.97 |
| 449 | CA | ASN | A | 44 | 47.202 | 55.868 | 28.040 | 1.00 | 29.76 |
| 451 | CB | ASN | A | 44 | 46.212 | 54.687 | 28.180 | 1.00 | 30.31 |
| 454 | CG | ASN | A | 44 | 46.513 | 53.535 | 27.210 | 1.00 | 31.66 |
| 455 | OD1 | ASN | A | 44 | 46.576 | 53.726 | 25.997 | 1.00 | 36.40 |
| 456 | ND2 | ASN | A | 44 | 46.694 | 52.342 | 27.748 | 1.00 | 32.76 |
| 459 | C | ASN | A | 44 | 46.937 | 56.948 | 29.094 | 1.00 | 29.56 |
| 460 | O | ASN | A | 44 | 45.842 | 57.041 | 29.631 | 1.00 | 29.84 |
| 461 | N | THR | A | 45 | 47.958 | 57.750 | 29.393 | 1.00 | 29.02 |
| 463 | CA | THR | A | 45 | 47.782 | 59.023 | 30.090 | 1.00 | 28.55 |
| 465 | CB | THR | A | 45 | 48.663 | 59.090 | 31.346 | 1.00 | 28.99 |
| 467 | OG1 | THR | A | 45 | 50.045 | 59.094 | 30.966 | 1.00 | 29.70 |
| 469 | CG2 | THR | A | 45 | 48.504 | 57.836 | 32.213 | 1.00 | 29.52 |
| 473 | C | THR | A | 45 | 48.173 | 60.135 | 29.107 | 1.00 | 27.72 |
| 474 | O | THR | A | 45 | 48.886 | 59.861 | 28.147 | 1.00 | 27.59 |
| 475 | N | PRO | A | 46 | 47.713 | 61.371 | 29.316 | 1.00 | 26.46 |
| 476 | CA | PRO | A | 46 | 47.961 | 62.453 | 28.351 | 1.00 | 25.93 |
| 478 | CB | PRO | A | 46 | 47.404 | 63.699 | 29.061 | 1.00 | 25.92 |
| 481 | CG | PRO | A | 46 | 46.331 | 63.155 | 29.974 | 1.00 | 26.20 |
| 484 | CD | PRO | A | 46 | 46.879 | 61.831 | 30.447 | 1.00 | 26.74 |
| 487 | C | PRO | A | 46 | 49.419 | 62.688 | 27.918 | 1.00 | 25.28 |
| 488 | O | PRO | A | 46 | 49.638 | 62.912 | 26.731 | 1.00 | 24.82 |
| 489 | N | VAL | A | 47 | 50.389 | 62.661 | 28.824 | 1.00 | 24.84 |
| 491 | CA | VAL | A | 47 | 51.766 | 62.944 | 28.412 | 1.00 | 24.49 |
| 493 | CB | VAL | A | 47 | 52.711 | 63.189 | 29.616 | 1.00 | 24.35 |
| 495 | CG1 | VAL | A | 47 | 52.934 | 61.920 | 30.414 | 1.00 | 25.47 |
| 499 | CG2 | VAL | A | 47 | 54.047 | 63.752 | 29.131 | 1.00 | 25.13 |
| 503 | C | VAL | A | 47 | 52.317 | 61.860 | 27.460 | 1.00 | 23.84 |

FIGURE 3 AF

| A | B | C | D | E | F | G | H | I | J |
|---|---|---|---|---|---|---|---|---|---|
| 504 | O | VAL | A | 47 | 52.962 | 62.172 | 26.462 | 1.00 | 23.42 |
| 505 | N | VAL | A | 48 | 52.046 | 60.594 | 27.752 | 1.00 | 23.38 |
| 507 | CA | VAL | A | 48 | 52.505 | 59.516 | 26.878 | 1.00 | 23.48 |
| 509 | CB | VAL | A | 48 | 52.449 | 58.146 | 27.567 | 1.00 | 23.07 |
| 511 | CG1 | VAL | A | 48 | 52.773 | 57.012 | 26.566 | 1.00 | 23.03 |
| 515 | CG2 | VAL | A | 48 | 53.409 | 58.125 | 28.740 | 1.00 | 23.55 |
| 519 | C | VAL | A | 48 | 51.725 | 59.512 | 25.567 | 1.00 | 23.67 |
| 520 | O | VAL | A | 48 | 52.297 | 59.299 | 24.510 | 1.00 | 23.73 |
| 521 | N | GLU | A | 49 | 50.427 | 59.782 | 25.632 | 1.00 | 23.99 |
| 523 | CA | GLU | A | 49 | 49.629 | 59.897 | 24.417 | 1.00 | 24.17 |
| 525 | CB | GLU | A | 49 | 48.155 | 60.087 | 24.761 | 1.00 | 24.86 |
| 528 | CG | GLU | A | 49 | 47.534 | 58.863 | 25.404 | 1.00 | 27.67 |
| 531 | CD | GLU | A | 49 | 46.125 | 59.115 | 25.899 | 1.00 | 33.01 |
| 532 | OE1 | GLU | A | 49 | 45.337 | 58.140 | 25.909 | 1.00 | 36.58 |
| 533 | OE2 | GLU | A | 49 | 45.806 | 60.274 | 26.278 | 1.00 | 35.89 |
| 534 | C | GLU | A | 49 | 50.115 | 61.066 | 23.562 | 1.00 | 22.99 |
| 535 | O | GLU | A | 49 | 50.099 | 60.980 | 22.345 | 1.00 | 21.91 |
| 536 | N | THR | A | 50 | 50.574 | 62.139 | 24.208 | 1.00 | 22.14 |
| 538 | CA | THR | A | 50 | 51.147 | 63.270 | 23.497 | 1.00 | 21.71 |
| 540 | CB | THR | A | 50 | 51.426 | 64.447 | 24.442 | 1.00 | 21.87 |
| 542 | OG1 | THR | A | 50 | 50.218 | 64.833 | 25.112 | 1.00 | 21.63 |
| 544 | CG2 | THR | A | 50 | 51.861 | 65.695 | 23.647 | 1.00 | 21.55 |
| 548 | C | THR | A | 50 | 52.435 | 62.833 | 22.813 | 1.00 | 21.19 |
| 549 | O | THR | A | 50 | 52.658 | 63.152 | 21.667 | 1.00 | 20.77 |
| 550 | N | MET | A | 51 | 53.268 | 62.075 | 23.515 | 1.00 | 21.45 |
| 552 | CA | MET | A | 51 | 54.525 | 61.583 | 22.936 | 1.00 | 21.16 |
| 554 | CB | MET | A | 51 | 55.321 | 60.768 | 23.965 | 1.00 | 21.28 |
| 557 | CG | MET | A | 51 | 55.825 | 61.558 | 25.165 | 1.00 | 21.06 |
| 560 | SD | MET | A | 51 | 56.503 | 60.485 | 26.448 | 1.00 | 21.92 |
| 561 | CE | MET | A | 51 | 58.036 | 59.941 | 25.581 | 1.00 | 18.94 |
| 565 | C | MET | A | 51 | 54.227 | 60.713 | 21.704 | 1.00 | 21.05 |
| 566 | O | MET | A | 51 | 54.873 | 60.858 | 20.676 | 1.00 | 21.01 |
| 567 | N | GLN | A | 52 | 53.228 | 59.835 | 21.812 | 1.00 | 21.04 |
| 569 | CA | GLN | A | 52 | 52.882 | 58.908 | 20.737 | 1.00 | 21.29 |
| 571 | CB | GLN | A | 52 | 51.862 | 57.889 | 21.229 | 1.00 | 21.77 |
| 574 | CG | GLN | A | 52 | 52.407 | 56.822 | 22.155 | 1.00 | 23.17 |
| 577 | CD | GLN | A | 52 | 51.297 | 55.954 | 22.728 | 1.00 | 26.61 |
| 578 | OE1 | GLN | A | 52 | 51.254 | 54.743 | 22.480 | 1.00 | 30.25 |
| 579 | NE2 | GLN | A | 52 | 50.389 | 56.569 | 23.474 | 1.00 | 24.83 |
| 582 | C | GLN | A | 52 | 52.299 | 59.642 | 19.526 | 1.00 | 21.06 |
| 583 | O | GLN | A | 52 | 52.547 | 59.291 | 18.371 | 1.00 | 19.85 |
| 584 | N | TYR | A | 53 | 51.495 | 60.656 | 19.804 | 1.00 | 20.82 |
| 586 | CA | TYR | A | 53 | 50.887 | 61.466 | 18.760 | 1.00 | 21.28 |
| 588 | CB | TYR | A | 53 | 49.946 | 62.447 | 19.433 | 1.00 | 21.43 |
| 591 | CG | TYR | A | 53 | 49.135 | 63.357 | 18.555 | 1.00 | 23.00 |
| 592 | CD1 | TYR | A | 53 | 47.838 | 63.002 | 18.154 | 1.00 | 24.56 |
| 594 | CE1 | TYR | A | 53 | 47.069 | 63.859 | 17.385 | 1.00 | 24.49 |
| 596 | CZ | TYR | A | 53 | 47.562 | 65.107 | 17.052 | 1.00 | 25.48 |
| 597 | OH | TYR | A | 53 | 46.793 | 65.965 | 16.292 | 1.00 | 24.53 |
| 599 | CE2 | TYR | A | 53 | 48.844 | 65.484 | 17.445 | 1.00 | 23.07 |
| 601 | CD2 | TYR | A | 53 | 49.604 | 64.618 | 18.212 | 1.00 | 23.55 |
| 603 | C | TYR | A | 53 | 51.967 | 62.218 | 18.002 | 1.00 | 20.79 |

FIGURE 3 AG

| A | B | C | D | E | F | G | H | I | J |
|---|---|---|---|---|---|---|---|---|---|
| 604 | O | TYR | A | 53 | 52.033 | 62.184 | 16.765 | 1.00 | 20.35 |
| 605 | N | GLY | A | 54 | 52.811 | 62.910 | 18.761 | 1.00 | 20.69 |
| 607 | CA | GLY | A | 54 | 53.840 | 63.751 | 18.187 | 1.00 | 20.90 |
| 610 | C | GLY | A | 54 | 54.963 | 62.972 | 17.526 | 1.00 | 21.30 |
| 611 | O | GLY | A | 54 | 55.596 | 63.495 | 16.627 | 1.00 | 21.54 |
| 612 | N | ALA | A | 55 | 55.215 | 61.732 | 17.955 | 1.00 | 21.95 |
| 614 | CA | ALA | A | 55 | 56.315 | 60.942 | 17.389 | 1.00 | 22.16 |
| 616 | CB | ALA | A | 55 | 56.981 | 60.100 | 18.480 | 1.00 | 22.04 |
| 620 | C | ALA | A | 55 | 55.862 | 60.033 | 16.242 | 1.00 | 22.84 |
| 621 | O | ALA | A | 55 | 56.609 | 59.808 | 15.282 | 1.00 | 22.77 |
| 622 | N | LEU | A | 56 | 54.645 | 59.506 | 16.337 | 1.00 | 23.82 |
| 624 | CA | LEU | A | 56 | 54.227 | 58.413 | 15.446 | 1.00 | 25.01 |
| 626 | CB | LEU | A | 56 | 53.718 | 57.229 | 16.272 | 1.00 | 25.40 |
| 629 | CG | LEU | A | 56 | 54.803 | 56.448 | 16.999 | 1.00 | 26.02 |
| 631 | CD1 | LEU | A | 56 | 54.192 | 55.617 | 18.110 | 1.00 | 27.58 |
| 635 | CD2 | LEU | A | 56 | 55.583 | 55.570 | 16.011 | 1.00 | 26.63 |
| 639 | C | LEU | A | 56 | 53.188 | 58.758 | 14.386 | 1.00 | 25.71 |
| 640 | O | LEU | A | 56 | 53.144 | 58.088 | 13.352 | 1.00 | 25.79 |
| 641 | N | LEU | A | 57 | 52.351 | 59.772 | 14.626 | 1.00 | 26.23 |
| 643 | CA | LEU | A | 57 | 51.244 | 60.076 | 13.712 | 1.00 | 26.84 |
| 645 | CB | LEU | A | 57 | 50.045 | 60.627 | 14.487 | 1.00 | 27.25 |
| 648 | CG | LEU | A | 57 | 48.675 | 60.380 | 13.836 | 1.00 | 29.61 |
| 650 | CD1 | LEU | A | 57 | 48.417 | 58.886 | 13.617 | 1.00 | 30.97 |
| 654 | CD2 | LEU | A | 57 | 47.544 | 60.990 | 14.672 | 1.00 | 31.15 |
| 658 | C | LEU | A | 57 | 51.660 | 61.041 | 12.589 | 1.00 | 26.56 |
| 659 | O | LEU | A | 57 | 51.650 | 62.260 | 12.762 | 1.00 | 26.92 |
| 660 | N | GLY | A | 58 | 52.014 | 60.471 | 11.441 | 1.00 | 26.04 |
| 662 | CA | GLY | A | 58 | 52.480 | 61.230 | 10.294 | 1.00 | 25.24 |
| 665 | C | GLY | A | 58 | 53.983 | 61.421 | 10.347 | 1.00 | 24.44 |
| 666 | O | GLY | A | 58 | 54.635 | 61.015 | 11.301 | 1.00 | 24.64 |
| 667 | N | GLY | A | 59 | 54.513 | 62.081 | 9.331 | 1.00 | 23.73 |
| 669 | CA | GLY | A | 59 | 55.938 | 62.322 | 9.195 | 1.00 | 23.06 |
| 672 | C | GLY | A | 59 | 56.553 | 61.359 | 8.209 | 1.00 | 22.26 |
| 673 | O | GLY | A | 59 | 56.162 | 60.194 | 8.133 | 1.00 | 22.42 |
| 674 | N | LYS | A | 60 | 57.547 | 61.842 | 7.478 | 1.00 | 22.13 |
| 676 | CA | LYS | A | 60 | 58.154 | 61.112 | 6.374 | 1.00 | 21.99 |
| 678 | CB | LYS | A | 60 | 58.759 | 62.101 | 5.373 | 1.00 | 22.38 |
| 681 | CG | LYS | A | 60 | 57.740 | 63.053 | 4.741 | 1.00 | 22.42 |
| 684 | CD | LYS | A | 60 | 58.397 | 63.946 | 3.700 | 1.00 | 22.36 |
| 687 | CE | LYS | A | 60 | 59.309 | 65.000 | 4.315 | 1.00 | 22.65 |
| 690 | NZ | LYS | A | 60 | 58.610 | 65.764 | 5.390 | 1.00 | 22.32 |
| 694 | C | LYS | A | 60 | 59.236 | 60.121 | 6.820 | 1.00 | 21.22 |
| 695 | O | LYS | A | 60 | 59.639 | 59.250 | 6.044 | 1.00 | 21.45 |
| 696 | N | ARG | A | 61 | 59.679 | 60.268 | 8.064 | 1.00 | 20.48 |
| 698 | CA | ARG | A | 61 | 60.763 | 59.494 | 8.657 | 1.00 | 19.82 |
| 700 | CB | ARG | A | 61 | 60.347 | 58.035 | 8.877 | 1.00 | 19.66 |
| 703 | CG | ARG | A | 61 | 59.138 | 57.855 | 9.723 | 1.00 | 20.10 |
| 706 | CD | ARG | A | 61 | 59.272 | 58.230 | 11.192 | 1.00 | 20.40 |
| 709 | NE | ARG | A | 61 | 57.948 | 58.049 | 11.781 | 1.00 | 20.92 |
| 711 | CZ | ARG | A | 61 | 57.037 | 58.991 | 11.934 | 1.00 | 22.13 |
| 712 | NH1 | ARG | A | 61 | 57.298 | 60.255 | 11.645 | 1.00 | 23.06 |
| 715 | NH2 | ARG | A | 61 | 55.840 | 58.667 | 12.421 | 1.00 | 22.86 |

FIGURE 3 AH

| A | B | C | D | E | F | G | H | I | J |
|---|---|---|---|---|---|---|---|---|---|
| 718 | C | ARG | A | 61 | 62.061 | 59.514 | 7.860 | 1.00 | 19.24 |
| 719 | O | ARG | A | 61 | 62.738 | 58.501 | 7.779 | 1.00 | 18.48 |
| 720 | N | LEU | A | 62 | 62.432 | 60.666 | 7.307 | 1.00 | 18.87 |
| 722 | CA | LEU | A | 62 | 63.630 | 60.734 | 6.485 | 1.00 | 18.40 |
| 724 | CB | LEU | A | 62 | 63.643 | 61.988 | 5.629 | 1.00 | 18.86 |
| 727 | CG | LEU | A | 62 | 62.430 | 62.083 | 4.708 | 1.00 | 18.30 |
| 729 | CD1 | LEU | A | 62 | 62.550 | 63.320 | 3.821 | 1.00 | 18.04 |
| 733 | CD2 | LEU | A | 62 | 62.266 | 60.815 | 3.896 | 1.00 | 19.13 |
| 737 | C | LEU | A | 62 | 64.908 | 60.646 | 7.296 | 1.00 | 18.46 |
| 738 | O | LEU | A | 62 | 65.933 | 60.241 | 6.772 | 1.00 | 18.88 |
| 739 | N | ARG | A | 63 | 64.866 | 61.017 | 8.562 | 1.00 | 17.65 |
| 741 | CA | ARG | A | 63 | 66.054 | 60.871 | 9.384 | 1.00 | 17.87 |
| 743 | CB | ARG | A | 63 | 66.000 | 61.756 | 10.611 | 1.00 | 17.85 |
| 746 | CG | ARG | A | 63 | 66.045 | 63.219 | 10.223 | 1.00 | 17.38 |
| 749 | CD | ARG | A | 63 | 65.459 | 64.177 | 11.253 | 1.00 | 17.84 |
| 752 | NE | ARG | A | 63 | 65.361 | 65.533 | 10.704 | 1.00 | 19.01 |
| 754 | CZ | ARG | A | 63 | 64.417 | 65.941 | 9.863 | 1.00 | 20.05 |
| 755 | NH1 | ARG | A | 63 | 64.422 | 67.193 | 9.411 | 1.00 | 22.90 |
| 758 | NH2 | ARG | A | 63 | 63.449 | 65.123 | 9.477 | 1.00 | 21.09 |
| 761 | C | ARG | A | 63 | 66.322 | 59.401 | 9.705 | 1.00 | 17.71 |
| 762 | O | ARG | A | 63 | 67.454 | 58.951 | 9.531 | 1.00 | 18.10 |
| 763 | N | PRO | A | 64 | 65.329 | 58.645 | 10.163 | 1.00 | 17.51 |
| 764 | CA | PRO | A | 64 | 65.476 | 57.180 | 10.192 | 1.00 | 17.45 |
| 766 | CB | PRO | A | 64 | 64.070 | 56.703 | 10.531 | 1.00 | 17.56 |
| 769 | CG | PRO | A | 64 | 63.506 | 57.791 | 11.356 | 1.00 | 17.73 |
| 772 | CD | PRO | A | 64 | 64.052 | 59.064 | 10.767 | 1.00 | 17.18 |
| 775 | C | PRO | A | 64 | 65.936 | 56.615 | 8.859 | 1.00 | 17.33 |
| 776 | O | PRO | A | 64 | 66.816 | 55.755 | 8.854 | 1.00 | 17.25 |
| 777 | N | PHE | A | 65 | 65.376 | 57.104 | 7.754 | 1.00 | 17.93 |
| 779 | CA | PHE | A | 65 | 65.781 | 56.677 | 6.427 | 1.00 | 18.40 |
| 781 | CB | PHE | A | 65 | 65.044 | 57.457 | 5.338 | 1.00 | 19.10 |
| 784 | CG | PHE | A | 65 | 65.198 | 56.872 | 3.941 | 1.00 | 19.82 |
| 785 | CD1 | PHE | A | 65 | 66.425 | 56.898 | 3.278 | 1.00 | 21.48 |
| 787 | CE1 | PHE | A | 65 | 66.558 | 56.356 | 1.990 | 1.00 | 24.16 |
| 789 | CZ | PHE | A | 65 | 65.456 | 55.801 | 1.354 | 1.00 | 23.70 |
| 791 | CE2 | PHE | A | 65 | 64.232 | 55.787 | 2.000 | 1.00 | 24.40 |
| 793 | CD2 | PHE | A | 65 | 64.112 | 56.329 | 3.289 | 1.00 | 21.85 |
| 795 | C | PHE | A | 65 | 67.288 | 56.831 | 6.274 | 1.00 | 18.39 |
| 796 | O | PHE | A | 65 | 67.951 | 55.920 | 5.814 | 1.00 | 18.40 |
| 797 | N | LEU | A | 66 | 67.820 | 57.973 | 6.683 | 1.00 | 18.52 |
| 799 | CA | LEU | A | 66 | 69.255 | 58.228 | 6.643 | 1.00 | 18.77 |
| 801 | CB | LEU | A | 66 | 69.554 | 59.650 | 7.101 | 1.00 | 19.16 |
| 804 | CG | LEU | A | 66 | 69.280 | 60.737 | 6.070 | 1.00 | 20.56 |
| 806 | CD1 | LEU | A | 66 | 69.409 | 62.108 | 6.739 | 1.00 | 21.70 |
| 810 | CD2 | LEU | A | 66 | 70.233 | 60.611 | 4.897 | 1.00 | 21.14 |
| 814 | C | LEU | A | 66 | 70.063 | 57.274 | 7.512 | 1.00 | 18.22 |
| 815 | O | LEU | A | 66 | 71.162 | 56.862 | 7.131 | 1.00 | 17.84 |
| 816 | N | VAL | A | 67 | 69.546 | 56.973 | 8.693 | 1.00 | 16.88 |
| 818 | CA | VAL | A | 67 | 70.235 | 56.066 | 9.609 | 1.00 | 17.06 |
| 820 | CB | VAL | A | 67 | 69.512 | 56.001 | 10.969 | 1.00 | 16.98 |
| 822 | CG1 | VAL | A | 67 | 70.075 | 54.909 | 11.865 | 1.00 | 17.14 |
| 826 | CG2 | VAL | A | 67 | 69.621 | 57.337 | 11.679 | 1.00 | 16.69 |

FIGURE 3 AI

| A | B | C | D | E | F | G | H | I | J |
|---|---|---|---|---|---|---|---|---|---|
| 830 | C | VAL | A | 67 | 70.315 | 54.667 | 8.984 | 1.00 | 17.43 |
| 831 | O | VAL | A | 67 | 71.391 | 54.087 | 8.924 | 1.00 | 16.85 |
| 832 | N | TYR | A | 68 | 69.171 | 54.175 | 8.504 | 1.00 | 17.82 |
| 834 | CA | TYR | A | 68 | 69.049 | 52.853 | 7.890 | 1.00 | 18.73 |
| 836 | CB | TYR | A | 68 | 67.590 | 52.546 | 7.534 | 1.00 | 18.65 |
| 839 | CG | TYR | A | 68 | 66.682 | 52.294 | 8.706 | 1.00 | 17.77 |
| 840 | CD1 | TYR | A | 68 | 66.993 | 51.343 | 9.670 | 1.00 | 18.53 |
| 842 | CE1 | TYR | A | 68 | 66.152 | 51.109 | 10.734 | 1.00 | 19.24 |
| 844 | CZ | TYR | A | 68 | 64.967 | 51.819 | 10.844 | 1.00 | 17.86 |
| 845 | OH | TYR | A | 68 | 64.123 | 51.616 | 11.915 | 1.00 | 16.87 |
| 847 | CE2 | TYR | A | 68 | 64.650 | 52.774 | 9.914 | 1.00 | 18.34 |
| 849 | CD2 | TYR | A | 68 | 65.492 | 52.988 | 8.835 | 1.00 | 18.14 |
| 851 | C | TYR | A | 68 | 69.878 | 52.741 | 6.626 | 1.00 | 19.22 |
| 852 | O | TYR | A | 68 | 70.627 | 51.788 | 6.466 | 1.00 | 20.65 |
| 853 | N | ALA | A | 69 | 69.762 | 53.725 | 5.744 | 1.00 | 19.41 |
| 855 | CA | ALA | A | 69 | 70.470 | 53.707 | 4.474 | 1.00 | 19.53 |
| 857 | CB | ALA | A | 69 | 70.035 | 54.875 | 3.616 | 1.00 | 20.02 |
| 861 | C | ALA | A | 69 | 71.975 | 53.744 | 4.695 | 1.00 | 20.18 |
| 862 | O | ALA | A | 69 | 72.721 | 53.053 | 4.011 | 1.00 | 21.39 |
| 863 | N | THR | A | 70 | 72.423 | 54.545 | 5.656 | 1.00 | 20.00 |
| 865 | CA | THR | A | 70 | 73.841 | 54.656 | 5.930 | 1.00 | 20.26 |
| 867 | CB | THR | A | 70 | 74.124 | 55.842 | 6.828 | 1.00 | 20.06 |
| 869 | OG1 | THR | A | 70 | 73.742 | 57.060 | 6.143 | 1.00 | 19.95 |
| 871 | CG2 | THR | A | 70 | 75.624 | 55.979 | 7.077 | 1.00 | 20.73 |
| 875 | C | THR | A | 70 | 74.371 | 53.370 | 6.527 | 1.00 | 20.27 |
| 876 | O | THR | A | 70 | 75.330 | 52.821 | 6.025 | 1.00 | 20.97 |
| 877 | N | GLY | A | 71 | 73.743 | 52.886 | 7.588 | 1.00 | 20.36 |
| 879 | CA | GLY | A | 71 | 74.136 | 51.630 | 8.199 | 1.00 | 20.44 |
| 882 | C | GLY | A | 71 | 74.090 | 50.470 | 7.229 | 1.00 | 20.43 |
| 883 | O | GLY | A | 71 | 74.966 | 49.600 | 7.242 | 1.00 | 21.38 |
| 884 | N | HIS | A | 72 | 73.061 | 50.442 | 6.393 | 1.00 | 21.26 |
| 886 | CA | HIS | A | 72 | 72.886 | 49.367 | 5.401 | 1.00 | 21.95 |
| 888 | CB | HIS | A | 72 | 71.577 | 49.530 | 4.623 | 1.00 | 22.16 |
| 891 | CG | HIS | A | 72 | 70.369 | 49.049 | 5.362 | 1.00 | 21.95 |
| 892 | ND1 | HIS | A | 72 | 69.094 | 49.468 | 5.051 | 1.00 | 23.29 |
| 894 | CE1 | HIS | A | 72 | 68.231 | 48.892 | 5.869 | 1.00 | 23.63 |
| 896 | NE2 | HIS | A | 72 | 68.899 | 48.097 | 6.687 | 1.00 | 21.16 |
| 898 | CD2 | HIS | A | 72 | 70.238 | 48.181 | 6.394 | 1.00 | 22.72 |
| 900 | C | HIS | A | 72 | 74.054 | 49.313 | 4.421 | 1.00 | 22.56 |
| 901 | O | HIS | A | 72 | 74.455 | 48.228 | 3.995 | 1.00 | 21.64 |
| 902 | N | MET | A | 73 | 74.610 | 50.477 | 4.080 | 1.00 | 23.05 |
| 904 | CA | MET | A | 73 | 75.782 | 50.536 | 3.201 | 1.00 | 23.89 |
| 906 | CB | MET | A | 73 | 76.282 | 51.961 | 3.027 | 1.00 | 24.12 |
| 909 | CG | MET | A | 73 | 75.546 | 52.765 | 2.016 | 1.00 | 26.38 |
| 912 | SD | MET | A | 73 | 76.590 | 54.090 | 1.347 | 1.00 | 31.06 |
| 913 | CE | MET | A | 73 | 77.179 | 54.849 | 2.837 | 1.00 | 30.61 |
| 917 | C | MET | A | 73 | 76.944 | 49.713 | 3.732 | 1.00 | 24.04 |
| 918 | O | MET | A | 73 | 77.740 | 49.208 | 2.945 | 1.00 | 24.70 |
| 919 | N | PHE | A | 74 | 77.052 | 49.617 | 5.057 | 1.00 | 24.12 |
| 921 | CA | PHE | A | 74 | 78.122 | 48.863 | 5.723 | 1.00 | 24.15 |
| 923 | CB | PHE | A | 74 | 78.644 | 49.693 | 6.881 | 1.00 | 24.28 |
| 926 | CG | PHE | A | 74 | 79.127 | 51.040 | 6.455 | 1.00 | 25.09 |

FIGURE 3 AJ

| A | B | C | D | E | F | G | H | I | J |
|---|---|---|---|---|---|---|---|---|---|
| 927 | CD1 | PHE | A | 74 | 78.410 | 52.183 | 6.759 | 1.00 | 25.88 |
| 929 | CE1 | PHE | A | 74 | 78.847 | 53.424 | 6.357 | 1.00 | 25.67 |
| 931 | CZ | PHE | A | 74 | 80.015 | 53.547 | 5.641 | 1.00 | 26.11 |
| 933 | CE2 | PHE | A | 74 | 80.751 | 52.415 | 5.330 | 1.00 | 26.51 |
| 935 | CD2 | PHE | A | 74 | 80.305 | 51.167 | 5.736 | 1.00 | 26.10 |
| 937 | C | PHE | A | 74 | 77.710 | 47.461 | 6.196 | 1.00 | 24.09 |
| 938 | O | PHE | A | 74 | 78.475 | 46.770 | 6.875 | 1.00 | 23.88 |
| 939 | N | GLY | A | 75 | 76.508 | 47.039 | 5.815 | 1.00 | 23.45 |
| 941 | CA | GLY | A | 75 | 76.025 | 45.708 | 6.114 | 1.00 | 23.38 |
| 944 | C | GLY | A | 75 | 75.544 | 45.539 | 7.545 | 1.00 | 23.11 |
| 945 | O | GLY | A | 75 | 75.412 | 44.415 | 8.032 | 1.00 | 22.14 |
| 946 | N | VAL | A | 76 | 75.261 | 46.636 | 8.241 | 1.00 | 22.50 |
| 948 | CA | VAL | A | 76 | 74.698 | 46.461 | 9.577 | 1.00 | 22.69 |
| 950 | CB | VAL | A | 76 | 75.093 | 47.576 | 10.642 | 1.00 | 22.92 |
| 952 | CG1 | VAL | A | 76 | 75.915 | 48.711 | 10.067 | 1.00 | 23.76 |
| 956 | CG2 | VAL | A | 76 | 73.908 | 48.074 | 11.396 | 1.00 | 22.71 |
| 960 | C | VAL | A | 76 | 73.194 | 46.144 | 9.484 | 1.00 | 21.96 |
| 961 | O | VAL | A | 76 | 72.487 | 46.604 | 8.591 | 1.00 | 21.42 |
| 962 | N | SER | A | 77 | 72.746 | 45.302 | 10.402 | 1.00 | 21.48 |
| 964 | CA | SER | A | 77 | 71.389 | 44.778 | 10.405 | 1.00 | 21.77 |
| 966 | CB | SER | A | 77 | 71.250 | 43.671 | 11.467 | 1.00 | 22.01 |
| 969 | OG | SER | A | 77 | 69.901 | 43.269 | 11.656 | 1.00 | 24.55 |
| 971 | C | SER | A | 77 | 70.388 | 45.893 | 10.669 | 1.00 | 21.66 |
| 972 | O | SER | A | 77 | 70.614 | 46.768 | 11.497 | 1.00 | 20.52 |
| 973 | N | THR | A | 78 | 69.280 | 45.849 | 9.950 | 1.00 | 21.30 |
| 975 | CA | THR | A | 78 | 68.197 | 46.782 | 10.145 | 1.00 | 21.37 |
| 977 | CB | THR | A | 78 | 67.041 | 46.395 | 9.243 | 1.00 | 21.59 |
| 979 | OG1 | THR | A | 78 | 67.522 | 46.238 | 7.898 | 1.00 | 20.65 |
| 981 | CG2 | THR | A | 78 | 66.004 | 47.531 | 9.175 | 1.00 | 21.88 |
| 985 | C | THR | A | 78 | 67.742 | 46.839 | 11.609 | 1.00 | 21.40 |
| 986 | O | THR | A | 78 | 67.457 | 47.919 | 12.127 | 1.00 | 20.26 |
| 987 | N | ASN | A | 79 | 67.712 | 45.681 | 12.273 | 1.00 | 20.85 |
| 989 | CA | ASN | A | 79 | 67.259 | 45.592 | 13.665 | 1.00 | 21.11 |
| 991 | CB | ASN | A | 79 | 67.155 | 44.113 | 14.110 | 1.00 | 20.78 |
| 994 | CG | ASN | A | 79 | 66.777 | 43.962 | 15.577 | 1.00 | 20.57 |
| 995 | OD1 | ASN | A | 79 | 65.629 | 44.176 | 15.960 | 1.00 | 20.74 |
| 996 | ND2 | ASN | A | 79 | 67.741 | 43.572 | 16.395 | 1.00 | 21.96 |
| 999 | C | ASN | A | 79 | 68.135 | 46.366 | 14.648 | 1.00 | 21.18 |
| 1000 | O | ASN | A | 79 | 67.630 | 46.935 | 15.589 | 1.00 | 21.24 |
| 1001 | N | THR | A | 80 | 69.445 | 46.363 | 14.445 | 1.00 | 21.31 |
| 1003 | CA | THR | A | 80 | 70.325 | 47.176 | 15.288 | 1.00 | 22.18 |
| 1005 | CB | THR | A | 80 | 71.831 | 46.719 | 15.233 | 1.00 | 23.07 |
| 1007 | OG1 | THR | A | 80 | 72.729 | 47.845 | 15.254 | 1.00 | 25.14 |
| 1009 | CG2 | THR | A | 80 | 72.163 | 46.051 | 13.972 | 1.00 | 25.36 |
| 1013 | C | THR | A | 80 | 70.149 | 48.653 | 14.952 | 1.00 | 21.28 |
| 1014 | O | THR | A | 80 | 70.191 | 49.488 | 15.836 | 1.00 | 21.18 |
| 1015 | N | LEU | A | 81 | 69.889 | 48.958 | 13.685 | 1.00 | 20.13 |
| 1017 | CA | LEU | A | 81 | 69.699 | 50.338 | 13.267 | 1.00 | 19.67 |
| 1019 | CB | LEU | A | 81 | 69.773 | 50.458 | 11.743 | 1.00 | 19.03 |
| 1022 | CG | LEU | A | 81 | 71.174 | 50.220 | 11.203 | 1.00 | 20.05 |
| 1024 | CD1 | LEU | A | 81 | 71.133 | 49.777 | 9.747 | 1.00 | 20.55 |
| 1028 | CD2 | LEU | A | 81 | 72.025 | 51.477 | 11.362 | 1.00 | 21.66 |

FIGURE 3 AK

| A | B | C | D | E | F | G | H | I | J |
|---|---|---|---|---|---|---|---|---|---|
| 1032 | C | LEU | A | 81 | 68.395 | 50.943 | 13.785 | 1.00 | 19.10 |
| 1033 | O | LEU | A | 81 | 68.266 | 52.154 | 13.797 | 1.00 | 17.73 |
| 1034 | N | ASP | A | 82 | 67.452 | 50.098 | 14.213 | 1.00 | 18.92 |
| 1036 | CA | ASP | A | 82 | 66.206 | 50.555 | 14.808 | 1.00 | 19.26 |
| 1038 | CB | ASP | A | 82 | 65.374 | 49.380 | 15.347 | 1.00 | 19.80 |
| 1041 | CG | ASP | A | 82 | 64.537 | 48.689 | 14.279 | 1.00 | 21.07 |
| 1042 | OD1 | ASP | A | 82 | 64.370 | 49.232 | 13.167 | 1.00 | 22.88 |
| 1043 | OD2 | ASP | A | 82 | 63.977 | 47.584 | 14.496 | 1.00 | 22.05 |
| 1044 | C | ASP | A | 82 | 66.491 | 51.503 | 15.972 | 1.00 | 18.72 |
| 1045 | O | ASP | A | 82 | 65.743 | 52.455 | 16.193 | 1.00 | 18.90 |
| 1046 | N | ALA | A | 83 | 67.551 | 51.227 | 16.724 | 1.00 | 18.47 |
| 1048 | CA | ALA | A | 83 | 67.879 | 52.031 | 17.902 | 1.00 | 18.05 |
| 1050 | CB | ALA | A | 83 | 68.957 | 51.350 | 18.777 | 1.00 | 18.08 |
| 1054 | C | ALA | A | 83 | 68.262 | 53.464 | 17.528 | 1.00 | 17.75 |
| 1055 | O | ALA | A | 83 | 67.571 | 54.391 | 17.954 | 1.00 | 16.58 |
| 1056 | N | PRO | A | 84 | 69.334 | 53.674 | 16.754 | 1.00 | 17.46 |
| 1057 | CA | PRO | A | 84 | 69.660 | 55.034 | 16.310 | 1.00 | 17.24 |
| 1059 | CB | PRO | A | 84 | 70.978 | 54.870 | 15.537 | 1.00 | 17.48 |
| 1062 | CG | PRO | A | 84 | 71.073 | 53.397 | 15.176 | 1.00 | 17.90 |
| 1065 | CD | PRO | A | 84 | 70.318 | 52.690 | 16.274 | 1.00 | 17.39 |
| 1068 | C | PRO | A | 84 | 68.570 | 55.674 | 15.452 | 1.00 | 17.54 |
| 1069 | O | PRO | A | 84 | 68.372 | 56.871 | 15.546 | 1.00 | 16.99 |
| 1070 | N | ALA | A | 85 | 67.881 | 54.899 | 14.617 | 1.00 | 17.55 |
| 1072 | CA | ALA | A | 85 | 66.786 | 55.439 | 13.827 | 1.00 | 17.51 |
| 1074 | CB | ALA | A | 85 | 66.196 | 54.371 | 12.908 | 1.00 | 17.15 |
| 1078 | C | ALA | A | 85 | 65.710 | 56.010 | 14.751 | 1.00 | 17.33 |
| 1079 | O | ALA | A | 85 | 65.235 | 57.120 | 14.540 | 1.00 | 17.48 |
| 1080 | N | ALA | A | 86 | 65.365 | 55.276 | 15.797 | 1.00 | 17.28 |
| 1082 | CA | ALA | A | 86 | 64.309 | 55.702 | 16.702 | 1.00 | 17.98 |
| 1084 | CB | ALA | A | 86 | 63.858 | 54.558 | 17.575 | 1.00 | 17.95 |
| 1088 | C | ALA | A | 86 | 64.764 | 56.881 | 17.559 | 1.00 | 18.07 |
| 1089 | O | ALA | A | 86 | 63.986 | 57.800 | 17.828 | 1.00 | 18.55 |
| 1090 | N | ALA | A | 87 | 66.027 | 56.852 | 17.965 | 1.00 | 17.63 |
| 1092 | CA | ALA | A | 87 | 66.612 | 57.905 | 18.776 | 1.00 | 17.90 |
| 1094 | CB | ALA | A | 87 | 68.016 | 57.551 | 19.129 | 1.00 | 17.89 |
| 1098 | C | ALA | A | 87 | 66.602 | 59.238 | 18.046 | 1.00 | 18.01 |
| 1099 | O | ALA | A | 87 | 66.199 | 60.258 | 18.611 | 1.00 | 16.96 |
| 1100 | N | VAL | A | 88 | 67.076 | 59.233 | 16.802 | 1.00 | 18.36 |
| 1102 | CA | VAL | A | 88 | 67.108 | 60.469 | 16.022 | 1.00 | 19.02 |
| 1104 | CB | VAL | A | 88 | 67.919 | 60.359 | 14.706 | 1.00 | 19.48 |
| 1106 | CG1 | VAL | A | 88 | 69.346 | 59.943 | 15.004 | 1.00 | 21.38 |
| 1110 | CG2 | VAL | A | 88 | 67.262 | 59.431 | 13.694 | 1.00 | 20.88 |
| 1114 | C | VAL | A | 88 | 65.697 | 60.984 | 15.728 | 1.00 | 18.91 |
| 1115 | O | VAL | A | 88 | 65.478 | 62.192 | 15.694 | 1.00 | 19.41 |
| 1116 | N | GLU | A | 89 | 64.755 | 60.075 | 15.506 | 1.00 | 18.77 |
| 1118 | CA | GLU | A | 89 | 63.371 | 60.460 | 15.281 | 1.00 | 19.03 |
| 1120 | CB | GLU | A | 89 | 62.580 | 59.307 | 14.672 | 1.00 | 19.35 |
| 1123 | CG | GLU | A | 89 | 61.202 | 59.659 | 14.140 | 1.00 | 20.47 |
| 1126 | CD | GLU | A | 89 | 61.187 | 60.686 | 13.014 | 1.00 | 23.08 |
| 1127 | OE1 | GLU | A | 89 | 60.085 | 61.188 | 12.699 | 1.00 | 21.79 |
| 1128 | OE2 | GLU | A | 89 | 62.243 | 61.001 | 12.436 | 1.00 | 22.95 |
| 1129 | C | GLU | A | 89 | 62.726 | 60.972 | 16.571 | 1.00 | 19.06 |

FIGURE 3 AL

| A | B | C | D | E | F | G | H | I | J |
|---|---|---|---|---|---|---|---|---|---|
| 1130 | O | GLU | A | 89 | 61.883 | 61.856 | 16.515 | 1.00 | 18.98 |
| 1131 | N | CYS | A | 90 | 63.154 | 60.466 | 17.724 | 1.00 | 19.07 |
| 1133 | CA | CYS | A | 90 | 62.684 | 61.026 | 18.999 | 1.00 | 19.48 |
| 1135 | CB | CYS | A | 90 | 63.154 | 60.218 | 20.204 | 1.00 | 19.62 |
| 1138 | SG | CYS | A | 90 | 62.240 | 58.692 | 20.462 | 1.00 | 21.40 |
| 1139 | C | CYS | A | 90 | 63.139 | 62.464 | 19.144 | 1.00 | 18.83 |
| 1140 | O | CYS | A | 90 | 62.348 | 63.311 | 19.526 | 1.00 | 19.11 |
| 1141 | N | ILE | A | 91 | 64.405 | 62.740 | 18.846 | 1.00 | 18.13 |
| 1143 | CA | ILE | A | 91 | 64.900 | 64.108 | 18.934 | 1.00 | 17.94 |
| 1145 | CB | ILE | A | 91 | 66.402 | 64.201 | 18.602 | 1.00 | 18.00 |
| 1147 | CG1 | ILE | A | 91 | 67.269 | 63.442 | 19.628 | 1.00 | 18.23 |
| 1150 | CD1 | ILE | A | 91 | 67.160 | 63.942 | 21.057 | 1.00 | 18.91 |
| 1154 | CG2 | ILE | A | 91 | 66.824 | 65.659 | 18.520 | 1.00 | 18.94 |
| 1158 | C | ILE | A | 91 | 64.117 | 64.994 | 17.959 | 1.00 | 17.15 |
| 1159 | O | ILE | A | 91 | 63.700 | 66.094 | 18.308 | 1.00 | 16.79 |
| 1160 | N | HIS | A | 92 | 63.952 | 64.506 | 16.732 | 1.00 | 16.32 |
| 1162 | CA | HIS | A | 92 | 63.238 | 65.238 | 15.701 | 1.00 | 16.58 |
| 1164 | CB | HIS | A | 92 | 63.182 | 64.438 | 14.409 | 1.00 | 16.65 |
| 1167 | CG | HIS | A | 92 | 62.424 | 65.119 | 13.321 | 1.00 | 16.27 |
| 1168 | ND1 | HIS | A | 92 | 61.352 | 64.536 | 12.675 | 1.00 | 17.53 |
| 1170 | CE1 | HIS | A | 92 | 60.892 | 65.378 | 11.761 | 1.00 | 15.88 |
| 1172 | NE2 | HIS | A | 92 | 61.620 | 66.480 | 11.800 | 1.00 | 17.29 |
| 1174 | CD2 | HIS | A | 92 | 62.573 | 66.348 | 12.779 | 1.00 | 15.01 |
| 1176 | C | HIS | A | 92 | 61.825 | 65.555 | 16.167 | 1.00 | 16.53 |
| 1177 | O | HIS | A | 92 | 61.399 | 66.712 | 16.151 | 1.00 | 16.57 |
| 1178 | N | ALA | A | 93 | 61.119 | 64.532 | 16.620 | 1.00 | 15.86 |
| 1180 | CA | ALA | A | 93 | 59.753 | 64.699 | 17.119 | 1.00 | 16.23 |
| 1182 | CB | ALA | A | 93 | 59.177 | 63.346 | 17.566 | 1.00 | 16.25 |
| 1186 | C | ALA | A | 93 | 59.671 | 65.720 | 18.251 | 1.00 | 16.36 |
| 1187 | O | ALA | A | 93 | 58.753 | 66.544 | 18.297 | 1.00 | 16.22 |
| 1188 | N | TYR | A | 94 | 60.632 | 65.668 | 19.168 | 1.00 | 16.81 |
| 1190 | CA | TYR | A | 94 | 60.653 | 66.585 | 20.289 | 1.00 | 17.25 |
| 1192 | CB | TYR | A | 94 | 61.742 | 66.187 | 21.312 | 1.00 | 18.09 |
| 1195 | CG | TYR | A | 94 | 62.785 | 67.233 | 21.639 | 1.00 | 18.65 |
| 1196 | CD1 | TYR | A | 94 | 62.444 | 68.391 | 22.309 | 1.00 | 20.51 |
| 1198 | CE1 | TYR | A | 94 | 63.388 | 69.341 | 22.613 | 1.00 | 22.48 |
| 1200 | CZ | TYR | A | 94 | 64.701 | 69.138 | 22.248 | 1.00 | 22.20 |
| 1201 | OH | TYR | A | 94 | 65.628 | 70.083 | 22.565 | 1.00 | 24.51 |
| 1203 | CE2 | TYR | A | 94 | 65.075 | 67.983 | 21.590 | 1.00 | 21.60 |
| 1205 | CD2 | TYR | A | 94 | 64.122 | 67.037 | 21.306 | 1.00 | 19.95 |
| 1207 | C | TYR | A | 94 | 60.837 | 68.001 | 19.766 | 1.00 | 17.28 |
| 1208 | O | TYR | A | 94 | 60.178 | 68.921 | 20.232 | 1.00 | 16.91 |
| 1209 | N | SER | A | 95 | 61.709 | 68.169 | 18.780 | 1.00 | 17.12 |
| 1211 | CA | SER | A | 95 | 62.028 | 69.486 | 18.281 | 1.00 | 17.61 |
| 1213 | CB | SER | A | 95 | 63.209 | 69.446 | 17.312 | 1.00 | 17.91 |
| 1216 | OG | SER | A | 95 | 62.859 | 68.946 | 16.045 | 1.00 | 19.03 |
| 1218 | C | SER | A | 95 | 60.787 | 70.161 | 17.665 | 1.00 | 18.18 |
| 1219 | O | SER | A | 95 | 60.591 | 71.367 | 17.826 | 1.00 | 17.08 |
| 1220 | N | LEU | A | 96 | 59.936 | 69.376 | 17.021 | 1.00 | 18.08 |
| 1222 | CA | LEU | A | 96 | 58.748 | 69.937 | 16.356 | 1.00 | 18.75 |
| 1224 | CB | LEU | A | 96 | 58.168 | 68.946 | 15.359 | 1.00 | 18.81 |
| 1227 | CG | LEU | A | 96 | 59.159 | 68.371 | 14.350 | 1.00 | 19.61 |

FIGURE 3 AM

| A | B | C | D | E | F | G | H | I | J |
|---|---|---|---|---|---|---|---|---|---|
| 1229 | CD1 | LEU | A | 96 | 58.421 | 67.472 | 13.385 | 1.00 | 19.87 |
| 1233 | CD2 | LEU | A | 96 | 59.901 | 69.477 | 13.628 | 1.00 | 20.82 |
| 1237 | C | LEU | A | 96 | 57.676 | 70.285 | 17.371 | 1.00 | 18.79 |
| 1238 | O | LEU | A | 96 | 56.928 | 71.252 | 17.192 | 1.00 | 19.67 |
| 1239 | N | ILE | A | 97 | 57.581 | 69.478 | 18.422 | 1.00 | 18.80 |
| 1241 | CA | ILE | A | 97 | 56.574 | 69.704 | 19.448 | 1.00 | 18.69 |
| 1243 | CB | ILE | A | 97 | 56.590 | 68.612 | 20.520 | 1.00 | 18.23 |
| 1245 | CG1 | ILE | A | 97 | 56.062 | 67.307 | 19.941 | 1.00 | 17.66 |
| 1248 | CD1 | ILE | A | 97 | 56.017 | 66.149 | 20.924 | 1.00 | 19.38 |
| 1252 | CG2 | ILE | A | 97 | 55.756 | 69.050 | 21.746 | 1.00 | 18.51 |
| 1256 | C | ILE | A | 97 | 56.844 | 71.069 | 20.071 | 1.00 | 19.44 |
| 1257 | O | ILE | A | 97 | 55.925 | 71.851 | 20.233 | 1.00 | 19.55 |
| 1258 | N | HIS | A | 98 | 58.108 | 71.358 | 20.383 | 1.00 | 19.42 |
| 1260 | CA | HIS | A | 98 | 58.452 | 72.609 | 21.039 | 1.00 | 20.66 |
| 1262 | CB | HIS | A | 98 | 59.797 | 72.507 | 21.730 | 1.00 | 21.50 |
| 1265 | CG | HIS | A | 98 | 59.735 | 71.795 | 23.045 | 1.00 | 25.90 |
| 1266 | ND1 | HIS | A | 98 | 59.610 | 70.432 | 23.149 | 1.00 | 34.19 |
| 1268 | CE1 | HIS | A | 98 | 59.570 | 70.087 | 24.425 | 1.00 | 32.41 |
| 1270 | NE2 | HIS | A | 98 | 59.660 | 71.175 | 25.149 | 1.00 | 32.34 |
| 1272 | CD2 | HIS | A | 98 | 59.748 | 72.261 | 24.312 | 1.00 | 32.88 |
| 1274 | C | HIS | A | 98 | 58.437 | 73.774 | 20.072 | 1.00 | 20.22 |
| 1275 | O | HIS | A | 98 | 58.095 | 74.880 | 20.444 | 1.00 | 20.04 |
| 1276 | N | ASP | A | 99 | 58.809 | 73.500 | 18.829 | 1.00 | 20.34 |
| 1278 | CA | ASP | A | 99 | 58.834 | 74.488 | 17.772 | 1.00 | 20.27 |
| 1280 | CB | ASP | A | 99 | 59.394 | 73.845 | 16.496 | 1.00 | 20.14 |
| 1283 | CG | ASP | A | 99 | 59.438 | 74.806 | 15.326 | 1.00 | 19.89 |
| 1284 | OD1 | ASP | A | 99 | 58.542 | 74.720 | 14.458 | 1.00 | 20.18 |
| 1285 | OD2 | ASP | A | 99 | 60.332 | 75.665 | 15.194 | 1.00 | 18.02 |
| 1286 | C | ASP | A | 99 | 57.447 | 75.081 | 17.512 | 1.00 | 20.91 |
| 1287 | O | ASP | A | 99 | 57.322 | 76.277 | 17.253 | 1.00 | 21.26 |
| 1288 | N | ASP | A | 100 | 56.410 | 74.254 | 17.580 | 1.00 | 21.41 |
| 1290 | CA | ASP | A | 100 | 55.037 | 74.718 | 17.328 | 1.00 | 21.41 |
| 1292 | CB | ASP | A | 100 | 54.098 | 73.551 | 17.048 | 1.00 | 21.45 |
| 1295 | CG | ASP | A | 100 | 54.436 | 72.819 | 15.799 | 1.00 | 20.29 |
| 1296 | OD1 | ASP | A | 100 | 54.167 | 71.594 | 15.734 | 1.00 | 20.18 |
| 1297 | OD2 | ASP | A | 100 | 54.978 | 73.379 | 14.841 | 1.00 | 19.29 |
| 1298 | C | ASP | A | 100 | 54.428 | 75.500 | 18.483 | 1.00 | 21.71 |
| 1299 | O | ASP | A | 100 | 53.395 | 76.123 | 18.301 | 1.00 | 22.06 |
| 1300 | N | LEU | A | 101 | 55.039 | 75.467 | 19.664 | 1.00 | 21.73 |
| 1302 | CA | LEU | A | 101 | 54.463 | 76.129 | 20.837 | 1.00 | 21.71 |
| 1304 | CB | LEU | A | 101 | 55.389 | 76.027 | 22.052 | 1.00 | 21.29 |
| 1307 | CG | LEU | A | 101 | 55.643 | 74.639 | 22.631 | 1.00 | 21.02 |
| 1309 | CD1 | LEU | A | 101 | 56.681 | 74.748 | 23.744 | 1.00 | 21.63 |
| 1313 | CD2 | LEU | A | 101 | 54.375 | 73.987 | 23.130 | 1.00 | 21.37 |
| 1317 | C | LEU | A | 101 | 54.173 | 77.611 | 20.587 | 1.00 | 22.13 |
| 1318 | O | LEU | A | 101 | 54.852 | 78.255 | 19.795 | 1.00 | 21.48 |
| 1319 | N | PRO | A | 102 | 53.167 | 78.152 | 21.273 | 1.00 | 23.19 |
| 1320 | CA | PRO | A | 102 | 52.850 | 79.588 | 21.175 | 1.00 | 23.59 |
| 1322 | CB | PRO | A | 102 | 51.811 | 79.779 | 22.282 | 1.00 | 24.00 |
| 1325 | CG | PRO | A | 102 | 51.099 | 78.464 | 22.308 | 1.00 | 23.90 |
| 1328 | CD | PRO | A | 102 | 52.216 | 77.443 | 22.149 | 1.00 | 22.62 |
| 1331 | C | PRO | A | 102 | 54.045 | 80.533 | 21.348 | 1.00 | 24.21 |

FIGURE 3 AN

| A | B | C | D | E | F | G | H | I | J |
|---|---|---|---|---|---|---|---|---|---|
| 1332 | O | PRO | A | 102 | 54.148 | 81.494 | 20.599 | 1.00 | 25.11 |
| 1333 | N | ALA | A | 103 | 54.943 | 80.255 | 22.285 | 1.00 | 24.74 |
| 1335 | CA | ALA | A | 103 | 56.123 | 81.094 | 22.516 | 1.00 | 25.23 |
| 1337 | CB | ALA | A | 103 | 56.753 | 80.737 | 23.867 | 1.00 | 25.78 |
| 1341 | C | ALA | A | 103 | 57.176 | 80.941 | 21.417 | 1.00 | 25.46 |
| 1342 | O | ALA | A | 103 | 58.093 | 81.742 | 21.317 | 1.00 | 24.70 |
| 1343 | N | MET | A | 104 | 57.053 | 79.879 | 20.626 | 1.00 | 25.19 |
| 1345 | CA | MET | A | 104 | 57.981 | 79.590 | 19.550 | 1.00 | 26.00 |
| 1347 | CB | MET | A | 104 | 58.362 | 78.109 | 19.598 | 1.00 | 25.79 |
| 1350 | CG | MET | A | 104 | 58.997 | 77.719 | 20.916 | 1.00 | 27.52 |
| 1353 | SD | MET | A | 104 | 60.690 | 78.194 | 20.987 | 1.00 | 31.55 |
| 1354 | CE | MET | A | 104 | 61.411 | 77.093 | 19.688 | 1.00 | 31.97 |
| 1358 | C | MET | A | 104 | 57.345 | 79.995 | 18.207 | 1.00 | 25.73 |
| 1359 | O | MET | A | 104 | 57.213 | 81.186 | 17.942 | 1.00 | 25.54 |
| 1360 | N | ASP | A | 105 | 56.937 | 79.038 | 17.374 | 1.00 | 25.29 |
| 1362 | CA | ASP | A | 105 | 56.373 | 79.388 | 16.061 | 1.00 | 25.81 |
| 1364 | CB | ASP | A | 105 | 56.832 | 78.419 | 14.969 | 1.00 | 25.24 |
| 1367 | CG | ASP | A | 105 | 58.319 | 78.496 | 14.716 | 1.00 | 24.83 |
| 1368 | OD1 | ASP | A | 105 | 58.853 | 77.642 | 13.954 | 1.00 | 22.09 |
| 1369 | OD2 | ASP | A | 105 | 59.049 | 79.364 | 15.253 | 1.00 | 25.62 |
| 1370 | C | ASP | A | 105 | 54.851 | 79.525 | 16.069 | 1.00 | 25.92 |
| 1371 | O | ASP | A | 105 | 54.289 | 80.054 | 15.126 | 1.00 | 26.07 |
| 1372 | N | ASP | A | 106 | 54.206 | 79.043 | 17.125 | 1.00 | 26.89 |
| 1374 | CA | ASP | A | 106 | 52.759 | 79.211 | 17.350 | 1.00 | 27.69 |
| 1376 | CB | ASP | A | 106 | 52.419 | 80.670 | 17.671 | 1.00 | 28.12 |
| 1379 | CG | ASP | A | 106 | 51.000 | 80.840 | 18.202 | 1.00 | 29.63 |
| 1380 | OD1 | ASP | A | 106 | 50.458 | 81.960 | 18.094 | 1.00 | 31.75 |
| 1381 | OD2 | ASP | A | 106 | 50.342 | 79.911 | 18.732 | 1.00 | 31.76 |
| 1382 | C | ASP | A | 106 | 51.952 | 78.715 | 16.157 | 1.00 | 28.05 |
| 1383 | O | ASP | A | 106 | 51.159 | 79.450 | 15.549 | 1.00 | 28.01 |
| 1384 | N | ASP | A | 107 | 52.190 | 77.456 | 15.809 | 1.00 | 28.07 |
| 1386 | CA | ASP | A | 107 | 51.534 | 76.822 | 14.686 | 1.00 | 27.99 |
| 1388 | CB | ASP | A | 107 | 52.553 | 76.037 | 13.855 | 1.00 | 28.56 |
| 1391 | CG | ASP | A | 107 | 53.069 | 76.830 | 12.677 | 1.00 | 29.78 |
| 1392 | OD1 | ASP | A | 107 | 52.257 | 77.111 | 11.774 | 1.00 | 33.36 |
| 1393 | OD2 | ASP | A | 107 | 54.255 | 77.210 | 12.549 | 1.00 | 31.90 |
| 1394 | C | ASP | A | 107 | 50.478 | 75.882 | 15.230 | 1.00 | 27.64 |
| 1395 | O | ASP | A | 107 | 50.693 | 75.218 | 16.248 | 1.00 | 26.98 |
| 1396 | N | ASP | A | 108 | 49.334 | 75.823 | 14.559 | 1.00 | 26.95 |
| 1398 | CA | ASP | A | 108 | 48.242 | 74.989 | 15.031 | 1.00 | 26.81 |
| 1400 | CB | ASP | A | 108 | 46.929 | 75.778 | 15.089 | 1.00 | 27.66 |
| 1403 | CG | ASP | A | 108 | 46.453 | 76.241 | 13.725 | 1.00 | 30.37 |
| 1404 | OD1 | ASP | A | 108 | 45.282 | 76.700 | 13.645 | 1.00 | 33.61 |
| 1405 | OD2 | ASP | A | 108 | 47.165 | 76.194 | 12.690 | 1.00 | 32.04 |
| 1406 | C | ASP | A | 108 | 48.075 | 73.702 | 14.236 | 1.00 | 25.96 |
| 1407 | O | ASP | A | 108 | 47.283 | 72.856 | 14.631 | 1.00 | 25.76 |
| 1408 | N | LEU | A | 109 | 48.818 | 73.559 | 13.136 | 1.00 | 25.04 |
| 1410 | CA | LEU | A | 109 | 48.751 | 72.367 | 12.298 | 1.00 | 24.85 |
| 1412 | CB | LEU | A | 109 | 48.106 | 72.694 | 10.945 | 1.00 | 25.33 |
| 1415 | CG | LEU | A | 109 | 46.598 | 72.821 | 10.810 | 1.00 | 26.83 |
| 1417 | CD1 | LEU | A | 109 | 46.260 | 73.283 | 9.399 | 1.00 | 29.44 |
| 1421 | CD2 | LEU | A | 109 | 45.903 | 71.492 | 11.089 | 1.00 | 27.95 |

FIGURE 3 AO

| A | B | C | D | E | F | G | H | I | J |
|---|---|---|---|---|---|---|---|---|---|
| 1425 | C | LEU | A | 109 | 50.144 | 71.781 | 12.034 | 1.00 | 23.64 |
| 1426 | O | LEU | A | 109 | 51.094 | 72.514 | 11.790 | 1.00 | 23.64 |
| 1427 | N | ARG | A | 110 | 50.237 | 70.454 | 12.081 | 1.00 | 22.79 |
| 1429 | CA | ARG | A | 110 | 51.401 | 69.715 | 11.603 | 1.00 | 22.20 |
| 1431 | CB | ARG | A | 110 | 52.479 | 69.644 | 12.672 | 1.00 | 21.90 |
| 1434 | CG | ARG | A | 110 | 53.742 | 69.015 | 12.166 | 1.00 | 21.62 |
| 1437 | CD | ARG | A | 110 | 54.820 | 68.975 | 13.195 | 1.00 | 21.16 |
| 1440 | NE | ARG | A | 110 | 55.377 | 70.290 | 13.472 | 1.00 | 19.55 |
| 1442 | CZ | ARG | A | 110 | 56.277 | 70.905 | 12.721 | 1.00 | 21.19 |
| 1443 | NH1 | ARG | A | 110 | 56.740 | 72.082 | 13.111 | 1.00 | 21.55 |
| 1446 | NH2 | ARG | A | 110 | 56.737 | 70.355 | 11.590 | 1.00 | 21.98 |
| 1449 | C | ARG | A | 110 | 50.997 | 68.301 | 11.215 | 1.00 | 21.87 |
| 1450 | O | ARG | A | 110 | 50.184 | 67.686 | 11.876 | 1.00 | 20.97 |
| 1451 | N | ARG | A | 111 | 51.566 | 67.807 | 10.122 | 1.00 | 22.79 |
| 1453 | CA | ARG | A | 111 | 51.237 | 66.489 | 9.580 | 1.00 | 23.42 |
| 1455 | CB | ARG | A | 111 | 51.814 | 65.407 | 10.477 | 1.00 | 23.33 |
| 1458 | CG | ARG | A | 111 | 53.310 | 65.424 | 10.531 | 1.00 | 22.10 |
| 1461 | CD | ARG | A | 111 | 53.841 | 64.752 | 11.768 | 1.00 | 21.59 |
| 1464 | NE | ARG | A | 111 | 55.282 | 64.632 | 11.726 | 1.00 | 21.10 |
| 1466 | CZ | ARG | A | 111 | 56.009 | 64.082 | 12.681 | 1.00 | 21.03 |
| 1467 | NH1 | ARG | A | 111 | 55.438 | 63.576 | 13.760 | 1.00 | 20.75 |
| 1470 | NH2 | ARG | A | 111 | 57.323 | 64.020 | 12.544 | 1.00 | 22.79 |
| 1473 | C | ARG | A | 111 | 49.733 | 66.284 | 9.374 | 1.00 | 24.49 |
| 1474 | O | ARG | A | 111 | 49.216 | 65.181 | 9.528 | 1.00 | 24.90 |
| 1475 | N | GLY | A | 112 | 49.048 | 67.375 | 9.037 | 1.00 | 25.84 |
| 1477 | CA | GLY | A | 112 | 47.641 | 67.363 | 8.673 | 1.00 | 26.45 |
| 1480 | C | GLY | A | 112 | 46.709 | 67.432 | 9.854 | 1.00 | 27.01 |
| 1481 | O | GLY | A | 112 | 45.500 | 67.383 | 9.663 | 1.00 | 27.66 |
| 1482 | N | LEU | A | 113 | 47.258 | 67.574 | 11.066 | 1.00 | 27.18 |
| 1484 | CA | LEU | A | 113 | 46.478 | 67.445 | 12.301 | 1.00 | 27.29 |
| 1486 | CB | LEU | A | 113 | 46.778 | 66.104 | 12.965 | 1.00 | 27.61 |
| 1489 | CG | LEU | A | 113 | 46.308 | 64.849 | 12.230 | 1.00 | 29.25 |
| 1491 | CD1 | LEU | A | 113 | 46.956 | 63.639 | 12.826 | 1.00 | 29.40 |
| 1495 | CD2 | LEU | A | 113 | 44.799 | 64.723 | 12.297 | 1.00 | 30.33 |
| 1499 | C | LEU | A | 113 | 46.783 | 68.580 | 13.279 | 1.00 | 26.95 |
| 1500 | O | LEU | A | 113 | 47.781 | 69.273 | 13.134 | 1.00 | 26.97 |
| 1501 | N | PRO | A | 114 | 45.911 | 68.807 | 14.256 | 1.00 | 26.77 |
| 1502 | CA | PRO | A | 114 | 46.242 | 69.737 | 15.341 | 1.00 | 26.42 |
| 1504 | CB | PRO | A | 114 | 45.151 | 69.465 | 16.391 | 1.00 | 26.39 |
| 1507 | CG | PRO | A | 114 | 43.997 | 68.927 | 15.636 | 1.00 | 27.10 |
| 1510 | CD | PRO | A | 114 | 44.540 | 68.278 | 14.377 | 1.00 | 27.03 |
| 1513 | C | PRO | A | 114 | 47.644 | 69.428 | 15.902 | 1.00 | 25.96 |
| 1514 | O | PRO | A | 114 | 47.988 | 68.247 | 16.088 | 1.00 | 25.12 |
| 1515 | N | THR | A | 115 | 48.433 | 70.470 | 16.131 | 1.00 | 25.63 |
| 1517 | CA | THR | A | 115 | 49.730 | 70.336 | 16.803 | 1.00 | 25.53 |
| 1519 | CB | THR | A | 115 | 50.478 | 71.668 | 16.835 | 1.00 | 25.67 |
| 1521 | OG1 | THR | A | 115 | 49.605 | 72.715 | 17.288 | 1.00 | 26.41 |
| 1523 | CG2 | THR | A | 115 | 50.901 | 72.085 | 15.442 | 1.00 | 25.77 |
| 1527 | C | THR | A | 115 | 49.531 | 69.838 | 18.228 | 1.00 | 25.27 |
| 1528 | O | THR | A | 115 | 48.430 | 69.941 | 18.787 | 1.00 | 24.78 |
| 1529 | N | CYS | A | 116 | 50.600 | 69.305 | 18.817 | 1.00 | 24.89 |
| 1531 | CA | CYS | A | 116 | 50.523 | 68.697 | 20.137 | 1.00 | 24.95 |

FIGURE 3 AP

| A | B | C | D | E | F | G | H | I | J |
|---|---|---|---|---|---|---|---|---|---|
| 1533 | CB | CYS | A | 116 | 51.895 | 68.165 | 20.581 | 1.00 | 24.90 |
| 1536 | SG | CYS | A | 116 | 52.285 | 66.565 | 19.821 | 1.00 | 24.91 |
| 1537 | C | CYS | A | 116 | 49.933 | 69.634 | 21.182 | 1.00 | 24.97 |
| 1538 | O | CYS | A | 116 | 49.096 | 69.228 | 21.971 | 1.00 | 24.71 |
| 1539 | N | HIS | A | 117 | 50.346 | 70.894 | 21.168 | 1.00 | 25.78 |
| 1541 | CA | HIS | A | 117 | 49.925 | 71.820 | 22.208 | 1.00 | 26.16 |
| 1543 | CB | HIS | A | 117 | 50.836 | 73.054 | 22.246 | 1.00 | 26.51 |
| 1546 | CG | HIS | A | 117 | 50.548 | 74.067 | 21.186 | 1.00 | 27.10 |
| 1547 | ND1 | HIS | A | 117 | 50.785 | 73.840 | 19.849 | 1.00 | 30.89 |
| 1549 | CE1 | HIS | A | 117 | 50.441 | 74.911 | 19.156 | 1.00 | 30.52 |
| 1551 | NE2 | HIS | A | 117 | 50.007 | 75.831 | 19.996 | 1.00 | 30.35 |
| 1553 | CD2 | HIS | A | 117 | 50.066 | 75.327 | 21.272 | 1.00 | 29.44 |
| 1555 | C | HIS | A | 117 | 48.433 | 72.162 | 22.054 | 1.00 | 26.69 |
| 1556 | O | HIS | A | 117 | 47.747 | 72.385 | 23.040 | 1.00 | 26.52 |
| 1557 | N | VAL | A | 118 | 47.938 | 72.180 | 20.820 | 1.00 | 27.17 |
| 1559 | CA | VAL | A | 118 | 46.510 | 72.380 | 20.577 | 1.00 | 27.86 |
| 1561 | CB | VAL | A | 118 | 46.217 | 72.617 | 19.078 | 1.00 | 27.70 |
| 1563 | CG1 | VAL | A | 118 | 44.701 | 72.510 | 18.774 | 1.00 | 28.86 |
| 1567 | CG2 | VAL | A | 118 | 46.737 | 73.972 | 18.645 | 1.00 | 28.14 |
| 1571 | C | VAL | A | 118 | 45.695 | 71.196 | 21.131 | 1.00 | 28.24 |
| 1572 | O | VAL | A | 118 | 44.784 | 71.396 | 21.935 | 1.00 | 28.47 |
| 1573 | N | LYS | A | 119 | 46.040 | 69.973 | 20.733 | 1.00 | 28.54 |
| 1575 | CA | LYS | A | 119 | 45.245 | 68.798 | 21.101 | 1.00 | 29.34 |
| 1577 | CB | LYS | A | 119 | 45.617 | 67.583 | 20.241 | 1.00 | 29.61 |
| 1580 | CG | LYS | A | 119 | 44.863 | 66.301 | 20.626 | 1.00 | 30.82 |
| 1583 | CD | LYS | A | 119 | 45.106 | 65.186 | 19.627 | 1.00 | 32.53 |
| 1586 | CE | LYS | A | 119 | 44.199 | 63.976 | 19.839 | 1.00 | 33.76 |
| 1589 | NZ | LYS | A | 119 | 43.344 | 64.050 | 21.054 | 1.00 | 36.05 |
| 1593 | C | LYS | A | 119 | 45.371 | 68.422 | 22.581 | 1.00 | 29.59 |
| 1594 | O | LYS | A | 119 | 44.383 | 68.012 | 23.194 | 1.00 | 29.82 |
| 1595 | N | PHE | A | 120 | 46.575 | 68.551 | 23.146 | 1.00 | 28.84 |
| 1597 | CA | PHE | A | 120 | 46.839 | 68.108 | 24.519 | 1.00 | 28.62 |
| 1599 | CB | PHE | A | 120 | 47.984 | 67.096 | 24.529 | 1.00 | 28.31 |
| 1602 | CG | PHE | A | 120 | 47.722 | 65.880 | 23.711 | 1.00 | 27.28 |
| 1603 | CD1 | PHE | A | 120 | 47.055 | 64.787 | 24.261 | 1.00 | 27.38 |
| 1605 | CE1 | PHE | A | 120 | 46.831 | 63.631 | 23.508 | 1.00 | 27.16 |
| 1607 | CZ | PHE | A | 120 | 47.271 | 63.563 | 22.198 | 1.00 | 27.58 |
| 1609 | CE2 | PHE | A | 120 | 47.932 | 64.648 | 21.636 | 1.00 | 27.23 |
| 1611 | CD2 | PHE | A | 120 | 48.163 | 65.804 | 22.399 | 1.00 | 27.44 |
| 1613 | C | PHE | A | 120 | 47.185 | 69.217 | 25.515 | 1.00 | 28.26 |
| 1614 | O | PHE | A | 120 | 47.341 | 68.943 | 26.706 | 1.00 | 29.25 |
| 1615 | N | GLY | A | 121 | 47.299 | 70.452 | 25.042 | 1.00 | 27.60 |
| 1617 | CA | GLY | A | 121 | 47.659 | 71.575 | 25.896 | 1.00 | 26.94 |
| 1620 | C | GLY | A | 121 | 49.155 | 71.840 | 25.860 | 1.00 | 26.46 |
| 1621 | O | GLY | A | 121 | 49.958 | 70.992 | 25.438 | 1.00 | 26.06 |
| 1622 | N | GLU | A | 122 | 49.536 | 73.009 | 26.340 | 1.00 | 25.72 |
| 1624 | CA | GLU | A | 122 | 50.910 | 73.462 | 26.248 | 1.00 | 25.58 |
| 1626 | CB | GLU | A | 122 | 51.007 | 74.958 | 26.519 | 1.00 | 25.87 |
| 1629 | CG | GLU | A | 122 | 50.483 | 75.783 | 25.358 | 1.00 | 29.11 |
| 1632 | CD | GLU | A | 122 | 50.355 | 77.241 | 25.698 | 1.00 | 33.26 |
| 1633 | OE1 | GLU | A | 122 | 51.247 | 77.754 | 26.399 | 1.00 | 35.51 |
| 1634 | OE2 | GLU | A | 122 | 49.349 | 77.861 | 25.269 | 1.00 | 37.97 |

FIGURE 3 AQ

| A | B | C | D | E | F | G | H | I | J |
|---|---|---|---|---|---|---|---|---|---|
| 1635 | C | GLU | A | 122 | 51.798 | 72.689 | 27.211 | 1.00 | 24.80 |
| 1636 | O | GLU | A | 122 | 52.899 | 72.300 | 26.840 | 1.00 | 24.40 |
| 1637 | N | ALA | A | 123 | 51.320 | 72.474 | 28.436 | 1.00 | 23.77 |
| 1639 | CA | ALA | A | 123 | 52.098 | 71.760 | 29.447 | 1.00 | 23.73 |
| 1641 | CB | ALA | A | 123 | 51.353 | 71.711 | 30.776 | 1.00 | 23.98 |
| 1645 | C | ALA | A | 123 | 52.441 | 70.343 | 28.968 | 1.00 | 23.81 |
| 1646 | O | ALA | A | 123 | 53.603 | 69.943 | 29.024 | 1.00 | 24.19 |
| 1647 | N | ASN | A | 124 | 51.442 | 69.609 | 28.479 | 1.00 | 22.86 |
| 1649 | CA | ASN | A | 124 | 51.654 | 68.270 | 27.947 | 1.00 | 22.86 |
| 1651 | CB | ASN | A | 124 | 50.345 | 67.623 | 27.491 | 1.00 | 23.02 |
| 1654 | CG | ASN | A | 124 | 49.539 | 67.041 | 28.635 | 1.00 | 24.68 |
| 1655 | OD1 | ASN | A | 124 | 48.304 | 67.110 | 28.640 | 1.00 | 27.85 |
| 1656 | ND2 | ASN | A | 124 | 50.220 | 66.461 | 29.600 | 1.00 | 25.67 |
| 1659 | C | ASN | A | 124 | 52.631 | 68.261 | 26.779 | 1.00 | 21.84 |
| 1660 | O | ASN | A | 124 | 53.428 | 67.339 | 26.667 | 1.00 | 22.15 |
| 1661 | N | ALA | A | 125 | 52.543 | 69.263 | 25.908 | 1.00 | 20.33 |
| 1663 | CA | ALA | A | 125 | 53.457 | 69.399 | 24.788 | 1.00 | 20.39 |
| 1665 | CB | ALA | A | 125 | 52.984 | 70.529 | 23.886 | 1.00 | 20.63 |
| 1669 | C | ALA | A | 125 | 54.925 | 69.621 | 25.250 | 1.00 | 19.95 |
| 1670 | O | ALA | A | 125 | 55.856 | 68.974 | 24.760 | 1.00 | 19.97 |
| 1671 | N | ILE | A | 126 | 55.117 | 70.509 | 26.218 | 1.00 | 19.41 |
| 1673 | CA | ILE | A | 126 | 56.434 | 70.769 | 26.790 | 1.00 | 19.39 |
| 1675 | CB | ILE | A | 126 | 56.357 | 71.842 | 27.880 | 1.00 | 19.07 |
| 1677 | CG1 | ILE | A | 126 | 56.032 | 73.214 | 27.267 | 1.00 | 20.58 |
| 1680 | CD1 | ILE | A | 126 | 55.450 | 74.180 | 28.244 | 1.00 | 22.11 |
| 1684 | CG2 | ILE | A | 126 | 57.668 | 71.944 | 28.623 | 1.00 | 19.77 |
| 1688 | C | ILE | A | 126 | 57.011 | 69.487 | 27.378 | 1.00 | 19.19 |
| 1689 | O | ILE | A | 126 | 58.134 | 69.105 | 27.069 | 1.00 | 18.97 |
| 1690 | N | LEU | A | 127 | 56.229 | 68.824 | 28.211 | 1.00 | 18.52 |
| 1692 | CA | LEU | A | 127 | 56.694 | 67.637 | 28.913 | 1.00 | 19.19 |
| 1694 | CB | LEU | A | 127 | 55.716 | 67.252 | 30.029 | 1.00 | 19.06 |
| 1697 | CG | LEU | A | 127 | 55.616 | 68.280 | 31.166 | 1.00 | 20.37 |
| 1699 | CD1 | LEU | A | 127 | 56.961 | 68.500 | 31.859 | 1.00 | 22.60 |
| 1703 | CD2 | LEU | A | 127 | 54.595 | 67.820 | 32.159 | 1.00 | 21.48 |
| 1707 | C | LEU | A | 127 | 56.907 | 66.470 | 27.966 | 1.00 | 18.53 |
| 1708 | O | LEU | A | 127 | 57.856 | 65.723 | 28.126 | 1.00 | 18.41 |
| 1709 | N | ALA | A | 128 | 56.033 | 66.320 | 26.973 | 1.00 | 17.92 |
| 1711 | CA | ALA | A | 128 | 56.179 | 65.228 | 26.012 | 1.00 | 17.62 |
| 1713 | CB | ALA | A | 128 | 54.947 | 65.115 | 25.104 | 1.00 | 17.67 |
| 1717 | C | ALA | A | 128 | 57.434 | 65.418 | 25.168 | 1.00 | 17.09 |
| 1718 | O | ALA | A | 128 | 58.108 | 64.461 | 24.828 | 1.00 | 17.12 |
| 1719 | N | GLY | A | 129 | 57.740 | 66.649 | 24.807 | 1.00 | 16.81 |
| 1721 | CA | GLY | A | 129 | 58.945 | 66.914 | 24.059 | 1.00 | 16.96 |
| 1724 | C | GLY | A | 129 | 60.155 | 66.651 | 24.946 | 1.00 | 17.30 |
| 1725 | O | GLY | A | 129 | 61.102 | 66.022 | 24.500 | 1.00 | 17.59 |
| 1726 | N | ASP | A | 130 | 60.106 | 67.121 | 26.193 | 1.00 | 17.16 |
| 1728 | CA | ASP | A | 130 | 61.139 | 66.853 | 27.190 | 1.00 | 17.77 |
| 1730 | CB | ASP | A | 130 | 60.717 | 67.383 | 28.562 | 1.00 | 18.20 |
| 1733 | CG | ASP | A | 130 | 60.801 | 68.881 | 28.661 | 1.00 | 19.18 |
| 1734 | OD1 | ASP | A | 130 | 61.407 | 69.492 | 27.759 | 1.00 | 21.99 |
| 1735 | OD2 | ASP | A | 130 | 60.295 | 69.527 | 29.612 | 1.00 | 19.91 |
| 1736 | C | ASP | A | 130 | 61.410 | 65.359 | 27.301 | 1.00 | 17.64 |

FIGURE 3 AR

| A | B | C | D | E | F | G | H | I | J |
|---|---|---|---|---|---|---|---|---|---|
| 1737 | O | ASP | A | 130 | 62.548 | 64.927 | 27.230 | 1.00 | 17.90 |
| 1738 | N | ALA | A | 131 | 60.343 | 64.584 | 27.447 | 1.00 | 17.42 |
| 1740 | CA | ALA | A | 131 | 60.438 | 63.146 | 27.633 | 1.00 | 17.39 |
| 1742 | CB | ALA | A | 131 | 59.098 | 62.582 | 28.089 | 1.00 | 17.97 |
| 1746 | C | ALA | A | 131 | 60.910 | 62.429 | 26.378 | 1.00 | 17.06 |
| 1747 | O | ALA | A | 131 | 61.576 | 61.425 | 26.482 | 1.00 | 16.51 |
| 1748 | N | LEU | A | 132 | 60.525 | 62.918 | 25.197 | 1.00 | 17.23 |
| 1750 | CA | LEU | A | 132 | 61.005 | 62.333 | 23.947 | 1.00 | 17.60 |
| 1752 | CB | LEU | A | 132 | 60.265 | 62.904 | 22.740 | 1.00 | 17.59 |
| 1755 | CG | LEU | A | 132 | 58.930 | 62.247 | 22.427 | 1.00 | 17.08 |
| 1757 | CD1 | LEU | A | 132 | 58.170 | 63.044 | 21.399 | 1.00 | 18.87 |
| 1761 | CD2 | LEU | A | 132 | 59.126 | 60.798 | 21.970 | 1.00 | 18.78 |
| 1765 | C | LEU | A | 132 | 62.515 | 62.534 | 23.779 | 1.00 | 17.74 |
| 1766 | O | LEU | A | 132 | 63.197 | 61.641 | 23.297 | 1.00 | 17.61 |
| 1767 | N | GLN | A | 133 | 63.036 | 63.695 | 24.185 | 1.00 | 17.96 |
| 1769 | CA | GLN | A | 133 | 64.483 | 63.926 | 24.148 | 1.00 | 18.23 |
| 1771 | CB | GLN | A | 133 | 64.894 | 65.366 | 24.559 | 1.00 | 18.28 |
| 1774 | CG | GLN | A | 133 | 66.427 | 65.512 | 24.520 | 1.00 | 19.50 |
| 1777 | CD | GLN | A | 133 | 67.021 | 66.816 | 25.074 | 1.00 | 22.38 |
| 1778 | OE1 | GLN | A | 133 | 66.350 | 67.833 | 25.237 | 1.00 | 19.65 |
| 1779 | NE2 | GLN | A | 133 | 68.322 | 66.768 | 25.346 | 1.00 | 23.26 |
| 1782 | C | GLN | A | 133 | 65.165 | 62.906 | 25.043 | 1.00 | 17.62 |
| 1783 | O | GLN | A | 133 | 66.132 | 62.284 | 24.645 | 1.00 | 17.06 |
| 1784 | N | THR | A | 134 | 64.650 | 62.736 | 26.258 | 1.00 | 18.05 |
| 1786 | CA | THR | A | 134 | 65.220 | 61.790 | 27.201 | 1.00 | 18.07 |
| 1788 | CB | THR | A | 134 | 64.461 | 61.797 | 28.520 | 1.00 | 18.89 |
| 1790 | OG1 | THR | A | 134 | 64.445 | 63.109 | 29.073 | 1.00 | 17.91 |
| 1792 | CG2 | THR | A | 134 | 65.189 | 60.940 | 29.551 | 1.00 | 18.65 |
| 1796 | C | THR | A | 134 | 65.165 | 60.373 | 26.665 | 1.00 | 17.74 |
| 1797 | O | THR | A | 134 | 66.111 | 59.615 | 26.829 | 1.00 | 17.70 |
| 1798 | N | LEU | A | 135 | 64.056 | 60.037 | 26.016 | 1.00 | 17.32 |
| 1800 | CA | LEU | A | 135 | 63.863 | 58.698 | 25.487 | 1.00 | 17.21 |
| 1802 | CB | LEU | A | 135 | 62.450 | 58.554 | 24.899 | 1.00 | 16.68 |
| 1805 | CG | LEU | A | 135 | 62.102 | 57.160 | 24.360 | 1.00 | 17.14 |
| 1807 | CD1 | LEU | A | 135 | 62.252 | 56.096 | 25.413 | 1.00 | 17.24 |
| 1811 | CD2 | LEU | A | 135 | 60.691 | 57.141 | 23.772 | 1.00 | 17.71 |
| 1815 | C | LEU | A | 135 | 64.934 | 58.362 | 24.443 | 1.00 | 16.99 |
| 1816 | O | LEU | A | 135 | 65.396 | 57.234 | 24.373 | 1.00 | 17.51 |
| 1817 | N | ALA | A | 136 | 65.311 | 59.345 | 23.637 | 1.00 | 16.86 |
| 1819 | CA | ALA | A | 136 | 66.350 | 59.191 | 22.640 | 1.00 | 16.98 |
| 1821 | CB | ALA | A | 136 | 66.617 | 60.525 | 21.936 | 1.00 | 16.96 |
| 1825 | C | ALA | A | 136 | 67.629 | 58.656 | 23.286 | 1.00 | 17.44 |
| 1826 | O | ALA | A | 136 | 68.269 | 57.772 | 22.741 | 1.00 | 17.77 |
| 1827 | N | PHE | A | 137 | 67.982 | 59.193 | 24.449 | 1.00 | 17.78 |
| 1829 | CA | PHE | A | 137 | 69.179 | 58.770 | 25.172 | 1.00 | 18.09 |
| 1831 | CB | PHE | A | 137 | 69.700 | 59.891 | 26.062 | 1.00 | 18.06 |
| 1834 | CG | PHE | A | 137 | 70.113 | 61.073 | 25.279 | 1.00 | 18.66 |
| 1835 | CD1 | PHE | A | 137 | 69.308 | 62.203 | 25.215 | 1.00 | 17.95 |
| 1837 | CE1 | PHE | A | 137 | 69.672 | 63.284 | 24.422 | 1.00 | 18.78 |
| 1839 | CZ | PHE | A | 137 | 70.834 | 63.241 | 23.689 | 1.00 | 18.81 |
| 1841 | CE2 | PHE | A | 137 | 71.647 | 62.108 | 23.742 | 1.00 | 19.03 |
| 1843 | CD2 | PHE | A | 137 | 71.277 | 61.031 | 24.526 | 1.00 | 19.55 |

FIGURE 3 AS

| A | B | C | D | E | F | G | H | I | J |
|---|---|---|---|---|---|---|---|---|---|
| 1845 | C | PHE | A | 137 | 69.000 | 57.481 | 25.944 | 1.00 | 17.78 |
| 1846 | O | PHE | A | 137 | 69.967 | 56.741 | 26.093 | 1.00 | 19.01 |
| 1847 | N | SER | A | 138 | 67.783 | 57.181 | 26.383 | 1.00 | 17.63 |
| 1849 | CA | SER | A | 138 | 67.480 | 55.853 | 26.930 | 1.00 | 17.81 |
| 1851 | CB | SER | A | 138 | 66.064 | 55.790 | 27.503 | 1.00 | 18.14 |
| 1854 | OG | SER | A | 138 | 65.998 | 56.474 | 28.749 | 1.00 | 19.62 |
| 1856 | C | SER | A | 138 | 67.634 | 54.788 | 25.860 | 1.00 | 17.61 |
| 1857 | O | SER | A | 138 | 68.139 | 53.706 | 26.127 | 1.00 | 17.31 |
| 1858 | N | ILE | A | 139 | 67.202 | 55.100 | 24.646 | 1.00 | 17.34 |
| 1860 | CA | ILE | A | 139 | 67.275 | 54.150 | 23.545 | 1.00 | 18.07 |
| 1862 | CB | ILE | A | 139 | 66.528 | 54.676 | 22.286 | 1.00 | 18.17 |
| 1864 | CG1 | ILE | A | 139 | 65.001 | 54.638 | 22.531 | 1.00 | 18.76 |
| 1867 | CD1 | ILE | A | 139 | 64.188 | 55.429 | 21.499 | 1.00 | 19.79 |
| 1871 | CG2 | ILE | A | 139 | 66.878 | 53.836 | 21.073 | 1.00 | 19.10 |
| 1875 | C | ILE | A | 139 | 68.732 | 53.827 | 23.237 | 1.00 | 17.54 |
| 1876 | O | ILE | A | 139 | 69.102 | 52.663 | 23.207 | 1.00 | 17.29 |
| 1877 | N | LEU | A | 140 | 69.556 | 54.854 | 23.081 | 1.00 | 17.52 |
| 1879 | CA | LEU | A | 140 | 70.961 | 54.677 | 22.710 | 1.00 | 18.26 |
| 1881 | CB | LEU | A | 140 | 71.607 | 56.028 | 22.388 | 1.00 | 18.48 |
| 1884 | CG | LEU | A | 140 | 71.151 | 56.649 | 21.066 | 1.00 | 18.76 |
| 1886 | CD1 | LEU | A | 140 | 71.890 | 57.952 | 20.786 | 1.00 | 19.92 |
| 1890 | CD2 | LEU | A | 140 | 71.349 | 55.663 | 19.939 | 1.00 | 19.54 |
| 1894 | C | LEU | A | 140 | 71.775 | 53.986 | 23.786 | 1.00 | 18.96 |
| 1895 | O | LEU | A | 140 | 72.715 | 53.265 | 23.476 | 1.00 | 18.14 |
| 1896 | N | SER | A | 141 | 71.414 | 54.201 | 25.046 | 1.00 | 19.45 |
| 1898 | CA | SER | A | 141 | 72.165 | 53.596 | 26.142 | 1.00 | 20.52 |
| 1900 | CB | SER | A | 141 | 72.125 | 54.482 | 27.404 | 1.00 | 20.39 |
| 1903 | OG | SER | A | 141 | 70.812 | 54.763 | 27.813 | 1.00 | 22.72 |
| 1905 | C | SER | A | 141 | 71.707 | 52.157 | 26.439 | 1.00 | 20.99 |
| 1906 | O | SER | A | 141 | 72.535 | 51.344 | 26.874 | 1.00 | 21.12 |
| 1907 | N | ASP | A | 142 | 70.435 | 51.840 | 26.157 | 1.00 | 20.94 |
| 1909 | CA | ASP | A | 142 | 69.803 | 50.583 | 26.617 | 1.00 | 21.52 |
| 1911 | CB | ASP | A | 142 | 68.510 | 50.885 | 27.360 | 1.00 | 21.35 |
| 1914 | CG | ASP | A | 142 | 68.740 | 51.573 | 28.668 | 1.00 | 23.16 |
| 1915 | OD1 | ASP | A | 142 | 67.745 | 52.038 | 29.261 | 1.00 | 22.75 |
| 1916 | OD2 | ASP | A | 142 | 69.871 | 51.678 | 29.188 | 1.00 | 24.41 |
| 1917 | C | ASP | A | 142 | 69.436 | 49.569 | 25.557 | 1.00 | 21.65 |
| 1918 | O | ASP | A | 142 | 69.308 | 48.382 | 25.850 | 1.00 | 20.45 |
| 1919 | N | ALA | A | 143 | 69.203 | 50.033 | 24.342 | 1.00 | 22.42 |
| 1921 | CA | ALA | A | 143 | 68.645 | 49.176 | 23.301 | 1.00 | 23.31 |
| 1923 | CB | ALA | A | 143 | 68.113 | 50.004 | 22.165 | 1.00 | 22.74 |
| 1927 | C | ALA | A | 143 | 69.698 | 48.200 | 22.795 | 1.00 | 24.09 |
| 1928 | O | ALA | A | 143 | 70.895 | 48.453 | 22.888 | 1.00 | 24.03 |
| 1929 | N | ASP | A | 144 | 69.228 | 47.087 | 22.256 | 1.00 | 25.84 |
| 1931 | CA | ASP | A | 144 | 70.096 | 46.051 | 21.707 | 1.00 | 27.11 |
| 1933 | CB | ASP | A | 144 | 69.309 | 44.768 | 21.402 | 1.00 | 27.68 |
| 1936 | CG | ASP | A | 144 | 68.293 | 44.426 | 22.469 | 1.00 | 31.56 |
| 1937 | OD1 | ASP | A | 144 | 67.116 | 44.829 | 22.309 | 1.00 | 38.25 |
| 1938 | OD2 | ASP | A | 144 | 68.558 | 43.752 | 23.487 | 1.00 | 35.92 |
| 1939 | C | ASP | A | 144 | 70.716 | 46.563 | 20.420 | 1.00 | 26.94 |
| 1940 | O | ASP | A | 144 | 69.995 | 46.966 | 19.504 | 1.00 | 27.42 |
| 1941 | N | MET | A | 145 | 72.044 | 46.586 | 20.374 | 1.00 | 27.00 |

FIGURE 3 AT

| A | B | C | D | E | F | G | H | I | J |
|---|---|---|---|---|---|---|---|---|---|
| 1943 | CA | MET | A | 145 | 72.794 | 46.828 | 19.148 | 1.00 | 27.40 |
| 1945 | CB | MET | A | 145 | 73.297 | 48.273 | 19.105 | 1.00 | 27.32 |
| 1948 | CG | MET | A | 145 | 72.199 | 49.301 | 19.048 | 1.00 | 27.17 |
| 1951 | SD | MET | A | 145 | 72.806 | 50.970 | 18.731 | 1.00 | 27.97 |
| 1952 | CE | MET | A | 145 | 73.747 | 51.294 | 20.169 | 1.00 | 26.35 |
| 1956 | C | MET | A | 145 | 73.972 | 45.850 | 19.125 | 1.00 | 28.08 |
| 1957 | O | MET | A | 145 | 75.099 | 46.213 | 19.487 | 1.00 | 27.86 |
| 1958 | N | PRO | A | 146 | 73.702 | 44.596 | 18.768 | 1.00 | 28.99 |
| 1959 | CA | PRO | A | 146 | 74.700 | 43.519 | 18.900 | 1.00 | 29.80 |
| 1961 | CB | PRO | A | 146 | 74.018 | 42.301 | 18.244 | 1.00 | 30.17 |
| 1964 | CG | PRO | A | 146 | 72.730 | 42.788 | 17.654 | 1.00 | 29.78 |
| 1967 | CD | PRO | A | 146 | 72.402 | 44.090 | 18.296 | 1.00 | 29.22 |
| 1970 | C | PRO | A | 146 | 76.088 | 43.778 | 18.280 | 1.00 | 29.90 |
| 1971 | O | PRO | A | 146 | 77.081 | 43.394 | 18.874 | 1.00 | 30.77 |
| 1972 | N | GLU | A | 147 | 76.176 | 44.452 | 17.149 | 1.00 | 30.07 |
| 1974 | CA | GLU | A | 147 | 77.488 | 44.605 | 16.495 | 1.00 | 30.29 |
| 1976 | CB | GLU | A | 147 | 77.348 | 44.666 | 14.970 | 1.00 | 30.88 |
| 1979 | CG | GLU | A | 147 | 76.419 | 43.625 | 14.368 | 1.00 | 33.60 |
| 1982 | CD | GLU | A | 147 | 74.996 | 44.126 | 14.226 | 1.00 | 36.03 |
| 1983 | OE1 | GLU | A | 147 | 74.447 | 44.088 | 13.102 | 1.00 | 38.00 |
| 1984 | OE2 | GLU | A | 147 | 74.433 | 44.556 | 15.252 | 1.00 | 37.12 |
| 1985 | C | GLU | A | 147 | 78.224 | 45.857 | 16.976 | 1.00 | 28.68 |
| 1986 | O | GLU | A | 147 | 79.335 | 46.129 | 16.528 | 1.00 | 28.50 |
| 1987 | N | VAL | A | 148 | 77.599 | 46.613 | 17.879 | 1.00 | 26.68 |
| 1989 | CA | VAL | A | 148 | 78.056 | 47.949 | 18.205 | 1.00 | 25.01 |
| 1991 | CB | VAL | A | 148 | 76.886 | 48.966 | 18.244 | 1.00 | 25.12 |
| 1993 | CG1 | VAL | A | 148 | 77.404 | 50.369 | 18.438 | 1.00 | 24.25 |
| 1997 | CG2 | VAL | A | 148 | 76.049 | 48.887 | 16.950 | 1.00 | 24.80 |
| 2001 | C | VAL | A | 148 | 78.819 | 47.927 | 19.526 | 1.00 | 23.84 |
| 2002 | O | VAL | A | 148 | 78.271 | 47.605 | 20.585 | 1.00 | 23.11 |
| 2003 | N | SER | A | 149 | 80.098 | 48.254 | 19.440 | 1.00 | 22.76 |
| 2005 | CA | SER | A | 149 | 80.952 | 48.338 | 20.613 | 1.00 | 22.78 |
| 2007 | CB | SER | A | 149 | 82.404 | 48.597 | 20.186 | 1.00 | 22.49 |
| 2010 | OG | SER | A | 149 | 82.568 | 49.915 | 19.707 | 1.00 | 21.57 |
| 2012 | C | SER | A | 149 | 80.458 | 49.448 | 21.539 | 1.00 | 23.11 |
| 2013 | O | SER | A | 149 | 79.794 | 50.402 | 21.099 | 1.00 | 21.95 |
| 2014 | N | ASP | A | 150 | 80.777 | 49.313 | 22.817 | 1.00 | 23.66 |
| 2016 | CA | ASP | A | 150 | 80.499 | 50.348 | 23.801 | 1.00 | 24.49 |
| 2018 | CB | ASP | A | 150 | 81.010 | 49.930 | 25.172 | 1.00 | 25.14 |
| 2021 | CG | ASP | A | 150 | 80.256 | 48.733 | 25.735 | 1.00 | 27.65 |
| 2022 | OD1 | ASP | A | 150 | 80.719 | 48.186 | 26.762 | 1.00 | 31.30 |
| 2023 | OD2 | ASP | A | 150 | 79.201 | 48.281 | 25.225 | 1.00 | 27.89 |
| 2024 | C | ASP | A | 150 | 81.115 | 51.680 | 23.394 | 1.00 | 24.45 |
| 2025 | O | ASP | A | 150 | 80.499 | 52.725 | 23.568 | 1.00 | 23.41 |
| 2026 | N | ARG | A | 151 | 82.319 | 51.639 | 22.827 | 1.00 | 24.28 |
| 2028 | CA | ARG | A | 151 | 82.973 | 52.844 | 22.355 | 1.00 | 24.79 |
| 2030 | CB | ARG | A | 151 | 84.352 | 52.508 | 21.759 | 1.00 | 26.00 |
| 2033 | CG | ARG | A | 151 | 85.134 | 53.699 | 21.268 | 1.00 | 28.93 |
| 2036 | CD | ARG | A | 151 | 85.432 | 54.712 | 22.350 | 1.00 | 34.80 |
| 2039 | NE | ARG | A | 151 | 84.576 | 55.893 | 22.233 | 1.00 | 38.89 |
| 2041 | CZ | ARG | A | 151 | 84.277 | 56.711 | 23.229 | 1.00 | 42.07 |
| 2042 | NH1 | ARG | A | 151 | 83.494 | 57.756 | 22.989 | 1.00 | 43.97 |

FIGURE 3 AU

| A | B | C | D | E | F | G | H | I | J |
|---|---|---|---|---|---|---|---|---|---|
| 2045 | NH2 | ARG | A | 151 | 84.754 | 56.502 | 24.462 | 1.00 | 42.69 |
| 2048 | C | ARG | A | 151 | 82.119 | 53.534 | 21.303 | 1.00 | 23.63 |
| 2049 | O | ARG | A | 151 | 81.949 | 54.749 | 21.330 | 1.00 | 22.68 |
| 2050 | N | ASP | A | 152 | 81.578 | 52.751 | 20.377 | 1.00 | 22.64 |
| 2052 | CA | ASP | A | 152 | 80.765 | 53.305 | 19.316 | 1.00 | 22.05 |
| 2054 | CB | ASP | A | 152 | 80.695 | 52.351 | 18.126 | 1.00 | 22.68 |
| 2057 | CG | ASP | A | 152 | 82.013 | 52.303 | 17.348 | 1.00 | 24.58 |
| 2058 | OD1 | ASP | A | 152 | 82.780 | 53.285 | 17.412 | 1.00 | 24.51 |
| 2059 | OD2 | ASP | A | 152 | 82.369 | 51.328 | 16.654 | 1.00 | 27.53 |
| 2060 | C | ASP | A | 152 | 79.380 | 53.730 | 19.832 | 1.00 | 20.89 |
| 2061 | O | ASP | A | 152 | 78.829 | 54.703 | 19.348 | 1.00 | 19.41 |
| 2062 | N | ARG | A | 153 | 78.855 | 53.043 | 20.844 | 1.00 | 19.83 |
| 2064 | CA | ARG | A | 153 | 77.577 | 53.435 | 21.459 | 1.00 | 18.66 |
| 2066 | CB | ARG | A | 153 | 77.116 | 52.390 | 22.450 | 1.00 | 18.96 |
| 2069 | CG | ARG | A | 153 | 75.734 | 52.644 | 23.008 | 1.00 | 18.87 |
| 2072 | CD | ARG | A | 153 | 75.377 | 51.687 | 24.112 | 1.00 | 19.73 |
| 2075 | NE | ARG | A | 153 | 75.180 | 50.322 | 23.630 | 1.00 | 20.07 |
| 2077 | CZ | ARG | A | 153 | 73.991 | 49.773 | 23.369 | 1.00 | 22.06 |
| 2078 | NH1 | ARG | A | 153 | 73.929 | 48.516 | 22.949 | 1.00 | 20.83 |
| 2081 | NH2 | ARG | A | 153 | 72.862 | 50.466 | 23.521 | 1.00 | 23.23 |
| 2084 | C | ARG | A | 153 | 77.724 | 54.771 | 22.171 | 1.00 | 18.18 |
| 2085 | O | ARG | A | 153 | 76.842 | 55.612 | 22.081 | 1.00 | 17.20 |
| 2086 | N | ILE | A | 154 | 78.847 | 54.959 | 22.869 | 1.00 | 17.73 |
| 2088 | CA | ILE | A | 154 | 79.141 | 56.223 | 23.542 | 1.00 | 18.41 |
| 2090 | CB | ILE | A | 154 | 80.414 | 56.100 | 24.449 | 1.00 | 18.14 |
| 2092 | CG1 | ILE | A | 154 | 80.092 | 55.249 | 25.684 | 1.00 | 19.24 |
| 2095 | CD1 | ILE | A | 154 | 81.307 | 54.703 | 26.408 | 1.00 | 20.01 |
| 2099 | CG2 | ILE | A | 154 | 80.932 | 57.468 | 24.875 | 1.00 | 19.53 |
| 2103 | C | ILE | A | 154 | 79.277 | 57.343 | 22.505 | 1.00 | 17.74 |
| 2104 | O | ILE | A | 154 | 78.757 | 58.424 | 22.698 | 1.00 | 18.17 |
| 2105 | N | SER | A | 155 | 79.934 | 57.063 | 21.388 | 1.00 | 18.18 |
| 2107 | CA | SER | A | 155 | 80.095 | 58.043 | 20.323 | 1.00 | 18.52 |
| 2109 | CB | SER | A | 155 | 81.020 | 57.511 | 19.236 | 1.00 | 18.63 |
| 2112 | OG | SER | A | 155 | 82.330 | 57.395 | 19.748 | 1.00 | 18.50 |
| 2114 | C | SER | A | 155 | 78.744 | 58.437 | 19.718 | 1.00 | 19.05 |
| 2115 | O | SER | A | 155 | 78.538 | 59.594 | 19.368 | 1.00 | 19.13 |
| 2116 | N | MET | A | 156 | 77.836 | 57.476 | 19.618 | 1.00 | 19.12 |
| 2118 | CA | MET | A | 156 | 76.482 | 57.743 | 19.135 | 1.00 | 19.40 |
| 2120 | CB | MET | A | 156 | 75.674 | 56.461 | 19.063 | 1.00 | 19.56 |
| 2123 | CG | MET | A | 156 | 76.083 | 55.564 | 17.948 | 1.00 | 22.23 |
| 2126 | SD | MET | A | 156 | 74.922 | 54.182 | 17.803 | 1.00 | 28.16 |
| 2127 | CE | MET | A | 156 | 75.814 | 53.241 | 16.666 | 1.00 | 26.77 |
| 2131 | C | MET | A | 156 | 75.746 | 58.693 | 20.039 | 1.00 | 18.61 |
| 2132 | O | MET | A | 156 | 75.101 | 59.609 | 19.567 | 1.00 | 18.79 |
| 2133 | N | ILE | A | 157 | 75.826 | 58.439 | 21.342 | 1.00 | 18.55 |
| 2135 | CA | ILE | A | 157 | 75.194 | 59.281 | 22.349 | 1.00 | 17.91 |
| 2137 | CB | ILE | A | 157 | 75.342 | 58.649 | 23.752 | 1.00 | 17.84 |
| 2139 | CG1 | ILE | A | 157 | 74.511 | 57.360 | 23.840 | 1.00 | 18.27 |
| 2142 | CD1 | ILE | A | 157 | 74.814 | 56.495 | 25.017 | 1.00 | 18.88 |
| 2146 | CG2 | ILE | A | 157 | 74.941 | 59.646 | 24.845 | 1.00 | 17.97 |
| 2150 | C | ILE | A | 157 | 75.804 | 60.685 | 22.313 | 1.00 | 17.61 |
| 2151 | O | ILE | A | 157 | 75.087 | 61.683 | 22.308 | 1.00 | 16.93 |

FIGURE 3 AV

| A | B | C | D | E | F | G | H | I | J |
|---|---|---|---|---|---|---|---|---|---|
| 2152 | N | SER | A | 158 | 77.136 | 60.749 | 22.290 | 1.00 | 17.36 |
| 2154 | CA | SER | A | 158 | 77.856 | 62.012 | 22.247 | 1.00 | 17.24 |
| 2156 | CB | SER | A | 158 | 79.372 | 61.759 | 22.292 | 1.00 | 17.57 |
| 2159 | OG | SER | A | 158 | 80.087 | 62.908 | 21.936 | 1.00 | 16.92 |
| 2161 | C | SER | A | 158 | 77.487 | 62.819 | 21.007 | 1.00 | 17.58 |
| 2162 | O | SER | A | 158 | 77.266 | 64.003 | 21.093 | 1.00 | 17.17 |
| 2163 | N | GLU | A | 159 | 77.408 | 62.163 | 19.856 | 1.00 | 18.38 |
| 2165 | CA | GLU | A | 159 | 77.042 | 62.833 | 18.616 | 1.00 | 18.63 |
| 2167 | CB | GLU | A | 159 | 77.242 | 61.904 | 17.409 | 1.00 | 19.18 |
| 2170 | CG | GLU | A | 159 | 76.518 | 62.361 | 16.145 | 1.00 | 20.77 |
| 2173 | CD | GLU | A | 159 | 76.979 | 63.726 | 15.666 | 1.00 | 23.75 |
| 2174 | OE1 | GLU | A | 159 | 78.105 | 64.141 | 16.022 | 1.00 | 24.45 |
| 2175 | OE2 | GLU | A | 159 | 76.233 | 64.384 | 14.918 | 1.00 | 26.52 |
| 2176 | C | GLU | A | 159 | 75.592 | 63.324 | 18.648 | 1.00 | 18.90 |
| 2177 | O | GLU | A | 159 | 75.311 | 64.455 | 18.224 | 1.00 | 18.41 |
| 2178 | N | LEU | A | 160 | 74.671 | 62.489 | 19.122 | 1.00 | 18.15 |
| 2180 | CA | LEU | A | 160 | 73.274 | 62.921 | 19.169 | 1.00 | 18.98 |
| 2182 | CB | LEU | A | 160 | 72.333 | 61.801 | 19.559 | 1.00 | 19.20 |
| 2185 | CG | LEU | A | 160 | 70.845 | 62.123 | 19.337 | 1.00 | 20.03 |
| 2187 | CD1 | LEU | A | 160 | 70.528 | 62.479 | 17.890 | 1.00 | 20.04 |
| 2191 | CD2 | LEU | A | 160 | 70.015 | 60.977 | 19.795 | 1.00 | 21.02 |
| 2195 | C | LEU | A | 160 | 73.119 | 64.115 | 20.113 | 1.00 | 19.39 |
| 2196 | O | LEU | A | 160 | 72.388 | 65.058 | 19.808 | 1.00 | 19.39 |
| 2197 | N | ALA | A | 161 | 73.832 | 64.078 | 21.234 | 1.00 | 19.92 |
| 2199 | CA | ALA | A | 161 | 73.814 | 65.162 | 22.208 | 1.00 | 20.54 |
| 2201 | CB | ALA | A | 161 | 74.591 | 64.764 | 23.463 | 1.00 | 20.76 |
| 2205 | C | ALA | A | 161 | 74.362 | 66.466 | 21.621 | 1.00 | 20.84 |
| 2206 | O | ALA | A | 161 | 73.690 | 67.496 | 21.678 | 1.00 | 21.05 |
| 2207 | N | SER | A | 162 | 75.554 | 66.431 | 21.027 | 1.00 | 21.51 |
| 2209 | CA | SER | A | 162 | 76.138 | 67.660 | 20.486 | 1.00 | 22.08 |
| 2211 | CB | SER | A | 162 | 77.614 | 67.492 | 20.063 | 1.00 | 22.37 |
| 2214 | OG | SER | A | 162 | 77.809 | 66.365 | 19.248 | 1.00 | 24.18 |
| 2216 | C | SER | A | 162 | 75.286 | 68.207 | 19.336 | 1.00 | 21.42 |
| 2217 | O | SER | A | 162 | 75.142 | 69.415 | 19.197 | 1.00 | 21.65 |
| 2218 | N | ALA | A | 163 | 74.700 | 67.316 | 18.539 | 1.00 | 20.43 |
| 2220 | CA | ALA | A | 163 | 73.906 | 67.716 | 17.379 | 1.00 | 20.07 |
| 2222 | CB | ALA | A | 163 | 73.732 | 66.523 | 16.438 | 1.00 | 20.07 |
| 2226 | C | ALA | A | 163 | 72.537 | 68.265 | 17.768 | 1.00 | 19.77 |
| 2227 | O | ALA | A | 163 | 71.937 | 69.041 | 17.026 | 1.00 | 18.96 |
| 2228 | N | SER | A | 164 | 72.026 | 67.836 | 18.922 | 1.00 | 19.92 |
| 2230 | CA | SER | A | 164 | 70.677 | 68.207 | 19.366 | 1.00 | 19.71 |
| 2232 | CB | SER | A | 164 | 70.061 | 67.027 | 20.112 | 1.00 | 20.08 |
| 2235 | OG | SER | A | 164 | 70.098 | 65.862 | 19.285 | 1.00 | 21.77 |
| 2237 | C | SER | A | 164 | 70.655 | 69.452 | 20.246 | 1.00 | 20.10 |
| 2238 | O | SER | A | 164 | 69.661 | 70.210 | 20.271 | 1.00 | 18.98 |
| 2239 | N | GLY | A | 165 | 71.757 | 69.676 | 20.958 | 1.00 | 19.76 |
| 2241 | CA | GLY | A | 165 | 71.846 | 70.733 | 21.939 | 1.00 | 20.35 |
| 2244 | C | GLY | A | 165 | 72.244 | 72.081 | 21.365 | 1.00 | 20.96 |
| 2245 | O | GLY | A | 165 | 71.982 | 72.393 | 20.203 | 1.00 | 20.86 |
| 2246 | N | ILE | A | 166 | 72.900 | 72.879 | 22.200 | 1.00 | 21.84 |
| 2248 | CA | ILE | A | 166 | 73.170 | 74.280 | 21.914 | 1.00 | 22.71 |
| 2250 | CB | ILE | A | 166 | 73.611 | 74.975 | 23.242 | 1.00 | 23.10 |

FIGURE 3 AW

| A | B | C | D | E | F | G | H | I | J |
|---|---|---|---|---|---|---|---|---|---|
| 2252 | CG1 | ILE | A | 166 | 73.194 | 76.437 | 23.239 | 1.00 | 23.87 |
| 2255 | CD1 | ILE | A | 166 | 71.710 | 76.610 | 23.444 | 1.00 | 23.14 |
| 2259 | CG2 | ILE | A | 166 | 75.109 | 74.770 | 23.489 | 1.00 | 25.44 |
| 2263 | C | ILE | A | 166 | 74.197 | 74.443 | 20.769 | 1.00 | 22.75 |
| 2264 | O | ILE | A | 166 | 74.206 | 75.456 | 20.057 | 1.00 | 23.12 |
| 2265 | N | ALA | A | 167 | 75.027 | 73.422 | 20.572 | 1.00 | 22.36 |
| 2267 | CA | ALA | A | 167 | 75.954 | 73.367 | 19.451 | 1.00 | 22.62 |
| 2269 | CB | ALA | A | 167 | 77.109 | 72.455 | 19.770 | 1.00 | 22.85 |
| 2273 | C | ALA | A | 167 | 75.285 | 72.916 | 18.152 | 1.00 | 22.34 |
| 2274 | O | ALA | A | 167 | 75.905 | 72.963 | 17.111 | 1.00 | 22.65 |
| 2275 | N | GLY | A | 168 | 74.028 | 72.488 | 18.212 | 1.00 | 21.57 |
| 2277 | CA | GLY | A | 168 | 73.304 | 72.064 | 17.022 | 1.00 | 21.12 |
| 2280 | C | GLY | A | 168 | 71.883 | 72.588 | 16.982 | 1.00 | 20.68 |
| 2281 | O | GLY | A | 168 | 71.665 | 73.785 | 16.956 | 1.00 | 19.79 |
| 2282 | N | MET | A | 169 | 70.914 | 71.682 | 17.005 | 1.00 | 20.95 |
| 2284 | CA | MET | A | 169 | 69.501 | 72.019 | 16.812 | 1.00 | 20.87 |
| 2286 | CB | MET | A | 169 | 68.655 | 70.757 | 16.927 | 1.00 | 21.21 |
| 2289 | CG | MET | A | 169 | 67.183 | 70.922 | 16.531 | 1.00 | 22.91 |
| 2292 | SD | MET | A | 169 | 66.208 | 71.479 | 17.897 | 1.00 | 28.34 |
| 2293 | CE | MET | A | 169 | 66.254 | 69.967 | 19.003 | 1.00 | 25.97 |
| 2297 | C | MET | A | 169 | 68.952 | 73.140 | 17.721 | 1.00 | 20.52 |
| 2298 | O | MET | A | 169 | 68.310 | 74.072 | 17.224 | 1.00 | 19.77 |
| 2299 | N | CYS | A | 170 | 69.200 | 73.059 | 19.028 | 1.00 | 20.60 |
| 2301 | CA | CYS | A | 170 | 68.689 | 74.061 | 19.977 | 1.00 | 20.42 |
| 2303 | CB | BCYS | A | 170 | 68.958 | 73.590 | 21.405 | 0.35 | 20.62 |
| 2304 | CB | ACYS | A | 170 | 68.958 | 73.668 | 21.427 | 0.65 | 20.89 |
| 2309 | SG | BCYS | A | 170 | 67.803 | 74.234 | 22.609 | 0.35 | 20.91 |
| 2310 | SG | ACYS | A | 170 | 67.804 | 72.489 | 22.098 | 0.65 | 22.71 |
| 2311 | C | CYS | A | 170 | 69.332 | 75.426 | 19.744 | 1.00 | 20.33 |
| 2312 | O | CYS | A | 170 | 68.665 | 76.459 | 19.811 | 1.00 | 18.74 |
| 2313 | N | GLY | A | 171 | 70.650 | 75.414 | 19.539 | 1.00 | 20.11 |
| 2315 | CA | GLY | A | 171 | 71.384 | 76.605 | 19.172 | 1.00 | 20.26 |
| 2318 | C | GLY | A | 171 | 70.807 | 77.252 | 17.932 | 1.00 | 20.35 |
| 2319 | O | GLY | A | 171 | 70.645 | 78.473 | 17.877 | 1.00 | 19.82 |
| 2320 | N | GLY | A | 172 | 70.470 | 76.425 | 16.948 | 1.00 | 20.20 |
| 2322 | CA | GLY | A | 172 | 69.875 | 76.891 | 15.715 | 1.00 | 20.43 |
| 2325 | C | GLY | A | 172 | 68.484 | 77.441 | 15.920 | 1.00 | 20.51 |
| 2326 | O | GLY | A | 172 | 68.117 | 78.435 | 15.303 | 1.00 | 20.93 |
| 2327 | N | GLN | A | 173 | 67.716 | 76.816 | 16.800 | 1.00 | 20.70 |
| 2329 | CA | GLN | A | 173 | 66.397 | 77.327 | 17.168 | 1.00 | 21.15 |
| 2331 | CB | GLN | A | 173 | 65.684 | 76.383 | 18.149 | 1.00 | 21.47 |
| 2334 | CG | GLN | A | 173 | 65.165 | 75.072 | 17.546 | 1.00 | 21.62 |
| 2337 | CD | GLN | A | 173 | 64.102 | 75.279 | 16.494 | 1.00 | 22.97 |
| 2338 | OE1 | GLN | A | 173 | 64.417 | 75.656 | 15.362 | 1.00 | 27.11 |
| 2339 | NE2 | GLN | A | 173 | 62.845 | 75.031 | 16.850 | 1.00 | 22.24 |
| 2342 | C | GLN | A | 173 | 66.514 | 78.725 | 17.794 | 1.00 | 21.59 |
| 2343 | O | GLN | A | 173 | 65.695 | 79.609 | 17.513 | 1.00 | 22.14 |
| 2344 | N | ALA | A | 174 | 67.532 | 78.931 | 18.622 | 1.00 | 21.59 |
| 2346 | CA | ALA | A | 174 | 67.766 | 80.245 | 19.230 | 1.00 | 21.99 |
| 2348 | CB | ALA | A | 174 | 68.847 | 80.166 | 20.296 | 1.00 | 22.20 |
| 2352 | C | ALA | A | 174 | 68.152 | 81.269 | 18.164 | 1.00 | 22.07 |
| 2353 | O | ALA | A | 174 | 67.683 | 82.380 | 18.206 | 1.00 | 21.87 |

FIGURE 3 AX

| A | B | C | D | E | F | G | H | I | J |
|---|---|---|---|---|---|---|---|---|---|
| 2354 | N | LEU | A | 175 | 69.001 | 80.885 | 17.212 | 1.00 | 22.13 |
| 2356 | CA | LEU | A | 175 | 69.369 | 81.776 | 16.106 | 1.00 | 23.00 |
| 2358 | CB | LEU | A | 175 | 70.449 | 81.144 | 15.233 | 1.00 | 23.09 |
| 2361 | CG | LEU | A | 175 | 71.824 | 80.871 | 15.840 | 1.00 | 22.66 |
| 2363 | CD1 | LEU | A | 175 | 72.668 | 80.085 | 14.817 | 1.00 | 24.29 |
| 2367 | CD2 | LEU | A | 175 | 72.522 | 82.155 | 16.235 | 1.00 | 22.45 |
| 2371 | C | LEU | A | 175 | 68.163 | 82.119 | 15.240 | 1.00 | 23.28 |
| 2372 | O | LEU | A | 175 | 68.003 | 83.265 | 14.805 | 1.00 | 23.62 |
| 2373 | N | ASP | A | 176 | 67.314 | 81.123 | 15.002 | 1.00 | 23.53 |
| 2375 | CA | ASP | A | 176 | 66.112 | 81.280 | 14.197 | 1.00 | 24.49 |
| 2377 | CB | ASP | A | 176 | 65.382 | 79.934 | 14.080 | 1.00 | 24.90 |
| 2380 | CG | ASP | A | 176 | 64.004 | 80.064 | 13.491 | 1.00 | 25.57 |
| 2381 | OD1 | ASP | A | 176 | 63.830 | 79.750 | 12.287 | 1.00 | 28.64 |
| 2382 | OD2 | ASP | A | 176 | 63.023 | 80.441 | 14.162 | 1.00 | 28.54 |
| 2383 | C | ASP | A | 176 | 65.187 | 82.320 | 14.841 | 1.00 | 24.97 |
| 2384 | O | ASP | A | 176 | 64.683 | 83.222 | 14.178 | 1.00 | 24.47 |
| 2385 | N | LEU | A | 177 | 64.974 | 82.168 | 16.138 | 1.00 | 25.23 |
| 2387 | CA | LEU | A | 177 | 64.127 | 83.083 | 16.905 | 1.00 | 26.68 |
| 2389 | CB | LEU | A | 177 | 63.977 | 82.575 | 18.343 | 1.00 | 26.78 |
| 2392 | CG | LEU | A | 177 | 62.658 | 81.902 | 18.734 | 1.00 | 28.22 |
| 2394 | CD1 | LEU | A | 177 | 62.016 | 81.077 | 17.633 | 1.00 | 29.14 |
| 2398 | CD2 | LEU | A | 177 | 62.892 | 81.055 | 19.970 | 1.00 | 29.13 |
| 2402 | C | LEU | A | 177 | 64.686 | 84.512 | 16.914 | 1.00 | 26.76 |
| 2403 | O | LEU | A | 177 | 63.936 | 85.474 | 16.784 | 1.00 | 26.89 |
| 2404 | N | ASP | A | 178 | 66.002 | 84.640 | 17.050 | 1.00 | 27.40 |
| 2406 | CA | ASP | A | 178 | 66.636 | 85.952 | 17.078 | 1.00 | 28.30 |
| 2408 | CB | ASP | A | 178 | 68.107 | 85.827 | 17.459 | 1.00 | 28.53 |
| 2411 | CG | ASP | A | 178 | 68.753 | 87.176 | 17.720 | 1.00 | 31.35 |
| 2412 | OD1 | ASP | A | 178 | 69.682 | 87.571 | 16.965 | 1.00 | 33.39 |
| 2413 | OD2 | ASP | A | 178 | 68.389 | 87.907 | 18.667 | 1.00 | 33.95 |
| 2414 | C | ASP | A | 178 | 66.513 | 86.681 | 15.734 | 1.00 | 28.03 |
| 2415 | O | ASP | A | 178 | 66.398 | 87.907 | 15.689 | 1.00 | 27.69 |
| 2416 | N | ALA | A | 179 | 66.525 | 85.915 | 14.648 | 1.00 | 27.46 |
| 2418 | CA | ALA | A | 179 | 66.499 | 86.467 | 13.300 | 1.00 | 27.69 |
| 2420 | CB | ALA | A | 179 | 67.174 | 85.479 | 12.330 | 1.00 | 27.70 |
| 2424 | C | ALA | A | 179 | 65.089 | 86.843 | 12.796 | 1.00 | 27.58 |
| 2425 | O | ALA | A | 179 | 64.946 | 87.351 | 11.683 | 1.00 | 27.80 |
| 2426 | N | GLU | A | 180 | 64.057 | 86.590 | 13.596 | 1.00 | 27.88 |
| 2428 | CA | GLU | A | 180 | 62.702 | 87.040 | 13.277 | 1.00 | 28.36 |
| 2430 | CB | GLU | A | 180 | 61.710 | 86.633 | 14.367 | 1.00 | 28.57 |
| 2433 | CG | GLU | A | 180 | 61.415 | 85.151 | 14.422 | 1.00 | 29.97 |
| 2436 | CD | GLU | A | 180 | 60.434 | 84.780 | 15.517 | 1.00 | 32.47 |
| 2437 | OE1 | GLU | A | 180 | 60.070 | 85.661 | 16.338 | 1.00 | 34.93 |
| 2438 | OE2 | GLU | A | 180 | 60.026 | 83.598 | 15.558 | 1.00 | 32.41 |
| 2439 | C | GLU | A | 180 | 62.695 | 88.560 | 13.162 | 1.00 | 28.40 |
| 2440 | O | GLU | A | 180 | 63.140 | 89.252 | 14.075 | 1.00 | 27.70 |
| 2441 | N | GLY | A | 181 | 62.227 | 89.057 | 12.020 | 1.00 | 28.55 |
| 2443 | CA | GLY | A | 181 | 62.105 | 90.477 | 11.766 | 1.00 | 29.05 |
| 2446 | C | GLY | A | 181 | 63.391 | 91.173 | 11.391 | 1.00 | 29.41 |
| 2447 | O | GLY | A | 181 | 63.379 | 92.382 | 11.129 | 1.00 | 30.34 |
| 2448 | N | LYS | A | 182 | 64.501 | 90.437 | 11.353 | 1.00 | 29.52 |
| 2450 | CA | LYS | A | 182 | 65.818 | 91.032 | 11.137 | 1.00 | 29.58 |

FIGURE 3 AY

| A | B | C | D | E | F | G | H | I | J |
|---|---|---|---|---|---|---|---|---|---|
| 2452 | CB | LYS | A | 182 | 66.807 | 90.510 | 12.175 | 1.00 | 30.25 |
| 2455 | CG | LYS | A | 182 | 66.415 | 90.819 | 13.604 | 1.00 | 31.19 |
| 2458 | CD | LYS | A | 182 | 67.528 | 90.474 | 14.569 | 1.00 | 33.42 |
| 2461 | CE | LYS | A | 182 | 67.168 | 90.894 | 16.009 | 1.00 | 34.43 |
| 2464 | NZ | LYS | A | 182 | 65.969 | 90.178 | 16.544 | 1.00 | 36.01 |
| 2468 | C | LYS | A | 182 | 66.375 | 90.797 | 9.730 | 1.00 | 29.61 |
| 2469 | O | LYS | A | 182 | 67.389 | 91.383 | 9.367 | 1.00 | 29.31 |
| 2470 | N | HIS | A | 183 | 65.725 | 89.944 | 8.947 | 1.00 | 29.18 |
| 2472 | CA | HIS | A | 183 | 66.098 | 89.736 | 7.546 | 1.00 | 29.54 |
| 2474 | CB | HIS | A | 183 | 65.574 | 90.895 | 6.688 | 1.00 | 29.50 |
| 2477 | CG | HIS | A | 183 | 64.099 | 91.086 | 6.806 | 1.00 | 29.04 |
| 2478 | ND1 | HIS | A | 183 | 63.217 | 90.679 | 5.835 | 1.00 | 29.33 |
| 2480 | CE1 | HIS | A | 183 | 61.982 | 90.944 | 6.226 | 1.00 | 30.87 |
| 2482 | NE2 | HIS | A | 183 | 62.033 | 91.486 | 7.429 | 1.00 | 30.77 |
| 2484 | CD2 | HIS | A | 183 | 63.346 | 91.580 | 7.816 | 1.00 | 30.69 |
| 2486 | C | HIS | A | 183 | 67.598 | 89.588 | 7.410 | 1.00 | 29.56 |
| 2487 | O | HIS | A | 183 | 68.261 | 90.375 | 6.732 | 1.00 | 29.82 |
| 2488 | N | VAL | A | 184 | 68.136 | 88.569 | 8.067 | 1.00 | 29.52 |
| 2490 | CA | VAL | A | 184 | 69.580 | 88.461 | 8.215 | 1.00 | 29.40 |
| 2492 | CB | VAL | A | 184 | 69.976 | 87.488 | 9.352 | 1.00 | 29.29 |
| 2494 | CG1 | VAL | A | 184 | 69.310 | 87.904 | 10.659 | 1.00 | 29.32 |
| 2498 | CG2 | VAL | A | 184 | 69.645 | 86.033 | 8.998 | 1.00 | 28.66 |
| 2502 | C | VAL | A | 184 | 70.233 | 88.072 | 6.886 | 1.00 | 29.41 |
| 2503 | O | VAL | A | 184 | 69.586 | 87.448 | 6.037 | 1.00 | 29.64 |
| 2504 | N | PRO | A | 185 | 71.501 | 88.441 | 6.701 | 1.00 | 29.70 |
| 2505 | CA | PRO | A | 185 | 72.217 | 88.146 | 5.458 | 1.00 | 29.74 |
| 2507 | CB | PRO | A | 185 | 73.565 | 88.851 | 5.643 | 1.00 | 29.72 |
| 2510 | CG | PRO | A | 185 | 73.389 | 89.766 | 6.777 | 1.00 | 30.18 |
| 2513 | CD | PRO | A | 185 | 72.357 | 89.168 | 7.653 | 1.00 | 30.09 |
| 2516 | C | PRO | A | 185 | 72.448 | 86.659 | 5.266 | 1.00 | 29.95 |
| 2517 | O | PRO | A | 185 | 72.317 | 85.896 | 6.224 | 1.00 | 29.23 |
| 2518 | N | LEU | A | 186 | 72.843 | 86.279 | 4.059 | 1.00 | 30.11 |
| 2520 | CA | LEU | A | 186 | 73.010 | 84.873 | 3.690 | 1.00 | 30.66 |
| 2522 | CB | LEU | A | 186 | 73.595 | 84.765 | 2.281 | 1.00 | 30.90 |
| 2525 | CG | LEU | A | 186 | 73.604 | 83.417 | 1.548 | 1.00 | 32.07 |
| 2527 | CD1 | LEU | A | 186 | 74.931 | 82.695 | 1.750 | 1.00 | 34.56 |
| 2531 | CD2 | LEU | A | 186 | 72.438 | 82.535 | 1.942 | 1.00 | 31.83 |
| 2535 | C | LEU | A | 186 | 73.875 | 84.071 | 4.670 | 1.00 | 30.74 |
| 2536 | O | LEU | A | 186 | 73.472 | 82.997 | 5.093 | 1.00 | 30.04 |
| 2537 | N | ASP | A | 187 | 75.058 | 84.584 | 5.009 | 1.00 | 30.98 |
| 2539 | CA | ASP | A | 187 | 75.951 | 83.903 | 5.945 | 1.00 | 31.77 |
| 2541 | CB | ASP | A | 187 | 77.278 | 84.667 | 6.143 | 1.00 | 32.58 |
| 2544 | CG | ASP | A | 187 | 77.097 | 86.128 | 6.641 | 1.00 | 34.74 |
| 2545 | OD1 | ASP | A | 187 | 75.963 | 86.630 | 6.812 | 1.00 | 37.70 |
| 2546 | OD2 | ASP | A | 187 | 78.079 | 86.866 | 6.881 | 1.00 | 39.45 |
| 2547 | C | ASP | A | 187 | 75.295 | 83.578 | 7.301 | 1.00 | 31.43 |
| 2548 | O | ASP | A | 187 | 75.516 | 82.494 | 7.847 | 1.00 | 31.36 |
| 2549 | N | ALA | A | 188 | 74.493 | 84.505 | 7.823 | 1.00 | 30.71 |
| 2551 | CA | ALA | A | 188 | 73.781 | 84.297 | 9.082 | 1.00 | 30.32 |
| 2553 | CB | ALA | A | 188 | 73.271 | 85.624 | 9.641 | 1.00 | 30.46 |
| 2557 | C | ALA | A | 188 | 72.627 | 83.331 | 8.870 | 1.00 | 29.80 |
| 2558 | O | ALA | A | 188 | 72.328 | 82.505 | 9.731 | 1.00 | 28.47 |

FIGURE 3 AZ

| A | B | C | D | E | F | G | H | I | J |
|---|---|---|---|---|---|---|---|---|---|
| 2559 | N | LEU | A | 189 | 71.990 | 83.427 | 7.708 | 1.00 | 29.23 |
| 2561 | CA | LEU | A | 189 | 70.902 | 82.529 | 7.358 | 1.00 | 29.70 |
| 2563 | CB | LEU | A | 189 | 70.360 | 82.867 | 5.971 | 1.00 | 30.15 |
| 2566 | CG | LEU | A | 189 | 68.870 | 83.128 | 5.772 | 1.00 | 31.79 |
| 2568 | CD1 | LEU | A | 189 | 68.545 | 82.912 | 4.280 | 1.00 | 32.57 |
| 2572 | CD2 | LEU | A | 189 | 67.958 | 82.296 | 6.672 | 1.00 | 32.39 |
| 2576 | C | LEU | A | 189 | 71.397 | 81.077 | 7.356 | 1.00 | 29.25 |
| 2577 | O | LEU | A | 189 | 70.766 | 80.182 | 7.923 | 1.00 | 27.68 |
| 2578 | N | GLU | A | 190 | 72.539 | 80.867 | 6.712 | 1.00 | 28.91 |
| 2580 | CA | GLU | A | 190 | 73.138 | 79.547 | 6.604 | 1.00 | 28.82 |
| 2582 | CB | GLU | A | 190 | 74.362 | 79.609 | 5.697 | 1.00 | 29.44 |
| 2585 | CG | GLU | A | 190 | 74.926 | 78.249 | 5.322 | 1.00 | 31.65 |
| 2588 | CD | GLU | A | 190 | 76.119 | 78.345 | 4.382 | 1.00 | 35.05 |
| 2589 | OE1 | GLU | A | 190 | 76.048 | 79.127 | 3.405 | 1.00 | 36.65 |
| 2590 | OE2 | GLU | A | 190 | 77.126 | 77.631 | 4.625 | 1.00 | 37.41 |
| 2591 | C | GLU | A | 190 | 73.524 | 78.996 | 7.972 | 1.00 | 28.22 |
| 2592 | O | GLU | A | 190 | 73.406 | 77.807 | 8.220 | 1.00 | 27.03 |
| 2593 | N | ARG | A | 191 | 74.001 | 79.866 | 8.856 | 1.00 | 27.79 |
| 2595 | CA | ARG | A | 191 | 74.342 | 79.454 | 10.210 | 1.00 | 27.69 |
| 2597 | CB | ARG | A | 191 | 75.021 | 80.585 | 10.988 | 1.00 | 28.29 |
| 2600 | CG | ARG | A | 191 | 76.429 | 80.908 | 10.483 | 1.00 | 32.30 |
| 2603 | CD | ARG | A | 191 | 77.323 | 81.682 | 11.474 | 1.00 | 35.96 |
| 2606 | NE | ARG | A | 191 | 78.509 | 80.902 | 11.831 | 1.00 | 39.49 |
| 2608 | CZ | ARG | A | 191 | 79.520 | 80.619 | 11.005 | 1.00 | 42.00 |
| 2609 | NH1 | ARG | A | 191 | 79.524 | 81.054 | 9.748 | 1.00 | 43.12 |
| 2612 | NH2 | ARG | A | 191 | 80.539 | 79.889 | 11.440 | 1.00 | 42.49 |
| 2615 | C | ARG | A | 191 | 73.100 | 78.970 | 10.948 | 1.00 | 26.20 |
| 2616 | O | ARG | A | 191 | 73.153 | 77.952 | 11.634 | 1.00 | 25.47 |
| 2617 | N | ILE | A | 192 | 71.985 | 79.681 | 10.787 | 1.00 | 25.12 |
| 2619 | CA | ILE | A | 192 | 70.719 | 79.254 | 11.387 | 1.00 | 24.45 |
| 2621 | CB | ILE | A | 192 | 69.546 | 80.183 | 11.009 | 1.00 | 24.28 |
| 2623 | CG1 | ILE | A | 192 | 69.717 | 81.579 | 11.619 | 1.00 | 25.03 |
| 2626 | CD1 | ILE | A | 192 | 68.851 | 82.624 | 10.981 | 1.00 | 25.02 |
| 2630 | CG2 | ILE | A | 192 | 68.222 | 79.577 | 11.474 | 1.00 | 24.54 |
| 2634 | C | ILE | A | 192 | 70.385 | 77.842 | 10.906 | 1.00 | 24.27 |
| 2635 | O | ILE | A | 192 | 70.205 | 76.928 | 11.699 | 1.00 | 23.05 |
| 2636 | N | HIS | A | 193 | 70.289 | 77.701 | 9.590 | 1.00 | 23.44 |
| 2638 | CA | HIS | A | 193 | 69.789 | 76.477 | 8.976 | 1.00 | 23.31 |
| 2640 | CB | HIS | A | 193 | 69.573 | 76.731 | 7.485 | 1.00 | 23.43 |
| 2643 | CG | HIS | A | 193 | 68.349 | 77.547 | 7.209 | 1.00 | 24.48 |
| 2644 | ND1 | HIS | A | 193 | 67.494 | 77.964 | 8.208 | 1.00 | 25.73 |
| 2646 | CE1 | HIS | A | 193 | 66.480 | 78.623 | 7.675 | 1.00 | 26.42 |
| 2648 | NE2 | HIS | A | 193 | 66.659 | 78.669 | 6.367 | 1.00 | 25.37 |
| 2650 | CD2 | HIS | A | 193 | 67.817 | 77.999 | 6.052 | 1.00 | 25.77 |
| 2652 | C | HIS | A | 193 | 70.678 | 75.264 | 9.230 | 1.00 | 22.37 |
| 2653 | O | HIS | A | 193 | 70.179 | 74.181 | 9.534 | 1.00 | 22.47 |
| 2654 | N | ARG | A | 194 | 71.986 | 75.445 | 9.128 | 1.00 | 21.53 |
| 2656 | CA | ARG | A | 194 | 72.919 | 74.362 | 9.391 | 1.00 | 21.47 |
| 2658 | CB | ARG | A | 194 | 74.358 | 74.778 | 9.120 | 1.00 | 20.83 |
| 2661 | CG | ARG | A | 194 | 74.700 | 74.835 | 7.656 | 1.00 | 21.22 |
| 2664 | CD | ARG | A | 194 | 76.180 | 74.847 | 7.423 | 1.00 | 22.88 |
| 2667 | NE | ARG | A | 194 | 76.501 | 75.077 | 6.022 | 1.00 | 24.27 |

FIGURE 3 BA

| A | B | C | D | E | F | G | H | I | J |
|---|---|---|---|---|---|---|---|---|---|
| 2669 | CZ | ARG | A | 194 | 76.459 | 74.147 | 5.092 | 1.00 | 25.12 |
| 2670 | NH1 | ARG | A | 194 | 76.120 | 72.904 | 5.398 | 1.00 | 25.42 |
| 2673 | NH2 | ARG | A | 194 | 76.784 | 74.455 | 3.840 | 1.00 | 28.83 |
| 2676 | C | ARG | A | 194 | 72.780 | 73.872 | 10.829 | 1.00 | 21.18 |
| 2677 | O | ARG | A | 194 | 72.861 | 72.681 | 11.071 | 1.00 | 20.79 |
| 2678 | N | HIS | A | 195 | 72.583 | 74.777 | 11.784 | 1.00 | 21.00 |
| 2680 | CA | HIS | A | 195 | 72.436 | 74.337 | 13.171 | 1.00 | 21.63 |
| 2682 | CB | HIS | A | 195 | 72.773 | 75.458 | 14.158 | 1.00 | 21.62 |
| 2685 | CG | HIS | A | 195 | 74.232 | 75.787 | 14.215 | 1.00 | 24.46 |
| 2686 | ND1 | HIS | A | 195 | 74.944 | 75.833 | 15.394 | 1.00 | 28.06 |
| 2688 | CE1 | HIS | A | 195 | 76.201 | 76.148 | 15.134 | 1.00 | 28.87 |
| 2690 | NE2 | HIS | A | 195 | 76.330 | 76.304 | 13.831 | 1.00 | 29.50 |
| 2692 | CD2 | HIS | A | 195 | 75.113 | 76.086 | 13.233 | 1.00 | 27.40 |
| 2694 | C | HIS | A | 195 | 71.050 | 73.751 | 13.451 | 1.00 | 21.00 |
| 2695 | O | HIS | A | 195 | 70.948 | 72.646 | 13.985 | 1.00 | 20.86 |
| 2696 | N | LYS | A | 196 | 69.985 | 74.462 | 13.087 | 1.00 | 20.63 |
| 2698 | CA | LYS | A | 196 | 68.642 | 74.022 | 13.489 | 1.00 | 20.10 |
| 2700 | CB | LYS | A | 196 | 67.590 | 75.123 | 13.367 | 1.00 | 19.88 |
| 2703 | CG | LYS | A | 196 | 66.987 | 75.363 | 11.997 | 1.00 | 19.59 |
| 2706 | CD | LYS | A | 196 | 65.944 | 76.473 | 12.065 | 1.00 | 19.02 |
| 2709 | CE | LYS | A | 196 | 65.416 | 76.847 | 10.672 | 1.00 | 18.63 |
| 2712 | NZ | LYS | A | 196 | 64.064 | 77.494 | 10.673 | 1.00 | 19.09 |
| 2716 | C | LYS | A | 196 | 68.215 | 72.756 | 12.758 | 1.00 | 20.00 |
| 2717 | O | LYS | A | 196 | 67.491 | 71.960 | 13.307 | 1.00 | 20.23 |
| 2718 | N | THR | A | 197 | 68.705 | 72.557 | 11.539 | 1.00 | 19.63 |
| 2720 | CA | THR | A | 197 | 68.278 | 71.433 | 10.726 | 1.00 | 19.13 |
| 2722 | CB | THR | A | 197 | 67.408 | 71.938 | 9.580 | 1.00 | 19.35 |
| 2724 | OG1 | THR | A | 197 | 66.166 | 72.400 | 10.127 | 1.00 | 18.33 |
| 2726 | CG2 | THR | A | 197 | 67.021 | 70.812 | 8.618 | 1.00 | 18.67 |
| 2730 | C | THR | A | 197 | 69.413 | 70.554 | 10.226 | 1.00 | 19.03 |
| 2731 | O | THR | A | 197 | 69.275 | 69.332 | 10.223 | 1.00 | 18.17 |
| 2732 | N | GLY | A | 198 | 70.522 | 71.167 | 9.812 | 1.00 | 19.30 |
| 2734 | CA | GLY | A | 198 | 71.667 | 70.421 | 9.316 | 1.00 | 19.16 |
| 2737 | C | GLY | A | 198 | 72.260 | 69.466 | 10.329 | 1.00 | 19.28 |
| 2738 | O | GLY | A | 198 | 72.580 | 68.330 | 9.987 | 1.00 | 19.12 |
| 2739 | N | ALA | A | 199 | 72.371 | 69.910 | 11.576 | 1.00 | 19.18 |
| 2741 | CA | ALA | A | 199 | 73.129 | 69.182 | 12.585 | 1.00 | 19.36 |
| 2743 | CB | ALA | A | 199 | 73.245 | 70.005 | 13.861 | 1.00 | 19.70 |
| 2747 | C | ALA | A | 199 | 72.505 | 67.816 | 12.897 | 1.00 | 19.34 |
| 2748 | O | ALA | A | 199 | 73.224 | 66.830 | 13.057 | 1.00 | 19.28 |
| 2749 | N | LEU | A | 200 | 71.177 | 67.768 | 12.994 | 1.00 | 19.51 |
| 2751 | CA | LEU | A | 200 | 70.476 | 66.522 | 13.302 | 1.00 | 19.63 |
| 2753 | CB | LEU | A | 200 | 69.016 | 66.775 | 13.700 | 1.00 | 19.77 |
| 2756 | CG | LEU | A | 200 | 68.261 | 65.516 | 14.183 | 1.00 | 20.34 |
| 2758 | CD1 | LEU | A | 200 | 68.918 | 64.931 | 15.431 | 1.00 | 20.63 |
| 2762 | CD2 | LEU | A | 200 | 66.799 | 65.855 | 14.449 | 1.00 | 20.55 |
| 2766 | C | LEU | A | 200 | 70.514 | 65.563 | 12.125 | 1.00 | 19.55 |
| 2767 | O | LEU | A | 200 | 70.590 | 64.336 | 12.312 | 1.00 | 19.72 |
| 2768 | N | ILE | A | 201 | 70.462 | 66.114 | 10.919 | 1.00 | 19.19 |
| 2770 | CA | ILE | A | 201 | 70.556 | 65.299 | 9.706 | 1.00 | 19.51 |
| 2772 | CB | ILE | A | 201 | 70.178 | 66.143 | 8.471 | 1.00 | 19.64 |
| 2774 | CG1 | ILE | A | 201 | 68.659 | 66.197 | 8.372 | 1.00 | 20.21 |

FIGURE 3 BB

| A | B | C | D | E | F | G | H | I | J |
|---|---|---|---|---|---|---|---|---|---|
| 2777 | CD1 | ILE | A | 201 | 68.149 | 67.249 | 7.449 | 1.00 | 21.65 |
| 2781 | CG2 | ILE | A | 201 | 70.782 | 65.578 | 7.169 | 1.00 | 20.92 |
| 2785 | C | ILE | A | 201 | 71.941 | 64.661 | 9.604 | 1.00 | 19.17 |
| 2786 | O | ILE | A | 201 | 72.066 | 63.504 | 9.227 | 1.00 | 18.77 |
| 2787 | N | ARG | A | 202 | 72.970 | 65.420 | 9.963 | 1.00 | 19.39 |
| 2789 | CA | ARG | A | 202 | 74.323 | 64.891 | 10.001 | 1.00 | 19.72 |
| 2791 | CB | ARG | A | 202 | 75.343 | 66.008 | 10.148 | 1.00 | 20.03 |
| 2794 | CG | ARG | A | 202 | 76.774 | 65.526 | 10.119 | 1.00 | 21.06 |
| 2797 | CD | ARG | A | 202 | 77.777 | 66.638 | 10.165 | 1.00 | 20.98 |
| 2800 | NE | ARG | A | 202 | 77.824 | 67.265 | 11.473 | 1.00 | 23.53 |
| 2802 | CZ | ARG | A | 202 | 78.617 | 68.294 | 11.789 | 1.00 | 25.30 |
| 2803 | NH1 | ARG | A | 202 | 78.580 | 68.800 | 13.012 | 1.00 | 23.66 |
| 2806 | NH2 | ARG | A | 202 | 79.445 | 68.815 | 10.891 | 1.00 | 26.69 |
| 2809 | C | ARG | A | 202 | 74.453 | 63.843 | 11.113 | 1.00 | 19.73 |
| 2810 | O | ARG | A | 202 | 75.153 | 62.859 | 10.935 | 1.00 | 19.84 |
| 2811 | N | ALA | A | 203 | 73.741 | 64.027 | 12.226 | 1.00 | 19.24 |
| 2813 | CA | ALA | A | 203 | 73.713 | 63.009 | 13.276 | 1.00 | 18.65 |
| 2815 | CB | ALA | A | 203 | 73.001 | 63.513 | 14.517 | 1.00 | 19.04 |
| 2819 | C | ALA | A | 203 | 73.097 | 61.696 | 12.824 | 1.00 | 18.20 |
| 2820 | O | ALA | A | 203 | 73.582 | 60.644 | 13.210 | 1.00 | 18.83 |
| 2821 | N | ALA | A | 204 | 72.025 | 61.740 | 12.043 | 1.00 | 18.01 |
| 2823 | CA | ALA | A | 204 | 71.441 | 60.524 | 11.485 | 1.00 | 18.08 |
| 2825 | CB | ALA | A | 204 | 70.268 | 60.868 | 10.588 | 1.00 | 18.17 |
| 2829 | C | ALA | A | 204 | 72.481 | 59.738 | 10.700 | 1.00 | 18.04 |
| 2830 | O | ALA | A | 204 | 72.645 | 58.522 | 10.879 | 1.00 | 17.73 |
| 2831 | N | VAL | A | 205 | 73.170 | 60.430 | 9.809 | 1.00 | 17.87 |
| 2833 | CA | VAL | A | 205 | 74.174 | 59.786 | 8.990 | 1.00 | 18.48 |
| 2835 | CB | VAL | A | 205 | 74.659 | 60.714 | 7.874 | 1.00 | 18.22 |
| 2837 | CG1 | VAL | A | 205 | 75.791 | 60.079 | 7.109 | 1.00 | 18.92 |
| 2841 | CG2 | VAL | A | 205 | 73.476 | 61.057 | 6.930 | 1.00 | 17.58 |
| 2845 | C | VAL | A | 205 | 75.314 | 59.238 | 9.852 | 1.00 | 18.69 |
| 2846 | O | VAL | A | 205 | 75.716 | 58.086 | 9.677 | 1.00 | 20.23 |
| 2847 | N | ARG | A | 206 | 75.783 | 60.032 | 10.808 | 1.00 | 18.74 |
| 2849 | CA | ARG | A | 206 | 76.862 | 59.629 | 11.702 | 1.00 | 18.96 |
| 2851 | CB | ARG | A | 206 | 77.274 | 60.778 | 12.615 | 1.00 | 18.76 |
| 2854 | CG | ARG | A | 206 | 78.157 | 61.792 | 11.948 | 1.00 | 19.71 |
| 2857 | CD | ARG | A | 206 | 78.477 | 63.008 | 12.803 | 1.00 | 19.66 |
| 2860 | NE | ARG | A | 206 | 79.481 | 63.857 | 12.167 | 1.00 | 21.03 |
| 2862 | CZ | ARG | A | 206 | 80.008 | 64.936 | 12.737 | 1.00 | 22.60 |
| 2863 | NH1 | ARG | A | 206 | 79.659 | 65.289 | 13.965 | 1.00 | 22.08 |
| 2866 | NH2 | ARG | A | 206 | 80.903 | 65.660 | 12.079 | 1.00 | 21.63 |
| 2869 | C | ARG | A | 206 | 76.481 | 58.427 | 12.549 | 1.00 | 19.18 |
| 2870 | O | ARG | A | 206 | 77.283 | 57.530 | 12.757 | 1.00 | 18.61 |
| 2871 | N | LEU | A | 207 | 75.244 | 58.394 | 13.014 | 1.00 | 19.73 |
| 2873 | CA | LEU | A | 207 | 74.790 | 57.288 | 13.850 | 1.00 | 20.29 |
| 2875 | CB | LEU | A | 207 | 73.426 | 57.600 | 14.481 | 1.00 | 20.21 |
| 2878 | CG | LEU | A | 207 | 73.432 | 58.067 | 15.944 | 1.00 | 21.69 |
| 2880 | CD1 | LEU | A | 207 | 74.453 | 59.147 | 16.210 | 1.00 | 22.70 |
| 2884 | CD2 | LEU | A | 207 | 72.044 | 58.554 | 16.298 | 1.00 | 23.52 |
| 2888 | C | LEU | A | 207 | 74.715 | 56.013 | 13.013 | 1.00 | 20.31 |
| 2889 | O | LEU | A | 207 | 75.049 | 54.941 | 13.486 | 1.00 | 19.90 |
| 2890 | N | GLY | A | 208 | 74.273 | 56.131 | 11.772 | 1.00 | 20.46 |

FIGURE 3 BC

| A | B | C | D | E | F | G | H | I | J |
|---|---|---|---|---|---|---|---|---|---|
| 2892 | CA | GLY | A | 208 | 74.297 | 55.000 | 10.861 | 1.00 | 21.15 |
| 2895 | C | GLY | A | 208 | 75.703 | 54.457 | 10.656 | 1.00 | 21.20 |
| 2896 | O | GLY | A | 208 | 75.933 | 53.240 | 10.737 | 1.00 | 22.15 |
| 2897 | N | ALA | A | 209 | 76.643 | 55.362 | 10.419 | 1.00 | 21.27 |
| 2899 | CA | ALA | A | 209 | 78.046 | 55.006 | 10.215 | 1.00 | 22.05 |
| 2901 | CB | ALA | A | 209 | 78.813 | 56.193 | 9.733 | 1.00 | 21.96 |
| 2905 | C | ALA | A | 209 | 78.700 | 54.419 | 11.480 | 1.00 | 22.41 |
| 2906 | O | ALA | A | 209 | 79.383 | 53.398 | 11.411 | 1.00 | 22.53 |
| 2907 | N | LEU | A | 210 | 78.471 | 55.041 | 12.635 | 1.00 | 22.29 |
| 2909 | CA | LEU | A | 210 | 79.090 | 54.580 | 13.877 | 1.00 | 22.51 |
| 2911 | CB | LEU | A | 210 | 78.775 | 55.522 | 15.039 | 1.00 | 22.37 |
| 2914 | CG | LEU | A | 210 | 79.513 | 56.853 | 14.977 | 1.00 | 22.40 |
| 2916 | CD1 | LEU | A | 210 | 78.845 | 57.900 | 15.863 | 1.00 | 22.42 |
| 2920 | CD2 | LEU | A | 210 | 81.004 | 56.689 | 15.372 | 1.00 | 22.32 |
| 2924 | C | LEU | A | 210 | 78.642 | 53.168 | 14.213 | 1.00 | 23.22 |
| 2925 | O | LEU | A | 210 | 79.383 | 52.408 | 14.830 | 1.00 | 23.30 |
| 2926 | N | SER | A | 211 | 77.430 | 52.809 | 13.786 | 1.00 | 24.01 |
| 2928 | CA | SER | A | 211 | 76.914 | 51.469 | 13.999 | 1.00 | 24.10 |
| 2930 | CB | SER | A | 211 | 75.478 | 51.347 | 13.496 | 1.00 | 24.10 |
| 2933 | OG | SER | A | 211 | 75.459 | 51.162 | 12.104 | 1.00 | 25.59 |
| 2935 | C | SER | A | 211 | 77.764 | 50.397 | 13.335 | 1.00 | 24.24 |
| 2936 | O | SER | A | 211 | 77.746 | 49.254 | 13.778 | 1.00 | 23.60 |
| 2937 | N | ALA | A | 212 | 78.464 | 50.782 | 12.269 | 1.00 | 24.79 |
| 2939 | CA | ALA | A | 212 | 79.332 | 49.906 | 11.496 | 1.00 | 25.88 |
| 2941 | CB | ALA | A | 212 | 79.361 | 50.376 | 10.050 | 1.00 | 26.06 |
| 2945 | C | ALA | A | 212 | 80.762 | 49.837 | 12.044 | 1.00 | 26.25 |
| 2946 | O | ALA | A | 212 | 81.602 | 49.130 | 11.490 | 1.00 | 27.04 |
| 2947 | N | GLY | A | 213 | 81.051 | 50.586 | 13.100 | 1.00 | 26.38 |
| 2949 | CA | GLY | A | 213 | 82.373 | 50.574 | 13.692 | 1.00 | 27.08 |
| 2952 | C | GLY | A | 213 | 83.427 | 51.209 | 12.809 | 1.00 | 27.54 |
| 2953 | O | GLY | A | 213 | 83.193 | 52.242 | 12.199 | 1.00 | 27.58 |
| 2954 | N | ASP | A | 214 | 84.584 | 50.570 | 12.718 | 1.00 | 28.92 |
| 2956 | CA | ASP | A | 214 | 85.758 | 51.188 | 12.105 | 1.00 | 29.67 |
| 2958 | CB | ASP | A | 214 | 86.993 | 50.294 | 12.281 | 1.00 | 30.31 |
| 2961 | CG | ASP | A | 214 | 87.596 | 50.413 | 13.666 | 1.00 | 33.03 |
| 2962 | OD1 | ASP | A | 214 | 88.445 | 49.568 | 14.020 | 1.00 | 37.45 |
| 2963 | OD2 | ASP | A | 214 | 87.285 | 51.318 | 14.478 | 1.00 | 35.85 |
| 2964 | C | ASP | A | 214 | 85.530 | 51.523 | 10.650 | 1.00 | 29.40 |
| 2965 | O | ASP | A | 214 | 85.907 | 52.596 | 10.203 | 1.00 | 29.23 |
| 2966 | N | LYS | A | 215 | 84.879 | 50.625 | 9.921 | 1.00 | 29.50 |
| 2968 | CA | LYS | A | 215 | 84.593 | 50.862 | 8.505 | 1.00 | 29.92 |
| 2970 | CB | LYS | A | 215 | 84.019 | 49.610 | 7.839 | 1.00 | 30.45 |
| 2973 | CG | LYS | A | 215 | 85.103 | 48.766 | 7.182 | 1.00 | 33.43 |
| 2976 | CD | LYS | A | 215 | 84.685 | 47.310 | 6.964 | 1.00 | 36.17 |
| 2979 | CE | LYS | A | 215 | 85.888 | 46.439 | 6.568 | 1.00 | 37.55 |
| 2982 | NZ | LYS | A | 215 | 85.967 | 45.213 | 7.416 | 1.00 | 39.13 |
| 2986 | C | LYS | A | 215 | 83.672 | 52.076 | 8.312 | 1.00 | 29.02 |
| 2987 | O | LYS | A | 215 | 83.851 | 52.860 | 7.384 | 1.00 | 27.84 |
| 2988 | N | GLY | A | 216 | 82.696 | 52.241 | 9.198 | 1.00 | 28.66 |
| 2990 | CA | GLY | A | 216 | 81.855 | 53.429 | 9.162 | 1.00 | 28.17 |
| 2993 | C | GLY | A | 216 | 82.647 | 54.692 | 9.471 | 1.00 | 27.77 |
| 2994 | O | GLY | A | 216 | 82.503 | 55.719 | 8.812 | 1.00 | 27.08 |

FIGURE 3 BD

| A | B | C | D | E | F | G | H | I | J |
|---|---|---|---|---|---|---|---|---|---|
| 2995 | N | ARG | A | 217 | 83.498 | 54.609 | 10.482 | 1.00 | 27.98 |
| 2997 | CA | ARG | A | 217 | 84.306 | 55.751 | 10.900 | 1.00 | 28.29 |
| 2999 | CB | ARG | A | 217 | 85.165 | 55.391 | 12.106 | 1.00 | 28.55 |
| 3002 | CG | ARG | A | 217 | 84.449 | 55.520 | 13.428 | 1.00 | 28.34 |
| 3005 | CD | ARG | A | 217 | 85.328 | 55.173 | 14.580 | 1.00 | 29.33 |
| 3008 | NE | ARG | A | 217 | 84.577 | 55.110 | 15.826 | 1.00 | 29.90 |
| 3010 | CZ | ARG | A | 217 | 84.375 | 56.148 | 16.637 | 1.00 | 29.01 |
| 3011 | NH1 | ARG | A | 217 | 84.836 | 57.359 | 16.334 | 1.00 | 29.10 |
| 3014 | NH2 | ARG | A | 217 | 83.671 | 55.980 | 17.743 | 1.00 | 28.00 |
| 3017 | C | ARG | A | 217 | 85.201 | 56.266 | 9.783 | 1.00 | 28.80 |
| 3018 | O | ARG | A | 217 | 85.367 | 57.476 | 9.645 | 1.00 | 28.97 |
| 3019 | N | ARG | A | 218 | 85.752 | 55.354 | 8.978 | 1.00 | 29.00 |
| 3021 | CA | ARG | A | 218 | 86.622 | 55.726 | 7.853 | 1.00 | 29.76 |
| 3023 | CB | ARG | A | 218 | 87.268 | 54.483 | 7.223 | 1.00 | 30.54 |
| 3026 | CG | ARG | A | 218 | 88.351 | 53.812 | 8.069 | 1.00 | 33.89 |
| 3029 | CD | ARG | A | 218 | 88.273 | 52.280 | 8.115 | 1.00 | 38.26 |
| 3032 | NE | ARG | A | 218 | 88.914 | 51.617 | 6.975 | 1.00 | 41.13 |
| 3034 | CZ | ARG | A | 218 | 88.318 | 51.290 | 5.817 | 1.00 | 44.61 |
| 3035 | NH1 | ARG | A | 218 | 89.023 | 50.681 | 4.862 | 1.00 | 46.06 |
| 3038 | NH2 | ARG | A | 218 | 87.037 | 51.564 | 5.587 | 1.00 | 45.97 |
| 3041 | C | ARG | A | 218 | 85.866 | 56.481 | 6.765 | 1.00 | 29.10 |
| 3042 | O | ARG | A | 218 | 86.460 | 57.283 | 6.034 | 1.00 | 29.09 |
| 3043 | N | ALA | A | 219 | 84.565 | 56.209 | 6.646 | 1.00 | 27.99 |
| 3045 | CA | ALA | A | 219 | 83.720 | 56.894 | 5.669 | 1.00 | 27.60 |
| 3047 | CB | ALA | A | 219 | 82.532 | 56.030 | 5.313 | 1.00 | 27.48 |
| 3051 | C | ALA | A | 219 | 83.234 | 58.253 | 6.142 | 1.00 | 27.24 |
| 3052 | O | ALA | A | 219 | 82.710 | 59.018 | 5.344 | 1.00 | 26.75 |
| 3053 | N | LEU | A | 220 | 83.394 | 58.543 | 7.433 | 1.00 | 27.30 |
| 3055 | CA | LEU | A | 220 | 82.807 | 59.736 | 8.036 | 1.00 | 27.51 |
| 3057 | CB | LEU | A | 220 | 83.061 | 59.804 | 9.546 | 1.00 | 27.81 |
| 3060 | CG | LEU | A | 220 | 82.127 | 58.960 | 10.416 | 1.00 | 29.69 |
| 3062 | CD1 | LEU | A | 220 | 82.573 | 59.004 | 11.889 | 1.00 | 30.50 |
| 3066 | CD2 | LEU | A | 220 | 80.677 | 59.411 | 10.271 | 1.00 | 30.60 |
| 3070 | C | LEU | A | 220 | 83.226 | 61.045 | 7.400 | 1.00 | 26.87 |
| 3071 | O | LEU | A | 220 | 82.380 | 61.901 | 7.232 | 1.00 | 27.16 |
| 3072 | N | PRO | A | 221 | 84.502 | 61.248 | 7.067 | 1.00 | 26.59 |
| 3073 | CA | PRO | A | 221 | 84.879 | 62.502 | 6.399 | 1.00 | 26.30 |
| 3075 | CB | PRO | A | 221 | 86.349 | 62.269 | 6.006 | 1.00 | 26.54 |
| 3078 | CG | PRO | A | 221 | 86.853 | 61.366 | 7.081 | 1.00 | 27.08 |
| 3081 | CD | PRO | A | 221 | 85.685 | 60.415 | 7.352 | 1.00 | 26.58 |
| 3084 | C | PRO | A | 221 | 83.996 | 62.758 | 5.195 | 1.00 | 25.66 |
| 3085 | O | PRO | A | 221 | 83.479 | 63.859 | 5.044 | 1.00 | 26.22 |
| 3086 | N | VAL | A | 222 | 83.770 | 61.735 | 4.381 | 1.00 | 24.71 |
| 3088 | CA | VAL | A | 222 | 82.965 | 61.910 | 3.181 | 1.00 | 24.34 |
| 3090 | CB | VAL | A | 222 | 83.272 | 60.835 | 2.139 | 1.00 | 24.09 |
| 3092 | CG1 | VAL | A | 222 | 82.302 | 60.927 | 0.999 | 1.00 | 23.94 |
| 3096 | CG2 | VAL | A | 222 | 84.718 | 60.988 | 1.655 | 1.00 | 25.44 |
| 3100 | C | VAL | A | 222 | 81.465 | 61.955 | 3.470 | 1.00 | 23.78 |
| 3101 | O | VAL | A | 222 | 80.754 | 62.771 | 2.885 | 1.00 | 23.40 |
| 3102 | N | LEU | A | 223 | 80.978 | 61.096 | 4.362 | 1.00 | 23.25 |
| 3104 | CA | LEU | A | 223 | 79.552 | 61.118 | 4.707 | 1.00 | 22.90 |
| 3106 | CB | LEU | A | 223 | 79.179 | 59.955 | 5.627 | 1.00 | 23.13 |

FIGURE 3 BE

| A | B | C | D | E | F | G | H | I | J |
|---|---|---|---|---|---|---|---|---|---|
| 3109 | CG | LEU | A | 223 | 79.130 | 58.583 | 4.947 | 1.00 | 22.78 |
| 3111 | CD1 | LEU | A | 223 | 79.022 | 57.462 | 5.987 | 1.00 | 23.57 |
| 3115 | CD2 | LEU | A | 223 | 77.991 | 58.484 | 3.975 | 1.00 | 23.72 |
| 3119 | C | LEU | A | 223 | 79.159 | 62.441 | 5.346 | 1.00 | 23.02 |
| 3120 | O | LEU | A | 223 | 78.023 | 62.903 | 5.182 | 1.00 | 22.74 |
| 3121 | N | ASP | A | 224 | 80.081 | 63.036 | 6.093 | 1.00 | 23.24 |
| 3123 | CA | ASP | A | 224 | 79.838 | 64.328 | 6.722 | 1.00 | 23.61 |
| 3125 | CB | ASP | A | 224 | 81.028 | 64.753 | 7.588 | 1.00 | 23.94 |
| 3128 | CG | ASP | A | 224 | 81.009 | 64.118 | 8.974 | 1.00 | 25.27 |
| 3129 | OD1 | ASP | A | 224 | 79.961 | 63.561 | 9.379 | 1.00 | 25.31 |
| 3130 | OD2 | ASP | A | 224 | 81.989 | 64.158 | 9.749 | 1.00 | 27.02 |
| 3131 | C | ASP | A | 224 | 79.568 | 65.385 | 5.654 | 1.00 | 23.60 |
| 3132 | O | ASP | A | 224 | 78.630 | 66.175 | 5.772 | 1.00 | 22.89 |
| 3133 | N | LYS | A | 225 | 80.373 | 65.377 | 4.599 | 1.00 | 23.58 |
| 3135 | CA | LYS | A | 225 | 80.234 | 66.391 | 3.557 | 1.00 | 24.32 |
| 3137 | CB | LYS | A | 225 | 81.439 | 66.381 | 2.594 | 1.00 | 24.94 |
| 3140 | CG | LYS | A | 225 | 82.825 | 66.478 | 3.298 | 1.00 | 27.64 |
| 3143 | CD | LYS | A | 225 | 83.113 | 67.828 | 4.009 | 1.00 | 31.84 |
| 3146 | CE | LYS | A | 225 | 83.516 | 67.719 | 5.546 | 1.00 | 32.28 |
| 3149 | NZ | LYS | A | 225 | 84.063 | 66.374 | 6.064 | 1.00 | 30.63 |
| 3153 | C | LYS | A | 225 | 78.901 | 66.207 | 2.842 | 1.00 | 23.43 |
| 3154 | O | LYS | A | 225 | 78.205 | 67.177 | 2.548 | 1.00 | 23.79 |
| 3155 | N | TYR | A | 226 | 78.521 | 64.955 | 2.612 | 1.00 | 22.64 |
| 3157 | CA | TYR | A | 226 | 77.214 | 64.632 | 2.063 | 1.00 | 21.59 |
| 3159 | CB | TYR | A | 226 | 77.075 | 63.114 | 1.881 | 1.00 | 21.93 |
| 3162 | CG | TYR | A | 226 | 75.645 | 62.633 | 1.753 | 1.00 | 20.62 |
| 3163 | CD1 | TYR | A | 226 | 75.021 | 62.606 | 0.523 | 1.00 | 21.37 |
| 3165 | CE1 | TYR | A | 226 | 73.736 | 62.160 | 0.386 | 1.00 | 20.90 |
| 3167 | CZ | TYR | A | 226 | 73.030 | 61.727 | 1.487 | 1.00 | 20.66 |
| 3168 | OH | TYR | A | 226 | 71.737 | 61.289 | 1.311 | 1.00 | 21.67 |
| 3170 | CE2 | TYR | A | 226 | 73.617 | 61.727 | 2.730 | 1.00 | 21.12 |
| 3172 | CD2 | TYR | A | 226 | 74.933 | 62.174 | 2.862 | 1.00 | 20.69 |
| 3174 | C | TYR | A | 226 | 76.098 | 65.121 | 2.979 | 1.00 | 21.19 |
| 3175 | O | TYR | A | 226 | 75.156 | 65.754 | 2.523 | 1.00 | 21.30 |
| 3176 | N | ALA | A | 227 | 76.208 | 64.804 | 4.261 | 1.00 | 20.68 |
| 3178 | CA | ALA | A | 227 | 75.173 | 65.126 | 5.240 | 1.00 | 20.41 |
| 3180 | CB | ALA | A | 227 | 75.503 | 64.513 | 6.581 | 1.00 | 20.07 |
| 3184 | C | ALA | A | 227 | 75.007 | 66.627 | 5.390 | 1.00 | 20.36 |
| 3185 | O | ALA | A | 227 | 73.893 | 67.123 | 5.485 | 1.00 | 19.95 |
| 3186 | N | GLU | A | 228 | 76.132 | 67.326 | 5.407 | 1.00 | 20.85 |
| 3188 | CA | GLU | A | 228 | 76.160 | 68.786 | 5.503 | 1.00 | 21.65 |
| 3190 | CB | GLU | A | 228 | 77.601 | 69.285 | 5.581 | 1.00 | 21.59 |
| 3193 | CG | GLU | A | 228 | 78.225 | 69.020 | 6.940 | 1.00 | 23.51 |
| 3196 | CD | GLU | A | 228 | 79.737 | 68.868 | 6.911 | 1.00 | 25.72 |
| 3197 | OE1 | GLU | A | 228 | 80.292 | 68.333 | 7.899 | 1.00 | 25.16 |
| 3198 | OE2 | GLU | A | 228 | 80.367 | 69.272 | 5.910 | 1.00 | 28.53 |
| 3199 | C | GLU | A | 228 | 75.411 | 69.428 | 4.340 | 1.00 | 21.53 |
| 3200 | O | GLU | A | 228 | 74.644 | 70.370 | 4.532 | 1.00 | 22.09 |
| 3201 | N | SER | A | 229 | 75.600 | 68.899 | 3.141 | 1.00 | 21.49 |
| 3203 | CA | SER | A | 229 | 74.922 | 69.459 | 1.985 | 1.00 | 21.57 |
| 3205 | CB | SER | A | 229 | 75.598 | 69.036 | 0.695 | 1.00 | 21.17 |
| 3208 | OG | SER | A | 229 | 76.870 | 69.647 | 0.589 | 1.00 | 22.38 |

FIGURE 3 BF

| A | B | C | D | E | F | G | H | I | J |
|---|---|---|---|---|---|---|---|---|---|
| 3210 | C | SER | A | 229 | 73.432 | 69.119 | 1.967 | 1.00 | 21.32 |
| 3211 | O | SER | A | 229 | 72.629 | 69.993 | 1.719 | 1.00 | 20.51 |
| 3212 | N | ILE | A | 230 | 73.044 | 67.871 | 2.238 | 1.00 | 21.52 |
| 3214 | CA | ILE | A | 230 | 71.610 | 67.562 | 2.236 | 1.00 | 21.70 |
| 3216 | CB | ILE | A | 230 | 71.318 | 66.049 | 2.154 | 1.00 | 21.58 |
| 3218 | CG1 | ILE | A | 230 | 71.881 | 65.279 | 3.347 | 1.00 | 22.85 |
| 3221 | CD1 | ILE | A | 230 | 71.069 | 64.038 | 3.669 | 1.00 | 22.81 |
| 3225 | CG2 | ILE | A | 230 | 71.815 | 65.486 | 0.849 | 1.00 | 21.97 |
| 3229 | C | ILE | A | 230 | 70.874 | 68.190 | 3.421 | 1.00 | 21.12 |
| 3230 | O | ILE | A | 230 | 69.684 | 68.467 | 3.337 | 1.00 | 21.31 |
| 3231 | N | GLY | A | 231 | 71.583 | 68.412 | 4.520 | 1.00 | 21.08 |
| 3233 | CA | GLY | A | 231 | 70.983 | 68.977 | 5.714 | 1.00 | 21.32 |
| 3236 | C | GLY | A | 231 | 70.607 | 70.441 | 5.534 | 1.00 | 21.14 |
| 3237 | O | GLY | A | 231 | 69.514 | 70.877 | 5.917 | 1.00 | 21.86 |
| 3238 | N | LEU | A | 232 | 71.513 | 71.205 | 4.939 | 1.00 | 21.35 |
| 3240 | CA | LEU | A | 232 | 71.214 | 72.583 | 4.595 | 1.00 | 21.18 |
| 3242 | CB | LEU | A | 232 | 72.467 | 73.318 | 4.127 | 1.00 | 21.49 |
| 3245 | CG | LEU | A | 232 | 72.250 | 74.769 | 3.712 | 1.00 | 21.63 |
| 3247 | CD1 | LEU | A | 232 | 71.601 | 75.564 | 4.829 | 1.00 | 22.56 |
| 3251 | CD2 | LEU | A | 232 | 73.571 | 75.361 | 3.320 | 1.00 | 23.37 |
| 3255 | C | LEU | A | 232 | 70.134 | 72.604 | 3.521 | 1.00 | 20.95 |
| 3256 | O | LEU | A | 232 | 69.171 | 73.324 | 3.659 | 1.00 | 20.57 |
| 3257 | N | ALA | A | 233 | 70.270 | 71.766 | 2.488 | 1.00 | 20.80 |
| 3259 | CA | ALA | A | 233 | 69.271 | 71.677 | 1.424 | 1.00 | 20.94 |
| 3261 | CB | ALA | A | 233 | 69.674 | 70.639 | 0.373 | 1.00 | 21.23 |
| 3265 | C | ALA | A | 233 | 67.885 | 71.350 | 1.966 | 1.00 | 20.81 |
| 3266 | O | ALA | A | 233 | 66.878 | 71.812 | 1.442 | 1.00 | 20.67 |
| 3267 | N | PHE | A | 234 | 67.840 | 70.554 | 3.029 | 1.00 | 20.67 |
| 3269 | CA | PHE | A | 234 | 66.568 | 70.166 | 3.634 | 1.00 | 20.70 |
| 3271 | CB | PHE | A | 234 | 66.798 | 69.201 | 4.785 | 1.00 | 20.78 |
| 3274 | CG | PHE | A | 234 | 65.600 | 68.375 | 5.131 | 1.00 | 22.14 |
| 3275 | CD1 | PHE | A | 234 | 65.546 | 67.041 | 4.768 | 1.00 | 23.74 |
| 3277 | CE1 | PHE | A | 234 | 64.455 | 66.267 | 5.103 | 1.00 | 25.17 |
| 3279 | CZ | PHE | A | 234 | 63.407 | 66.817 | 5.797 | 1.00 | 23.85 |
| 3281 | CE2 | PHE | A | 234 | 63.462 | 68.143 | 6.173 | 1.00 | 23.26 |
| 3283 | CD2 | PHE | A | 234 | 64.551 | 68.907 | 5.851 | 1.00 | 21.11 |
| 3285 | C | PHE | A | 234 | 65.812 | 71.378 | 4.147 | 1.00 | 20.30 |
| 3286 | O | PHE | A | 234 | 64.590 | 71.496 | 3.939 | 1.00 | 19.63 |
| 3287 | N | GLN | A | 235 | 66.523 | 72.269 | 4.835 | 1.00 | 20.63 |
| 3289 | CA | GLN | A | 235 | 65.874 | 73.456 | 5.381 | 1.00 | 21.12 |
| 3291 | CB | GLN | A | 235 | 66.699 | 74.091 | 6.503 | 1.00 | 21.39 |
| 3294 | CG | GLN | A | 235 | 65.944 | 75.205 | 7.276 | 1.00 | 21.45 |
| 3297 | CD | GLN | A | 235 | 64.668 | 74.715 | 7.926 | 1.00 | 23.00 |
| 3298 | OE1 | GLN | A | 235 | 64.650 | 73.654 | 8.548 | 1.00 | 23.23 |
| 3299 | NE2 | GLN | A | 235 | 63.595 | 75.490 | 7.795 | 1.00 | 20.99 |
| 3302 | C | GLN | A | 235 | 65.546 | 74.494 | 4.300 | 1.00 | 21.77 |
| 3303 | O | GLN | A | 235 | 64.511 | 75.148 | 4.375 | 1.00 | 22.39 |
| 3304 | N | VAL | A | 236 | 66.402 | 74.641 | 3.299 | 1.00 | 22.51 |
| 3306 | CA | VAL | A | 236 | 66.066 | 75.543 | 2.184 | 1.00 | 22.92 |
| 3308 | CB | VAL | A | 236 | 67.260 | 75.840 | 1.212 | 1.00 | 23.27 |
| 3310 | CG1 | VAL | A | 236 | 68.054 | 74.664 | 0.922 | 1.00 | 26.25 |
| 3314 | CG2 | VAL | A | 236 | 66.794 | 76.486 | -0.102 | 1.00 | 23.71 |

FIGURE 3 BG

| A | B | C | D | E | F | G | H | I | J |
|---|---|---|---|---|---|---|---|---|---|
| 3318 | C | VAL | A | 236 | 64.794 | 75.075 | 1.478 | 1.00 | 22.84 |
| 3319 | O | VAL | A | 236 | 63.936 | 75.893 | 1.150 | 1.00 | 22.34 |
| 3320 | N | GLN | A | 237 | 64.635 | 73.761 | 1.307 | 1.00 | 23.02 |
| 3322 | CA | GLN | A | 237 | 63.413 | 73.222 | 0.738 | 1.00 | 23.04 |
| 3324 | CB | GLN | A | 237 | 63.538 | 71.727 | 0.418 | 1.00 | 23.87 |
| 3327 | CG | GLN | A | 237 | 62.276 | 71.128 | -0.198 | 1.00 | 25.59 |
| 3330 | CD | GLN | A | 237 | 62.058 | 71.593 | -1.623 | 1.00 | 29.42 |
| 3331 | OE1 | GLN | A | 237 | 62.818 | 72.426 | -2.133 | 1.00 | 30.57 |
| 3332 | NE2 | GLN | A | 237 | 61.025 | 71.053 | -2.275 | 1.00 | 28.29 |
| 3335 | C | GLN | A | 237 | 62.241 | 73.441 | 1.671 | 1.00 | 22.23 |
| 3336 | O | GLN | A | 237 | 61.140 | 73.709 | 1.213 | 1.00 | 22.37 |
| 3337 | N | ASP | A | 238 | 62.467 | 73.315 | 2.977 | 1.00 | 21.60 |
| 3339 | CA | ASP | A | 238 | 61.409 | 73.564 | 3.954 | 1.00 | 21.14 |
| 3341 | CB | ASP | A | 238 | 61.898 | 73.263 | 5.372 | 1.00 | 20.81 |
| 3344 | CG | ASP | A | 238 | 60.808 | 73.400 | 6.393 | 1.00 | 20.15 |
| 3345 | OD1 | ASP | A | 238 | 59.877 | 72.588 | 6.376 | 1.00 | 22.40 |
| 3346 | OD2 | ASP | A | 238 | 60.774 | 74.310 | 7.250 | 1.00 | 23.26 |
| 3347 | C | ASP | A | 238 | 60.904 | 75.018 | 3.848 | 1.00 | 21.37 |
| 3348 | O | ASP | A | 238 | 59.701 | 75.260 | 3.866 | 1.00 | 21.86 |
| 3349 | N | ASP | A | 239 | 61.820 | 75.966 | 3.694 | 1.00 | 21.89 |
| 3351 | CA | ASP | A | 239 | 61.446 | 77.379 | 3.534 | 1.00 | 22.75 |
| 3353 | CB | ASP | A | 239 | 62.674 | 78.275 | 3.478 | 1.00 | 22.66 |
| 3356 | CG | ASP | A | 239 | 63.436 | 78.375 | 4.789 | 1.00 | 23.92 |
| 3357 | OD1 | ASP | A | 239 | 62.965 | 77.899 | 5.859 | 1.00 | 26.27 |
| 3358 | OD2 | ASP | A | 239 | 64.542 | 78.966 | 4.821 | 1.00 | 23.49 |
| 3359 | C | ASP | A | 239 | 60.679 | 77.596 | 2.219 | 1.00 | 23.14 |
| 3360 | O | ASP | A | 239 | 59.719 | 78.357 | 2.158 | 1.00 | 23.09 |
| 3361 | N | ILE | A | 240 | 61.129 | 76.934 | 1.162 | 1.00 | 24.22 |
| 3363 | CA | ILE | A | 240 | 60.507 | 77.067 | -0.150 | 1.00 | 24.50 |
| 3365 | CB | ILE | A | 240 | 61.358 | 76.356 | -1.230 | 1.00 | 24.79 |
| 3367 | CG1 | ILE | A | 240 | 62.593 | 77.200 | -1.545 | 1.00 | 25.00 |
| 3370 | CD1 | ILE | A | 240 | 63.697 | 76.444 | -2.246 | 1.00 | 25.62 |
| 3374 | CG2 | ILE | A | 240 | 60.548 | 76.118 | -2.518 | 1.00 | 24.83 |
| 3378 | C | ILE | A | 240 | 59.094 | 76.529 | -0.095 | 1.00 | 24.74 |
| 3379 | O | ILE | A | 240 | 58.168 | 77.162 | -0.598 | 1.00 | 24.41 |
| 3380 | N | LEU | A | 241 | 58.920 | 75.380 | 0.561 | 1.00 | 24.90 |
| 3382 | CA | LEU | A | 241 | 57.608 | 74.763 | 0.702 | 1.00 | 25.47 |
| 3384 | CB | LEU | A | 241 | 57.721 | 73.376 | 1.346 | 1.00 | 25.41 |
| 3387 | CG | LEU | A | 241 | 58.364 | 72.296 | 0.469 | 1.00 | 26.20 |
| 3389 | CD1 | LEU | A | 241 | 58.592 | 71.012 | 1.275 | 1.00 | 26.19 |
| 3393 | CD2 | LEU | A | 241 | 57.523 | 72.032 | -0.762 | 1.00 | 26.28 |
| 3397 | C | LEU | A | 241 | 56.677 | 75.637 | 1.517 | 1.00 | 25.82 |
| 3398 | O | LEU | A | 241 | 55.463 | 75.646 | 1.296 | 1.00 | 26.02 |
| 3399 | N | ASP | A | 242 | 57.238 | 76.375 | 2.461 | 1.00 | 26.06 |
| 3401 | CA | ASP | A | 242 | 56.422 | 77.233 | 3.298 | 1.00 | 27.02 |
| 3403 | CB | ASP | A | 242 | 57.239 | 77.832 | 4.426 | 1.00 | 26.69 |
| 3406 | CG | ASP | A | 242 | 56.390 | 78.176 | 5.607 | 1.00 | 28.82 |
| 3407 | OD1 | ASP | A | 242 | 55.886 | 79.319 | 5.636 | 1.00 | 29.75 |
| 3408 | OD2 | ASP | A | 242 | 56.148 | 77.365 | 6.534 | 1.00 | 31.49 |
| 3409 | C | ASP | A | 242 | 55.765 | 78.333 | 2.458 | 1.00 | 27.65 |
| 3410 | O | ASP | A | 242 | 54.622 | 78.689 | 2.698 | 1.00 | 28.08 |
| 3411 | N | VAL | A | 243 | 56.481 | 78.823 | 1.454 | 1.00 | 28.57 |

FIGURE 3 BH

| A | B | C | D | E | F | G | H | I | J |
|---|---|---|---|---|---|---|---|---|---|
| 3413 | CA | VAL | A | 243 | 55.949 | 79.838 | 0.542 | 1.00 | 29.59 |
| 3415 | CB | VAL | A | 243 | 57.091 | 80.577 | -0.188 | 1.00 | 29.49 |
| 3417 | CG1 | VAL | A | 243 | 56.537 | 81.656 | -1.140 | 1.00 | 29.98 |
| 3421 | CG2 | VAL | A | 243 | 58.062 | 81.200 | 0.825 | 1.00 | 29.51 |
| 3425 | C | VAL | A | 243 | 54.951 | 79.248 | -0.477 | 1.00 | 30.63 |
| 3426 | O | VAL | A | 243 | 53.791 | 79.669 | -0.525 | 1.00 | 30.78 |
| 3427 | N | VAL | A | 244 | 55.388 | 78.253 | -1.250 | 1.00 | 31.44 |
| 3429 | CA | VAL | A | 244 | 54.642 | 77.785 | -2.427 | 1.00 | 32.17 |
| 3431 | CB | VAL | A | 244 | 55.605 | 77.525 | -3.617 | 1.00 | 32.40 |
| 3433 | CG1 | VAL | A | 244 | 56.588 | 78.680 | -3.768 | 1.00 | 32.66 |
| 3437 | CG2 | VAL | A | 244 | 56.349 | 76.185 | -3.462 | 1.00 | 32.82 |
| 3441 | C | VAL | A | 244 | 53.766 | 76.543 | -2.233 | 1.00 | 32.47 |
| 3442 | O | VAL | A | 244 | 52.963 | 76.204 | -3.110 | 1.00 | 32.70 |
| 3443 | N | GLY | A | 245 | 53.915 | 75.854 | -1.105 | 1.00 | 32.77 |
| 3445 | CA | GLY | A | 245 | 53.200 | 74.611 | -0.879 | 1.00 | 33.14 |
| 3448 | C | GLY | A | 245 | 51.784 | 74.871 | -0.407 | 1.00 | 33.82 |
| 3449 | O | GLY | A | 245 | 51.515 | 75.920 | 0.162 | 1.00 | 34.10 |
| 3450 | N | ASP | A | 246 | 50.887 | 73.920 | -0.656 | 1.00 | 34.38 |
| 3452 | CA | ASP | A | 246 | 49.489 | 73.995 | -0.211 | 1.00 | 34.75 |
| 3454 | CB | ASP | A | 246 | 48.602 | 73.159 | -1.151 | 1.00 | 35.30 |
| 3457 | CG | ASP | A | 246 | 47.185 | 73.699 | -1.272 | 1.00 | 38.65 |
| 3458 | OD1 | ASP | A | 246 | 46.738 | 73.925 | -2.425 | 1.00 | 42.04 |
| 3459 | OD2 | ASP | A | 246 | 46.433 | 73.914 | -0.284 | 1.00 | 42.91 |
| 3460 | C | ASP | A | 246 | 49.431 | 73.410 | 1.198 | 1.00 | 33.97 |
| 3461 | O | ASP | A | 246 | 50.088 | 72.411 | 1.456 | 1.00 | 33.79 |
| 3462 | N | THR | A | 247 | 48.643 | 74.009 | 2.089 | 1.00 | 33.08 |
| 3464 | CA | THR | A | 247 | 48.489 | 73.517 | 3.465 | 1.00 | 32.87 |
| 3466 | CB | THR | A | 247 | 47.476 | 74.394 | 4.249 | 1.00 | 32.46 |
| 3468 | OG1 | THR | A | 247 | 48.002 | 75.710 | 4.420 | 1.00 | 32.70 |
| 3470 | CG2 | THR | A | 247 | 47.288 | 73.901 | 5.684 | 1.00 | 32.42 |
| 3474 | C | THR | A | 247 | 48.061 | 72.041 | 3.542 | 1.00 | 32.67 |
| 3475 | O | THR | A | 247 | 48.561 | 71.297 | 4.377 | 1.00 | 32.65 |
| 3476 | N | ALA | A | 248 | 47.141 | 71.617 | 2.677 | 1.00 | 32.34 |
| 3478 | CA | ALA | A | 248 | 46.651 | 70.240 | 2.709 | 1.00 | 32.14 |
| 3480 | CB | ALA | A | 248 | 45.388 | 70.095 | 1.857 | 1.00 | 32.51 |
| 3484 | C | ALA | A | 248 | 47.724 | 69.228 | 2.271 | 1.00 | 31.60 |
| 3485 | O | ALA | A | 248 | 47.692 | 68.073 | 2.678 | 1.00 | 31.38 |
| 3486 | N | THR | A | 249 | 48.668 | 69.666 | 1.447 | 1.00 | 31.12 |
| 3488 | CA | THR | A | 249 | 49.785 | 68.815 | 1.025 | 1.00 | 31.09 |
| 3490 | CB | THR | A | 249 | 50.269 | 69.251 | -0.371 | 1.00 | 31.32 |
| 3492 | OG1 | THR | A | 249 | 49.192 | 69.112 | -1.313 | 1.00 | 33.79 |
| 3494 | CG2 | THR | A | 249 | 51.348 | 68.308 | -0.917 | 1.00 | 31.41 |
| 3498 | C | THR | A | 249 | 50.943 | 68.825 | 2.045 | 1.00 | 30.23 |
| 3499 | O | THR | A | 249 | 51.483 | 67.768 | 2.391 | 1.00 | 30.03 |
| 3500 | N | LEU | A | 250 | 51.312 | 70.017 | 2.520 | 1.00 | 29.30 |
| 3502 | CA | LEU | A | 250 | 52.358 | 70.175 | 3.539 | 1.00 | 28.64 |
| 3504 | CB | LEU | A | 250 | 52.668 | 71.653 | 3.766 | 1.00 | 28.31 |
| 3507 | CG | LEU | A | 250 | 53.253 | 72.412 | 2.577 | 1.00 | 29.19 |
| 3509 | CD1 | LEU | A | 250 | 53.329 | 73.903 | 2.883 | 1.00 | 29.07 |
| 3513 | CD2 | LEU | A | 250 | 54.620 | 71.880 | 2.197 | 1.00 | 29.56 |
| 3517 | C | LEU | A | 250 | 52.007 | 69.554 | 4.880 | 1.00 | 27.73 |
| 3518 | O | LEU | A | 250 | 52.877 | 69.038 | 5.578 | 1.00 | 27.92 |

FIGURE 3 BI

| A | B | C | D | E | F | G | H | I | J |
|---|---|---|---|---|---|---|---|---|---|
| 3519 | N | GLY | A | 251 | 50.732 | 69.613 | 5.240 | 1.00 | 26.76 |
| 3521 | CA | GLY | A | 251 | 50.277 | 69.195 | 6.546 | 1.00 | 26.19 |
| 3524 | C | GLY | A | 251 | 50.485 | 70.266 | 7.601 | 1.00 | 25.80 |
| 3525 | O | GLY | A | 251 | 50.150 | 70.053 | 8.757 | 1.00 | 24.95 |
| 3526 | N | LYS | A | 252 | 51.071 | 71.388 | 7.197 | 1.00 | 25.86 |
| 3528 | CA | LYS | A | 252 | 51.273 | 72.556 | 8.052 | 1.00 | 26.53 |
| 3530 | CB | LYS | A | 252 | 52.701 | 72.588 | 8.628 | 1.00 | 25.80 |
| 3533 | CG | LYS | A | 252 | 53.804 | 72.498 | 7.579 | 1.00 | 25.64 |
| 3536 | CD | LYS | A | 252 | 55.183 | 72.231 | 8.200 | 1.00 | 23.61 |
| 3539 | CE | LYS | A | 252 | 56.297 | 72.507 | 7.205 | 1.00 | 22.86 |
| 3542 | NZ | LYS | A | 252 | 57.604 | 71.866 | 7.602 | 1.00 | 21.94 |
| 3546 | C | LYS | A | 252 | 50.992 | 73.813 | 7.223 | 1.00 | 27.55 |
| 3547 | O | LYS | A | 252 | 51.046 | 73.781 | 5.982 | 1.00 | 28.12 |
| 3548 | N | ARG | A | 253 | 50.721 | 74.918 | 7.905 | 1.00 | 28.61 |
| 3550 | CA | ARG | A | 253 | 50.217 | 76.128 | 7.249 | 1.00 | 29.63 |
| 3552 | CB | ARG | A | 253 | 49.658 | 77.096 | 8.287 | 1.00 | 30.10 |
| 3555 | CG | ARG | A | 253 | 48.370 | 76.612 | 8.875 | 1.00 | 32.12 |
| 3558 | CD | ARG | A | 253 | 47.441 | 77.693 | 9.362 | 1.00 | 35.28 |
| 3561 | NE | ARG | A | 253 | 46.380 | 77.104 | 10.175 | 1.00 | 38.07 |
| 3563 | CZ | ARG | A | 253 | 45.308 | 76.476 | 9.688 | 1.00 | 40.08 |
| 3564 | NH1 | ARG | A | 253 | 45.095 | 76.378 | 8.376 | 1.00 | 39.60 |
| 3567 | NH2 | ARG | A | 253 | 44.419 | 75.962 | 10.533 | 1.00 | 40.97 |
| 3570 | C | ARG | A | 253 | 51.223 | 76.852 | 6.360 | 1.00 | 29.71 |
| 3571 | O | ARG | A | 253 | 52.306 | 77.274 | 6.806 | 1.00 | 29.38 |
| 3572 | N | GLN | A | 254 | 50.847 | 76.966 | 5.084 | 1.00 | 30.10 |
| 3574 | CA | GLN | A | 254 | 51.544 | 77.794 | 4.108 | 1.00 | 29.94 |
| 3576 | CB | GLN | A | 254 | 50.816 | 77.731 | 2.754 | 1.00 | 30.17 |
| 3579 | CG | GLN | A | 254 | 51.436 | 78.643 | 1.649 | 1.00 | 31.83 |
| 3582 | CD | GLN | A | 254 | 50.618 | 78.716 | 0.357 | 1.00 | 34.25 |
| 3583 | OE1 | GLN | A | 254 | 51.157 | 79.057 | -0.705 | 1.00 | 35.57 |
| 3584 | NE2 | GLN | A | 254 | 49.333 | 78.396 | 0.439 | 1.00 | 35.68 |
| 3587 | C | GLN | A | 254 | 51.586 | 79.238 | 4.601 | 1.00 | 29.79 |
| 3588 | O | GLN | A | 254 | 50.625 | 79.733 | 5.193 | 1.00 | 29.82 |
| 3589 | N | GLY | A | 255 | 52.705 | 79.907 | 4.369 | 1.00 | 29.23 |
| 3591 | CA | GLY | A | 255 | 52.843 | 81.298 | 4.740 | 1.00 | 29.36 |
| 3594 | C | GLY | A | 255 | 53.063 | 81.513 | 6.230 | 1.00 | 29.17 |
| 3595 | O | GLY | A | 255 | 52.963 | 82.630 | 6.708 | 1.00 | 28.41 |
| 3596 | N | ALA | A | 256 | 53.372 | 80.453 | 6.971 | 1.00 | 29.32 |
| 3598 | CA | ALA | A | 256 | 53.670 | 80.594 | 8.395 | 1.00 | 29.31 |
| 3600 | CB | ALA | A | 256 | 53.865 | 79.216 | 9.032 | 1.00 | 29.54 |
| 3604 | C | ALA | A | 256 | 54.900 | 81.481 | 8.638 | 1.00 | 29.48 |
| 3605 | O | ALA | A | 256 | 54.915 | 82.276 | 9.569 | 1.00 | 30.09 |
| 3606 | N | ASP | A | 257 | 55.925 | 81.350 | 7.805 | 1.00 | 29.41 |
| 3608 | CA | ASP | A | 257 | 57.170 | 82.079 | 8.006 | 1.00 | 29.43 |
| 3610 | CB | ASP | A | 257 | 58.242 | 81.581 | 7.053 | 1.00 | 29.35 |
| 3613 | CG | ASP | A | 257 | 58.770 | 80.208 | 7.420 | 1.00 | 28.93 |
| 3614 | OD1 | ASP | A | 257 | 58.493 | 79.724 | 8.552 | 1.00 | 27.10 |
| 3615 | OD2 | ASP | A | 257 | 59.480 | 79.562 | 6.613 | 1.00 | 25.07 |
| 3616 | C | ASP | A | 257 | 56.992 | 83.576 | 7.772 | 1.00 | 30.15 |
| 3617 | O | ASP | A | 257 | 57.516 | 84.404 | 8.505 | 1.00 | 28.74 |
| 3618 | N | GLN | A | 258 | 56.258 | 83.887 | 6.717 | 1.00 | 31.27 |
| 3620 | CA | GLN | A | 258 | 56.003 | 85.254 | 6.311 | 1.00 | 32.11 |

FIGURE 3 BJ

| A | B | C | D | E | F | G | H | I | J |
|---|---|---|---|---|---|---|---|---|---|
| 3622 | CB | BGLN | A | 258 | 55.223 | 85.271 | 4.997 | 0.35 | 32.00 |
| 3623 | CB | AGLN | A | 258 | 55.313 | 85.259 | 4.930 | 0.65 | 32.18 |
| 3628 | CG | BGLN | A | 258 | 55.115 | 86.632 | 4.342 | 0.35 | 31.76 |
| 3629 | CG | AGLN | A | 258 | 56.317 | 84.920 | 3.801 | 0.65 | 32.43 |
| 3634 | CD | BGLN | A | 258 | 54.771 | 86.519 | 2.876 | 0.35 | 31.23 |
| 3635 | CD | AGLN | A | 258 | 55.724 | 84.264 | 2.547 | 0.65 | 32.97 |
| 3636 | OE1 | BGLN | A | 258 | 55.645 | 86.639 | 2.016 | 0.35 | 30.93 |
| 3637 | OE1 | AGLN | A | 258 | 54.977 | 83.279 | 2.618 | 0.65 | 32.08 |
| 3638 | NE2 | BGLN | A | 258 | 53.503 | 86.266 | 2.585 | 0.35 | 30.18 |
| 3639 | NE2 | AGLN | A | 258 | 56.103 | 84.792 | 1.389 | 0.65 | 33.37 |
| 3644 | C | GLN | A | 258 | 55.203 | 85.967 | 7.400 | 1.00 | 32.82 |
| 3645 | O | GLN | A | 258 | 55.460 | 87.123 | 7.720 | 1.00 | 33.46 |
| 3646 | N | GLN | A | 259 | 54.266 | 85.249 | 8.000 | 1.00 | 33.70 |
| 3648 | CA | GLN | A | 259 | 53.452 | 85.780 | 9.084 | 1.00 | 34.64 |
| 3650 | CB | GLN | A | 259 | 52.395 | 84.756 | 9.463 | 1.00 | 35.35 |
| 3653 | CG | GLN | A | 259 | 51.346 | 85.257 | 10.436 | 1.00 | 38.57 |
| 3656 | CD | GLN | A | 259 | 50.161 | 84.331 | 10.482 | 1.00 | 42.61 |
| 3657 | OE1 | GLN | A | 259 | 49.161 | 84.555 | 9.787 | 1.00 | 45.33 |
| 3658 | NE2 | GLN | A | 259 | 50.272 | 83.263 | 11.278 | 1.00 | 44.63 |
| 3661 | C | GLN | A | 259 | 54.281 | 86.173 | 10.320 | 1.00 | 34.20 |
| 3662 | O | GLN | A | 259 | 53.948 | 87.154 | 10.990 | 1.00 | 33.93 |
| 3663 | N | LEU | A | 260 | 55.347 | 85.419 | 10.613 | 1.00 | 33.21 |
| 3665 | CA | LEU | A | 260 | 56.247 | 85.737 | 11.734 | 1.00 | 32.74 |
| 3667 | CB | LEU | A | 260 | 56.676 | 84.463 | 12.474 | 1.00 | 32.73 |
| 3670 | CG | LEU | A | 260 | 55.629 | 83.549 | 13.112 | 1.00 | 34.09 |
| 3672 | CD1 | LEU | A | 260 | 56.300 | 82.734 | 14.206 | 1.00 | 35.07 |
| 3676 | CD2 | LEU | A | 260 | 54.412 | 84.295 | 13.676 | 1.00 | 35.20 |
| 3680 | C | LEU | A | 260 | 57.514 | 86.495 | 11.326 | 1.00 | 31.74 |
| 3681 | O | LEU | A | 260 | 58.348 | 86.790 | 12.172 | 1.00 | 31.90 |
| 3682 | N | GLY | A | 261 | 57.670 | 86.808 | 10.043 | 1.00 | 30.66 |
| 3684 | CA | GLY | A | 261 | 58.858 | 87.495 | 9.565 | 1.00 | 29.51 |
| 3687 | C | GLY | A | 261 | 60.157 | 86.732 | 9.759 | 1.00 | 28.74 |
| 3688 | O | GLY | A | 261 | 61.198 | 87.333 | 9.998 | 1.00 | 28.52 |
| 3689 | N | LYS | A | 262 | 60.099 | 85.405 | 9.649 | 1.00 | 27.62 |
| 3691 | CA | LYS | A | 262 | 61.296 | 84.575 | 9.707 | 1.00 | 26.77 |
| 3693 | CB | LYS | A | 262 | 60.934 | 83.092 | 9.572 | 1.00 | 26.29 |
| 3696 | CG | LYS | A | 262 | 60.021 | 82.536 | 10.642 | 1.00 | 25.90 |
| 3699 | CD | LYS | A | 262 | 60.797 | 82.141 | 11.884 | 1.00 | 26.17 |
| 3702 | CE | LYS | A | 262 | 59.882 | 81.593 | 12.965 | 1.00 | 26.68 |
| 3705 | NZ | LYS | A | 262 | 60.644 | 81.319 | 14.214 | 1.00 | 25.74 |
| 3709 | C | LYS | A | 262 | 62.280 | 84.943 | 8.595 | 1.00 | 26.39 |
| 3710 | O | LYS | A | 262 | 61.884 | 85.161 | 7.445 | 1.00 | 26.03 |
| 3711 | N | SER | A | 263 | 63.563 | 85.005 | 8.943 | 1.00 | 26.23 |
| 3713 | CA | SER | A | 263 | 64.629 | 85.019 | 7.944 | 1.00 | 26.10 |
| 3715 | CB | SER | A | 263 | 65.975 | 85.311 | 8.586 | 1.00 | 26.43 |
| 3718 | OG | SER | A | 263 | 65.979 | 86.581 | 9.207 | 1.00 | 26.96 |
| 3720 | C | SER | A | 263 | 64.666 | 83.652 | 7.247 | 1.00 | 26.21 |
| 3721 | O | SER | A | 263 | 64.899 | 82.629 | 7.898 | 1.00 | 25.19 |
| 3722 | N | THR | A | 264 | 64.388 | 83.642 | 5.942 | 1.00 | 25.65 |
| 3724 | CA | THR | A | 264 | 64.408 | 82.408 | 5.149 | 1.00 | 25.89 |
| 3726 | CB | THR | A | 264 | 62.975 | 81.922 | 4.812 | 1.00 | 26.14 |
| 3728 | OG1 | THR | A | 264 | 62.368 | 82.789 | 3.847 | 1.00 | 26.91 |

FIGURE 3 BK

| A | B | C | D | E | F | G | H | I | J |
|---|---|---|---|---|---|---|---|---|---|
| 3730 | CG2 | THR | A | 264 | 62.046 | 81.992 | 6.033 | 1.00 | 26.45 |
| 3734 | C | THR | A | 264 | 65.189 | 82.591 | 3.856 | 1.00 | 25.77 |
| 3735 | O | THR | A | 264 | 65.538 | 83.722 | 3.472 | 1.00 | 25.52 |
| 3736 | N | TYR | A | 265 | 65.479 | 81.471 | 3.195 | 1.00 | 25.31 |
| 3738 | CA | TYR | A | 265 | 66.114 | 81.507 | 1.886 | 1.00 | 25.24 |
| 3740 | CB | TYR | A | 265 | 66.555 | 80.104 | 1.428 | 1.00 | 24.84 |
| 3743 | CG | TYR | A | 265 | 67.953 | 79.767 | 1.902 | 1.00 | 24.29 |
| 3744 | CD1 | TYR | A | 265 | 69.012 | 79.698 | 1.010 | 1.00 | 23.63 |
| 3746 | CE1 | TYR | A | 265 | 70.282 | 79.407 | 1.423 | 1.00 | 24.04 |
| 3748 | CZ | TYR | A | 265 | 70.545 | 79.200 | 2.759 | 1.00 | 24.29 |
| 3749 | OH | TYR | A | 265 | 71.827 | 78.928 | 3.168 | 1.00 | 24.41 |
| 3751 | CE2 | TYR | A | 265 | 69.521 | 79.276 | 3.685 | 1.00 | 24.92 |
| 3753 | CD2 | TYR | A | 265 | 68.225 | 79.566 | 3.250 | 1.00 | 23.77 |
| 3755 | C | TYR | A | 265 | 65.240 | 82.222 | 0.843 | 1.00 | 25.25 |
| 3756 | O | TYR | A | 265 | 65.717 | 83.149 | 0.211 | 1.00 | 25.83 |
| 3757 | N | PRO | A | 266 | 63.982 | 81.823 | 0.658 | 1.00 | 25.61 |
| 3758 | CA | PRO | A | 266 | 63.108 | 82.515 | -0.307 | 1.00 | 25.70 |
| 3760 | CB | PRO | A | 266 | 61.812 | 81.700 | -0.284 | 1.00 | 26.04 |
| 3763 | CG | PRO | A | 266 | 61.876 | 80.854 | 0.923 | 1.00 | 26.04 |
| 3766 | CD | PRO | A | 266 | 63.311 | 80.683 | 1.293 | 1.00 | 25.37 |
| 3769 | C | PRO | A | 266 | 62.825 | 83.980 | 0.027 | 1.00 | 25.95 |
| 3770 | O | PRO | A | 266 | 62.702 | 84.784 | -0.900 | 1.00 | 25.00 |
| 3771 | N | ALA | A | 267 | 62.738 | 84.326 | 1.311 | 1.00 | 26.04 |
| 3773 | CA | ALA | A | 267 | 62.503 | 85.719 | 1.697 | 1.00 | 26.33 |
| 3775 | CB | ALA | A | 267 | 62.193 | 85.853 | 3.166 | 1.00 | 26.37 |
| 3779 | C | ALA | A | 267 | 63.694 | 86.578 | 1.309 | 1.00 | 26.47 |
| 3780 | O | ALA | A | 267 | 63.512 | 87.637 | 0.734 | 1.00 | 26.90 |
| 3781 | N | LEU | A | 268 | 64.906 | 86.094 | 1.574 | 1.00 | 26.35 |
| 3783 | CA | LEU | A | 268 | 66.124 | 86.814 | 1.213 | 1.00 | 26.27 |
| 3785 | CB | LEU | A | 268 | 67.337 | 86.201 | 1.924 | 1.00 | 26.30 |
| 3788 | CG | LEU | A | 268 | 68.691 | 86.873 | 1.690 | 1.00 | 27.65 |
| 3790 | CD1 | LEU | A | 268 | 68.728 | 88.322 | 2.211 | 1.00 | 28.07 |
| 3794 | CD2 | LEU | A | 268 | 69.803 | 86.053 | 2.316 | 1.00 | 28.26 |
| 3798 | C | LEU | A | 268 | 66.386 | 86.828 | -0.294 | 1.00 | 26.01 |
| 3799 | O | LEU | A | 268 | 66.541 | 87.899 | -0.898 | 1.00 | 25.44 |
| 3800 | N | LEU | A | 269 | 66.439 | 85.633 | -0.881 | 1.00 | 25.58 |
| 3802 | CA | LEU | A | 269 | 66.963 | 85.430 | -2.234 | 1.00 | 25.43 |
| 3804 | CB | LEU | A | 269 | 67.755 | 84.113 | -2.298 | 1.00 | 25.44 |
| 3807 | CG | LEU | A | 269 | 68.906 | 83.896 | -1.320 | 1.00 | 26.67 |
| 3809 | CD1 | LEU | A | 269 | 69.520 | 82.486 | -1.510 | 1.00 | 25.96 |
| 3813 | CD2 | LEU | A | 269 | 69.960 | 84.976 | -1.479 | 1.00 | 27.24 |
| 3817 | C | LEU | A | 269 | 65.902 | 85.380 | -3.316 | 1.00 | 24.91 |
| 3818 | O | LEU | A | 269 | 66.226 | 85.454 | -4.490 | 1.00 | 24.92 |
| 3819 | N | GLY | A | 270 | 64.640 | 85.253 | -2.933 | 1.00 | 24.87 |
| 3821 | CA | GLY | A | 270 | 63.584 | 84.945 | -3.884 | 1.00 | 24.94 |
| 3824 | C | GLY | A | 270 | 63.529 | 83.446 | -4.151 | 1.00 | 25.33 |
| 3825 | O | GLY | A | 270 | 64.488 | 82.724 | -3.871 | 1.00 | 25.08 |
| 3826 | N | LEU | A | 271 | 62.415 | 82.985 | -4.699 | 1.00 | 25.79 |
| 3828 | CA | LEU | A | 271 | 62.170 | 81.567 | -4.899 | 1.00 | 26.67 |
| 3830 | CB | LEU | A | 271 | 60.732 | 81.320 | -5.383 | 1.00 | 27.35 |
| 3833 | CG | LEU | A | 271 | 59.602 | 81.477 | -4.365 | 1.00 | 28.42 |
| 3835 | CD1 | LEU | A | 271 | 58.252 | 81.403 | -5.068 | 1.00 | 29.93 |

FIGURE 3 BL

| A | B | C | D | E | F | G | H | I | J |
|---|---|---|---|---|---|---|---|---|---|
| 3839 | CD2 | LEU | A | 271 | 59.687 | 80.413 | -3.279 | 1.00 | 28.63 |
| 3843 | C | LEU | A | 271 | 63.162 | 80.914 | -5.853 | 1.00 | 27.13 |
| 3844 | O | LEU | A | 271 | 63.593 | 79.796 | -5.591 | 1.00 | 27.11 |
| 3845 | N | GLU | A | 272 | 63.536 | 81.599 | -6.938 | 1.00 | 27.48 |
| 3847 | CA | GLU | A | 272 | 64.429 | 81.018 | -7.956 | 1.00 | 28.05 |
| 3849 | CB | GLU | A | 272 | 64.488 | 81.905 | -9.229 | 1.00 | 28.98 |
| 3852 | CG | GLU | A | 272 | 65.687 | 81.611 | -10.148 | 1.00 | 31.69 |
| 3855 | CD | GLU | A | 272 | 65.592 | 82.253 | -11.528 | 1.00 | 35.38 |
| 3856 | OE1 | GLU | A | 272 | 66.103 | 81.648 | -12.499 | 1.00 | 39.00 |
| 3857 | OE2 | GLU | A | 272 | 65.013 | 83.354 | -11.655 | 1.00 | 37.35 |
| 3858 | C | GLU | A | 272 | 65.850 | 80.739 | -7.455 | 1.00 | 27.43 |
| 3859 | O | GLU | A | 272 | 66.427 | 79.668 | -7.745 | 1.00 | 27.14 |
| 3860 | N | GLN | A | 273 | 66.432 | 81.697 | -6.743 | 1.00 | 26.16 |
| 3862 | CA | GLN | A | 273 | 67.799 | 81.563 | -6.250 | 1.00 | 26.17 |
| 3864 | CB | GLN | A | 273 | 68.364 | 82.909 | -5.793 | 1.00 | 26.14 |
| 3867 | CG | GLN | A | 273 | 68.642 | 83.881 | -6.920 | 1.00 | 29.26 |
| 3870 | CD | GLN | A | 273 | 69.025 | 85.266 | -6.418 | 1.00 | 32.23 |
| 3871 | OE1 | GLN | A | 273 | 69.828 | 85.405 | -5.485 | 1.00 | 34.54 |
| 3872 | NE2 | GLN | A | 273 | 68.464 | 86.295 | -7.046 | 1.00 | 34.59 |
| 3875 | C | GLN | A | 273 | 67.854 | 80.566 | -5.092 | 1.00 | 25.40 |
| 3876 | O | GLN | A | 273 | 68.856 | 79.905 | -4.900 | 1.00 | 25.15 |
| 3877 | N | ALA | A | 274 | 66.776 | 80.485 | -4.318 | 1.00 | 25.33 |
| 3879 | CA | ALA | A | 274 | 66.681 | 79.514 | -3.239 | 1.00 | 25.32 |
| 3881 | CB | ALA | A | 274 | 65.429 | 79.770 | -2.427 | 1.00 | 25.59 |
| 3885 | C | ALA | A | 274 | 66.665 | 78.097 | -3.837 | 1.00 | 25.68 |
| 3886 | O | ALA | A | 274 | 67.388 | 77.213 | -3.385 | 1.00 | 25.35 |
| 3887 | N | ARG | A | 275 | 65.860 | 77.913 | -4.878 | 1.00 | 25.78 |
| 3889 | CA | ARG | A | 275 | 65.753 | 76.631 | -5.564 | 1.00 | 26.49 |
| 3891 | CB | ARG | A | 275 | 64.725 | 76.697 | -6.683 | 1.00 | 26.59 |
| 3894 | CG | ARG | A | 275 | 63.311 | 76.604 | -6.197 | 1.00 | 27.19 |
| 3897 | CD | ARG | A | 275 | 62.284 | 76.791 | -7.294 | 1.00 | 29.91 |
| 3900 | NE | ARG | A | 275 | 60.926 | 76.575 | -6.799 | 1.00 | 31.85 |
| 3902 | CZ | ARG | A | 275 | 59.886 | 77.379 | -7.009 | 1.00 | 34.22 |
| 3903 | NH1 | ARG | A | 275 | 59.998 | 78.504 | -7.720 | 1.00 | 35.16 |
| 3906 | NH2 | ARG | A | 275 | 58.706 | 77.047 | -6.491 | 1.00 | 35.99 |
| 3909 | C | ARG | A | 275 | 67.091 | 76.201 | -6.109 | 1.00 | 26.94 |
| 3910 | O | ARG | A | 275 | 67.468 | 75.039 | -5.985 | 1.00 | 27.03 |
| 3911 | N | LYS | A | 276 | 67.816 | 77.155 | -6.679 | 1.00 | 27.58 |
| 3913 | CA | LYS | A | 276 | 69.145 | 76.929 | -7.218 | 1.00 | 28.35 |
| 3915 | CB | LYS | A | 276 | 69.641 | 78.193 | -7.934 | 1.00 | 29.25 |
| 3918 | CG | LYS | A | 276 | 71.101 | 78.163 | -8.408 | 1.00 | 31.10 |
| 3921 | CD | LYS | A | 276 | 71.288 | 77.283 | -9.637 | 1.00 | 34.04 |
| 3924 | CE | LYS | A | 276 | 72.514 | 77.689 | -10.473 | 1.00 | 35.05 |
| 3927 | NZ | LYS | A | 276 | 73.803 | 77.493 | -9.748 | 1.00 | 35.48 |
| 3931 | C | LYS | A | 276 | 70.130 | 76.552 | -6.132 | 1.00 | 28.37 |
| 3932 | O | LYS | A | 276 | 70.987 | 75.692 | -6.347 | 1.00 | 28.80 |
| 3933 | N | LYS | A | 277 | 70.054 | 77.222 | -4.986 | 1.00 | 28.08 |
| 3935 | CA | LYS | A | 277 | 70.938 | 76.890 | -3.873 | 1.00 | 27.92 |
| 3937 | CB | LYS | A | 277 | 70.723 | 77.824 | -2.675 | 1.00 | 28.22 |
| 3940 | CG | LYS | A | 277 | 71.163 | 79.279 | -2.921 | 1.00 | 30.08 |
| 3943 | CD | LYS | A | 277 | 72.546 | 79.581 | -2.376 | 1.00 | 31.98 |
| 3946 | CE | LYS | A | 277 | 72.871 | 81.085 | -2.414 | 1.00 | 32.86 |

FIGURE 3 BM

| A | B | C | D | E | F | G | H | I | J |
|---|---|---|---|---|---|---|---|---|---|
| 3949 | NZ | LYS | A | 277 | 74.277 | 81.323 | -2.846 | 1.00 | 33.80 |
| 3953 | C | LYS | A | 277 | 70.680 | 75.438 | -3.453 | 1.00 | 27.24 |
| 3954 | O | LYS | A | 277 | 71.620 | 74.699 | -3.201 | 1.00 | 26.52 |
| 3955 | N | ALA | A | 278 | 69.411 | 75.041 | -3.393 | 1.00 | 26.71 |
| 3957 | CA | ALA | A | 278 | 69.053 | 73.682 | -2.960 | 1.00 | 26.99 |
| 3959 | CB | ALA | A | 278 | 67.544 | 73.546 | -2.823 | 1.00 | 26.84 |
| 3963 | C | ALA | A | 278 | 69.589 | 72.651 | -3.949 | 1.00 | 27.26 |
| 3964 | O | ALA | A | 278 | 70.141 | 71.636 | -3.566 | 1.00 | 26.69 |
| 3965 | N | ARG | A | 279 | 69.427 | 72.948 | -5.234 | 1.00 | 27.61 |
| 3967 | CA | ARG | A | 279 | 69.869 | 72.070 | -6.311 | 1.00 | 28.16 |
| 3969 | CB | ARG | A | 279 | 69.332 | 72.603 | -7.641 | 1.00 | 28.87 |
| 3972 | CG | ARG | A | 279 | 69.910 | 71.996 | -8.886 | 1.00 | 32.19 |
| 3975 | CD | ARG | A | 279 | 69.160 | 72.414 | -10.158 | 1.00 | 35.33 |
| 3978 | NE | ARG | A | 279 | 68.039 | 73.319 | -9.871 | 1.00 | 38.00 |
| 3980 | CZ | ARG | A | 279 | 68.005 | 74.632 | -10.133 | 1.00 | 38.95 |
| 3981 | NH1 | ARG | A | 279 | 69.027 | 75.256 | -10.711 | 1.00 | 40.27 |
| 3984 | NH2 | ARG | A | 279 | 66.924 | 75.329 | -9.815 | 1.00 | 38.71 |
| 3987 | C | ARG | A | 279 | 71.389 | 71.923 | -6.336 | 1.00 | 27.24 |
| 3988 | O | ARG | A | 279 | 71.885 | 70.819 | -6.512 | 1.00 | 27.02 |
| 3989 | N | ASP | A | 280 | 72.116 | 73.021 | -6.128 | 1.00 | 26.36 |
| 3991 | CA | ASP | A | 280 | 73.586 | 72.995 | -6.059 | 1.00 | 25.90 |
| 3993 | CB | ASP | A | 280 | 74.150 | 74.420 | -6.005 | 1.00 | 26.39 |
| 3996 | CG | ASP | A | 280 | 74.006 | 75.175 | -7.335 | 1.00 | 28.03 |
| 3997 | OD1 | ASP | A | 280 | 74.090 | 76.423 | -7.315 | 1.00 | 30.25 |
| 3998 | OD2 | ASP | A | 280 | 73.790 | 74.623 | -8.433 | 1.00 | 28.83 |
| 3999 | C | ASP | A | 280 | 74.086 | 72.217 | -4.828 | 1.00 | 25.37 |
| 4000 | O | ASP | A | 280 | 75.128 | 71.557 | -4.873 | 1.00 | 24.74 |
| 4001 | N | LEU | A | 281 | 73.346 | 72.307 | -3.727 | 1.00 | 24.45 |
| 4003 | CA | LEU | A | 281 | 73.688 | 71.553 | -2.529 | 1.00 | 24.47 |
| 4005 | CB | LEU | A | 281 | 72.825 | 71.999 | -1.335 | 1.00 | 24.55 |
| 4008 | CG | LEU | A | 281 | 73.246 | 73.324 | -0.700 | 1.00 | 23.94 |
| 4010 | CD1 | LEU | A | 281 | 72.129 | 73.904 | 0.129 | 1.00 | 23.80 |
| 4014 | CD2 | LEU | A | 281 | 74.506 | 73.133 | 0.150 | 1.00 | 23.78 |
| 4018 | C | LEU | A | 281 | 73.526 | 70.048 | -2.781 | 1.00 | 24.25 |
| 4019 | O | LEU | A | 281 | 74.364 | 69.262 | -2.353 | 1.00 | 23.54 |
| 4020 | N | ILE | A | 282 | 72.459 | 69.660 | -3.475 | 1.00 | 24.75 |
| 4022 | CA | ILE | A | 282 | 72.221 | 68.242 | -3.788 | 1.00 | 25.66 |
| 4024 | CB | ILE | A | 282 | 70.771 | 67.998 | -4.289 | 1.00 | 25.32 |
| 4026 | CG1 | ILE | A | 282 | 69.745 | 68.291 | -3.185 | 1.00 | 25.41 |
| 4029 | CD1 | ILE | A | 282 | 70.153 | 67.917 | -1.800 | 1.00 | 25.34 |
| 4033 | CG2 | ILE | A | 282 | 70.592 | 66.548 | -4.826 | 1.00 | 25.27 |
| 4037 | C | ILE | A | 282 | 73.241 | 67.719 | -4.788 | 1.00 | 26.42 |
| 4038 | O | ILE | A | 282 | 73.728 | 66.602 | -4.641 | 1.00 | 26.98 |
| 4039 | N | ASP | A | 283 | 73.571 | 68.511 | -5.802 | 1.00 | 27.38 |
| 4041 | CA | ASP | A | 283 | 74.607 | 68.111 | -6.753 | 1.00 | 28.16 |
| 4043 | CB | ASP | A | 283 | 74.799 | 69.165 | -7.851 | 1.00 | 28.99 |
| 4046 | CG | ASP | A | 283 | 73.578 | 69.319 | -8.758 | 1.00 | 31.72 |
| 4047 | OD1 | ASP | A | 283 | 73.510 | 70.341 | -9.477 | 1.00 | 36.96 |
| 4048 | OD2 | ASP | A | 283 | 72.644 | 68.493 | -8.830 | 1.00 | 35.17 |
| 4049 | C | ASP | A | 283 | 75.929 | 67.903 | -5.997 | 1.00 | 27.86 |
| 4050 | O | ASP | A | 283 | 76.696 | 67.003 | -6.319 | 1.00 | 27.48 |
| 4051 | N | ASP | A | 284 | 76.189 | 68.740 | -4.988 | 1.00 | 27.56 |

FIGURE 3 BN

| A | B | C | D | E | F | G | H | I | J |
|---|---|---|---|---|---|---|---|---|---|
| 4053 | CA | ASP | A | 284 | 77.405 | 68.623 | -4.177 | 1.00 | 27.43 |
| 4055 | CB | ASP | A | 284 | 77.573 | 69.869 | -3.296 | 1.00 | 27.98 |
| 4058 | CG | ASP | A | 284 | 78.753 | 69.774 | -2.351 | 1.00 | 29.55 |
| 4059 | OD1 | ASP | A | 284 | 79.871 | 70.166 | -2.754 | 1.00 | 34.48 |
| 4060 | OD2 | ASP | A | 284 | 78.662 | 69.347 | -1.179 | 1.00 | 30.96 |
| 4061 | C | ASP | A | 284 | 77.344 | 67.351 | -3.320 | 1.00 | 26.91 |
| 4062 | O | ASP | A | 284 | 78.347 | 66.666 | -3.137 | 1.00 | 26.70 |
| 4063 | N | ALA | A | 285 | 76.154 | 67.039 | -2.817 | 1.00 | 26.35 |
| 4065 | CA | ALA | A | 285 | 75.935 | 65.830 | -2.041 | 1.00 | 26.26 |
| 4067 | CB | ALA | A | 285 | 74.514 | 65.811 | -1.452 | 1.00 | 26.18 |
| 4071 | C | ALA | A | 285 | 76.164 | 64.607 | -2.913 | 1.00 | 26.41 |
| 4072 | O | ALA | A | 285 | 76.774 | 63.648 | -2.469 | 1.00 | 26.46 |
| 4073 | N | ARG | A | 286 | 75.687 | 64.647 | -4.156 | 1.00 | 26.93 |
| 4075 | CA | ARG | A | 286 | 75.888 | 63.543 | -5.095 | 1.00 | 27.77 |
| 4077 | CB | ARG | A | 286 | 75.153 | 63.778 | -6.413 | 1.00 | 28.06 |
| 4080 | CG | ARG | A | 286 | 73.650 | 63.500 | -6.353 | 1.00 | 30.42 |
| 4083 | CD | ARG | A | 286 | 72.949 | 63.511 | -7.727 | 1.00 | 33.16 |
| 4086 | NE | ARG | A | 286 | 71.739 | 62.694 | -7.695 | 1.00 | 35.04 |
| 4088 | CZ | ARG | A | 286 | 71.709 | 61.365 | -7.828 | 1.00 | 37.56 |
| 4089 | NH1 | ARG | A | 286 | 72.820 | 60.653 | -8.041 | 1.00 | 37.77 |
| 4092 | NH2 | ARG | A | 286 | 70.544 | 60.731 | -7.757 | 1.00 | 37.95 |
| 4095 | C | ARG | A | 286 | 77.377 | 63.333 | -5.364 | 1.00 | 28.02 |
| 4096 | O | ARG | A | 286 | 77.837 | 62.202 | -5.438 | 1.00 | 27.64 |
| 4097 | N | GLN | A | 287 | 78.120 | 64.427 | -5.478 | 1.00 | 28.41 |
| 4099 | CA | GLN | A | 287 | 79.550 | 64.352 | -5.768 | 1.00 | 29.05 |
| 4101 | CB | GLN | A | 287 | 80.163 | 65.742 | -5.984 | 1.00 | 29.26 |
| 4104 | CG | GLN | A | 287 | 79.870 | 66.348 | -7.343 | 1.00 | 31.16 |
| 4107 | CD | GLN | A | 287 | 80.342 | 65.469 | -8.494 | 1.00 | 34.10 |
| 4108 | OE1 | GLN | A | 287 | 81.544 | 65.280 | -8.687 | 1.00 | 36.57 |
| 4109 | NE2 | GLN | A | 287 | 79.396 | 64.921 | -9.248 | 1.00 | 34.65 |
| 4112 | C | GLN | A | 287 | 80.260 | 63.638 | -4.645 | 1.00 | 28.84 |
| 4113 | O | GLN | A | 287 | 81.060 | 62.747 | -4.898 | 1.00 | 29.43 |
| 4114 | N | SER | A | 288 | 79.946 | 64.002 | -3.403 | 1.00 | 28.72 |
| 4116 | CA | SER | A | 288 | 80.514 | 63.331 | -2.234 | 1.00 | 28.70 |
| 4118 | CB | SER | A | 288 | 79.948 | 63.912 | -0.930 | 1.00 | 28.50 |
| 4121 | OG | SER | A | 288 | 80.451 | 65.214 | -0.693 | 1.00 | 28.19 |
| 4123 | C | SER | A | 288 | 80.254 | 61.824 | -2.255 | 1.00 | 28.86 |
| 4124 | O | SER | A | 288 | 81.143 | 61.046 | -1.948 | 1.00 | 28.79 |
| 4125 | N | LEU | A | 289 | 79.028 | 61.428 | -2.579 | 1.00 | 29.44 |
| 4127 | CA | LEU | A | 289 | 78.666 | 60.005 | -2.650 | 1.00 | 29.79 |
| 4129 | CB | LEU | A | 289 | 77.163 | 59.818 | -2.910 | 1.00 | 29.50 |
| 4132 | CG | LEU | A | 289 | 76.184 | 60.273 | -1.815 | 1.00 | 28.59 |
| 4134 | CD1 | LEU | A | 289 | 74.747 | 60.026 | -2.249 | 1.00 | 28.94 |
| 4138 | CD2 | LEU | A | 289 | 76.473 | 59.585 | -0.493 | 1.00 | 27.92 |
| 4142 | C | LEU | A | 289 | 79.472 | 59.246 | -3.717 | 1.00 | 30.81 |
| 4143 | O | LEU | A | 289 | 79.732 | 58.062 | -3.545 | 1.00 | 30.71 |
| 4144 | N | LYS | A | 290 | 79.870 | 59.919 | -4.800 | 1.00 | 31.59 |
| 4146 | CA | LYS | A | 290 | 80.704 | 59.288 | -5.837 | 1.00 | 32.26 |
| 4148 | CB | LYS | A | 290 | 80.998 | 60.268 | -6.989 | 1.00 | 32.55 |
| 4151 | CG | LYS | A | 290 | 79.794 | 60.560 | -7.898 | 1.00 | 34.13 |
| 4154 | CD | LYS | A | 290 | 80.188 | 61.386 | -9.153 | 1.00 | 35.23 |
| 4157 | CE | LYS | A | 290 | 79.129 | 61.238 | -10.259 | 1.00 | 36.81 |

FIGURE 3 BO

| A | B | C | D | E | F | G | H | I | J |
|---|---|---|---|---|---|---|---|---|---|
| 4160 | NZ | LYS | A | 290 | 79.083 | 62.387 | -11.229 | 1.00 | 37.86 |
| 4164 | C | LYS | A | 290 | 82.012 | 58.741 | -5.256 | 1.00 | 32.60 |
| 4165 | O | LYS | A | 290 | 82.471 | 57.679 | -5.650 | 1.00 | 33.03 |
| 4166 | N | GLN | A | 291 | 82.589 | 59.462 | -4.300 | 1.00 | 33.38 |
| 4168 | CA | GLN | A | 291 | 83.796 | 59.026 | -3.599 | 1.00 | 34.01 |
| 4170 | CB | GLN | A | 291 | 84.253 | 60.103 | -2.607 | 1.00 | 34.60 |
| 4173 | CG | GLN | A | 291 | 84.614 | 61.448 | -3.230 | 1.00 | 35.87 |
| 4176 | CD | GLN | A | 291 | 85.108 | 62.446 | -2.197 | 1.00 | 37.47 |
| 4177 | OE1 | GLN | A | 291 | 86.039 | 62.155 | -1.446 | 1.00 | 39.36 |
| 4178 | NE2 | GLN | A | 291 | 84.483 | 63.615 | -2.149 | 1.00 | 39.06 |
| 4181 | C | GLN | A | 291 | 83.589 | 57.715 | -2.830 | 1.00 | 34.18 |
| 4182 | O | GLN | A | 291 | 84.513 | 56.909 | -2.707 | 1.00 | 34.15 |
| 4183 | N | LEU | A | 292 | 82.385 | 57.520 | -2.294 | 1.00 | 33.99 |
| 4185 | CA | LEU | A | 292 | 82.047 | 56.287 | -1.591 | 1.00 | 34.26 |
| 4187 | CB | LEU | A | 292 | 80.849 | 56.509 | -0.670 | 1.00 | 33.95 |
| 4190 | CG | LEU | A | 292 | 81.061 | 57.578 | 0.398 | 1.00 | 33.40 |
| 4192 | CD1 | LEU | A | 292 | 79.805 | 57.720 | 1.223 | 1.00 | 33.09 |
| 4196 | CD2 | LEU | A | 292 | 82.269 | 57.242 | 1.274 | 1.00 | 33.91 |
| 4200 | C | LEU | A | 292 | 81.738 | 55.137 | -2.533 | 1.00 | 34.79 |
| 4201 | O | LEU | A | 292 | 82.073 | 53.989 | -2.239 | 1.00 | 34.64 |
| 4202 | N | ALA | A | 293 | 81.072 | 55.445 | -3.642 | 1.00 | 35.56 |
| 4204 | CA | ALA | A | 293 | 80.741 | 54.450 | -4.660 | 1.00 | 36.49 |
| 4206 | CB | ALA | A | 293 | 79.825 | 55.061 | -5.712 | 1.00 | 36.38 |
| 4210 | C | ALA | A | 293 | 82.012 | 53.886 | -5.311 | 1.00 | 37.32 |
| 4211 | O | ALA | A | 293 | 82.015 | 52.758 | -5.799 | 1.00 | 37.70 |
| 4212 | N | GLU | A | 294 | 83.075 | 54.690 | -5.296 | 1.00 | 38.52 |
| 4214 | CA | GLU | A | 294 | 84.421 | 54.297 | -5.744 | 1.00 | 39.54 |
| 4216 | CB | GLU | A | 294 | 85.353 | 55.513 | -5.677 | 1.00 | 39.78 |
| 4219 | CG | GLU | A | 294 | 86.404 | 55.572 | -6.767 | 1.00 | 41.97 |
| 4222 | CD | GLU | A | 294 | 86.407 | 56.897 | -7.488 | 1.00 | 43.76 |
| 4223 | OE1 | GLU | A | 294 | 86.681 | 57.915 | -6.825 | 1.00 | 46.66 |
| 4224 | OE2 | GLU | A | 294 | 86.129 | 56.921 | -8.705 | 1.00 | 45.53 |
| 4225 | C | GLU | A | 294 | 85.034 | 53.179 | -4.895 | 1.00 | 39.49 |
| 4226 | O | GLU | A | 294 | 85.883 | 52.422 | -5.363 | 1.00 | 40.00 |
| 4227 | N | GLN | A | 295 | 84.617 | 53.112 | -3.638 | 1.00 | 39.43 |
| 4229 | CA | GLN | A | 295 | 85.085 | 52.109 | -2.700 | 1.00 | 39.30 |
| 4231 | CB | GLN | A | 295 | 85.306 | 52.752 | -1.324 | 1.00 | 39.51 |
| 4234 | CG | GLN | A | 295 | 86.094 | 54.061 | -1.348 | 1.00 | 40.85 |
| 4237 | CD | GLN | A | 295 | 86.003 | 54.825 | -0.033 | 1.00 | 42.68 |
| 4238 | OE1 | GLN | A | 295 | 85.958 | 54.217 | 1.037 | 1.00 | 44.83 |
| 4239 | NE2 | GLN | A | 295 | 85.983 | 56.156 | -0.110 | 1.00 | 42.30 |
| 4242 | C | GLN | A | 295 | 84.087 | 50.944 | -2.594 | 1.00 | 38.62 |
| 4243 | O | GLN | A | 295 | 84.083 | 50.210 | -1.605 | 1.00 | 38.99 |
| 4244 | N | SER | A | 296 | 83.250 | 50.794 | -3.616 | 1.00 | 37.61 |
| 4246 | CA | SER | A | 296 | 82.260 | 49.718 | -3.721 | 1.00 | 36.98 |
| 4248 | CB | SER | A | 296 | 82.963 | 48.362 | -3.884 | 1.00 | 37.17 |
| 4251 | OG | SER | A | 296 | 83.487 | 48.241 | -5.197 | 1.00 | 38.77 |
| 4253 | C | SER | A | 296 | 81.210 | 49.685 | -2.598 | 1.00 | 35.68 |
| 4254 | O | SER | A | 296 | 80.722 | 48.617 | -2.206 | 1.00 | 35.55 |
| 4255 | N | LEU | A | 297 | 80.867 | 50.865 | -2.092 | 1.00 | 34.25 |
| 4257 | CA | LEU | A | 297 | 79.710 | 51.032 | -1.218 | 1.00 | 32.88 |
| 4259 | CB | LEU | A | 297 | 79.997 | 52.090 | -0.161 | 1.00 | 32.92 |

FIGURE 3 BP

| A | B | C | D | E | F | G | H | I | J |
|---|---|---|---|---|---|---|---|---|---|
| 4262 | CG | LEU | A | 297 | 81.178 | 51.793 | 0.755 | 1.00 | 33.21 |
| 4264 | CD1 | LEU | A | 297 | 81.567 | 53.040 | 1.532 | 1.00 | 33.05 |
| 4268 | CD2 | LEU | A | 297 | 80.872 | 50.609 | 1.704 | 1.00 | 33.61 |
| 4272 | C | LEU | A | 297 | 78.507 | 51.432 | -2.074 | 1.00 | 31.66 |
| 4273 | O | LEU | A | 297 | 78.621 | 52.255 | -2.988 | 1.00 | 31.32 |
| 4274 | N | ASP | A | 298 | 77.361 | 50.827 | -1.799 | 1.00 | 30.63 |
| 4276 | CA | ASP | A | 298 | 76.127 | 51.123 | -2.528 | 1.00 | 29.60 |
| 4278 | CB | ASP | A | 298 | 75.150 | 49.956 | -2.371 | 1.00 | 29.83 |
| 4281 | CG | ASP | A | 298 | 73.911 | 50.089 | -3.251 | 1.00 | 30.98 |
| 4282 | OD1 | ASP | A | 298 | 73.673 | 51.177 | -3.843 | 1.00 | 30.78 |
| 4283 | OD2 | ASP | A | 298 | 73.117 | 49.135 | -3.407 | 1.00 | 32.78 |
| 4284 | C | ASP | A | 298 | 75.516 | 52.431 | -2.021 | 1.00 | 28.62 |
| 4285 | O | ASP | A | 298 | 74.919 | 52.474 | -0.953 | 1.00 | 27.93 |
| 4286 | N | THR | A | 299 | 75.655 | 53.496 | -2.801 | 1.00 | 27.78 |
| 4288 | CA | THR | A | 299 | 75.152 | 54.812 | -2.395 | 1.00 | 27.48 |
| 4290 | CB | THR | A | 299 | 76.121 | 55.907 | -2.850 | 1.00 | 27.79 |
| 4292 | OG1 | THR | A | 299 | 76.198 | 55.923 | -4.282 | 1.00 | 27.64 |
| 4294 | CG2 | THR | A | 299 | 77.522 | 55.612 | -2.397 | 1.00 | 27.86 |
| 4298 | C | THR | A | 299 | 73.775 | 55.130 | -2.963 | 1.00 | 26.98 |
| 4299 | O | THR | A | 299 | 73.314 | 56.269 | -2.852 | 1.00 | 26.90 |
| 4300 | N | SER | A | 300 | 73.115 | 54.136 | -3.549 | 1.00 | 25.87 |
| 4302 | CA | SER | A | 300 | 71.884 | 54.371 | -4.303 | 1.00 | 25.78 |
| 4304 | CB | SER | A | 300 | 71.469 | 53.116 | -5.083 | 1.00 | 25.66 |
| 4307 | OG | SER | A | 300 | 71.181 | 52.042 | -4.210 | 1.00 | 28.03 |
| 4309 | C | SER | A | 300 | 70.718 | 54.922 | -3.460 | 1.00 | 24.86 |
| 4310 | O | SER | A | 300 | 69.989 | 55.799 | -3.922 | 1.00 | 24.04 |
| 4311 | N | ALA | A | 301 | 70.538 | 54.423 | -2.237 | 1.00 | 24.31 |
| 4313 | CA | ALA | A | 301 | 69.491 | 54.957 | -1.356 | 1.00 | 23.85 |
| 4315 | CB | ALA | A | 301 | 69.266 | 54.058 | -0.138 | 1.00 | 23.74 |
| 4319 | C | ALA | A | 301 | 69.813 | 56.402 | -0.925 | 1.00 | 23.51 |
| 4320 | O | ALA | A | 301 | 68.927 | 57.234 | -0.865 | 1.00 | 22.49 |
| 4321 | N | LEU | A | 302 | 71.082 | 56.696 | -0.670 | 1.00 | 23.59 |
| 4323 | CA | LEU | A | 302 | 71.476 | 58.050 | -0.254 | 1.00 | 24.04 |
| 4325 | CB | LEU | A | 302 | 72.893 | 58.059 | 0.321 | 1.00 | 23.68 |
| 4328 | CG | LEU | A | 302 | 73.047 | 57.380 | 1.677 | 1.00 | 24.07 |
| 4330 | CD1 | LEU | A | 302 | 74.495 | 57.511 | 2.165 | 1.00 | 25.59 |
| 4334 | CD2 | LEU | A | 302 | 72.085 | 57.972 | 2.680 | 1.00 | 24.26 |
| 4338 | C | LEU | A | 302 | 71.375 | 59.070 | -1.370 | 1.00 | 24.05 |
| 4339 | O | LEU | A | 302 | 71.128 | 60.238 | -1.104 | 1.00 | 24.30 |
| 4340 | N | GLU | A | 303 | 71.575 | 58.648 | -2.614 | 1.00 | 24.92 |
| 4342 | CA | GLU | A | 303 | 71.455 | 59.578 | -3.734 | 1.00 | 25.79 |
| 4344 | CB | GLU | A | 303 | 72.238 | 59.158 | -4.988 | 1.00 | 26.38 |
| 4347 | CG | GLU | A | 303 | 72.152 | 57.732 | -5.448 | 1.00 | 28.99 |
| 4350 | CD | GLU | A | 303 | 73.344 | 57.345 | -6.333 | 1.00 | 31.29 |
| 4351 | OE1 | GLU | A | 303 | 73.673 | 58.127 | -7.247 | 1.00 | 31.21 |
| 4352 | OE2 | GLU | A | 303 | 73.966 | 56.274 | -6.098 | 1.00 | 33.39 |
| 4353 | C | GLU | A | 303 | 69.982 | 59.834 | -4.045 | 1.00 | 25.52 |
| 4354 | O | GLU | A | 303 | 69.605 | 60.961 | -4.347 | 1.00 | 25.13 |
| 4355 | N | ALA | A | 304 | 69.152 | 58.797 | -3.927 | 1.00 | 25.73 |
| 4357 | CA | ALA | A | 304 | 67.709 | 58.953 | -4.149 | 1.00 | 25.33 |
| 4359 | CB | ALA | A | 304 | 67.020 | 57.609 | -4.201 | 1.00 | 25.75 |
| 4363 | C | ALA | A | 304 | 67.099 | 59.830 | -3.059 | 1.00 | 25.32 |

FIGURE 3 BQ

| A | B | C | D | E | F | G | H | I | J |
|---|---|---|---|---|---|---|---|---|---|
| 4364 | O | ALA | A | 304 | 66.202 | 60.633 | -3.328 | 1.00 | 24.76 |
| 4365 | N | LEU | A | 305 | 67.591 | 59.677 | -1.828 | 1.00 | 25.18 |
| 4367 | CA | LEU | A | 305 | 67.117 | 60.499 | -0.711 | 1.00 | 25.23 |
| 4369 | CB | LEU | A | 305 | 67.707 | 59.988 | 0.608 | 1.00 | 25.28 |
| 4372 | CG | LEU | A | 305 | 67.209 | 60.548 | 1.945 | 1.00 | 27.23 |
| 4374 | CD1 | LEU | A | 305 | 67.788 | 61.919 | 2.199 | 1.00 | 29.43 |
| 4378 | CD2 | LEU | A | 305 | 65.687 | 60.595 | 2.012 | 1.00 | 28.69 |
| 4382 | C | LEU | A | 305 | 67.520 | 61.954 | -0.959 | 1.00 | 24.32 |
| 4383 | O | LEU | A | 305 | 66.719 | 62.872 | -0.780 | 1.00 | 23.70 |
| 4384 | N | ALA | A | 306 | 68.758 | 62.146 | -1.399 | 1.00 | 23.80 |
| 4386 | CA | ALA | A | 306 | 69.282 | 63.481 | -1.672 | 1.00 | 24.14 |
| 4388 | CB | ALA | A | 306 | 70.733 | 63.405 | -2.153 | 1.00 | 24.17 |
| 4392 | C | ALA | A | 306 | 68.410 | 64.218 | -2.687 | 1.00 | 24.07 |
| 4393 | O | ALA | A | 306 | 68.063 | 65.382 | -2.480 | 1.00 | 23.69 |
| 4394 | N | ASP | A | 307 | 68.027 | 63.538 | -3.761 | 1.00 | 24.24 |
| 4396 | CA | ASP | A | 307 | 67.146 | 64.143 | -4.772 | 1.00 | 24.99 |
| 4398 | CB | ASP | A | 307 | 67.015 | 63.231 | -5.990 | 1.00 | 25.46 |
| 4401 | CG | ASP | A | 307 | 68.259 | 63.225 | -6.840 | 1.00 | 27.73 |
| 4402 | OD1 | ASP | A | 307 | 68.311 | 62.445 | -7.819 | 1.00 | 32.11 |
| 4403 | OD2 | ASP | A | 307 | 69.231 | 63.968 | -6.614 | 1.00 | 30.06 |
| 4404 | C | ASP | A | 307 | 65.751 | 64.427 | -4.242 | 1.00 | 24.15 |
| 4405 | O | ASP | A | 307 | 65.146 | 65.464 | -4.565 | 1.00 | 23.53 |
| 4406 | N | TYR | A | 308 | 65.233 | 63.497 | -3.445 | 1.00 | 23.64 |
| 4408 | CA | TYR | A | 308 | 63.890 | 63.636 | -2.889 | 1.00 | 23.49 |
| 4410 | CB | TYR | A | 308 | 63.465 | 62.369 | -2.150 | 1.00 | 23.53 |
| 4413 | CG | TYR | A | 308 | 62.066 | 62.432 | -1.543 | 1.00 | 23.83 |
| 4414 | CD1 | TYR | A | 308 | 61.882 | 62.358 | -0.171 | 1.00 | 24.83 |
| 4416 | CE1 | TYR | A | 308 | 60.607 | 62.425 | 0.392 | 1.00 | 25.12 |
| 4418 | CZ | TYR | A | 308 | 59.501 | 62.553 | -0.424 | 1.00 | 26.00 |
| 4419 | OH | TYR | A | 308 | 58.239 | 62.602 | 0.134 | 1.00 | 26.70 |
| 4421 | CE2 | TYR | A | 308 | 59.660 | 62.622 | -1.798 | 1.00 | 25.30 |
| 4423 | CD2 | TYR | A | 308 | 60.939 | 62.568 | -2.344 | 1.00 | 23.99 |
| 4425 | C | TYR | A | 308 | 63.824 | 64.844 | -1.957 | 1.00 | 23.57 |
| 4426 | O | TYR | A | 308 | 62.829 | 65.529 | -1.919 | 1.00 | 22.72 |
| 4427 | N | ILE | A | 309 | 64.902 | 65.112 | -1.229 | 1.00 | 24.12 |
| 4429 | CA | ILE | A | 309 | 64.949 | 66.247 | -0.301 | 1.00 | 24.93 |
| 4431 | CB | ILE | A | 309 | 66.333 | 66.304 | 0.411 | 1.00 | 24.90 |
| 4433 | CG1 | ILE | A | 309 | 66.333 | 65.285 | 1.553 | 1.00 | 25.34 |
| 4436 | CD1 | ILE | A | 309 | 67.675 | 65.077 | 2.197 | 1.00 | 27.41 |
| 4440 | CG2 | ILE | A | 309 | 66.639 | 67.710 | 0.943 | 1.00 | 25.11 |
| 4444 | C | ILE | A | 309 | 64.575 | 67.576 | -0.977 | 1.00 | 25.41 |
| 4445 | O | ILE | A | 309 | 64.017 | 68.468 | -0.326 | 1.00 | 25.21 |
| 4446 | N | ILE | A | 310 | 64.848 | 67.702 | -2.274 | 1.00 | 25.98 |
| 4448 | CA | ILE | A | 310 | 64.481 | 68.928 | -3.003 | 1.00 | 26.46 |
| 4450 | CB | ILE | A | 310 | 65.736 | 69.586 | -3.590 | 1.00 | 26.50 |
| 4452 | CG1 | ILE | A | 310 | 66.349 | 68.722 | -4.700 | 1.00 | 26.76 |
| 4455 | CD1 | ILE | A | 310 | 67.350 | 69.472 | -5.530 | 1.00 | 27.27 |
| 4459 | CG2 | ILE | A | 310 | 66.729 | 69.819 | -2.491 | 1.00 | 26.11 |
| 4463 | C | ILE | A | 310 | 63.393 | 68.781 | -4.066 | 1.00 | 26.91 |
| 4464 | O | ILE | A | 310 | 62.930 | 69.779 | -4.622 | 1.00 | 26.80 |
| 4465 | N | GLN | A | 311 | 62.982 | 67.543 | -4.337 | 1.00 | 26.94 |
| 4467 | CA | GLN | A | 311 | 61.911 | 67.267 | -5.284 | 1.00 | 27.25 |

FIGURE 3 BR

| A | B | C | D | E | F | G | H | I | J |
|---|---|---|---|---|---|---|---|---|---|
| 4469 | CB | GLN | A | 311 | 62.217 | 65.999 | -6.089 | 1.00 | 27.44 |
| 4472 | CG | GLN | A | 311 | 63.241 | 66.219 | -7.186 | 1.00 | 30.05 |
| 4475 | CD | GLN | A | 311 | 63.720 | 64.922 | -7.830 | 1.00 | 33.37 |
| 4476 | OE1 | GLN | A | 311 | 64.730 | 64.920 | -8.521 | 1.00 | 36.33 |
| 4477 | NE2 | GLN | A | 311 | 62.999 | 63.828 | -7.606 | 1.00 | 34.01 |
| 4480 | C | GLN | A | 311 | 60.573 | 67.102 | -4.575 | 1.00 | 26.71 |
| 4481 | O | GLN | A | 311 | 59.514 | 67.225 | -5.193 | 1.00 | 27.01 |
| 4482 | N | ARG | A | 312 | 60.620 | 66.825 | -3.280 | 1.00 | 26.09 |
| 4484 | CA | ARG | A | 312 | 59.418 | 66.570 | -2.503 | 1.00 | 25.94 |
| 4486 | CB | ARG | A | 312 | 59.774 | 66.077 | -1.098 | 1.00 | 25.87 |
| 4489 | CG | ARG | A | 312 | 60.382 | 67.160 | -0.225 | 1.00 | 25.06 |
| 4492 | CD | ARG | A | 312 | 61.211 | 66.630 | 0.914 | 1.00 | 23.99 |
| 4495 | NE | ARG | A | 312 | 61.963 | 67.704 | 1.555 | 1.00 | 22.64 |
| 4497 | CZ | ARG | A | 312 | 61.503 | 68.481 | 2.528 | 1.00 | 19.61 |
| 4498 | NH1 | ARG | A | 312 | 62.286 | 69.429 | 3.025 | 1.00 | 20.15 |
| 4501 | NH2 | ARG | A | 312 | 60.289 | 68.325 | 3.008 | 1.00 | 19.15 |
| 4504 | C | ARG | A | 312 | 58.558 | 67.817 | -2.386 | 1.00 | 26.24 |
| 4505 | O | ARG | A | 312 | 59.053 | 68.938 | -2.448 | 1.00 | 25.48 |
| 4506 | N | ASN | A | 313 | 57.269 | 67.601 | -2.191 | 1.00 | 26.97 |
| 4508 | CA | ASN | A | 313 | 56.321 | 68.702 | -2.054 | 1.00 | 28.44 |
| 4510 | CB | ASN | A | 313 | 55.255 | 68.594 | -3.128 | 1.00 | 28.90 |
| 4513 | CG | ASN | A | 313 | 55.820 | 68.829 | -4.487 | 1.00 | 31.25 |
| 4514 | OD1 | ASN | A | 313 | 56.328 | 69.921 | -4.771 | 1.00 | 36.72 |
| 4515 | ND2 | ASN | A | 313 | 55.782 | 67.807 | -5.337 | 1.00 | 35.16 |
| 4518 | C | ASN | A | 313 | 55.711 | 68.729 | -0.676 | 1.00 | 28.47 |
| 4519 | O | ASN | A | 313 | 54.731 | 69.426 | -0.440 | 1.00 | 28.00 |
| 4520 | N | LYS | A | 314 | 56.326 | 67.972 | 0.234 | 1.00 | 29.44 |
| 4522 | CA | LYS | A | 314 | 55.925 | 67.944 | 1.642 | 1.00 | 30.19 |
| 4524 | CB | LYS | A | 314 | 54.722 | 67.029 | 1.835 | 1.00 | 30.27 |
| 4527 | CG | LYS | A | 314 | 54.874 | 65.638 | 1.202 | 1.00 | 32.14 |
| 4530 | CD | LYS | A | 314 | 54.635 | 64.498 | 2.180 | 1.00 | 34.17 |
| 4533 | CE | LYS | A | 314 | 53.660 | 63.459 | 1.652 | 1.00 | 35.54 |
| 4536 | NZ | LYS | A | 314 | 54.228 | 62.656 | 0.542 | 1.00 | 36.19 |
| 4540 | C | LYS | A | 314 | 57.081 | 67.487 | 2.528 | 1.00 | 30.38 |
| 4541 | O | LYS | A | 314 | 56.992 | 67.504 | 3.759 | 1.00 | 30.94 |
| 4542 | OXT | LYS | A | 314 | 58.130 | 67.081 | 2.028 | 1.00 | 30.00 |
| 4543 | N | ASP | B | 17 | 19.060 | 6.498 | -16.010 | 1.00 | 36.37 |
| 4545 | CA | ASP | B | 17 | 17.827 | 7.340 | -15.968 | 1.00 | 36.07 |
| 4547 | CB | ASP | B | 17 | 16.585 | 6.454 | -15.910 | 1.00 | 36.75 |
| 4550 | CG | ASP | B | 17 | 15.301 | 7.258 | -15.889 | 1.00 | 38.21 |
| 4551 | OD1 | ASP | B | 17 | 15.288 | 8.356 | -16.476 | 1.00 | 42.09 |
| 4552 | OD2 | ASP | B | 17 | 14.258 | 6.882 | -15.321 | 1.00 | 41.73 |
| 4553 | C | ASP | B | 17 | 17.853 | 8.266 | -14.742 | 1.00 | 35.62 |
| 4554 | O | ASP | B | 17 | 17.713 | 7.800 | -13.603 | 1.00 | 35.09 |
| 4557 | N | PHE | B | 18 | 18.002 | 9.572 | -14.969 | 1.00 | 34.42 |
| 4559 | CA | PHE | B | 18 | 18.233 | 10.472 | -13.845 | 1.00 | 33.65 |
| 4561 | CB | PHE | B | 18 | 18.831 | 11.812 | -14.264 | 1.00 | 33.54 |
| 4564 | CG | PHE | B | 18 | 19.286 | 12.629 | -13.097 | 1.00 | 32.06 |
| 4565 | CD1 | PHE | B | 18 | 20.342 | 12.202 | -12.312 | 1.00 | 31.59 |
| 4567 | CE1 | PHE | B | 18 | 20.747 | 12.940 | -11.217 | 1.00 | 31.53 |
| 4569 | CZ | PHE | B | 18 | 20.080 | 14.100 | -10.888 | 1.00 | 30.24 |
| 4571 | CE2 | PHE | B | 18 | 19.029 | 14.516 | -11.638 | 1.00 | 31.16 |

FIGURE 3 BS

| A | B | C | D | E | F | G | H | I | J |
|---|---|---|---|---|---|---|---|---|---|
| 4573 | CD2 | PHE | B | 18 | 18.621 | 13.779 | -12.739 | 1.00 | 32.52 |
| 4575 | C | PHE | B | 18 | 17.015 | 10.695 | -12.946 | 1.00 | 33.05 |
| 4576 | O | PHE | B | 18 | 17.179 | 10.672 | -11.738 | 1.00 | 32.55 |
| 4577 | N | PRO | B | 19 | 15.817 | 10.901 | -13.503 | 1.00 | 32.85 |
| 4578 | CA | PRO | B | 19 | 14.606 | 11.056 | -12.680 | 1.00 | 32.66 |
| 4580 | CB | PRO | B | 19 | 13.497 | 11.261 | -13.722 | 1.00 | 32.79 |
| 4583 | CG | PRO | B | 19 | 14.213 | 11.795 | -14.914 | 1.00 | 33.05 |
| 4586 | CD | PRO | B | 19 | 15.508 | 11.051 | -14.936 | 1.00 | 32.96 |
| 4589 | C | PRO | B | 19 | 14.285 | 9.869 | -11.768 | 1.00 | 32.36 |
| 4590 | O | PRO | B | 19 | 13.759 | 10.093 | -10.685 | 1.00 | 31.80 |
| 4591 | N | GLN | B | 20 | 14.594 | 8.643 | -12.190 | 1.00 | 31.98 |
| 4593 | CA | GLN | B | 20 | 14.399 | 7.478 | -11.329 | 1.00 | 32.12 |
| 4595 | CB | GLN | B | 20 | 14.282 | 6.175 | -12.145 | 1.00 | 32.62 |
| 4598 | CG | GLN | B | 20 | 12.872 | 5.922 | -12.758 | 1.00 | 35.79 |
| 4601 | CD | GLN | B | 20 | 11.784 | 5.507 | -11.736 | 1.00 | 38.90 |
| 4602 | OE1 | GLN | B | 20 | 11.382 | 4.327 | -11.677 | 1.00 | 40.51 |
| 4603 | NE2 | GLN | B | 20 | 11.292 | 6.479 | -10.956 | 1.00 | 40.37 |
| 4606 | C | GLN | B | 20 | 15.524 | 7.368 | -10.279 | 1.00 | 30.90 |
| 4607 | O | GLN | B | 20 | 15.304 | 6.829 | -9.213 | 1.00 | 30.46 |
| 4608 | N | GLN | B | 21 | 16.715 | 7.872 | -10.583 | 1.00 | 30.18 |
| 4610 | CA | GLN | B | 21 | 17.778 | 7.963 | -9.575 | 1.00 | 30.30 |
| 4612 | CB | GLN | B | 21 | 19.108 | 8.421 | -10.180 | 1.00 | 30.56 |
| 4615 | CG | GLN | B | 21 | 19.929 | 7.310 | -10.799 | 1.00 | 33.30 |
| 4618 | CD | GLN | B | 21 | 20.971 | 6.745 | -9.843 | 1.00 | 36.37 |
| 4619 | OE1 | GLN | B | 21 | 21.903 | 7.457 | -9.441 | 1.00 | 39.14 |
| 4620 | NE2 | GLN | B | 21 | 20.822 | 5.474 | -9.479 | 1.00 | 36.91 |
| 4623 | C | GLN | B | 21 | 17.364 | 8.924 | -8.464 | 1.00 | 29.14 |
| 4624 | O | GLN | B | 21 | 17.509 | 8.604 | -7.285 | 1.00 | 29.47 |
| 4625 | N | LEU | B | 22 | 16.838 | 10.086 | -8.841 | 1.00 | 27.84 |
| 4627 | CA | LEU | B | 22 | 16.384 | 11.074 | -7.864 | 1.00 | 27.57 |
| 4629 | CB | LEU | B | 22 | 15.793 | 12.309 | -8.546 | 1.00 | 27.88 |
| 4632 | CG | LEU | B | 22 | 16.740 | 13.324 | -9.180 | 1.00 | 28.18 |
| 4634 | CD1 | LEU | B | 22 | 15.884 | 14.370 | -9.884 | 1.00 | 28.62 |
| 4638 | CD2 | LEU | B | 22 | 17.667 | 13.973 | -8.145 | 1.00 | 28.38 |
| 4642 | C | LEU | B | 22 | 15.317 | 10.478 | -6.961 | 1.00 | 27.38 |
| 4643 | O | LEU | B | 22 | 15.364 | 10.643 | -5.741 | 1.00 | 26.09 |
| 4644 | N | GLU | B | 23 | 14.358 | 9.786 | -7.573 | 1.00 | 27.02 |
| 4646 | CA | GLU | B | 23 | 13.207 | 9.269 | -6.847 | 1.00 | 27.65 |
| 4648 | CB | GLU | B | 23 | 12.098 | 8.855 | -7.825 | 1.00 | 28.49 |
| 4651 | CG | GLU | B | 23 | 11.022 | 7.981 | -7.212 | 1.00 | 32.02 |
| 4654 | CD | GLU | B | 23 | 9.646 | 8.256 | -7.782 | 1.00 | 37.15 |
| 4655 | OE1 | GLU | B | 23 | 9.109 | 9.364 | -7.545 | 1.00 | 42.58 |
| 4656 | OE2 | GLU | B | 23 | 9.100 | 7.363 | -8.463 | 1.00 | 41.15 |
| 4657 | C | GLU | B | 23 | 13.618 | 8.112 | -5.938 | 1.00 | 26.50 |
| 4658 | O | GLU | B | 23 | 13.115 | 8.008 | -4.823 | 1.00 | 26.62 |
| 4659 | N | ALA | B | 24 | 14.513 | 7.250 | -6.421 | 1.00 | 25.43 |
| 4661 | CA | ALA | B | 24 | 15.092 | 6.179 | -5.610 | 1.00 | 24.85 |
| 4663 | CB | ALA | B | 24 | 16.021 | 5.297 | -6.443 | 1.00 | 24.98 |
| 4667 | C | ALA | B | 24 | 15.864 | 6.765 | -4.421 | 1.00 | 24.65 |
| 4668 | O | ALA | B | 24 | 15.827 | 6.211 | -3.318 | 1.00 | 23.25 |
| 4669 | N | CYS | B | 25 | 16.556 | 7.885 | -4.650 | 1.00 | 24.00 |
| 4671 | CA | CYS | B | 25 | 17.315 | 8.544 | -3.589 | 1.00 | 23.64 |

FIGURE 3 BT

| A | B | C | D | E | F | G | H | I | J |
|---|---|---|---|---|---|---|---|---|---|
| 4673 | CB | CYS | B | 25 | 18.217 | 9.650 | -4.152 | 1.00 | 23.72 |
| 4676 | SG | CYS | B | 25 | 19.117 | 10.582 | -2.885 | 1.00 | 22.22 |
| 4677 | C | CYS | B | 25 | 16.374 | 9.096 | -2.524 | 1.00 | 23.27 |
| 4678 | O | CYS | B | 25 | 16.578 | 8.876 | -1.336 | 1.00 | 23.22 |
| 4679 | N | VAL | B | 26 | 15.323 | 9.779 | -2.945 | 1.00 | 23.25 |
| 4681 | CA | VAL | B | 26 | 14.334 | 10.280 | -2.006 | 1.00 | 23.43 |
| 4683 | CB | VAL | B | 26 | 13.175 | 10.997 | -2.725 | 1.00 | 23.51 |
| 4685 | CG1 | VAL | B | 26 | 12.005 | 11.220 | -1.804 | 1.00 | 24.68 |
| 4689 | CG2 | VAL | B | 26 | 13.650 | 12.324 | -3.276 | 1.00 | 23.07 |
| 4693 | C | VAL | B | 26 | 13.811 | 9.132 | -1.138 | 1.00 | 23.73 |
| 4694 | O | VAL | B | 26 | 13.641 | 9.300 | 0.067 | 1.00 | 23.38 |
| 4695 | N | LYS | B | 27 | 13.581 | 7.964 | -1.737 | 1.00 | 23.54 |
| 4697 | CA | LYS | B | 27 | 13.012 | 6.852 | -0.972 | 1.00 | 24.03 |
| 4699 | CB | LYS | B | 27 | 12.440 | 5.765 | -1.891 | 1.00 | 24.27 |
| 4702 | CG | LYS | B | 27 | 10.995 | 6.086 | -2.256 | 1.00 | 27.21 |
| 4705 | CD | LYS | B | 27 | 10.544 | 5.567 | -3.606 | 1.00 | 31.82 |
| 4708 | CE | LYS | B | 27 | 9.032 | 5.811 | -3.762 | 1.00 | 33.94 |
| 4711 | NZ | LYS | B | 27 | 8.488 | 5.279 | -5.045 | 1.00 | 37.62 |
| 4715 | C | LYS | B | 27 | 14.026 | 6.287 | -0.004 | 1.00 | 22.89 |
| 4716 | O | LYS | B | 27 | 13.699 | 6.017 | 1.145 | 1.00 | 23.39 |
| 4717 | N | GLN | B | 28 | 15.257 | 6.124 | -0.468 | 1.00 | 22.27 |
| 4719 | CA | GLN | B | 28 | 16.335 | 5.645 | 0.380 | 1.00 | 21.89 |
| 4721 | CB | GLN | B | 28 | 17.623 | 5.496 | -0.423 | 1.00 | 21.61 |
| 4724 | CG | GLN | B | 28 | 18.810 | 4.946 | 0.352 | 1.00 | 21.80 |
| 4727 | CD | GLN | B | 28 | 18.683 | 3.471 | 0.705 | 1.00 | 23.69 |
| 4728 | OE1 | GLN | B | 28 | 19.316 | 2.999 | 1.657 | 1.00 | 25.82 |
| 4729 | NE2 | GLN | B | 28 | 17.882 | 2.742 | -0.054 | 1.00 | 22.57 |
| 4732 | C | GLN | B | 28 | 16.518 | 6.604 | 1.561 | 1.00 | 21.61 |
| 4733 | O | GLN | B | 28 | 16.596 | 6.163 | 2.704 | 1.00 | 21.00 |
| 4734 | N | ALA | B | 29 | 16.556 | 7.906 | 1.285 | 1.00 | 21.58 |
| 4736 | CA | ALA | B | 29 | 16.835 | 8.916 | 2.323 | 1.00 | 21.82 |
| 4738 | CB | ALA | B | 29 | 17.120 | 10.295 | 1.691 | 1.00 | 21.91 |
| 4742 | C | ALA | B | 29 | 15.684 | 9.025 | 3.317 | 1.00 | 21.73 |
| 4743 | O | ALA | B | 29 | 15.897 | 9.174 | 4.508 | 1.00 | 21.94 |
| 4744 | N | ASN | B | 30 | 14.461 | 8.963 | 2.822 | 1.00 | 22.10 |
| 4746 | CA | ASN | B | 30 | 13.289 | 8.996 | 3.699 | 1.00 | 22.38 |
| 4748 | CB | ASN | B | 30 | 12.013 | 9.035 | 2.869 | 1.00 | 22.05 |
| 4751 | CG | ASN | B | 30 | 11.720 | 10.416 | 2.319 | 1.00 | 23.08 |
| 4752 | OD1 | ASN | B | 30 | 12.374 | 11.387 | 2.689 | 1.00 | 22.74 |
| 4753 | ND2 | ASN | B | 30 | 10.732 | 10.510 | 1.424 | 1.00 | 22.09 |
| 4756 | C | ASN | B | 30 | 13.237 | 7.812 | 4.655 | 1.00 | 22.64 |
| 4757 | O | ASN | B | 30 | 12.857 | 7.962 | 5.811 | 1.00 | 22.97 |
| 4758 | N | GLN | B | 31 | 13.604 | 6.637 | 4.160 | 1.00 | 22.84 |
| 4760 | CA | GLN | B | 31 | 13.624 | 5.438 | 4.978 | 1.00 | 23.34 |
| 4762 | CB | GLN | B | 31 | 13.859 | 4.210 | 4.085 | 1.00 | 23.43 |
| 4765 | CG | GLN | B | 31 | 14.118 | 2.893 | 4.795 | 1.00 | 26.33 |
| 4768 | CD | GLN | B | 31 | 14.528 | 1.795 | 3.815 | 1.00 | 28.80 |
| 4769 | OE1 | GLN | B | 31 | 15.700 | 1.679 | 3.443 | 1.00 | 33.07 |
| 4770 | NE2 | GLN | B | 31 | 13.560 | 1.007 | 3.378 | 1.00 | 32.12 |
| 4773 | C | GLN | B | 31 | 14.720 | 5.582 | 6.039 | 1.00 | 23.12 |
| 4774 | O | GLN | B | 31 | 14.542 | 5.183 | 7.178 | 1.00 | 23.43 |
| 4775 | N | ALA | B | 32 | 15.855 | 6.146 | 5.653 | 1.00 | 22.32 |

FIGURE 3 BU

| A | B | C | D | E | F | G | H | I | J |
|---|---|---|---|---|---|---|---|---|---|
| 4777 | CA | ALA | B | 32 | 16.974 | 6.318 | 6.569 | 1.00 | 22.90 |
| 4779 | CB | ALA | B | 32 | 18.199 | 6.814 | 5.818 | 1.00 | 22.55 |
| 4783 | C | ALA | B | 32 | 16.590 | 7.296 | 7.679 | 1.00 | 22.66 |
| 4784 | O | ALA | B | 32 | 16.750 | 6.992 | 8.861 | 1.00 | 22.59 |
| 4785 | N | LEU | B | 33 | 16.069 | 8.457 | 7.288 | 1.00 | 22.88 |
| 4787 | CA | LEU | B | 33 | 15.603 | 9.462 | 8.244 | 1.00 | 23.19 |
| 4789 | CB | LEU | B | 33 | 14.980 | 10.661 | 7.521 | 1.00 | 23.23 |
| 4792 | CG | LEU | B | 33 | 15.948 | 11.654 | 6.869 | 1.00 | 24.18 |
| 4794 | CD1 | LEU | B | 33 | 15.253 | 12.531 | 5.850 | 1.00 | 25.04 |
| 4798 | CD2 | LEU | B | 33 | 16.610 | 12.528 | 7.925 | 1.00 | 25.95 |
| 4802 | C | LEU | B | 33 | 14.565 | 8.869 | 9.206 | 1.00 | 23.67 |
| 4803 | O | LEU | B | 33 | 14.665 | 9.037 | 10.415 | 1.00 | 22.94 |
| 4804 | N | SER | B | 34 | 13.573 | 8.180 | 8.654 | 1.00 | 24.43 |
| 4806 | CA | SER | B | 34 | 12.506 | 7.580 | 9.458 | 1.00 | 25.35 |
| 4808 | CB | SER | B | 34 | 11.490 | 6.887 | 8.551 | 1.00 | 25.51 |
| 4811 | OG | SER | B | 34 | 10.877 | 7.830 | 7.706 | 1.00 | 26.80 |
| 4813 | C | SER | B | 34 | 13.043 | 6.579 | 10.487 | 1.00 | 25.98 |
| 4814 | O | SER | B | 34 | 12.547 | 6.525 | 11.610 | 1.00 | 26.04 |
| 4815 | N | ARG | B | 35 | 14.062 | 5.813 | 10.094 | 1.00 | 26.60 |
| 4817 | CA | ARG | B | 35 | 14.700 | 4.820 | 10.962 | 1.00 | 27.70 |
| 4819 | CB | ARG | B | 35 | 15.743 | 3.993 | 10.185 | 1.00 | 28.27 |
| 4822 | CG | ARG | B | 35 | 15.205 | 2.761 | 9.484 | 1.00 | 31.67 |
| 4825 | CD | ARG | B | 35 | 16.207 | 1.605 | 9.357 | 1.00 | 34.70 |
| 4828 | NE | ARG | B | 35 | 17.593 | 2.056 | 9.140 | 1.00 | 36.06 |
| 4830 | CZ | ARG | B | 35 | 18.083 | 2.498 | 7.984 | 1.00 | 33.83 |
| 4831 | NH1 | ARG | B | 35 | 17.320 | 2.570 | 6.914 | 1.00 | 34.48 |
| 4834 | NH2 | ARG | B | 35 | 19.354 | 2.876 | 7.903 | 1.00 | 33.58 |
| 4837 | C | ARG | B | 35 | 15.407 | 5.464 | 12.148 | 1.00 | 27.46 |
| 4838 | O | ARG | B | 35 | 15.465 | 4.877 | 13.237 | 1.00 | 27.43 |
| 4839 | N | PHE | B | 36 | 15.967 | 6.655 | 11.926 | 1.00 | 27.31 |
| 4841 | CA | PHE | B | 36 | 16.692 | 7.373 | 12.965 | 1.00 | 26.91 |
| 4843 | CB | PHE | B | 36 | 17.758 | 8.289 | 12.356 | 1.00 | 26.72 |
| 4846 | CG | PHE | B | 36 | 18.835 | 7.547 | 11.623 | 1.00 | 24.89 |
| 4847 | CD1 | PHE | B | 36 | 19.206 | 7.916 | 10.343 | 1.00 | 22.57 |
| 4849 | CE1 | PHE | B | 36 | 20.201 | 7.220 | 9.656 | 1.00 | 22.79 |
| 4851 | CZ | PHE | B | 36 | 20.845 | 6.150 | 10.267 | 1.00 | 23.00 |
| 4853 | CE2 | PHE | B | 36 | 20.493 | 5.777 | 11.546 | 1.00 | 24.18 |
| 4855 | CD2 | PHE | B | 36 | 19.488 | 6.473 | 12.224 | 1.00 | 24.53 |
| 4857 | C | PHE | B | 36 | 15.763 | 8.164 | 13.851 | 1.00 | 27.56 |
| 4858 | O | PHE | B | 36 | 16.136 | 8.505 | 14.964 | 1.00 | 28.14 |
| 4859 | N | ILE | B | 37 | 14.563 | 8.457 | 13.357 | 1.00 | 28.06 |
| 4861 | CA | ILE | B | 37 | 13.570 | 9.208 | 14.113 | 1.00 | 29.01 |
| 4863 | CB | ILE | B | 37 | 12.677 | 10.054 | 13.160 | 1.00 | 29.24 |
| 4865 | CG1 | ILE | B | 37 | 13.470 | 11.240 | 12.608 | 1.00 | 28.43 |
| 4868 | CD1 | ILE | B | 37 | 12.767 | 12.003 | 11.524 | 1.00 | 29.06 |
| 4872 | CG2 | ILE | B | 37 | 11.412 | 10.552 | 13.876 | 1.00 | 30.14 |
| 4876 | C | ILE | B | 37 | 12.719 | 8.257 | 14.959 | 1.00 | 29.75 |
| 4877 | O | ILE | B | 37 | 12.120 | 8.678 | 15.948 | 1.00 | 30.10 |
| 4878 | N | ALA | B | 38 | 12.698 | 6.977 | 14.580 | 1.00 | 30.36 |
| 4880 | CA | ALA | B | 38 | 11.784 | 5.995 | 15.172 | 1.00 | 30.63 |
| 4882 | CB | ALA | B | 38 | 11.849 | 4.666 | 14.409 | 1.00 | 30.80 |
| 4886 | C | ALA | B | 38 | 12.021 | 5.762 | 16.651 | 1.00 | 30.90 |

FIGURE 3 BV

| A | B | C | D | E | F | G | H | I | J |
|---|---|---|---|---|---|---|---|---|---|
| 4887 | O | ALA | B | 38 | 11.052 | 5.739 | 17.415 | 1.00 | 31.31 |
| 4888 | N | PRO | B | 39 | 13.278 | 5.595 | 17.074 | 1.00 | 31.28 |
| 4889 | CA | PRO | B | 39 | 13.573 | 5.370 | 18.494 | 1.00 | 31.54 |
| 4891 | CB | PRO | B | 39 | 15.045 | 4.922 | 18.489 | 1.00 | 31.77 |
| 4894 | CG | PRO | B | 39 | 15.425 | 4.741 | 17.062 | 1.00 | 32.00 |
| 4897 | CD | PRO | B | 39 | 14.512 | 5.594 | 16.270 | 1.00 | 31.28 |
| 4900 | C | PRO | B | 39 | 13.423 | 6.610 | 19.377 | 1.00 | 31.62 |
| 4901 | O | PRO | B | 39 | 13.551 | 6.466 | 20.594 | 1.00 | 32.39 |
| 4902 | N | LEU | B | 40 | 13.184 | 7.790 | 18.794 | 1.00 | 30.70 |
| 4904 | CA | LEU | B | 40 | 13.053 | 9.012 | 19.575 | 1.00 | 30.07 |
| 4906 | CB | LEU | B | 40 | 12.980 | 10.253 | 18.670 | 1.00 | 30.11 |
| 4909 | CG | LEU | B | 40 | 14.228 | 10.593 | 17.836 | 1.00 | 30.37 |
| 4911 | CD1 | LEU | B | 40 | 13.985 | 11.886 | 17.056 | 1.00 | 30.25 |
| 4915 | CD2 | LEU | B | 40 | 15.502 | 10.691 | 18.687 | 1.00 | 30.52 |
| 4919 | C | LEU | B | 40 | 11.801 | 8.963 | 20.448 | 1.00 | 29.37 |
| 4920 | O | LEU | B | 40 | 10.747 | 8.494 | 20.005 | 1.00 | 29.73 |
| 4921 | N | PRO | B | 41 | 11.903 | 9.477 | 21.669 | 1.00 | 28.40 |
| 4922 | CA | PRO | B | 41 | 10.738 | 9.551 | 22.553 | 1.00 | 28.09 |
| 4924 | CB | PRO | B | 41 | 11.355 | 9.872 | 23.921 | 1.00 | 28.24 |
| 4927 | CG | PRO | B | 41 | 12.658 | 10.565 | 23.613 | 1.00 | 28.08 |
| 4930 | CD | PRO | B | 41 | 13.115 | 10.033 | 22.301 | 1.00 | 28.09 |
| 4933 | C | PRO | B | 41 | 9.796 | 10.657 | 22.100 | 1.00 | 27.75 |
| 4934 | O | PRO | B | 41 | 10.119 | 11.411 | 21.154 | 1.00 | 26.90 |
| 4935 | N | PHE | B | 42 | 8.630 | 10.724 | 22.739 | 1.00 | 27.16 |
| 4937 | CA | PHE | B | 42 | 7.644 | 11.774 | 22.477 | 1.00 | 27.19 |
| 4939 | CB | PHE | B | 42 | 8.224 | 13.158 | 22.776 | 1.00 | 27.06 |
| 4942 | CG | PHE | B | 42 | 8.887 | 13.259 | 24.118 | 1.00 | 27.64 |
| 4943 | CD1 | PHE | B | 42 | 8.136 | 13.124 | 25.279 | 1.00 | 28.66 |
| 4945 | CE1 | PHE | B | 42 | 8.732 | 13.207 | 26.518 | 1.00 | 29.45 |
| 4947 | CZ | PHE | B | 42 | 10.096 | 13.439 | 26.617 | 1.00 | 28.49 |
| 4949 | CE2 | PHE | B | 42 | 10.863 | 13.574 | 25.475 | 1.00 | 27.66 |
| 4951 | CD2 | PHE | B | 42 | 10.260 | 13.485 | 24.226 | 1.00 | 27.57 |
| 4953 | C | PHE | B | 42 | 7.094 | 11.730 | 21.053 | 1.00 | 27.15 |
| 4954 | O | PHE | B | 42 | 6.729 | 12.755 | 20.491 | 1.00 | 26.43 |
| 4955 | N | GLN | B | 43 | 7.015 | 10.534 | 20.489 | 1.00 | 27.91 |
| 4957 | CA | GLN | B | 43 | 6.310 | 10.320 | 19.224 | 1.00 | 28.60 |
| 4959 | CB | GLN | B | 43 | 6.294 | 8.834 | 18.858 | 1.00 | 28.40 |
| 4962 | CG | GLN | B | 43 | 7.659 | 8.201 | 18.665 | 1.00 | 28.70 |
| 4965 | CD | GLN | B | 43 | 8.379 | 8.718 | 17.438 | 1.00 | 28.74 |
| 4966 | OE1 | GLN | B | 43 | 7.765 | 8.927 | 16.394 | 1.00 | 29.53 |
| 4967 | NE2 | GLN | B | 43 | 9.685 | 8.915 | 17.558 | 1.00 | 28.45 |
| 4970 | C | GLN | B | 43 | 4.868 | 10.796 | 19.363 | 1.00 | 29.43 |
| 4971 | O | GLN | B | 43 | 4.275 | 10.720 | 20.449 | 1.00 | 30.02 |
| 4972 | N | ASN | B | 44 | 4.311 | 11.291 | 18.268 | 1.00 | 30.07 |
| 4974 | CA | ASN | B | 44 | 2.942 | 11.787 | 18.226 | 1.00 | 30.82 |
| 4976 | CB | ASN | B | 44 | 1.943 | 10.631 | 18.396 | 1.00 | 31.34 |
| 4979 | CG | ASN | B | 44 | 2.264 | 9.445 | 17.492 | 1.00 | 32.36 |
| 4980 | OD1 | ASN | B | 44 | 2.338 | 9.579 | 16.261 | 1.00 | 35.83 |
| 4981 | ND2 | ASN | B | 44 | 2.480 | 8.288 | 18.096 | 1.00 | 33.67 |
| 4984 | C | ASN | B | 44 | 2.684 | 12.898 | 19.244 | 1.00 | 30.94 |
| 4985 | O | ASN | B | 44 | 1.596 | 12.983 | 19.805 | 1.00 | 31.98 |
| 4986 | N | THR | B | 45 | 3.705 | 13.716 | 19.507 | 1.00 | 30.13 |

FIGURE 3 BW

| A | B | C | D | E | F | G | H | I | J |
|---|---|---|---|---|---|---|---|---|---|
| 4988 | CA | THR | B | 45 | 3.529 | 14.982 | 20.201 | 1.00 | 29.44 |
| 4990 | CB | THR | B | 45 | 4.399 | 15.055 | 21.470 | 1.00 | 29.55 |
| 4992 | OG1 | THR | B | 45 | 5.790 | 15.106 | 21.123 | 1.00 | 29.59 |
| 4994 | CG2 | THR | B | 45 | 4.249 | 13.787 | 22.313 | 1.00 | 30.13 |
| 4998 | C | THR | B | 45 | 3.901 | 16.083 | 19.216 | 1.00 | 28.76 |
| 4999 | O | THR | B | 45 | 4.574 | 15.800 | 18.231 | 1.00 | 29.08 |
| 5000 | N | PRO | B | 46 | 3.458 | 17.318 | 19.450 | 1.00 | 28.09 |
| 5001 | CA | PRO | B | 46 | 3.684 | 18.421 | 18.494 | 1.00 | 27.28 |
| 5003 | CB | PRO | B | 46 | 3.174 | 19.652 | 19.252 | 1.00 | 27.82 |
| 5006 | CG | PRO | B | 46 | 2.115 | 19.111 | 20.181 | 1.00 | 28.40 |
| 5009 | CD | PRO | B | 46 | 2.640 | 17.750 | 20.605 | 1.00 | 28.19 |
| 5012 | C | PRO | B | 46 | 5.135 | 18.643 | 18.041 | 1.00 | 26.19 |
| 5013 | O | PRO | B | 46 | 5.357 | 18.854 | 16.853 | 1.00 | 25.60 |
| 5014 | N | VAL | B | 47 | 6.100 | 18.595 | 18.957 | 1.00 | 24.76 |
| 5016 | CA | VAL | B | 47 | 7.479 | 18.902 | 18.602 | 1.00 | 23.94 |
| 5018 | CB | VAL | B | 47 | 8.365 | 19.173 | 19.859 | 1.00 | 24.25 |
| 5020 | CG1 | VAL | B | 47 | 8.593 | 17.904 | 20.684 | 1.00 | 24.46 |
| 5024 | CG2 | VAL | B | 47 | 9.678 | 19.801 | 19.452 | 1.00 | 25.37 |
| 5028 | C | VAL | B | 47 | 8.074 | 17.824 | 17.690 | 1.00 | 22.86 |
| 5029 | O | VAL | B | 47 | 8.719 | 18.150 | 16.704 | 1.00 | 21.98 |
| 5030 | N | VAL | B | 48 | 7.822 | 16.549 | 17.991 | 1.00 | 22.17 |
| 5032 | CA | VAL | B | 48 | 8.303 | 15.456 | 17.145 | 1.00 | 22.05 |
| 5034 | CB | VAL | B | 48 | 8.227 | 14.101 | 17.872 | 1.00 | 22.22 |
| 5036 | CG1 | VAL | B | 48 | 8.620 | 12.960 | 16.951 | 1.00 | 22.38 |
| 5040 | CG2 | VAL | B | 48 | 9.132 | 14.128 | 19.090 | 1.00 | 22.62 |
| 5044 | C | VAL | B | 48 | 7.547 | 15.414 | 15.816 | 1.00 | 22.15 |
| 5045 | O | VAL | B | 48 | 8.108 | 15.076 | 14.775 | 1.00 | 21.53 |
| 5046 | N | GLU | B | 49 | 6.273 | 15.760 | 15.844 | 1.00 | 22.30 |
| 5048 | CA | GLU | B | 49 | 5.501 | 15.839 | 14.612 | 1.00 | 23.31 |
| 5050 | CB | GLU | B | 49 | 4.020 | 16.062 | 14.906 | 1.00 | 23.97 |
| 5053 | CG | GLU | B | 49 | 3.349 | 14.847 | 15.529 | 1.00 | 27.97 |
| 5056 | CD | GLU | B | 49 | 1.902 | 15.107 | 15.899 | 1.00 | 32.93 |
| 5057 | OE1 | GLU | B | 49 | 1.410 | 16.237 | 15.650 | 1.00 | 37.74 |
| 5058 | OE2 | GLU | B | 49 | 1.263 | 14.182 | 16.446 | 1.00 | 36.88 |
| 5059 | C | GLU | B | 49 | 6.023 | 16.965 | 13.727 | 1.00 | 22.40 |
| 5060 | O | GLU | B | 49 | 6.016 | 16.837 | 12.516 | 1.00 | 21.26 |
| 5061 | N | THR | B | 50 | 6.497 | 18.044 | 14.344 | 1.00 | 21.39 |
| 5063 | CA | THR | B | 50 | 7.105 | 19.143 | 13.607 | 1.00 | 21.78 |
| 5065 | CB | THR | B | 50 | 7.382 | 20.353 | 14.534 | 1.00 | 22.24 |
| 5067 | OG1 | THR | B | 50 | 6.174 | 20.767 | 15.191 | 1.00 | 21.33 |
| 5069 | CG2 | THR | B | 50 | 7.803 | 21.573 | 13.727 | 1.00 | 22.96 |
| 5073 | C | THR | B | 50 | 8.406 | 18.684 | 12.964 | 1.00 | 21.83 |
| 5074 | O | THR | B | 50 | 8.671 | 19.001 | 11.808 | 1.00 | 21.23 |
| 5075 | N | MET | B | 51 | 9.220 | 17.953 | 13.728 | 1.00 | 21.95 |
| 5077 | CA | MET | B | 51 | 10.470 | 17.408 | 13.215 | 1.00 | 21.91 |
| 5079 | CB | MET | B | 51 | 11.207 | 16.630 | 14.299 | 1.00 | 21.87 |
| 5082 | CG | MET | B | 51 | 11.735 | 17.485 | 15.441 | 1.00 | 20.93 |
| 5085 | SD | MET | B | 51 | 12.315 | 16.444 | 16.774 | 1.00 | 22.35 |
| 5086 | CE | MET | B | 51 | 13.754 | 15.689 | 16.047 | 1.00 | 23.07 |
| 5090 | C | MET | B | 51 | 10.221 | 16.502 | 12.014 | 1.00 | 22.56 |
| 5091 | O | MET | B | 51 | 10.951 | 16.565 | 11.024 | 1.00 | 22.83 |
| 5092 | N | GLN | B | 52 | 9.179 | 15.676 | 12.088 | 1.00 | 23.09 |

FIGURE 3 BX

| A | B | C | D | E | F | G | H | I | J |
|---|---|---|---|---|---|---|---|---|---|
| 5094 | CA  | GLN | B | 52 | 8.895  | 14.714 | 11.016 | 1.00 | 23.09 |
| 5096 | CB  | GLN | B | 52 | 7.843  | 13.694 | 11.460 | 1.00 | 23.18 |
| 5099 | CG  | GLN | B | 52 | 8.386  | 12.700 | 12.456 | 1.00 | 24.11 |
| 5102 | CD  | GLN | B | 52 | 7.334  | 11.743 | 12.961 | 1.00 | 26.66 |
| 5103 | OE1 | GLN | B | 52 | 7.463  | 10.525 | 12.791 | 1.00 | 28.62 |
| 5104 | NE2 | GLN | B | 52 | 6.304  | 12.280 | 13.601 | 1.00 | 23.91 |
| 5107 | C   | GLN | B | 52 | 8.393  | 15.435 | 9.787  | 1.00 | 22.65 |
| 5108 | O   | GLN | B | 52 | 8.764  | 15.123 | 8.661  | 1.00 | 22.15 |
| 5109 | N   | TYR | B | 53 | 7.531  | 16.402 | 10.028 | 1.00 | 22.64 |
| 5111 | CA  | TYR | B | 53 | 6.942  | 17.213 | 8.974  | 1.00 | 22.81 |
| 5113 | CB  | TYR | B | 53 | 5.939  | 18.145 | 9.647  | 1.00 | 23.23 |
| 5116 | CG  | TYR | B | 53 | 5.133  | 19.066 | 8.784  | 1.00 | 24.77 |
| 5117 | CD1 | TYR | B | 53 | 3.855  | 18.706 | 8.346  | 1.00 | 27.29 |
| 5119 | CE1 | TYR | B | 53 | 3.089  | 19.572 | 7.587  | 1.00 | 28.69 |
| 5121 | CZ  | TYR | B | 53 | 3.582  | 20.820 | 7.286  | 1.00 | 28.49 |
| 5122 | OH  | TYR | B | 53 | 2.827  | 21.673 | 6.537  | 1.00 | 28.74 |
| 5124 | CE2 | TYR | B | 53 | 4.844  | 21.209 | 7.727  | 1.00 | 27.93 |
| 5126 | CD2 | TYR | B | 53 | 5.600  | 20.335 | 8.477  | 1.00 | 26.79 |
| 5128 | C   | TYR | B | 53 | 8.051  | 17.978 | 8.237  | 1.00 | 22.85 |
| 5129 | O   | TYR | B | 53 | 8.114  | 17.976 | 7.010  | 1.00 | 22.68 |
| 5130 | N   | GLY | B | 54 | 8.948  | 18.591 | 9.005  | 1.00 | 22.75 |
| 5132 | CA  | GLY | B | 54 | 10.014 | 19.408 | 8.455  | 1.00 | 22.25 |
| 5135 | C   | GLY | B | 54 | 11.071 | 18.608 | 7.738  | 1.00 | 22.08 |
| 5136 | O   | GLY | B | 54 | 11.669 | 19.088 | 6.782  | 1.00 | 21.36 |
| 5137 | N   | ALA | B | 55 | 11.310 | 17.384 | 8.201  | 1.00 | 22.33 |
| 5139 | CA  | ALA | B | 55 | 12.382 | 16.568 | 7.656  | 1.00 | 22.52 |
| 5141 | CB  | ALA | B | 55 | 12.996 | 15.714 | 8.733  | 1.00 | 22.31 |
| 5145 | C   | ALA | B | 55 | 11.925 | 15.698 | 6.492  | 1.00 | 23.07 |
| 5146 | O   | ALA | B | 55 | 12.692 | 15.487 | 5.548  | 1.00 | 22.77 |
| 5147 | N   | LEU | B | 56 | 10.682 | 15.220 | 6.538  | 1.00 | 23.33 |
| 5149 | CA  | LEU | B | 56 | 10.265 | 14.079 | 5.705  | 1.00 | 24.30 |
| 5151 | CB  | LEU | B | 56 | 9.706  | 12.960 | 6.586  | 1.00 | 24.12 |
| 5154 | CG  | LEU | B | 56 | 10.789 | 12.220 | 7.367  | 1.00 | 24.95 |
| 5156 | CD1 | LEU | B | 56 | 10.177 | 11.362 | 8.448  | 1.00 | 25.81 |
| 5160 | CD2 | LEU | B | 56 | 11.624 | 11.386 | 6.415  | 1.00 | 25.72 |
| 5164 | C   | LEU | B | 56 | 9.241  | 14.390 | 4.610  | 1.00 | 24.83 |
| 5165 | O   | LEU | B | 56 | 9.168  | 13.668 | 3.615  | 1.00 | 24.82 |
| 5166 | N   | LEU | B | 57 | 8.480  | 15.459 | 4.784  | 1.00 | 25.44 |
| 5168 | CA  | LEU | B | 57 | 7.363  | 15.761 | 3.890  | 1.00 | 26.38 |
| 5170 | CB  | LEU | B | 57 | 6.196  | 16.353 | 4.683  | 1.00 | 26.51 |
| 5173 | CG  | LEU | B | 57 | 4.851  | 15.625 | 4.607  | 1.00 | 29.53 |
| 5175 | CD1 | LEU | B | 57 | 4.953  | 14.108 | 4.807  | 1.00 | 30.58 |
| 5179 | CD2 | LEU | B | 57 | 3.880  | 16.228 | 5.625  | 1.00 | 30.77 |
| 5183 | C   | LEU | B | 57 | 7.833  | 16.671 | 2.741  | 1.00 | 26.06 |
| 5184 | O   | LEU | B | 57 | 7.862  | 17.895 | 2.846  | 1.00 | 27.01 |
| 5185 | N   | GLY | B | 58 | 8.237  | 16.048 | 1.651  | 1.00 | 25.60 |
| 5187 | CA  | GLY | B | 58 | 8.677  | 16.778 | 0.477  | 1.00 | 25.47 |
| 5190 | C   | GLY | B | 58 | 10.152 | 17.095 | 0.529  | 1.00 | 24.67 |
| 5191 | O   | GLY | B | 58 | 10.821 | 16.878 | 1.542  | 1.00 | 24.85 |
| 5192 | N   | GLY | B | 59 | 10.655 | 17.628 | -0.575 | 1.00 | 24.17 |
| 5194 | CA  | GLY | B | 59 | 12.046 | 18.001 | -0.702 | 1.00 | 23.50 |
| 5197 | C   | GLY | B | 59 | 12.688 | 17.037 | -1.671 | 1.00 | 23.34 |

FIGURE 3 BY

| A | B | C | D | E | F | G | H | I | J |
|---|---|---|---|---|---|---|---|---|---|
| 5198 | O | GLY | B | 59 | 12.221 | 15.901 | -1.822 | 1.00 | 23.79 |
| 5199 | N | LYS | B | 60 | 13.776 | 17.465 | -2.305 | 1.00 | 22.25 |
| 5201 | CA | LYS | B | 60 | 14.378 | 16.698 | -3.397 | 1.00 | 21.47 |
| 5203 | CB | LYS | B | 60 | 14.964 | 17.634 | -4.446 | 1.00 | 21.33 |
| 5206 | CG | LYS | B | 60 | 13.989 | 18.633 | -5.009 | 1.00 | 21.64 |
| 5209 | CD | LYS | B | 60 | 14.690 | 19.563 | -5.983 | 1.00 | 20.05 |
| 5212 | CE | LYS | B | 60 | 15.503 | 20.635 | -5.285 | 1.00 | 20.61 |
| 5215 | NZ | LYS | B | 60 | 14.661 | 21.571 | -4.488 | 1.00 | 18.47 |
| 5219 | C | LYS | B | 60 | 15.473 | 15.764 | -2.916 | 1.00 | 20.81 |
| 5220 | O | LYS | B | 60 | 15.930 | 14.904 | -3.680 | 1.00 | 19.71 |
| 5221 | N | ARG | B | 61 | 15.873 | 15.934 | -1.651 | 1.00 | 19.67 |
| 5223 | CA | ARG | B | 61 | 16.956 | 15.168 | -1.037 | 1.00 | 19.66 |
| 5225 | CB | ARG | B | 61 | 16.531 | 13.713 | -0.785 | 1.00 | 19.62 |
| 5228 | CG | ARG | B | 61 | 15.280 | 13.581 | 0.031 | 1.00 | 20.32 |
| 5231 | CD | ARG | B | 61 | 15.456 | 13.814 | 1.534 | 1.00 | 21.36 |
| 5234 | NE | ARG | B | 61 | 14.145 | 13.667 | 2.159 | 1.00 | 22.35 |
| 5236 | CZ | ARG | B | 61 | 13.232 | 14.625 | 2.243 | 1.00 | 24.57 |
| 5237 | NH1 | ARG | B | 61 | 13.491 | 15.867 | 1.836 | 1.00 | 25.55 |
| 5240 | NH2 | ARG | B | 61 | 12.042 | 14.347 | 2.754 | 1.00 | 25.42 |
| 5243 | C | ARG | B | 61 | 18.218 | 15.188 | -1.878 | 1.00 | 19.19 |
| 5244 | O | ARG | B | 61 | 18.871 | 14.162 | -2.042 | 1.00 | 19.59 |
| 5245 | N | LEU | B | 62 | 18.575 | 16.345 | -2.419 | 1.00 | 18.57 |
| 5247 | CA | LEU | B | 62 | 19.781 | 16.421 | -3.233 | 1.00 | 18.09 |
| 5249 | CB | LEU | B | 62 | 19.801 | 17.700 | -4.043 | 1.00 | 18.16 |
| 5252 | CG | LEU | B | 62 | 18.659 | 17.854 | -5.069 | 1.00 | 17.75 |
| 5254 | CD1 | LEU | B | 62 | 18.918 | 19.010 | -5.960 | 1.00 | 17.68 |
| 5258 | CD2 | LEU | B | 62 | 18.460 | 16.582 | -5.902 | 1.00 | 17.92 |
| 5262 | C | LEU | B | 62 | 21.050 | 16.265 | -2.398 | 1.00 | 18.27 |
| 5263 | O | LEU | B | 62 | 22.075 | 15.828 | -2.904 | 1.00 | 19.36 |
| 5264 | N | ARG | B | 63 | 20.984 | 16.589 | -1.118 | 1.00 | 18.60 |
| 5266 | CA | ARG | B | 63 | 22.152 | 16.472 | -0.263 | 1.00 | 18.77 |
| 5268 | CB | ARG | B | 63 | 22.052 | 17.389 | 0.948 | 1.00 | 18.34 |
| 5271 | CG | ARG | B | 63 | 22.255 | 18.855 | 0.557 | 1.00 | 18.92 |
| 5274 | CD | ARG | B | 63 | 21.763 | 19.861 | 1.576 | 1.00 | 19.63 |
| 5277 | NE | ARG | B | 63 | 21.626 | 21.189 | 0.993 | 1.00 | 18.86 |
| 5279 | CZ | ARG | B | 63 | 20.623 | 21.574 | 0.213 | 1.00 | 20.23 |
| 5280 | NH1 | ARG | B | 63 | 20.591 | 22.816 | -0.258 | 1.00 | 20.75 |
| 5283 | NH2 | ARG | B | 63 | 19.642 | 20.736 | -0.106 | 1.00 | 20.23 |
| 5286 | C | ARG | B | 63 | 22.421 | 14.999 | 0.076 | 1.00 | 19.10 |
| 5287 | O | ARG | B | 63 | 23.547 | 14.561 | -0.077 | 1.00 | 19.88 |
| 5288 | N | PRO | B | 64 | 21.423 | 14.225 | 0.504 | 1.00 | 19.43 |
| 5289 | CA | PRO | B | 64 | 21.571 | 12.764 | 0.495 | 1.00 | 19.41 |
| 5291 | CB | PRO | B | 64 | 20.168 | 12.271 | 0.822 | 1.00 | 20.11 |
| 5294 | CG | PRO | B | 64 | 19.619 | 13.337 | 1.712 | 1.00 | 19.65 |
| 5297 | CD | PRO | B | 64 | 20.136 | 14.628 | 1.091 | 1.00 | 19.55 |
| 5300 | C | PRO | B | 64 | 22.061 | 12.230 | -0.851 | 1.00 | 18.78 |
| 5301 | O | PRO | B | 64 | 22.971 | 11.411 | -0.850 | 1.00 | 19.31 |
| 5302 | N | PHE | B | 65 | 21.512 | 12.708 | -1.965 | 1.00 | 18.78 |
| 5304 | CA | PHE | B | 65 | 21.994 | 12.301 | -3.290 | 1.00 | 18.13 |
| 5306 | CB | PHE | B | 65 | 21.301 | 13.089 | -4.406 | 1.00 | 18.17 |
| 5309 | CG | PHE | B | 65 | 21.440 | 12.462 | -5.768 | 1.00 | 19.67 |
| 5310 | CD1 | PHE | B | 65 | 22.618 | 12.595 | -6.496 | 1.00 | 21.70 |

FIGURE 3 BZ

| A | B | C | D | E | F | G | H | I | J |
|---|---|---|---|---|---|---|---|---|---|
| 5312 | CE1 | PHE | B | 65 | 22.745 | 12.007 | -7.755 | 1.00 | 22.62 |
| 5314 | CZ | PHE | B | 65 | 21.697 | 11.280 | -8.296 | 1.00 | 23.33 |
| 5316 | CE2 | PHE | B | 65 | 20.532 | 11.138 | -7.587 | 1.00 | 23.93 |
| 5318 | CD2 | PHE | B | 65 | 20.400 | 11.730 | -6.324 | 1.00 | 22.20 |
| 5320 | C | PHE | B | 65 | 23.518 | 12.444 | -3.401 | 1.00 | 18.01 |
| 5321 | O | PHE | B | 65 | 24.194 | 11.528 | -3.851 | 1.00 | 17.71 |
| 5322 | N | LEU | B | 66 | 24.042 | 13.591 | -2.986 | 1.00 | 17.36 |
| 5324 | CA | LEU | B | 66 | 25.470 | 13.851 | -3.011 | 1.00 | 17.79 |
| 5326 | CB | LEU | B | 66 | 25.775 | 15.297 | -2.615 | 1.00 | 17.54 |
| 5329 | CG | LEU | B | 66 | 25.431 | 16.355 | -3.650 | 1.00 | 18.09 |
| 5331 | CD1 | LEU | B | 66 | 25.477 | 17.733 | -3.004 | 1.00 | 20.27 |
| 5335 | CD2 | LEU | B | 66 | 26.378 | 16.312 | -4.830 | 1.00 | 18.85 |
| 5339 | C | LEU | B | 66 | 26.245 | 12.913 | -2.104 | 1.00 | 17.24 |
| 5340 | O | LEU | B | 66 | 27.325 | 12.470 | -2.464 | 1.00 | 17.66 |
| 5341 | N | VAL | B | 67 | 25.717 | 12.633 | -0.920 | 1.00 | 16.80 |
| 5343 | CA | VAL | B | 67 | 26.388 | 11.711 | -0.011 | 1.00 | 16.74 |
| 5345 | CB | VAL | B | 67 | 25.658 | 11.640 | 1.340 | 1.00 | 16.98 |
| 5347 | CG1 | VAL | B | 67 | 26.180 | 10.504 | 2.196 | 1.00 | 16.26 |
| 5351 | CG2 | VAL | B | 67 | 25.754 | 13.004 | 2.088 | 1.00 | 17.68 |
| 5355 | C | VAL | B | 67 | 26.465 | 10.322 | -0.656 | 1.00 | 16.74 |
| 5356 | O | VAL | B | 67 | 27.536 | 9.725 | -0.718 | 1.00 | 15.63 |
| 5357 | N | TYR | B | 68 | 25.315 | 9.830 | -1.120 | 1.00 | 17.27 |
| 5359 | CA | TYR | B | 68 | 25.226 | 8.520 | -1.767 | 1.00 | 18.14 |
| 5361 | CB | TYR | B | 68 | 23.790 | 8.181 | -2.162 | 1.00 | 18.15 |
| 5364 | CG | TYR | B | 68 | 22.884 | 7.903 | -1.001 | 1.00 | 17.89 |
| 5365 | CD1 | TYR | B | 68 | 23.205 | 6.940 | -0.059 | 1.00 | 19.51 |
| 5367 | CE1 | TYR | B | 68 | 22.357 | 6.678 | 1.022 | 1.00 | 18.10 |
| 5369 | CZ | TYR | B | 68 | 21.198 | 7.396 | 1.155 | 1.00 | 18.28 |
| 5370 | OH | TYR | B | 68 | 20.351 | 7.135 | 2.215 | 1.00 | 19.90 |
| 5372 | CE2 | TYR | B | 68 | 20.866 | 8.363 | 0.221 | 1.00 | 18.45 |
| 5374 | CD2 | TYR | B | 68 | 21.699 | 8.599 | -0.846 | 1.00 | 18.98 |
| 5376 | C | TYR | B | 68 | 26.082 | 8.438 | -3.015 | 1.00 | 17.83 |
| 5377 | O | TYR | B | 68 | 26.788 | 7.478 | -3.201 | 1.00 | 17.93 |
| 5378 | N | ALA | B | 69 | 26.031 | 9.456 | -3.868 | 1.00 | 18.14 |
| 5380 | CA | ALA | B | 69 | 26.687 | 9.377 | -5.168 | 1.00 | 17.87 |
| 5382 | CB | ALA | B | 69 | 26.264 | 10.525 | -6.039 | 1.00 | 18.36 |
| 5386 | C | ALA | B | 69 | 28.200 | 9.387 | -4.975 | 1.00 | 18.40 |
| 5387 | O | ALA | B | 69 | 28.960 | 8.703 | -5.696 | 1.00 | 18.10 |
| 5388 | N | THR | B | 70 | 28.639 | 10.155 | -3.985 | 1.00 | 18.02 |
| 5390 | CA | THR | B | 70 | 30.055 | 10.258 | -3.691 | 1.00 | 18.66 |
| 5392 | CB | THR | B | 70 | 30.300 | 11.424 | -2.750 | 1.00 | 17.72 |
| 5394 | OG1 | THR | B | 70 | 29.858 | 12.636 | -3.373 | 1.00 | 18.73 |
| 5396 | CG2 | THR | B | 70 | 31.801 | 11.638 | -2.534 | 1.00 | 19.07 |
| 5400 | C | THR | B | 70 | 30.634 | 8.968 | -3.097 | 1.00 | 19.24 |
| 5401 | O | THR | B | 70 | 31.644 | 8.449 | -3.592 | 1.00 | 19.75 |
| 5402 | N | GLY | B | 71 | 29.999 | 8.474 | -2.036 | 1.00 | 19.50 |
| 5404 | CA | GLY | B | 71 | 30.432 | 7.259 | -1.389 | 1.00 | 20.08 |
| 5407 | C | GLY | B | 71 | 30.417 | 6.071 | -2.343 | 1.00 | 20.27 |
| 5408 | O | GLY | B | 71 | 31.314 | 5.231 | -2.310 | 1.00 | 20.87 |
| 5409 | N | HIS | B | 72 | 29.379 | 6.008 | -3.169 | 1.00 | 20.75 |
| 5411 | CA | HIS | B | 72 | 29.201 | 4.952 | -4.163 | 1.00 | 21.28 |
| 5413 | CB | HIS | B | 72 | 27.909 | 5.167 | -4.955 | 1.00 | 20.79 |

FIGURE 3 CA

| A | B | C | D | E | F | G | H | I | J |
|---|---|---|---|---|---|---|---|---|---|
| 5416 | CG | HIS | B | 72 | 26.666 | 4.749 | -4.233 | 1.00 | 20.15 |
| 5417 | ND1 | HIS | B | 72 | 25.407 | 4.975 | -4.744 | 1.00 | 18.98 |
| 5419 | CE1 | HIS | B | 72 | 24.500 | 4.502 | -3.911 | 1.00 | 20.13 |
| 5421 | NE2 | HIS | B | 72 | 25.126 | 3.949 | -2.887 | 1.00 | 20.74 |
| 5423 | CD2 | HIS | B | 72 | 26.482 | 4.101 | -3.059 | 1.00 | 21.64 |
| 5425 | C | HIS | B | 72 | 30.361 | 4.878 | -5.151 | 1.00 | 21.89 |
| 5426 | O | HIS | B | 72 | 30.692 | 3.791 | -5.606 | 1.00 | 21.76 |
| 5427 | N | MET | B | 73 | 30.960 | 6.023 | -5.493 | 1.00 | 22.15 |
| 5429 | CA | MET | B | 73 | 32.157 | 6.051 | -6.357 | 1.00 | 23.42 |
| 5431 | CB | MET | B | 73 | 32.672 | 7.481 | -6.565 | 1.00 | 23.57 |
| 5434 | CG | MET | B | 73 | 31.804 | 8.325 | -7.471 | 1.00 | 24.99 |
| 5437 | SD | MET | B | 73 | 32.611 | 9.844 | -8.067 | 1.00 | 26.07 |
| 5438 | CE | MET | B | 73 | 33.270 | 10.463 | -6.588 | 1.00 | 25.93 |
| 5442 | C | MET | B | 73 | 33.303 | 5.200 | -5.819 | 1.00 | 23.68 |
| 5443 | O | MET | B | 73 | 34.094 | 4.657 | -6.595 | 1.00 | 24.77 |
| 5444 | N | PHE | B | 74 | 33.405 | 5.105 | -4.502 | 1.00 | 23.69 |
| 5446 | CA | PHE | B | 74 | 34.474 | 4.342 | -3.856 | 1.00 | 23.70 |
| 5448 | CB | PHE | B | 74 | 35.073 | 5.171 | -2.720 | 1.00 | 23.12 |
| 5451 | CG | PHE | B | 74 | 35.419 | 6.571 | -3.134 | 1.00 | 23.22 |
| 5452 | CD1 | PHE | B | 74 | 34.539 | 7.620 | -2.887 | 1.00 | 22.52 |
| 5454 | CE1 | PHE | B | 74 | 34.842 | 8.909 | -3.297 | 1.00 | 21.95 |
| 5456 | CZ | PHE | B | 74 | 36.029 | 9.160 | -3.967 | 1.00 | 23.61 |
| 5458 | CE2 | PHE | B | 74 | 36.910 | 8.116 | -4.230 | 1.00 | 22.42 |
| 5460 | CD2 | PHE | B | 74 | 36.604 | 6.834 | -3.818 | 1.00 | 23.20 |
| 5462 | C | PHE | B | 74 | 34.016 | 2.986 | -3.339 | 1.00 | 23.73 |
| 5463 | O | PHE | B | 74 | 34.751 | 2.309 | -2.625 | 1.00 | 23.67 |
| 5464 | N | GLY | B | 75 | 32.791 | 2.607 | -3.686 | 1.00 | 23.96 |
| 5466 | CA | GLY | B | 75 | 32.273 | 1.287 | -3.397 | 1.00 | 24.04 |
| 5469 | C | GLY | B | 75 | 31.674 | 1.153 | -2.023 | 1.00 | 23.99 |
| 5470 | O | GLY | B | 75 | 31.462 | 0.038 | -1.543 | 1.00 | 23.68 |
| 5471 | N | VAL | B | 76 | 31.385 | 2.278 | -1.375 | 1.00 | 23.71 |
| 5473 | CA | VAL | B | 76 | 30.866 | 2.207 | -0.020 | 1.00 | 23.08 |
| 5475 | CB | BVAL | B | 76 | 31.048 | 3.547 | 0.736 | 0.35 | 22.92 |
| 5476 | CB | AVAL | B | 76 | 31.192 | 3.459 | 0.840 | 0.65 | 23.42 |
| 5479 | CG1 | BVAL | B | 76 | 30.368 | 3.508 | 2.114 | 0.35 | 22.09 |
| 5480 | CG1 | AVAL | B | 76 | 32.625 | 3.934 | 0.590 | 0.65 | 23.81 |
| 5487 | CG2 | BVAL | B | 76 | 32.527 | 3.883 | 0.872 | 0.35 | 23.15 |
| 5488 | CG2 | AVAL | B | 76 | 30.219 | 4.544 | 0.625 | 0.65 | 24.67 |
| 5495 | C | VAL | B | 76 | 29.387 | 1.847 | -0.088 | 1.00 | 22.55 |
| 5496 | O | VAL | B | 76 | 28.660 | 2.300 | -0.965 | 1.00 | 21.42 |
| 5497 | N | SER | B | 77 | 28.987 | 0.968 | 0.819 | 1.00 | 22.22 |
| 5499 | CA | SER | B | 77 | 27.645 | 0.429 | 0.868 | 1.00 | 22.25 |
| 5501 | CB | SER | B | 77 | 27.539 | -0.621 | 1.979 | 1.00 | 22.22 |
| 5504 | OG | SER | B | 77 | 26.202 | -1.078 | 2.137 | 1.00 | 22.42 |
| 5506 | C | SER | B | 77 | 26.656 | 1.550 | 1.108 | 1.00 | 22.33 |
| 5507 | O | SER | B | 77 | 26.919 | 2.462 | 1.898 | 1.00 | 21.77 |
| 5508 | N | THR | B | 78 | 25.534 | 1.480 | 0.394 | 1.00 | 21.99 |
| 5510 | CA | THR | B | 78 | 24.431 | 2.400 | 0.559 | 1.00 | 22.06 |
| 5512 | CB | THR | B | 78 | 23.259 | 1.990 | -0.367 | 1.00 | 22.16 |
| 5514 | OG1 | THR | B | 78 | 23.685 | 2.032 | -1.732 | 1.00 | 23.21 |
| 5516 | CG2 | THR | B | 78 | 22.126 | 2.999 | -0.303 | 1.00 | 22.58 |
| 5520 | C | THR | B | 78 | 23.949 | 2.433 | 1.997 | 1.00 | 21.59 |

FIGURE 3 CB

| A | B | C | D | E | F | G | H | I | J |
|---|---|---|---|---|---|---|---|---|---|
| 5521 | O | THR | B | 78 | 23.618 | 3.500 | 2.527 | 1.00 | 21.04 |
| 5522 | N | ASN | B | 79 | 23.897 | 1.261 | 2.628 | 1.00 | 21.29 |
| 5524 | CA | ASN | B | 79 | 23.467 | 1.170 | 4.022 | 1.00 | 21.08 |
| 5526 | CB | ASN | B | 79 | 23.358 | -0.293 | 4.454 | 1.00 | 21.68 |
| 5529 | CG | ASN | B | 79 | 23.046 | -0.442 | 5.923 | 1.00 | 21.92 |
| 5530 | OD1 | ASN | B | 79 | 21.903 | -0.297 | 6.343 | 1.00 | 23.33 |
| 5531 | ND2 | ASN | B | 79 | 24.060 | -0.747 | 6.706 | 1.00 | 22.60 |
| 5534 | C | ASN | B | 79 | 24.404 | 1.930 | 4.963 | 1.00 | 20.60 |
| 5535 | O | ASN | B | 79 | 23.950 | 2.532 | 5.920 | 1.00 | 19.95 |
| 5536 | N | THR | B | 80 | 25.708 | 1.876 | 4.708 | 1.00 | 20.20 |
| 5538 | CA | THR | B | 80 | 26.661 | 2.698 | 5.453 | 1.00 | 20.29 |
| 5540 | CB | THR | B | 80 | 28.086 | 2.339 | 5.017 | 1.00 | 20.31 |
| 5542 | OG1 | THR | B | 80 | 28.386 | 1.014 | 5.482 | 1.00 | 20.98 |
| 5544 | CG2 | THR | B | 80 | 29.139 | 3.242 | 5.699 | 1.00 | 21.55 |
| 5548 | C | THR | B | 80 | 26.390 | 4.199 | 5.257 | 1.00 | 20.17 |
| 5549 | O | THR | B | 80 | 26.440 | 4.994 | 6.218 | 1.00 | 20.64 |
| 5550 | N | LEU | B | 81 | 26.078 | 4.560 | 4.013 | 1.00 | 19.46 |
| 5552 | CA | LEU | B | 81 | 25.883 | 5.947 | 3.604 | 1.00 | 19.22 |
| 5554 | CB | LEU | B | 81 | 25.952 | 6.044 | 2.077 | 1.00 | 18.97 |
| 5557 | CG | LEU | B | 81 | 27.376 | 5.905 | 1.533 | 1.00 | 19.26 |
| 5559 | CD1 | LEU | B | 81 | 27.370 | 5.638 | 0.037 | 1.00 | 20.15 |
| 5563 | CD2 | LEU | B | 81 | 28.251 | 7.121 | 1.875 | 1.00 | 20.46 |
| 5567 | C | LEU | B | 81 | 24.584 | 6.574 | 4.113 | 1.00 | 19.19 |
| 5568 | O | LEU | B | 81 | 24.445 | 7.794 | 4.139 | 1.00 | 18.91 |
| 5569 | N | ASP | B | 82 | 23.641 | 5.746 | 4.523 | 1.00 | 19.51 |
| 5571 | CA | ASP | B | 82 | 22.393 | 6.219 | 5.106 | 1.00 | 19.28 |
| 5573 | CB | ASP | B | 82 | 21.559 | 5.046 | 5.616 | 1.00 | 19.89 |
| 5576 | CG | ASP | B | 82 | 20.654 | 4.406 | 4.552 | 1.00 | 21.00 |
| 5577 | OD1 | ASP | B | 82 | 20.591 | 4.823 | 3.365 | 1.00 | 21.03 |
| 5578 | OD2 | ASP | B | 82 | 19.938 | 3.431 | 4.867 | 1.00 | 24.24 |
| 5579 | C | ASP | B | 82 | 22.645 | 7.167 | 6.297 | 1.00 | 18.72 |
| 5580 | O | ASP | B | 82 | 21.924 | 8.147 | 6.462 | 1.00 | 18.18 |
| 5581 | N | ALA | B | 83 | 23.639 | 6.861 | 7.130 | 1.00 | 18.70 |
| 5583 | CA | ALA | B | 83 | 23.955 | 7.700 | 8.290 | 1.00 | 19.48 |
| 5585 | CB | ALA | B | 83 | 25.006 | 7.061 | 9.204 | 1.00 | 19.64 |
| 5589 | C | ALA | B | 83 | 24.360 | 9.113 | 7.894 | 1.00 | 19.16 |
| 5590 | O | ALA | B | 83 | 23.679 | 10.049 | 8.257 | 1.00 | 18.92 |
| 5591 | N | PRO | B | 84 | 25.451 | 9.305 | 7.163 | 1.00 | 19.56 |
| 5592 | CA | PRO | B | 84 | 25.781 | 10.672 | 6.739 | 1.00 | 19.16 |
| 5594 | CB | PRO | B | 84 | 27.114 | 10.519 | 6.004 | 1.00 | 19.21 |
| 5597 | CG | PRO | B | 84 | 27.166 | 9.070 | 5.606 | 1.00 | 19.67 |
| 5600 | CD | PRO | B | 84 | 26.446 | 8.323 | 6.694 | 1.00 | 19.64 |
| 5603 | C | PRO | B | 84 | 24.692 | 11.299 | 5.856 | 1.00 | 18.58 |
| 5604 | O | PRO | B | 84 | 24.509 | 12.510 | 5.924 | 1.00 | 18.13 |
| 5605 | N | ALA | B | 85 | 23.975 | 10.506 | 5.063 | 1.00 | 18.37 |
| 5607 | CA | ALA | B | 85 | 22.891 | 11.038 | 4.225 | 1.00 | 18.51 |
| 5609 | CB | ALA | B | 85 | 22.314 | 9.952 | 3.312 | 1.00 | 18.83 |
| 5613 | C | ALA | B | 85 | 21.790 | 11.644 | 5.073 | 1.00 | 18.64 |
| 5614 | O | ALA | B | 85 | 21.313 | 12.749 | 4.811 | 1.00 | 19.06 |
| 5615 | N | ALA | B | 86 | 21.407 | 10.928 | 6.114 | 1.00 | 18.40 |
| 5617 | CA | ALA | B | 86 | 20.360 | 11.383 | 7.010 | 1.00 | 18.11 |
| 5619 | CB | ALA | B | 86 | 19.906 | 10.245 | 7.903 | 1.00 | 18.05 |

FIGURE 3 CC

| A | B | C | D | E | F | G | H | I | J |
|---|---|---|---|---|---|---|---|---|---|
| 5623 | C | ALA | B | 86 | 20.855 | 12.566 | 7.841 | 1.00 | 17.48 |
| 5624 | O | ALA | B | 86 | 20.123 | 13.505 | 8.071 | 1.00 | 16.95 |
| 5625 | N | ALA | B | 87 | 22.105 | 12.525 | 8.281 | 1.00 | 17.41 |
| 5627 | CA | ALA | B | 87 | 22.630 | 13.600 | 9.115 | 1.00 | 17.40 |
| 5629 | CB | ALA | B | 87 | 23.982 | 13.244 | 9.638 | 1.00 | 17.13 |
| 5633 | C | ALA | B | 87 | 22.680 | 14.917 | 8.335 | 1.00 | 17.61 |
| 5634 | O | ALA | B | 87 | 22.298 | 15.947 | 8.858 | 1.00 | 17.33 |
| 5635 | N | VAL | B | 88 | 23.143 | 14.893 | 7.091 | 1.00 | 18.42 |
| 5637 | CA | VAL | B | 88 | 23.208 | 16.146 | 6.304 | 1.00 | 18.96 |
| 5639 | CB | BVAL | B | 88 | 24.038 | 16.002 | 4.993 | 0.35 | 18.97 |
| 5640 | CB | AVAL | B | 88 | 23.983 | 16.016 | 4.957 | 0.65 | 19.14 |
| 5643 | CG1 | BVAL | B | 88 | 23.256 | 15.295 | 3.906 | 0.35 | 19.73 |
| 5644 | CG1 | AVAL | B | 88 | 25.429 | 15.726 | 5.214 | 0.65 | 19.11 |
| 5651 | CG2 | BVAL | B | 88 | 24.517 | 17.378 | 4.509 | 0.35 | 18.57 |
| 5652 | CG2 | AVAL | B | 88 | 23.381 | 14.977 | 4.031 | 0.65 | 20.34 |
| 5659 | C | VAL | B | 88 | 21.813 | 16.685 | 6.031 | 1.00 | 19.05 |
| 5660 | O | VAL | B | 88 | 21.610 | 17.902 | 6.048 | 1.00 | 19.83 |
| 5661 | N | GLU | B | 89 | 20.858 | 15.786 | 5.828 | 1.00 | 18.96 |
| 5663 | CA | GLU | B | 89 | 19.479 | 16.181 | 5.611 | 1.00 | 19.29 |
| 5665 | CB | GLU | B | 89 | 18.657 | 15.024 | 5.045 | 1.00 | 19.83 |
| 5668 | CG | GLU | B | 89 | 17.271 | 15.429 | 4.550 | 1.00 | 20.18 |
| 5671 | CD | GLU | B | 89 | 17.276 | 16.380 | 3.353 | 1.00 | 21.04 |
| 5672 | OE1 | GLU | B | 89 | 16.175 | 16.831 | 2.956 | 1.00 | 20.80 |
| 5673 | OE2 | GLU | B | 89 | 18.352 | 16.669 | 2.784 | 1.00 | 22.55 |
| 5674 | C | GLU | B | 89 | 18.816 | 16.727 | 6.868 | 1.00 | 19.09 |
| 5675 | O | GLU | B | 89 | 17.964 | 17.587 | 6.761 | 1.00 | 18.76 |
| 5676 | N | CYS | B | 90 | 19.205 | 16.246 | 8.053 | 1.00 | 19.19 |
| 5678 | CA | CYS | B | 90 | 18.694 | 16.808 | 9.313 | 1.00 | 18.68 |
| 5680 | CB | CYS | B | 90 | 19.186 | 16.019 | 10.519 | 1.00 | 19.12 |
| 5683 | SG | CYS | B | 90 | 18.326 | 14.474 | 10.771 | 1.00 | 22.59 |
| 5684 | C | CYS | B | 90 | 19.160 | 18.255 | 9.485 | 1.00 | 17.90 |
| 5685 | O | CYS | B | 90 | 18.407 | 19.095 | 9.978 | 1.00 | 17.58 |
| 5686 | N | ILE | B | 91 | 20.416 | 18.524 | 9.129 | 1.00 | 16.55 |
| 5688 | CA | ILE | B | 91 | 20.951 | 19.877 | 9.214 | 1.00 | 16.20 |
| 5690 | CB | ILE | B | 91 | 22.468 | 19.934 | 8.896 | 1.00 | 15.98 |
| 5692 | CG1 | ILE | B | 91 | 23.261 | 19.204 | 9.970 | 1.00 | 15.40 |
| 5695 | CD1 | ILE | B | 91 | 23.203 | 19.886 | 11.342 | 1.00 | 17.23 |
| 5699 | CG2 | ILE | B | 91 | 22.941 | 21.391 | 8.777 | 1.00 | 15.29 |
| 5703 | C | ILE | B | 91 | 20.200 | 20.722 | 8.215 | 1.00 | 15.87 |
| 5704 | O | ILE | B | 91 | 19.770 | 21.815 | 8.533 | 1.00 | 15.70 |
| 5705 | N | HIS | B | 92 | 20.067 | 20.215 | 6.992 | 1.00 | 15.91 |
| 5707 | CA | HIS | B | 92 | 19.330 | 20.914 | 5.957 | 1.00 | 16.10 |
| 5709 | CB | HIS | B | 92 | 19.247 | 20.072 | 4.687 | 1.00 | 16.66 |
| 5712 | CG | HIS | B | 92 | 18.572 | 20.782 | 3.567 | 1.00 | 15.86 |
| 5713 | ND1 | HIS | B | 92 | 17.518 | 20.240 | 2.860 | 1.00 | 19.53 |
| 5715 | CE1 | HIS | B | 92 | 17.127 | 21.104 | 1.941 | 1.00 | 17.62 |
| 5717 | NE2 | HIS | B | 92 | 17.871 | 22.190 | 2.043 | 1.00 | 19.93 |
| 5719 | CD2 | HIS | B | 92 | 18.776 | 22.017 | 3.057 | 1.00 | 15.34 |
| 5721 | C | HIS | B | 92 | 17.923 | 21.259 | 6.424 | 1.00 | 17.04 |
| 5722 | O | HIS | B | 92 | 17.524 | 22.425 | 6.412 | 1.00 | 16.67 |
| 5723 | N | ALA | B | 93 | 17.193 | 20.243 | 6.885 | 1.00 | 17.19 |
| 5725 | CA | ALA | B | 93 | 15.809 | 20.414 | 7.334 | 1.00 | 17.14 |

FIGURE 3 CD

| A | B | C | D | E | F | G | H | I | J |
|---|---|---|---|---|---|---|---|---|---|
| 5727 | CB | ALA | B | 93 | 15.236 | 19.074 | 7.793 | 1.00 | 17.69 |
| 5731 | C | ALA | B | 93 | 15.681 | 21.456 | 8.452 | 1.00 | 17.97 |
| 5732 | O | ALA | B | 93 | 14.806 | 22.325 | 8.400 | 1.00 | 17.24 |
| 5733 | N | TYR | B | 94 | 16.570 | 21.389 | 9.449 | 1.00 | 17.80 |
| 5735 | CA | TYR | B | 94 | 16.550 | 22.348 | 10.560 | 1.00 | 17.32 |
| 5737 | CB | TYR | B | 94 | 17.580 | 21.968 | 11.647 | 1.00 | 18.17 |
| 5740 | CG | TYR | B | 94 | 18.635 | 23.015 | 11.933 | 1.00 | 19.38 |
| 5741 | CD1 | TYR | B | 94 | 18.308 | 24.219 | 12.556 | 1.00 | 22.96 |
| 5743 | CE1 | TYR | B | 94 | 19.290 | 25.186 | 12.809 | 1.00 | 23.47 |
| 5745 | CZ | TYR | B | 94 | 20.601 | 24.932 | 12.424 | 1.00 | 23.58 |
| 5746 | OH | TYR | B | 94 | 21.596 | 25.839 | 12.653 | 1.00 | 22.83 |
| 5748 | CE2 | TYR | B | 94 | 20.935 | 23.736 | 11.815 | 1.00 | 21.94 |
| 5750 | CD2 | TYR | B | 94 | 19.963 | 22.802 | 11.571 | 1.00 | 20.83 |
| 5752 | C | TYR | B | 94 | 16.810 | 23.765 | 10.042 | 1.00 | 16.90 |
| 5753 | O | TYR | B | 94 | 16.187 | 24.727 | 10.489 | 1.00 | 16.75 |
| 5754 | N | SER | B | 95 | 17.730 | 23.891 | 9.098 | 1.00 | 16.44 |
| 5756 | CA | SER | B | 95 | 18.097 | 25.192 | 8.581 | 1.00 | 17.14 |
| 5758 | CB | SER | B | 95 | 19.263 | 25.083 | 7.593 | 1.00 | 16.73 |
| 5761 | OG | SER | B | 95 | 18.840 | 24.597 | 6.337 | 1.00 | 18.73 |
| 5763 | C | SER | B | 95 | 16.887 | 25.851 | 7.924 | 1.00 | 17.47 |
| 5764 | O | SER | B | 95 | 16.686 | 27.050 | 8.047 | 1.00 | 17.44 |
| 5765 | N | LEU | B | 96 | 16.089 | 25.064 | 7.224 | 1.00 | 18.06 |
| 5767 | CA | LEU | B | 96 | 14.897 | 25.584 | 6.562 | 1.00 | 18.72 |
| 5769 | CB | LEU | B | 96 | 14.324 | 24.528 | 5.642 | 1.00 | 19.20 |
| 5772 | CG | LEU | B | 96 | 15.224 | 23.982 | 4.548 | 1.00 | 19.55 |
| 5774 | CD1 | LEU | B | 96 | 14.392 | 23.084 | 3.642 | 1.00 | 21.29 |
| 5778 | CD2 | LEU | B | 96 | 15.912 | 25.114 | 3.771 | 1.00 | 19.66 |
| 5782 | C | LEU | B | 96 | 13.814 | 26.018 | 7.551 | 1.00 | 18.78 |
| 5783 | O | LEU | B | 96 | 13.179 | 27.057 | 7.360 | 1.00 | 19.38 |
| 5784 | N | ILE | B | 97 | 13.607 | 25.227 | 8.599 | 1.00 | 18.35 |
| 5786 | CA | ILE | B | 97 | 12.581 | 25.536 | 9.612 | 1.00 | 18.39 |
| 5788 | CB | ILE | B | 97 | 12.525 | 24.456 | 10.724 | 1.00 | 18.49 |
| 5790 | CG1 | ILE | B | 97 | 12.050 | 23.122 | 10.161 | 1.00 | 19.38 |
| 5793 | CD1 | ILE | B | 97 | 12.339 | 21.950 | 11.075 | 1.00 | 20.40 |
| 5797 | CG2 | ILE | B | 97 | 11.617 | 24.887 | 11.862 | 1.00 | 18.22 |
| 5801 | C | ILE | B | 97 | 12.874 | 26.891 | 10.247 | 1.00 | 18.35 |
| 5802 | O | ILE | B | 97 | 11.976 | 27.698 | 10.437 | 1.00 | 18.38 |
| 5803 | N | HIS | B | 98 | 14.142 | 27.127 | 10.568 | 1.00 | 18.85 |
| 5805 | CA | HIS | B | 98 | 14.554 | 28.377 | 11.204 | 1.00 | 18.52 |
| 5807 | CB | HIS | B | 98 | 15.891 | 28.199 | 11.898 | 1.00 | 19.08 |
| 5810 | CG | HIS | B | 98 | 15.787 | 27.494 | 13.204 | 1.00 | 18.65 |
| 5811 | ND1 | HIS | B | 98 | 16.798 | 27.505 | 14.135 | 1.00 | 19.24 |
| 5813 | CE1 | HIS | B | 98 | 16.422 | 26.803 | 15.188 | 1.00 | 20.04 |
| 5815 | NE2 | HIS | B | 98 | 15.204 | 26.341 | 14.976 | 1.00 | 19.64 |
| 5817 | CD2 | HIS | B | 98 | 14.785 | 26.756 | 13.738 | 1.00 | 20.54 |
| 5819 | C | HIS | B | 98 | 14.588 | 29.526 | 10.189 | 1.00 | 18.70 |
| 5820 | O | HIS | B | 98 | 14.261 | 30.658 | 10.527 | 1.00 | 18.65 |
| 5821 | N | ASP | B | 99 | 14.949 | 29.218 | 8.946 | 1.00 | 18.55 |
| 5823 | CA | ASP | B | 99 | 14.971 | 30.199 | 7.861 | 1.00 | 18.61 |
| 5825 | CB | ASP | B | 99 | 15.515 | 29.530 | 6.605 | 1.00 | 18.44 |
| 5828 | CG | ASP | B | 99 | 15.629 | 30.470 | 5.456 | 1.00 | 18.37 |
| 5829 | OD1 | ASP | B | 99 | 14.710 | 30.462 | 4.590 | 1.00 | 16.28 |

FIGURE 3 CE

| A | B | C | D | E | F | G | H | I | J |
|---|---|---|---|---|---|---|---|---|---|
| 5830 | OD2 | ASP | B | 99  | 16.618 | 31.233 | 5.324  | 1.00 | 20.63 |
| 5831 | C   | ASP | B | 99  | 13.581 | 30.809 | 7.572  | 1.00 | 18.97 |
| 5832 | O   | ASP | B | 99  | 13.471 | 31.985 | 7.256  | 1.00 | 19.10 |
| 5833 | N   | ASP | B | 100 | 12.537 | 30.007 | 7.703  | 1.00 | 19.32 |
| 5835 | CA  | ASP | B | 100 | 11.172 | 30.446 | 7.448  | 1.00 | 20.42 |
| 5837 | CB  | ASP | B | 100 | 10.283 | 29.224 | 7.206  | 1.00 | 20.29 |
| 5840 | CG  | ASP | B | 100 | 10.566 | 28.544 | 5.883  | 1.00 | 20.45 |
| 5841 | OD1 | ASP | B | 100 | 10.363 | 27.303 | 5.791  | 1.00 | 21.30 |
| 5842 | OD2 | ASP | B | 100 | 10.981 | 29.158 | 4.885  | 1.00 | 20.64 |
| 5843 | C   | ASP | B | 100 | 10.524 | 31.287 | 8.577  | 1.00 | 20.97 |
| 5844 | O   | ASP | B | 100 | 9.465  | 31.874 | 8.372  | 1.00 | 21.34 |
| 5845 | N   | LEU | B | 101 | 11.150 | 31.332 | 9.748  | 1.00 | 21.55 |
| 5847 | CA  | LEU | B | 101 | 10.588 | 31.991 | 10.925 | 1.00 | 22.27 |
| 5849 | CB  | LEU | B | 101 | 11.551 | 31.861 | 12.120 | 1.00 | 22.07 |
| 5852 | CG  | LEU | B | 101 | 11.746 | 30.451 | 12.684 | 1.00 | 22.57 |
| 5854 | CD1 | LEU | B | 101 | 12.901 | 30.397 | 13.690 | 1.00 | 21.96 |
| 5858 | CD2 | LEU | B | 101 | 10.471 | 29.947 | 13.317 | 1.00 | 23.63 |
| 5862 | C   | LEU | B | 101 | 10.313 | 33.470 | 10.646 | 1.00 | 22.59 |
| 5863 | O   | LEU | B | 101 | 11.025 | 34.078 | 9.870  | 1.00 | 22.10 |
| 5864 | N   | PRO | B | 102 | 9.262  | 34.035 | 11.242 | 1.00 | 23.34 |
| 5865 | CA  | PRO | B | 102 | 8.959  | 35.467 | 11.096 | 1.00 | 23.88 |
| 5867 | CB  | PRO | B | 102 | 7.886  | 35.698 | 12.152 | 1.00 | 23.65 |
| 5870 | CG  | PRO | B | 102 | 7.151  | 34.422 | 12.154 | 1.00 | 24.22 |
| 5873 | CD  | PRO | B | 102 | 8.225  | 33.347 | 12.024 | 1.00 | 23.27 |
| 5876 | C   | PRO | B | 102 | 10.131 | 36.428 | 11.282 | 1.00 | 24.08 |
| 5877 | O   | PRO | B | 102 | 10.211 | 37.387 | 10.523 | 1.00 | 24.64 |
| 5878 | N   | ALA | B | 103 | 11.019 | 36.183 | 12.243 | 1.00 | 24.21 |
| 5880 | CA  | ALA | B | 103 | 12.179 | 37.054 | 12.450 | 1.00 | 24.56 |
| 5882 | CB  | ALA | B | 103 | 12.804 | 36.795 | 13.823 | 1.00 | 24.65 |
| 5886 | C   | ALA | B | 103 | 13.235 | 36.885 | 11.364 | 1.00 | 24.37 |
| 5887 | O   | ALA | B | 103 | 14.092 | 37.756 | 11.188 | 1.00 | 25.00 |
| 5888 | N   | MET | B | 104 | 13.193 | 35.747 | 10.674 | 1.00 | 23.93 |
| 5890 | CA  | MET | B | 104 | 14.111 | 35.445 | 9.578  | 1.00 | 24.35 |
| 5892 | CB  | MET | B | 104 | 14.527 | 33.969 | 9.642  | 1.00 | 24.14 |
| 5895 | CG  | MET | B | 104 | 15.317 | 33.629 | 10.912 | 1.00 | 26.61 |
| 5898 | SD  | MET | B | 104 | 17.063 | 34.058 | 10.820 | 1.00 | 29.08 |
| 5899 | CE  | MET | B | 104 | 17.584 | 33.058 | 9.452  | 1.00 | 29.15 |
| 5903 | C   | MET | B | 104 | 13.463 | 35.845 | 8.237  | 1.00 | 23.69 |
| 5904 | O   | MET | B | 104 | 13.310 | 37.040 | 7.995  | 1.00 | 23.79 |
| 5905 | N   | ASP | B | 105 | 13.044 | 34.885 | 7.404  | 1.00 | 23.23 |
| 5907 | CA  | ASP | B | 105 | 12.489 | 35.198 | 6.073  | 1.00 | 22.98 |
| 5909 | CB  | ASP | B | 105 | 12.936 | 34.167 | 5.016  | 1.00 | 22.62 |
| 5912 | CG  | ASP | B | 105 | 14.429 | 34.138 | 4.838  | 1.00 | 21.61 |
| 5913 | OD1 | ASP | B | 105 | 14.957 | 33.260 | 4.090  | 1.00 | 18.84 |
| 5914 | OD2 | ASP | B | 105 | 15.163 | 34.963 | 5.413  | 1.00 | 21.22 |
| 5915 | C   | ASP | B | 105 | 10.967 | 35.289 | 6.067  | 1.00 | 23.49 |
| 5916 | O   | ASP | B | 105 | 10.365 | 35.645 | 5.054  | 1.00 | 22.75 |
| 5917 | N   | ASP | B | 106 | 10.348 | 34.950 | 7.185  | 1.00 | 23.98 |
| 5919 | CA  | ASP | B | 106 | 8.907  | 35.099 | 7.339  | 1.00 | 25.41 |
| 5921 | CB  | ASP | B | 106 | 8.567  | 36.597 | 7.503  | 1.00 | 25.60 |
| 5924 | CG  | ASP | B | 106 | 7.203  | 36.817 | 8.103  | 1.00 | 27.51 |
| 5925 | OD1 | ASP | B | 106 | 6.682  | 37.941 | 7.973  | 1.00 | 29.77 |

FIGURE 3 CF

| A | B | C | D | E | F | G | H | I | J |
|---|---|---|---|---|---|---|---|---|---|
| 5926 | OD2 | ASP | B | 106 | 6.583 | 35.930 | 8.728 | 1.00 | 28.05 |
| 5927 | C | ASP | B | 106 | 8.126 | 34.503 | 6.172 | 1.00 | 25.57 |
| 5928 | O | ASP | B | 106 | 7.385 | 35.206 | 5.498 | 1.00 | 25.87 |
| 5929 | N | ASP | B | 107 | 8.309 | 33.203 | 5.936 | 1.00 | 26.04 |
| 5931 | CA | ASP | B | 107 | 7.630 | 32.487 | 4.861 | 1.00 | 25.95 |
| 5933 | CB | ASP | B | 107 | 8.641 | 31.685 | 4.032 | 1.00 | 26.04 |
| 5936 | CG | ASP | B | 107 | 9.212 | 32.477 | 2.895 | 1.00 | 26.93 |
| 5937 | OD1 | ASP | B | 107 | 8.428 | 32.869 | 2.004 | 1.00 | 30.09 |
| 5938 | OD2 | ASP | B | 107 | 10.426 | 32.755 | 2.786 | 1.00 | 25.96 |
| 5939 | C | ASP | B | 107 | 6.573 | 31.549 | 5.403 | 1.00 | 26.02 |
| 5940 | O | ASP | B | 107 | 6.773 | 30.883 | 6.425 | 1.00 | 26.50 |
| 5941 | N | ASP | B | 108 | 5.443 | 31.487 | 4.703 | 1.00 | 25.79 |
| 5943 | CA | ASP | B | 108 | 4.331 | 30.628 | 5.107 | 1.00 | 25.53 |
| 5945 | CB | ASP | B | 108 | 3.012 | 31.404 | 5.131 | 1.00 | 25.80 |
| 5948 | CG | ASP | B | 108 | 2.611 | 31.970 | 3.766 | 1.00 | 28.04 |
| 5949 | OD1 | ASP | B | 108 | 1.460 | 32.426 | 3.651 | 1.00 | 30.10 |
| 5950 | OD2 | ASP | B | 108 | 3.356 | 32.024 | 2.762 | 1.00 | 28.90 |
| 5951 | C | ASP | B | 108 | 4.183 | 29.359 | 4.260 | 1.00 | 24.50 |
| 5952 | O | ASP | B | 108 | 3.362 | 28.516 | 4.588 | 1.00 | 23.73 |
| 5953 | N | LEU | B | 109 | 4.975 | 29.228 | 3.197 | 1.00 | 23.97 |
| 5955 | CA | LEU | B | 109 | 4.939 | 28.054 | 2.323 | 1.00 | 23.69 |
| 5957 | CB | LEU | B | 109 | 4.386 | 28.414 | 0.940 | 1.00 | 24.10 |
| 5960 | CG | LEU | B | 109 | 2.907 | 28.201 | 0.569 | 1.00 | 27.09 |
| 5962 | CD1 | LEU | B | 109 | 2.748 | 28.570 | -0.917 | 1.00 | 27.23 |
| 5966 | CD2 | LEU | B | 109 | 2.367 | 26.794 | 0.840 | 1.00 | 25.73 |
| 5970 | C | LEU | B | 109 | 6.329 | 27.462 | 2.103 | 1.00 | 22.98 |
| 5971 | O | LEU | B | 109 | 7.271 | 28.178 | 1.813 | 1.00 | 22.51 |
| 5972 | N | ARG | B | 110 | 6.426 | 26.146 | 2.208 | 1.00 | 22.68 |
| 5974 | CA | ARG | B | 110 | 7.609 | 25.422 | 1.776 | 1.00 | 22.37 |
| 5976 | CB | ARG | B | 110 | 8.662 | 25.359 | 2.878 | 1.00 | 22.08 |
| 5979 | CG | ARG | B | 110 | 9.916 | 24.624 | 2.441 | 1.00 | 21.74 |
| 5982 | CD | ARG | B | 110 | 11.021 | 24.622 | 3.487 | 1.00 | 19.15 |
| 5985 | NE | ARG | B | 110 | 11.586 | 25.949 | 3.737 | 1.00 | 17.98 |
| 5987 | CZ | ARG | B | 110 | 12.421 | 26.579 | 2.911 | 1.00 | 18.36 |
| 5988 | NH1 | ARG | B | 110 | 12.900 | 27.771 | 3.239 | 1.00 | 19.16 |
| 5991 | NH2 | ARG | B | 110 | 12.789 | 26.027 | 1.770 | 1.00 | 18.06 |
| 5994 | C | ARG | B | 110 | 7.210 | 24.022 | 1.382 | 1.00 | 22.36 |
| 5995 | O | ARG | B | 110 | 6.409 | 23.385 | 2.071 | 1.00 | 22.81 |
| 5996 | N | ARG | B | 111 | 7.789 | 23.549 | 0.283 | 1.00 | 22.18 |
| 5998 | CA | ARG | B | 111 | 7.542 | 22.212 | -0.244 | 1.00 | 22.54 |
| 6000 | CB | ARG | B | 111 | 8.143 | 21.147 | 0.679 | 1.00 | 22.32 |
| 6003 | CG | ARG | B | 111 | 9.662 | 21.147 | 0.734 | 1.00 | 21.77 |
| 6006 | CD | ARG | B | 111 | 10.202 | 20.545 | 2.021 | 1.00 | 21.80 |
| 6009 | NE | ARG | B | 111 | 11.633 | 20.275 | 1.973 | 1.00 | 20.78 |
| 6011 | CZ | ARG | B | 111 | 12.305 | 19.671 | 2.947 | 1.00 | 20.45 |
| 6012 | NH1 | ARG | B | 111 | 11.688 | 19.269 | 4.048 | 1.00 | 18.82 |
| 6015 | NH2 | ARG | B | 111 | 13.608 | 19.464 | 2.826 | 1.00 | 19.98 |
| 6018 | C | ARG | B | 111 | 6.042 | 21.973 | -0.465 | 1.00 | 23.08 |
| 6019 | O | ARG | B | 111 | 5.544 | 20.861 | -0.338 | 1.00 | 22.39 |
| 6020 | N | GLY | B | 112 | 5.335 | 23.042 | -0.807 | 1.00 | 23.92 |
| 6022 | CA | GLY | B | 112 | 3.921 | 22.975 | -1.135 | 1.00 | 24.69 |
| 6025 | C | GLY | B | 112 | 3.010 | 23.023 | 0.070 | 1.00 | 24.98 |

FIGURE 3 CG

| A | B | C | D | E | F | G | H | I | J |
|---|---|---|---|---|---|---|---|---|---|
| 6026 | O | GLY | B | 112 | 1.808 | 22.978 | -0.089 | 1.00 | 25.54 |
| 6027 | N | LEU | B | 113 | 3.578 | 23.126 | 1.268 | 1.00 | 25.57 |
| 6029 | CA | LEU | B | 113 | 2.813 | 23.045 | 2.508 | 1.00 | 25.94 |
| 6031 | CB | LEU | B | 113 | 3.226 | 21.797 | 3.283 | 1.00 | 26.65 |
| 6034 | CG | LEU | B | 113 | 3.068 | 20.468 | 2.548 | 1.00 | 29.36 |
| 6036 | CD1 | LEU | B | 113 | 3.750 | 19.369 | 3.338 | 1.00 | 31.10 |
| 6040 | CD2 | LEU | B | 113 | 1.599 | 20.127 | 2.336 | 1.00 | 31.06 |
| 6044 | C | LEU | B | 113 | 3.043 | 24.272 | 3.388 | 1.00 | 25.32 |
| 6045 | O | LEU | B | 113 | 4.027 | 24.999 | 3.216 | 1.00 | 24.34 |
| 6046 | N | PRO | B | 114 | 2.153 | 24.497 | 4.355 | 1.00 | 25.34 |
| 6047 | CA | PRO | B | 114 | 2.425 | 25.500 | 5.383 | 1.00 | 24.92 |
| 6049 | CB | PRO | B | 114 | 1.261 | 25.331 | 6.348 | 1.00 | 25.42 |
| 6052 | CG | PRO | B | 114 | 0.165 | 24.734 | 5.503 | 1.00 | 25.33 |
| 6055 | CD | PRO | B | 114 | 0.862 | 23.812 | 4.575 | 1.00 | 25.09 |
| 6058 | C | PRO | B | 114 | 3.764 | 25.201 | 6.077 | 1.00 | 24.65 |
| 6059 | O | PRO | B | 114 | 4.051 | 24.057 | 6.403 | 1.00 | 24.29 |
| 6060 | N | THR | B | 115 | 4.583 | 26.222 | 6.259 | 1.00 | 24.42 |
| 6062 | CA | THR | B | 115 | 5.850 | 26.062 | 6.966 | 1.00 | 24.49 |
| 6064 | CB | THR | B | 115 | 6.635 | 27.364 | 6.990 | 1.00 | 24.32 |
| 6066 | OG1 | THR | B | 115 | 5.798 | 28.437 | 7.465 | 1.00 | 26.32 |
| 6068 | CG2 | THR | B | 115 | 7.058 | 27.773 | 5.573 | 1.00 | 24.50 |
| 6072 | C | THR | B | 115 | 5.607 | 25.577 | 8.387 | 1.00 | 24.50 |
| 6073 | O | THR | B | 115 | 4.512 | 25.721 | 8.944 | 1.00 | 23.20 |
| 6074 | N | CYS | B | 116 | 6.641 | 24.995 | 8.969 | 1.00 | 24.26 |
| 6076 | CA | CYS | B | 116 | 6.537 | 24.419 | 10.297 | 1.00 | 24.93 |
| 6078 | CB | CYS | B | 116 | 7.885 | 23.869 | 10.759 | 1.00 | 24.70 |
| 6081 | SG | CYS | B | 116 | 8.346 | 22.384 | 9.881 | 1.00 | 26.74 |
| 6082 | C | CYS | B | 116 | 6.002 | 25.412 | 11.305 | 1.00 | 24.67 |
| 6083 | O | CYS | B | 116 | 5.204 | 25.042 | 12.148 | 1.00 | 25.48 |
| 6084 | N | HIS | B | 117 | 6.408 | 26.672 | 11.212 | 1.00 | 24.78 |
| 6086 | CA | HIS | B | 117 | 5.981 | 27.647 | 12.214 | 1.00 | 25.04 |
| 6088 | CB | HIS | B | 117 | 6.888 | 28.867 | 12.233 | 1.00 | 25.27 |
| 6091 | CG | HIS | B | 117 | 6.649 | 29.828 | 11.116 | 1.00 | 25.24 |
| 6092 | ND1 | HIS | B | 117 | 5.983 | 31.018 | 11.293 | 1.00 | 26.70 |
| 6094 | CE1 | HIS | B | 117 | 5.924 | 31.663 | 10.141 | 1.00 | 27.42 |
| 6096 | NE2 | HIS | B | 117 | 6.532 | 30.935 | 9.226 | 1.00 | 26.41 |
| 6098 | CD2 | HIS | B | 117 | 6.985 | 29.776 | 9.807 | 1.00 | 26.27 |
| 6100 | C | HIS | B | 117 | 4.539 | 28.076 | 12.018 | 1.00 | 25.01 |
| 6101 | O | HIS | B | 117 | 3.891 | 28.466 | 12.971 | 1.00 | 25.49 |
| 6102 | N | VAL | B | 118 | 4.051 | 28.021 | 10.784 | 1.00 | 25.12 |
| 6104 | CA | VAL | B | 118 | 2.631 | 28.253 | 10.508 | 1.00 | 25.25 |
| 6106 | CB | VAL | B | 118 | 2.394 | 28.567 | 9.018 | 1.00 | 25.46 |
| 6108 | CG1 | VAL | B | 118 | 0.884 | 28.609 | 8.673 | 1.00 | 26.21 |
| 6112 | CG2 | VAL | B | 118 | 3.035 | 29.894 | 8.681 | 1.00 | 25.70 |
| 6116 | C | VAL | B | 118 | 1.786 | 27.078 | 10.999 | 1.00 | 25.08 |
| 6117 | O | VAL | B | 118 | 0.821 | 27.285 | 11.720 | 1.00 | 24.86 |
| 6118 | N | LYS | B | 119 | 2.167 | 25.856 | 10.639 | 1.00 | 25.25 |
| 6120 | CA | LYS | B | 119 | 1.439 | 24.654 | 11.042 | 1.00 | 25.87 |
| 6122 | CB | LYS | B | 119 | 1.935 | 23.428 | 10.263 | 1.00 | 26.25 |
| 6125 | CG | LYS | B | 119 | 0.884 | 22.726 | 9.418 | 1.00 | 28.80 |
| 6128 | CD | LYS | B | 119 | -0.165 | 22.025 | 10.250 | 1.00 | 31.95 |
| 6131 | CE | LYS | B | 119 | -0.978 | 21.015 | 9.432 | 1.00 | 33.31 |

FIGURE 3 CH

| A | B | C | D | E | F | G | H | I | J |
|---|---|---|---|---|---|---|---|---|---|
| 6134 | NZ | LYS | B | 119 | -1.864 | 21.671 | 8.417 | 1.00 | 34.97 |
| 6138 | C | LYS | B | 119 | 1.468 | 24.365 | 12.564 | 1.00 | 25.31 |
| 6139 | O | LYS | B | 119 | 0.445 | 24.061 | 13.161 | 1.00 | 24.99 |
| 6140 | N | PHE | B | 120 | 2.626 | 24.488 | 13.193 | 1.00 | 24.69 |
| 6142 | CA | PHE | B | 120 | 2.789 | 24.032 | 14.567 | 1.00 | 24.30 |
| 6144 | CB | PHE | B | 120 | 3.908 | 22.993 | 14.616 | 1.00 | 24.16 |
| 6147 | CG | PHE | B | 120 | 3.639 | 21.763 | 13.799 | 1.00 | 24.65 |
| 6148 | CD1 | PHE | B | 120 | 2.915 | 20.704 | 14.332 | 1.00 | 26.16 |
| 6150 | CE1 | PHE | B | 120 | 2.690 | 19.541 | 13.582 | 1.00 | 25.66 |
| 6152 | CZ | PHE | B | 120 | 3.192 | 19.441 | 12.311 | 1.00 | 25.37 |
| 6154 | CE2 | PHE | B | 120 | 3.930 | 20.494 | 11.767 | 1.00 | 24.54 |
| 6156 | CD2 | PHE | B | 120 | 4.158 | 21.637 | 12.513 | 1.00 | 25.35 |
| 6158 | C | PHE | B | 120 | 3.084 | 25.165 | 15.565 | 1.00 | 23.77 |
| 6159 | O | PHE | B | 120 | 3.155 | 24.927 | 16.752 | 1.00 | 23.66 |
| 6160 | N | GLY | B | 121 | 3.250 | 26.391 | 15.083 | 1.00 | 23.69 |
| 6162 | CA | GLY | B | 121 | 3.622 | 27.516 | 15.935 | 1.00 | 23.51 |
| 6165 | C | GLY | B | 121 | 5.130 | 27.773 | 15.955 | 1.00 | 23.55 |
| 6166 | O | GLY | B | 121 | 5.927 | 26.892 | 15.652 | 1.00 | 22.34 |
| 6167 | N | GLU | B | 122 | 5.518 | 28.986 | 16.320 | 1.00 | 23.70 |
| 6169 | CA | GLU | B | 122 | 6.934 | 29.381 | 16.314 | 1.00 | 24.67 |
| 6171 | CB | GLU | B | 122 | 7.091 | 30.868 | 16.639 | 1.00 | 24.89 |
| 6174 | CG | GLU | B | 122 | 6.990 | 31.777 | 15.427 | 1.00 | 27.84 |
| 6177 | CD | GLU | B | 122 | 7.069 | 33.248 | 15.796 | 1.00 | 30.34 |
| 6178 | OE1 | GLU | B | 122 | 8.174 | 33.721 | 16.136 | 1.00 | 35.10 |
| 6179 | OE2 | GLU | B | 122 | 6.033 | 33.931 | 15.743 | 1.00 | 32.39 |
| 6180 | C | GLU | B | 122 | 7.792 | 28.558 | 17.283 | 1.00 | 24.12 |
| 6181 | O | GLU | B | 122 | 8.925 | 28.199 | 16.955 | 1.00 | 23.74 |
| 6182 | N | ALA | B | 123 | 7.249 | 28.292 | 18.469 | 1.00 | 23.52 |
| 6184 | CA | ALA | B | 123 | 7.968 | 27.587 | 19.526 | 1.00 | 23.88 |
| 6186 | CB | ALA | B | 123 | 7.156 | 27.594 | 20.816 | 1.00 | 23.93 |
| 6190 | C | ALA | B | 123 | 8.287 | 26.159 | 19.098 | 1.00 | 23.98 |
| 6191 | O | ALA | B | 123 | 9.417 | 25.688 | 19.247 | 1.00 | 22.97 |
| 6192 | N | ASN | B | 124 | 7.290 | 25.494 | 18.524 | 1.00 | 23.86 |
| 6194 | CA | ASN | B | 124 | 7.484 | 24.159 | 17.980 | 1.00 | 24.09 |
| 6196 | CB | ASN | B | 124 | 6.165 | 23.561 | 17.486 | 1.00 | 24.26 |
| 6199 | CG | ASN | B | 124 | 5.365 | 22.896 | 18.601 | 1.00 | 26.12 |
| 6200 | OD1 | ASN | B | 124 | 4.125 | 22.946 | 18.602 | 1.00 | 27.70 |
| 6201 | ND2 | ASN | B | 124 | 6.064 | 22.278 | 19.561 | 1.00 | 23.40 |
| 6204 | C | ASN | B | 124 | 8.508 | 24.168 | 16.849 | 1.00 | 23.11 |
| 6205 | O | ASN | B | 124 | 9.294 | 23.250 | 16.750 | 1.00 | 22.29 |
| 6206 | N | ALA | B | 125 | 8.496 | 25.208 | 16.015 | 1.00 | 22.58 |
| 6208 | CA | ALA | B | 125 | 9.430 | 25.303 | 14.896 | 1.00 | 22.31 |
| 6210 | CB | ALA | B | 125 | 9.043 | 26.425 | 13.953 | 1.00 | 23.02 |
| 6214 | C | ALA | B | 125 | 10.836 | 25.526 | 15.405 | 1.00 | 21.81 |
| 6215 | O | ALA | B | 125 | 11.766 | 24.906 | 14.932 | 1.00 | 21.37 |
| 6216 | N | ILE | B | 126 | 10.985 | 26.419 | 16.371 | 1.00 | 21.15 |
| 6218 | CA | ILE | B | 126 | 12.293 | 26.701 | 16.936 | 1.00 | 20.84 |
| 6220 | CB | ILE | B | 126 | 12.177 | 27.795 | 18.007 | 1.00 | 20.71 |
| 6222 | CG1 | ILE | B | 126 | 11.994 | 29.168 | 17.339 | 1.00 | 21.50 |
| 6225 | CD1 | ILE | B | 126 | 11.342 | 30.199 | 18.243 | 1.00 | 22.29 |
| 6229 | CG2 | ILE | B | 126 | 13.395 | 27.816 | 18.903 | 1.00 | 21.11 |
| 6233 | C | ILE | B | 126 | 12.888 | 25.423 | 17.523 | 1.00 | 19.99 |

FIGURE 3 CI

| A | B | C | D | E | F | G | H | I | J |
|---|---|---|---|---|---|---|---|---|---|
| 6234 | O | ILE | B | 126 | 14.037 | 25.072 | 17.234 | 1.00 | 19.91 |
| 6235 | N | LEU | B | 127 | 12.094 | 24.746 | 18.342 | 1.00 | 19.38 |
| 6237 | CA | LEU | B | 127 | 12.522 | 23.553 | 19.061 | 1.00 | 19.20 |
| 6239 | CB | LEU | B | 127 | 11.477 | 23.141 | 20.106 | 1.00 | 19.23 |
| 6242 | CG | LEU | B | 127 | 11.417 | 24.029 | 21.357 | 1.00 | 20.75 |
| 6244 | CD1 | LEU | B | 127 | 12.776 | 24.131 | 22.047 | 1.00 | 22.13 |
| 6248 | CD2 | LEU | B | 127 | 10.382 | 23.528 | 22.321 | 1.00 | 22.65 |
| 6252 | C | LEU | B | 127 | 12.776 | 22.413 | 18.096 | 1.00 | 19.26 |
| 6253 | O | LEU | B | 127 | 13.757 | 21.682 | 18.244 | 1.00 | 19.51 |
| 6254 | N | ALA | B | 128 | 11.926 | 22.286 | 17.082 | 1.00 | 18.61 |
| 6256 | CA | ALA | B | 128 | 12.073 | 21.218 | 16.108 | 1.00 | 19.13 |
| 6258 | CB | ALA | B | 128 | 10.873 | 21.183 | 15.181 | 1.00 | 18.64 |
| 6262 | C | ALA | B | 128 | 13.373 | 21.368 | 15.315 | 1.00 | 18.57 |
| 6263 | O | ALA | B | 128 | 14.079 | 20.387 | 15.065 | 1.00 | 18.99 |
| 6264 | N | GLY | B | 129 | 13.685 | 22.595 | 14.916 | 1.00 | 18.91 |
| 6266 | CA | GLY | B | 129 | 14.948 | 22.879 | 14.272 | 1.00 | 18.59 |
| 6269 | C | GLY | B | 129 | 16.117 | 22.574 | 15.200 | 1.00 | 18.99 |
| 6270 | O | GLY | B | 129 | 17.098 | 21.959 | 14.790 | 1.00 | 18.66 |
| 6271 | N | ASP | B | 130 | 16.001 | 22.986 | 16.459 | 1.00 | 19.11 |
| 6273 | CA | ASP | B | 130 | 17.061 | 22.771 | 17.457 | 1.00 | 19.02 |
| 6275 | CB | ASP | B | 130 | 16.652 | 23.327 | 18.829 | 1.00 | 18.48 |
| 6278 | CG | ASP | B | 130 | 16.654 | 24.851 | 18.881 | 1.00 | 20.10 |
| 6279 | OD1 | ASP | B | 130 | 17.086 | 25.482 | 17.880 | 1.00 | 19.13 |
| 6280 | OD2 | ASP | B | 130 | 16.221 | 25.488 | 19.889 | 1.00 | 20.44 |
| 6281 | C | ASP | B | 130 | 17.344 | 21.283 | 17.586 | 1.00 | 18.66 |
| 6282 | O | ASP | B | 130 | 18.481 | 20.860 | 17.541 | 1.00 | 18.36 |
| 6283 | N | ALA | B | 131 | 16.274 | 20.506 | 17.675 | 1.00 | 18.43 |
| 6285 | CA | ALA | B | 131 | 16.347 | 19.069 | 17.878 | 1.00 | 18.51 |
| 6287 | CB | ALA | B | 131 | 15.012 | 18.540 | 18.344 | 1.00 | 18.33 |
| 6291 | C | ALA | B | 131 | 16.808 | 18.315 | 16.629 | 1.00 | 18.44 |
| 6292 | O | ALA | B | 131 | 17.407 | 17.248 | 16.748 | 1.00 | 18.67 |
| 6293 | N | LEU | B | 132 | 16.518 | 18.850 | 15.445 | 1.00 | 18.17 |
| 6295 | CA | LEU | B | 132 | 16.970 | 18.235 | 14.207 | 1.00 | 18.20 |
| 6297 | CB | LEU | B | 132 | 16.213 | 18.786 | 12.995 | 1.00 | 18.38 |
| 6300 | CG | LEU | B | 132 | 14.853 | 18.138 | 12.732 | 1.00 | 17.74 |
| 6302 | CD1 | LEU | B | 132 | 14.127 | 18.905 | 11.651 | 1.00 | 17.44 |
| 6306 | CD2 | LEU | B | 132 | 15.017 | 16.674 | 12.341 | 1.00 | 18.02 |
| 6310 | C | LEU | B | 132 | 18.467 | 18.452 | 14.034 | 1.00 | 18.06 |
| 6311 | O | LEU | B | 132 | 19.167 | 17.572 | 13.544 | 1.00 | 18.16 |
| 6312 | N | GLN | B | 133 | 18.969 | 19.610 | 14.447 | 1.00 | 17.91 |
| 6314 | CA | GLN | B | 133 | 20.412 | 19.804 | 14.412 | 1.00 | 18.74 |
| 6316 | CB | GLN | B | 133 | 20.838 | 21.223 | 14.800 | 1.00 | 18.78 |
| 6319 | CG | GLN | B | 133 | 22.358 | 21.369 | 14.668 | 1.00 | 21.69 |
| 6322 | CD | GLN | B | 133 | 22.953 | 22.631 | 15.232 | 1.00 | 23.34 |
| 6323 | OE1 | GLN | B | 133 | 22.274 | 23.644 | 15.458 | 1.00 | 24.32 |
| 6324 | NE2 | GLN | B | 133 | 24.255 | 22.578 | 15.452 | 1.00 | 26.40 |
| 6327 | C | GLN | B | 133 | 21.094 | 18.762 | 15.319 | 1.00 | 18.33 |
| 6328 | O | GLN | B | 133 | 22.086 | 18.144 | 14.926 | 1.00 | 18.38 |
| 6329 | N | THR | B | 134 | 20.542 | 18.560 | 16.508 | 1.00 | 17.86 |
| 6331 | CA | THR | B | 134 | 21.121 | 17.657 | 17.476 | 1.00 | 18.15 |
| 6333 | CB | THR | B | 134 | 20.384 | 17.734 | 18.820 | 1.00 | 18.21 |
| 6335 | OG1 | THR | B | 134 | 20.296 | 19.101 | 19.283 | 1.00 | 18.94 |

FIGURE 3 CJ

| A | B | C | D | E | F | G | H | I | J |
|---|---|---|---|---|---|---|---|---|---|
| 6337 | CG2 | THR | B | 134 | 21.169 | 17.017 | 19.864 | 1.00 | 19.06 |
| 6341 | C | THR | B | 134 | 21.060 | 16.225 | 16.950 | 1.00 | 18.22 |
| 6342 | O | THR | B | 134 | 22.014 | 15.474 | 17.106 | 1.00 | 18.09 |
| 6343 | N | LEU | B | 135 | 19.936 | 15.870 | 16.322 | 1.00 | 17.83 |
| 6345 | CA | LEU | B | 135 | 19.739 | 14.530 | 15.781 | 1.00 | 17.43 |
| 6347 | CB | LEU | B | 135 | 18.336 | 14.416 | 15.184 | 1.00 | 17.61 |
| 6350 | CG | LEU | B | 135 | 18.006 | 13.113 | 14.455 | 1.00 | 18.78 |
| 6352 | CD1 | LEU | B | 135 | 18.167 | 11.908 | 15.367 | 1.00 | 18.23 |
| 6356 | CD2 | LEU | B | 135 | 16.619 | 13.201 | 13.912 | 1.00 | 19.31 |
| 6360 | C | LEU | B | 135 | 20.818 | 14.186 | 14.743 | 1.00 | 16.77 |
| 6361 | O | LEU | B | 135 | 21.287 | 13.045 | 14.664 | 1.00 | 16.01 |
| 6362 | N | ALA | B | 136 | 21.243 | 15.179 | 13.970 | 1.00 | 16.82 |
| 6364 | CA | ALA | B | 136 | 22.280 | 14.960 | 12.974 | 1.00 | 16.89 |
| 6366 | CB | ALA | B | 136 | 22.581 | 16.241 | 12.231 | 1.00 | 17.47 |
| 6370 | C | ALA | B | 136 | 23.548 | 14.406 | 13.625 | 1.00 | 17.27 |
| 6371 | O | ALA | B | 136 | 24.184 | 13.484 | 13.091 | 1.00 | 17.46 |
| 6372 | N | PHE | B | 137 | 23.888 | 14.943 | 14.789 | 1.00 | 17.08 |
| 6374 | CA | PHE | B | 137 | 25.088 | 14.528 | 15.496 | 1.00 | 17.65 |
| 6376 | CB | PHE | B | 137 | 25.593 | 15.666 | 16.381 | 1.00 | 18.03 |
| 6379 | CG | PHE | B | 137 | 26.007 | 16.880 | 15.584 | 1.00 | 18.67 |
| 6380 | CD1 | PHE | B | 137 | 25.230 | 18.019 | 15.566 | 1.00 | 18.86 |
| 6382 | CE1 | PHE | B | 137 | 25.605 | 19.122 | 14.809 | 1.00 | 19.97 |
| 6384 | CZ | PHE | B | 137 | 26.757 | 19.070 | 14.029 | 1.00 | 19.23 |
| 6386 | CE2 | PHE | B | 137 | 27.526 | 17.940 | 14.023 | 1.00 | 19.82 |
| 6388 | CD2 | PHE | B | 137 | 27.140 | 16.835 | 14.788 | 1.00 | 21.06 |
| 6390 | C | PHE | B | 137 | 24.848 | 13.218 | 16.260 | 1.00 | 17.89 |
| 6391 | O | PHE | B | 137 | 25.764 | 12.440 | 16.419 | 1.00 | 17.92 |
| 6392 | N | SER | B | 138 | 23.613 | 12.966 | 16.699 | 1.00 | 18.09 |
| 6394 | CA | SER | B | 138 | 23.275 | 11.661 | 17.269 | 1.00 | 18.71 |
| 6396 | CB | SER | B | 138 | 21.839 | 11.634 | 17.769 | 1.00 | 18.28 |
| 6399 | OG | SER | B | 138 | 21.712 | 12.386 | 18.950 | 1.00 | 19.32 |
| 6401 | C | SER | B | 138 | 23.466 | 10.571 | 16.212 | 1.00 | 18.94 |
| 6402 | O | SER | B | 138 | 24.084 | 9.555 | 16.485 | 1.00 | 19.25 |
| 6403 | N | ILE | B | 139 | 22.967 | 10.819 | 15.001 | 1.00 | 19.22 |
| 6405 | CA | ILE | B | 139 | 23.123 | 9.884 | 13.890 | 1.00 | 19.25 |
| 6407 | CB | ILE | B | 139 | 22.430 | 10.403 | 12.622 | 1.00 | 19.39 |
| 6409 | CG1 | ILE | B | 139 | 20.916 | 10.363 | 12.822 | 1.00 | 18.95 |
| 6412 | CD1 | ILE | B | 139 | 20.144 | 11.100 | 11.805 | 1.00 | 21.43 |
| 6416 | CG2 | ILE | B | 139 | 22.848 | 9.571 | 11.387 | 1.00 | 17.88 |
| 6420 | C | ILE | B | 139 | 24.606 | 9.609 | 13.612 | 1.00 | 19.87 |
| 6421 | O | ILE | B | 139 | 25.021 | 8.461 | 13.593 | 1.00 | 19.68 |
| 6422 | N | LEU | B | 140 | 25.397 | 10.648 | 13.393 | 1.00 | 19.88 |
| 6424 | CA | LEU | B | 140 | 26.799 | 10.451 | 13.025 | 1.00 | 20.40 |
| 6426 | CB | LEU | B | 140 | 27.452 | 11.764 | 12.620 | 1.00 | 20.25 |
| 6429 | CG | LEU | B | 140 | 27.071 | 12.298 | 11.246 | 1.00 | 20.51 |
| 6431 | CD1 | LEU | B | 140 | 27.798 | 13.593 | 11.005 | 1.00 | 23.24 |
| 6435 | CD2 | LEU | B | 140 | 27.402 | 11.299 | 10.149 | 1.00 | 21.98 |
| 6439 | C | LEU | B | 140 | 27.600 | 9.803 | 14.145 | 1.00 | 20.89 |
| 6440 | O | LEU | B | 140 | 28.572 | 9.088 | 13.876 | 1.00 | 21.00 |
| 6441 | N | SER | B | 141 | 27.211 | 10.045 | 15.396 | 1.00 | 21.26 |
| 6443 | CA | SER | B | 141 | 27.933 | 9.439 | 16.514 | 1.00 | 22.16 |
| 6445 | CB | SER | B | 141 | 27.926 | 10.329 | 17.756 | 1.00 | 21.93 |

FIGURE 3 CK

|  A   | B   | C   | D | E   | F      | G      | H      | I    | J     |
|------|-----|-----|---|-----|--------|--------|--------|------|-------|
| 6448 | OG  | SER | B | 141 | 26.615 | 10.552 | 18.225 | 1.00 | 23.99 |
| 6450 | C   | SER | B | 141 | 27.456 | 8.023  | 16.856 | 1.00 | 22.90 |
| 6451 | O   | SER | B | 141 | 28.248 | 7.250  | 17.390 | 1.00 | 22.85 |
| 6452 | N   | ASP | B | 142 | 26.203 | 7.678  | 16.538 | 1.00 | 23.91 |
| 6454 | CA  | ASP | B | 142 | 25.580 | 6.411  | 16.991 | 1.00 | 24.85 |
| 6456 | CB  | ASP | B | 142 | 24.270 | 6.674  | 17.745 | 1.00 | 25.39 |
| 6459 | CG  | ASP | B | 142 | 24.464 | 7.509  | 18.995 | 1.00 | 26.64 |
| 6460 | OD1 | ASP | B | 142 | 23.535 | 8.249  | 19.365 | 1.00 | 25.98 |
| 6461 | OD2 | ASP | B | 142 | 25.516 | 7.497  | 19.667 | 1.00 | 29.60 |
| 6462 | C   | ASP | B | 142 | 25.262 | 5.407  | 15.890 | 1.00 | 25.42 |
| 6463 | O   | ASP | B | 142 | 25.185 | 4.202  | 16.158 | 1.00 | 25.21 |
| 6464 | N   | ALA | B | 143 | 25.052 | 5.887  | 14.663 | 1.00 | 25.69 |
| 6466 | CA  | ALA | B | 143 | 24.533 | 5.031  | 13.592 | 1.00 | 26.20 |
| 6468 | CB  | ALA | B | 143 | 24.187 | 5.840  | 12.367 | 1.00 | 26.13 |
| 6472 | C   | ALA | B | 143 | 25.542 | 3.965  | 13.226 | 1.00 | 26.52 |
| 6473 | O   | ALA | B | 143 | 26.739 | 4.190  | 13.292 | 1.00 | 26.08 |
| 6474 | N   | ASP | B | 144 | 25.051 | 2.790  | 12.862 | 1.00 | 27.00 |
| 6476 | CA  | ASP | B | 144 | 25.908 | 1.760  | 12.308 | 1.00 | 27.79 |
| 6478 | CB  | ASP | B | 144 | 25.084 | 0.487  | 12.088 | 1.00 | 28.61 |
| 6481 | CG  | ASP | B | 144 | 25.935 | -0.733 | 11.853 | 1.00 | 30.23 |
| 6482 | OD1 | ASP | B | 144 | 27.147 | -0.714 | 12.160 | 1.00 | 33.26 |
| 6483 | OD2 | ASP | B | 144 | 25.452 | -1.776 | 11.358 | 1.00 | 34.68 |
| 6484 | C   | ASP | B | 144 | 26.531 | 2.247  | 10.992 | 1.00 | 27.76 |
| 6485 | O   | ASP | B | 144 | 25.825 | 2.652  | 10.050 | 1.00 | 27.93 |
| 6486 | N   | MET | B | 145 | 27.856 | 2.247  | 10.951 | 1.00 | 27.25 |
| 6488 | CA  | MET | B | 145 | 28.612 | 2.526  | 9.743  | 1.00 | 27.33 |
| 6490 | CB  | MET | B | 145 | 29.181 | 3.936  | 9.772  | 1.00 | 26.88 |
| 6493 | CG  | MET | B | 145 | 28.129 | 5.014  | 9.664  | 1.00 | 26.79 |
| 6496 | SD  | MET | B | 145 | 28.859 | 6.646  | 9.270  | 1.00 | 27.26 |
| 6497 | CE  | MET | B | 145 | 29.830 | 6.916  | 10.701 | 1.00 | 23.05 |
| 6501 | C   | MET | B | 145 | 29.737 | 1.508  | 9.657  | 1.00 | 27.62 |
| 6502 | O   | MET | B | 145 | 30.895 | 1.812  | 9.936  | 1.00 | 26.26 |
| 6503 | N   | PRO | B | 146 | 29.393 | 0.291  | 9.256  | 1.00 | 28.79 |
| 6504 | CA  | PRO | B | 146 | 30.354 | -0.815 | 9.234  | 1.00 | 29.73 |
| 6506 | CB  | PRO | B | 146 | 29.669 | -1.832 | 8.320  | 1.00 | 29.99 |
| 6509 | CG  | PRO | B | 146 | 28.228 | -1.630 | 8.593  | 1.00 | 29.30 |
| 6512 | CD  | PRO | B | 146 | 28.060 | -0.137 | 8.799  | 1.00 | 29.11 |
| 6515 | C   | PRO | B | 146 | 31.733 | -0.464 | 8.696  | 1.00 | 30.46 |
| 6516 | O   | PRO | B | 146 | 32.732 | -0.822 | 9.317  | 1.00 | 30.83 |
| 6517 | N   | GLU | B | 147 | 31.801 | 0.253  | 7.586  | 1.00 | 31.81 |
| 6519 | CA  | GLU | B | 147 | 33.089 | 0.431  | 6.905  | 1.00 | 33.36 |
| 6521 | CB  | GLU | B | 147 | 32.889 | 0.840  | 5.426  | 1.00 | 34.57 |
| 6524 | CG  | GLU | B | 147 | 31.629 | 0.304  | 4.730  | 1.00 | 37.40 |
| 6527 | CD  | GLU | B | 147 | 31.768 | 0.264  | 3.209  | 1.00 | 41.76 |
| 6528 | OE1 | GLU | B | 147 | 30.918 | -0.387 | 2.543  | 1.00 | 42.19 |
| 6529 | OE2 | GLU | B | 147 | 32.733 | 0.877  | 2.676  | 1.00 | 43.49 |
| 6530 | C   | GLU | B | 147 | 34.030 | 1.449  | 7.587  | 1.00 | 32.65 |
| 6531 | O   | GLU | B | 147 | 35.172 | 1.605  | 7.155  | 1.00 | 33.17 |
| 6532 | N   | VAL | B | 148 | 33.572 | 2.099  | 8.660  | 1.00 | 31.25 |
| 6534 | CA  | VAL | B | 148 | 34.097 | 3.410  | 9.043  | 1.00 | 30.18 |
| 6536 | CB  | VAL | B | 148 | 32.970 | 4.456  | 9.012  | 1.00 | 30.21 |
| 6538 | CG1 | VAL | B | 148 | 33.501 | 5.842  | 9.381  | 1.00 | 29.95 |

FIGURE 3 CL

| A | B | C | D | E | F | G | H | I | J |
|---|---|---|---|---|---|---|---|---|---|
| 6542 | CG2 | VAL | B | 148 | 32.310 | 4.467 | 7.634 | 1.00 | 30.63 |
| 6546 | C | VAL | B | 148 | 34.767 | 3.425 | 10.417 | 1.00 | 28.89 |
| 6547 | O | VAL | B | 148 | 34.131 | 3.174 | 11.431 | 1.00 | 27.43 |
| 6548 | N | SER | B | 149 | 36.057 | 3.755 | 10.435 | 1.00 | 28.02 |
| 6550 | CA | SER | B | 149 | 36.806 | 3.836 | 11.681 | 1.00 | 27.32 |
| 6552 | CB | SER | B | 149 | 38.302 | 4.022 | 11.413 | 1.00 | 27.23 |
| 6555 | OG | SER | B | 149 | 38.554 | 5.276 | 10.811 | 1.00 | 25.67 |
| 6557 | C | SER | B | 149 | 36.295 | 4.984 | 12.540 | 1.00 | 27.03 |
| 6558 | O | SER | B | 149 | 35.651 | 5.906 | 12.045 | 1.00 | 26.50 |
| 6559 | N | ASP | B | 150 | 36.601 | 4.899 | 13.831 | 1.00 | 26.71 |
| 6561 | CA | ASP | B | 150 | 36.236 | 5.914 | 14.810 | 1.00 | 26.65 |
| 6563 | CB | ASP | B | 150 | 36.729 | 5.509 | 16.194 | 1.00 | 26.35 |
| 6566 | CG | ASP | B | 150 | 35.776 | 4.575 | 16.906 | 1.00 | 28.03 |
| 6567 | OD1 | ASP | B | 150 | 36.086 | 4.216 | 18.054 | 1.00 | 30.17 |
| 6568 | OD2 | ASP | B | 150 | 34.692 | 4.157 | 16.424 | 1.00 | 29.62 |
| 6569 | C | ASP | B | 150 | 36.824 | 7.253 | 14.407 | 1.00 | 26.23 |
| 6570 | O | ASP | B | 150 | 36.146 | 8.269 | 14.454 | 1.00 | 25.29 |
| 6571 | N | ARG | B | 151 | 38.077 | 7.229 | 13.970 | 1.00 | 26.28 |
| 6573 | CA | ARG | B | 151 | 38.745 | 8.409 | 13.442 | 1.00 | 26.55 |
| 6575 | CB | ARG | B | 151 | 40.172 | 8.069 | 13.019 | 1.00 | 27.45 |
| 6578 | CG | ARG | B | 151 | 41.099 | 9.254 | 13.054 | 1.00 | 30.78 |
| 6581 | CD | ARG | B | 151 | 41.726 | 9.500 | 14.416 | 1.00 | 34.73 |
| 6584 | NE | ARG | B | 151 | 41.001 | 10.520 | 15.179 | 1.00 | 38.97 |
| 6586 | CZ | ARG | B | 151 | 41.152 | 11.835 | 15.043 | 1.00 | 42.64 |
| 6587 | NH1 | ARG | B | 151 | 42.000 | 12.354 | 14.148 | 1.00 | 45.06 |
| 6590 | NH2 | ARG | B | 151 | 40.435 | 12.651 | 15.801 | 1.00 | 43.15 |
| 6593 | C | ARG | B | 151 | 38.004 | 9.052 | 12.268 | 1.00 | 25.50 |
| 6594 | O | ARG | B | 151 | 37.870 | 10.265 | 12.211 | 1.00 | 25.19 |
| 6595 | N | ASP | B | 152 | 37.540 | 8.252 | 11.315 | 1.00 | 24.83 |
| 6597 | CA | ASP | B | 152 | 36.823 | 8.813 | 10.171 | 1.00 | 24.18 |
| 6599 | CB | ASP | B | 152 | 36.747 | 7.809 | 9.030 | 1.00 | 24.78 |
| 6602 | CG | ASP | B | 152 | 38.117 | 7.499 | 8.443 | 1.00 | 26.32 |
| 6603 | OD1 | ASP | B | 152 | 39.074 | 8.280 | 8.679 | 1.00 | 29.38 |
| 6604 | OD2 | ASP | B | 152 | 38.329 | 6.479 | 7.758 | 1.00 | 28.43 |
| 6605 | C | ASP | B | 152 | 35.427 | 9.290 | 10.562 | 1.00 | 22.75 |
| 6606 | O | ASP | B | 152 | 34.923 | 10.240 | 10.007 | 1.00 | 22.39 |
| 6607 | N | ARG | B | 153 | 34.810 | 8.619 | 11.521 | 1.00 | 21.86 |
| 6609 | CA | ARG | B | 153 | 33.532 | 9.053 | 12.064 | 1.00 | 20.79 |
| 6611 | CB | ARG | B | 153 | 33.022 | 8.054 | 13.088 | 1.00 | 20.74 |
| 6614 | CG | ARG | B | 153 | 31.647 | 8.375 | 13.651 | 1.00 | 20.82 |
| 6617 | CD | ARG | B | 153 | 31.205 | 7.399 | 14.704 | 1.00 | 20.94 |
| 6620 | NE | ARG | B | 153 | 30.980 | 6.045 | 14.173 | 1.00 | 22.48 |
| 6622 | CZ | ARG | B | 153 | 29.790 | 5.511 | 13.895 | 1.00 | 23.71 |
| 6623 | NH1 | ARG | B | 153 | 29.723 | 4.256 | 13.448 | 1.00 | 25.23 |
| 6626 | NH2 | ARG | B | 153 | 28.671 | 6.205 | 14.046 | 1.00 | 20.67 |
| 6629 | C | ARG | B | 153 | 33.676 | 10.426 | 12.714 | 1.00 | 20.58 |
| 6630 | O | ARG | B | 153 | 32.833 | 11.297 | 12.519 | 1.00 | 18.98 |
| 6631 | N | ILE | B | 154 | 34.752 | 10.610 | 13.483 | 1.00 | 20.29 |
| 6633 | CA | ILE | B | 154 | 35.016 | 11.891 | 14.124 | 1.00 | 20.38 |
| 6635 | CB | ILE | B | 154 | 36.209 | 11.808 | 15.090 | 1.00 | 20.21 |
| 6637 | CG1 | ILE | B | 154 | 35.848 | 10.962 | 16.319 | 1.00 | 20.02 |
| 6640 | CD1 | ILE | B | 154 | 37.077 | 10.390 | 17.035 | 1.00 | 21.78 |

FIGURE 3 CM

| A | B | C | D | E | F | G | H | I | J |
|---|---|---|---|---|---|---|---|---|---|
| 6644 | CG2 | ILE | B | 154 | 36.656 | 13.203 | 15.514 | 1.00 | 21.46 |
| 6648 | C | ILE | B | 154 | 35.247 | 12.940 | 13.051 | 1.00 | 20.53 |
| 6649 | O | ILE | B | 154 | 34.737 | 14.018 | 13.158 | 1.00 | 20.41 |
| 6650 | N | SER | B | 155 | 35.976 | 12.593 | 11.996 | 1.00 | 21.07 |
| 6652 | CA | SER | B | 155 | 36.182 | 13.485 | 10.864 | 1.00 | 21.78 |
| 6654 | CB | SER | B | 155 | 37.097 | 12.822 | 9.824 | 1.00 | 22.36 |
| 6657 | OG | SER | B | 155 | 38.452 | 13.117 | 10.107 | 1.00 | 25.91 |
| 6659 | C | SER | B | 155 | 34.867 | 13.924 | 10.186 | 1.00 | 21.46 |
| 6660 | O | SER | B | 155 | 34.771 | 15.053 | 9.711 | 1.00 | 21.56 |
| 6661 | N | MET | B | 156 | 33.886 | 13.029 | 10.125 | 1.00 | 21.47 |
| 6663 | CA | MET | B | 156 | 32.569 | 13.337 | 9.576 | 1.00 | 21.23 |
| 6665 | CB | MET | B | 156 | 31.726 | 12.079 | 9.403 | 1.00 | 21.94 |
| 6668 | CG | MET | B | 156 | 32.183 | 11.183 | 8.281 | 1.00 | 24.79 |
| 6671 | SD | MET | B | 156 | 31.189 | 9.677 | 8.224 | 1.00 | 31.73 |
| 6672 | CE | MET | B | 156 | 32.337 | 8.674 | 7.553 | 1.00 | 32.04 |
| 6676 | C | MET | B | 156 | 31.815 | 14.278 | 10.480 | 1.00 | 20.18 |
| 6677 | O | MET | B | 156 | 31.164 | 15.191 | 10.005 | 1.00 | 20.12 |
| 6678 | N | ILE | B | 157 | 31.894 | 14.045 | 11.782 | 1.00 | 20.00 |
| 6680 | CA | ILE | B | 157 | 31.238 | 14.915 | 12.744 | 1.00 | 19.69 |
| 6682 | CB | ILE | B | 157 | 31.290 | 14.326 | 14.178 | 1.00 | 19.62 |
| 6684 | CG1 | ILE | B | 157 | 30.466 | 13.047 | 14.259 | 1.00 | 19.47 |
| 6687 | CD1 | ILE | B | 157 | 30.741 | 12.182 | 15.483 | 1.00 | 21.29 |
| 6691 | CG2 | ILE | B | 157 | 30.763 | 15.332 | 15.177 | 1.00 | 18.69 |
| 6695 | C | ILE | B | 157 | 31.878 | 16.289 | 12.688 | 1.00 | 19.80 |
| 6696 | O | ILE | B | 157 | 31.182 | 17.300 | 12.684 | 1.00 | 20.00 |
| 6697 | N | SER | B | 158 | 33.204 | 16.340 | 12.640 | 1.00 | 19.73 |
| 6699 | CA | SER | B | 158 | 33.894 | 17.619 | 12.559 | 1.00 | 19.44 |
| 6701 | CB | SER | B | 158 | 35.410 | 17.419 | 12.507 | 1.00 | 19.53 |
| 6704 | OG | SER | B | 158 | 36.053 | 18.665 | 12.347 | 1.00 | 19.74 |
| 6706 | C | SER | B | 158 | 33.469 | 18.403 | 11.325 | 1.00 | 19.46 |
| 6707 | O | SER | B | 158 | 33.193 | 19.587 | 11.408 | 1.00 | 18.61 |
| 6708 | N | GLU | B | 159 | 33.429 | 17.734 | 10.181 | 1.00 | 20.02 |
| 6710 | CA | GLU | B | 159 | 33.084 | 18.384 | 8.932 | 1.00 | 20.06 |
| 6712 | CB | GLU | B | 159 | 33.224 | 17.423 | 7.757 | 1.00 | 20.49 |
| 6715 | CG | GLU | B | 159 | 32.576 | 17.922 | 6.472 | 1.00 | 21.89 |
| 6718 | CD | GLU | B | 159 | 33.103 | 19.290 | 6.041 | 1.00 | 23.61 |
| 6719 | OE1 | GLU | B | 159 | 34.281 | 19.584 | 6.322 | 1.00 | 24.99 |
| 6720 | OE2 | GLU | B | 159 | 32.347 | 20.067 | 5.426 | 1.00 | 25.28 |
| 6721 | C | GLU | B | 159 | 31.658 | 18.934 | 8.990 | 1.00 | 19.72 |
| 6722 | O | GLU | B | 159 | 31.422 | 20.062 | 8.577 | 1.00 | 19.69 |
| 6723 | N | LEU | B | 160 | 30.720 | 18.140 | 9.494 | 1.00 | 18.90 |
| 6725 | CA | LEU | B | 160 | 29.324 | 18.550 | 9.526 | 1.00 | 18.94 |
| 6727 | CB | LEU | B | 160 | 28.406 | 17.404 | 9.956 | 1.00 | 18.87 |
| 6730 | CG | LEU | B | 160 | 26.915 | 17.695 | 9.771 | 1.00 | 19.53 |
| 6732 | CD1 | LEU | B | 160 | 26.644 | 18.166 | 8.357 | 1.00 | 19.83 |
| 6736 | CD2 | LEU | B | 160 | 26.076 | 16.470 | 10.093 | 1.00 | 20.63 |
| 6740 | C | LEU | B | 160 | 29.158 | 19.736 | 10.458 | 1.00 | 18.48 |
| 6741 | O | LEU | B | 160 | 28.486 | 20.694 | 10.130 | 1.00 | 18.99 |
| 6742 | N | ALA | B | 161 | 29.803 | 19.673 | 11.612 | 1.00 | 18.69 |
| 6744 | CA | ALA | B | 161 | 29.769 | 20.773 | 12.560 | 1.00 | 18.51 |
| 6746 | CB | ALA | B | 161 | 30.446 | 20.384 | 13.872 | 1.00 | 18.21 |
| 6750 | C | ALA | B | 161 | 30.377 | 22.045 | 11.970 | 1.00 | 19.04 |

FIGURE 3 CN

| A | B | C | D | E | F | G | H | I | J |
|---|---|---|---|---|---|---|---|---|---|
| 6751 | O | ALA | B | 161 | 29.749 | 23.095 | 12.012 | 1.00 | 18.97 |
| 6752 | N | SER | B | 162 | 31.573 | 21.976 | 11.387 | 1.00 | 19.49 |
| 6754 | CA | SER | B | 162 | 32.161 | 23.190 | 10.838 | 1.00 | 19.97 |
| 6756 | CB | SER | B | 162 | 33.630 | 22.988 | 10.472 | 1.00 | 20.60 |
| 6759 | OG | SER | B | 162 | 33.756 | 21.975 | 9.518 | 1.00 | 24.18 |
| 6761 | C | SER | B | 162 | 31.348 | 23.734 | 9.643 | 1.00 | 19.40 |
| 6762 | O | SER | B | 162 | 31.186 | 24.958 | 9.482 | 1.00 | 18.70 |
| 6763 | N | ALA | B | 163 | 30.813 | 22.832 | 8.825 | 1.00 | 19.19 |
| 6765 | CA | ALA | B | 163 | 29.974 | 23.225 | 7.690 | 1.00 | 18.98 |
| 6767 | CB | ALA | B | 163 | 29.671 | 22.011 | 6.798 | 1.00 | 19.19 |
| 6771 | C | ALA | B | 163 | 28.672 | 23.907 | 8.081 | 1.00 | 18.85 |
| 6772 | O | ALA | B | 163 | 28.157 | 24.742 | 7.341 | 1.00 | 19.30 |
| 6773 | N | SER | B | 164 | 28.135 | 23.537 | 9.228 | 1.00 | 18.81 |
| 6775 | CA | SER | B | 164 | 26.788 | 23.931 | 9.638 | 1.00 | 18.52 |
| 6777 | CB | SER | B | 164 | 26.128 | 22.787 | 10.405 | 1.00 | 18.45 |
| 6780 | OG | SER | B | 164 | 26.073 | 21.610 | 9.622 | 1.00 | 18.06 |
| 6782 | C | SER | B | 164 | 26.780 | 25.159 | 10.526 | 1.00 | 18.48 |
| 6783 | O | SER | B | 164 | 25.779 | 25.828 | 10.630 | 1.00 | 18.20 |
| 6784 | N | GLY | B | 165 | 27.902 | 25.438 | 11.177 | 1.00 | 19.42 |
| 6786 | CA | GLY | B | 165 | 27.950 | 26.481 | 12.175 | 1.00 | 19.70 |
| 6789 | C | GLY | B | 165 | 28.359 | 27.810 | 11.598 | 1.00 | 20.33 |
| 6790 | O | GLY | B | 165 | 28.096 | 28.122 | 10.441 | 1.00 | 19.41 |
| 6791 | N | ILE | B | 166 | 29.018 | 28.604 | 12.424 | 1.00 | 21.45 |
| 6793 | CA | ILE | B | 166 | 29.348 | 29.976 | 12.074 | 1.00 | 22.91 |
| 6795 | CB | ILE | B | 166 | 29.846 | 30.707 | 13.354 | 1.00 | 23.50 |
| 6797 | CG1 | ILE | B | 166 | 29.737 | 32.206 | 13.173 | 1.00 | 25.77 |
| 6800 | CD1 | ILE | B | 166 | 28.314 | 32.688 | 13.353 | 1.00 | 25.49 |
| 6804 | CG2 | ILE | B | 166 | 31.229 | 30.245 | 13.727 | 1.00 | 24.89 |
| 6808 | C | ILE | B | 166 | 30.354 | 30.068 | 10.916 | 1.00 | 22.56 |
| 6809 | O | ILE | B | 166 | 30.335 | 31.016 | 10.141 | 1.00 | 22.77 |
| 6810 | N | ALA | B | 167 | 31.207 | 29.059 | 10.771 | 1.00 | 22.49 |
| 6812 | CA | ALA | B | 167 | 32.152 | 29.006 | 9.656 | 1.00 | 22.06 |
| 6814 | CB | ALA | B | 167 | 33.324 | 28.148 | 10.023 | 1.00 | 21.92 |
| 6818 | C | ALA | B | 167 | 31.490 | 28.488 | 8.383 | 1.00 | 22.04 |
| 6819 | O | ALA | B | 167 | 32.146 | 28.318 | 7.376 | 1.00 | 22.97 |
| 6820 | N | GLY | B | 168 | 30.181 | 28.252 | 8.430 | 1.00 | 21.24 |
| 6822 | CA | GLY | B | 168 | 29.464 | 27.684 | 7.313 | 1.00 | 20.53 |
| 6825 | C | GLY | B | 168 | 28.034 | 28.189 | 7.292 | 1.00 | 20.28 |
| 6826 | O | GLY | B | 168 | 27.804 | 29.394 | 7.295 | 1.00 | 19.03 |
| 6827 | N | MET | B | 169 | 27.082 | 27.265 | 7.340 | 1.00 | 20.39 |
| 6829 | CA | MET | B | 169 | 25.676 | 27.559 | 7.077 | 1.00 | 21.14 |
| 6831 | CB | MET | B | 169 | 24.855 | 26.298 | 7.278 | 1.00 | 21.40 |
| 6834 | CG | MET | B | 169 | 23.410 | 26.392 | 6.837 | 1.00 | 23.14 |
| 6837 | SD | MET | B | 169 | 22.401 | 27.153 | 8.090 | 1.00 | 26.74 |
| 6838 | CE | MET | B | 169 | 22.407 | 25.862 | 9.410 | 1.00 | 26.17 |
| 6842 | C | MET | B | 169 | 25.147 | 28.696 | 7.938 | 1.00 | 21.67 |
| 6843 | O | MET | B | 169 | 24.556 | 29.644 | 7.436 | 1.00 | 21.21 |
| 6844 | N | CYS | B | 170 | 25.367 | 28.594 | 9.239 | 1.00 | 22.13 |
| 6846 | CA | CYS | B | 170 | 24.827 | 29.556 | 10.170 | 1.00 | 22.50 |
| 6848 | CB | BCYS | B | 170 | 25.042 | 29.096 | 11.614 | 0.35 | 22.49 |
| 6849 | CB | ACYS | B | 170 | 25.010 | 29.057 | 11.596 | 0.65 | 22.96 |
| 6854 | SG | BCYS | B | 170 | 23.609 | 28.307 | 12.340 | 0.35 | 22.05 |

FIGURE 3 CO

| A | B | C | D | E | F | G | H | I | J |
|---|---|---|---|---|---|---|---|---|---|
| 6855 | SG | ACYS | B | 170 | 24.028 | 29.996 | 12.749 | 0.65 | 25.42 |
| 6856 | C | CYS | B | 170 | 25.460 | 30.935 | 9.997 | 1.00 | 21.94 |
| 6857 | O | CYS | B | 170 | 24.775 | 31.934 | 10.105 | 1.00 | 22.08 |
| 6858 | N | GLY | B | 171 | 26.767 | 30.980 | 9.758 | 1.00 | 21.27 |
| 6860 | CA | GLY | B | 171 | 27.453 | 32.231 | 9.504 | 1.00 | 21.35 |
| 6863 | C | GLY | B | 171 | 26.951 | 32.858 | 8.218 | 1.00 | 20.97 |
| 6864 | O | GLY | B | 171 | 26.839 | 34.081 | 8.111 | 1.00 | 20.81 |
| 6865 | N | GLY | B | 172 | 26.643 | 32.009 | 7.249 | 1.00 | 20.08 |
| 6867 | CA | GLY | B | 172 | 26.027 | 32.440 | 6.009 | 1.00 | 19.62 |
| 6870 | C | GLY | B | 172 | 24.641 | 33.007 | 6.215 | 1.00 | 19.25 |
| 6871 | O | GLY | B | 172 | 24.288 | 34.011 | 5.605 | 1.00 | 18.27 |
| 6872 | N | GLN | B | 173 | 23.858 | 32.380 | 7.084 | 1.00 | 18.75 |
| 6874 | CA | GLN | B | 173 | 22.535 | 32.890 | 7.404 | 1.00 | 19.22 |
| 6876 | CB | GLN | B | 173 | 21.787 | 31.947 | 8.348 | 1.00 | 19.67 |
| 6879 | CG | GLN | B | 173 | 21.349 | 30.652 | 7.682 | 1.00 | 20.18 |
| 6882 | CD | GLN | B | 173 | 20.333 | 30.899 | 6.597 | 1.00 | 20.92 |
| 6883 | OE1 | GLN | B | 173 | 20.701 | 31.297 | 5.496 | 1.00 | 21.77 |
| 6884 | NE2 | GLN | B | 173 | 19.047 | 30.712 | 6.914 | 1.00 | 19.90 |
| 6887 | C | GLN | B | 173 | 22.632 | 34.281 | 8.002 | 1.00 | 19.31 |
| 6888 | O | GLN | B | 173 | 21.805 | 35.146 | 7.691 | 1.00 | 18.98 |
| 6889 | N | ALA | B | 174 | 23.667 | 34.503 | 8.810 | 1.00 | 19.26 |
| 6891 | CA | ALA | B | 174 | 23.894 | 35.813 | 9.437 | 1.00 | 20.09 |
| 6893 | CB | ALA | B | 174 | 24.956 | 35.725 | 10.526 | 1.00 | 19.57 |
| 6897 | C | ALA | B | 174 | 24.292 | 36.845 | 8.387 | 1.00 | 20.47 |
| 6898 | O | ALA | B | 174 | 23.826 | 37.969 | 8.440 | 1.00 | 21.60 |
| 6899 | N | LEU | B | 175 | 25.143 | 36.464 | 7.436 | 1.00 | 21.00 |
| 6901 | CA | LEU | B | 175 | 25.561 | 37.384 | 6.371 | 1.00 | 21.21 |
| 6903 | CB | LEU | B | 175 | 26.646 | 36.753 | 5.497 | 1.00 | 21.41 |
| 6906 | CG | LEU | B | 175 | 28.026 | 36.557 | 6.121 | 1.00 | 23.45 |
| 6908 | CD1 | LEU | B | 175 | 28.948 | 35.855 | 5.138 | 1.00 | 24.47 |
| 6912 | CD2 | LEU | B | 175 | 28.630 | 37.913 | 6.562 | 1.00 | 24.78 |
| 6916 | C | LEU | B | 175 | 24.358 | 37.776 | 5.519 | 1.00 | 21.36 |
| 6917 | O | LEU | B | 175 | 24.210 | 38.942 | 5.118 | 1.00 | 20.88 |
| 6918 | N | ASP | B | 176 | 23.498 | 36.794 | 5.258 | 1.00 | 21.82 |
| 6920 | CA | ASP | B | 176 | 22.291 | 36.980 | 4.466 | 1.00 | 22.30 |
| 6922 | CB | ASP | B | 176 | 21.615 | 35.625 | 4.252 | 1.00 | 22.47 |
| 6925 | CG | ASP | B | 176 | 20.205 | 35.739 | 3.779 | 1.00 | 21.57 |
| 6926 | OD1 | ASP | B | 176 | 19.938 | 35.449 | 2.588 | 1.00 | 22.94 |
| 6927 | OD2 | ASP | B | 176 | 19.281 | 36.072 | 4.540 | 1.00 | 25.04 |
| 6928 | C | ASP | B | 176 | 21.356 | 37.989 | 5.138 | 1.00 | 23.38 |
| 6929 | O | ASP | B | 176 | 20.856 | 38.927 | 4.499 | 1.00 | 23.61 |
| 6930 | N | LEU | B | 177 | 21.131 | 37.814 | 6.429 | 1.00 | 24.61 |
| 6932 | CA | LEU | B | 177 | 20.296 | 38.751 | 7.181 | 1.00 | 26.08 |
| 6934 | CB | LEU | B | 177 | 20.112 | 38.267 | 8.621 | 1.00 | 26.86 |
| 6937 | CG | LEU | B | 177 | 18.842 | 37.475 | 8.968 | 1.00 | 28.65 |
| 6939 | CD1 | LEU | B | 177 | 18.029 | 36.990 | 7.768 | 1.00 | 30.94 |
| 6943 | CD2 | LEU | B | 177 | 19.243 | 36.330 | 9.825 | 1.00 | 29.29 |
| 6947 | C | LEU | B | 177 | 20.891 | 40.147 | 7.193 | 1.00 | 26.38 |
| 6948 | O | LEU | B | 177 | 20.176 | 41.134 | 7.048 | 1.00 | 27.18 |
| 6949 | N | ASP | B | 178 | 22.203 | 40.228 | 7.355 | 1.00 | 27.07 |
| 6951 | CA | ASP | B | 178 | 22.893 | 41.513 | 7.389 | 1.00 | 27.97 |
| 6953 | CB | ASP | B | 178 | 24.336 | 41.337 | 7.864 | 1.00 | 28.49 |

FIGURE 3 CP

| A | B | C | D | E | F | G | H | I | J |
|---|---|---|---|---|---|---|---|---|---|
| 6956 | CG | ASP | B | 178 | 24.926 | 42.624 | 8.427 | 1.00 | 31.55 |
| 6957 | OD1 | ASP | B | 178 | 25.937 | 43.106 | 7.874 | 1.00 | 34.43 |
| 6958 | OD2 | ASP | B | 178 | 24.447 | 43.218 | 9.419 | 1.00 | 36.43 |
| 6959 | C | ASP | B | 178 | 22.865 | 42.228 | 6.034 | 1.00 | 27.98 |
| 6960 | O | ASP | B | 178 | 22.853 | 43.454 | 5.993 | 1.00 | 27.47 |
| 6961 | N | ALA | B | 179 | 22.828 | 41.462 | 4.936 | 1.00 | 27.64 |
| 6963 | CA | ALA | B | 179 | 22.818 | 42.026 | 3.576 | 1.00 | 27.64 |
| 6965 | CB | ALA | B | 179 | 23.397 | 41.024 | 2.579 | 1.00 | 27.26 |
| 6969 | C | ALA | B | 179 | 21.415 | 42.474 | 3.118 | 1.00 | 27.90 |
| 6970 | O | ALA | B | 179 | 21.288 | 43.142 | 2.109 | 1.00 | 27.38 |
| 6971 | N | GLU | B | 180 | 20.374 | 42.097 | 3.852 | 1.00 | 28.50 |
| 6973 | CA | GLU | B | 180 | 19.006 | 42.515 | 3.535 | 1.00 | 29.13 |
| 6975 | CB | GLU | B | 180 | 18.031 | 42.069 | 4.629 | 1.00 | 29.71 |
| 6978 | CG | GLU | B | 180 | 17.071 | 40.969 | 4.234 | 1.00 | 31.66 |
| 6981 | CD | GLU | B | 180 | 16.175 | 40.534 | 5.384 | 1.00 | 33.14 |
| 6982 | OE1 | GLU | B | 180 | 15.509 | 41.400 | 5.995 | 1.00 | 35.30 |
| 6983 | OE2 | GLU | B | 180 | 16.149 | 39.324 | 5.684 | 1.00 | 32.62 |
| 6984 | C | GLU | B | 180 | 18.922 | 44.041 | 3.418 | 1.00 | 29.49 |
| 6985 | O | GLU | B | 180 | 19.290 | 44.755 | 4.348 | 1.00 | 28.60 |
| 6986 | N | GLY | B | 181 | 18.454 | 44.518 | 2.264 | 1.00 | 29.61 |
| 6988 | CA | GLY | B | 181 | 18.279 | 45.935 | 1.997 | 1.00 | 29.83 |
| 6991 | C | GLY | B | 181 | 19.560 | 46.670 | 1.658 | 1.00 | 30.04 |
| 6992 | O | GLY | B | 181 | 19.532 | 47.871 | 1.420 | 1.00 | 30.48 |
| 6993 | N | LYS | B | 182 | 20.681 | 45.954 | 1.622 | 1.00 | 30.21 |
| 6995 | CA | LYS | B | 182 | 21.992 | 46.573 | 1.506 | 1.00 | 30.46 |
| 6997 | CB | LYS | B | 182 | 22.959 | 45.982 | 2.526 | 1.00 | 30.97 |
| 7000 | CG | LYS | B | 182 | 22.593 | 46.287 | 3.973 | 1.00 | 32.58 |
| 7003 | CD | LYS | B | 182 | 23.830 | 46.343 | 4.864 | 1.00 | 34.32 |
| 7006 | CE | LYS | B | 182 | 23.490 | 46.882 | 6.259 | 1.00 | 35.98 |
| 7009 | NZ | LYS | B | 182 | 23.339 | 45.804 | 7.290 | 1.00 | 36.88 |
| 7013 | C | LYS | B | 182 | 22.573 | 46.427 | 0.116 | 1.00 | 30.22 |
| 7014 | O | LYS | B | 182 | 23.559 | 47.083 | -0.203 | 1.00 | 30.23 |
| 7015 | N | HIS | B | 183 | 21.984 | 45.555 | -0.700 | 1.00 | 29.28 |
| 7017 | CA | HIS | B | 183 | 22.375 | 45.441 | -2.093 | 1.00 | 29.34 |
| 7019 | CB | HIS | B | 183 | 21.892 | 46.684 | -2.856 | 1.00 | 29.70 |
| 7022 | CG | HIS | B | 183 | 20.410 | 46.833 | -2.832 | 1.00 | 30.08 |
| 7023 | ND1 | HIS | B | 183 | 19.699 | 47.003 | -1.668 | 1.00 | 32.28 |
| 7025 | CE1 | HIS | B | 183 | 18.412 | 47.068 | -1.942 | 1.00 | 31.16 |
| 7027 | NE2 | HIS | B | 183 | 18.261 | 46.940 | -3.244 | 1.00 | 32.50 |
| 7029 | CD2 | HIS | B | 183 | 19.497 | 46.782 | -3.821 | 1.00 | 32.70 |
| 7031 | C | HIS | B | 183 | 23.887 | 45.297 | -2.191 | 1.00 | 28.93 |
| 7032 | O | HIS | B | 183 | 24.558 | 46.097 | -2.847 | 1.00 | 29.19 |
| 7033 | N | VAL | B | 184 | 24.415 | 44.274 | -1.522 | 1.00 | 27.85 |
| 7035 | CA | VAL | B | 184 | 25.850 | 44.103 | -1.417 | 1.00 | 27.29 |
| 7037 | CB | VAL | B | 184 | 26.247 | 43.065 | -0.319 | 1.00 | 27.33 |
| 7039 | CG1 | VAL | B | 184 | 25.636 | 43.452 | 1.052 | 1.00 | 27.10 |
| 7043 | CG2 | VAL | B | 184 | 25.860 | 41.634 | -0.722 | 1.00 | 27.05 |
| 7047 | C | VAL | B | 184 | 26.419 | 43.723 | -2.779 | 1.00 | 26.86 |
| 7048 | O | VAL | B | 184 | 25.733 | 43.075 | -3.577 | 1.00 | 26.12 |
| 7049 | N | PRO | B | 185 | 27.663 | 44.126 | -3.051 | 1.00 | 26.31 |
| 7050 | CA | PRO | B | 185 | 28.314 | 43.792 | -4.319 | 1.00 | 26.16 |
| 7052 | CB | PRO | B | 185 | 29.596 | 44.623 | -4.284 | 1.00 | 26.24 |

FIGURE 3 CQ

| A | B | C | D | E | F | G | H | I | J |
|---|---|---|---|---|---|---|---|---|---|
| 7055 | CG | PRO | B | 185 | 29.892 | 44.801 | -2.835 | 1.00 | 26.65 |
| 7058 | CD | PRO | B | 185 | 28.552 | 44.905 | -2.168 | 1.00 | 26.81 |
| 7061 | C | PRO | B | 185 | 28.646 | 42.297 | -4.436 | 1.00 | 25.85 |
| 7062 | O | PRO | B | 185 | 28.521 | 41.553 | -3.475 | 1.00 | 24.67 |
| 7063 | N | LEU | B | 186 | 29.106 | 41.908 | -5.616 | 1.00 | 26.22 |
| 7065 | CA | LEU | B | 186 | 29.284 | 40.509 | -6.002 | 1.00 | 26.42 |
| 7067 | CB | LEU | B | 186 | 29.859 | 40.422 | -7.424 | 1.00 | 26.65 |
| 7070 | CG | LEU | B | 186 | 29.462 | 39.279 | -8.371 | 1.00 | 28.07 |
| 7072 | CD1 | LEU | B | 186 | 30.565 | 39.033 | -9.399 | 1.00 | 29.61 |
| 7076 | CD2 | LEU | B | 186 | 29.105 | 38.004 | -7.671 | 1.00 | 28.33 |
| 7080 | C | LEU | B | 186 | 30.183 | 39.726 | -5.048 | 1.00 | 26.27 |
| 7081 | O | LEU | B | 186 | 29.890 | 38.580 | -4.737 | 1.00 | 25.80 |
| 7082 | N | ASP | B | 187 | 31.286 | 40.317 | -4.590 | 1.00 | 26.90 |
| 7084 | CA | ASP | B | 187 | 32.198 | 39.558 | -3.721 | 1.00 | 27.11 |
| 7086 | CB | ASP | B | 187 | 33.567 | 40.236 | -3.526 | 1.00 | 27.85 |
| 7089 | CG | ASP | B | 187 | 33.480 | 41.648 | -2.951 | 1.00 | 30.82 |
| 7090 | OD1 | ASP | B | 187 | 34.555 | 42.173 | -2.574 | 1.00 | 36.51 |
| 7091 | OD2 | ASP | B | 187 | 32.435 | 42.331 | -2.848 | 1.00 | 35.53 |
| 7092 | C | ASP | B | 187 | 31.554 | 39.180 | -2.380 | 1.00 | 26.24 |
| 7093 | O | ASP | B | 187 | 31.729 | 38.053 | -1.900 | 1.00 | 25.65 |
| 7094 | N | ALA | B | 188 | 30.809 | 40.117 | -1.799 | 1.00 | 25.42 |
| 7096 | CA | ALA | B | 188 | 30.097 | 39.892 | -0.548 | 1.00 | 24.85 |
| 7098 | CB | ALA | B | 188 | 29.610 | 41.221 | 0.019 | 1.00 | 24.84 |
| 7102 | C | ALA | B | 188 | 28.915 | 38.951 | -0.774 | 1.00 | 24.38 |
| 7103 | O | ALA | B | 188 | 28.578 | 38.154 | 0.081 | 1.00 | 24.14 |
| 7104 | N | LEU | B | 189 | 28.291 | 39.059 | -1.942 | 1.00 | 24.33 |
| 7106 | CA | LEU | B | 189 | 27.156 | 38.230 | -2.286 | 1.00 | 24.42 |
| 7108 | CB | LEU | B | 189 | 26.530 | 38.741 | -3.577 | 1.00 | 24.99 |
| 7111 | CG | LEU | B | 189 | 25.509 | 37.865 | -4.268 | 1.00 | 25.94 |
| 7113 | CD1 | LEU | B | 189 | 24.317 | 37.593 | -3.350 | 1.00 | 26.65 |
| 7117 | CD2 | LEU | B | 189 | 25.072 | 38.566 | -5.566 | 1.00 | 26.30 |
| 7121 | C | LEU | B | 189 | 27.607 | 36.783 | -2.435 | 1.00 | 23.85 |
| 7122 | O | LEU | B | 189 | 26.965 | 35.863 | -1.918 | 1.00 | 23.56 |
| 7123 | N | GLU | B | 190 | 28.727 | 36.590 | -3.115 | 1.00 | 23.22 |
| 7125 | CA | GLU | B | 190 | 29.301 | 35.269 | -3.280 | 1.00 | 23.29 |
| 7127 | CB | GLU | B | 190 | 30.566 | 35.331 | -4.135 | 1.00 | 23.75 |
| 7130 | CG | GLU | B | 190 | 31.070 | 33.963 | -4.535 | 1.00 | 25.63 |
| 7133 | CD | GLU | B | 190 | 32.356 | 33.994 | -5.339 | 1.00 | 28.46 |
| 7134 | OE1 | GLU | B | 190 | 33.201 | 33.121 | -5.090 | 1.00 | 31.64 |
| 7135 | OE2 | GLU | B | 190 | 32.522 | 34.854 | -6.226 | 1.00 | 32.12 |
| 7136 | C | GLU | B | 190 | 29.625 | 34.655 | -1.917 | 1.00 | 22.85 |
| 7137 | O | GLU | B | 190 | 29.434 | 33.459 | -1.699 | 1.00 | 20.62 |
| 7138 | N | ARG | B | 191 | 30.114 | 35.490 | -1.009 | 1.00 | 22.57 |
| 7140 | CA | ARG | B | 191 | 30.499 | 35.041 | 0.315 | 1.00 | 22.97 |
| 7142 | CB | ARG | B | 191 | 31.169 | 36.171 | 1.077 | 1.00 | 23.59 |
| 7145 | CG | ARG | B | 191 | 31.646 | 35.789 | 2.444 | 1.00 | 26.56 |
| 7148 | CD | ARG | B | 191 | 32.707 | 36.714 | 3.004 | 1.00 | 31.42 |
| 7151 | NE | ARG | B | 191 | 32.158 | 37.666 | 3.962 | 1.00 | 35.82 |
| 7153 | CZ | ARG | B | 191 | 32.874 | 38.304 | 4.891 | 1.00 | 38.83 |
| 7154 | NH1 | ARG | B | 191 | 34.184 | 38.105 | 5.012 | 1.00 | 39.90 |
| 7157 | NH2 | ARG | B | 191 | 32.270 | 39.150 | 5.712 | 1.00 | 40.92 |
| 7160 | C | ARG | B | 191 | 29.282 | 34.546 | 1.087 | 1.00 | 21.94 |

FIGURE 3 CR

| A | B | C | D | E | F | G | H | I | J |
|---|---|---|---|---|---|---|---|---|---|
| 7161 | O | ARG | B | 191 | 29.357 | 33.536 | 1.770 | 1.00 | 22.24 |
| 7162 | N | ILE | B | 192 | 28.160 | 35.246 | 0.947 | 1.00 | 21.11 |
| 7164 | CA | ILE | B | 192 | 26.916 | 34.836 | 1.574 | 1.00 | 19.99 |
| 7166 | CB | ILE | B | 192 | 25.763 | 35.775 | 1.186 | 1.00 | 19.92 |
| 7168 | CG1 | ILE | B | 192 | 25.925 | 37.151 | 1.835 | 1.00 | 20.88 |
| 7171 | CD1 | ILE | B | 192 | 25.092 | 38.196 | 1.195 | 1.00 | 21.97 |
| 7175 | CG2 | ILE | B | 192 | 24.408 | 35.196 | 1.598 | 1.00 | 19.49 |
| 7179 | C | ILE | B | 192 | 26.589 | 33.421 | 1.107 | 1.00 | 19.95 |
| 7180 | O | ILE | B | 192 | 26.387 | 32.538 | 1.914 | 1.00 | 19.48 |
| 7181 | N | HIS | B | 193 | 26.542 | 33.231 | -0.207 | 1.00 | 19.56 |
| 7183 | CA | HIS | B | 193 | 26.027 | 31.999 | -0.802 | 1.00 | 18.94 |
| 7185 | CB | HIS | B | 193 | 25.801 | 32.209 | -2.298 | 1.00 | 19.11 |
| 7188 | CG | HIS | B | 193 | 24.584 | 33.024 | -2.606 | 1.00 | 17.67 |
| 7189 | ND1 | HIS | B | 193 | 23.920 | 33.755 | -1.647 | 1.00 | 19.83 |
| 7191 | CE1 | HIS | B | 193 | 22.873 | 34.349 | -2.191 | 1.00 | 19.06 |
| 7193 | NE2 | HIS | B | 193 | 22.821 | 34.013 | -3.467 | 1.00 | 19.16 |
| 7195 | CD2 | HIS | B | 193 | 23.882 | 33.186 | -3.754 | 1.00 | 19.39 |
| 7197 | C | HIS | B | 193 | 26.913 | 30.802 | -0.543 | 1.00 | 18.45 |
| 7198 | O | HIS | B | 193 | 26.422 | 29.700 | -0.294 | 1.00 | 18.16 |
| 7199 | N | ARG | B | 194 | 28.221 | 31.017 | -0.579 | 1.00 | 18.21 |
| 7201 | CA | ARG | B | 194 | 29.157 | 29.954 | -0.301 | 1.00 | 18.14 |
| 7203 | CB | ARG | B | 194 | 30.582 | 30.396 | -0.588 | 1.00 | 18.28 |
| 7206 | CG | ARG | B | 194 | 30.894 | 30.549 | -2.059 | 1.00 | 18.14 |
| 7209 | CD | ARG | B | 194 | 32.368 | 30.534 | -2.332 | 1.00 | 19.86 |
| 7212 | NE | ARG | B | 194 | 32.685 | 30.696 | -3.740 | 1.00 | 20.51 |
| 7214 | CZ | ARG | B | 194 | 32.656 | 29.723 | -4.648 | 1.00 | 23.08 |
| 7215 | NH1 | ARG | B | 194 | 32.326 | 28.482 | -4.320 | 1.00 | 24.68 |
| 7218 | NH2 | ARG | B | 194 | 32.981 | 29.995 | -5.900 | 1.00 | 25.18 |
| 7221 | C | ARG | B | 194 | 29.003 | 29.465 | 1.143 | 1.00 | 18.28 |
| 7222 | O | ARG | B | 194 | 29.037 | 28.267 | 1.392 | 1.00 | 18.15 |
| 7223 | N | HIS | B | 195 | 28.782 | 30.390 | 2.079 | 1.00 | 18.49 |
| 7225 | CA | HIS | B | 195 | 28.558 | 30.036 | 3.479 | 1.00 | 18.76 |
| 7227 | CB | HIS | B | 195 | 28.786 | 31.251 | 4.390 | 1.00 | 18.80 |
| 7230 | CG | HIS | B | 195 | 30.224 | 31.612 | 4.533 | 1.00 | 19.89 |
| 7231 | ND1 | HIS | B | 195 | 30.934 | 32.241 | 3.533 | 1.00 | 21.51 |
| 7233 | CE1 | HIS | B | 195 | 32.186 | 32.408 | 3.925 | 1.00 | 21.57 |
| 7235 | NE2 | HIS | B | 195 | 32.311 | 31.910 | 5.142 | 1.00 | 21.37 |
| 7237 | CD2 | HIS | B | 195 | 31.103 | 31.395 | 5.541 | 1.00 | 21.40 |
| 7239 | C | HIS | B | 195 | 27.170 | 29.430 | 3.697 | 1.00 | 18.88 |
| 7240 | O | HIS | B | 195 | 27.050 | 28.298 | 4.182 | 1.00 | 19.41 |
| 7241 | N | LYS | B | 196 | 26.117 | 30.122 | 3.293 | 1.00 | 18.32 |
| 7243 | CA | LYS | B | 196 | 24.778 | 29.672 | 3.686 | 1.00 | 18.29 |
| 7245 | CB | LYS | B | 196 | 23.725 | 30.764 | 3.506 | 1.00 | 18.11 |
| 7248 | CG | LYS | B | 196 | 23.241 | 31.027 | 2.080 | 1.00 | 17.45 |
| 7251 | CD | LYS | B | 196 | 22.081 | 32.049 | 2.131 | 1.00 | 17.15 |
| 7254 | CE | LYS | B | 196 | 21.634 | 32.547 | 0.768 | 1.00 | 15.61 |
| 7257 | NZ | LYS | B | 196 | 20.235 | 33.122 | 0.794 | 1.00 | 15.01 |
| 7261 | C | LYS | B | 196 | 24.322 | 28.389 | 3.006 | 1.00 | 18.44 |
| 7262 | O | LYS | B | 196 | 23.466 | 27.688 | 3.541 | 1.00 | 18.43 |
| 7263 | N | THR | B | 197 | 24.898 | 28.098 | 1.841 | 1.00 | 17.92 |
| 7265 | CA | THR | B | 197 | 24.454 | 27.009 | 0.983 | 1.00 | 18.22 |
| 7267 | CB | THR | B | 197 | 23.686 | 27.598 | -0.203 | 1.00 | 17.81 |

FIGURE 3 CS

| A | B | C | D | E | F | G | H | I | J |
|---|---|---|---|---|---|---|---|---|---|
| 7269 | OG1 | THR | B | 197 | 22.429 | 28.070 | 0.261 | 1.00 | 18.26 |
| 7271 | CG2 | THR | B | 197 | 23.322 | 26.539 | -1.246 | 1.00 | 18.58 |
| 7275 | C | THR | B | 197 | 25.601 | 26.129 | 0.504 | 1.00 | 17.84 |
| 7276 | O | THR | B | 197 | 25.482 | 24.907 | 0.475 | 1.00 | 18.55 |
| 7277 | N | GLY | B | 198 | 26.703 | 26.746 | 0.104 | 1.00 | 17.60 |
| 7279 | CA | GLY | B | 198 | 27.854 | 26.006 | -0.358 | 1.00 | 17.04 |
| 7282 | C | GLY | B | 198 | 28.469 | 25.112 | 0.708 | 1.00 | 16.72 |
| 7283 | O | GLY | B | 198 | 28.863 | 23.993 | 0.415 | 1.00 | 15.65 |
| 7284 | N | ALA | B | 199 | 28.523 | 25.581 | 1.951 | 1.00 | 16.19 |
| 7286 | CA | ALA | B | 199 | 29.239 | 24.837 | 2.993 | 1.00 | 16.23 |
| 7288 | CB | ALA | B | 199 | 29.265 | 25.611 | 4.271 | 1.00 | 16.00 |
| 7292 | C | ALA | B | 199 | 28.633 | 23.441 | 3.200 | 1.00 | 16.09 |
| 7293 | O | ALA | B | 199 | 29.357 | 22.445 | 3.312 | 1.00 | 16.00 |
| 7294 | N | LEU | B | 200 | 27.309 | 23.363 | 3.200 | 1.00 | 15.80 |
| 7296 | CA | LEU | B | 200 | 26.623 | 22.126 | 3.536 | 1.00 | 16.20 |
| 7298 | CB | LEU | B | 200 | 25.202 | 22.408 | 4.018 | 1.00 | 16.05 |
| 7301 | CG | LEU | B | 200 | 24.363 | 21.238 | 4.540 | 1.00 | 18.16 |
| 7303 | CD1 | LEU | B | 200 | 25.019 | 20.573 | 5.727 | 1.00 | 18.85 |
| 7307 | CD2 | LEU | B | 200 | 22.989 | 21.735 | 4.928 | 1.00 | 18.03 |
| 7311 | C | LEU | B | 200 | 26.593 | 21.206 | 2.332 | 1.00 | 16.19 |
| 7312 | O | LEU | B | 200 | 26.544 | 19.993 | 2.479 | 1.00 | 15.79 |
| 7313 | N | ILE | B | 201 | 26.615 | 21.769 | 1.136 | 1.00 | 16.74 |
| 7315 | CA | ILE | B | 201 | 26.723 | 20.928 | -0.052 | 1.00 | 17.10 |
| 7317 | CB | ILE | B | 201 | 26.341 | 21.713 | -1.305 | 1.00 | 17.41 |
| 7319 | CG1 | ILE | B | 201 | 24.806 | 21.764 | -1.403 | 1.00 | 18.09 |
| 7322 | CD1 | ILE | B | 201 | 24.283 | 22.985 | -2.120 | 1.00 | 19.65 |
| 7326 | CG2 | ILE | B | 201 | 26.936 | 21.073 | -2.581 | 1.00 | 16.41 |
| 7330 | C | ILE | B | 201 | 28.130 | 20.312 | -0.110 | 1.00 | 17.27 |
| 7331 | O | ILE | B | 201 | 28.289 | 19.126 | -0.436 | 1.00 | 16.47 |
| 7332 | N | ARG | B | 202 | 29.139 | 21.098 | 0.240 | 1.00 | 17.03 |
| 7334 | CA | ARG | B | 202 | 30.468 | 20.539 | 0.389 | 1.00 | 17.33 |
| 7336 | CB | ARG | B | 202 | 31.516 | 21.598 | 0.645 | 1.00 | 17.65 |
| 7339 | CG | ARG | B | 202 | 32.956 | 20.997 | 0.625 | 1.00 | 18.08 |
| 7342 | CD | ARG | B | 202 | 34.038 | 22.029 | 0.637 | 1.00 | 19.46 |
| 7345 | NE | ARG | B | 202 | 33.985 | 22.829 | 1.854 | 1.00 | 21.33 |
| 7347 | CZ | ARG | B | 202 | 34.772 | 23.882 | 2.089 | 1.00 | 22.51 |
| 7348 | NH1 | ARG | B | 202 | 34.662 | 24.547 | 3.222 | 1.00 | 23.90 |
| 7351 | NH2 | ARG | B | 202 | 35.663 | 24.271 | 1.199 | 1.00 | 21.54 |
| 7354 | C | ARG | B | 202 | 30.517 | 19.475 | 1.475 | 1.00 | 17.44 |
| 7355 | O | ARG | B | 202 | 31.179 | 18.451 | 1.295 | 1.00 | 17.53 |
| 7356 | N | ALA | B | 203 | 29.804 | 19.689 | 2.580 | 1.00 | 17.13 |
| 7358 | CA | ALA | B | 203 | 29.776 | 18.709 | 3.658 | 1.00 | 16.93 |
| 7360 | CB | ALA | B | 203 | 28.967 | 19.200 | 4.832 | 1.00 | 17.56 |
| 7364 | C | ALA | B | 203 | 29.211 | 17.389 | 3.179 | 1.00 | 17.03 |
| 7365 | O | ALA | B | 203 | 29.704 | 16.351 | 3.574 | 1.00 | 15.70 |
| 7366 | N | ALA | B | 204 | 28.154 | 17.439 | 2.368 | 1.00 | 16.79 |
| 7368 | CA | ALA | B | 204 | 27.548 | 16.224 | 1.799 | 1.00 | 17.41 |
| 7370 | CB | ALA | B | 204 | 26.386 | 16.572 | 0.915 | 1.00 | 17.51 |
| 7374 | C | ALA | B | 204 | 28.560 | 15.419 | 1.002 | 1.00 | 17.70 |
| 7375 | O | ALA | B | 204 | 28.698 | 14.197 | 1.200 | 1.00 | 17.88 |
| 7376 | N | VAL | B | 205 | 29.268 | 16.107 | 0.109 | 1.00 | 17.07 |
| 7378 | CA | VAL | B | 205 | 30.282 | 15.471 | -0.724 | 1.00 | 17.54 |

FIGURE 3 CT

| A | B | C | D | E | F | G | H | I | J |
|---|---|---|---|---|---|---|---|---|---|
| 7380 | CB | VAL | B | 205 | 30.849 | 16.429 | -1.793 | 1.00 | 17.01 |
| 7382 | CG1 | VAL | B | 205 | 31.962 | 15.769 | -2.607 | 1.00 | 17.61 |
| 7386 | CG2 | VAL | B | 205 | 29.750 | 16.884 | -2.730 | 1.00 | 17.80 |
| 7390 | C | VAL | B | 205 | 31.400 | 14.924 | 0.150 | 1.00 | 18.04 |
| 7391 | O | VAL | B | 205 | 31.802 | 13.766 | -0.005 | 1.00 | 17.71 |
| 7392 | N | ARG | B | 206 | 31.887 | 15.748 | 1.078 | 1.00 | 18.26 |
| 7394 | CA | ARG | B | 206 | 32.974 | 15.348 | 1.963 | 1.00 | 18.54 |
| 7396 | CB | ARG | B | 206 | 33.393 | 16.497 | 2.878 | 1.00 | 19.04 |
| 7399 | CG | ARG | B | 206 | 34.211 | 17.532 | 2.179 | 1.00 | 18.96 |
| 7402 | CD | ARG | B | 206 | 34.665 | 18.637 | 3.113 | 1.00 | 20.46 |
| 7405 | NE | ARG | B | 206 | 35.712 | 19.448 | 2.531 | 1.00 | 20.99 |
| 7407 | CZ | ARG | B | 206 | 36.218 | 20.545 | 3.102 | 1.00 | 21.01 |
| 7408 | NH1 | ARG | B | 206 | 35.771 | 20.974 | 4.275 | 1.00 | 20.38 |
| 7411 | NH2 | ARG | B | 206 | 37.190 | 21.204 | 2.495 | 1.00 | 20.62 |
| 7414 | C | ARG | B | 206 | 32.582 | 14.152 | 2.795 | 1.00 | 18.87 |
| 7415 | O | ARG | B | 206 | 33.368 | 13.219 | 2.935 | 1.00 | 18.67 |
| 7416 | N | LEU | B | 207 | 31.346 | 14.136 | 3.289 | 1.00 | 19.33 |
| 7418 | CA | LEU | B | 207 | 30.896 | 13.036 | 4.141 | 1.00 | 20.12 |
| 7420 | CB | LEU | B | 207 | 29.516 | 13.310 | 4.738 | 1.00 | 19.99 |
| 7423 | CG | LEU | B | 207 | 29.431 | 13.776 | 6.203 | 1.00 | 22.44 |
| 7425 | CD1 | LEU | B | 207 | 30.464 | 14.770 | 6.559 | 1.00 | 24.69 |
| 7429 | CD2 | LEU | B | 207 | 28.046 | 14.364 | 6.440 | 1.00 | 24.61 |
| 7433 | C | LEU | B | 207 | 30.887 | 11.715 | 3.370 | 1.00 | 20.21 |
| 7434 | O | LEU | B | 207 | 31.247 | 10.668 | 3.922 | 1.00 | 20.74 |
| 7435 | N | GLY | B | 208 | 30.461 | 11.750 | 2.110 | 1.00 | 20.90 |
| 7437 | CA | GLY | B | 208 | 30.546 | 10.578 | 1.246 | 1.00 | 21.11 |
| 7440 | C | GLY | B | 208 | 31.979 | 10.097 | 1.066 | 1.00 | 21.83 |
| 7441 | O | GLY | B | 208 | 32.263 | 8.898 | 1.152 | 1.00 | 22.91 |
| 7442 | N | ALA | B | 209 | 32.892 | 11.029 | 0.821 | 1.00 | 21.98 |
| 7444 | CA | ALA | B | 209 | 34.292 | 10.688 | 0.627 | 1.00 | 22.48 |
| 7446 | CB | ALA | B | 209 | 35.059 | 11.868 | 0.052 | 1.00 | 22.44 |
| 7450 | C | ALA | B | 209 | 34.934 | 10.189 | 1.928 | 1.00 | 23.19 |
| 7451 | O | ALA | B | 209 | 35.703 | 9.232 | 1.906 | 1.00 | 23.21 |
| 7452 | N | LEU | B | 210 | 34.582 | 10.804 | 3.058 | 1.00 | 23.38 |
| 7454 | CA | LEU | B | 210 | 35.144 | 10.429 | 4.355 | 1.00 | 23.77 |
| 7456 | CB | LEU | B | 210 | 34.733 | 11.429 | 5.440 | 1.00 | 23.69 |
| 7459 | CG | LEU | B | 210 | 35.459 | 12.768 | 5.355 | 1.00 | 23.52 |
| 7461 | CD1 | LEU | B | 210 | 34.830 | 13.745 | 6.336 | 1.00 | 22.14 |
| 7465 | CD2 | LEU | B | 210 | 36.962 | 12.569 | 5.630 | 1.00 | 24.32 |
| 7469 | C | LEU | B | 210 | 34.721 | 9.031 | 4.780 | 1.00 | 24.42 |
| 7470 | O | LEU | B | 210 | 35.379 | 8.410 | 5.603 | 1.00 | 24.38 |
| 7471 | N | SER | B | 211 | 33.627 | 8.541 | 4.211 | 1.00 | 25.75 |
| 7473 | CA | SER | B | 211 | 33.176 | 7.180 | 4.458 | 1.00 | 26.29 |
| 7475 | CB | BSER | B | 211 | 31.724 | 6.990 | 3.992 | 0.35 | 26.33 |
| 7476 | CB | ASER | B | 211 | 31.733 | 7.003 | 3.960 | 0.65 | 26.73 |
| 7481 | OG | BSER | B | 211 | 31.635 | 6.814 | 2.589 | 0.35 | 25.17 |
| 7482 | OG | ASER | B | 211 | 30.884 | 8.043 | 4.437 | 0.65 | 28.22 |
| 7485 | C | SER | B | 211 | 34.096 | 6.146 | 3.779 | 1.00 | 26.79 |
| 7486 | O | SER | B | 211 | 33.943 | 4.960 | 4.011 | 1.00 | 27.11 |
| 7487 | N | ALA | B | 212 | 35.052 | 6.609 | 2.971 | 1.00 | 27.48 |
| 7489 | CA | ALA | B | 212 | 35.807 | 5.765 | 2.045 | 1.00 | 28.00 |
| 7491 | CB | ALA | B | 212 | 35.502 | 6.200 | 0.610 | 1.00 | 27.64 |

FIGURE 3 CU

| A | B | C | D | E | F | G | H | I | J |
|---|---|---|---|---|---|---|---|---|---|
| 7495 | C | ALA | B | 212 | 37.330 | 5.735 | 2.259 | 1.00 | 28.36 |
| 7496 | O | ALA | B | 212 | 38.075 | 5.478 | 1.305 | 1.00 | 28.63 |
| 7497 | N | GLY | B | 213 | 37.793 | 6.017 | 3.480 | 1.00 | 28.63 |
| 7499 | CA | GLY | B | 213 | 39.190 | 5.812 | 3.848 | 1.00 | 28.66 |
| 7502 | C | GLY | B | 213 | 40.160 | 6.623 | 3.013 | 1.00 | 29.30 |
| 7503 | O | GLY | B | 213 | 39.829 | 7.754 | 2.628 | 1.00 | 29.18 |
| 7504 | N | ASP | B | 214 | 41.337 | 6.047 | 2.725 | 1.00 | 29.91 |
| 7506 | CA | ASP | B | 214 | 42.401 | 6.716 | 1.945 | 1.00 | 30.40 |
| 7508 | CB | ASP | B | 214 | 43.629 | 5.798 | 1.749 | 1.00 | 31.13 |
| 7511 | CG | ASP | B | 214 | 44.248 | 5.315 | 3.055 | 1.00 | 32.74 |
| 7512 | OD1 | ASP | B | 214 | 44.060 | 5.963 | 4.113 | 1.00 | 34.47 |
| 7513 | OD2 | ASP | B | 214 | 44.958 | 4.280 | 3.097 | 1.00 | 35.20 |
| 7514 | C | ASP | B | 214 | 41.960 | 7.157 | 0.541 | 1.00 | 30.05 |
| 7515 | O | ASP | B | 214 | 42.333 | 8.224 | 0.068 | 1.00 | 29.72 |
| 7516 | N | LYS | B | 215 | 41.203 | 6.319 | -0.150 | 1.00 | 30.05 |
| 7518 | CA | LYS | B | 215 | 40.854 | 6.614 | -1.546 | 1.00 | 29.92 |
| 7520 | CB | LYS | B | 215 | 40.230 | 5.391 | -2.199 | 1.00 | 30.71 |
| 7523 | CG | LYS | B | 215 | 40.214 | 5.394 | -3.723 | 1.00 | 32.45 |
| 7526 | CD | LYS | B | 215 | 39.887 | 3.980 | -4.222 | 1.00 | 34.64 |
| 7529 | CE | LYS | B | 215 | 39.790 | 3.882 | -5.732 | 1.00 | 36.80 |
| 7532 | NZ | LYS | B | 215 | 39.315 | 2.521 | -6.190 | 1.00 | 38.07 |
| 7536 | C | LYS | B | 215 | 39.906 | 7.821 | -1.634 | 1.00 | 28.89 |
| 7537 | O | LYS | B | 215 | 40.045 | 8.661 | -2.525 | 1.00 | 28.45 |
| 7538 | N | GLY | B | 216 | 38.972 | 7.902 | -0.689 | 1.00 | 27.81 |
| 7540 | CA | GLY | B | 216 | 38.049 | 9.018 | -0.591 | 1.00 | 27.11 |
| 7543 | C | GLY | B | 216 | 38.781 | 10.292 | -0.243 | 1.00 | 26.53 |
| 7544 | O | GLY | B | 216 | 38.559 | 11.333 | -0.840 | 1.00 | 26.52 |
| 7545 | N | ARG | B | 217 | 39.690 | 10.198 | 0.720 | 1.00 | 26.28 |
| 7547 | CA | ARG | B | 217 | 40.519 | 11.340 | 1.099 | 1.00 | 25.74 |
| 7549 | CB | ARG | B | 217 | 41.263 | 11.018 | 2.393 | 1.00 | 25.35 |
| 7552 | CG | ARG | B | 217 | 40.332 | 11.005 | 3.598 | 1.00 | 28.38 |
| 7555 | CD | ARG | B | 217 | 40.945 | 10.453 | 4.857 | 1.00 | 31.47 |
| 7558 | NE | ARG | B | 217 | 40.208 | 10.787 | 6.078 | 1.00 | 33.37 |
| 7560 | CZ | ARG | B | 217 | 40.258 | 11.974 | 6.697 | 1.00 | 36.00 |
| 7561 | NH1 | ARG | B | 217 | 40.977 | 12.979 | 6.200 | 1.00 | 39.28 |
| 7564 | NH2 | ARG | B | 217 | 39.575 | 12.170 | 7.810 | 1.00 | 34.96 |
| 7567 | C | ARG | B | 217 | 41.471 | 11.800 | -0.027 | 1.00 | 24.69 |
| 7568 | O | ARG | B | 217 | 41.743 | 12.983 | -0.161 | 1.00 | 24.52 |
| 7569 | N | ARG | B | 218 | 41.956 | 10.873 | -0.844 | 1.00 | 24.21 |
| 7571 | CA | ARG | B | 218 | 42.809 | 11.210 | -1.983 | 1.00 | 23.79 |
| 7573 | CB | ARG | B | 218 | 43.340 | 9.927 | -2.637 | 1.00 | 24.37 |
| 7576 | CG | ARG | B | 218 | 44.257 | 10.097 | -3.872 | 1.00 | 27.47 |
| 7579 | CD | ARG | B | 218 | 43.908 | 9.115 | -5.003 | 1.00 | 32.66 |
| 7582 | NE | ARG | B | 218 | 45.013 | 8.799 | -5.908 | 1.00 | 36.58 |
| 7584 | CZ | ARG | B | 218 | 45.406 | 9.552 | -6.933 | 1.00 | 39.40 |
| 7585 | NH1 | ARG | B | 218 | 46.425 | 9.145 | -7.688 | 1.00 | 40.57 |
| 7588 | NH2 | ARG | B | 218 | 44.809 | 10.714 | -7.204 | 1.00 | 39.74 |
| 7591 | C | ARG | B | 218 | 42.025 | 12.047 | -3.005 | 1.00 | 22.91 |
| 7592 | O | ARG | B | 218 | 42.599 | 12.928 | -3.640 | 1.00 | 22.18 |
| 7593 | N | ALA | B | 219 | 40.726 | 11.759 | -3.149 | 1.00 | 21.70 |
| 7595 | CA | ALA | B | 219 | 39.845 | 12.476 | -4.066 | 1.00 | 21.49 |
| 7597 | CB | ALA | B | 219 | 38.667 | 11.618 | -4.422 | 1.00 | 21.35 |

FIGURE 3 CV

| A | B | C | D | E | F | G | H | I | J |
|---|---|---|---|---|---|---|---|---|---|
| 7601 | C | ALA | B | 219 | 39.340 | 13.818 | -3.523 | 1.00 | 21.64 |
| 7602 | O | ALA | B | 219 | 38.756 | 14.587 | -4.270 | 1.00 | 20.84 |
| 7603 | N | LEU | B | 220 | 39.563 | 14.090 | -2.240 | 1.00 | 21.58 |
| 7605 | CA | LEU | B | 220 | 39.003 | 15.285 | -1.600 | 1.00 | 22.20 |
| 7607 | CB | LEU | B | 220 | 39.340 | 15.335 | -0.110 | 1.00 | 22.43 |
| 7610 | CG | LEU | B | 220 | 38.407 | 14.580 | 0.840 | 1.00 | 22.95 |
| 7612 | CD1 | LEU | B | 220 | 38.991 | 14.642 | 2.244 | 1.00 | 24.14 |
| 7616 | CD2 | LEU | B | 220 | 37.002 | 15.153 | 0.810 | 1.00 | 24.62 |
| 7620 | C | LEU | B | 220 | 39.364 | 16.616 | -2.239 | 1.00 | 21.85 |
| 7621 | O | LEU | B | 220 | 38.482 | 17.438 | -2.393 | 1.00 | 22.54 |
| 7622 | N | PRO | B | 221 | 40.627 | 16.872 | -2.583 | 1.00 | 22.19 |
| 7623 | CA | PRO | B | 221 | 40.969 | 18.150 | -3.227 | 1.00 | 22.28 |
| 7625 | CB | PRO | B | 221 | 42.442 | 17.987 | -3.589 | 1.00 | 22.39 |
| 7628 | CG | PRO | B | 221 | 42.951 | 16.960 | -2.616 | 1.00 | 23.34 |
| 7631 | CD | PRO | B | 221 | 41.812 | 16.025 | -2.379 | 1.00 | 22.27 |
| 7634 | C | PRO | B | 221 | 40.115 | 18.420 | -4.460 | 1.00 | 21.79 |
| 7635 | O | PRO | B | 221 | 39.580 | 19.513 | -4.592 | 1.00 | 21.54 |
| 7636 | N | VAL | B | 222 | 39.945 | 17.431 | -5.331 | 1.00 | 21.34 |
| 7638 | CA | VAL | B | 222 | 39.131 | 17.616 | -6.533 | 1.00 | 20.96 |
| 7640 | CB | VAL | B | 222 | 39.431 | 16.533 | -7.601 | 1.00 | 21.09 |
| 7642 | CG1 | VAL | B | 222 | 38.492 | 16.664 | -8.787 | 1.00 | 20.79 |
| 7646 | CG2 | VAL | B | 222 | 40.885 | 16.668 | -8.085 | 1.00 | 22.50 |
| 7650 | C | VAL | B | 222 | 37.620 | 17.635 | -6.214 | 1.00 | 20.48 |
| 7651 | O | VAL | B | 222 | 36.877 | 18.411 | -6.804 | 1.00 | 20.29 |
| 7652 | N | LEU | B | 223 | 37.172 | 16.773 | -5.307 | 1.00 | 20.17 |
| 7654 | CA | LEU | B | 223 | 35.750 | 16.717 | -4.924 | 1.00 | 19.91 |
| 7656 | CB | LEU | B | 223 | 35.466 | 15.562 | -3.957 | 1.00 | 20.52 |
| 7659 | CG | LEU | B | 223 | 35.293 | 14.173 | -4.587 | 1.00 | 21.95 |
| 7661 | CD1 | LEU | B | 223 | 35.296 | 13.095 | -3.512 | 1.00 | 22.04 |
| 7665 | CD2 | LEU | B | 223 | 34.039 | 14.111 | -5.407 | 1.00 | 23.07 |
| 7669 | C | LEU | B | 223 | 35.327 | 18.015 | -4.253 | 1.00 | 19.72 |
| 7670 | O | LEU | B | 223 | 34.188 | 18.456 | -4.381 | 1.00 | 19.07 |
| 7671 | N | ASP | B | 224 | 36.250 | 18.599 | -3.503 | 1.00 | 19.68 |
| 7673 | CA | ASP | B | 224 | 36.042 | 19.893 | -2.883 | 1.00 | 19.94 |
| 7675 | CB | ASP | B | 224 | 37.272 | 20.287 | -2.069 | 1.00 | 19.86 |
| 7678 | CG | ASP | B | 224 | 37.289 | 19.671 | -0.705 | 1.00 | 22.67 |
| 7679 | OD1 | ASP | B | 224 | 36.256 | 19.094 | -0.288 | 1.00 | 23.35 |
| 7680 | OD2 | ASP | B | 224 | 38.304 | 19.744 | 0.036 | 1.00 | 25.14 |
| 7681 | C | ASP | B | 224 | 35.778 | 20.972 | -3.908 | 1.00 | 19.81 |
| 7682 | O | ASP | B | 224 | 34.910 | 21.795 | -3.702 | 1.00 | 19.95 |
| 7683 | N | LYS | B | 225 | 36.541 | 20.990 | -4.996 | 1.00 | 19.94 |
| 7685 | CA | LYS | B | 225 | 36.368 | 22.027 | -6.013 | 1.00 | 20.31 |
| 7687 | CB | LYS | B | 225 | 37.525 | 22.048 | -7.022 | 1.00 | 20.63 |
| 7690 | CG | LYS | B | 225 | 38.973 | 22.184 | -6.439 | 1.00 | 22.72 |
| 7693 | CD | BLYS | B | 225 | 39.100 | 23.053 | -5.155 | 0.35 | 21.46 |
| 7694 | CD | ALYS | B | 225 | 39.001 | 22.753 | -5.014 | 0.65 | 25.09 |
| 7699 | CE | BLYS | B | 225 | 39.223 | 22.270 | -3.837 | 0.35 | 19.92 |
| 7700 | CE | ALYS | B | 225 | 39.871 | 23.974 | -4.801 | 0.65 | 25.51 |
| 7705 | NZ | BLYS | B | 225 | 40.570 | 21.728 | -3.502 | 0.35 | 14.63 |
| 7706 | NZ | ALYS | B | 225 | 39.377 | 24.575 | -3.546 | 0.65 | 24.29 |
| 7713 | C | LYS | B | 225 | 35.049 | 21.804 | -6.718 | 1.00 | 19.81 |
| 7714 | O | LYS | B | 225 | 34.320 | 22.762 | -6.982 | 1.00 | 19.64 |

FIGURE 3 CW

| A | B | C | D | E | F | G | H | I | J |
|---|---|---|---|---|---|---|---|---|---|
| 7715 | N | TYR | B | 226 | 34.733 | 20.536 | -6.979 | 1.00 | 19.10 |
| 7717 | CA | TYR | B | 226 | 33.437 | 20.151 | -7.525 | 1.00 | 18.47 |
| 7719 | CB | TYR | B | 226 | 33.307 | 18.624 | -7.646 | 1.00 | 18.62 |
| 7722 | CG | TYR | B | 226 | 31.883 | 18.168 | -7.875 | 1.00 | 17.81 |
| 7723 | CD1 | TYR | B | 226 | 31.300 | 18.256 | -9.132 | 1.00 | 17.52 |
| 7725 | CE1 | TYR | B | 226 | 29.994 | 17.859 | -9.337 | 1.00 | 20.05 |
| 7727 | CZ | TYR | B | 226 | 29.232 | 17.374 | -8.279 | 1.00 | 18.47 |
| 7728 | OH | TYR | B | 226 | 27.919 | 16.982 | -8.500 | 1.00 | 17.52 |
| 7730 | CE2 | TYR | B | 226 | 29.785 | 17.299 | -7.026 | 1.00 | 17.57 |
| 7732 | CD2 | TYR | B | 226 | 31.112 | 17.694 | -6.829 | 1.00 | 17.49 |
| 7734 | C | TYR | B | 226 | 32.331 | 20.699 | -6.643 | 1.00 | 18.41 |
| 7735 | O | TYR | B | 226 | 31.452 | 21.411 | -7.122 | 1.00 | 18.11 |
| 7736 | N | ALA | B | 227 | 32.417 | 20.408 | -5.345 | 1.00 | 18.13 |
| 7738 | CA | ALA | B | 227 | 31.403 | 20.799 | -4.377 | 1.00 | 18.18 |
| 7740 | CB | ALA | B | 227 | 31.723 | 20.221 | -3.021 | 1.00 | 17.94 |
| 7744 | C | ALA | B | 227 | 31.281 | 22.316 | -4.251 | 1.00 | 18.61 |
| 7745 | O | ALA | B | 227 | 30.196 | 22.851 | -4.063 | 1.00 | 18.11 |
| 7746 | N | GLU | B | 228 | 32.407 | 22.996 | -4.328 | 1.00 | 19.06 |
| 7748 | CA | GLU | B | 228 | 32.418 | 24.439 | -4.177 | 1.00 | 20.24 |
| 7750 | CB | GLU | B | 228 | 33.864 | 24.949 | -4.123 | 1.00 | 20.64 |
| 7753 | CG | GLU | B | 228 | 34.451 | 24.809 | -2.730 | 1.00 | 23.29 |
| 7756 | CD | GLU | B | 228 | 35.947 | 24.586 | -2.731 | 1.00 | 26.70 |
| 7757 | OE1 | GLU | B | 228 | 36.464 | 23.942 | -1.768 | 1.00 | 29.92 |
| 7758 | OE2 | GLU | B | 228 | 36.592 | 25.044 | -3.686 | 1.00 | 27.85 |
| 7759 | C | GLU | B | 228 | 31.636 | 25.080 | -5.300 | 1.00 | 20.03 |
| 7760 | O | GLU | B | 228 | 30.842 | 25.982 | -5.063 | 1.00 | 20.42 |
| 7761 | N | SER | B | 229 | 31.824 | 24.584 | -6.521 | 1.00 | 20.10 |
| 7763 | CA | SER | B | 229 | 31.140 | 25.146 | -7.663 | 1.00 | 20.21 |
| 7765 | CB | SER | B | 229 | 31.838 | 24.755 | -8.958 | 1.00 | 20.74 |
| 7768 | OG | SER | B | 229 | 33.134 | 25.319 | -8.986 | 1.00 | 21.81 |
| 7770 | C | SER | B | 229 | 29.655 | 24.795 | -7.704 | 1.00 | 19.69 |
| 7771 | O | SER | B | 229 | 28.845 | 25.675 | -7.972 | 1.00 | 19.58 |
| 7772 | N | ILE | B | 230 | 29.283 | 23.538 | -7.451 | 1.00 | 19.26 |
| 7774 | CA | ILE | B | 230 | 27.855 | 23.173 | -7.467 | 1.00 | 19.00 |
| 7776 | CB | ILE | B | 230 | 27.588 | 21.634 | -7.493 | 1.00 | 19.39 |
| 7778 | CG1 | ILE | B | 230 | 28.132 | 20.922 | -6.249 | 1.00 | 19.42 |
| 7781 | CD1 | ILE | B | 230 | 27.348 | 19.661 | -5.883 | 1.00 | 19.21 |
| 7785 | CG2 | ILE | B | 230 | 28.145 | 20.996 | -8.778 | 1.00 | 20.74 |
| 7789 | C | ILE | B | 230 | 27.118 | 23.798 | -6.292 | 1.00 | 18.75 |
| 7790 | O | ILE | B | 230 | 25.934 | 24.062 | -6.404 | 1.00 | 18.69 |
| 7791 | N | GLY | B | 231 | 27.825 | 24.000 | -5.179 | 1.00 | 17.92 |
| 7793 | CA | GLY | B | 231 | 27.260 | 24.588 | -3.977 | 1.00 | 18.54 |
| 7796 | C | GLY | B | 231 | 26.885 | 26.044 | -4.189 | 1.00 | 18.41 |
| 7797 | O | GLY | B | 231 | 25.776 | 26.467 | -3.838 | 1.00 | 18.39 |
| 7798 | N | LEU | B | 232 | 27.791 | 26.809 | -4.801 | 1.00 | 18.03 |
| 7800 | CA | LEU | B | 232 | 27.463 | 28.191 | -5.176 | 1.00 | 17.92 |
| 7802 | CB | LEU | B | 232 | 28.697 | 28.973 | -5.644 | 1.00 | 17.76 |
| 7805 | CG | LEU | B | 232 | 28.471 | 30.416 | -6.137 | 1.00 | 18.58 |
| 7807 | CD1 | LEU | B | 232 | 27.676 | 31.245 | -5.123 | 1.00 | 20.10 |
| 7811 | CD2 | LEU | B | 232 | 29.783 | 31.085 | -6.471 | 1.00 | 19.77 |
| 7815 | C | LEU | B | 232 | 26.371 | 28.184 | -6.232 | 1.00 | 17.69 |
| 7816 | O | LEU | B | 232 | 25.391 | 28.929 | -6.125 | 1.00 | 17.69 |

FIGURE 3 CX

| A | B | C | D | E | F | G | H | I | J |
|---|---|---|---|---|---|---|---|---|---|
| 7817 | N | ALA | B | 233 | 26.520 | 27.332 | -7.243 | 1.00 | 17.54 |
| 7819 | CA | ALA | B | 233 | 25.535 | 27.255 | -8.330 | 1.00 | 17.52 |
| 7821 | CB | ALA | B | 233 | 25.937 | 26.175 | -9.322 | 1.00 | 17.72 |
| 7825 | C | ALA | B | 233 | 24.133 | 26.996 | -7.801 | 1.00 | 16.87 |
| 7826 | O | ALA | B | 233 | 23.149 | 27.503 | -8.321 | 1.00 | 16.72 |
| 7827 | N | PHE | B | 234 | 24.055 | 26.207 | -6.738 | 1.00 | 17.20 |
| 7829 | CA | PHE | B | 234 | 22.796 | 25.770 | -6.175 | 1.00 | 17.20 |
| 7831 | CB | PHE | B | 234 | 23.077 | 24.798 | -5.020 | 1.00 | 17.86 |
| 7834 | CG | PHE | B | 234 | 21.913 | 23.952 | -4.635 | 1.00 | 19.19 |
| 7835 | CD1 | PHE | B | 234 | 21.908 | 22.595 | -4.939 | 1.00 | 23.96 |
| 7837 | CE1 | PHE | B | 234 | 20.833 | 21.786 | -4.576 | 1.00 | 25.08 |
| 7839 | CZ | PHE | B | 234 | 19.753 | 22.346 | -3.895 | 1.00 | 23.44 |
| 7841 | CE2 | PHE | B | 234 | 19.766 | 23.705 | -3.578 | 1.00 | 21.13 |
| 7843 | CD2 | PHE | B | 234 | 20.837 | 24.489 | -3.936 | 1.00 | 19.81 |
| 7845 | C | PHE | B | 234 | 22.023 | 26.972 | -5.659 | 1.00 | 17.12 |
| 7846 | O | PHE | B | 234 | 20.817 | 27.075 | -5.856 | 1.00 | 16.09 |
| 7847 | N | GLN | B | 235 | 22.724 | 27.860 | -4.969 | 1.00 | 16.71 |
| 7849 | CA | GLN | B | 235 | 22.093 | 29.040 | -4.427 | 1.00 | 17.18 |
| 7851 | CB | GLN | B | 235 | 22.918 | 29.661 | -3.304 | 1.00 | 16.88 |
| 7854 | CG | GLN | B | 235 | 22.173 | 30.781 | -2.566 | 1.00 | 16.78 |
| 7857 | CD | GLN | B | 235 | 20.856 | 30.332 | -1.970 | 1.00 | 18.18 |
| 7858 | OE1 | GLN | B | 235 | 20.783 | 29.271 | -1.353 | 1.00 | 17.96 |
| 7859 | NE2 | GLN | B | 235 | 19.818 | 31.140 | -2.138 | 1.00 | 15.32 |
| 7862 | C | GLN | B | 235 | 21.821 | 30.089 | -5.501 | 1.00 | 16.98 |
| 7863 | O | GLN | B | 235 | 20.842 | 30.800 | -5.392 | 1.00 | 16.15 |
| 7864 | N | VAL | B | 236 | 22.640 | 30.184 | -6.544 | 1.00 | 17.46 |
| 7866 | CA | VAL | B | 236 | 22.265 | 31.160 | -7.590 | 1.00 | 18.23 |
| 7868 | CB | VAL | B | 236 | 23.405 | 31.708 | -8.547 | 1.00 | 18.68 |
| 7870 | CG1 | VAL | B | 236 | 24.747 | 31.119 | -8.271 | 1.00 | 19.87 |
| 7874 | CG2 | VAL | B | 236 | 23.019 | 31.733 | -10.030 | 1.00 | 19.70 |
| 7878 | C | VAL | B | 236 | 21.003 | 30.665 | -8.279 | 1.00 | 17.45 |
| 7879 | O | VAL | B | 236 | 20.139 | 31.457 | -8.531 | 1.00 | 17.04 |
| 7880 | N | GLN | B | 237 | 20.856 | 29.350 | -8.447 | 1.00 | 17.88 |
| 7882 | CA | GLN | B | 237 | 19.649 | 28.785 | -9.035 | 1.00 | 18.28 |
| 7884 | CB | GLN | B | 237 | 19.783 | 27.288 | -9.337 | 1.00 | 18.86 |
| 7887 | CG | GLN | B | 237 | 18.561 | 26.715 | -10.056 | 1.00 | 20.61 |
| 7890 | CD | GLN | B | 237 | 18.402 | 27.211 | -11.478 | 1.00 | 23.91 |
| 7891 | OE1 | GLN | B | 237 | 19.207 | 27.995 | -11.962 | 1.00 | 27.71 |
| 7892 | NE2 | GLN | B | 237 | 17.361 | 26.738 | -12.157 | 1.00 | 25.53 |
| 7895 | C | GLN | B | 237 | 18.469 | 29.005 | -8.135 | 1.00 | 17.68 |
| 7896 | O | GLN | B | 237 | 17.381 | 29.326 | -8.612 | 1.00 | 18.18 |
| 7897 | N | ASP | B | 238 | 18.673 | 28.830 | -6.832 | 1.00 | 16.95 |
| 7899 | CA | ASP | B | 238 | 17.624 | 29.133 | -5.872 | 1.00 | 16.59 |
| 7901 | CB | ASP | B | 238 | 18.084 | 28.803 | -4.452 | 1.00 | 15.86 |
| 7904 | CG | ASP | B | 238 | 16.988 | 28.976 | -3.451 | 1.00 | 16.32 |
| 7905 | OD1 | ASP | B | 238 | 16.037 | 28.162 | -3.445 | 1.00 | 17.49 |
| 7906 | OD2 | ASP | B | 238 | 16.959 | 29.929 | -2.651 | 1.00 | 18.97 |
| 7907 | C | ASP | B | 238 | 17.186 | 30.610 | -5.985 | 1.00 | 16.34 |
| 7908 | O | ASP | B | 238 | 16.001 | 30.905 | -5.932 | 1.00 | 15.59 |
| 7909 | N | ASP | B | 239 | 18.135 | 31.526 | -6.146 | 1.00 | 17.76 |
| 7911 | CA | ASP | B | 239 | 17.799 | 32.959 | -6.321 | 1.00 | 18.83 |
| 7913 | CB | ASP | B | 239 | 19.044 | 33.819 | -6.384 | 1.00 | 19.28 |

FIGURE 3 CY

| A | B | C | D | E | F | G | H | I | J |
|---|---|---|---|---|---|---|---|---|---|
| 7916 | CG | ASP | B | 239 | 19.766 | 33.928 | -5.070 | 1.00 | 19.95 |
| 7917 | OD1 | ASP | B | 239 | 19.251 | 33.447 | -4.018 | 1.00 | 23.46 |
| 7918 | OD2 | ASP | B | 239 | 20.886 | 34.480 | -5.016 | 1.00 | 19.63 |
| 7919 | C | ASP | B | 239 | 17.021 | 33.192 | -7.610 | 1.00 | 19.87 |
| 7920 | O | ASP | B | 239 | 16.020 | 33.917 | -7.629 | 1.00 | 20.25 |
| 7921 | N | ILE | B | 240 | 17.492 | 32.570 | -8.687 | 1.00 | 19.96 |
| 7923 | CA | ILE | B | 240 | 16.845 | 32.676 | -9.986 | 1.00 | 20.61 |
| 7925 | CB | ILE | B | 240 | 17.647 | 31.902 | -11.039 | 1.00 | 20.77 |
| 7927 | CG1 | ILE | B | 240 | 18.945 | 32.645 | -11.363 | 1.00 | 20.81 |
| 7930 | CD1 | ILE | B | 240 | 19.974 | 31.792 | -11.997 | 1.00 | 21.71 |
| 7934 | CG2 | ILE | B | 240 | 16.821 | 31.682 | -12.304 | 1.00 | 21.31 |
| 7938 | C | ILE | B | 240 | 15.413 | 32.161 | -9.932 | 1.00 | 20.80 |
| 7939 | O | ILE | B | 240 | 14.506 | 32.784 | -10.482 | 1.00 | 20.05 |
| 7940 | N | LEU | B | 241 | 15.214 | 31.014 | -9.283 | 1.00 | 21.23 |
| 7942 | CA | LEU | B | 241 | 13.904 | 30.394 | -9.206 | 1.00 | 21.82 |
| 7944 | CB | LEU | B | 241 | 14.009 | 28.986 | -8.620 | 1.00 | 22.08 |
| 7947 | CG | LEU | B | 241 | 14.569 | 27.953 | -9.600 | 1.00 | 23.04 |
| 7949 | CD1 | LEU | B | 241 | 14.635 | 26.592 | -8.926 | 1.00 | 25.03 |
| 7953 | CD2 | LEU | B | 241 | 13.740 | 27.874 | -10.869 | 1.00 | 23.91 |
| 7957 | C | LEU | B | 241 | 12.955 | 31.226 | -8.384 | 1.00 | 22.17 |
| 7958 | O | LEU | B | 241 | 11.759 | 31.219 | -8.613 | 1.00 | 22.86 |
| 7959 | N | ASP | B | 242 | 13.487 | 31.928 | -7.401 | 1.00 | 22.89 |
| 7961 | CA | ASP | B | 242 | 12.680 | 32.816 | -6.597 | 1.00 | 23.68 |
| 7963 | CB | ASP | B | 242 | 13.538 | 33.476 | -5.526 | 1.00 | 24.26 |
| 7966 | CG | ASP | B | 242 | 12.782 | 33.732 | -4.261 | 1.00 | 26.59 |
| 7967 | OD1 | ASP | B | 242 | 12.339 | 34.885 | -4.081 | 1.00 | 29.09 |
| 7968 | OD2 | ASP | B | 242 | 12.586 | 32.842 | -3.395 | 1.00 | 30.35 |
| 7969 | C | ASP | B | 242 | 12.018 | 33.889 | -7.468 | 1.00 | 24.03 |
| 7970 | O | ASP | B | 242 | 10.872 | 34.264 | -7.225 | 1.00 | 23.75 |
| 7971 | N | VAL | B | 243 | 12.722 | 34.380 | -8.478 | 1.00 | 24.22 |
| 7973 | CA | VAL | B | 243 | 12.133 | 35.431 | -9.334 | 1.00 | 25.09 |
| 7975 | CB | BVAL | B | 243 | 13.207 | 36.455 | -9.871 | 0.35 | 24.92 |
| 7976 | CB | AVAL | B | 243 | 13.180 | 36.479 | -9.849 | 0.65 | 25.18 |
| 7979 | CG1 | BVAL | B | 243 | 14.454 | 35.767 | -10.368 | 0.35 | 24.74 |
| 7980 | CG1 | AVAL | B | 243 | 14.270 | 36.727 | -8.817 | 0.65 | 24.27 |
| 7987 | CG2 | BVAL | B | 243 | 12.633 | 37.361 | -10.975 | 0.35 | 23.96 |
| 7988 | CG2 | AVAL | B | 243 | 13.775 | 36.088 | -11.166 | 0.65 | 25.87 |
| 7995 | C | VAL | B | 243 | 11.271 | 34.851 | -10.474 | 1.00 | 25.74 |
| 7996 | O | VAL | B | 243 | 10.167 | 35.330 | -10.688 | 1.00 | 25.89 |
| 7997 | N | VAL | B | 244 | 11.745 | 33.812 | -11.160 | 1.00 | 26.96 |
| 7999 | CA | VAL | B | 244 | 11.065 | 33.282 | -12.350 | 1.00 | 27.89 |
| 8001 | CB | VAL | B | 244 | 12.069 | 32.914 | -13.472 | 1.00 | 28.15 |
| 8003 | CG1 | VAL | B | 244 | 12.996 | 34.083 | -13.769 | 1.00 | 29.48 |
| 8007 | CG2 | VAL | B | 244 | 12.852 | 31.642 | -13.143 | 1.00 | 28.31 |
| 8011 | C | VAL | B | 244 | 10.158 | 32.066 | -12.136 | 1.00 | 28.41 |
| 8012 | O | VAL | B | 244 | 9.330 | 31.776 | -12.983 | 1.00 | 28.51 |
| 8013 | N | GLY | B | 245 | 10.331 | 31.335 | -11.038 | 1.00 | 29.07 |
| 8015 | CA | GLY | B | 245 | 9.583 | 30.107 | -10.813 | 1.00 | 29.72 |
| 8018 | C | GLY | B | 245 | 8.131 | 30.378 | -10.460 | 1.00 | 30.36 |
| 8019 | O | GLY | B | 245 | 7.793 | 31.482 | -10.070 | 1.00 | 31.39 |
| 8020 | N | ASP | B | 246 | 7.276 | 29.376 | -10.613 | 1.00 | 30.83 |
| 8022 | CA | ASP | B | 246 | 5.885 | 29.465 | -10.194 | 1.00 | 31.66 |

FIGURE 3 CZ

| A | B | C | D | E | F | G | H | I | J |
|---|---|---|---|---|---|---|---|---|---|
| 8024 | CB | ASP | B | 246 | 4.996 | 28.632 | -11.128 | 1.00 | 32.32 |
| 8027 | CG | ASP | B | 246 | 3.527 | 29.006 | -11.027 | 1.00 | 35.80 |
| 8028 | OD1 | ASP | B | 246 | 2.981 | 29.516 | -12.041 | 1.00 | 41.36 |
| 8029 | OD2 | ASP | B | 246 | 2.818 | 28.820 | -9.997 | 1.00 | 39.19 |
| 8030 | C | ASP | B | 246 | 5.782 | 28.894 | -8.790 | 1.00 | 30.65 |
| 8031 | O | ASP | B | 246 | 6.321 | 27.842 | -8.546 | 1.00 | 30.56 |
| 8032 | N | THR | B | 247 | 5.072 | 29.572 | -7.892 | 1.00 | 29.92 |
| 8034 | CA | THR | B | 247 | 4.846 | 29.080 | -6.533 | 1.00 | 29.76 |
| 8036 | CB | THR | B | 247 | 3.814 | 29.975 | -5.811 | 1.00 | 29.87 |
| 8038 | OG1 | THR | B | 247 | 4.378 | 31.272 | -5.593 | 1.00 | 31.54 |
| 8040 | CG2 | THR | B | 247 | 3.502 | 29.459 | -4.399 | 1.00 | 30.40 |
| 8044 | C | THR | B | 247 | 4.401 | 27.611 | -6.492 | 1.00 | 28.88 |
| 8045 | O | THR | B | 247 | 4.911 | 26.844 | -5.685 | 1.00 | 28.30 |
| 8046 | N | ALA | B | 248 | 3.465 | 27.222 | -7.358 | 1.00 | 28.23 |
| 8048 | CA | ALA | B | 248 | 2.932 | 25.852 | -7.367 | 1.00 | 28.33 |
| 8050 | CB | ALA | B | 248 | 1.809 | 25.708 | -8.391 | 1.00 | 28.17 |
| 8054 | C | ALA | B | 248 | 4.007 | 24.805 | -7.644 | 1.00 | 28.26 |
| 8055 | O | ALA | B | 248 | 3.925 | 23.687 | -7.143 | 1.00 | 28.69 |
| 8056 | N | THR | B | 249 | 4.985 | 25.172 | -8.466 | 1.00 | 27.77 |
| 8058 | CA | THR | B | 249 | 6.091 | 24.292 | -8.824 | 1.00 | 27.75 |
| 8060 | CB | THR | B | 249 | 6.638 | 24.726 | -10.188 | 1.00 | 27.90 |
| 8062 | OG1 | THR | B | 249 | 5.596 | 24.624 | -11.164 | 1.00 | 30.21 |
| 8064 | CG2 | THR | B | 249 | 7.706 | 23.767 | -10.678 | 1.00 | 28.58 |
| 8068 | C | THR | B | 249 | 7.223 | 24.275 | -7.773 | 1.00 | 26.85 |
| 8069 | O | THR | B | 249 | 7.671 | 23.202 | -7.356 | 1.00 | 26.31 |
| 8070 | N | LEU | B | 250 | 7.654 | 25.463 | -7.348 | 1.00 | 25.98 |
| 8072 | CA | LEU | B | 250 | 8.706 | 25.627 | -6.328 | 1.00 | 25.67 |
| 8074 | CB | LEU | B | 250 | 8.994 | 27.116 | -6.091 | 1.00 | 25.92 |
| 8077 | CG | LEU | B | 250 | 9.408 | 28.030 | -7.239 | 1.00 | 27.52 |
| 8079 | CD1 | LEU | B | 250 | 9.656 | 29.433 | -6.691 | 1.00 | 27.93 |
| 8083 | CD2 | LEU | B | 250 | 10.625 | 27.516 | -7.954 | 1.00 | 28.70 |
| 8087 | C | LEU | B | 250 | 8.359 | 25.039 | -4.965 | 1.00 | 24.61 |
| 8088 | O | LEU | B | 250 | 9.244 | 24.625 | -4.217 | 1.00 | 22.99 |
| 8089 | N | GLY | B | 251 | 7.077 | 25.078 | -4.612 | 1.00 | 23.96 |
| 8091 | CA | GLY | B | 251 | 6.636 | 24.759 | -3.265 | 1.00 | 23.66 |
| 8094 | C | GLY | B | 251 | 6.808 | 25.892 | -2.263 | 1.00 | 23.66 |
| 8095 | O | GLY | B | 251 | 6.449 | 25.748 | -1.105 | 1.00 | 23.25 |
| 8096 | N | LYS | B | 252 | 7.310 | 27.036 | -2.721 | 1.00 | 23.45 |
| 8098 | CA | LYS | B | 252 | 7.499 | 28.207 | -1.881 | 1.00 | 23.55 |
| 8100 | CB | LYS | B | 252 | 8.913 | 28.217 | -1.262 | 1.00 | 23.19 |
| 8103 | CG | LYS | B | 252 | 10.065 | 28.100 | -2.279 | 1.00 | 22.81 |
| 8106 | CD | LYS | B | 252 | 11.443 | 27.892 | -1.587 | 1.00 | 21.30 |
| 8109 | CE | LYS | B | 252 | 12.575 | 28.125 | -2.537 | 1.00 | 19.95 |
| 8112 | NZ | LYS | B | 252 | 13.876 | 27.549 | -2.087 | 1.00 | 18.06 |
| 8116 | C | LYS | B | 252 | 7.248 | 29.466 | -2.729 | 1.00 | 24.42 |
| 8117 | O | LYS | B | 252 | 7.280 | 29.414 | -3.961 | 1.00 | 24.38 |
| 8118 | N | ARG | B | 253 | 7.024 | 30.592 | -2.066 | 1.00 | 25.44 |
| 8120 | CA | ARG | B | 253 | 6.534 | 31.795 | -2.744 | 1.00 | 26.73 |
| 8122 | CB | ARG | B | 253 | 6.006 | 32.830 | -1.737 | 1.00 | 27.67 |
| 8125 | CG | ARG | B | 253 | 4.510 | 33.101 | -1.907 | 1.00 | 31.24 |
| 8128 | CD | ARG | B | 253 | 3.825 | 33.710 | -0.700 | 1.00 | 35.52 |
| 8131 | NE | ARG | B | 253 | 3.150 | 32.704 | 0.116 | 1.00 | 37.39 |

FIGURE 3 DA

| A | B | C | D | E | F | G | H | I | J |
|---|---|---|---|---|---|---|---|---|---|
| 8133 | CZ | ARG | B | 253 | 2.036 | 32.056 | -0.235 | 1.00 | 39.88 |
| 8134 | NH1 | ARG | B | 253 | 1.451 | 32.263 | -1.417 | 1.00 | 41.43 |
| 8137 | NH2 | ARG | B | 253 | 1.518 | 31.167 | 0.605 | 1.00 | 41.57 |
| 8140 | C | ARG | B | 253 | 7.550 | 32.432 | -3.685 | 1.00 | 25.93 |
| 8141 | O | ARG | B | 253 | 8.642 | 32.852 | -3.283 | 1.00 | 25.79 |
| 8142 | N | GLN | B | 254 | 7.176 | 32.480 | -4.955 | 1.00 | 25.68 |
| 8144 | CA | GLN | B | 254 | 7.848 | 33.323 | -5.931 | 1.00 | 25.41 |
| 8146 | CB | GLN | B | 254 | 7.076 | 33.337 | -7.255 | 1.00 | 25.85 |
| 8149 | CG B | GLN | B | 254 | 7.707 | 34.187 | -8.363 | 0.35 | 25.46 |
| 8150 | CG A | GLN | B | 254 | 7.696 | 34.266 | -8.323 | 0.65 | 26.52 |
| 8155 | CD B | GLN | B | 254 | 7.388 | 35.665 | -8.261 | 0.35 | 25.75 |
| 8156 | CD A | GLN | B | 254 | 6.858 | 34.376 | -9.595 | 0.65 | 29.40 |
| 8157 | OE1B | GLN | B | 254 | 8.227 | 36.501 | -8.593 | 0.35 | 26.04 |
| 8158 | OE1A | GLN | B | 254 | 7.335 | 34.901 | -10.609 | 0.65 | 30.77 |
| 8159 | NE2B | GLN | B | 254 | 6.180 | 35.993 | -7.809 | 0.35 | 25.98 |
| 8160 | NE2A | GLN | B | 254 | 5.622 | 33.888 | -9.547 | 0.65 | 29.10 |
| 8165 | C | GLN | B | 254 | 7.900 | 34.730 | -5.369 | 1.00 | 24.67 |
| 8166 | O | GLN | B | 254 | 6.942 | 35.184 | -4.755 | 1.00 | 24.03 |
| 8167 | N | GLY | B | 255 | 9.023 | 35.413 | -5.565 | 1.00 | 24.23 |
| 8169 | CA | GLY | B | 255 | 9.107 | 36.829 | -5.264 | 1.00 | 24.15 |
| 8172 | C | GLY | B | 255 | 9.417 | 37.151 | -3.816 | 1.00 | 24.34 |
| 8173 | O | GLY | B | 255 | 9.464 | 38.307 | -3.465 | 1.00 | 24.07 |
| 8174 | N | ALA | B | 256 | 9.656 | 36.142 | -2.983 | 1.00 | 24.66 |
| 8176 | CA | ALA | B | 256 | 9.909 | 36.359 | -1.559 | 1.00 | 25.08 |
| 8178 | CB | ALA | B | 256 | 9.978 | 35.024 | -0.833 | 1.00 | 24.93 |
| 8182 | C | ALA | B | 256 | 11.179 | 37.180 | -1.288 | 1.00 | 25.56 |
| 8183 | O | ALA | B | 256 | 11.213 | 37.979 | -0.353 | 1.00 | 26.42 |
| 8184 | N | ASP | B | 257 | 12.210 | 37.000 | -2.105 | 1.00 | 25.88 |
| 8186 | CA | ASP | B | 257 | 13.466 | 37.739 | -1.932 | 1.00 | 26.25 |
| 8188 | CB | ASP | B | 257 | 14.564 | 37.191 | -2.848 | 1.00 | 26.11 |
| 8191 | CG | ASP | B | 257 | 15.025 | 35.791 | -2.463 | 1.00 | 26.45 |
| 8192 | OD1 | ASP | B | 257 | 14.815 | 35.353 | -1.299 | 1.00 | 26.12 |
| 8193 | OD2 | ASP | B | 257 | 15.602 | 35.054 | -3.292 | 1.00 | 25.40 |
| 8194 | C | ASP | B | 257 | 13.286 | 39.221 | -2.241 | 1.00 | 27.05 |
| 8195 | O | ASP | B | 257 | 13.823 | 40.074 | -1.549 | 1.00 | 26.45 |
| 8196 | N | GLN | B | 258 | 12.545 | 39.520 | -3.304 | 1.00 | 28.65 |
| 8198 | CA | GLN | B | 258 | 12.278 | 40.908 | -3.691 | 1.00 | 29.67 |
| 8200 | CB B | GLN | B | 258 | 11.590 | 40.972 | -5.061 | 0.35 | 29.64 |
| 8201 | CB A | GLN | B | 258 | 11.557 | 40.939 | -5.046 | 0.65 | 30.10 |
| 8206 | CG B | GLN | B | 258 | 12.546 | 40.710 | -6.226 | 0.35 | 29.64 |
| 8207 | CG A | GLN | B | 258 | 11.357 | 42.333 | -5.625 | 0.65 | 31.67 |
| 8212 | CD B | GLN | B | 258 | 11.961 | 41.060 | -7.589 | 0.35 | 29.88 |
| 8213 | CD A | GLN | B | 258 | 9.896 | 42.666 | -5.883 | 0.65 | 33.37 |
| 8214 | OE1B | GLN | B | 258 | 12.242 | 40.380 | -8.581 | 0.35 | 29.18 |
| 8215 | OE1A | GLN | B | 258 | 9.502 | 42.893 | -7.025 | 0.65 | 34.64 |
| 8216 | NE2B | GLN | B | 258 | 11.163 | 42.126 | -7.646 | 0.35 | 29.79 |
| 8217 | NE2A | GLN | B | 258 | 9.094 | 42.705 | -4.820 | 0.65 | 34.91 |
| 8222 | C | GLN | B | 258 | 11.455 | 41.638 | -2.614 | 1.00 | 29.97 |
| 8223 | O | GLN | B | 258 | 11.755 | 42.780 | -2.274 | 1.00 | 29.34 |
| 8224 | N | GLN | B | 259 | 10.439 | 40.957 | -2.080 | 1.00 | 30.70 |
| 8226 | CA | GLN | B | 259 | 9.658 | 41.427 | -0.922 | 1.00 | 31.61 |
| 8228 | CB | GLN | B | 259 | 8.769 | 40.285 | -0.410 | 1.00 | 32.41 |

FIGURE 3 DB

| A | B | C | D | E | F | G | H | I | J |
|---|---|---|---|---|---|---|---|---|---|
| 8231 | CG | GLN | B | 259 | 7.466 | 40.703 | 0.244 | 1.00 | 35.31 |
| 8234 | CD | GLN | B | 259 | 6.317 | 40.769 | -0.744 | 1.00 | 39.68 |
| 8235 | OE1 | GLN | B | 259 | 5.925 | 41.861 | -1.174 | 1.00 | 43.25 |
| 8236 | NE2 | GLN | B | 259 | 5.780 | 39.605 | -1.119 | 1.00 | 42.40 |
| 8239 | C | GLN | B | 259 | 10.546 | 41.934 | 0.242 | 1.00 | 31.29 |
| 8240 | O | GLN | B | 259 | 10.321 | 43.032 | 0.776 | 1.00 | 31.47 |
| 8241 | N | LEU | B | 260 | 11.552 | 41.135 | 0.612 | 1.00 | 30.18 |
| 8243 | CA | LEU | B | 260 | 12.421 | 41.420 | 1.761 | 1.00 | 29.88 |
| 8245 | CB | LEU | B | 260 | 12.851 | 40.109 | 2.446 | 1.00 | 29.79 |
| 8248 | CG | LEU | B | 260 | 11.792 | 39.268 | 3.160 | 1.00 | 30.18 |
| 8250 | CD1 | LEU | B | 260 | 12.453 | 38.363 | 4.192 | 1.00 | 29.62 |
| 8254 | CD2 | LEU | B | 260 | 10.742 | 40.140 | 3.817 | 1.00 | 31.47 |
| 8258 | C | LEU | B | 260 | 13.681 | 42.207 | 1.413 | 1.00 | 28.94 |
| 8259 | O | LEU | B | 260 | 14.431 | 42.593 | 2.307 | 1.00 | 29.69 |
| 8260 | N | GLY | B | 261 | 13.921 | 42.429 | 0.128 | 1.00 | 27.95 |
| 8262 | CA | GLY | B | 261 | 15.133 | 43.084 | -0.333 | 1.00 | 26.93 |
| 8265 | C | GLY | B | 261 | 16.398 | 42.279 | -0.094 | 1.00 | 25.88 |
| 8266 | O | GLY | B | 261 | 17.436 | 42.845 | 0.261 | 1.00 | 25.61 |
| 8267 | N | LYS | B | 262 | 16.325 | 40.959 | -0.277 | 1.00 | 24.82 |
| 8269 | CA | LYS | B | 262 | 17.501 | 40.115 | -0.136 | 1.00 | 23.75 |
| 8271 | CB | LYS | B | 262 | 17.153 | 38.627 | -0.295 | 1.00 | 23.56 |
| 8274 | CG | LYS | B | 262 | 16.230 | 38.069 | 0.762 | 1.00 | 23.25 |
| 8277 | CD | LYS | B | 262 | 16.916 | 37.862 | 2.096 | 1.00 | 21.56 |
| 8280 | CE | LYS | B | 262 | 15.901 | 37.433 | 3.158 | 1.00 | 23.14 |
| 8283 | NZ | LYS | B | 262 | 16.536 | 37.070 | 4.482 | 1.00 | 21.85 |
| 8287 | C | LYS | B | 262 | 18.515 | 40.497 | -1.195 | 1.00 | 23.58 |
| 8288 | O | LYS | B | 262 | 18.145 | 40.845 | -2.337 | 1.00 | 23.29 |
| 8289 | N | SER | B | 263 | 19.785 | 40.474 | -0.803 | 1.00 | 22.82 |
| 8291 | CA | SER | B | 263 | 20.885 | 40.514 | -1.746 | 1.00 | 22.51 |
| 8293 | CB | SER | B | 263 | 22.206 | 40.785 | -1.035 | 1.00 | 22.93 |
| 8296 | OG | SER | B | 263 | 22.263 | 42.141 | -0.613 | 1.00 | 23.10 |
| 8298 | C | SER | B | 263 | 20.934 | 39.170 | -2.452 | 1.00 | 22.79 |
| 8299 | O | SER | B | 263 | 21.051 | 38.122 | -1.784 | 1.00 | 22.61 |
| 8300 | N | THR | B | 264 | 20.786 | 39.194 | -3.782 | 1.00 | 21.90 |
| 8302 | CA | THR | B | 264 | 20.764 | 37.973 | -4.593 | 1.00 | 22.01 |
| 8304 | CB | THR | B | 264 | 19.304 | 37.496 | -4.909 | 1.00 | 22.17 |
| 8306 | OG1 | THR | B | 264 | 18.667 | 38.392 | -5.827 | 1.00 | 23.42 |
| 8308 | CG2 | THR | B | 264 | 18.386 | 37.525 | -3.707 | 1.00 | 21.68 |
| 8312 | C | THR | B | 264 | 21.499 | 38.175 | -5.908 | 1.00 | 21.99 |
| 8313 | O | THR | B | 264 | 21.731 | 39.306 | -6.354 | 1.00 | 21.16 |
| 8314 | N | TYR | B | 265 | 21.841 | 37.066 | -6.553 | 1.00 | 21.84 |
| 8316 | CA | TYR | B | 265 | 22.470 | 37.134 | -7.864 | 1.00 | 22.04 |
| 8318 | CB | TYR | B | 265 | 22.959 | 35.754 | -8.319 | 1.00 | 21.34 |
| 8321 | CG | TYR | B | 265 | 24.340 | 35.435 | -7.803 | 1.00 | 20.33 |
| 8322 | CD1 | TYR | B | 265 | 25.430 | 35.422 | -8.654 | 1.00 | 20.38 |
| 8324 | CE1 | TYR | B | 265 | 26.686 | 35.129 | -8.197 | 1.00 | 20.95 |
| 8326 | CZ | TYR | B | 265 | 26.877 | 34.859 | -6.866 | 1.00 | 20.10 |
| 8327 | OH | TYR | B | 265 | 28.142 | 34.576 | -6.417 | 1.00 | 24.40 |
| 8329 | CE2 | TYR | B | 265 | 25.818 | 34.876 | -5.989 | 1.00 | 19.89 |
| 8331 | CD2 | TYR | B | 265 | 24.561 | 35.161 | -6.455 | 1.00 | 18.52 |
| 8333 | C | TYR | B | 265 | 21.588 | 37.816 | -8.933 | 1.00 | 22.40 |
| 8334 | O | TYR | B | 265 | 22.075 | 38.711 | -9.612 | 1.00 | 22.20 |

FIGURE 3 DC

| A | B | C | D | E | F | G | H | I | J |
|---|---|---|---|---|---|---|---|---|---|
| 8335 | N | PRO | B | 266 | 20.328 | 37.413 | -9.102 | 1.00 | 22.68 |
| 8336 | CA | PRO | B | 266 | 19.448 | 38.083 | -10.073 | 1.00 | 23.28 |
| 8338 | CB | PRO | B | 266 | 18.131 | 37.309 | -9.984 | 1.00 | 23.44 |
| 8341 | CG | PRO | B | 266 | 18.438 | 36.064 | -9.253 | 1.00 | 23.26 |
| 8344 | CD | PRO | B | 266 | 19.635 | 36.319 | -8.412 | 1.00 | 23.08 |
| 8347 | C | PRO | B | 266 | 19.193 | 39.550 | -9.744 | 1.00 | 23.45 |
| 8348 | O | PRO | B | 266 | 19.084 | 40.350 | -10.668 | 1.00 | 23.18 |
| 8349 | N | ALA | B | 267 | 19.099 | 39.890 | -8.460 | 1.00 | 23.47 |
| 8351 | CA | ALA | B | 267 | 18.821 | 41.268 | -8.062 | 1.00 | 23.58 |
| 8353 | CB | ALA | B | 267 | 18.569 | 41.386 | -6.560 | 1.00 | 23.84 |
| 8357 | C | ALA | B | 267 | 19.962 | 42.155 | -8.483 | 1.00 | 23.82 |
| 8358 | O | ALA | B | 267 | 19.742 | 43.216 | -9.062 | 1.00 | 24.38 |
| 8359 | N | LEU | B | 268 | 21.184 | 41.692 | -8.247 | 1.00 | 23.53 |
| 8361 | CA | LEU | B | 268 | 22.375 | 42.447 | -8.586 | 1.00 | 23.59 |
| 8363 | CB | LEU | B | 268 | 23.566 | 41.908 | -7.798 | 1.00 | 23.51 |
| 8366 | CG | LEU | B | 268 | 24.934 | 42.511 | -8.113 | 1.00 | 23.92 |
| 8368 | CD1 | LEU | B | 268 | 24.947 | 44.021 | -7.830 | 1.00 | 24.92 |
| 8372 | CD2 | LEU | B | 268 | 26.012 | 41.800 | -7.318 | 1.00 | 24.12 |
| 8376 | C | LEU | B | 268 | 22.704 | 42.437 | -10.082 | 1.00 | 23.25 |
| 8377 | O | LEU | B | 268 | 22.964 | 43.479 | -10.664 | 1.00 | 23.31 |
| 8378 | N | LEU | B | 269 | 22.693 | 41.253 | -10.683 | 1.00 | 22.76 |
| 8380 | CA | LEU | B | 269 | 23.281 | 41.018 | -11.995 | 1.00 | 22.56 |
| 8382 | CB | LEU | B | 269 | 24.093 | 39.726 | -11.983 | 1.00 | 22.53 |
| 8385 | CG | LEU | B | 269 | 25.314 | 39.686 | -11.062 | 1.00 | 24.16 |
| 8387 | CD1 | LEU | B | 269 | 25.881 | 38.277 | -11.022 | 1.00 | 25.08 |
| 8391 | CD2 | LEU | B | 269 | 26.394 | 40.674 | -11.518 | 1.00 | 25.88 |
| 8395 | C | LEU | B | 269 | 22.237 | 40.925 | -13.089 | 1.00 | 21.93 |
| 8396 | O | LEU | B | 269 | 22.567 | 40.925 | -14.273 | 1.00 | 21.98 |
| 8397 | N | GLY | B | 270 | 20.981 | 40.880 | -12.696 | 1.00 | 21.10 |
| 8399 | CA | GLY | B | 270 | 19.925 | 40.537 | -13.619 | 1.00 | 21.48 |
| 8402 | C | GLY | B | 270 | 19.923 | 39.035 | -13.860 | 1.00 | 21.79 |
| 8403 | O | GLY | B | 270 | 20.883 | 38.320 | -13.530 | 1.00 | 20.41 |
| 8404 | N | LEU | B | 271 | 18.831 | 38.570 | -14.445 | 1.00 | 22.27 |
| 8406 | CA | LEU | B | 271 | 18.587 | 37.145 | -14.645 | 1.00 | 23.11 |
| 8408 | CB | LEU | B | 271 | 17.169 | 36.923 | -15.161 | 1.00 | 23.57 |
| 8411 | CG | LEU | B | 271 | 16.145 | 36.966 | -14.051 | 1.00 | 23.96 |
| 8413 | CD1 | LEU | B | 271 | 14.712 | 36.988 | -14.638 | 1.00 | 25.68 |
| 8417 | CD2 | LEU | B | 271 | 16.375 | 35.748 | -13.152 | 1.00 | 24.82 |
| 8421 | C | LEU | B | 271 | 19.554 | 36.493 | -15.601 | 1.00 | 23.62 |
| 8422 | O | LEU | B | 271 | 19.999 | 35.393 | -15.348 | 1.00 | 22.96 |
| 8423 | N | GLU | B | 272 | 19.885 | 37.158 | -16.704 | 1.00 | 24.28 |
| 8425 | CA | GLU | B | 272 | 20.703 | 36.498 | -17.715 | 1.00 | 25.35 |
| 8427 | CB | GLU | B | 272 | 20.712 | 37.237 | -19.049 | 1.00 | 26.22 |
| 8430 | CG | GLU | B | 272 | 21.247 | 36.373 | -20.184 | 1.00 | 30.72 |
| 8433 | CD | GLU | B | 272 | 20.177 | 35.523 | -20.858 | 1.00 | 36.13 |
| 8434 | OE1 | GLU | B | 272 | 19.801 | 35.857 | -22.020 | 1.00 | 40.61 |
| 8435 | OE2 | GLU | B | 272 | 19.725 | 34.513 | -20.244 | 1.00 | 38.13 |
| 8436 | C | GLU | B | 272 | 22.116 | 36.293 | -17.220 | 1.00 | 24.46 |
| 8437 | O | GLU | B | 272 | 22.658 | 35.215 | -17.405 | 1.00 | 23.99 |
| 8438 | N | GLN | B | 273 | 22.707 | 37.305 | -16.582 | 1.00 | 23.54 |
| 8440 | CA | GLN | B | 273 | 24.052 | 37.148 | -16.019 | 1.00 | 23.89 |
| 8442 | CB | GLN | B | 273 | 24.640 | 38.488 | -15.569 | 1.00 | 23.95 |

FIGURE 3 DD

| A | B | C | D | E | F | G | H | I | J |
|---|---|---|---|---|---|---|---|---|---|
| 8445 | CG | GLN | B | 273 | 25.057 | 39.407 | -16.701 | 1.00 | 26.62 |
| 8448 | CD | GLN | B | 273 | 25.436 | 40.804 | -16.197 | 1.00 | 29.62 |
| 8449 | OE1 | GLN | B | 273 | 26.041 | 40.939 | -15.140 | 1.00 | 29.56 |
| 8450 | NE2 | GLN | B | 273 | 25.046 | 41.834 | -16.941 | 1.00 | 32.63 |
| 8453 | C | GLN | B | 273 | 24.042 | 36.157 | -14.848 | 1.00 | 23.16 |
| 8454 | O | GLN | B | 273 | 24.994 | 35.428 | -14.656 | 1.00 | 23.94 |
| 8455 | N | ALA | B | 274 | 22.968 | 36.130 | -14.071 | 1.00 | 22.86 |
| 8457 | CA | ALA | B | 274 | 22.852 | 35.161 | -12.985 | 1.00 | 22.78 |
| 8459 | CB | ALA | B | 274 | 21.591 | 35.413 | -12.169 | 1.00 | 22.56 |
| 8463 | C | ALA | B | 274 | 22.848 | 33.738 | -13.565 | 1.00 | 22.60 |
| 8464 | O | ALA | B | 274 | 23.542 | 32.873 | -13.071 | 1.00 | 22.64 |
| 8465 | N | ARG | B | 275 | 22.085 | 33.520 | -14.632 | 1.00 | 22.89 |
| 8467 | CA | ARG | B | 275 | 22.048 | 32.213 | -15.299 | 1.00 | 23.30 |
| 8469 | CB | ARG | B | 275 | 21.012 | 32.205 | -16.431 | 1.00 | 23.67 |
| 8472 | CG | ARG | B | 275 | 19.594 | 32.090 | -15.944 | 1.00 | 25.28 |
| 8475 | CD | ARG | B | 275 | 18.542 | 32.199 | -17.031 | 1.00 | 27.92 |
| 8478 | NE | ARG | B | 275 | 17.209 | 31.888 | -16.503 | 1.00 | 30.36 |
| 8480 | CZ | ARG | B | 275 | 16.104 | 32.616 | -16.697 | 1.00 | 32.35 |
| 8481 | NH1 | ARG | B | 275 | 16.121 | 33.727 | -17.423 | 1.00 | 31.95 |
| 8484 | NH2 | ARG | B | 275 | 14.954 | 32.217 | -16.160 | 1.00 | 34.03 |
| 8487 | C | ARG | B | 275 | 23.424 | 31.827 | -15.854 | 1.00 | 23.20 |
| 8488 | O | ARG | B | 275 | 23.843 | 30.669 | -15.783 | 1.00 | 22.27 |
| 8489 | N | LYS | B | 276 | 24.111 | 32.807 | -16.421 | 1.00 | 23.01 |
| 8491 | CA | LYS | B | 276 | 25.418 | 32.595 | -16.998 | 1.00 | 22.90 |
| 8493 | CB | LYS | B | 276 | 25.870 | 33.833 | -17.774 | 1.00 | 23.16 |
| 8496 | CG | LYS | B | 276 | 27.307 | 33.794 | -18.251 | 1.00 | 24.89 |
| 8499 | CD | LYS | B | 276 | 27.542 | 32.619 | -19.190 | 1.00 | 28.29 |
| 8502 | CE | LYS | B | 276 | 28.672 | 32.892 | -20.166 | 1.00 | 29.58 |
| 8505 | NZ | LYS | B | 276 | 29.948 | 33.113 | -19.451 | 1.00 | 30.99 |
| 8509 | C | LYS | B | 276 | 26.422 | 32.253 | -15.893 | 1.00 | 22.40 |
| 8510 | O | LYS | B | 276 | 27.270 | 31.400 | -16.086 | 1.00 | 22.05 |
| 8511 | N | LYS | B | 277 | 26.312 | 32.901 | -14.742 | 1.00 | 21.92 |
| 8513 | CA | LYS | B | 277 | 27.191 | 32.604 | -13.612 | 1.00 | 22.26 |
| 8515 | CB | LYS | B | 277 | 26.959 | 33.566 | -12.444 | 1.00 | 22.86 |
| 8518 | CG | LYS | B | 277 | 27.325 | 35.029 | -12.759 | 1.00 | 26.57 |
| 8521 | CD | LYS | B | 277 | 28.574 | 35.530 | -12.019 | 1.00 | 30.08 |
| 8524 | CE | LYS | B | 277 | 29.067 | 36.885 | -12.583 | 1.00 | 31.95 |
| 8527 | NZ | LYS | B | 277 | 30.540 | 37.060 | -12.449 | 1.00 | 33.10 |
| 8531 | C | LYS | B | 277 | 26.982 | 31.151 | -13.175 | 1.00 | 21.47 |
| 8532 | O | LYS | B | 277 | 27.939 | 30.422 | -12.944 | 1.00 | 21.43 |
| 8533 | N | ALA | B | 278 | 25.725 | 30.729 | -13.101 | 1.00 | 20.57 |
| 8535 | CA | ALA | B | 278 | 25.408 | 29.366 | -12.697 | 1.00 | 20.64 |
| 8537 | CB | ALA | B | 278 | 23.881 | 29.171 | -12.552 | 1.00 | 20.42 |
| 8541 | C | ALA | B | 278 | 25.990 | 28.377 | -13.699 | 1.00 | 20.27 |
| 8542 | O | ALA | B | 278 | 26.607 | 27.383 | -13.306 | 1.00 | 19.24 |
| 8543 | N | ARG | B | 279 | 25.819 | 28.639 | -14.990 | 1.00 | 20.74 |
| 8545 | CA | ARG | B | 279 | 26.307 | 27.695 | -15.997 | 1.00 | 21.12 |
| 8547 | CB | ARG | B | 279 | 25.765 | 28.003 | -17.392 | 1.00 | 21.76 |
| 8550 | CG | ARG | B | 279 | 26.088 | 26.897 | -18.402 | 1.00 | 22.89 |
| 8553 | CD | ARG | B | 279 | 25.654 | 27.222 | -19.814 | 1.00 | 25.89 |
| 8556 | NE | ARG | B | 279 | 26.498 | 28.272 | -20.382 | 1.00 | 26.63 |
| 8558 | CZ | ARG | B | 279 | 26.296 | 28.833 | -21.562 | 1.00 | 26.13 |

FIGURE 3 DE

| A | B | C | D | E | F | G | H | I | J |
|---|---|---|---|---|---|---|---|---|---|
| 8559 | NH1 | ARG | B | 279 | 25.253 | 28.490 | -22.311 | 1.00 | 24.20 |
| 8562 | NH2 | ARG | B | 279 | 27.138 | 29.760 | -21.981 | 1.00 | 25.45 |
| 8565 | C | ARG | B | 279 | 27.831 | 27.650 | -16.001 | 1.00 | 21.30 |
| 8566 | O | ARG | B | 279 | 28.416 | 26.590 | -16.177 | 1.00 | 21.07 |
| 8567 | N | ASP | B | 280 | 28.461 | 28.795 | -15.766 | 1.00 | 21.40 |
| 8569 | CA | ASP | B | 280 | 29.915 | 28.874 | -15.595 | 1.00 | 21.87 |
| 8571 | CB | ASP | B | 280 | 30.335 | 30.327 | -15.313 | 1.00 | 22.54 |
| 8574 | CG | ASP | B | 280 | 30.370 | 31.200 | -16.579 | 1.00 | 25.24 |
| 8575 | OD1 | ASP | B | 280 | 30.630 | 32.424 | -16.457 | 1.00 | 28.05 |
| 8576 | OD2 | ASP | B | 280 | 30.138 | 30.759 | -17.724 | 1.00 | 26.91 |
| 8577 | C | ASP | B | 280 | 30.401 | 27.958 | -14.456 | 1.00 | 21.04 |
| 8578 | O | ASP | B | 280 | 31.440 | 27.297 | -14.562 | 1.00 | 20.76 |
| 8579 | N | LEU | B | 281 | 29.633 | 27.922 | -13.372 | 1.00 | 20.21 |
| 8581 | CA | LEU | B | 281 | 29.994 | 27.151 | -12.188 | 1.00 | 19.69 |
| 8583 | CB | LEU | B | 281 | 29.141 | 27.569 | -10.992 | 1.00 | 19.82 |
| 8586 | CG | LEU | B | 281 | 29.530 | 28.953 | -10.452 | 1.00 | 18.53 |
| 8588 | CD1 | LEU | B | 281 | 28.423 | 29.532 | -9.589 | 1.00 | 19.63 |
| 8592 | CD2 | LEU | B | 281 | 30.812 | 28.869 | -9.646 | 1.00 | 19.99 |
| 8596 | C | LEU | B | 281 | 29.838 | 25.670 | -12.468 | 1.00 | 19.73 |
| 8597 | O | LEU | B | 281 | 30.671 | 24.889 | -12.094 | 1.00 | 20.05 |
| 8598 | N | ILE | B | 282 | 28.774 | 25.295 | -13.150 | 1.00 | 20.33 |
| 8600 | CA | ILE | B | 282 | 28.597 | 23.906 | -13.555 | 1.00 | 21.14 |
| 8602 | CB | ILE | B | 282 | 27.190 | 23.672 | -14.076 | 1.00 | 21.02 |
| 8604 | CG1 | ILE | B | 282 | 26.178 | 23.925 | -12.949 | 1.00 | 22.56 |
| 8607 | CD1 | ILE | B | 282 | 26.532 | 23.265 | -11.610 | 1.00 | 22.71 |
| 8611 | CG2 | ILE | B | 282 | 27.041 | 22.244 | -14.624 | 1.00 | 21.66 |
| 8615 | C | ILE | B | 282 | 29.659 | 23.477 | -14.566 | 1.00 | 21.32 |
| 8616 | O | ILE | B | 282 | 30.149 | 22.359 | -14.488 | 1.00 | 21.92 |
| 8617 | N | ASP | B | 283 | 30.032 | 24.358 | -15.487 | 1.00 | 21.87 |
| 8619 | CA | ASP | B | 283 | 31.112 | 24.056 | -16.430 | 1.00 | 22.32 |
| 8621 | CB | ASP | B | 283 | 31.436 | 25.261 | -17.330 | 1.00 | 22.60 |
| 8624 | CG | ASP | B | 283 | 30.410 | 25.503 | -18.417 | 1.00 | 23.70 |
| 8625 | OD1 | ASP | B | 283 | 30.445 | 26.623 | -18.989 | 1.00 | 26.27 |
| 8626 | OD2 | ASP | B | 283 | 29.548 | 24.676 | -18.786 | 1.00 | 22.23 |
| 8627 | C | ASP | B | 283 | 32.369 | 23.705 | -15.624 | 1.00 | 22.25 |
| 8628 | O | ASP | B | 283 | 33.066 | 22.756 | -15.928 | 1.00 | 21.47 |
| 8629 | N | ASP | B | 284 | 32.636 | 24.490 | -14.588 | 1.00 | 22.34 |
| 8631 | CA | ASP | B | 284 | 33.793 | 24.291 | -13.731 | 1.00 | 23.23 |
| 8633 | CB | ASP | B | 284 | 33.980 | 25.509 | -12.820 | 1.00 | 23.34 |
| 8636 | CG | ASP | B | 284 | 35.161 | 25.368 | -11.918 | 1.00 | 26.31 |
| 8637 | OD1 | ASP | B | 284 | 36.305 | 25.530 | -12.420 | 1.00 | 28.34 |
| 8638 | OD2 | ASP | B | 284 | 35.037 | 25.088 | -10.697 | 1.00 | 28.06 |
| 8639 | C | ASP | B | 284 | 33.670 | 22.986 | -12.925 | 1.00 | 22.69 |
| 8640 | O | ASP | B | 284 | 34.641 | 22.234 | -12.816 | 1.00 | 22.49 |
| 8641 | N | ALA | B | 285 | 32.474 | 22.703 | -12.405 | 1.00 | 22.19 |
| 8643 | CA | ALA | B | 285 | 32.204 | 21.431 | -11.725 | 1.00 | 22.57 |
| 8645 | CB | ALA | B | 285 | 30.752 | 21.361 | -11.263 | 1.00 | 22.03 |
| 8649 | C | ALA | B | 285 | 32.524 | 20.233 | -12.631 | 1.00 | 22.99 |
| 8650 | O | ALA | B | 285 | 33.151 | 19.270 | -12.190 | 1.00 | 22.66 |
| 8651 | N | ARG | B | 286 | 32.115 | 20.321 | -13.895 | 1.00 | 23.78 |
| 8653 | CA | ARG | B | 286 | 32.394 | 19.283 | -14.883 | 1.00 | 25.16 |
| 8655 | CB | ARG | B | 286 | 31.628 | 19.550 | -16.180 | 1.00 | 25.91 |

FIGURE 3 DF

| A | B | C | D | E | F | G | H | I | J |
|---|---|---|---|---|---|---|---|---|---|
| 8658 | CG | ARG | B | 286 | 30.138 | 19.170 | -16.097 | 1.00 | 28.32 |
| 8661 | CD | BARG | B | 286 | 29.468 | 18.992 | -17.466 | 0.35 | 29.52 |
| 8662 | CD | AARG | B | 286 | 29.453 | 19.007 | -17.451 | 0.65 | 30.92 |
| 8667 | NE | BARG | B | 286 | 29.262 | 20.264 | -18.163 | 0.35 | 29.83 |
| 8668 | NE | AARG | B | 286 | 28.271 | 18.146 | -17.365 | 0.65 | 31.71 |
| 8671 | CZ | BARG | B | 286 | 28.839 | 20.386 | -19.423 | 0.35 | 30.53 |
| 8672 | CZ | AARG | B | 286 | 28.231 | 16.856 | -17.684 | 0.65 | 33.32 |
| 8673 | NH1 | BARG | B | 286 | 28.567 | 19.313 | -20.165 | 0.35 | 30.23 |
| 8674 | NH1 | AARG | B | 286 | 29.309 | 16.209 | -18.125 | 0.65 | 33.00 |
| 8679 | NH2 | BARG | B | 286 | 28.688 | 21.596 | -19.951 | 0.35 | 30.87 |
| 8680 | NH2 | AARG | B | 286 | 27.089 | 16.195 | -17.563 | 0.65 | 33.96 |
| 8685 | C | ARG | B | 286 | 33.894 | 19.108 | -15.170 | 1.00 | 25.22 |
| 8686 | O | ARG | B | 286 | 34.349 | 17.988 | -15.388 | 1.00 | 24.81 |
| 8687 | N | GLN | B | 287 | 34.651 | 20.204 | -15.171 | 1.00 | 25.23 |
| 8689 | CA | GLN | B | 287 | 36.100 | 20.116 | -15.322 | 1.00 | 25.93 |
| 8691 | CB | GLN | B | 287 | 36.756 | 21.497 | -15.472 | 1.00 | 26.28 |
| 8694 | CG | GLN | B | 287 | 36.425 | 22.206 | -16.775 | 1.00 | 29.31 |
| 8697 | CD | GLN | B | 287 | 37.009 | 21.533 | -18.012 | 1.00 | 32.74 |
| 8698 | OE1 | GLN | B | 287 | 38.047 | 20.880 | -17.945 | 1.00 | 35.76 |
| 8699 | NE2 | GLN | B | 287 | 36.340 | 21.706 | -19.144 | 1.00 | 35.59 |
| 8702 | C | GLN | B | 287 | 36.706 | 19.364 | -14.131 | 1.00 | 25.31 |
| 8703 | O | GLN | B | 287 | 37.565 | 18.521 | -14.333 | 1.00 | 24.00 |
| 8704 | N | SER | B | 288 | 36.241 | 19.658 | -12.905 | 1.00 | 25.12 |
| 8706 | CA | SER | B | 288 | 36.665 | 18.911 | -11.720 | 1.00 | 25.39 |
| 8708 | CB | SER | B | 288 | 36.105 | 19.510 | -10.414 | 1.00 | 25.38 |
| 8711 | OG | SER | B | 288 | 36.557 | 20.834 | -10.215 | 1.00 | 24.82 |
| 8713 | C | SER | B | 288 | 36.289 | 17.433 | -11.820 | 1.00 | 25.78 |
| 8714 | O | SER | B | 288 | 37.077 | 16.569 | -11.459 | 1.00 | 25.49 |
| 8715 | N | LEU | B | 289 | 35.098 | 17.125 | -12.321 | 1.00 | 26.38 |
| 8717 | CA | LEU | B | 289 | 34.709 | 15.726 | -12.441 | 1.00 | 27.10 |
| 8719 | CB | LEU | B | 289 | 33.237 | 15.580 | -12.838 | 1.00 | 26.93 |
| 8722 | CG | LEU | B | 289 | 32.258 | 15.977 | -11.729 | 1.00 | 25.30 |
| 8724 | CD1 | LEU | B | 289 | 30.821 | 15.804 | -12.200 | 1.00 | 25.85 |
| 8728 | CD2 | LEU | B | 289 | 32.524 | 15.189 | -10.431 | 1.00 | 25.23 |
| 8732 | C | LEU | B | 289 | 35.635 | 14.995 | -13.425 | 1.00 | 28.16 |
| 8733 | O | LEU | B | 289 | 35.998 | 13.854 | -13.186 | 1.00 | 28.16 |
| 8734 | N | LYS | B | 290 | 36.053 | 15.677 | -14.487 | 1.00 | 29.02 |
| 8736 | CA | LYS | B | 290 | 36.961 | 15.096 | -15.481 | 1.00 | 30.79 |
| 8738 | CB | LYS | B | 290 | 37.313 | 16.118 | -16.587 | 1.00 | 30.97 |
| 8741 | CG | LYS | B | 290 | 36.966 | 15.687 | -18.011 | 1.00 | 33.97 |
| 8744 | CD | LYS | B | 290 | 36.614 | 16.900 | -18.921 | 1.00 | 36.64 |
| 8747 | CE | LYS | B | 290 | 35.099 | 17.019 | -19.182 | 1.00 | 37.79 |
| 8750 | NZ | LYS | B | 290 | 34.637 | 18.445 | -19.343 | 1.00 | 38.84 |
| 8754 | C | LYS | B | 290 | 38.244 | 14.611 | -14.809 | 1.00 | 31.28 |
| 8755 | O | LYS | B | 290 | 38.750 | 13.544 | -15.141 | 1.00 | 31.44 |
| 8756 | N | GLN | B | 291 | 38.759 | 15.401 | -13.869 | 1.00 | 32.13 |
| 8758 | CA | GLN | B | 291 | 39.978 | 15.054 | -13.152 | 1.00 | 33.58 |
| 8760 | CB | GLN | B | 291 | 40.470 | 16.251 | -12.326 | 1.00 | 33.80 |
| 8763 | CG | GLN | B | 291 | 40.818 | 17.493 | -13.167 | 1.00 | 35.12 |
| 8766 | CD | GLN | B | 291 | 40.846 | 18.775 | -12.353 | 1.00 | 36.83 |
| 8767 | OE1 | GLN | B | 291 | 41.175 | 18.756 | -11.168 | 1.00 | 36.95 |
| 8768 | NE2 | GLN | B | 291 | 40.495 | 19.893 | -12.985 | 1.00 | 38.40 |

FIGURE 3 DG

| A | B | C | D | E | F | G | H | I | J |
|---|---|---|---|---|---|---|---|---|---|
| 8771 | C | GLN | B | 291 | 39.800 | 13.810 | -12.265 | 1.00 | 34.42 |
| 8772 | O | GLN | B | 291 | 40.764 | 13.098 | -12.013 | 1.00 | 34.62 |
| 8773 | N | LEU | B | 292 | 38.577 | 13.568 | -11.784 | 1.00 | 35.42 |
| 8775 | CA | LEU | B | 292 | 38.248 | 12.364 | -10.999 | 1.00 | 36.35 |
| 8777 | CB | LEU | B | 292 | 36.931 | 12.542 | -10.251 | 1.00 | 36.39 |
| 8780 | CG | LEU | B | 292 | 36.924 | 13.515 | -9.082 | 1.00 | 36.49 |
| 8782 | CD1 | LEU | B | 292 | 35.562 | 13.491 | -8.411 | 1.00 | 36.85 |
| 8786 | CD2 | LEU | B | 292 | 38.023 | 13.153 | -8.101 | 1.00 | 36.84 |
| 8790 | C | LEU | B | 292 | 38.141 | 11.088 | -11.820 | 1.00 | 37.54 |
| 8791 | O | LEU | B | 292 | 38.519 | 10.015 | -11.352 | 1.00 | 37.33 |
| 8792 | N | ALA | B | 293 | 37.598 | 11.193 | -13.028 | 1.00 | 38.95 |
| 8794 | CA | ALA | B | 293 | 37.635 | 10.088 | -13.974 | 1.00 | 40.14 |
| 8796 | CB | ALA | B | 293 | 36.587 | 10.291 | -15.078 | 1.00 | 40.36 |
| 8800 | C | ALA | B | 293 | 39.045 | 9.950 | -14.565 | 1.00 | 40.76 |
| 8801 | O | ALA | B | 293 | 39.206 | 9.462 | -15.677 | 1.00 | 41.94 |
| 8802 | N | GLU | B | 294 | 40.045 | 10.442 | -13.834 | 1.00 | 41.22 |
| 8804 | CA | GLU | B | 294 | 41.456 | 10.118 | -14.039 | 1.00 | 41.53 |
| 8806 | CB | GLU | B | 294 | 42.240 | 11.402 | -14.318 | 1.00 | 41.94 |
| 8809 | CG | GLU | B | 294 | 43.620 | 11.186 | -14.911 | 1.00 | 44.01 |
| 8812 | CD | GLU | B | 294 | 44.144 | 12.428 | -15.604 | 1.00 | 45.96 |
| 8813 | OE1 | GLU | B | 294 | 44.166 | 13.499 | -14.953 | 1.00 | 48.06 |
| 8814 | OE2 | GLU | B | 294 | 44.528 | 12.332 | -16.794 | 1.00 | 47.73 |
| 8815 | C | GLU | B | 294 | 42.047 | 9.414 | -12.808 | 1.00 | 40.89 |
| 8816 | O | GLU | B | 294 | 43.185 | 8.941 | -12.846 | 1.00 | 41.57 |
| 8817 | N | GLN | B | 295 | 41.295 | 9.399 | -11.705 | 1.00 | 39.90 |
| 8819 | CA | GLN | B | 295 | 41.549 | 8.516 | -10.565 | 1.00 | 38.66 |
| 8821 | CB | GLN | B | 295 | 41.248 | 9.243 | -9.243 | 1.00 | 38.65 |
| 8824 | CG | GLN | B | 295 | 41.958 | 10.592 | -9.083 | 1.00 | 38.47 |
| 8827 | CD | GLN | B | 295 | 41.556 | 11.354 | -7.816 | 1.00 | 37.66 |
| 8828 | OE1 | GLN | B | 295 | 41.179 | 10.751 | -6.807 | 1.00 | 36.11 |
| 8829 | NE2 | GLN | B | 295 | 41.658 | 12.686 | -7.867 | 1.00 | 36.75 |
| 8832 | C | GLN | B | 295 | 40.681 | 7.258 | -10.689 | 1.00 | 37.75 |
| 8833 | O | GLN | B | 295 | 40.432 | 6.560 | -9.698 | 1.00 | 37.50 |
| 8834 | N | SER | B | 296 | 40.220 | 6.995 | -11.914 | 1.00 | 36.44 |
| 8836 | CA | SER | B | 296 | 39.373 | 5.852 | -12.261 | 1.00 | 35.92 |
| 8838 | CB | SER | B | 296 | 40.117 | 4.541 | -12.022 | 1.00 | 36.22 |
| 8841 | OG | SER | B | 296 | 39.666 | 3.572 | -12.955 | 1.00 | 38.05 |
| 8843 | C | SER | B | 296 | 38.003 | 5.810 | -11.566 | 1.00 | 34.56 |
| 8844 | O | SER | B | 296 | 37.551 | 4.753 | -11.143 | 1.00 | 34.47 |
| 8845 | N | LEU | B | 297 | 37.330 | 6.952 | -11.485 | 1.00 | 32.72 |
| 8847 | CA | LEU | B | 297 | 36.060 | 7.022 | -10.773 | 1.00 | 31.10 |
| 8849 | CB | LEU | B | 297 | 36.114 | 8.107 | -9.699 | 1.00 | 30.86 |
| 8852 | CG | LEU | B | 297 | 37.166 | 7.891 | -8.611 | 1.00 | 30.39 |
| 8854 | CD1 | LEU | B | 297 | 37.381 | 9.150 | -7.786 | 1.00 | 30.04 |
| 8858 | CD2 | LEU | B | 297 | 36.771 | 6.739 | -7.721 | 1.00 | 30.69 |
| 8862 | C | LEU | B | 297 | 34.910 | 7.286 | -11.724 | 1.00 | 30.21 |
| 8863 | O | LEU | B | 297 | 35.045 | 8.047 | -12.684 | 1.00 | 29.81 |
| 8864 | N | ASP | B | 298 | 33.776 | 6.655 | -11.425 | 1.00 | 28.91 |
| 8866 | CA | ASP | B | 298 | 32.541 | 6.834 | -12.171 | 1.00 | 28.55 |
| 8868 | CB | ASP | B | 298 | 31.659 | 5.597 | -12.005 | 1.00 | 28.67 |
| 8871 | CG | ASP | B | 298 | 30.377 | 5.661 | -12.823 | 1.00 | 30.58 |
| 8872 | OD1 | ASP | B | 298 | 30.141 | 6.682 | -13.512 | 1.00 | 31.79 |

FIGURE 3 DH

| A | B | C | D | E | F | G | H | I | J |
|---|---|---|---|---|---|---|---|---|---|
| 8873 | OD2 | ASP | B | 298 | 29.534 | 4.729 | -12.815 | 1.00 | 33.35 |
| 8874 | C | ASP | B | 298 | 31.830 | 8.086 | -11.662 | 1.00 | 27.64 |
| 8875 | O | ASP | B | 298 | 31.132 | 8.050 | -10.649 | 1.00 | 26.94 |
| 8876 | N | THR | B | 299 | 32.007 | 9.187 | -12.390 | 1.00 | 26.96 |
| 8878 | CA | THR | B | 299 | 31.424 | 10.478 | -12.020 | 1.00 | 26.33 |
| 8880 | CB | THR | B | 299 | 32.352 | 11.615 | -12.471 | 1.00 | 26.05 |
| 8882 | OG1 | THR | B | 299 | 32.571 | 11.538 | -13.882 | 1.00 | 27.18 |
| 8884 | CG2 | THR | B | 299 | 33.740 | 11.457 | -11.879 | 1.00 | 26.15 |
| 8888 | C | THR | B | 299 | 30.006 | 10.704 | -12.588 | 1.00 | 25.98 |
| 8889 | O | THR | B | 299 | 29.464 | 11.785 | -12.453 | 1.00 | 25.98 |
| 8890 | N | SER | B | 300 | 29.392 | 9.682 | -13.176 | 1.00 | 25.39 |
| 8892 | CA | SER | B | 300 | 28.130 | 9.855 | -13.906 | 1.00 | 25.11 |
| 8894 | CB | SER | B | 300 | 27.672 | 8.535 | -14.531 | 1.00 | 25.29 |
| 8897 | OG | SER | B | 300 | 27.346 | 7.581 | -13.529 | 1.00 | 27.52 |
| 8899 | C | SER | B | 300 | 27.004 | 10.479 | -13.077 | 1.00 | 24.18 |
| 8900 | O | SER | B | 300 | 26.340 | 11.391 | -13.553 | 1.00 | 23.89 |
| 8901 | N | ALA | B | 301 | 26.788 | 10.001 | -11.850 | 1.00 | 23.33 |
| 8903 | CA | ALA | B | 301 | 25.756 | 10.590 | -10.983 | 1.00 | 22.98 |
| 8905 | CB | ALA | B | 301 | 25.555 | 9.776 | -9.736 | 1.00 | 22.98 |
| 8909 | C | ALA | B | 301 | 26.051 | 12.044 | -10.605 | 1.00 | 22.43 |
| 8910 | O | ALA | B | 301 | 25.138 | 12.850 | -10.585 | 1.00 | 21.51 |
| 8911 | N | LEU | B | 302 | 27.321 | 12.361 | -10.309 | 1.00 | 22.10 |
| 8913 | CA | LEU | B | 302 | 27.705 | 13.698 | -9.887 | 1.00 | 21.91 |
| 8915 | CB | LEU | B | 302 | 29.102 | 13.715 | -9.268 | 1.00 | 21.74 |
| 8918 | CG | LEU | B | 302 | 29.295 | 12.964 | -7.951 | 1.00 | 22.89 |
| 8920 | CD1 | LEU | B | 302 | 30.736 | 13.126 | -7.523 | 1.00 | 23.47 |
| 8924 | CD2 | LEU | B | 302 | 28.338 | 13.420 | -6.858 | 1.00 | 23.02 |
| 8928 | C | LEU | B | 302 | 27.651 | 14.663 | -11.058 | 1.00 | 22.32 |
| 8929 | O | LEU | B | 302 | 27.411 | 15.858 | -10.863 | 1.00 | 21.59 |
| 8930 | N | GLU | B | 303 | 27.861 | 14.144 | -12.270 | 1.00 | 22.83 |
| 8932 | CA | GLU | B | 303 | 27.716 | 14.933 | -13.480 | 1.00 | 23.58 |
| 8934 | CB | GLU | B | 303 | 28.227 | 14.192 | -14.720 | 1.00 | 24.19 |
| 8937 | CG | GLU | B | 303 | 29.708 | 13.867 | -14.789 | 1.00 | 27.75 |
| 8940 | CD | GLU | B | 303 | 30.025 | 12.941 | -15.962 | 1.00 | 31.36 |
| 8941 | OE1 | GLU | B | 303 | 29.515 | 13.205 | -17.070 | 1.00 | 34.68 |
| 8942 | OE2 | GLU | B | 303 | 30.758 | 11.938 | -15.784 | 1.00 | 33.57 |
| 8943 | C | GLU | B | 303 | 26.241 | 15.247 | -13.705 | 1.00 | 23.21 |
| 8944 | O | GLU | B | 303 | 25.897 | 16.382 | -14.000 | 1.00 | 23.30 |
| 8945 | N | ALA | B | 304 | 25.378 | 14.238 | -13.592 | 1.00 | 22.93 |
| 8947 | CA | ALA | B | 304 | 23.954 | 14.418 | -13.865 | 1.00 | 23.17 |
| 8949 | CB | ALA | B | 304 | 23.219 | 13.063 | -13.846 | 1.00 | 23.72 |
| 8953 | C | ALA | B | 304 | 23.348 | 15.383 | -12.844 | 1.00 | 22.99 |
| 8954 | O | ALA | B | 304 | 22.530 | 16.240 | -13.186 | 1.00 | 22.84 |
| 8955 | N | LEU | B | 305 | 23.786 | 15.250 | -11.596 | 1.00 | 22.47 |
| 8957 | CA | LEU | B | 305 | 23.331 | 16.111 | -10.518 | 1.00 | 22.39 |
| 8959 | CB | LEU | B | 305 | 23.841 | 15.623 | -9.166 | 1.00 | 22.42 |
| 8962 | CG | LEU | B | 305 | 23.319 | 16.420 | -7.973 | 1.00 | 23.49 |
| 8964 | CD1 | LEU | B | 305 | 21.813 | 16.473 | -7.938 | 1.00 | 26.09 |
| 8968 | CD2 | LEU | B | 305 | 23.835 | 15.859 | -6.701 | 1.00 | 25.91 |
| 8972 | C | LEU | B | 305 | 23.766 | 17.540 | -10.732 | 1.00 | 21.68 |
| 8973 | O | LEU | B | 305 | 22.993 | 18.452 | -10.511 | 1.00 | 21.68 |
| 8974 | N | ALA | B | 306 | 25.002 | 17.742 | -11.173 | 1.00 | 21.62 |

FIGURE 3 DI

| A | B | C | D | E | F | G | H | I | J |
|---|---|---|---|---|---|---|---|---|---|
| 8976 | CA | ALA | B | 306 | 25.507 | 19.094 | -11.401 | 1.00 | 21.18 |
| 8978 | CB | ALA | B | 306 | 26.970 | 19.055 | -11.829 | 1.00 | 20.99 |
| 8982 | C | ALA | B | 306 | 24.649 | 19.827 | -12.437 | 1.00 | 21.29 |
| 8983 | O | ALA | B | 306 | 24.260 | 20.978 | -12.221 | 1.00 | 20.84 |
| 8984 | N | ASP | B | 307 | 24.356 | 19.157 | -13.557 | 1.00 | 21.52 |
| 8986 | CA | ASP | B | 307 | 23.462 | 19.700 | -14.575 | 1.00 | 21.89 |
| 8988 | CB | ASP | B | 307 | 23.298 | 18.717 | -15.749 | 1.00 | 22.19 |
| 8991 | CG | ASP | B | 307 | 24.484 | 18.721 | -16.695 | 1.00 | 24.91 |
| 8992 | OD1 | ASP | B | 307 | 25.217 | 19.734 | -16.774 | 1.00 | 27.76 |
| 8993 | OD2 | ASP | B | 307 | 24.754 | 17.744 | -17.418 | 1.00 | 28.49 |
| 8994 | C | ASP | B | 307 | 22.091 | 19.989 | -13.985 | 1.00 | 21.17 |
| 8995 | O | ASP | B | 307 | 21.517 | 21.065 | -14.199 | 1.00 | 21.04 |
| 8996 | N | TYR | B | 308 | 21.566 | 19.037 | -13.226 | 1.00 | 20.68 |
| 8998 | CA | TYR | B | 308 | 20.230 | 19.196 | -12.667 | 1.00 | 21.00 |
| 9000 | CB | TYR | B | 308 | 19.804 | 17.946 | -11.921 | 1.00 | 20.75 |
| 9003 | CG | TYR | B | 308 | 18.419 | 18.039 | -11.344 | 1.00 | 21.19 |
| 9004 | CD1 | TYR | B | 308 | 18.220 | 18.052 | -9.966 | 1.00 | 20.91 |
| 9006 | CE1 | TYR | B | 308 | 16.956 | 18.127 | -9.432 | 1.00 | 21.89 |
| 9008 | CZ | TYR | B | 308 | 15.853 | 18.187 | -10.268 | 1.00 | 24.30 |
| 9009 | OH | TYR | B | 308 | 14.587 | 18.254 | -9.704 | 1.00 | 26.37 |
| 9011 | CE2 | TYR | B | 308 | 16.020 | 18.192 | -11.643 | 1.00 | 23.04 |
| 9013 | CD2 | TYR | B | 308 | 17.299 | 18.112 | -12.174 | 1.00 | 22.71 |
| 9015 | C | TYR | B | 308 | 20.145 | 20.397 | -11.726 | 1.00 | 21.05 |
| 9016 | O | TYR | B | 308 | 19.109 | 21.018 | -11.613 | 1.00 | 20.68 |
| 9017 | N | ILE | B | 309 | 21.239 | 20.713 | -11.043 | 1.00 | 21.13 |
| 9019 | CA | ILE | B | 309 | 21.245 | 21.825 | -10.102 | 1.00 | 21.51 |
| 9021 | CB | ILE | B | 309 | 22.635 | 21.881 | -9.382 | 1.00 | 21.42 |
| 9023 | CG1 | ILE | B | 309 | 22.663 | 20.817 | -8.279 | 1.00 | 21.51 |
| 9026 | CD1 | ILE | B | 309 | 24.007 | 20.664 | -7.593 | 1.00 | 22.06 |
| 9030 | CG2 | ILE | B | 309 | 22.891 | 23.256 | -8.766 | 1.00 | 22.35 |
| 9034 | C | ILE | B | 309 | 20.874 | 23.159 | -10.774 | 1.00 | 21.80 |
| 9035 | O | ILE | B | 309 | 20.237 | 24.017 | -10.162 | 1.00 | 21.41 |
| 9036 | N | ILE | B | 310 | 21.245 | 23.328 | -12.041 | 1.00 | 22.74 |
| 9038 | CA | ILE | B | 310 | 20.886 | 24.542 | -12.765 | 1.00 | 23.55 |
| 9040 | CB | ILE | B | 310 | 22.148 | 25.209 | -13.364 | 1.00 | 23.89 |
| 9042 | CG1 | ILE | B | 310 | 22.714 | 24.400 | -14.540 | 1.00 | 24.25 |
| 9045 | CD1 | ILE | B | 310 | 23.776 | 25.141 | -15.342 | 1.00 | 24.35 |
| 9049 | CG2 | ILE | B | 310 | 23.190 | 25.406 | -12.269 | 1.00 | 24.66 |
| 9053 | C | ILE | B | 310 | 19.799 | 24.344 | -13.828 | 1.00 | 23.85 |
| 9054 | O | ILE | B | 310 | 19.400 | 25.315 | -14.470 | 1.00 | 24.70 |
| 9055 | N | GLN | B | 311 | 19.319 | 23.110 | -14.015 | 1.00 | 23.74 |
| 9057 | CA | GLN | B | 311 | 18.251 | 22.833 | -14.990 | 1.00 | 23.91 |
| 9059 | CB | GLN | B | 311 | 18.584 | 21.602 | -15.821 | 1.00 | 24.17 |
| 9062 | CG | GLN | B | 311 | 19.713 | 21.884 | -16.815 | 1.00 | 26.77 |
| 9065 | CD | GLN | B | 311 | 20.172 | 20.670 | -17.588 | 1.00 | 28.31 |
| 9066 | OE1 | GLN | B | 311 | 21.115 | 20.760 | -18.367 | 1.00 | 33.64 |
| 9067 | NE2 | GLN | B | 311 | 19.520 | 19.540 | -17.382 | 1.00 | 32.21 |
| 9070 | C | GLN | B | 311 | 16.887 | 22.687 | -14.329 | 1.00 | 23.46 |
| 9071 | O | GLN | B | 311 | 15.857 | 22.873 | -14.981 | 1.00 | 23.30 |
| 9072 | N | ARG | B | 312 | 16.889 | 22.369 | -13.033 | 1.00 | 23.14 |
| 9074 | CA | ARG | B | 312 | 15.666 | 22.175 | -12.249 | 1.00 | 22.83 |
| 9076 | CB | ARG | B | 312 | 16.010 | 21.784 | -10.806 | 1.00 | 22.67 |

FIGURE 3 DJ

| A | B | C | D | E | F | G | H | I | J |
|---|---|---|---|---|---|---|---|---|---|
| 9079 | CG | ARG | B | 312 | 16.722 | 22.887 | -10.002 | 1.00 | 21.91 |
| 9082 | CD | ARG | B | 312 | 17.584 | 22.348 | -8.871 | 1.00 | 20.80 |
| 9085 | NE | ARG | B | 312 | 18.319 | 23.405 | -8.180 | 1.00 | 19.32 |
| 9087 | CZ | ARG | B | 312 | 17.807 | 24.145 | -7.212 | 1.00 | 19.88 |
| 9088 | NH1 | ARG | B | 312 | 18.559 | 25.083 | -6.640 | 1.00 | 20.86 |
| 9091 | NH2 | ARG | B | 312 | 16.547 | 23.956 | -6.806 | 1.00 | 18.83 |
| 9094 | C | ARG | B | 312 | 14.826 | 23.434 | -12.199 | 1.00 | 23.29 |
| 9095 | O | ARG | B | 312 | 15.361 | 24.542 | -12.222 | 1.00 | 22.52 |
| 9096 | N | ASN | B | 313 | 13.513 | 23.232 | -12.116 | 1.00 | 24.23 |
| 9098 | CA | ASN | B | 313 | 12.519 | 24.294 | -11.967 | 1.00 | 25.30 |
| 9100 | CB | ASN | B | 313 | 11.404 | 24.132 | -13.023 | 1.00 | 25.73 |
| 9103 | CG | ASN | B | 313 | 10.586 | 22.855 | -12.843 | 1.00 | 27.06 |
| 9104 | OD1 | ASN | B | 313 | 10.893 | 22.015 | -12.003 | 1.00 | 30.28 |
| 9105 | ND2 | ASN | B | 313 | 9.526 | 22.712 | -13.642 | 1.00 | 30.33 |
| 9108 | C | ASN | B | 313 | 11.922 | 24.303 | -10.550 | 1.00 | 26.15 |
| 9109 | O | ASN | B | 313 | 10.931 | 24.991 | -10.282 | 1.00 | 26.07 |
| 9110 | N | LYS | B | 314 | 12.523 | 23.510 | -9.663 | 1.00 | 26.76 |
| 9112 | CA | LYS | B | 314 | 12.057 | 23.349 | -8.295 | 1.00 | 27.55 |
| 9114 | CB | LYS | B | 314 | 10.997 | 22.245 | -8.214 | 1.00 | 28.24 |
| 9117 | CG | LYS | B | 314 | 11.437 | 20.876 | -8.748 | 1.00 | 30.42 |
| 9120 | CD | LYS | B | 314 | 10.388 | 19.777 | -8.483 | 1.00 | 34.02 |
| 9123 | CE | LYS | B | 314 | 9.281 | 19.733 | -9.557 | 1.00 | 35.81 |
| 9126 | NZ | LYS | B | 314 | 9.763 | 19.297 | -10.914 | 1.00 | 37.55 |
| 9130 | C | LYS | B | 314 | 13.212 | 23.017 | -7.370 | 1.00 | 27.53 |
| 9131 | O | LYS | B | 314 | 13.045 | 23.018 | -6.148 | 1.00 | 27.94 |
| 9132 | OXT | LYS | B | 314 | 14.311 | 22.729 | -7.848 | 1.00 | 26.55 |
| 9133 | O9 | ipp | X | 900 | 59.879 | 67.784 | 6.844 | 1.00 | 22.62 |
| 9134 | P7 | ipp | X | 900 | 60.281 | 67.030 | 8.078 | 1.00 | 20.44 |
| 9135 | O8 | ipp | X | 900 | 61.128 | 65.793 | 7.905 | 1.00 | 20.16 |
| 9136 | O10 | ipp | X | 900 | 58.921 | 66.747 | 8.923 | 1.00 | 20.32 |
| 9137 | P11 | ipp | X | 900 | 58.096 | 65.364 | 9.039 | 1.00 | 20.72 |
| 9138 | O13 | ipp | X | 900 | 58.271 | 64.667 | 7.712 | 1.00 | 21.48 |
| 9139 | O12 | ipp | X | 900 | 58.760 | 64.598 | 10.167 | 1.00 | 20.42 |
| 9140 | O14 | ipp | X | 900 | 56.677 | 65.719 | 9.388 | 1.00 | 19.87 |
| 9141 | O6 | ipp | X | 900 | 61.085 | 68.067 | 9.000 | 1.00 | 23.40 |
| 9142 | C5 | ipp | X | 900 | 60.446 | 69.278 | 9.396 | 1.00 | 22.55 |
| 9145 | C4 | ipp | X | 900 | 61.386 | 70.077 | 10.277 | 1.00 | 23.87 |
| 9148 | C2 | ipp | X | 900 | 62.729 | 70.303 | 9.627 | 1.00 | 24.00 |
| 9149 | C3 | ipp | X | 900 | 62.847 | 70.872 | 8.237 | 1.00 | 23.48 |
| 9153 | C1 | ipp | X | 900 | 63.818 | 70.021 | 10.311 | 1.00 | 24.77 |
| 9156 | O12 | ris | X | 901 | 57.820 | 74.304 | 11.572 | 1.00 | 21.28 |
| 9157 | P9 | ris | X | 901 | 58.623 | 73.691 | 10.433 | 1.00 | 21.35 |
| 9158 | O11 | ris | X | 901 | 58.329 | 74.511 | 8.992 | 1.00 | 22.29 |
| 9160 | O10 | ris | X | 901 | 58.206 | 72.094 | 10.263 | 1.00 | 22.10 |
| 9162 | C8 | ris | X | 901 | 60.334 | 73.798 | 10.791 | 1.00 | 20.58 |
| 9163 | O13 | ris | X | 901 | 61.051 | 73.167 | 9.710 | 1.00 | 21.47 |
| 9165 | P14 | ris | X | 901 | 60.832 | 75.467 | 10.955 | 1.00 | 21.49 |
| 9166 | O16 | ris | X | 901 | 60.487 | 76.175 | 9.664 | 1.00 | 20.67 |
| 9167 | O15 | ris | X | 901 | 60.014 | 76.127 | 12.259 | 1.00 | 20.29 |
| 9169 | O17 | ris | X | 901 | 62.473 | 75.654 | 11.235 | 1.00 | 16.79 |
| 9171 | C7 | ris | X | 901 | 60.517 | 73.036 | 12.110 | 1.00 | 20.01 |
| 9174 | C2 | ris | X | 901 | 61.916 | 72.843 | 12.658 | 1.00 | 20.04 |

FIGURE 3 DK

| A | B | C | D | E | F | G | H | I | J |
|---|---|---|---|---|---|---|---|---|---|
| 9175 | C1 | ris | X | 901 | 62.030 | 72.693 | 14.038 | 1.00 | 22.23 |
| 9177 | C6 | ris | X | 901 | 63.284 | 72.496 | 14.614 | 1.00 | 21.92 |
| 9179 | C5 | ris | X | 901 | 64.396 | 72.454 | 13.790 | 1.00 | 21.90 |
| 9181 | N4 | ris | X | 901 | 64.272 | 72.597 | 12.461 | 1.00 | 20.50 |
| 9182 | C3 | ris | X | 901 | 63.073 | 72.787 | 11.887 | 1.00 | 20.38 |
| 9184 | O9 | ipp | X | 902 | 16.064 | 23.295 | -2.975 | 1.00 | 21.48 |
| 9185 | P7 | ipp | X | 902 | 16.496 | 22.587 | -1.731 | 1.00 | 20.32 |
| 9186 | O8 | ipp | X | 902 | 17.402 | 21.368 | -1.817 | 1.00 | 20.60 |
| 9187 | O10 | ipp | X | 902 | 15.180 | 22.297 | -0.852 | 1.00 | 19.29 |
| 9188 | P11 | ipp | X | 902 | 14.357 | 20.933 | -0.731 | 1.00 | 21.41 |
| 9189 | O13 | ipp | X | 902 | 14.501 | 20.303 | -2.099 | 1.00 | 21.14 |
| 9190 | O12 | ipp | X | 902 | 15.018 | 20.139 | 0.361 | 1.00 | 19.56 |
| 9191 | O14 | ipp | X | 902 | 12.943 | 21.318 | -0.386 | 1.00 | 20.18 |
| 9192 | O6 | ipp | X | 902 | 17.282 | 23.658 | -0.828 | 1.00 | 21.57 |
| 9193 | C5 | ipp | X | 902 | 16.665 | 24.901 | -0.520 | 1.00 | 20.59 |
| 9196 | C4 | ipp | X | 902 | 17.539 | 25.684 | 0.451 | 1.00 | 20.72 |
| 9199 | C2 | ipp | X | 902 | 18.923 | 25.954 | -0.086 | 1.00 | 20.12 |
| 9200 | C3 | ipp | X | 902 | 19.094 | 26.613 | -1.425 | 1.00 | 20.10 |
| 9204 | C1 | ipp | X | 902 | 19.970 | 25.641 | 0.637 | 1.00 | 19.72 |
| 9207 | O12 | ris | X | 903 | 13.949 | 29.944 | 1.653 | 1.00 | 18.96 |
| 9208 | P9 | ris | X | 903 | 14.827 | 29.319 | 0.595 | 1.00 | 18.15 |
| 9209 | O11 | ris | X | 903 | 14.564 | 30.066 | -0.891 | 1.00 | 17.76 |
| 9211 | O10 | ris | X | 903 | 14.479 | 27.699 | 0.371 | 1.00 | 17.12 |
| 9213 | C8 | ris | X | 903 | 16.543 | 29.484 | 1.000 | 1.00 | 16.83 |
| 9214 | O13 | ris | X | 903 | 17.268 | 28.905 | -0.099 | 1.00 | 14.71 |
| 9216 | P14 | ris | X | 903 | 17.105 | 31.143 | 1.147 | 1.00 | 16.07 |
| 9217 | O16 | ris | X | 903 | 16.424 | 31.703 | 2.361 | 1.00 | 18.08 |
| 9218 | O15 | ris | X | 903 | 18.754 | 31.239 | 1.421 | 1.00 | 20.15 |
| 9220 | O17 | ris | X | 903 | 16.681 | 31.883 | -0.303 | 1.00 | 17.24 |
| 9222 | C7 | ris | X | 903 | 16.736 | 28.711 | 2.310 | 1.00 | 15.64 |
| 9225 | C2 | ris | X | 903 | 18.144 | 28.461 | 2.843 | 1.00 | 17.89 |
| 9226 | C1 | ris | X | 903 | 18.231 | 28.146 | 4.193 | 1.00 | 17.51 |
| 9228 | C6 | ris | X | 903 | 19.477 | 27.908 | 4.776 | 1.00 | 17.87 |
| 9230 | C5 | ris | X | 903 | 20.612 | 27.985 | 3.980 | 1.00 | 18.68 |
| 9232 | N4 | ris | X | 903 | 20.535 | 28.281 | 2.665 | 1.00 | 18.45 |
| 9233 | C3 | ris | X | 903 | 19.332 | 28.506 | 2.084 | 1.00 | 18.77 |
| 9235 | MG | MG | X | 904 | 15.574 | 31.310 | -1.873 | 1.00 | 21.07 |
| 9236 | MG | MG | X | 905 | 17.080 | 32.751 | 3.968 | 1.00 | 17.94 |
| 9237 | MG | MG | X | 906 | 14.279 | 31.564 | 2.944 | 1.00 | 18.98 |
| 9238 | MG | MG | X | 907 | 58.027 | 75.928 | 12.811 | 1.00 | 21.97 |
| 9239 | MG | MG | X | 908 | 59.508 | 75.731 | 8.080 | 1.00 | 25.32 |
| 9240 | MG | MG | X | 909 | 60.807 | 77.116 | 13.792 | 1.00 | 19.86 |
| 9241 | OW0 | HOH | X | 1 | 69.581 | 70.101 | 13.536 | 1.00 | 18.91 |
| 9244 | OW0 | HOH | X | 2 | 62.678 | 62.339 | 10.204 | 1.00 | 15.42 |
| 9247 | OW0 | HOH | X | 3 | 25.799 | 25.747 | 3.926 | 1.00 | 15.73 |
| 9250 | OW0 | HOH | X | 4 | 59.333 | 62.010 | 10.213 | 1.00 | 18.17 |
| 9253 | OW0 | HOH | X | 5 | 18.822 | 17.964 | 0.386 | 1.00 | 18.32 |
| 9256 | OW0 | HOH | X | 6 | 13.596 | 24.842 | -2.548 | 1.00 | 13.98 |
| 9259 | OW0 | HOH | X | 7 | 60.443 | 70.120 | 5.487 | 1.00 | 20.05 |
| 9262 | OW0 | HOH | X | 8 | 67.024 | 68.022 | 10.947 | 1.00 | 18.31 |
| 9265 | OW0 | HOH | X | 9 | 75.891 | 66.532 | 13.529 | 1.00 | 16.24 |
| 9268 | OW0 | HOH | X | 10 | 61.389 | 59.407 | 28.540 | 1.00 | 15.76 |

FIGURE 3 DL

| A | B | C | D | E | F | G | H | I | J |
|---|---|---|---|---|---|---|---|---|---|
| 9271 | OW0 | HOH | X | 11 | 16.713 | 25.479 | -4.403 | 1.00 | 16.69 |
| 9274 | OW0 | HOH | X | 12 | 17.228 | 19.008 | -1.948 | 1.00 | 17.97 |
| 9277 | OW0 | HOH | X | 13 | 60.948 | 63.338 | 7.816 | 1.00 | 17.21 |
| 9280 | OW0 | HOH | X | 14 | 12.537 | 21.690 | 6.873 | 1.00 | 20.29 |
| 9283 | OW0 | HOH | X | 15 | 17.395 | 34.432 | 2.680 | 1.00 | 15.95 |
| 9286 | OW0 | HOH | X | 16 | 22.715 | 24.983 | 3.509 | 1.00 | 21.00 |
| 9289 | OW0 | HOH | X | 17 | 23.103 | 23.679 | 1.175 | 1.00 | 16.66 |
| 9292 | OW0 | HOH | X | 18 | 60.488 | 77.235 | 6.934 | 1.00 | 16.27 |
| 9295 | OW0 | HOH | X | 19 | 57.327 | 69.233 | 7.233 | 1.00 | 17.06 |
| 9298 | OW0 | HOH | X | 20 | 15.505 | 17.649 | 0.655 | 1.00 | 17.89 |
| 9301 | OW0 | HOH | X | 21 | 34.673 | 22.728 | -9.839 | 1.00 | 22.21 |
| 9304 | OW0 | HOH | X | 22 | 12.191 | 23.940 | -0.324 | 1.00 | 14.99 |
| 9307 | OW0 | HOH | X | 23 | 4.461 | 26.280 | 19.031 | 1.00 | 23.20 |
| 9310 | OW0 | HOH | X | 24 | 72.420 | 88.509 | 2.009 | 1.00 | 28.92 |
| 9313 | OW0 | HOH | X | 25 | 73.365 | 71.690 | 24.882 | 1.00 | 15.83 |
| 9316 | OW0 | HOH | X | 26 | 9.311 | 27.134 | 10.014 | 1.00 | 16.86 |
| 9319 | OW0 | HOH | X | 27 | 33.303 | 4.388 | 14.111 | 1.00 | 23.61 |
| 9322 | OW0 | HOH | X | 28 | 9.972 | 29.039 | 2.416 | 1.00 | 19.40 |
| 9325 | OW0 | HOH | X | 29 | 20.315 | 24.167 | 4.178 | 1.00 | 21.86 |
| 9328 | OW0 | HOH | X | 30 | 23.161 | 10.579 | 20.659 | 1.00 | 23.73 |
| 9331 | OW0 | HOH | X | 31 | 62.889 | 76.521 | 13.608 | 1.00 | 18.10 |
| 9334 | OW0 | HOH | X | 32 | 14.368 | 17.510 | 4.944 | 1.00 | 24.43 |
| 9337 | OW0 | HOH | X | 33 | 31.222 | 26.334 | 11.934 | 1.00 | 21.87 |
| 9340 | OW0 | HOH | X | 34 | 17.123 | 34.428 | -0.050 | 1.00 | 18.82 |
| 9343 | OW0 | HOH | X | 35 | 65.244 | 84.346 | -6.827 | 1.00 | 23.12 |
| 9346 | OW0 | HOH | X | 36 | 53.273 | 71.292 | 19.938 | 1.00 | 20.38 |
| 9349 | OW0 | HOH | X | 37 | 75.108 | 70.654 | 21.698 | 1.00 | 19.01 |
| 9352 | OW0 | HOH | X | 38 | 61.370 | 78.383 | 15.450 | 1.00 | 24.45 |
| 9355 | OW0 | HOH | X | 39 | 64.170 | 68.585 | 13.753 | 1.00 | 23.11 |
| 9358 | OW0 | HOH | X | 40 | 15.187 | 3.524 | -3.226 | 1.00 | 21.48 |
| 9361 | OW0 | HOH | X | 41 | 20.358 | 39.276 | 1.884 | 1.00 | 22.25 |
| 9364 | OW0 | HOH | X | 42 | 59.729 | 80.370 | 3.839 | 1.00 | 25.41 |
| 9367 | OW0 | HOH | X | 43 | 9.394 | 25.625 | 7.660 | 1.00 | 19.98 |
| 9370 | OW0 | HOH | X | 44 | 19.279 | 13.591 | 19.445 | 1.00 | 25.74 |
| 9373 | OW0 | HOH | X | 45 | 18.592 | 28.894 | 9.372 | 1.00 | 21.52 |
| 9376 | OW0 | HOH | X | 46 | 16.733 | 32.742 | -2.993 | 1.00 | 17.70 |
| 9379 | OW0 | HOH | X | 47 | 28.337 | 35.553 | 9.793 | 1.00 | 24.55 |
| 9382 | OW0 | HOH | X | 48 | 71.766 | 52.024 | 1.660 | 1.00 | 25.10 |
| 9385 | OW0 | HOH | X | 49 | 5.509 | 18.812 | 21.857 | 1.00 | 25.11 |
| 9388 | OW0 | HOH | X | 50 | 25.249 | 44.467 | -11.635 | 1.00 | 22.90 |
| 9391 | OW0 | HOH | X | 51 | 16.089 | 35.932 | -5.867 | 1.00 | 20.15 |
| 9394 | OW0 | HOH | X | 52 | 50.870 | 75.101 | 10.886 | 1.00 | 22.51 |
| 9397 | OW0 | HOH | X | 53 | 58.111 | 59.051 | 3.773 | 1.00 | 23.52 |
| 9400 | OW0 | HOH | X | 54 | 84.343 | 49.350 | 23.069 | 1.00 | 19.58 |
| 9403 | OW0 | HOH | X | 55 | 56.087 | 75.553 | 13.615 | 1.00 | 15.17 |
| 9406 | OW0 | HOH | X | 56 | 19.494 | 34.654 | -1.382 | 1.00 | 20.86 |
| 9409 | OW0 | HOH | X | 57 | 8.799 | 19.400 | 4.773 | 1.00 | 21.44 |
| 9412 | OW0 | HOH | X | 58 | 39.726 | 12.512 | 12.694 | 1.00 | 37.61 |
| 9415 | OW0 | HOH | X | 59 | 12.786 | 3.396 | 7.777 | 1.00 | 28.21 |
| 9418 | OW0 | HOH | X | 61 | 33.547 | 28.085 | -16.167 | 1.00 | 24.17 |
| 9421 | OW0 | HOH | X | 62 | 60.548 | 68.421 | 32.431 | 1.00 | 22.66 |
| 9424 | OW0 | HOH | X | 63 | 52.652 | 63.594 | 14.580 | 1.00 | 21.16 |

FIGURE 3 DM

| A | B | C | D | E | F | G | H | I | J |
|---|---|---|---|---|---|---|---|---|---|
| 9427 | OW0 | HOH | X | 64 | 63.267 | 78.956 | 8.228 | 1.00 | 23.96 |
| 9430 | OW0 | HOH | X | 65 | 21.674 | 40.154 | -16.591 | 1.00 | 19.82 |
| 9433 | OW0 | HOH | X | 66 | 62.524 | 73.265 | 19.235 | 1.00 | 24.72 |
| 9436 | OW0 | HOH | X | 67 | 50.175 | 67.476 | 14.681 | 1.00 | 24.07 |
| 9439 | OW0 | HOH | X | 68 | 16.317 | 24.542 | 22.592 | 1.00 | 24.88 |
| 9442 | OW0 | HOH | X | 70 | 13.596 | 32.913 | 1.425 | 1.00 | 18.95 |
| 9445 | OW0 | HOH | X | 71 | 33.743 | 4.683 | -9.292 | 1.00 | 21.88 |
| 9448 | OW0 | HOH | X | 72 | 84.877 | 52.105 | 15.691 | 1.00 | 35.89 |
| 9451 | OW0 | HOH | X | 73 | 28.069 | 7.721 | -7.921 | 1.00 | 22.28 |
| 9454 | OW0 | HOH | X | 74 | 29.256 | 1.053 | 13.166 | 1.00 | 28.61 |
| 9457 | OW0 | HOH | X | 75 | 26.790 | -1.137 | 5.597 | 1.00 | 33.71 |
| 9460 | OW0 | HOH | X | 76 | 33.840 | 27.398 | -6.991 | 1.00 | 26.70 |
| 9463 | OW0 | HOH | X | 77 | 20.039 | 38.545 | -21.843 | 1.00 | 59.27 |
| 9466 | OW0 | HOH | X | 78 | 49.910 | 55.142 | 25.447 | 1.00 | 26.46 |
| 9469 | OW0 | HOH | X | 79 | 9.843 | 14.477 | -1.615 | 1.00 | 27.96 |
| 9472 | OW0 | HOH | X | 80 | 36.808 | 16.350 | 8.648 | 1.00 | 22.19 |
| 9475 | OW0 | HOH | X | 81 | 43.245 | 14.999 | 0.753 | 1.00 | 22.13 |
| 9478 | OW0 | HOH | X | 82 | 57.361 | 79.956 | 11.239 | 1.00 | 25.78 |
| 9481 | OW0 | HOH | X | 83 | 9.775 | 24.342 | -1.506 | 1.00 | 22.49 |
| 9484 | OW0 | HOH | X | 84 | 68.131 | 69.501 | 22.346 | 1.00 | 28.17 |
| 9487 | OW0 | HOH | X | 85 | 64.173 | 83.689 | 11.530 | 1.00 | 19.53 |
| 9490 | OW0 | HOH | X | 86 | 58.920 | 48.042 | 6.438 | 1.00 | 22.32 |
| 9493 | OW0 | HOH | X | 87 | 57.493 | 77.168 | 11.232 | 1.00 | 19.16 |
| 9496 | OW0 | HOH | X | 88 | 77.326 | 71.627 | 2.643 | 1.00 | 27.72 |
| 9499 | OW0 | HOH | X | 89 | 74.547 | 71.580 | 7.451 | 1.00 | 24.66 |
| 9502 | OW0 | HOH | X | 91 | 48.469 | 59.380 | 21.046 | 1.00 | 23.24 |
| 9505 | OW0 | HOH | X | 92 | 59.723 | 83.049 | 3.647 | 1.00 | 26.08 |
| 9508 | OW0 | HOH | X | 93 | 29.853 | 24.288 | -1.800 | 1.00 | 33.40 |
| 9511 | O | HOH | X | 94 | 56.128 | 56.547 | -0.069 | 1.00 | 31.76 |
| 9514 | O | HOH | X | 95 | 60.992 | 57.155 | 5.055 | 1.00 | 25.17 |
| 9517 | O | HOH | X | 96 | 57.412 | 60.876 | 1.767 | 1.00 | 27.49 |
| 9520 | O | HOH | X | 98 | 10.425 | 34.341 | 14.720 | 1.00 | 25.28 |
| 9523 | O | HOH | X | 99 | 58.393 | 61.924 | 14.465 | 1.00 | 21.57 |
| 9526 | O | HOH | X | 100 | 15.514 | 40.203 | -8.447 | 1.00 | 25.83 |
| 9529 | O | HOH | X | 101 | 71.395 | 44.872 | 6.706 | 1.00 | 23.21 |
| 9532 | O | HOH | X | 102 | 59.088 | 84.453 | 1.416 | 1.00 | 21.13 |
| 9535 | O | HOH | X | 103 | 10.805 | 35.476 | 2.484 | 1.00 | 30.21 |
| 9538 | O | HOH | X | 104 | 78.675 | 67.094 | -0.168 | 1.00 | 30.94 |
| 9541 | O | HOH | X | 105 | 53.216 | 69.834 | 17.573 | 1.00 | 21.88 |
| 9544 | O | HOH | X | 106 | 11.540 | 21.193 | -2.775 | 1.00 | 23.63 |
| 9547 | O | HOH | X | 107 | 56.434 | 66.036 | 16.603 | 1.00 | 21.18 |
| 9550 | O | HOH | X | 108 | 53.589 | 69.002 | 8.469 | 1.00 | 26.03 |
| 9553 | O | HOH | X | 109 | 22.171 | 2.588 | 12.364 | 1.00 | 25.07 |
| 9556 | O | HOH | X | 110 | 77.332 | 49.094 | 0.357 | 1.00 | 25.35 |
| 9559 | O | HOH | X | 111 | 33.771 | 36.319 | -2.063 | 1.00 | 30.82 |
| 9562 | O | HOH | X | 112 | 12.214 | 37.251 | -5.519 | 1.00 | 20.62 |
| 9565 | O | HOH | X | 113 | 68.012 | 47.978 | 18.112 | 1.00 | 22.53 |
| 9568 | O | HOH | X | 114 | 52.583 | 66.344 | 14.741 | 1.00 | 24.60 |
| 9571 | O | HOH | X | 115 | 54.317 | 78.524 | 24.510 | 1.00 | 28.76 |
| 9574 | O | HOH | X | 116 | 17.315 | 3.665 | 4.180 | 1.00 | 31.96 |
| 9577 | O | HOH | X | 117 | 41.900 | 14.903 | -5.570 | 1.00 | 23.73 |
| 9580 | O | HOH | X | 118 | 25.232 | 6.606 | -7.167 | 1.00 | 24.37 |

FIGURE 3 DN

| A | B | C | D | E | F | G | H | I | J |
|---|---|---|---|---|---|---|---|---|---|
| 9583 | O | HOH | X | 119 | 69.198 | 51.022 | 2.442 | 1.00 | 32.30 |
| 9586 | O | HOH | X | 120 | 54.454 | 75.970 | 7.898 | 1.00 | 29.61 |
| 9589 | O | HOH | X | 121 | 72.835 | 54.092 | -0.028 | 1.00 | 28.37 |
| 9592 | O | HOH | X | 122 | 13.624 | 16.407 | -7.904 | 1.00 | 26.27 |
| 9595 | O | HOH | X | 123 | 52.606 | 51.548 | 23.966 | 1.00 | 31.75 |
| 9598 | O | HOH | X | 124 | 64.545 | 60.261 | -5.452 | 1.00 | 26.24 |
| 9601 | O | HOH | X | 125 | 48.485 | 73.411 | 29.403 | 1.00 | 35.53 |
| 9604 | O | HOH | X | 126 | 73.394 | 45.286 | 22.697 | 1.00 | 31.73 |
| 9607 | O | HOH | X | 127 | 1.619 | 16.387 | 23.748 | 1.00 | 35.87 |
| 9610 | O | HOH | X | 128 | 51.331 | 52.037 | 31.882 | 1.00 | 32.80 |
| 9613 | O | HOH | X | 130 | 59.702 | 84.785 | 5.880 | 1.00 | 28.09 |
| 9616 | O | HOH | X | 131 | 35.875 | 32.733 | -2.230 | 1.00 | 41.90 |
| 9619 | O | HOH | X | 132 | 56.078 | 68.294 | 9.410 | 1.00 | 23.25 |
| 9622 | O | HOH | X | 133 | 68.940 | 88.925 | -1.936 | 1.00 | 24.65 |
| 9625 | O | HOH | X | 134 | 66.234 | 47.041 | 21.983 | 1.00 | 27.75 |
| 9628 | O | HOH | X | 135 | 61.333 | 46.476 | 6.833 | 1.00 | 25.98 |
| 9631 | O | HOH | X | 136 | 67.556 | 54.792 | 30.084 | 1.00 | 27.45 |
| 9634 | O | HOH | X | 137 | 40.092 | 4.846 | 14.202 | 1.00 | 33.56 |
| 9637 | O | HOH | X | 138 | 6.434 | 23.324 | 4.635 | 1.00 | 23.23 |
| 9640 | O | HOH | X | 139 | 53.326 | 52.199 | 10.569 | 1.00 | 27.46 |
| 9643 | O | HOH | X | 140 | 16.797 | 40.699 | -15.388 | 1.00 | 31.25 |
| 9646 | O | HOH | X | 141 | 55.505 | 68.569 | 5.472 | 1.00 | 31.05 |
| 9649 | O | HOH | X | 142 | 19.829 | 28.141 | -14.550 | 1.00 | 32.03 |
| 9652 | O | HOH | X | 143 | 72.192 | 80.036 | 19.386 | 1.00 | 26.69 |
| 9655 | O | HOH | X | 144 | 49.567 | 62.818 | 10.675 | 1.00 | 36.36 |
| 9658 | O | HOH | X | 145 | 77.624 | 80.795 | 7.572 | 1.00 | 30.84 |
| 9661 | O | HOH | X | 146 | 70.251 | 84.697 | 14.333 | 1.00 | 29.10 |
| 9664 | O | HOH | X | 147 | 22.147 | 28.439 | -15.860 | 1.00 | 25.06 |
| 9667 | O | HOH | X | 149 | 13.634 | 35.572 | 1.265 | 1.00 | 25.62 |
| 9670 | O | HOH | X | 150 | 82.244 | 46.629 | 23.769 | 1.00 | 35.68 |
| 9673 | O | HOH | X | 151 | 63.846 | 88.990 | 3.561 | 1.00 | 28.36 |
| 9676 | O | HOH | X | 152 | 64.405 | 73.293 | -9.004 | 1.00 | 59.74 |
| 9679 | O | HOH | X | 153 | 19.585 | 44.233 | -0.968 | 1.00 | 31.22 |
| 9682 | O | HOH | X | 154 | 17.128 | 12.637 | -4.589 | 1.00 | 25.38 |
| 9685 | O | HOH | X | 155 | 5.113 | 33.908 | 7.713 | 1.00 | 38.08 |
| 9688 | O | HOH | X | 156 | 30.306 | 34.937 | -7.899 | 1.00 | 34.44 |
| 9691 | O | HOH | X | 157 | 3.129 | 22.986 | -4.541 | 1.00 | 39.21 |
| 9694 | O | HOH | X | 158 | 66.626 | 69.399 | 13.372 | 1.00 | 23.00 |
| 9697 | O | HOH | X | 159 | 63.446 | 57.641 | 29.205 | 1.00 | 27.23 |
| 9700 | O | HOH | X | 160 | 54.243 | 50.317 | 14.175 | 1.00 | 34.68 |
| 9703 | O | HOH | X | 161 | 66.368 | 78.182 | -9.856 | 1.00 | 26.10 |
| 9706 | O | HOH | X | 162 | 53.159 | 57.048 | 10.179 | 1.00 | 27.95 |
| 9709 | O | HOH | X | 163 | 44.219 | 16.007 | -6.192 | 1.00 | 25.11 |
| 9712 | O | HOH | X | 164 | 80.589 | 61.008 | 18.291 | 1.00 | 25.88 |
| 9715 | O | HOH | X | 165 | 28.989 | 38.706 | 2.563 | 1.00 | 25.75 |
| 9718 | O | HOH | X | 166 | 11.238 | 30.773 | 0.615 | 1.00 | 24.14 |
| 9721 | O | HOH | X | 167 | 53.608 | 73.127 | 12.234 | 1.00 | 26.24 |
| 9724 | O | HOH | X | 169 | 63.586 | 45.033 | 14.349 | 1.00 | 31.13 |
| 9727 | O | HOH | X | 170 | 77.596 | 48.785 | 23.097 | 1.00 | 26.73 |
| 9730 | O | HOH | X | 171 | 84.848 | 48.026 | 14.304 | 1.00 | 29.46 |
| 9733 | O | HOH | X | 172 | 4.265 | 15.315 | 11.290 | 1.00 | 29.33 |
| 9736 | O | HOH | X | 173 | 3.381 | 31.069 | 16.737 | 1.00 | 33.72 |

FIGURE 3 DO

| A | B | C | D | E | F | G | H | I | J |
|---|---|---|---|---|---|---|---|---|---|
| 9739 | O | HOH | X | 174 | 55.238 | 65.487 | 7.142 | 1.00 | 31.03 |
| 9742 | O | HOH | X | 175 | 9.341 | 26.913 | -11.288 | 1.00 | 29.49 |
| 9745 | O | HOH | X | 176 | 53.199 | 53.483 | 20.584 | 1.00 | 32.49 |
| 9748 | O | HOH | X | 177 | 14.338 | 14.643 | -5.988 | 1.00 | 23.99 |
| 9751 | O | HOH | X | 178 | 38.329 | 22.112 | -11.565 | 1.00 | 45.14 |
| 9754 | O | HOH | X | 179 | 39.337 | 18.256 | 2.081 | 1.00 | 27.57 |
| 9757 | O | HOH | X | 180 | 56.191 | 81.845 | 4.467 | 1.00 | 30.98 |
| 9760 | O | HOH | X | 181 | 20.859 | 16.036 | -15.248 | 1.00 | 24.19 |
| 9763 | O | HOH | X | 182 | 52.592 | 52.636 | 34.412 | 1.00 | 33.36 |
| 9766 | O | HOH | X | 183 | 8.751 | 22.025 | 4.991 | 1.00 | 21.08 |
| 9769 | O | HOH | X | 184 | 63.183 | 88.654 | 8.668 | 1.00 | 32.88 |
| 9772 | O | HOH | X | 185 | 23.296 | 39.123 | 11.088 | 1.00 | 28.53 |
| 9775 | O | HOH | X | 186 | 21.029 | 42.374 | -4.623 | 1.00 | 40.24 |
| 9778 | O | HOH | X | 187 | 61.193 | 73.706 | -5.808 | 1.00 | 35.26 |
| 9781 | O | HOH | X | 188 | 55.468 | 47.798 | 19.949 | 1.00 | 28.75 |
| 9784 | O | HOH | X | 189 | 35.734 | 28.370 | -1.891 | 1.00 | 42.91 |
| 9787 | O | HOH | X | 190 | 28.941 | 9.752 | -9.745 | 1.00 | 28.83 |
| 9790 | O | HOH | X | 191 | 60.836 | 85.243 | -5.478 | 1.00 | 33.63 |
| 9793 | O | HOH | X | 193 | 85.606 | 61.921 | 11.265 | 1.00 | 33.58 |
| 9796 | O | HOH | X | 194 | 78.387 | 74.119 | -1.722 | 1.00 | 50.78 |
| 9799 | O | HOH | X | 195 | 7.183 | 30.679 | 0.916 | 1.00 | 33.15 |
| 9802 | O | HOH | X | 196 | 32.652 | 28.076 | -18.831 | 1.00 | 28.06 |
| 9805 | O | HOH | X | 197 | 53.948 | 51.530 | 21.729 | 1.00 | 30.16 |
| 9808 | O | HOH | X | 198 | 3.740 | 12.442 | 13.203 | 1.00 | 38.10 |
| 9811 | O | HOH | X | 199 | 81.671 | 47.299 | 9.794 | 1.00 | 39.29 |
| 9814 | O | HOH | X | 200 | 76.149 | 46.441 | 21.909 | 1.00 | 32.74 |
| 9817 | O | HOH | X | 201 | 61.151 | 42.663 | 13.748 | 1.00 | 62.81 |
| 9820 | O | HOH | X | 202 | 54.688 | 79.719 | 12.391 | 1.00 | 30.29 |
| 9823 | O | HOH | X | 203 | 51.275 | 79.190 | 10.957 | 1.00 | 40.83 |
| 9826 | O | HOH | X | 204 | 14.506 | 30.823 | -3.503 | 1.00 | 21.42 |
| 9829 | O | HOH | X | 205 | 14.195 | 32.814 | -1.332 | 1.00 | 19.33 |
| 9832 | O | HOH | X | 206 | 12.434 | 31.396 | 3.683 | 1.00 | 16.08 |
| 9835 | O | HOH | X | 207 | 18.969 | 32.213 | 3.765 | 1.00 | 20.53 |
| 9838 | O | HOH | X | 208 | 17.536 | 34.005 | 5.600 | 1.00 | 16.75 |
| 9841 | O | HOH | X | 209 | 33.461 | 39.878 | 0.879 | 1.00 | 48.09 |
| 9844 | O | HOH | X | 210 | 78.263 | 66.876 | 16.527 | 1.00 | 37.29 |
| 9847 | O | HOH | X | 211 | 80.975 | 67.293 | 15.894 | 1.00 | 39.50 |
| 9850 | O | HOH | X | 212 | 82.405 | 67.613 | 13.856 | 1.00 | 46.74 |
| 9853 | O | HOH | X | 213 | 50.671 | 57.527 | 11.069 | 1.00 | 40.42 |
| 9856 | O | HOH | X | 214 | 51.601 | 55.517 | 13.513 | 1.00 | 33.26 |
| 9859 | O | HOH | X | 215 | 62.729 | 54.517 | 30.771 | 1.00 | 40.62 |
| 9862 | O | HOH | X | 216 | 60.331 | 52.329 | 31.300 | 1.00 | 52.01 |
| 9865 | O | HOH | X | 217 | 31.078 | 32.997 | -9.951 | 1.00 | 29.54 |
| 9868 | O | HOH | X | 218 | 33.614 | 33.829 | -1.558 | 1.00 | 23.66 |
| 9871 | O | HOH | X | 219 | 3.882 | 31.855 | 12.746 | 1.00 | 38.99 |
| 9874 | O | HOH | X | 220 | 15.840 | 40.330 | -3.855 | 1.00 | 26.18 |
| 9877 | O | HOH | X | 221 | 15.995 | 38.459 | -6.211 | 1.00 | 24.53 |
| 9880 | O | HOH | X | 222 | 63.555 | 73.039 | -4.552 | 1.00 | 36.76 |
| 9883 | O | HOH | X | 223 | 65.686 | 72.948 | -6.046 | 1.00 | 30.87 |
| 9886 | O | HOH | X | 224 | 61.071 | 89.367 | 2.768 | 1.00 | 33.44 |
| 9889 | O | HOH | X | 225 | 85.368 | 50.306 | 25.290 | 1.00 | 39.68 |
| 9892 | O | HOH | X | 226 | 10.770 | 31.661 | -1.862 | 1.00 | 30.59 |

FIGURE 3 DP

| A | B | C | D | E | F | G | H | I | J |
|---|---|---|---|---|---|---|---|---|---|
| 9895 | O | HOH | X | 227 | 67.074 | 86.090 | 20.611 | 1.00 | 47.90 |
| 9898 | O | HOH | X | 228 | 72.225 | 82.393 | 20.309 | 1.00 | 28.15 |
| 9901 | O | HOH | X | 229 | 23.258 | 30.948 | -19.639 | 1.00 | 37.49 |
| 9904 | O | HOH | X | 230 | 18.514 | 43.214 | -15.138 | 1.00 | 25.15 |
| 9907 | O | HOH | X | 231 | 18.316 | 39.793 | -17.580 | 1.00 | 30.27 |
| 9910 | O | HOH | X | 232 | 18.565 | 40.376 | -20.157 | 1.00 | 27.88 |
| 9913 | O | HOH | X | 233 | 10.124 | 22.994 | 6.965 | 1.00 | 22.65 |
| 9916 | O | HOH | X | 234 | 40.682 | 5.559 | 16.461 | 1.00 | 35.43 |
| 9919 | O | HOH | X | 235 | 60.087 | 44.060 | 7.813 | 1.00 | 29.04 |
| 9922 | O | HOH | X | 236 | 65.753 | 46.800 | 19.256 | 1.00 | 33.55 |
| 9925 | O | HOH | X | 237 | 47.350 | 74.880 | 26.880 | 1.00 | 40.56 |
| 9928 | O | HOH | X | 238 | 48.590 | 70.295 | 28.815 | 1.00 | 22.47 |
| 9931 | O | HOH | X | 239 | 62.111 | 62.571 | -5.691 | 1.00 | 41.29 |
| 9934 | O | HOH | X | 240 | 58.266 | 75.096 | 6.385 | 1.00 | 20.97 |
| 9937 | O | HOH | X | 241 | 57.930 | 77.196 | 8.555 | 1.00 | 21.06 |
| 9940 | O | HOH | X | 242 | 60.766 | 78.814 | 9.905 | 1.00 | 24.54 |
| 9943 | O | HOH | X | 243 | 61.087 | 78.751 | 12.516 | 1.00 | 17.96 |
| 9946 | O | HOH | X | 244 | 66.063 | 45.873 | 5.892 | 1.00 | 30.86 |
| 9949 | O | HOH | X | 245 | 68.834 | 44.595 | 6.140 | 1.00 | 27.12 |
| 9952 | O | HOH | X | 246 | 40.240 | 21.104 | -0.696 | 1.00 | 29.77 |
| 9955 | O | HOH | X | 247 | 54.038 | 67.321 | 16.979 | 1.00 | 23.18 |
| 9958 | O | HOH | X | 248 | 6.161 | 36.828 | -2.610 | 1.00 | 45.75 |
| 9961 | O | HOH | X | 249 | 32.414 | 42.931 | -5.770 | 1.00 | 26.20 |
| 9964 | O | HOH | X | 250 | 8.263 | 18.675 | -2.300 | 1.00 | 37.46 |
| 9967 | O | HOH | X | 251 | 57.682 | 88.576 | 6.524 | 1.00 | 41.67 |
| 9970 | O | HOH | X | 252 | 9.403 | 38.851 | 14.485 | 1.00 | 38.72 |
| 9973 | O | HOH | X | 253 | 7.150 | 40.262 | 16.390 | 1.00 | 45.72 |
| 9976 | O | HOH | X | 254 | 53.657 | 64.735 | -1.870 | 1.00 | 50.87 |
| 9979 | O | HOH | X | 255 | 54.909 | 49.982 | 11.303 | 1.00 | 29.97 |
| 9982 | O | HOH | X | 256 | 54.469 | 48.142 | 15.766 | 1.00 | 35.94 |
| 9985 | O | HOH | X | 257 | 64.819 | 51.877 | 25.591 | 1.00 | 48.64 |
| 9988 | O | HOH | X | 258 | 48.466 | 60.211 | 34.761 | 1.00 | 34.69 |
| 9991 | O | HOH | X | 259 | 50.594 | 60.418 | 33.231 | 1.00 | 29.29 |
| 9994 | O | HOH | X | 260 | 44.303 | 61.380 | 23.666 | 1.00 | 50.60 |
| 9997 | O | HOH | X | 261 | 42.915 | 58.238 | 26.279 | 1.00 | 44.44 |
| 10000 | O | HOH | X | 262 | 52.554 | 63.196 | 6.954 | 1.00 | 45.59 |
| 10003 | O | HOH | X | 263 | 75.789 | 43.073 | 11.027 | 1.00 | 45.52 |
| 10006 | O | HOH | X | 264 | 63.099 | 46.831 | 5.108 | 1.00 | 38.28 |
| 10009 | O | HOH | X | 265 | 44.196 | 64.994 | 15.827 | 1.00 | 37.65 |
| 10012 | O | HOH | X | 266 | 43.951 | 62.363 | 16.102 | 1.00 | 46.48 |
| 10015 | O | HOH | X | 267 | 39.222 | 63.891 | 21.996 | 1.00 | 52.12 |
| 10018 | O | HOH | X | 268 | 42.850 | 63.664 | 23.396 | 1.00 | 50.80 |
| 10021 | O | HOH | X | 269 | 48.526 | 74.293 | 31.675 | 1.00 | 36.34 |
| 10024 | O | HOH | X | 270 | 67.670 | 48.672 | 31.258 | 1.00 | 51.39 |
| 10027 | O | HOH | X | 271 | 81.199 | 48.984 | 16.751 | 1.00 | 28.66 |
| 10030 | O | HOH | X | 272 | 79.911 | 47.943 | 14.775 | 1.00 | 31.46 |
| 10033 | O | HOH | X | 273 | 85.017 | 50.279 | 19.126 | 1.00 | 30.80 |
| 10036 | O | HOH | X | 274 | 64.657 | 81.303 | 10.384 | 1.00 | 30.96 |
| 10039 | O | HOH | X | 275 | 62.329 | 87.607 | 6.341 | 1.00 | 31.55 |
| 10042 | O | HOH | X | 276 | 64.640 | 86.808 | 5.080 | 1.00 | 34.11 |
| 10045 | O | HOH | X | 277 | 60.179 | 93.225 | 8.295 | 1.00 | 40.09 |
| 10048 | O | HOH | X | 278 | 73.593 | 79.168 | 1.381 | 1.00 | 35.41 |

FIGURE 3 DQ

| A | B | C | D | E | F | G | H | I | J |
|---|---|---|---|---|---|---|---|---|---|
| 10051 | O | HOH | X | 279 | 74.858 | 77.325 | -0.481 | 1.00 | 41.75 |
| 10054 | O | HOH | X | 280 | 77.068 | 76.446 | 0.836 | 1.00 | 38.59 |
| 10057 | O | HOH | X | 281 | 74.159 | 76.085 | -2.785 | 1.00 | 31.06 |
| 10060 | O | HOH | X | 282 | 79.283 | 78.702 | 16.390 | 1.00 | 38.20 |
| 10063 | O | HOH | X | 283 | 77.257 | 76.993 | 10.420 | 1.00 | 32.78 |
| 10066 | O | HOH | X | 284 | 77.239 | 78.246 | 8.067 | 1.00 | 37.50 |
| 10069 | O | HOH | X | 285 | 73.948 | 68.872 | 7.682 | 1.00 | 33.72 |
| 10072 | O | HOH | X | 286 | 77.608 | 62.256 | 8.543 | 1.00 | 45.53 |
| 10075 | O | HOH | X | 287 | 84.634 | 47.863 | 10.649 | 1.00 | 33.57 |
| 10078 | O | HOH | X | 288 | 89.171 | 59.221 | 10.145 | 1.00 | 51.60 |
| 10081 | O | HOH | X | 289 | 88.540 | 58.568 | 7.606 | 1.00 | 57.77 |
| 10084 | O | HOH | X | 290 | 44.965 | 73.834 | 1.582 | 1.00 | 48.13 |
| 10087 | O | HOH | X | 291 | 49.561 | 81.495 | 7.222 | 1.00 | 45.30 |
| 10090 | O | HOH | X | 292 | 70.469 | 68.660 | -8.004 | 1.00 | 41.08 |
| 10093 | O | HOH | X | 293 | 81.881 | 67.174 | -2.963 | 1.00 | 39.74 |
| 10096 | O | HOH | X | 294 | 77.288 | 57.817 | -5.855 | 1.00 | 32.90 |
| 10099 | O | HOH | X | 295 | 76.204 | 60.286 | -6.405 | 1.00 | 33.62 |
| 10102 | O | HOH | X | 296 | 72.178 | 51.978 | -1.088 | 1.00 | 40.76 |
| 10105 | O | HOH | X | 297 | 69.367 | 55.952 | -6.441 | 1.00 | 41.52 |
| 10108 | O | HOH | X | 298 | 66.145 | 60.092 | -7.585 | 1.00 | 37.64 |
| 10111 | O | HOH | X | 299 | 58.836 | 67.727 | -7.779 | 1.00 | 45.55 |
| 10114 | O | HOH | X | 300 | 13.363 | 3.105 | -5.157 | 1.00 | 38.92 |
| 10117 | O | HOH | X | 301 | 13.794 | 2.664 | -0.805 | 1.00 | 33.87 |
| 10120 | O | HOH | X | 302 | 15.442 | 1.396 | 0.758 | 1.00 | 53.73 |
| 10123 | O | HOH | X | 303 | 17.525 | -0.047 | 0.589 | 1.00 | 35.96 |
| 10126 | O | HOH | X | 304 | 13.277 | 5.297 | -9.056 | 1.00 | 41.07 |
| 10129 | O | HOH | X | 305 | 10.451 | 8.808 | -4.245 | 1.00 | 33.55 |
| 10132 | O | HOH | X | 306 | 11.127 | 5.641 | 1.860 | 1.00 | 28.72 |
| 10135 | O | HOH | X | 307 | 17.465 | 2.139 | -2.799 | 1.00 | 30.54 |
| 10138 | O | HOH | X | 308 | 19.535 | 2.393 | -4.513 | 1.00 | 33.31 |
| 10141 | O | HOH | X | 309 | 9.312 | 12.628 | 0.396 | 1.00 | 37.60 |
| 10144 | O | HOH | X | 310 | 7.665 | 11.510 | 3.549 | 1.00 | 34.31 |
| 10147 | O | HOH | X | 311 | 6.051 | 11.080 | 6.071 | 1.00 | 39.84 |
| 10150 | O | HOH | X | 312 | 10.116 | 7.158 | 11.883 | 1.00 | 33.40 |
| 10153 | O | HOH | X | 313 | 9.385 | 9.324 | 10.796 | 1.00 | 36.05 |
| 10156 | O | HOH | X | 314 | 14.622 | 2.412 | 13.739 | 1.00 | 31.45 |
| 10159 | O | HOH | X | 315 | 13.037 | 2.160 | 16.038 | 1.00 | 41.01 |
| 10162 | O | HOH | X | 316 | 5.930 | 10.969 | 15.786 | 1.00 | 34.44 |
| 10165 | O | HOH | X | 317 | 4.581 | 9.801 | 22.907 | 1.00 | 46.13 |
| 10168 | O | HOH | X | 318 | 1.584 | 18.885 | -1.559 | 1.00 | 52.72 |
| 10171 | O | HOH | X | 319 | 37.184 | 2.115 | -2.954 | 1.00 | 43.48 |
| 10174 | O | HOH | X | 320 | 36.733 | 3.493 | -6.561 | 1.00 | 45.09 |
| 10177 | O | HOH | X | 321 | 20.082 | 0.677 | 4.712 | 1.00 | 26.47 |
| 10180 | O | HOH | X | 322 | 20.457 | 8.134 | 16.042 | 1.00 | 46.78 |
| 10183 | O | HOH | X | 323 | 19.090 | 10.262 | 18.888 | 1.00 | 37.59 |
| 10186 | O | HOH | X | 324 | 24.214 | 25.499 | 12.581 | 1.00 | 29.01 |
| 10189 | O | HOH | X | 325 | 14.989 | 39.048 | 7.973 | 1.00 | 31.76 |
| 10192 | O | HOH | X | 326 | 11.756 | 39.045 | 9.415 | 1.00 | 50.88 |
| 10195 | O | HOH | X | 327 | 7.810 | 36.884 | 3.543 | 1.00 | 43.84 |
| 10198 | O | HOH | X | 328 | 3.242 | 25.497 | -3.703 | 1.00 | 29.56 |
| 10201 | O | HOH | X | 329 | 1.219 | 33.875 | 16.266 | 1.00 | 46.56 |
| 10204 | O | HOH | X | 330 | 1.544 | 29.687 | 13.872 | 1.00 | 40.23 |

FIGURE 3 DR

| A | B | C | D | E | F | G | H | I | J |
|---|---|---|---|---|---|---|---|---|---|
| 10207 | O | HOH | X | 331 | -0.474 | 27.413 | 15.144 | 1.00 | 54.89 |
| 10210 | O | HOH | X | 332 | 4.337 | 28.953 | 19.199 | 1.00 | 36.94 |
| 10213 | O | HOH | X | 333 | -1.539 | 27.356 | 11.980 | 1.00 | 45.30 |
| 10216 | O | HOH | X | 334 | -2.107 | 24.658 | 12.397 | 1.00 | 38.86 |
| 10219 | O | HOH | X | 335 | 2.398 | 22.547 | 20.759 | 1.00 | 43.49 |
| 10222 | O | HOH | X | 336 | 4.084 | 16.237 | 25.067 | 1.00 | 35.34 |
| 10225 | O | HOH | X | 337 | 3.978 | 13.588 | 25.815 | 1.00 | 45.80 |
| 10228 | O | HOH | X | 338 | 3.094 | 17.271 | 27.390 | 1.00 | 40.72 |
| 10231 | O | HOH | X | 339 | 4.241 | 24.783 | 21.717 | 1.00 | 35.53 |
| 10234 | O | HOH | X | 340 | 37.329 | 4.276 | 7.908 | 1.00 | 35.31 |
| 10237 | O | HOH | X | 341 | 39.684 | 14.815 | 17.121 | 1.00 | 27.65 |
| 10240 | O | HOH | X | 342 | 36.317 | 20.283 | 10.218 | 1.00 | 40.32 |
| 10243 | O | HOH | X | 343 | 32.070 | 22.082 | 3.932 | 1.00 | 19.26 |
| 10246 | O | HOH | X | 344 | 32.703 | 24.069 | 5.500 | 1.00 | 30.65 |
| 10249 | O | HOH | X | 345 | 21.195 | 37.054 | 0.700 | 1.00 | 23.85 |
| 10252 | O | HOH | X | 346 | 26.360 | 48.147 | -1.801 | 1.00 | 37.57 |
| 10255 | O | HOH | X | 347 | 23.190 | 43.465 | -4.592 | 1.00 | 34.90 |
| 10258 | O | HOH | X | 348 | 18.440 | 43.181 | -3.522 | 1.00 | 30.15 |
| 10261 | O | HOH | X | 349 | 15.607 | 42.903 | -4.850 | 1.00 | 31.05 |
| 10264 | O | HOH | X | 350 | 13.692 | 44.194 | -3.391 | 1.00 | 41.66 |
| 10267 | O | HOH | X | 351 | 31.128 | 44.045 | -7.531 | 1.00 | 41.41 |
| 10270 | O | HOH | X | 352 | 31.689 | 47.433 | -4.627 | 1.00 | 30.20 |
| 10273 | O | HOH | X | 353 | 32.993 | 49.163 | -3.190 | 1.00 | 38.18 |
| 10276 | O | HOH | X | 354 | 27.426 | 44.095 | -10.304 | 1.00 | 33.92 |
| 10279 | O | HOH | X | 355 | 43.796 | 13.725 | 3.108 | 1.00 | 23.99 |
| 10282 | O | HOH | X | 356 | 42.070 | 17.335 | 1.525 | 1.00 | 30.43 |
| 10285 | O | HOH | X | 357 | 43.287 | 19.448 | 0.553 | 1.00 | 33.75 |
| 10288 | O | HOH | X | 358 | 39.828 | 16.002 | 5.397 | 1.00 | 35.08 |
| 10291 | O | HOH | X | 359 | 38.165 | 17.818 | 4.577 | 1.00 | 37.82 |
| 10294 | O | HOH | X | 360 | 33.950 | 17.800 | -1.148 | 1.00 | 45.50 |
| 10297 | O | HOH | X | 361 | 11.762 | 24.758 | -4.528 | 1.00 | 31.90 |
| 10300 | O | HOH | X | 362 | 3.975 | 32.061 | -8.760 | 1.00 | 36.38 |
| 10303 | O | HOH | X | 363 | 15.528 | 42.830 | -7.772 | 1.00 | 35.25 |
| 10306 | O | HOH | X | 364 | 14.500 | 29.223 | -15.075 | 1.00 | 41.38 |
| 10309 | O | HOH | X | 365 | 32.850 | 21.982 | -18.707 | 1.00 | 37.44 |
| 10312 | O | HOH | X | 366 | 40.592 | 8.573 | -5.209 | 1.00 | 37.21 |
| 10315 | O | HOH | X | 367 | 25.811 | 11.663 | -16.176 | 1.00 | 30.06 |
| 10318 | O | HOH | X | 368 | 26.945 | 13.028 | -17.719 | 1.00 | 49.20 |
| 10321 | O | HOH | X | 369 | 24.479 | 22.182 | -17.748 | 1.00 | 49.87 |
| 10324 | O | HOH | X | 370 | 21.021 | 17.997 | -19.491 | 1.00 | 46.80 |
| 10327 | O | HOH | X | 371 | 23.217 | 19.367 | -20.360 | 1.00 | 51.32 |
| 10330 | O | HOH | X | 372 | 22.674 | 25.397 | -19.288 | 1.00 | 43.41 |
| 10333 | O | HOH | X | 373 | 12.811 | 20.249 | -12.633 | 1.00 | 35.30 |
| 10336 | O | HOH | X | 374 | 55.709 | 88.998 | 19.001 | 1.00 | 47.10 |
| 10339 | O | HOH | X | 375 | 54.100 | 84.683 | 17.666 | 1.00 | 43.29 |
| 10342 | O | HOH | X | 376 | 48.970 | 77.908 | 17.748 | 1.00 | 39.82 |
| 10345 | O | HOH | X | 377 | 41.899 | 65.707 | 18.118 | 1.00 | 46.67 |
| 10348 | O | HOH | X | 378 | 48.368 | 58.949 | 18.441 | 1.00 | 30.58 |
| 10351 | O | HOH | X | 379 | 48.070 | 56.991 | 22.120 | 1.00 | 35.54 |
| 10354 | O | HOH | X | 380 | 47.998 | 54.800 | 20.225 | 1.00 | 42.38 |
| 10357 | O | HOH | X | 381 | 50.349 | 57.710 | 17.797 | 1.00 | 39.16 |
| 10360 | O | HOH | X | 382 | 32.392 | 26.723 | 0.642 | 1.00 | 35.35 |

FIGURE 3 DS

| A | B | C | D | E | F | G | H | I | J |
|---|---|---|---|---|---|---|---|---|---|
| 10363 | O | HOH | X | 383 | 30.720 | 27.097 | -2.250 | 1.00 | 27.18 |
| 10366 | O | HOH | X | 384 | 37.015 | 26.821 | 2.778 | 1.00 | 49.37 |
| 10369 | O | HOH | X | 385 | 38.443 | 23.443 | 3.534 | 1.00 | 33.87 |
| 10372 | O | HOH | X | 386 | 38.669 | 19.697 | 6.394 | 1.00 | 36.31 |
| 10375 | O | HOH | X | 387 | 30.186 | -3.337 | 5.179 | 1.00 | 43.04 |
| 10378 | O | HOH | X | 388 | 36.379 | 2.179 | 1.556 | 1.00 | 42.15 |
| 10381 | O | HOH | X | 389 | 41.111 | 3.324 | 0.448 | 1.00 | 36.90 |
| 10384 | O | HOH | X | 390 | 43.161 | 2.676 | -1.085 | 1.00 | 38.66 |
| 10387 | O | HOH | X | 391 | 62.047 | 69.399 | 25.389 | 1.00 | 88.66 |
| 10390 | O | HOH | X | 392 | 64.141 | 69.344 | 27.823 | 1.00 | 41.19 |
| 10393 | O | HOH | X | 393 | 58.875 | 89.405 | 12.710 | 1.00 | 64.96 |
| 10396 | O | HOH | X | 394 | 52.351 | 74.162 | -4.548 | 1.00 | 47.29 |
| 10399 | O | HOH | X | 395 | 53.730 | 70.282 | -5.715 | 1.00 | 55.71 |
| 10402 | O | HOH | X | 396 | 47.666 | 76.863 | 1.325 | 1.00 | 34.63 |
| 10405 | O | HOH | X | 397 | 59.660 | 75.843 | -9.785 | 1.00 | 41.09 |
| 10408 | O | HOH | X | 398 | 62.561 | 78.886 | -9.940 | 1.00 | 50.51 |
| 10411 | O | HOH | X | 399 | 30.260 | 2.431 | -11.763 | 1.00 | 34.80 |
| 10414 | O | HOH | X | 400 | 27.528 | 3.971 | -14.875 | 1.00 | 45.91 |
| 10417 | O | HOH | X | 401 | 33.506 | 13.418 | -15.971 | 1.00 | 38.77 |
| 10420 | O | HOH | X | 402 | 41.028 | 6.141 | -7.128 | 1.00 | 49.46 |
| 10423 | O | HOH | X | 403 | 28.710 | 29.035 | -18.837 | 1.00 | 26.44 |
| 10426 | O | HOH | X | 404 | 29.796 | 34.872 | -15.688 | 1.00 | 37.98 |
| 10429 | O | HOH | X | 405 | 27.243 | 36.476 | -15.645 | 1.00 | 37.96 |
| 10432 | O | HOH | X | 406 | 31.047 | 35.920 | -10.224 | 1.00 | 55.58 |
| 10435 | O | HOH | X | 407 | 33.680 | 38.851 | -7.405 | 1.00 | 50.01 |
| 10438 | O | HOH | X | 408 | 25.402 | 37.066 | -19.531 | 1.00 | 37.00 |
| 10441 | O | HOH | X | 409 | 35.153 | 33.776 | 5.764 | 1.00 | 48.02 |
| 10444 | O | HOH | X | 410 | 35.151 | 34.064 | 2.494 | 1.00 | 34.05 |
| 10447 | O | HOH | X | 411 | 34.154 | 30.349 | 7.013 | 1.00 | 44.18 |
| 10450 | O | HOH | X | 412 | 8.762 | 37.486 | 1.397 | 1.00 | 38.43 |
| 10453 | O | HOH | X | 413 | 7.201 | 35.165 | 1.535 | 1.00 | 41.39 |
| 10456 | O | HOH | X | 414 | 26.384 | 40.391 | 4.437 | 1.00 | 36.18 |
| 10459 | O | HOH | X | 415 | 51.309 | 51.810 | -0.301 | 1.00 | 39.62 |
| 10462 | O | HOH | X | 416 | 29.679 | 4.776 | 17.263 | 1.00 | 29.29 |
| 10465 | O | HOH | X | 417 | 28.029 | 5.806 | 20.001 | 1.00 | 42.73 |
| 10468 | O | HOH | X | 418 | 20.603 | 24.902 | 18.280 | 1.00 | 45.48 |
| 10471 | O | HOH | X | 419 | 56.231 | 57.185 | 2.974 | 1.00 | 32.25 |
| 10474 | O | HOH | X | 420 | 53.164 | 57.686 | 5.692 | 1.00 | 35.05 |
| 10477 | O | HOH | X | 421 | 65.428 | 51.862 | 28.325 | 1.00 | 40.33 |

CRYSTALLINE COMPOSITION OF FARSENYL PYROPHOSPHATE SYNTHASE (ISPA)

FIELD OF THE INVENTION

The present invention relates to a mevalonate pathway enzyme responsible for the synthesis of farnesyl pyrophosphate (FPP), and more specifically to IspA also known as farnesyl pyrophophate synthase (FPPS) and farnesyl diphosphate synthase (FDPS), referred to herein as IspA. Provided is IspA in crystalline form, methods of forming crystals comprising IspA, methods of using crystals comprising IspA, a crystal structure of IspA, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising IspA and particularly crystals comprising IspA that have sufficient size and quality to obtain useful information about the structural properties of IspA and molecules or complexes that may associate with IspA.

In one embodiment, a composition is provided that comprises a protein in crystalline form wherein the protein has 55%, 65%, 78%, 85%, 90%, 95%, 97%, 99% or greater identity with residues 16-314 of SEQ. ID No. 1.

In one variation, the protein has activity characteristic of IspA. For example, the protein may optionally be inhibited by inhibitors of the *E. coli* form of IspA.

The protein crystal may also diffract X-rays for a determination of structure coordinates to a resolution of 4 Å, 3.5 Å, 3.0 Å or less.

In one variation, the protein crystal has a crystal lattice in a $P4_122$ space group. The protein crystal may also have a crystal lattice having unit cell dimensions, +/−5%, of a=88.80 Å, b=88.80 Å and c=174.99 Å; $\alpha=\beta=\gamma=90$.

In one variation, the protein has activity characteristic of IspA. For example, the protein may optionally be inhibited by inhibitors of the *E. coli* or human forms of IspA.

The present invention is also directed to crystallizing IspA. The present invention is also directed to the conditions useful for crystallizing IspA. It should be recognized that a wide variety of crystallization methods can be used in combination with the crystallization conditions to form crystals comprising IspA including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein that has at least 55% identity with residues 16-314 of SEQ. ID No. 1 in a concentration between 1 mg/ml and 50 mg/ml; 5-50% w/v of precipitant wherein the precipitant comprises one or more members of the group consisting of PEG MME having a molecular weight range between 300-10000, and PEG having a molecular weight range between 100-10000; optionally 0.05 to 2.5M additives wherein the additives comprise a monovalent and/or divalent salt (for example, sodium, lithium, magnesium, calcium, and the like); and storing the crystallization volume under conditions suitable for crystal formation. The method also optionally further includes performing the crystallization at a temperature between 1° C.-37° C. The method may optionally further comprise forming a protein crystal that has a crystal lattice in a $P4_122$ space group. The method also optionally further comprises forming a protein crystal that has a crystal lattice having unit cell dimensions, +/−5%, of a=88.80 Å, b=88.80 Å and c=174.99 Å; $\alpha=\beta=\gamma=90$. The invention also relates to protein crystals formed by these methods.

The present invention is also directed to structure coordinates for IspA as well as structure coordinates that are comparatively similar to these structure coordinates. It is noted that these comparatively similar structure coordinates may encompass proteins with similar sequences and/or structures, such as other IspA homologs. For example, machine-readable data storage media is provided having data storage material encoded with machine-readable data that comprises structure coordinates that are comparatively similar to the structure coordinates of IspA. The present invention is also directed to a machine readable data storage medium having data storage material encoded with machine readable data, which, when read by an appropriate machine, can display a three dimensional representation of all or a portion of a structure of IspA or a model that is comparatively similar to the structure of all or a portion of IspA.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.27 Å, 0.18 Å or 0.13 Å when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| IPP BINDING POCKET | | | | |
| Table 2 (4 Angstrom set) | alpha-carbon atoms[1] | 0.27 | 0.18 | 0.13 |
|  | main-chain atoms[1] | 0.27 | 0.19 | 0.13 |
|  | all non-hydrogen[2] | 0.57 | 0.37 | 0.28 |
| Table 3 (7 Angstrom set) | alpha-carbon atoms[1] | 0.90 | 0.60 | 0.45 |
|  | main-chain atoms[1] | 0.92 | 0.61 | 0.46 |
|  | all non-hydrogen[2] | 1.06 | 0.70 | 0.53 |
| Table 4 (10 Angstrom set) | alpha-carbon atoms[1] | 1.63 | 1.08 | 0.82 |
|  | main-chain atoms[1] | 1.61 | 1.06 | 0.81 |
|  | all non-hydrogen[2] | 1.02 | 0.67 | 0.51 |
| RISEDRONATE BINDING POCKET | | | | |
| Table 5 (4 Angstrom set) | alpha-carbon atoms[1] | 1.63 | 1.08 | 0.82 |
|  | main-chain atoms[1] | 1.61 | 1.06 | 0.81 |
|  | all non-hydrogen[2] | 1.02 | 0.67 | 0.51 |
| Table 6 (7 Angstrom set) | alpha-carbon atoms[1] | 1.63 | 1.08 | 0.82 |
|  | main-chain atoms[1] | 1.61 | 1.06 | 0.81 |
|  | all non-hydrogen[2] | 1.02 | 0.67 | 0.51 |
| Table 7 (10 Angstrom set) | alpha-carbon atoms[1] | 1.63 | 1.08 | 0.82 |
|  | main-chain atoms[1] | 1.61 | 1.06 | 0.81 |
|  | all non-hydrogen[2] | 1.02 | 0.67 | 0.51 |
| ENTIRE PROTEIN | | | | |
| 16-314 of SEQ. ID No. 1 | alpha-carbon atoms[1] | 1.61 | 1.06 | 0.81 |
|  | main-chain atoms[1] | 1.59 | 1.05 | 0.80 |
|  | all non-hydrogen[2] | 1.52 | 1.00 | 0.76 |

[1]the RMSD computed between the atoms of all amino acids that are common to both the target and the reference in the aligned and superposed structure. The amino acids need not to be identical.
[2]the RMSD computed only between identical amino acids, which are common to both the target and the reference in the aligned and superposed structure.

The present invention is also directed to a three-dimensional structure of all or a portion of IspA. This three-dimensional structure may be used to identify binding sites, to provide mutants having desirable binding properties, and ultimately, to design, characterize, or identify ligands capable of interacting with IspA. Ligands that interact with IspA may be any type of atom, compound, protein or chemical group that binds to or otherwise associates with the protein. Examples of types of ligands include natural substrates for IspA, inhibitors of IspA, and heavy atoms. The inhibitors of IspA may optionally be used as drugs to treat therapeutic indications by modifying the in vivo activity of IspA.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of IspA.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of IspA, in particular the structure coordinates of IspA and the surface contour defined by them, in methods for screening, designing, or optimizing molecules or other chemical entities that interact with and preferably inhibit IspA.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of IspA and/or its structure coordinates to evaluate the ability of entities to associate with IspA. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein having at least 55% identity with residues 16-314 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein having at least 55% identity with residues 16-314 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for IspA, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for IspA, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of IspA. For example, the protein may optionally be inhibited by inhibitors of the E. coli or human forms of IspA.

In another embodiment, a method is provided for identifying an entity that associates with a protein comprising: taking structure coordinates from diffraction data obtained from a crystal of a protein that has at least 55%, 65%, 78%, 85%, 90%, 95%, 97%, 99% or more identity with the residues 16-314 of SEQ. ID No. 1; and performing rational drug design using a three dimensional structure that is based on the obtained structure coordinates. The protein crystals may optionally have a crystal lattice having unit cell dimensions, +/−5%, of a=88.80 Å, b=88.80 Å and c=174.99 Å; $\alpha=\beta=\gamma=90$. The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1 and 2 referred to in this application.

FIG. 3 lists a set of atomic structure coordinates for IspA (the amino acid numbers of column E correlate to residues 16-314 of SEQ. ID No. 1) as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
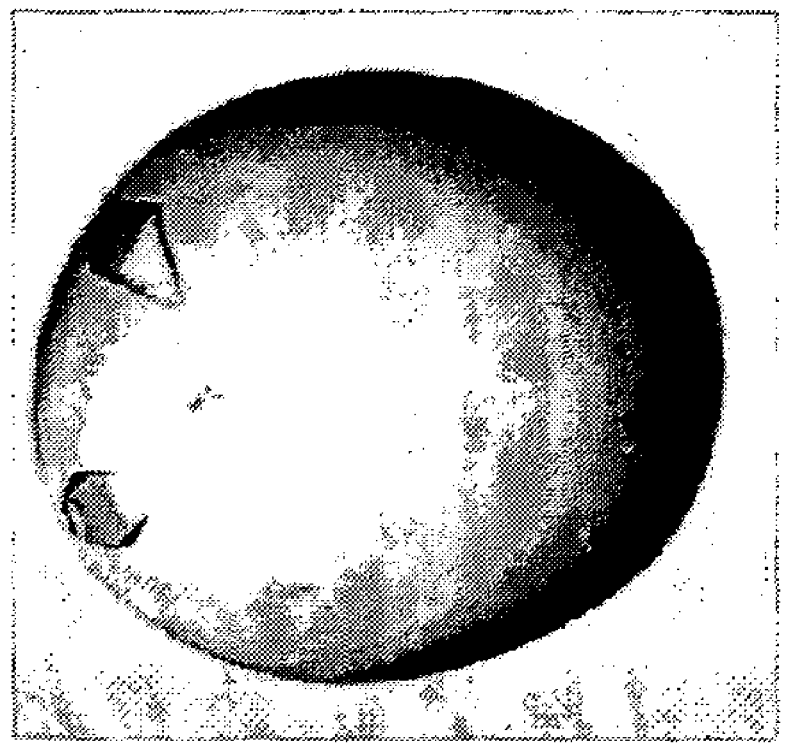
FIG. 2 illustrates crystal of IspA corresponding to SEQ. ID No. 1, having a crystal lattice in a $P4_122$ space group and unit cell dimensions, +/−5%, of a=88.80 Å, b=88.80 Å and c=174.99 Å; $\alpha=\beta=\gamma=90$.

The present invention relates to a mevalonate pathway enzyme responsible for the synthesis of farnesyl pyrophosphate (FPP), and more specifically to IspA also known as farnesyl pyrophophate synthase (FPPS) and farnesyl diphosphate synthase (FDPS), referred to herein as IspA. Provided is IspA in crystalline form, methods of forming crystals comprising IspA, methods of using crystals comprising IspA, a crystal structure of IspA, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. IspA

IspA, also known as farnesyl pyrophophate synthase (FPPS) and farnesyl diphosphate synthase (FDPS), is a mevalonate pathway enzyme responsible for the synthesis of farnesyl pyrophosphate (FPP), a key branchpoint intermediate for the biosynthesis of cholesterol, prenylated proteins, ubiquinones, dolichols, and heme a. The enzyme belongs to the larger family of isoprenoid diphosphate synthases that catalyze prenyl transfer to isopentyl pyrophosphate (IPP). Although different isoprenoid diphosphate synthase family members catalyze different reactions, all members of the family possess two conserved ASP rich motifs (DDXXD and DDXXXXD) crucial for catalysis. In cells, IspA synthesizes the C15 isoprenoid FPP through two sequential condensations of allylic and homoallyic isoprenoid units. In the first reaction isopentyl pyrophosphate (IPP) and dimethylallyl pyrophosphate (DMAPP) are condensed to form the C10 isoprenoid geranyl pyrophosphate (GPP). In the second reaction GPP is condensed with another molecule of IPP to form FPP, completing the C5 to C15 isoprenoid elongation.

Close homologues of the IspA enzyme are found in organism from all the three kingdoms of life, including a human enzyme that shares ~26% sequence identity. Notably, residues identified as contacting the allylic and homoallyic substrates are highly conserved among homologues indicating that the substrate-bound form of the E. coli enzyme will be useful for ligand design directed at the human enzyme.

Human FPPS is the molecular target of the N-containing bisphosphonate drugs used to treat osteoporosis. Bisphosphonates are analogs of pyrophophate (P—O—P) in which the central pyrophoshphate oxygen is replaced by a carbon with various side chains. The highly charged phosphate groups target and concentrate bisphosphonates on bone surfaces where they are absorbed by osteoclastic cells responsible for bone resorption. The biological consequences of bisphosphonate-mediated FPPS inhibition is thought to be a direct result of reduced intracellular levels of FPP and the C20 isoprenoid geranylgeranyl pyrophosphate (GGPP). These two molecules are substrates for prenyl:protein transferases that attach an isoprenoid lipid onto the C-terminus of small GTPases (such as Ras, Rac, Rho, and CDC42) to direct there subcellular localization and influence key protein:protein interactions. Disruption of these activities through bisphosphonate-mediated isoprenoid depletion disrupts the function of the osteoclast, which undergoes apoptosis, resulting in reduced bone resorption and lower bone turnover.

The bisphosphonate-mediated reduction of FPP has parallels with the statin family of drugs that inhibit HMG-CoA reductase, a mevalonate pathway enzyme that acts upstream of IspA. Statins, unlike bisphosphonates are highly lipophilic, and as such are targeted to the liver rather than bone. In the liver, statin-mediated HMG-CoA reductase inhibition indirectly reduces IspA levels and thus decreases the rate of cholesterol biosynthesis. The beneficial effects of statins, however, are not only mediated through a reduction in serum cholesterol, but also by disruption of trimeric G-protein signaling. Thus, like bisphosphonate-mediated inhibition of FPPS, these cholesterol-independent effects of statins' result from a reduction in the synthesis of key isoprenoid intermediates. As such, bisphosphonate-mediated inhibition of FPPS and statin mediated inhibition of HMG-CoA is currently being investigated for the treatment of a diverse range of clinical indications including cell proliferation and metastases, angiogenesis, inflammation, obesity and the treatment of parasitic diseases.

In one embodiment, IspA comprises the *E. coli* form of full length IspA (residues 16-314 of SEQ. ID No. 1) (GenBank Accession Number NM_D00694) with an N-terminal His-tag (MGSDKIIHHHHHHTL (residues 1-15 of SEQ ID No: 1).

In another embodiment, IspA comprises residues 16-314 of SEQ. ID No. 1 which comprises the active site domain of wild-type IspA that is represented in the set of structural coordinates shown in FIG. 3.

It should be recognized that the invention may be readily extended to various variants of wild-type IspA and variants of fragments thereof. In another embodiment, IspA comprises a sequence that has at least 55% identity, preferably at least 65%, 78%, 85%, 90%, 95%, 97%, 99% or higher identity with SEQ. ID No. 1.

It is also noted that the above sequences of IspA are also intended to encompass isoforms, mutants and fusion proteins of these sequences.

With the crystal structure provided herein, it is now known where amino acid residues are positioned in the structure. As a result, the impact of different substitutions can be more easily predicted and understood.

For example, based on the crystal structure, applicants have determined that the IspA amino acids shown in Table 2 encompass a 4-Angstrom radius around the IspA active site and thus likely to interact with any active site inhibitor of IspA. Applicants have also determined that the amino acids of Table 3 encompass a 7-Angstrom radius around the IspA active site. Further it has been determined that the amino acids of Table 4 encompass a 10-Angstrom radius around the IspA active site. It is noted that there is one IspA molecule in the asymmetric unit, referred to as chain A. Structural coordinates appear in FIG. 3. It is noted that the sequence and structure of the residues in the active site may also be conserved and hence pertinent to other homologues of IspA.

One or more of the sets of amino acids set forth in the tables is preferably conserved in a variant of IspA. Hence, IspA may optionally comprise a sequence that has at least 55% identity, preferably at least 65%, 78%, 85%, 90%, 95%, 97%, 99% or higher identity with any one of the above sequences (e.g., all of SEQ. ID No. 1 or residues 16-314 of SEQ. ID No. 1) where at least the residues shown in Tables 2, 3, 4, 5, 6 and/or 7 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the IPP binding pocket.

| GLY | 65 | LYS | 66 | ARG | 69 | HIS | 98 |
| LEU | 102 | ARG | 117 | THR | 203 | PHE | 240 |
| GLN | 241 | ASP | 244 | ARG | 318 | | |

TABLE 3

Amino Acids encompassed by a 7-Angstrom radius around the IPP binding pocket.

| LEU | 63 | GLY | 64 | GLY | 65 | LYS | 66 | ARG | 67 |
| LEU | 68 | ARG | 69 | GLU | 95 | HIS | 98 | ALA | 99 |
| SER | 101 | LEU | 102 | ASP | 105 | ARG | 116 | ARG | 117 |
| LYS | 202 | THR | 203 | GLY | 204 | LEU | 206 | ILE | 207 |
| PHE | 240 | GLN | 241 | ASP | 244 | ASP | 245 | LEU | 247 |
| LEU | 256 | LYS | 258 | ARG | 318 | LYS | 320 | | |

TABLE 4

Amino Acids encompassed by a 10-Angstrom radius around the IPP binding pocket.

| LEU | 28 | VAL | 32 | ASN | 36 | LEU | 39 | TYR | 59 |
| GLY | 60 | ALA | 61 | LEU | 62 | LEU | 63 | GLY | 64 |
| GLY | 65 | LYS | 66 | ARG | 67 | LEU | 68 | ARG | 69 |
| PRO | 70 | PHE | 71 | LEU | 72 | VAL | 94 | GLU | 95 |
| CYS | 96 | ILE | 97 | HIS | 98 | ALA | 99 | TYR | 100 |
| SER | 101 | LEU | 102 | ILE | 103 | ASP | 105 | ASP | 106 |
| ASP | 111 | LEU | 115 | ARG | 116 | ARG | 117 | GLY | 118 |
| LEU | 119 | MET | 175 | GLN | 179 | ASP | 182 | ILE | 198 |
| HIS | 199 | ARG | 200 | HIS | 201 | LYS | 202 | THR | 203 |
| GLY | 204 | ALA | 205 | LEU | 206 | ILE | 207 | ILE | 236 |
| GLY | 237 | LEU | 238 | ALA | 239 | PHE | 240 | GLN | 241 |
| VAL | 242 | GLN | 243 | ASP | 244 | ASP | 245 | ILE | 246 |
| LEU | 247 | ASP | 248 | THR | 255 | LEU | 256 | GLY | 257 |
| LYS | 258 | ASP | 263 | LEU | 311 | TYR | 314 | ILE | 315 |
| ARG | 318 | ASN | 319 | LYS | 320 | | | | |

TABLE 5

Amino Acids encompassed by a 4-Angstrom radius around the Risedronate binding pocket.

| SER | 101 | LEU | 102 | ASP | 105 | ASP | 111 | ARG | 116 |
| GLN | 179 | LYS | 202 | THR | 203 | GLN | 241 | ASP | 244 |
| LYS | 288 | | | | | | | | |

TABLE 6

Amino Acids encompassed by a 7-Angstrom radius around the Risedronate binding pocket.

| ARG | 69 | HIS | 98 | SER | 101 | LEU | 102 | ASP | 105 |
| ASP | 106 | ASP | 111 | ASP | 113 | LEU | 115 | ARG | 116 |
| MET | 175 | GLY | 178 | GLN | 179 | ASP | 182 | ILE | 198 |
| HIS | 199 | HIS | 201 | LYS | 202 | THR | 203 | GLY | 204 |
| PHE | 240 | GLN | 241 | ASP | 244 | ASP | 245 | ASP | 248 |
| LYS | 258 | ARG | 259 | ALA | 262 | ASP | 263 | LYS | 268 |

TABLE 7

Amino Acids encompassed by a 10-Angstrom radius around the Risedronate binding pocket.

| LYS | 66 | ARG | 69 | ILE | 97 | HIS | 98 | ALA | 99 |
|---|---|---|---|---|---|---|---|---|---|
| TYR | 100 | SER | 101 | LEU | 102 | ILE | 103 | HIS | 104 |
| ASP | 105 | ASP | 106 | LEU | 107 | MET | 110 | ASP | 111 |
| ASP | 112 | ASP | 113 | ASP | 114 | LEU | 115 | ARG | 116 |
| ARG | 117 | THR | 121 | ALA | 169 | SER | 170 | GLY | 171 |
| GLY | 174 | MET | 175 | CYS | 176 | GLY | 177 | GLY | 178 |
| GLN | 179 | ALA | 180 | LEU | 181 | ASP | 182 | LEU | 183 |
| GLU | 186 | LEU | 195 | ILE | 198 | HIS | 199 | ARG | 200 |
| HIS | 201 | LYS | 202 | THR | 203 | GLY | 204 | ALA | 205 |
| LEU | 206 | ILE | 207 | GLY | 237 | PHE | 240 | GLN | 241 |
| VAL | 242 | GLN | 243 | ASP | 244 | ASP | 245 | ILE | 246 |
| LEU | 247 | ASP | 248 | VAL | 249 | LEU | 256 | GLY | 257 |
| LYS | 258 | ARG | 259 | GLN | 260 | GLY | 261 | ALA | 262 |
| ASP | 263 | GLN | 264 | LEU | 266 | LYS | 268 | SER | 269 |
| THR | 270 | TYR | 271 | PRO | 272 | ARG | 318 | LYS | 320 |

With the benefit of the crystal structure and guidance provided by Tables 2, 3, 4, 5, 6 and 7, a wide variety of IspA variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of IspA.

Variants of IspA may be insertional variants in which one or more amino acid residues are introduced into a predetermined site in the IspA sequence. For instance, insertional variants can be fusions of heterologous proteins or polypeptides to the amino or carboxyl terminus of the subunits.

Variants of IspA also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Asp→Glu, Ser→Cys, and Cys→Ser for example.

Another class of variants is deletional variants, which are characterized by the removal of one or more amino acid residues from the IspA sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea, 2,4-pentanedione; and transaminaseN catalyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$, or $^{131}I$, to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding IspA may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of *E. coli* IspA is functional in the sense that the resulting protein is capable of associating with at least one same chemical entity that is also capable of selectively associating with a protein comprising the *E. coli* IspA (e.g., residues 16-314 of SEQ. ID No. 1) since this common associative ability evidences that at least a portion of the native structure has been conserved.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of IspA, and the atomic structure coordinates obtained there from, can be used to identify compounds that bind to the native domain. These compounds may affect the activity of the native domain.

Amino acid substitutions, deletions and additions that do not significantly interfere with the three-dimensional structure of IspA will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of IspA will be apparent to those having skills in the art, particularly in view of the three dimensional structure of IspA provided herein.

2. Cloning, Expression and Purification of IspA

The gene encoding IspA can be isolated from RNA, cDNA or cDNA libraries. In this case, the portion of the gene encoding amino acid residues 16-314 (SEQ. ID No. 1), corresponding to *E. coli*IspA, was isolated and is shown as residues 46-945 of SEQ. ID No. 2.

Construction of expression vectors and recombinant proteins from the DNA sequence encoding IspA may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of IspA. Example 1 provides one such expression system.

Once expressed, purification steps are employed to produce IspA in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

3. Crystallization and Crystals Comprising IspA

One aspect of the present invention relates to methods for forming crystals comprising IspA as well as crystals comprising IspA.

In one embodiment, a method for forming crystals comprising IspA is provided comprising forming a crystallization volume comprising IspA, one or more precipitants, optionally a buffer, optionally a monovalent and/or divalent salt and optionally an organic solvent; and storing the crystallization volume under conditions suitable for crystal formation.

In yet another embodiment, a method for forming crystals comprising IspA is provided comprising forming a crystallization volume comprising IspA in solution comprising the components shown in Table 8; and storing the crystallization volume under conditions suitable for crystal formation.

TABLE 8

Precipitant 5-65% w/v of precipitant wherein the precipitant comprises one or more members of the group consisting of PEG MME having a molecular weight range between 500-10000, PEG having a molecular weight range between 100-10000, MPD, and ethanol. 0.3-2.0 M Sodium, potassium or ammonium phosphate.

pH pH 4-10. Buffers that may be used include, but are not limited to tris, bicine, phosphate, cacodylate, acetate, citrate, HEPES, PIPES, MES and combinations thereof.

Additives

Optionally 0.05 to 2.5 M additives wherein the additives comprise a monovalent and/or divalent salt (for example, sodium, lithium, magnesium, calcium, and the like)

Protein Concentration 1 mg/ml-50 mg/ml

Temperature

1° C.-25° C.

In yet another embodiment, a method for forming crystals comprising IspA is provided comprising forming a crystallization volume comprising IspA; introducing crystals comprising IspA as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising IspA and crystals comprising IspA according to the invention are not intended to be limited to the *E. coli* form of IspA shown in SEQ. ID No. 1 and fragments comprising residues 16-314 of SEQ. ID No. 1. Rather, it should be recognized that the invention may be extended to various other fragments and variants of wild-type IspA as described above.

It should also be understood that forming crystals comprising IspA and crystals comprising IspA according to the invention may be such that IspA is optionally complexed with one or more ligands and one or more copies of the same ligand. The ligand used to form the complex may be any ligand capable of binding to IspA. In one variation, the ligand is a natural substrate. In another variation, the ligand is an inhibitor.

In one particular embodiment, IspA crystals have a crystal lattice in the P4,22 space group. IspA crystals may also optionally have unit cell dimensions, +/−5%, of a=88.80 Å, b=88.80 Å and c=174.99 Å; $\alpha=\beta=\gamma=90$. IspA crystals also preferably are capable of diffracting X-rays for determination of atomic coordinates to a resolution of 4 Å, 3.5 Å, 3.0 Å or better.

Crystals comprising IspA may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, $2^{nd}$ Ed. (1999), Academic Press Inc. Further descriptions regarding performing crystallization experiments are provided in Stevens, et al. (2000) *Curr. Opin. Struct. Biol.:* 10(5):558-63, and U.S. Pat. Nos. 6,296,673, 5,419,278, and 5,096,676.

In one variation, crystals comprising IspA are formed by mixing substantially pure IspA with an aqueous buffer containing a precipitant at a concentration just below a concentration necessary to precipitate the protein. One suitable precipitant for crystallizing IspA is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a IspA complex were obtained. In order to accomplish this, systematic broad screen crystallization trials were performed on an IspA complex using the sitting drop technique. Over 1000 individual trials were performed in which pH, temperature and precipitants were varied. In each experiment, a 100 mL mixture of IspA complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect IspA crystallization was obtained. Based on this understanding, a series of crystallization conditions were identified that may be used to form crystals comprising IspA. These conditions are summarized in Table 8. A particular example of crystallization conditions that may be used to form diffraction quality crystals of the IspA complex is detailed in Example 2. FIG. 2 illustrates crystals of the IspA complex formed using the crystallization conditions provided in Table 8.

One skilled in the art will recognize that the crystallization conditions provided in Table 8 and Example 2 can be varied and still yield protein crystals comprising IspA. For example, it is noted that variations on the crystallization conditions described herein can be readily determined by taking the conditions provided in Table 8 and performing fine screens around those conditions by varying the type and concentration of the components in order to determine additional suitable conditions for crystallizing IspA, variants of IspA, and ligand complexes thereof.

Crystals comprising IspA have a wide range of uses. For example, now that crystals comprising IspA have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising IspA according to the present invention, the crystals so formed can be used by this crystallization technique to initiate crystal growth of other IspA comprising crystals, including IspA complexed to other ligands.

As will be described herein in greater detail, crystals may also be used to perform X-ray or neutron diffraction analysis in order to determine the three-dimensional structure of IspA and, in particular, to assist in the identification of its active site. Knowledge of the binding site region allows rational design and construction of ligands including inhibitors. Crystallization and structural determination of IspA mutants having altered bioactivity allows the evaluation of whether such changes are caused by general structure deformation or by side chain alterations at the substitution site.

4. X-Ray Data Collection and Structure Determination

Crystals comprising IspA may be obtained as described above in Section 3. As described herein, these crystals may then be used to perform X-ray data collection and for structure determination.

In one embodiment, described in Example 2, crystals of IspA were obtained where IspA has the sequence of residues shown in SEQ. ID No. 1. These particular crystals were used to determine the three dimensional structure of IspA. However, it is noted that other crystals comprising IspA including different IspA variants, fragments, and complexes thereof may also be used.

Diffraction data was collected from cryocooled crystals (100K) of IspA_Ec at the Advanced Light Source beam line 5.0.3 using an ADSC CCD detector. The diffraction pattern of IspA displayed symmetry consistent with a $P4_122$ space group, with unit cell dimensions a=88.80 Å, b=88.00 Å and c=174.99 Å. Data were collected and integrated to 1.95 Å with DENZO and scaled with SCALEPACK.

All crystallographic calculations were performed using the CCP4 program package (Collaborative Computational Project, N. The CCP4 Suite: Programs for Protein Crystallography. *Acta Cryst.* D50, 760-763 (1994)). The initial phases for IspA_Ec were obtained by the molecular replacement method using the program AMORE. The coordinates of an unliganded IspA from *S. Aureus* (NCBI accession code—NP_646291), which were determined at Syrrx using MAD techniques, were used as a search model. The highest solution from the translational function was subjected to a rigid body rotation followed by positional refinement against the maximum likelihood method as implemented in REFMAC5 (CCP4). Overall refinement employed iterative rounds of manual model building with Xfit (McRee, D. E. XtalView/Xfit-A versatile program for manipulating atomic coordinates and electron density *J. Struct. Biol.* 125, 156-65 (1999)) followed by positional refinement with REFMAC5 (CCP4). All stages of model refinement were carried with bulk solvent correction and anisotropic scaling. The data collection and data refinement statistics are given in Table 9.

TABLE 9

|  |  | IspA_Ec |
|---|---|---|
| Data collection |  |  |
| X-ray source |  | ALS-BL5.0.3 |
| Wavelength [Å] |  | 1.0 |
| Resolution [Å] |  | 87-1.95 |
| Observations (unique) |  | 51703 |
| Redundancy |  | 7.6 |
| Completeness | overall (outer shell) | 99.3% (96.2%) |
| I/σ (I) | overall (outer shell) | 27.8 (3.0) |
| $R_{symm}$[1] | overall (outer shell) | 7.7% (51.6%) |
| Refinement |  |  |
| Reflections used |  | 49037 |
| R-factor |  | 20.6% |
| $R_{free}$ |  | 23.9% |
| r.m.s bonds |  | 0.010 |
| r.m.s angles |  | 1.23 |

[1] $R_{symm} = \Sigma_{hkl}\Sigma_i |I(hkl)_i - \langle I(hkl) \rangle| / \Sigma_{hkl}\Sigma_i \langle I(hkl)_i \rangle$ over I observations of a reflection hkl During structure determination, it was realized that the asymmetric unit comprised two IspA molecules. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 1. Structure coordinates are reported for residues 16-314.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the IspA structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of IspA would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap. Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v.2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for IspA, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1FPS was identified as having the smallest RMSD values relative to the structure coordinates provided herein. Table 10 below provides a series of RMSD values that were calculated by the above described process using the structure coordinates in FIG. 3 as the reference protein and the structure coordinates from PDB code: 1FPS as the target protein.

TABLE 10

| AA RESIDUES USED TO PERFORM RMSD COMPARISON WITH PDB:1FPS | PORTION OF EACH AA RESIDUE USED TO PERFORM RMSD COMPARISON WITH PDB:1FPS | RMSD [Å] |
|---|---|---|
| IPP BINDING POCKET | | |
| Table 2 (4 Angstrom set) | alpha-carbon atoms[1] | 2.41 |
| | main-chain atoms[1] | 2.37 |
| | all non-hydrogen[2] | 4.17 |
| Table 3 (7 Angstrom set) | alpha-carbon atoms[1] | 3.41 |
| | main-chain atoms[1] | 3.47 |
| | all non-hydrogen[2] | 4.68 |
| Table 4 (10 Angstrom set) | alpha-carbon atoms[1] | 3.02 |
| | main-chain atoms[1] | 3.05 |
| | all non-hydrogen[2] | 3.87 |
| RISEDRONATE BINDING POCKET | | |
| Table 5 (4 Angstrom set) | alpha-carbon atoms[1] | 1.88 |
| | main-chain atoms[1] | 1.83 |
| | all non-hydrogen[2] | 2.19 |
| Table 6 (7 Angstrom set) | alpha-carbon atoms[1] | 2.04 |
| | main-chain atoms[1] | 1.99 |
| | all non-hydrogen[2] | 2.41 |
| Table 7 (10 Angstrom set) | alpha-carbon atoms[1] | 2.66 |
| | main-chain atoms[1] | 2.73 |
| | all non-hydrogen[2] | 3.61 |
| ENTIRE PROTEIN | | |
| 16-314 of SEQ. ID No. 1 | alpha-carbon atoms[1] | 3.64 |
| | main-chain atoms[1] | 3.59 |
| | all non-hydrogen[2] | 4.06 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

It is noted that mutants, homologs and variants of IspA are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the IspA structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. IspA Structure

The present invention is also directed to a three-dimensional crystal structure of IspA. This crystal structure may be used to identify binding sites, to provide mutants having desirable binding properties, and ultimately, to design, characterize, or identify ligands that interact with IspA as well as homologs and other closely related proteins.

The three-dimensional crystal structure of IspA may be generated, as is known in the art, from the structure coordinates shown in FIG. 3 and similar such coordinates.

During the course of structure solution it became evident that the crystals of IspA of the present invention contained two IspA molecules in the asymmetric unit. These two molecules interact to form the biological dimer.

The final refined coordinates include amino acid residues 16-314 (FIG. 3).

Figure 4:
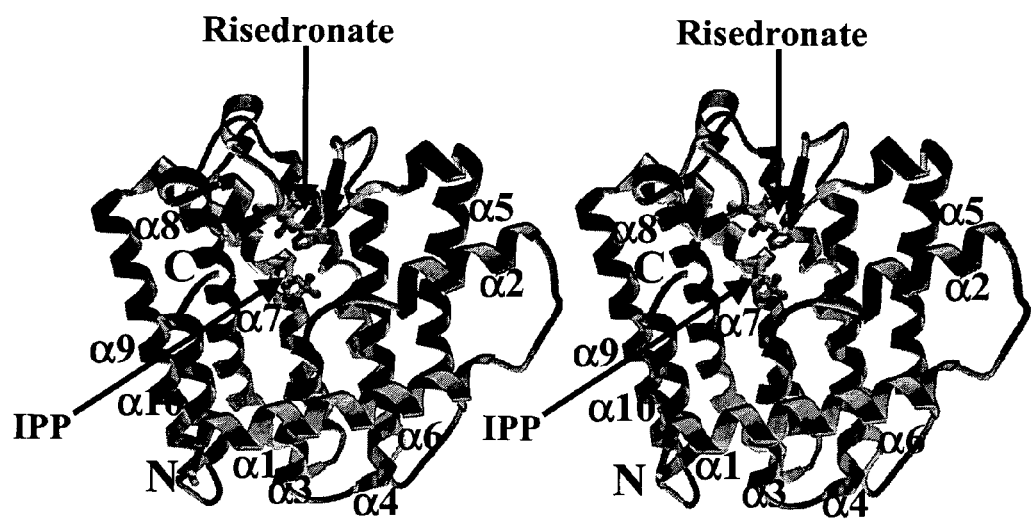
FIG. 4 illustrates a ribbon diagram overview of the structure of IspA, highlighting secondary structural elements of the protein.

FIG. 4 illustrates a ribbon diagram overview of the structure of IspA, highlighting the secondary structural elements of the protein. Aside from significant differences in ligand and inhibitor-binding active site residues, the overall secondary structure of IspA_Ec resembles that of avian farnesyl pyrophosphate synthase (pdb code 1FPS; Biochemistry (1994): 33, 10871) which shares 26% sequence identity. The enzyme forms a long and somewhat flat all-α helical structure that packs to form 3 distinct layers. The first layer is formed by helices 1 and 2 and is orthogonal to the two others. The second layer contains helices 3, 4, 5 and 10, and the third is formed by helices 6, 7, 8, and 9. Helices 4 and 8 are located in the center of the protein core and contain the conserved Asp rich motifs that identify IspA_Ec as a member of the isoprenoid diphosphate synthase family.

6. IspA Active Site and Ligand Interaction

The term "binding site" or "binding pocket", as the terms are used herein, refers to a region of a protein that, as a result of its shape, favorably associates with a ligand or substrate. The term "IspA-like binding pocket" refers to a portion of a molecule or molecular complex whose shape is sufficiently similar to the IspA binding pockets as to bind common ligands. This commonality of shape may be quantitatively defined based on a comparison to a reference point, that reference point being the structure coordinates provided herein. For example the commonality of shape may be quantitatively defined based on a root mean square deviation (RMSD) from the structure coordinates of the backbone atoms of the amino acids that make up the binding pockets in IspA (as set forth in FIG. 3).

The "active site binding pockets" or "active site" of IspA refers to the area on the surface of IspA where the substrate binds.

A major feature of the IspA structure is a large centrally located cavity that binds the allyic and homoallylic isoprenoid substrates as well as bisphosphonate inhibitors. DMAPP and inhibitor binding is mediated by a trinuclear Mg center that is ligated by conserved protein side chains that emanate from the two Aps rich motifs located on opposite walls of the cavity. In the active site all three Mg atoms are octahedraly coordinated by protein, pyrophosphate and water oxygens. The Mg1 site is coordinated by the side chain of Asp244 from the second DDXXD motif, two diphosphate oxygen atoms, and three water molecules. The side chain of Asp105 and Asp111 form the first DDXXD motif, two diphosphate oxygens, and two water molecules coordinate Mg2. Notably, both of these metal centers form 6 membered-ring chelate structures with the risedronate diphosphate. These interactions anchor the inhibitor to the enzyme active site and constrain the geometry of its diphosphate such that the nonbridging oxygens on adjacent phosphates are maintained in a coplanar arrangement. Asp105 and Asp111, as well as a diphosphate oxygen and three water molecules coordinate the third active site Mg (Mg3). In addition to multiple metal coordination interactions, the inhibitor diphosphate makes ionic interactions with the side chains of conserved Arg116, Lys202, and Lys258.

This risedronate:IPP ternary complex reveals that the FPPS C-terminus participates in catalysis by organizing conserved residues that interact with the IPP pyrophosphate. Notably, a salt bridge between the C-terminus and Lys66 positions its side chain NZ atom in an optimal location to interact with two nonbridging oxygens on adjacent phosphates. Arg318, which is also positioned by a C-terminal salt bridge, forms a water mediated interaction to a single diphosphate oxygen. Additional interactions, including hydrogen bonds from the Gly65 backbone amide and the side chain of His98, and salt bridges between Arg69 and Arg117, stabilize the enzyme bound IPP diphosphate conformation.

The pyridyl side chain of the bisphosphonate inhibitor binds in a large hydrophobic pocket that accommodates the growing hydrocarbon tail of the isoprenyl product. Stacking interactions with Gln 179 and Lys 202 on one side and Ser 101 and Leu 102 on the other, as well as a hydrogen bond to conserved Thr 203, position the inhibitor pyridyl group within vanderwalls distance of the C1, C2, C3, and C4 atoms of IPP. The pocket extends to the dimer interface with residues from helix 4 (Tyr100, Ser101, His104, and Met110), helix 6 (Met175 and Cys176), and helix 5 of the adjacent subunit forming the walls of the pocket.

Figure 5A:
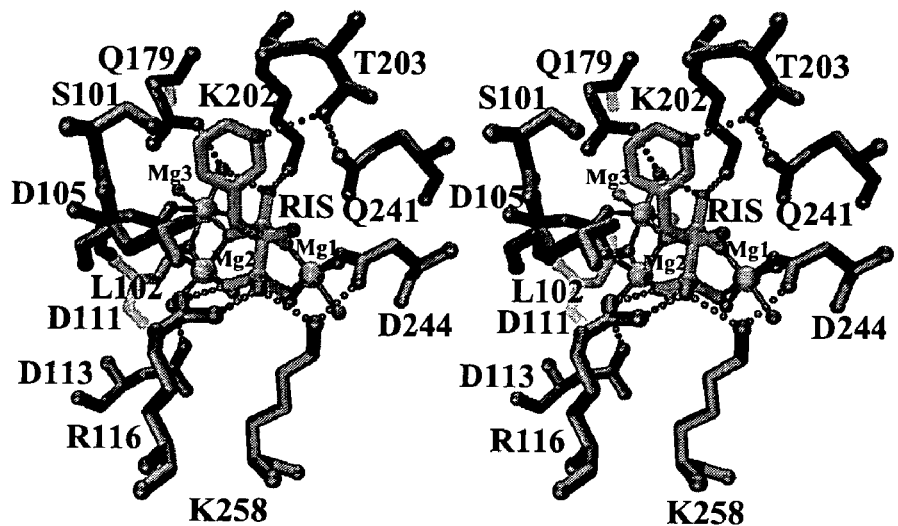
FIG. 5A illustrates residues within 4.0 Å of the IPP binding pocket for IspA.
Figure 5B:
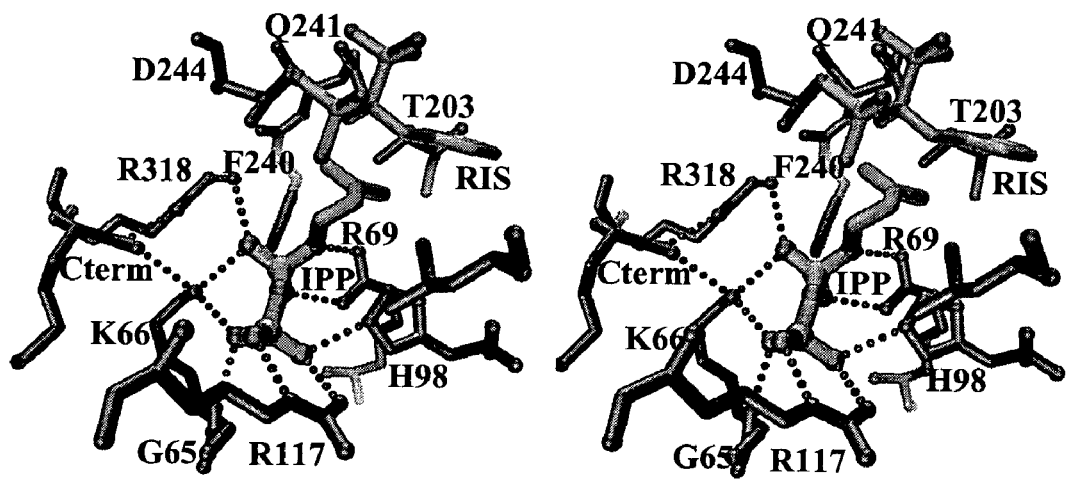
FIG. 5B illustrates residues within 4.0 Å of the Risedronate binding pocket for IspA.

FIG. 5A illustrates residues within 4.0 A of the IPP binding pocket for IspA. FIG. 5B illustrates residues within 4.0 A of the Risedronate binding pocket for IspA.

In resolving the crystal structure of IspA, applicants determined that IspA amino acids shown in Table 2 (above) are encompassed within a 4-Angstrom radius around the IspA active site and therefore are likely close enough to interact with an active site inhibitor of IspA. Applicants have also determined that the amino acids shown in Table 3 (above) are encompassed within a 7-Angstrom radius around the IspA active site. Further, the amino acids shown in Table 4 (above) are encompassed within a 10-Angstrom radius around the IspA active site. Due to their proximity to the active site, the amino acids in the 4, 7, and/or 10 Angstroms sets are preferably conserved in variants of IspA. While it is desirable to largely conserve these residues, it should be recognized however that variants may also involve varying 1, 2, 3, 4 or more of the residues set forth in Tables 2, 3, 4, 5, 6 and 7 in order to evaluate the roles these amino acids play in the binding pocket.

With the knowledge of the IspA crystal structure provided herein, Applicants are able to know the contour of an IspA binding pocket based on the relative positioning of the 4, 7, and/or 10 Angstroms sets of amino acids. Again, it is noted that it may be desirable to form variants where 1, 2, 3 4 or more of the residues set forth in Tables 2, 3, 4, 5, 6 and 7 are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted above, there are many different ways to express the surface contours of the IspA structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It will be readily apparent to those of skill in the art that the numbering of amino acids in other isoforms of IspA may be different than that set forth for IspA. Corresponding amino acids in other isoforms of IspA are easily identified by visual inspection of the amino acid sequences or by using commercially available homology software programs, as further described below.

7. System for Displaying the Three Dimensional Structure of IspA

The present invention is also directed to machine-readable data storage media having data storage material encoded with machine-readable data that comprises structure coordinates for IspA. The present invention is also directed to a machine readable data storage media having data storage material encoded with machine readable data, which, when read by an appropriate machine, can display a three dimensional representation of a structure of IspA.

All or a portion of the IspA coordinate data shown in FIG. 3, when used in conjunction with a computer programmed with software to translate those coordinates into the three-dimensional structure of IspA may be used for a variety of purposes, especially for purposes relating to drug discovery. Softwares for generating three-dimensional graphical representations are known and commercially available. The ready use of the coordinate data requires that it be stored in a computer-readable format. Thus, in accordance with the present invention, data capable of being displayed as the three-dimensional structure of IspA and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an IspA-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising IspA or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other IspA-like enzymes, and isoforms of IspA.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
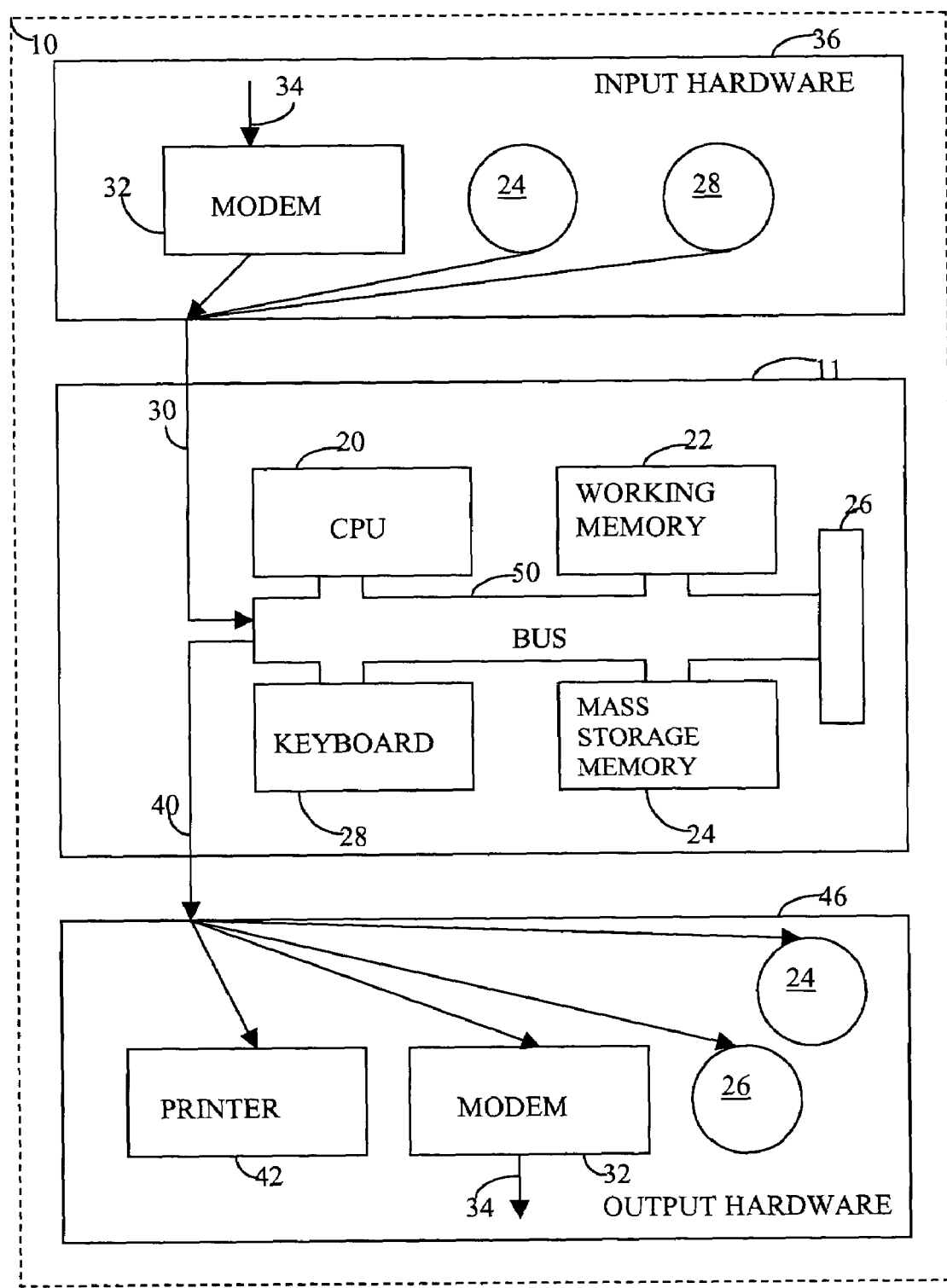
FIG. 6 illustrates a system that may be used to carry out instructions for displaying a crystal structure of IspA encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of IspA described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of IspA

The three-dimensional crystal structure of the present invention may be used to identify IspA binding sites, be used as a molecular replacement model to solve the structure of unknown crystallized proteins, to design mutants having desirable binding properties, and ultimately, to design, characterize, identify entities capable of interacting with IspA and other related homologs, as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The IspA structure coordinates provided herein are useful for screening and identifying drugs that inhibit IspA and other related homologs. For example, the structure encoded by the data may be computationally evaluated for its ability to associate with putative substrates or ligands. Such compounds that associate with IspA may inhibit IspA, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with IspA or a fragment or variant thereof by using all or a portion of the structure coordinates provided in FIG. 3 or functional equivalents thereof. A method is also provided for evaluating the potential of an entity to associate with IspA or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3, 4, 5, 6 and 7 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an IspA-like binding pocket. One embodiment of the method comprises: using all or a portion of the structure coordinates provided herein to generate a three-dimensional structure of an IspA-like binding pocket; employing the three-dimensional structure to design or select a potential ligand; synthesizing the potential ligand; and contacting the synthesized potential ligand with a protein comprising an IspA-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 1, 2 and/or 3 that are present.

As noted previously, the three-dimensional structure of an IspA-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an IspA-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for IspA, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an IspA-like binding pocket with the synthesized entity.

With the structure provided herein, the present invention for the first time permits the use of molecular design techniques to identify, select or design potential inhibitors of IspA, based on the structure of an IspA-like binding pocket. Such a predictive model is valuable in light of the high costs associated with the preparation and testing of the many diverse compounds that may possibly bind to the IspA protein.

According to this invention, a potential IspA inhibitor may now be evaluated for its ability to bind an IspA-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an IspA-like binding pocket may be computationally evaluated using a series of steps in which chemical entities or fragments are screened and selected for their ability to associate with the IspA-like binding pockets.

One skilled in the art may use one of several methods to screen entities (whether chemical or protein) for their ability to associate with an IspA-like binding pocket. This process may begin by visual inspection of, for example, an IspA-like binding pocket on a computer screen based on the IspA structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of IspA. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of an IspA-like binding pocket in a step-wise fashion one fragment or entity at a time as described above, inhibitory or other IspA binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an IspA binding pocket may be tested and optimized by computational evaluation. For example, an effective IspA binding pocket inhibitor preferably demonstrates a relatively small difference in energy between its bound and free states (i.e., a small deformation energy of binding). Thus, the most efficient IspA binding pocket inhibitors should preferably be designed with deformation energy of binding of not greater than about 10 kcal/mole, more preferably, not greater than 7 kcal/mole. IspA binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an IspA binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRIGHT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an IspA binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an IspA-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the IspA provided by this invention (and set forth in FIG. 3) can be used to determine the structure of another crystallized molecule or molecular complex more quickly and efficiently than attempting an ab initio structure determination. One particular use includes use with other related IspA homologs. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of IspA according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of IspA can be resolved by this method.

In one embodiment, the method of molecular replacement is utilized to obtain structural information about the present invention and any other IspA-like molecule. The structure coordinates of IspA, as provided by this invention, are particularly useful in solving the structure of other isoforms of IspA or IspA complexes.

The structure coordinates of IspA as provided by this invention are useful in solving the structure of IspA variants that have amino acid substitutions, additions and/or deletions (referred to collectively as "IspA mutants", as compared to naturally occurring IspA). These IspA mutants may optionally be crystallized in co-complex with a ligand, such as an inhibitor, substrate analogue or a suicide substrate. The crystal structures of a series of such complexes may then be solved by molecular replacement and compared with that of IspA. Potential sites for modification within the various binding sites of the enzyme may thus be identified. This information provides an additional tool for determining the most efficient binding interactions such as, for example, increased hydrophobic interactions, between IspA and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known IspA inhibitors, and more importantly, to design new IspA inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of IspA

Crystals, crystallization conditions and the diffraction pattern of IspA that can be generated from the crystals also have a range of uses. One particular use relates to screening entities that are not known ligands of IspA for their ability to bind to IspA. For example, with the availability of crystallization conditions, crystals and diffraction patterns of IspA provided according to the present invention, it is possible to take a crystal of IspA; expose the crystal to one or more entities that may be a ligand of IspA; and determine whether a ligand/IspA complex is formed. The crystals of IspA may be exposed to potential ligands by various methods, including but not limited to, soaking a crystal in a solution of one or more potential ligands or co-crystallizing IspA in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/IspA complex(es) may be used to design new ligands that bind tighter, bind more specifically, have better biological activity or have better safety profile than known ligands.

In one embodiment, a method is provided for identifying a ligand that binds to IspA comprising: (a) attempting to crystallize a protein that comprises a sequence with 55%, 65%, 78%, 85%, 90%, 95%, 97%, 99% or greater identity with SEQ. ID No. 1 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to IspA comprising: soaking a crystal of a protein that comprises a sequence with 55%, 65%, 78%, 85%, 90%, 95%, 97%, 99% or greater identity with SEQ. ID No. 1 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-IspA complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of IspA_Ec

This example describes the expression of IspA_Ec. It should be noted that a variety of other expression systems and hosts are also suitable for the expression of IspA_Ec, as would be readily appreciated by one of skill in the art.

The gene encoding residues 16-314 of SEQ. ID No. 1, which corresponds to the full-length IspA from *E. coli*, was isolated by PCR from *E. coli* genomic DNA (DH10B-1r strain) and cloned into the TOPO-activated cloning site of pSX28 vector. This DNA sequence along with residues encoding the N-terminal His-tag (residues 1-15 of SEQ ID No: 1) is presented in SEQ. ID No. 2. Expression of SEQ. ID No:2 in the pSX28 vector generated a fusion of the full-length IspA with a non-cleavable amino-terminal six histidine tag (SEQ ID No: 1). The amino acid sequence of the tag is shown, underlined, in FIG. 1 (residues 1-15 of SEQ. ID No.1).

Biomass for purification of recombinant IspA_Ec was generated using 96-well fermentor. Cells from a single 70 ml fermentor tubes was thawed by addition of 21 ml of lysis buffer (50 mM Tris/HCl pH 7.9, 50 mM NaCl, 1 mM $MgCl_2$) containing hen egg white lysozyme (0.6 mg/ml) and Benzonase (2.5 U/ml) and sonicated using Sonic Hedgehog robot. The sonicate was allowed to stand for 30 minutes at ~4° C. Total lysate was clarified by centrifugation and 2 mL of 5M NaCl were added to the cleared lysate. The cleared lysate from a single fermentor tubes was applied to 3 ml bed ProBond column that had been equilibrated to 50 mM Potassium Phosphate pH 7.8, 0.4 M NaCl, 0.1 M KCl, 20 mM imidazole, 10% glycerol, 0.25 mM TCEP. The solution was passed through the column using gravity flow and the column was washed with 6 bed volumes of 50 mM Potassium Phosphate pH 7.8, 0.4 M NaCl, 0.1 M KCl, 40 mM imidazole, 10% glycerol, 0.25 mM TCEP. The product was eluted with 12 ml of 50 mM Potassium Phosphate pH 7.4, 0.4 M NaCl, 0.1 M KCl, 200 mM imidazole, 10% glycerol, 0.25 mM TCEP. The eluted protein was concentrated and buffer-exchanged into 25 mM Tris pH 7.9, 150 mM NaCl by using Vivaspin centrifugal concentrators. Following three five-fold dilution buffer-exchanges, the IMAC purified IspA_Ec was concentrated to 12.1 mg/ml with a total volume of 1.08 ml. The purified protein had the correct molecular mass as determined by Mass Spectrograph (MS) analysis (33,812 observed and 33,810 expected without N-terminal methionine), was monomeric by analytical size-exclusion chromatography (SEC) and exhibited a major band by both isoelectric focusing (IEF) and by sodium-dodecyl-sulfate polyacrylamide gel electrophoresis (SDS-PAGE) analyses.

Passage 2 HTS was used to infect a 5-liter culture of *Spodoptera frugiperda* Sf9 insect cells (at a density of approx. $3\times10^6$ cells/ml) in a 10 liter Wave BioReactor grown in ESF-921 serum-free medium at a multiplicity of infection (moi) of approximately 5 (empirical value based on usual HTS viral counts). Cell growth/infection proceeded for two days after which time the cells were pelleted by centrifugation and the cell pellet stored at –80C until required. Frozen cell pellets from two such 5-liter cultures were removed from the –80C freezer and each suspended in 150 ml of Lysis Buffer (50 mM Tris-HCl, pH 7.9, 200 mM NaCl, 0.25 mM TCEP, 1 mM PMSF and 2 'Complete-EDTA' Roche Protease Inhibitor tablets). The suspensions were stirred for 45 min at 4C followed by centrifugation at 7,000 g for 1 h. To each supernatant were added 8 ml of a 50% slurry of ProBond (InVitrogen) resin that had been equilibrated in Lysis Buffer without protease inhibitors. The suspensions were mixed for 90 min followed by centrifugation at 640 g for 5 min. The supernatants were discarded and the resin pellets washed three times with 50 mM potassium phosphate, pH 7.9, 400 mM NaCl, 0.25 mM TCEP and 1 ug/mL leupeptin. Each resin sample was transferred to an OMNI chromatography column (10 cm×1.5 cm diameter) at 4C and washed with 50 column volumes of 50 mM potassium phosphate, pH 7.9, 400 mM NaCl, 20 mM imidazole-HCl, pH 7.9, 0.25 mM TCEP and 1 ug/mL leupeptin. The columns were subsequently washed with 5 column volumes of 50 mM Tris-HCl, pH 7.9, 400 mM NaCl, 0.25 mM TCEP and 1 ug/mL leupeptin. Target elution was effected by the addition of 50 mM Tris-HCl, pH 7.9, 400 mM NaCl, 200 mM imidazole-HCl, pH 7.9, 0.25 mM TCEP, 1 ug/mL leupeptin. The eluates were pooled (the yield at this stage was 25.3 mg total protein in 36 ml) and the polyhistidine purification tag removed by cleavage overnight with 100 u/ml TEV protease during dialysis against 50 mM Tris-HCl, pH 7.9, 400 mM NaCl, 20 mM imidazole-HCl, pH 7.9, 0.25 mM TCEP and 1 ug/mL leupeptin at 4C. The TEV-treated sample was passed by gravity flow through an 8 ml bed volume of ProBond chelating resin charged with Ni that had been equilibrated in 50 mM Tris-HCl, pH 7.9, 400 mM NaCl, 20 mM imidazole-HCl, pH 7.9, 0.25 mM TCEP and 1 ug/mL leupeptin at 4C. The unbound flow-through material was concentrated and buffer-exchanged into 25 mM Tris-HCl buffer, pH 7.6, 250 mM NaCl, 5 mM DTT and 1 mM EDTA-NaOH, pH 8.0, by using Vivaspin centrifugal concentrators. Following three five-fold dilution buffer-exchanges, the purified IspA was concentrated to 10.6 mg/ml with a total volume of 1.68 ml (17.8 mg purified IspA). The purified protein had the correct molecular mass as determined by Mass Spectrograph (MS) analysis (38,705 expected and 38,700 observed), was monomeric by analytical size-exclusion chromatography (SEC) and exhibited a major band by both isoelectric focusing (IEF) and by sodium-dodecyl-sulfate polyacrylamide gel electrophoresis (SDS-PAGE) analyses.

Example 2

Crystallization of IspA

This example describes the crystallization of IspA. It is noted that the precise crystallization conditions used may be further varied, for example by performing a fine screen based on these crystallization conditions.

IspA protein samples (corresponding to residues 1-314 of SEQ. ID No. 1) were concentrated to the final concentration of 12 mg/ml, incubated with 0.5-2.50 mM $MgCl_2$ and ligands before initiating crystallization trials. Several combinations of ligands in the 0.5-2.5 mM range produced crystals useful for structural analysis. The ligand combinations included: 1) isopentyl pyrophosphate (IPP)+dimethylallyl S-thiolodiphosphate (DMASPP), 2) IPP+farnesyl S-thiolodiphosphate (FSPP), 3) geranyl diphosphate (GPP), 4) IPP+geranyl S-thiolodiphosphate, 5) IPP+Risedronate, 6) IPP+Pamidronate, and 7) Risedronate. Interestingly, it was found that crystallization was facilitated by the presence of ligands.

50 nL of protein was mixed with 50 nL of reservoir solution and incubated in sitting drops over a period of one month using the vapor diffusion method. Crystals were obtained after an extensive and broad screen of conditions, followed by optimization. The reservoir conditions which produced crystal used for data collection were: 10% methyl pentanediol (MPD), 0.1M MES pH 6.0

Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of IspA complexed with IPP+Risedronate is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein, isopentyl pyrophosphate and Risedronate complex in co-crystalline form, wherein the protein of the complex consists of residues 1-314 of SEQ ID NO: 1, wherein said protein is in complex with isopentyl pyrophosphate and Risedronate, and wherein the co-crystal has a crystal lattice in a $P4_122$ space group and unit cell dimensions, +/−5%, of a=88.80 Å b=88.80 Å and c=174.99 Å, $\alpha=\beta=\gamma=90°$.

2. The composition according to claim 1 wherein the co-crystal diffracts X-rays for a determination of structure coordinates to a resolution of a value equal to or less than 3.0 Å.

3. A method for forming a co-crystal of a protein, isopentyl pyrophosphate and Risedronate comprising:

forming a crystallization volume comprising a precipitant solution, isopentyl pyrophosphate, Risedronate and a protein that consists of residues 1-314 of SEQ ID NO: 1, wherein said protein is in complex with isopentyl pyrophosphate and Risedronate; and storing the crystallization volume under conditions suitable for formation of a protein, isopentyl pyrophosphate and Risedronate complex co-crystal, wherein the co-crystal has a crystal lattice in a $P4_122$ space group and unit cell dimensions, +/−5%, of a=88.80 Å, b=88.80 Å and c=174.99 Å, $\alpha=\beta=\gamma=90°$.

4. The method according to claim 3 wherein the co-crystal diffracts X-rays for a determination of structure coordinates to a resolution of a value equal to or less than 3.0 Å.

5. A method of solving a structure of a protein comprising:

forming a crystallization volume comprising a precipitant solution, isopentyl pyrophosphate, Risedronate and a protein that consists of residues 1-314 of SEQ ID NO: 1, wherein said protein is in complex with isopentyl pyrophosphate and Risedronate;

storing the crystallization volume under conditions suitable for formation of a protein, isopentyl pyrophosphate and Risedronate complex co-crystal, wherein the co-crystal has a crystal lattice in a $P4_122$ space group and unit cell dimensions, +/−5%, of a=88.80 Å, b=88.80 Å and c=174.99 Å, $\alpha=\beta=\gamma=90°$;

diffracting the co-crystal to produce a diffraction pattern; and solving the structure of the protein from the diffraction pattern.

6. A non-crystalline protein consisting of residues 1-314 of SEQ ID NO: 1.

7. A method of identifying an entity that potentially associates with a protein comprising:

forming a crystallization volume comprising a precipitant solution, isopentyl pyrophosphate, Risedronate and a protein that consists of residues 1-314 of SEQ ID NO: 1, wherein said protein is in complex with isopentyl pyrophosphate and Risedronate;

storing the crystallization volume under conditions suitable for formation of a protein, isopentyl pyrophosphate and Risedronate complex co-crystal, wherein the co-crystal has a crystal lattice in a $P4_122$ space group and unit cell dimensions, +/−5%, of a=88.80 Å b=88.80 Å and c=174.99 Å, $\alpha=\beta=\gamma=90°$;

diffracting the co-crystal to produce a diffraction pattern;

solving the structure of the protein from the diffraction pattern;

performing rational drug design using the solved structure; and identifying an entity that associates with the protein.

8. The method according to claim 7 further comprising selecting one or more entities based on the rational drug design and contacting the selected entities with the protein.

9. The method according to claim 8 further comprising measuring an activity of the protein when contacted with the one or more entities.

10. An isolated non-crystalline protein consisting of residues 1-314 of SEQ ID NO: 1.

* * * * *

SEQUENCE LISTING

```
<160> NUMBER OF SEQ ID NOS: 2

<210> SEQ ID NO 1
<211> LENGTH: 314
<212> TYPE: PRT
<213> ORGANISM: Artificial
<220> FEATURE:
<223> OTHER INFORMATION: Amino acid sequence for full-length E. coli
      IspA with an N-terminal His-tag
<220> FEATURE:
<221> NAME/KEY: MISC_FEATURE
<222> LOCATION: (1)..(15)
<223> OTHER INFORMATION: N-terminal His-tag
<220> FEATURE:
<221> NAME/KEY: MISC_FEATURE
<222> LOCATION: (16)..(314)
<223> OTHER INFORMATION: Full-length E. coli IspA

<400> SEQUENCE: 1

Met Gly Ser Asp Lys Ile Ile His His His His His His Thr Leu Met
1               5                   10                  15

Asp Phe Pro Gln Gln Leu Glu Ala Cys Val Lys Gln Ala Asn Gln Ala
            20                  25                  30

Leu Ser Arg Phe Ile Ala Pro Leu Pro Phe Gln Asn Thr Pro Val Val
        35                  40                  45

Glu Thr Met Gln Tyr Gly Ala Leu Leu Gly Gly Lys Arg Leu Arg Pro
    50                  55                  60

Phe Leu Val Tyr Ala Thr Gly His Met Phe Gly Val Ser Thr Asn Thr
65                  70                  75                  80

Leu Asp Ala Pro Ala Ala Ala Val Glu Cys Ile His Ala Tyr Ser Leu
            85                  90                  95

Ile His Asp Asp Leu Pro Ala Met Asp Asp Asp Leu Arg Arg Gly
            100                 105                 110

Leu Pro Thr Cys His Val Lys Phe Gly Glu Ala Asn Ala Ile Leu Ala
        115                 120                 125

Gly Asp Ala Leu Gln Thr Leu Ala Phe Ser Ile Leu Ser Asp Ala Asp
```

-continued

```
                130                 135                 140
Met Pro Glu Val Ser Asp Arg Asp Arg Ile Ser Met Ile Ser Glu Leu
145                 150                 155                 160

Ala Ser Ala Ser Gly Ile Ala Gly Met Cys Gly Gly Gln Ala Leu Asp
                165                 170                 175

Leu Asp Ala Glu Gly Lys His Val Pro Leu Asp Ala Leu Glu Arg Ile
                180                 185                 190

His Arg His Lys Thr Gly Ala Leu Ile Arg Ala Ala Val Arg Leu Gly
            195                 200                 205

Ala Leu Ser Ala Gly Asp Lys Gly Arg Arg Ala Leu Pro Val Leu Asp
        210                 215                 220

Lys Tyr Ala Glu Ser Ile Gly Leu Ala Phe Gln Val Gln Asp Asp Ile
225                 230                 235                 240

Leu Asp Val Val Gly Asp Thr Ala Thr Leu Gly Lys Arg Gln Gly Ala
                245                 250                 255

Asp Gln Gln Leu Gly Lys Ser Thr Tyr Pro Ala Leu Leu Gly Leu Glu
                260                 265                 270

Gln Ala Arg Lys Lys Ala Arg Asp Leu Ile Asp Asp Ala Arg Gln Ser
            275                 280                 285

Leu Lys Gln Leu Ala Glu Gln Ser Leu Asp Thr Ser Ala Leu Glu Ala
        290                 295                 300

Leu Ala Asp Tyr Ile Ile Gln Arg Asn Lys
305                 310
```

```
<210> SEQ ID NO 2
<211> LENGTH: 945
<212> TYPE: DNA
<213> ORGANISM: Artificial
<220> FEATURE:
<223> OTHER INFORMATION: cDNA sequence encoding IspA with an N-terminal
      His-tag
<220> FEATURE:
<221> NAME/KEY: misc_feature
<222> LOCATION: (1)..(45)
<223> OTHER INFORMATION: Sequence encoding N-terminal His-tag
<220> FEATURE:
<221> NAME/KEY: misc_feature
<222> LOCATION: (46)..(945)
<223> OTHER INFORMATION: Sequence encoding full-length E. coli IspA

<400> SEQUENCE: 2
atgggatctg ataaaattat tcaccatcac catcaccata cccttatgga ctttccgcag    60
caactcgaag cctgcgttaa gcaggccaac caggcgctga ccgttttat cgccccactg    120 cccttcaga acactcccgt ggtcgaaacc atgcagtatg gcgcattatt aggtggtaag    180
cgcctgcgac ctttcctggt ttatgccacc ggtcatatgt tcggcgttag cacaaacacg    240
ctggacgcac ccgctgccgc cgttgagtgt atccacgctt actcattaat tcatgatgat    300
ttaccggcaa tggatgatga cgatctgcgt gcggtttgc caacctgcca tgtgaagttt    360
ggcgaagcaa acgcgattct cgctggcgac gctttacaaa cgctggcgtt ctcgattta    420 agcgatgccg atatgccgga agtgtcggac gcgacagaa tttcgatgat ttctgaactg    480
gcgagcgcca gtggtattgc cggaatgtgc ggtggtcagg cattagattt agacgcggaa    540
ggcaaacacg tacctctgga cgcgcttgag cgtattcatc gtcataaaac cggcgcattg    600
attcgcgccg ccgttcgcct ggtgcatta agcgccggag ataaaggacg tcgtgctctg    660
ccggtactcg acaagtatgc agagagcatc ggccttgcct tccaggttca ggatgacatc    720
ctggatgtgg tgggagatac tgcaacgttg ggaaaacgcc aggtgccga ccagcaactt    780
```

```
ggtaaaagta  cctaccctgc  acttctgggt  cttgagcaag  cccggaagaa  agcccgggat      840
ctgatcgacg  atgcccgtca  gtcgctgaaa  caactggctg  aacagtcact  cgatacctcg      900
gcactggaag  cgctagcgga  ctacatcatc  cagcgtaata  aataa                       945
```